US011858996B2

(12) United States Patent
Sainson et al.

(10) Patent No.: US 11,858,996 B2
(45) **Date of Patent: *Jan. 2, 2024**

(54) ANTI-ICOS ANTIBODIES

(71) Applicant: Kymab Limited, Cambridge (GB)

(72) Inventors: Richard Charles Alfred Sainson, Cambridge (GB); Stephen John Arkinstall, Cambridge (GB); Jamie Iain Campbell, Cambridge (GB); Mohammed Hanif Ali, Cambridge (GB); E-Chiang Lee, Cambridge (GB); Matthew John McCourt, Cambridge (GB); Volker Germaschewski, Cambridge (GB); Ian Kirby, Cambridge (GB); Miha Kosmac, Cambridge (GB); Nahida Parveen, Cambridge (GB); Robert Rowlands, Cambridge (GB); Gwenoline Borhis, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 459 days.

This patent is subject to a terminal disclaimer.

(21) Appl. No.: 16/323,980

(22) PCT Filed: Aug. 9, 2017

(86) PCT No.: PCT/GB2017/052352

§ 371 (c)(1),
(2) Date: Feb. 7, 2019

(87) PCT Pub. No.: WO2018/029474

PCT Pub. Date: Feb. 15, 2018

(65) Prior Publication Data

US 2019/0330345 A1 Oct. 31, 2019

(30) Foreign Application Priority Data

| | | |
|---|---|---|
| Aug. 9, 2016 | (GB) | 1613683 |
| Sep. 7, 2016 | (GB) | 1615224 |
| Sep. 9, 2016 | (GB) | 1615335 |
| Dec. 1, 2016 | (GB) | 1620414 |
| Dec. 20, 2016 | (GB) | 1621782 |
| Feb. 13, 2017 | (GB) | 1702338 |
| Feb. 13, 2017 | (GB) | 1702339 |
| Feb. 24, 2017 | (GB) | 1703071 |
| Jun. 20, 2017 | (GB) | 1709818 |
| Jun. 20, 2017 | (TW) | 106120562 |
| Jun. 20, 2017 | (TW) | 106120563 |
| Jun. 20, 2017 | (TW) | 106120564 |
| Jun. 20, 2017 | (WO) | PCT/GB2017/051794 |
| Jun. 20, 2017 | (WO) | PCT/GB2017/051795 |
| Jun. 20, 2017 | (WO) | PCT/GB2017/051796 |

(51) Int. Cl.

| | |
|---|---|
| ***C07K 16/02*** | (2006.01) |
| ***A61K 39/395*** | (2006.01) |
| ***A61P 35/00*** | (2006.01) |
| ***C07K 16/28*** | (2006.01) |
| ***A61K 47/68*** | (2017.01) |

(Continued)

(52) U.S. Cl.

CPC ........ *C07K 16/2818* (2013.01); *A61K 31/282* (2013.01); *A61K 39/395* (2013.01); *A61K 47/6849* (2017.08); *A61P 35/00* (2018.01); *C07K 14/55* (2013.01); *C07K 16/2827* (2013.01); *C07K 16/468* (2013.01); *G01N 33/5026* (2013.01); *A61K 2039/505* (2013.01); *A61K 2039/507* (2013.01); *A61K 2039/545* (2013.01); *C07K 2317/21* (2013.01); *C07K 2317/31* (2013.01); *C07K 2317/33* (2013.01); *C07K 2317/40* (2013.01); *C07K 2317/52* (2013.01); *C07K 2317/565* (2013.01); *C07K 2317/567* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 5,869,046 | A | 2/1999 | Presta et al. |
| 6,121,022 | A | 9/2000 | Presta et al. |

(Continued)

FOREIGN PATENT DOCUMENTS

| | | | |
|---|---|---|---|
| CN | 101861168 | A | 10/2010 |
| CN | 104826106 | A | 8/2015 |

(Continued)

OTHER PUBLICATIONS

Colman, "Effects of amino acid sequence changes on antibody-antigen interactions", Research in Immunology, Jan. 1994, 145(1): 33-36.

(Continued)

*Primary Examiner* — Ilia I Ouspenski

(74) *Attorney, Agent, or Firm* — LATHROP GPM LLP; James H. Velema, Esq.

(57) ABSTRACT

Antibodies that bind ICOS (Inducible T cell Co-Stimulator). Therapeutic use of anti-ICOS antibodies for modulating the ratio between regulatory T cells and effector T cells, to stimulate the immune system of patients, including use in treating cancers. Methods of producing anti-ICOS antibodies, including species cross-reactive antibodies, using transgenic knock-out mice.

29 Claims, 61 Drawing Sheets

Specification includes a Sequence Listing.

(51) Int. Cl.

| | |
|---|---|
| ***A61K 31/282*** | (2006.01) |
| ***C07K 14/55*** | (2006.01) |
| ***C07K 16/46*** | (2006.01) |
| ***G01N 33/50*** | (2006.01) |
| *A61K 39/00* | (2006.01) |

(56) References Cited

U.S. PATENT DOCUMENTS

| | | | |
|---|---|---|---|
| 6,803,039 | B2 | 10/2004 | Tsuji et al. |
| 7,030,225 | B1 | 4/2006 | Tamatani et al. |
| 7,045,615 | B2 | 5/2006 | Tamatani et al. |
| 7,125,551 | B2 | 10/2006 | Kroczek |
| 7,132,099 | B2 | 11/2006 | Kroczek |
| 7,166,283 | B2 | 1/2007 | Tsuji et al. |
| 7,196,175 | B2 | 3/2007 | Tamatani et al. |
| 7,226,909 | B2 | 6/2007 | Tamatani et al. |
| 7,259,247 | B1 | 8/2007 | Kroczek |
| 7,279,560 | B2 | 10/2007 | Tamatani et al. |
| 7,306,800 | B2 | 12/2007 | Kroczek |
| 7,438,905 | B2 | 10/2008 | Suzuki et al. |
| 7,465,445 | B2 | 12/2008 | Tezuka et al. |
| 7,722,872 | B2 | 5/2010 | Kroczek |
| 7,794,710 | B2 | 9/2010 | Chen et al. |
| 7,892,540 | B2 | 2/2011 | Chen et al. |
| 7,932,358 | B2 | 4/2011 | Tamatani et al. |
| 7,988,965 | B2 | 8/2011 | Tsuji et al. |
| 7,998,478 | B2 | 8/2011 | Tezuka et al. |
| 8,168,179 | B2 | 5/2012 | Honjo et al. |
| 8,318,905 | B2 | 11/2012 | Kroczek |
| 8,389,690 | B2 | 3/2013 | Tamatani et al. |
| 8,840,889 | B2 | 9/2014 | Chen |
| 8,916,155 | B2 | 12/2014 | Kroczek |
| 9,102,725 | B2 | 8/2015 | Korman et al. |
| 9,376,493 | B2 | 6/2016 | Faget et al. |
| 9,567,399 | B1 | 2/2017 | Campbell et al. |
| 9,617,338 | B1 | 4/2017 | Campbell et al. |
| 9,810,837 | B2 | 11/2017 | Benabid et al. |
| 9,957,323 | B2 * | 5/2018 | Sainson ............. C07K 16/2827 |
| 10,266,608 | B2 | 4/2019 | Wu |
| 10,517,949 | B2 | 12/2019 | Wang |
| 10,793,632 | B2 | 10/2020 | Bernett et al. |
| 10,981,992 | B2 | 4/2021 | Bernett et al. |
| 11,629,189 | B2 | 4/2023 | McCourt et al. |
| 2002/0156242 | A1 | 10/2002 | Tamatani et al. |
| 2003/0124149 | A1 | 7/2003 | Shalaby et al. |
| 2005/0085433 | A1 | 4/2005 | Breidenstein et al. |
| 2006/0002929 | A1 | 1/2006 | Khare et al. |
| 2007/0122378 | A1 | 5/2007 | Freeman et al. |
| 2008/0069795 | A1 | 3/2008 | Rabb |
| 2009/0055944 | A1 | 2/2009 | Korman et al. |
| 2010/0166740 | A1 | 7/2010 | Endl et al. |
| 2010/0203056 | A1 | 8/2010 | Irving et al. |
| 2011/0065902 | A1 | 3/2011 | Sleeman et al. |
| 2015/0239978 | A1 | 8/2015 | Marodon et al. |
| 2015/0307620 | A1 | 10/2015 | Vella et al. |
| 2016/0002336 | A1 | 1/2016 | Chen |
| 2016/0024211 | A1 | 1/2016 | Chen |
| 2016/0145344 | A1 | 5/2016 | Akbari |
| 2016/0215059 | A1 | 7/2016 | Liu et al. |
| 2016/0264666 | A1 | 9/2016 | Faget et al. |
| 2016/0304610 | A1 | 10/2016 | Sazinsky et al. |
| 2016/0355608 | A1 | 12/2016 | Bernett et al. |
| 2019/0202917 | A1 * | 7/2019 | Campbell .......... C07K 16/2803 |
| 2019/0330345 | A1 | 10/2019 | Sainson et al. |
| 2019/0338032 | A1 * | 11/2019 | Campbell .......... C07K 16/2803 |
| 2020/0131267 | A1 * | 4/2020 | Carvalho .......... C07K 16/2803 |
| 2020/0190191 | A1 * | 6/2020 | Campbell .......... C07K 16/2818 |
| 2020/0317786 | A1 * | 10/2020 | Labokha ............ C07K 16/2827 |
| 2020/0407446 | A1 * | 12/2020 | McCourt ................. A61P 35/00 |
| 2021/0139590 | A1 | 5/2021 | Tuna |
| 2021/0380699 | A1 * | 12/2021 | Campbell ............... A61P 25/16 |
| 2022/0380467 | A1 | 12/2022 | Sainson et al. |
| 2022/0396623 | A1 | 12/2022 | Sainson |
| 2022/0403029 | A1 | 12/2022 | Sainson et al. |
| 2023/0176060 | A1 | 6/2023 | Sainson et al. |

FOREIGN PATENT DOCUMENTS

| | | | |
|---|---|---|---|
| CN | 110579836 | B | 10/2020 |
| EP | 0984023 | A1 | 3/2000 |
| EP | 1125585 | A1 | 8/2001 |
| EP | 1158004 | A2 | 11/2001 |
| EP | 1374901 | A1 | 1/2004 |
| EP | 1502920 | A2 | 2/2005 |
| EP | 1286668 | B1 | 4/2005 |
| EP | 1740617 | B1 | 10/2013 |
| EP | 2691419 | B1 | 11/2016 |
| EP | 2482849 | B1 | 6/2018 |
| FR | 3006774 | A1 | 12/2014 |
| GB | 2583352 | A | 10/2020 |
| JP | 2013-506690 | A | 2/2013 |
| RU | 2540490 | C2 | 2/2015 |
| WO | WO-1998/003821 | A2 | 1/1998 |
| WO | WO-1999/015553 | A2 | 4/1999 |
| WO | WO-2001/014424 | A2 | 3/2001 |
| WO | WO 2001/077342 | A1 | 10/2001 |
| WO | WO-2001/087981 | A2 | 11/2001 |
| WO | WO-2005/103086 | A1 | 11/2005 |
| WO | WO-2006/133396 | A2 | 12/2006 |
| WO | WO 2007/005874 | A2 | 1/2007 |
| WO | WO-2007/005874 | A2 | 1/2007 |
| WO | WO-2007/113648 | A2 | 10/2007 |
| WO | WO-2007/133290 | A2 | 11/2007 |
| WO | WO 2008/003103 | A2 | 1/2008 |
| WO | WO-2008/083174 | A2 | 7/2008 |
| WO | WO-2008/137915 | A2 | 11/2008 |
| WO | WO 2008/137915 | A2 | 11/2008 |
| WO | WO-2009/070642 | A1 | 6/2009 |
| WO | WO-2009/126688 | A2 | 10/2009 |
| WO | WO-2009/141239 | A1 | 11/2009 |
| WO | WO-2010/036959 | A2 | 4/2010 |
| WO | WO-2010/056804 | A1 | 5/2010 |
| WO | WO-2010/077634 | A1 | 7/2010 |
| WO | WO-2010/089411 | A2 | 8/2010 |
| WO | WO-2011/004192 | A1 | 1/2011 |
| WO | WO-2011/020024 | A2 | 2/2011 |
| WO | WO 2011/041613 | A2 | 4/2011 |
| WO | WO-2011/041613 | A2 | 4/2011 |
| WO | WO-2011/066389 | A1 | 6/2011 |
| WO | WO-2011/071871 | A1 | 6/2011 |
| WO | WO-2011/073180 | A1 | 6/2011 |
| WO | WO-2011/097477 | A1 | 8/2011 |
| WO | WO-2011/158009 | A1 | 12/2011 |
| WO | WO-2012/131004 | A2 | 10/2012 |
| WO | WO-2012/145493 | A1 | 10/2012 |
| WO | WO-2012/174338 | A2 | 12/2012 |
| WO | WO-2013/061078 | A1 | 5/2013 |
| WO | WO-2013/061098 | A2 | 5/2013 |
| WO | WO-2013/079174 | A1 | 6/2013 |
| WO | WO-2013/173223 | A1 | 11/2013 |
| WO | WO-2013/181634 | A2 | 12/2013 |
| WO | WO-2014/033327 | A1 | 3/2014 |
| WO | WO-2014/055897 | A2 | 4/2014 |
| WO | WO-2014/089113 | A1 | 6/2014 |
| WO | WO-2014/100079 | A1 | 6/2014 |
| WO | WO-2014/116846 | A2 | 7/2014 |
| WO | WO-2014/159562 | A1 | 10/2014 |
| WO | WO-2014/165082 | A2 | 10/2014 |
| WO | WO-2015/040401 | A1 | 3/2015 |
| WO | WO-2015/049537 | A1 | 4/2015 |
| WO | WO-2015/061668 | A1 | 4/2015 |
| WO | WO 2015/103072 | A1 | 7/2015 |
| WO | WO-2015/109124 | A2 | 7/2015 |
| WO | WO-2015/112800 | A1 | 7/2015 |
| WO | WO-2015/112805 | A1 | 7/2015 |
| WO | WO 2015/112805 | A1 | 7/2015 |
| WO | WO-2015/112900 | A1 | 7/2015 |
| WO | WO-2015/132580 | A1 | 9/2015 |
| WO | WO-2015/136541 | A2 | 9/2015 |
| WO | WO-2015/173267 | A1 | 11/2015 |
| WO | WO-2015/179654 | A1 | 11/2015 |
| WO | WO-2015/181342 | A1 | 12/2015 |
| WO | WO-2016/000619 | A1 | 1/2016 |
| WO | WO-2016/007235 | A1 | 1/2016 |
| WO | WO-2016/022630 | A1 | 2/2016 |

(56) References Cited

FOREIGN PATENT DOCUMENTS

| | | | |
|---|---|---|---|
| WO | WO-2016/028656 | A1 | 2/2016 |
| WO | WO-2016/030350 | A1 | 3/2016 |
| WO | WO-2016/061142 | A1 | 4/2016 |
| WO | WO 2016/068801 | A1 | 5/2016 |
| WO | WO-2016/106302 | A1 | 6/2016 |
| WO | WO-2016/111645 | A1 | 7/2016 |
| WO | WO-2016/120789 | A1 | 8/2016 |
| WO | WO-2016/149201 | A2 | 9/2016 |
| WO | WO-2016/154177 | A2 | 9/2016 |
| WO | WO-2016/160792 | A1 | 10/2016 |
| WO | WO-2016/191643 | A2 | 12/2016 |
| WO | WO-2016/197367 | A1 | 12/2016 |
| WO | WO-2017/020291 | A1 | 2/2017 |
| WO | WO-2017/020801 | A1 | 2/2017 |
| WO | WO-2017/020858 | A1 | 2/2017 |
| WO | WO 2017/025871 | A1 | 2/2017 |
| WO | WO-2017/030823 | A2 | 2/2017 |
| WO | WO-2017/034916 | A1 | 3/2017 |
| WO | WO-2017/037707 | A1 | 3/2017 |
| WO | WO-2017/053748 | A2 | 3/2017 |
| WO | WO-2017/059095 | A1 | 4/2017 |
| WO | WO-2017/070423 | A1 | 4/2017 |
| WO | WO-2017/087587 | A1 | 5/2017 |
| WO | WO-2017/213695 | A1 | 12/2017 |
| WO | WO-2017/220988 | A1 | 12/2017 |
| WO | WO-2018/025221 | A1 | 2/2018 |
| WO | WO 2018/029474 | A2 | 2/2018 |
| WO | WO-2018/045110 | A1 | 3/2018 |
| WO | WO-2018/047178 | A1 | 3/2018 |
| WO | WO-2018/085358 | A1 | 5/2018 |
| WO | WO-2018/115859 | A1 | 6/2018 |
| WO | WO-2018/187191 | A1 | 10/2018 |
| WO | WO-2018/187613 | A1 | 10/2018 |
| WO | WO 2018/225033 | A1 | 12/2018 |
| WO | WO 2019/121906 | A1 | 6/2019 |
| WO | WO 2019/122882 | A1 | 6/2019 |
| WO | WO 2019/122884 | A1 | 6/2019 |
| WO | WO 2021/043961 | A1 | 3/2021 |

OTHER PUBLICATIONS

Muto et al., "Improving the Cross-Reactivity of an Antibody Using Site-Directed Mutagenesis", Tosoh Research and Technology Review, Dec. 31, 2012, 56: 3-9.
Rudikoff et al., "Single amino acid substitution altering antigen-binding specificity", PNAS USA, Mar. 1982, 79(6): 1979-1983.
Stewart et al., "Identification and Characterization of MEDI4736, an Antagonistic Anti-PD-L1 Monoclonal Antibody", Cancer Immunology Research, Sep. 2015, 3(9): 1052-1062.
Abcam Product Datasheet, Anti-ICOS antibody [C398.4A) ab81459, 2 pages.
Abiko et al., "PD-L 1 on tumor cells is induced in ascites and promotes peritoneal dissemination of ovarian cancer through CTL dysfunction", Clin Cancer Res, 19(6):1363-74 (2013).
Affymetrix eBioscience, Anti-Human CD278 (ICOS) Purified, 1 page.
Alexandrov et al. "Signatures of mutational processes in human cancer. " Nature. Aug. 22, 2013;500(7463):415-21.
Barbie, et al., "Systematic RNA interference reveals that oncogenic KRAS-driven cancers require TBK1." Nature, 2009; 462(7269)108-12, plus 22 pages supplemental materials.
Baruch et al. "PD-1 immune checkpoint blockade reduces pathology and improves memory in mouse models of Alzheimer's disease." Nat Med, 2016; 22(2):135-9, plus 296 pages supplemental material.
Beer et al., "Randomized, Double-Blind, Phase III Trial of Ipilimumab Versus Placebo in Asymptomatic or Minimally Symptomatic Patients with Metastatic Chemotherapy-Naïve Castration-Resistant Prostate Cancer," Journal of Clinical Oncology, 35(1): 40-51 (2019).
Beier et al. "Induction, binding specificity and function of human ICOS." Eur J Immunol. Dec. 2000;30(12):3707-17.
Binnewies et al., "Understanding the tumor immune microenvironment (TIME) for effective therapy," Nature Medicine, Published online Apr. 23, 2018 (10 pages).
Blank et al., "PD-L1/B7H-1 inhibits the effector phase of tumor rejection by T cell receptor (TCR) transgenic COB+ T cells" 64(3):1140-5 (2004).
Bos et al., "Transient regulatory T cell ablation deters oncogene-driven breast cancer and enhances radiotherapy," J Exp Med 210(11):2434-2446 2013.
Boschetti et al., "Therapy with Anti-TNFα Antibody Enhances Number and Function of FOXP3+ Regulatory T Cells in Inflammatory Bowel Diseases," AGA Abstracts, S-743 (2010).
Brahmer et al., "Phase I study of single-agent anti-programmed death-1 (MDX-1106) in refractory solid tumors: safety, clinical activity, pharmacodynamics, and immunologic correlates", J Clin Oncol, 28(19):3167-75 (2010).
Brahmer et al., "Safety and activity of anti-PD-L 1 antibody in patients with advanced cancer", N Engl J Med, 366 (26):2455-65 (2012).
Briskin, "Efficacy of Anti-ICOS Agonist Monoclonal Antibodies in Preclinical Models Provides a Rationale for Clinical Development for cancer immunotherapy," Presentation SITC 2015, 22 pages.
Brown et al., "Blockade of programmed death-1 ligands on dendritic cells enhances T cell activation and cytokine production", J Immunol, 170(3):1257-66 (2003).
Buonfiglio et al., "The T cell activation molecule H4 and the CD28-like molecule ICOS are identical," Eur. J. Immunol., 30:3463-3467 (2000).
Burmeister et al., "ICOS Controls the Pool Size of Effector-Memory and Regulatory T Cells," J. Immunol., 180(2): 774-782 (2008).
Burris III et al., "Phase 1 Safety of ICOS Agonist Antibody JTX-2011 Alone and with Nivolumab (Nivo) in Advanced Solid Tumors; Predicted vs. Observed Pharmacokinetics (PK) in ICONIC" (2017).
Butte et al., "Programmed death-1 ligand 1 interacts specifically with the B7-1 costimulatory molecule to inhibit T cell responses", Immunity, 27(1):111-22 (2007).
Camus et al., "Coordination of Intratumoral Immune Reaction and Human Colorectal Cancer Recurrence," Cancer Res 69:2685-93 (2009).
Carthon et al. Preoperative CTLA-4 blockade: Tolerability and immune monitoring in the setting of a presurgical clinical trial. Clin. Cancer Res. 16:2861-2871.
Chattopadhyay et al., "Structural Basis of Inducible Costimulatory Ligand Function: Determination of the Cell Surface Oligomeric State and Functional Mapping of the Receptor Binding Site of the Protein," J. Immunol. 177(6):3920-3929 2006.
Chevalier et al., "Phenotype Alterations in Regulatory T-Cell Subsets in Primary HIV Infection and Identification of Tr1-like Cells at the Main Interleukin 10-Producing CD4+ T Cells," JID, 211: 769-779 (2015).
Collin, "Immune checkpoint inhibitors: a patent review" Expert Opinion on Therapeutic Patents, 26(5): 555-564 (2016).
Conrad et al., "Plasmacytoid dendritic cells and regulatory T cells in the tumor microenvironment: A dangerous liaison." Oncoimmunology. May 1, 2013;2(5):e2388.
Coyle et al. "The CD28-related molecule ICOS is required for effective T cell-dependent immune responses." Immunity. Jul. 2000;13(1):95-105.
Crotty, "T follicular helper cell differentiation, function, and roles in disease." Immunity. Oct. 16, 2014;41(4):529-42.
Curran et al., "PD-1 and CTLA-4 combination blockade expands infiltrating cells and reduces regulatory T and myeloid cells within B16 melanoma tumors", PNAS, 107(9): 4275-4280 (2010).
Currie et al. "Dual Control of Antitumor CD8 T Cells through the Programmed Death-1/Programmed Death-Ligand 1 Pathway and Immunosuppressive CD4 T Cells: Regulation and Counterregulation," J. Immunol., 183(12): 7898-7908 (2009).
Dall et al., "Increasing the affinity of a human IgG1 for the neonatal Fc receptor: Biological consequences." Immunol 2002; 169:5171-5180.

(56) References Cited

OTHER PUBLICATIONS

Dana Farber Blog, "Enhancing Immunotherapy: The Race to Make 'Cold' Tumors 'Hot,'" Published Jun. 6, 2018 at https://blog.dana.farber.org/insight/2018/06/enhancing-immunotherapy-race-make-cold-tumors-hot/ (7 pages).
Declaration of Dr. Anil K. Thotakura submitted with Statement of Opposition filed at European Patent Office against European Patent No. EP2482849 on Mar. 6, 2019 (27 pages).
Declaration of Dr. Gwenoline Borhis submitted with Statement of Opposition filed at European Patent Office against European Patent No. EP2482849 on Mar. 6, 2019 (10 pages).
Declaration of Dr. Richard C.A. Sainson, submitted with Statement of Opposition filed at European Patent Office against European Patent No. EP2482849 on Mar. 6, 2019 (8 pages).
Deng et al., "An Agonist Human ICOS Monoclonal Antibody that Induces T Cell Activation and Inhibits Proliferation of a Myeloma Cell Line," Hybridoma and Hybridomics, 23(3): 176-182 (2004).
Deng et al., "Extrafollicular CD4+ T-B interactions are sufficient for inducing autoimmune-like chronic graft- versus-host disease," Nature Communications 2017, 18:978, (17 pages).
Dong et al., "B7-H1, a third member ofthe B7 family, co-stimulates T-cell proliferation and interleukin-10 secretion" Nat Med, 5(12):1365-9 (1999).
Dong et al. "ICOS co-stimulatory receptor is essential for T-cell activation and function." Nature. 2001; 409(6816):97-101.
Dong et al., "Tumor-associated B7-H1 promotes T-cell apoptosis: a potential mechanism of immune evasion", Nat Med, 8(8):793-800 (2002).
Dranoff et al., "Vaccination with irradiated tumor cells engineered to secrete murine granulocyte-macrophage colony-stimulating factor stimulates potent, specific, and long-lasting anti-tumor immunity," Proc. Natl. Acad. Sci. USA 90: 3539-3543 (1993).
Driessens et al., "Costimulatory and coinhibitory receptors in anti-tumor immunity," Immunol. Rev. 229(1):126-144 (2009).
Eager et al., "GM-CSF Gene-Transduced Tumor Vaccines," Molecular Therapy 12(1): 18-27 (2005).
Elpek et al., "Abstract A059: Efficacy of anti-ICOS agonist monoclonal antibodies in preclinical tumor models proves a rationale for clinical development as cancer immunotherapeutics," Cancer Immunology Research, (2016).
EuropeanBiotechnology.com, "Roche's anti-PD-L1 fails in bladder cancer," Published May 10, 2017 at https://european-biotechnology.com/up-to-date/latest-news/news/roches-anti-pd-l1-fails-in-bladder-cancer.html (2 pages).
Faget et al., "ICOS-Ligand Expression on Plasmacytoid Dendritic Cells Supports Breast Cancer Progression by Promoting the Accumulation of Immunosuppressive CD4+ T Cells," Cancer Res., 72(23): (2012).
Fan et al. "Engagement ofthe ICOS pathway markedly enhances efficacy of CTLA-4 blockade in cancer immunotherapy." J Exp Med. Apr. 7, 2014;211(4):715-25.
Fehrenbacher et al., "Atezolizumab versus docetaxel for patients with previously treated non-small-cell lung cancer (POPLAR): a multicentre, open-label, phase 2 randomised controlled trial", Lancet, 387(10030):1837-46 (2016).
Feyler et al., "Tumour Cell Generation of Inducible Regulatory T-Cells in Multiple Myeloma is Contact-Dependent and Antigen-Presenting Cell-Independent," PLoS ONE, 7(5): 10 pages (2012).
Francisco et al., "PD-L1 regulates the development, maintenance, and function of induced regulatory T cells," J. Exp. Med. 206(13): 3015-3029 (2009).
Freeman et al., "Engagement of the PD-1 immunoinhibitory receptor by a novel B7 family member leads to negative regulation of lymphocyte activation", J Exp Med, 192(7): 1027-34 (2000).
French et al., "What is conservative substitution?" J. Mol. Evol. 1983; 19;171-5.
Fu et al., "The ICOS/ICOSL pathway is required for optimal antitumor responses mediated by anti-CTLA-4 therapy." Cancer Res. Aug. 15, 2011;71(16):5445-54.
Galluzzi et al, "Immunological mechanisms underneath the efficacy of cancer therapy." Canc. Imm. Res. 4:895-902 2016.
Galon et al., "Approaches to treat immune hot, altered and cold tumours with combination immunotherapies," Nature Reviews Drug Discovery, Published online Jan. 4, 2019 (22 pages).
Gerritsen et al., "A dose-escalation trial of GM-CSF-gene transduced allogeneic prostate cancer cellular immunotherapy in combination with a fully human anti-CTLA antibody (MDX-010, ipilimumab) in patients with metastatic hormone-refractory prostate cancer (mHRPC)" Journal of Clinical Oncology, 24(18), Published online Dec. 12, 2016 at http://ascopubs.org/doi/abs/10.1200/jco.2006.24.18_suppl.2500 (5 pages).
Hamada et al., "Carrier Cell-mediated Delivery of a Replication-competent Adenovirus for Cancer Gene Therapy," Molecular Therapy 15(6): 1121-1128 (2007).
Hänzelmann, et al., "GSVA: gene set variation analysis for microarray and RNA-Seq data," BMC Bioinformatics, vol. 14, No. 1, p. 7, 2013.
Harvey et al., "Efficacy of Anti-ICOS Agonist Monoclonal Antibodies in Preclinical Models Provides a Rationale for Clinical Development for cancer immunotherapy," Journal for Immunotherapy of Cancer 3(Suppl 2):O9 (2015).
Hasenhindl et al., "Creating stable stem regions for loop elongation in Fcabs—Insights from combining yeast surface display, in silico loop reconstruction and molecular dynamics simulations", Biochimica et Biophysica Acta 1844: 1530-1540 (2014).
Helfand, "AstraZeneca's Imfinzi fails key Mystic trial in lung cancer. What now?" Published online Nov. 16, 2018 at https://www.fiercepharma.com/pharma/astrazeneca-s-imfinzi-fails-key-mystic-trial-lung-cancer-what-now (4 pages).
Herbst et al., "Predictive correlates of response to the anti-PD-L 1 antibody MPDL3280A in cancer patients", Nature, 515(7528):563-7 (2014).
Hirano et al., "Blockade of B7-H1 and PD-1 by monoclonal antibodies potentiates cancer therapeutic immunity", Cancer Res, 65(3):1089-96 (2005).
Hirsch et al., "Biomarker Driven Indication Selection in JTX-2011 ICONIC Clinical Trial," poster presented at the American Society of Clinical Oncology (ASCO) Annual Meeting, Jun. 2-6, 2017 in Chicago, Illinois.
Hirsch, "A biomarker-driven approach for the development of the ICOS agonist antibody, JTX-2011, presentation for the Society for Immunotherapy of Cancer," Nov. 8, 2017 in National Harbor, Maryland, 11 pages.
Hodge et al., "Multiple Costimulatory Modalities Enhance CTL Avidity," J. Immunol. 174: 5994-6004 (2005).
Hodi et al., "Immunologic and clinical effects of antibody blockade of cytotoxic T lymphocyte-associated antigen 4 in previously vaccinated cancer patients." PNAS Feb. 26, 2008;105(8):3005-10.
Houot et al., "Therapeutic effect of CD137 immunomodulation in lymphoma and its enhancement by Treg depletion," Blood 114:3431-3438 2009.
Hutloff et al. "ICOS is an inducible T-cell co-stimulator structurally and functionally related to CD28." Nature. 1999; 397(6716):263-6.
Idusogie et al., "Engineered antibodies with increased activity to recruit complement." J. Immunol., 2001, 166:2571-2575.
Inman, "Costimulation, Coinhibition, and Cancer." Current Cancer Drug Targets, 7, 15-30 (2007).
International Search Report & Written Opinion dated Sep. 22, 2017; PCT/GB2017/051794.
International Search Report & Written Opinion dated Sep. 25, 2017; PCT/GB2017/051795.
International Search Report & Written Opinion dated Oct. 4, 2017; PCT/GB2017/051796.
International Search Report & Written Opinion dated Feb. 5, 2018; PCT/GB2017/052352.
International Search Report & Written Opinion dated May 3, 2018; PCT/GB2017/053826.
International Search Report & Written Opinion dated May 7, 2019; PCT/GB2018/051714.
International Search Report & Written Opinion dated Apr. 1, 2019, PCT/GB2018/053698.

(56) References Cited

OTHER PUBLICATIONS

International Search Report & Written Opinion dated May 27, 2019, PCT/GB2018/053701.
Iwai et al., "Involvement of PD-L 1 on tumor cells in the escape from host immune system and tumor immunotherapy by PD-L 1 blockade", Proc Nall Acad Sci USA, 99(19):12293-7 (2002).
Janke et al., "Eminent role of ICOS costimulation for T cells interacting with plasmacytoid dendritic cells," Immunology, 11: 353-360 (2006).
Jian-Fei et al., "Regulatory T cells, especially !COS+ FOXP3(+) regulatory T cells, are increased in the hepatocellular carcinoma microenvironment and predict reduced survival", Scientific Reports, vol. 6, Oct. 2.
Jounce Therapeutics, "Advancing Cancer Immunotherapy Worldwide" Presentation for SITC Conference, Nov. 8-12, 2017.
Jounce Therapeutics Press Release, Jounce Therapeutics Initiates Phase 2 Portion of ICONIC Study of JTX-2011 in Patients with Advanced Solid Tumors, Apr. 20, 2017, 3 pages.
Jounce Therapeutics Press Release, Jounce Therapeutics Initiates Phase 1/2 ICONIC Study of JTX-2011 in Patients with Advanced Solid Tumors, Sep. 7, 2016, 2 pages.
Jounce Therapeutics Press Release, Jounce Therapeutics Presents Data Highlighting Advances From Two Programs in its Immune-Oncology Pipeline at the 2016 AACR Annual Meeting, Apr. 17, 2016, 2 pages.
Jounce Therapeutics Press Release, Jounce Therapeutics Presents Phase 1 Data from ICONIC Study of JTX-2011 in Patients with Advanced Solid Tumors at 2017 ASCO Annual Meeting, Jun. 5, 2017, 6 pages.
Jounce Therapeutics Press Release, Jounce Therapeutics to Present Program Updates at AACR Annual Meeting 2016, Mar. 16, 2016, 2 pages.
Jounce Therapeutics Press Release, Jounce Therapeutics to Present at AACR Annual Meeting on JTX-2011 Cancer Immunotherapy Program, Mar. 22, 2017, 5 pages.
Jounce Therapeutics Press Release, Jounce Therapeutics to Present Phase 1 Data from JTX-2011 ICONIC Trial at 2017 American Society of Clinical Oncology Annual Meeting, May 17, 2017, 5 pages.
Kaiser et al., "Reduced tumor-antigen density leads to PD-1/PD-L 1-mediated impairment of partially exhausted COB+ T cells", Eur J Immunol, 42(3):662-71 (2012).
Keir et al., "PD-1 and Its Ligands in Tolerance and Immunity," Annu. Rev. Immunol. 26: 677-704 (2008).
Kilpatrick et al., "Rapid development of affinity matured monoclonal antibodies using RIMMS;" Hybridoma, 1997; 16(4):381-9.
Kraman et al. "A LAG-3/PD-L1 bispecific antibody inhibits tumour growth in two syngeneic colon carcinoma patients," Keystone Symposium, 2017, Poster 3005.
Kroemer et al. "Immunologic Cell Death in Cancer Therapy," Ann Rev Immunol. 2013; 31:51-72.
Langer, "New methods of drug delivery." (1990) Science 249:1527-1533.
Lazar et al., "Engineered antibody Fc variants with enhanced effector function," 2006, Proc. Natl. Acad. Sci. U.S.A., Mar. 14; 103(11):4005-10.
Le et al., "Follicular B Lymphomas Generate Regulatory T Cells via the ICOS/ICOSL Pathway and Are Susceptible to Treatment by Anti-ICOS/ICOSL Therapy," Cancer Res., 76(16):4648-4660 (2016).
Lee et al, "Complete humanization of the mouse immunoglobulin loci enables efficient therapeutic antibody discovery." Nature Biotechnology, 2014; 32:6-363.
Lefranc "IMGT unique numbering for immunoglobulin and T cell receptor variable domains and lg superfamily V-like domains," Dev Comp Immunol. 2003; 27(1):55-77.
Liakou et al. "CTLA-4 blockade increases IFNgamma-producing CD4+ICOShi cells to shift the ratio of effector to regulatory T cells in cancer patients." Proc Natl Acad Sci U S A. Sep. 30, 2008;105(39):14987-92.
Lin et al., "The PD-1/PD-L 1 complex resembles the antigen-binding Fv domains ofantibodies and T cell receptors", Proc Nall Acad Sci USA, 105(8):3011-6 (2008).
Liston et al., "Dicer-dependent microRNA pathway safeguards regulatory T cell function," J Exp Med 205(9):1993-2004 (2008).
Löhning et al., "Expression of ICOS in Vivo Defines CD4+ Effector T Cells with High Inflammatory Potential and a Strong Bias for Secretion of Interleukin 10," J. Exp. Med., 197(2): 181-193 (2003).
Mak et al.. "Costimulation through the inducible costimulator ligand is essential for both T helper and B cell functions in T cell-dependent B cell responses." Nat Immunol. 2003; 4(8):765-72.
Martin-Orozco et al., "Melanoma Cells Express ICOS Ligand to Promote the Activation and Expansion of T-Regulatory Cells," Cancer Research 70(23):9581-9590 2010.
McAdam et al., "Mouse Inducible Costimulatory Molecule (ICOS) Expression is Enhanced by CD28 Costimulation and Regulates Differentiation of CD4+ T Cells," J. Immunology, 165:5035-5040 (2000).
McCourt et al., "KY1055, a novel anti-ICOS/PD-L1 bispecific antibody, enhances T cell activation and delivers potent monotherapy anti-tumour responses in vivo," poster, 1 page.
McCourt et al., "KY1055, a novel anti-ICOS/PD-L1 bispecific antibody, enhances T cell activation and delivers potent monotherapy anti-tumour responses in vivo," powerpoint, 13 pages.
Metzger et al., "ICOS Promotes the Function of $CD4^+$ Effector T Cells during Anti-OX40-Mediated Tumor Rejection," Cancer Res, 76(13): 3684-3689 (2016).
Michaelson, "Preclinical Assessment of JTX-2011, An Agonist Antibody Targeting ICOS, Supports Evaluation in ICONIC Clinical Trial," Presentation 2017, 27 pages.
Moore et al., "Anti-PD1 x anti-ICOS bispecific antibody XmAb23104 brings together PD1 blockade and ICOS costimulation to promote human T cell activation and proliferation" SITC 2017 Poster P347.
Moynihan et al., "Eradication of large established tumors in mice by combination immunotherapy that engages innate and adaptive immune responses," Nature Medicine, 12 pages (2016).
Nair et al., "A simple practice guide for dose conversion between animals and human." J Basic Clin Pharma 2016;7:27-31.
Natsume et al., "Engineered Antibodies of IgG1/IgG3 Mixed Isotype with Enhanced Cytotoxic Activities." Cancer Res., 68: 3863-3872.
Natsume et al., "Improving effector functions of antibodies for cancer treatment : Enhancing ADCC and CDC," 2009, Drug Des. Devel. Ther., 3:7-16.
Nemunaitis, "Vaccines in Cancer: GVAX®, a GM-CSF gene vaccine," Expert Rev. Vaccines 4(3): 259-274 (2005).
Neri et al., "Immunocytokines for cancer treatment: past, present and future", Current Opinion in Immunology, Elsevier, Oxford, GB vol. 40, Apr. 6, 2016 (Apr. 6, 2016), pp. 96-102.
Odegard et al., "ICOS Controls Effector Function but Not Trafficking Receptor Expression of Kidney-Infiltrating Effector T Cells in Murine Lupus," J Immunology 182:4076-84 (2009).
Ohaegbulam et al., "Human cancer immunotherapy with antibodies to the PD-1 and PD-L1 pathway," Trends Mol Med., 21(1): 24-33, 23 pages (2014).
Powell et al. "Compendium of excipients for parenteral formulations" PDA J Pharm Sci Technol, 1998; 52:238-311.
Preston, et al., "The ratios of CD8+ T cells to CD4+CD25+ FOXP3+ and FOXP3-T cells correlate with poor clinical outcome in human serous ovarian cancer." PLoS One Nov. 14;8(11):e80063 (2013).
Pühler et al., "Generation of a recombinant oncolytic Newcastle disease virus and expression of a full IgG antibody from two transgenes," Gene Ther. 15: 371-383 (2008).
Quezada et al., "CTLA4 blockade and GM-CSF combination immunotherapy alters the intratumor balance of effector and regulatory T cells," Journal of Clinical Investigation, 116(7): 1935-45 (2006).
Redoglia et al., "Characterization of H4: a mouse T Lymphocyte activation molecule functionally associated with the DC3/T cell receptor," Eur. J. Immunol., 11: 2781-9 (1996) (abstract only).
Rosenberg et al., "Atezolizumab in patients with locally advanced and metastatic urothelial carcinoma who have regressed following

(56) References Cited

OTHER PUBLICATIONS treatment with platinum-based chemotherapy: a single-arm, multicentre, phase 2 trial", Lancet, 387(10031):1909-20 (2016).
Rossi et al., "Optimization of multivalent bispecific antibodies and immunocytokines with improved in vivo properties", Bioconjug Chem, 24(1):63-71 (2013).
Rubio, et al. "Ex vivo identification, isolation and analysis of tumor-cytolytic T cells." Nat Med. 2003;9(11):1377-82, plus 9 pages supplemental material.
Rudikoff et al., "Single Amino Acid Substitution Altering Antigen-Binding Specificity," Proc. Natl. Acad. Sci., 79: 1978-1983 (1982).
Sainson et al., "KY1044, a novel anti-ICOS antibody, elicits long term in vivo anti-tumour efficacy as monotherapy and in combination with immune checkpoint inhibitors", 1 page.
Sainson et al., "KY1055, a novel ICOS/PD-L1 bispecific antibody, efficiently enhances T cell activation and delivers a potent anti-tumour response in vivo", 1 page.
Sainson et al., "A novel antibody targeting ICOS increases intratumoural cytotoxic to regulatory T cell ratio and induces tumour regression," bioRxiv preprint first posted online Sep. 16, 2019, https://www.biorxiv.org/content/biorxiv/early/2019/09/16/771493.full.pdf—Retrieved Oct. 21, 2019 (80 pages).
Sanmamed et al., "Agonists of Co-stimulation in Cancer Immunotherapy Directed Against CD137, OX40, GITR, CD27, CD28, and ICOS," Seminars in Oncology, 42(4): 640-655 (2015).
Sato et al., "Spatially selective depletion of tumor-associated regulatory T cells with near-infrared photoimmunotherapy," Science Translational Medicine, 2016; 8(352):1-12, plus 27 pages supplemental material.
Sears et al., "ICONIC: Phase 1/2 Trial of ICOS Agonist JTX-2011 Alone and in Combination with Nivolumab (nivo)" (2017).
Selby et al., "Anti-CTLA-4 antibodies of IgGZa isotype enhance antitumor activity through reduction of intratumoral regulatory T cells." Cancer immunoloqv research, 1(1):32-42 2013.
Seshasayee et al., "In vivo blockade of OX40 ligand inhibits thymic stromal lymphopoietin driven atopic inflammation," J Clin Invest 117(12): 3868-3878 (2007).
Sharma et al., "Immune Checkpoint Targeting in Cancer Therapy: Toward Combination Strategies with Curative Potential," Cell, 161: 205-214 (2015).
Sharma et al., "The future of immune checkpoint therapy," Science, 348(6230): 56-61 (2015).
Shields et al., "High resolution mapping of the binding site on human IgG1 for Fc gamma RI, Fc gamma RII, Fc gamma RIII, and FcRn and design of IgG1 variants with improved binding to the Fc gamma R." 2001, J. Biol. Chem., Mar. 2; 276(9):6591-604).
Shields et al. "Lack of Fucose on Human IgG1 N-Linked Oligosaccharide Improves Binding to Human FcγRIII and Antibody-dependent Cellular Toxicity" (2002) JBC 277:26733.
Shirakawa, "The Current Status of Adenovirus-based Cancer Gene Therapy," Mol. Cells, 25(4): 462-466 (2008).
Sim et al., "IL-2 therapy promotes suppressive ICOS+ Treg expansion in melanoma patients," J Clin Invest, 124(1): 99-110 (2014).
Sim et al., "IL-2 variant circumvents ICOS+ regulatory T cell expansion and promotes NK cell activation," Cancer Immunol Res 2016.
Simpson et al., "Regulation of CD4 T cell activation and effector function by inducible costimulatory (ICOS)," Current Opinion in Immunology 22: 326-332 (2010).
Simpson et al., "Fc-dependent depletion of tumor-infiltrating regulatory T cells co-defines the efficacy of anti-CTLA-4 therapy against melanoma." J. Exp. Med. 210(9):1695-1710 2013.
Solomon et al., "TIGIT: a novel immunotherapy target moving from bench to bedside," Cancer Immunol Immunother; 67(11):1659-1667 (2018).
Song et al., "Overexpression of B7-H1 correlates with malignant cell proliferation in pancreatic cancer", Oncol Rep, 31(3):1191-8 (2014).
Statement of Opposition filed at European Patent Office against European Patent No. EP2482849 on Mar. 6, 2019 (62 pages).
Strauss et al., "Expression of ICOS on Human Melanoma-Infiltrating $CD4^+CD25^{high}Foxp3^+$ T Regulatory Cells: Implications and Impact on Tumor-Mediated Immune Suppression," J. Immunol 180(5): 2967-2980 (2008).
Strohl, "Fusion Proteins for Half-Life Extension of Biologics as a Strategy to Make Biobetters." BioDrugs (2015) 29:215-239.
Swallow et al., "B7h, a novel costimulatory homolog of B7.1 and B7.2, is induced by TNFalpha." Immunity. Oct. 1999;11(4):423-32.
Taylor et al, "The classification of amino acid conservation." J. Theor. Biol., 1986; 119;205-218.
Taylor, "AstraZeneca tremelimumab fails another phase 3 cancertrial," Published online Dec. 7, 2018 at https://fiercebiotech.com/biotech/astrazeneca-s-tremelimumab-fails-another-phase-3-cancer-trial (4 pages).
Thompson et al., "Tumor B7-H1 is associated with poor prognosis in renal cell carcinoma patients with long-term follow-up", Cancer Res, 66(7):3381-5 (2006).
Topalian et al., "Safety, activity, and immune correlates of anti-PD-1 antibody in cancer", N Engl J Med, 366(26):2443-54 (2012).
Tu et al., "Regulatory T cells, especially ICOS FOXP3+ regulatory T cells, are increased in the hepatocellular carcinoma microenvironment and predict reduced survival," Scientific Reports, 6:35056 (2016).
Ueha et al., "Robust Antitumor Effects of Combined Anti-CD4-Depleting Antibody and Anti-PD-1/PD-LI Immune Checkpoint Antibody Treatment in Mice," Cancer Immunology Research, 3(6); pp. 631-640 (2015).
U.S. National Library of Medicine, "Anti-ICOS Monoclonal Antibody MEDI-570 in Treating Patients with Relapsed or Refractory Peripheral T-cell Lymphoma Follicular Variant or Angioimmunoblastic T-cell Lymphoma," ClinicalTrials.gov Identifier No. NCT02520791. First posted Aug. 13, 2015. Retrieved at https://clinicaltrials.gov/ct2/show/NCT02520791.
Van Berkel et al., "CD28 and ICOS: Similar or separate costimulators of T cells?" Immunology Letters 105: 115-122 (2006).
Van Elsas et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection of Subcutaneous and Metastatic Tumors Accompanied by Autoimmune Depigmentation," J Exp Med 190(3): 355-66 (1999).
Vazquez-Lombardi et al., "Potent antitumour activity of interleukin-2-Fc fusion proteins requires Fc-mediated depletion of regulatory T-cells," Nature Communications, vol. 8, May 12, 2017 (May 12, 2017), pp. 1-12.
Vetterman et al., "A signalling-enhanced chimeric receptor to activate the ICOS pathway in T cells," Journal of Immunological Methods 424: 14-19 (2015).
Vonderheide et al. 2010. "Tremelimumab in combination with exemestane in patients with advanced breast cancer and treatment-associated modulation of inducible costimulator expression on patient T cells." Clin. Cancer Res. 16:3485-3494.
Wang et al. "Costimulation of T cells by B7-H2, a B7-like molecule that binds ICOS." Blood. Oct. 15, 2000;96(8):2808-13.
Wang et al., "In Vitro Characterization of the Anti-PD-1 Antibody Nivolumab, BMS-936558, and In Vivo Toxicology in Non-Human Primates", Cancer Immunology Research, vol. 2, No. 9, May 28, 2014 (May 28, 2014), pp. 846-856.
Ward et al., "Targeting Costimulatory Pathways for Tumor Immunotherapy," International Reviews of Immunology, 26:161-196 (2007).
West et al., "PD-L 1 blockade synergizes with IL-2 therapy in reinvigorating exhausted T cells", J Clin Invest, 123(6):2604-15 (2013).
Wozniak-Knopp et al., "Introducing antigen-binding sites in structural loops of immunoglobulin constant domains : Fc fragments with engineered HER2/neu-binding sites and antibody properties," Protein Engineering, Design & Selection, 23(4) ; 289-297 (2010).
Yang et al., "Programmed cell death-ligand 1 expression in surgically resected stage I pulmonary adenocarcinoma and its correlation with driver mutations and clinical outcomes", Eur J Cancer, 50(7):1361-9 (2014).

(56) References Cited

OTHER PUBLICATIONS

Yap et al., "ICONIC : Biologic and clinical activity of first in class ICOS against antibody JTX-2011 +/− nivolumab (nivo) in patients with advanced cancers," Presented at 2018 ASCO Annual Meeting (18 pages).
Yusa K, et al. "A hyperactive piggyBac transposase for mammalian applications," Proc Natl Acad Sci U S A. Jan. 25, 2011.
Zang et al., "The B7 family and cancertherapy: costimulation and coinhibition," Clinical Cancer Research, 13(18): 5271-5279 (2007).
Baruch, et al., Aging-Induced type I Interferon Response at the Choroid Plexus Negatively Affects Brain Function, Science 346(6205): 89-93 (2014).
Baruch, et al., Breaking Immune Tolerance by Targeting Foxp3(+) Regulatory T Cells Mitigates Alzheimer's Disease Pathology, Nat Commun. 6: 7967-7978 (2015).
Baruch, et al., Cerebral Nitric Oxide Represses Choroid Plexus NFκB-Dependent Gateway Activity for Leukocyte Trafficking, EMBO J. 34(13): 1816-1828 (2015).
Baruch, et al., CNS-Specific Immunity at the Choroid Plexus Shifts Toward Destructive Th2 Inflammation in Brain Aging, Proc. Natl. Acad. Sci. U. S. A. 110 (6): 2264-2269 (2013).
Baruch and Schwartz, CNS-specific T Cells Shape Brain Function via the Choroid Plexus, Brain Behav. Immun. 34: 11-16 (2013).
Cauvin et al. (2015) Advantages and Limitations of Commonly Used Nonhuman Primate Species in Research and Development of Biopharmaceuticals in the Nonhuman Primate in Nonclinical Drug Development and Safety Assessment (Academic Press), 379-395.
Kunis, et al., IFN-γ-Dependent Activation of the Brain's Choroid Plexus for CNS Immune Surveillance and Repair, Brain 136: 3427-3440 (2013).
Kunis, et al., Immunization with a Myelin-Derived Antigen Activates the Brain's Choroid Plexus for Recruitment of Immunoregulatory Cells to the CNS and Attenuates Disease Progression in a Mouse Model of ALS, J. Neurosci. 35(16): 6381-6393 (2015).
Rosenzweig, et al., PD-1/PD-L1 Checkpoint Blockade Harnesses Monocyte-Derived Macrophages to Combat Cognitive Impairment in a Tauopathy Mouse Model, Nat Commun. 10(1): 465-479 (2019).
Schwartz and Baruch, The Resolution of Neuroinflammation in Neurodegeneration: Leukocyte Recruitment via the Choroid Plexus, EMBO J. 33(1): 7-20 (2014).
Bowie, et al., "Deciphering the Message in Protein Sequences: Tolerance to Amino Acid Substitutions", Science, 1990, vol. 247, No. 4948, pp. 1306-1310.
Kussie, et al., "A Single Engineered Amino Acid Substitution Changes Antibody Fine Specificity", The Journal of Immunology, 1994, vol. 152, No. 1, pp. 146-152.
Sela-Culang, et al., "The Structural Basis of Antibody-antigen Recognition", Frontiers in Immunology, Oct. 8, 2013, vol. 4, No. 302, pp. 1-13.
Sirin, et al., "AB-bind: Antibody Binding Mutational Database for Computational Affinity Predictions", Protein Science, Feb. 2016, vol. 25, No. 2, pp. 393-409.
Wikenheiser, et al., "ICOS Co-Stimulation: Friend or Foe?", Frontiers in Immunology, Aug. 10, 2016, vol. 7, No. 304, pp. 1-16.
Winkler, et al., "Changing the antigen binding specificity by single point mutations of an anti-p24 (HIV-1) antibody", Journal of Immunology, Oct. 15, 2000, vol. 165, No. 8, pp. 4505-4514.
Almagro & Fransson, Humanization of antibodies, Frontiers in Bioscience, 13: 1619-1633 (2008).
Brinkmann et al., The making of bispecific antibodies, MABS 9(2): 182-212 (2017).
Chemical Society of Japan Lecture Proceedings, 2014, 94(3): 974 (Japanese language only).
Chen et al., Human monoclonal antibodies targeting the haemagglutinin glycoprotein can neutralize H7N9 influenza virus. Nat Commun. Mar. 30, 2015;6:6714.
Enzyme Engineering News, Jun. 2014, 75: 11-14 (Japanese language only).
Eun et al., Prolonged Survival in Rat Composite Tissue Allografts Treated with Combined Administration of ICOS-Ig and CTLA4-Ig, The Journal of Japanese Society for Surgery of the Hand, 2005, 22(1): S86 (1-Pb-7).
General Presentation Poster, The Japanese Journal of Nephrology, 2004, 46(3): 249 (P-113), obtained from https://www.jstage.jst.go.jp/article/jpnjnephrol1959/46/3/46_3_231/_pdf/-char/en.
Gul et al., Antibody-Dependent Phagocytosis of Tumor Cells by Macrophages: A Potent Effector Mechanism of Monoclonal Antibody Therapy of Cancer, Cancer Res., 75(23), Dec. 1, 2015.
International Search Report and Written Opinion for PCT International Patent Application No. PCT/EP2022/063450, dated Sep. 12, 2022.
Jachimowicz et al., Multi-specific antibodies for cancer immunotherapy. BioDrugs. 2014, 28(4): 331-343.
Kubo et al., Dendritic Cell and Cancer Immune Checkpoint, The Japanese Journal of Clinical Immunology, 2016, 39(5): 468-472.
Pan et al., Further Study of Anti-ICOS Immunotherapy for Rat Cardiac Allograft Rejection, Surgery Today, 2008, 38(9): 815-825.
Akce et al., A Phase 1 multiple-ascending dose study to evaluate the safety and tolerability of XmAb23104 (PD-1 x ICOS) in subjects with selected advanced solid tumors (DUET-3) (NCT03752398), Abstract 2604, 2022 ASCO Annual Meeting I, Journ Clin Oncology, 40(16 Suppl): 2604-2604.
Chen, "Anti-CTLA-4 therapy results in higher CD4+ICOShi T cell frequency and IFN-γ levels in both nonmalignant and malignant prostate tissues", PNAS, 2009,106(8): 2729-2734.
Collis et al., "Analysis of the antigen combining site: correlations between length and sequence composition of the hypervariable loops and the nature of the antigen", J Mol Biol., Jan. 10, 2003, 325(2): 337-354.
Del Bano et al., "Taking up Cancer Immunotherapy Challenges: Bispecific Antibodies, the Path Forward?", Antibodies, 2016, 5(1): 1-23.
Dondelinger et al., "Understanding the Significance and Implications of Antibody Numbering and Antigen-Binding Surface/Residue Definition", Front. Immunol./, Oct. 16, 2018, Sec. Vaccines and Molecular Therapeutics, 2018, 9: 2278.
Tsuchiya et al., "The diversity of H3 loops determines the antigen-binding tendencies of antibody CDR loops", Protein Sci., Apr. 2016, 25(4): 815-825.
Wei, "Distinct Cellular Mechanisms Underlie Anti-CTLA-4 and Anti-PD-1 Checkpoint Blockade", Cell, 2017, 170(6): 1120-1133.
Wu et al., Fab-based bispecific antibody formats with robust biophysical properties and biological activity, mAbs, May/Jun. 2015, 7(3): 470-482.
U.S. Appl. No. 17/727,288 2022/0380467, filed Apr. 22, 2022 Nov. 17, 2022, Richard Charles Alfred Sainson, Anti-ICOS Antibodies.
U.S. Appl. No. 17/727,309 2022/0403029, filed Apr. 22, 2022 Dec. 22, 2022, Richard Charles Alfred Sainson, Anti-ICOS Antibodies.
U.S. Appl. No. 16/955,197 2020/0317786, filed Jun. 18, 2020 Oct. 8, 2020, Aksana Labokha, Anti-ICOS Antibodies.
U.S. Appl. No. 16/311,421 2019/0202917, filed Dec. 19, 2018 Jul. 4, 2019, Jamie Campbell, Antibodies to ICOS.
U.S. Appl. No. 17/901,800, filed Sep. 1, 2022, Jamie Campbell, Multispecific Antibodies for Immuno-Oncology.
U.S. Appl. No. 16/955,219 2020/0407446 U.S. Pat. No. 11,629,189, filed Jun. 18, 2020 Dec. 31, 2020 Apr. 18, 2023, Matthew John McCourt, Multispecific Antibodies for Immuno-Oncology.
U.S. Appl. No. 18/174,925, filed Feb. 27, 2023, Matthew John McCourt, Multispecific Antibodies for Immuno-Oncology.
U.S. Appl. No. 16/471,161 2020/0190191, filed Jun. 19, 2019 Jun. 18, 2020, Jamie Iain Campbell, Bispecific Antibody for ICOS and PD-L1.
U.S. Appl. No. 17/747,886 2022/0396623, filed May 18, 2022 Dec. 15, 2022, Richard Charles Alfred Sainson, Multispecific Antibody with Combination Therapy for Immuno-Oncology.
U.S. Appl. No. 17/921,822 2023/0176060, filed May 13, 2021 Jun. 8, 2023, Richard Charles Alfred Sainson, Uses of Anti-ICOS Antibodies.

* cited by examiner

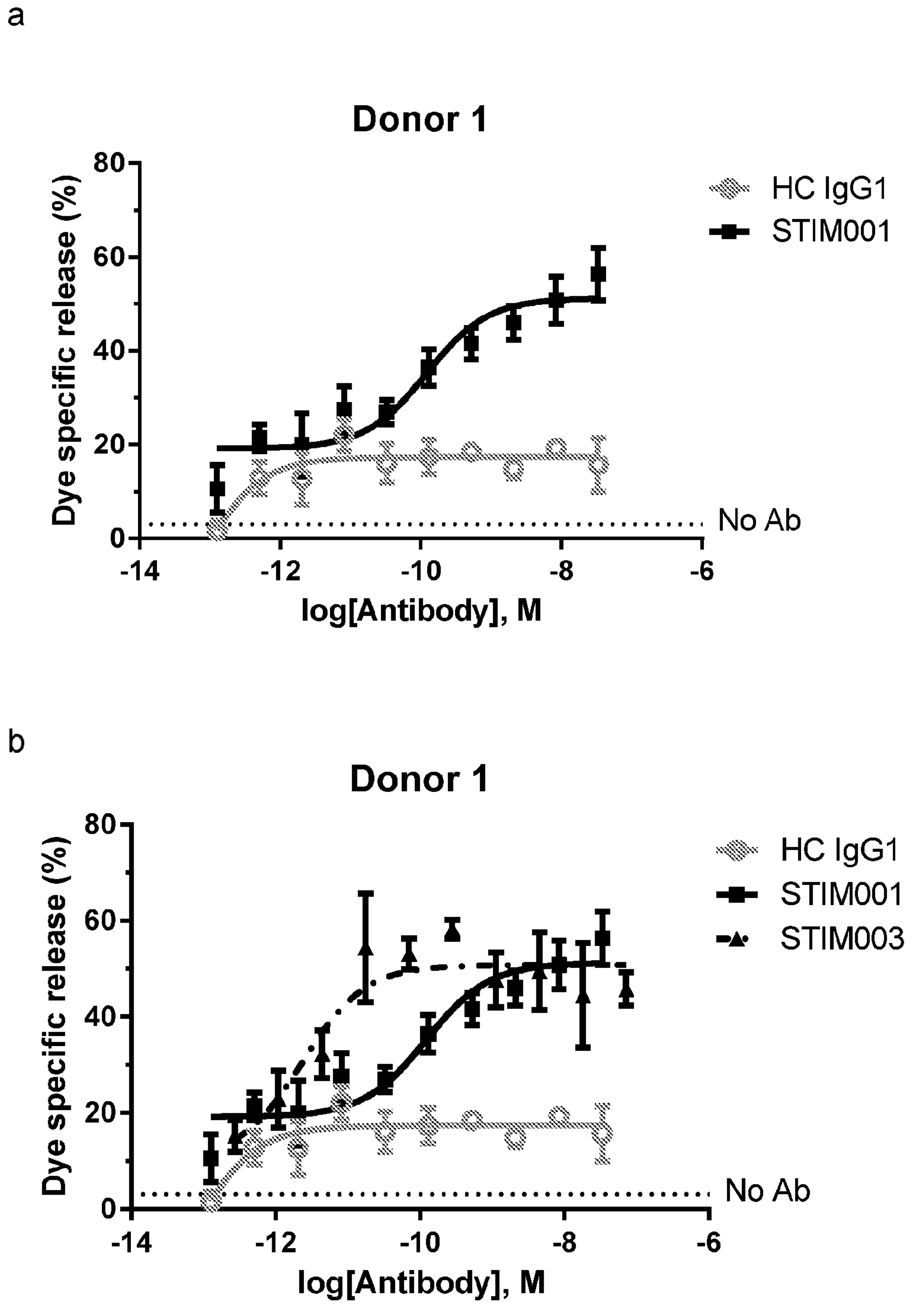
Figure 6 a and b c
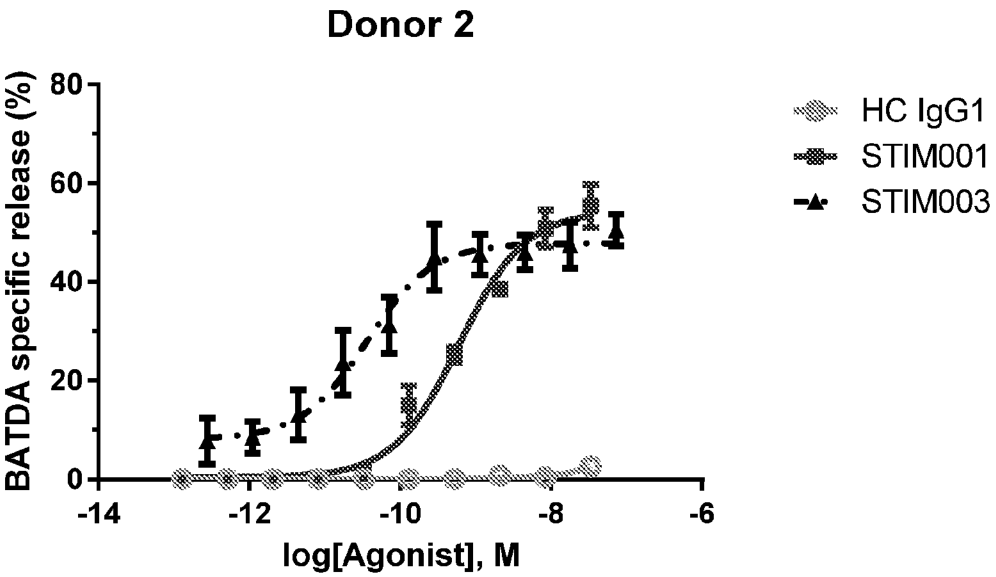
d
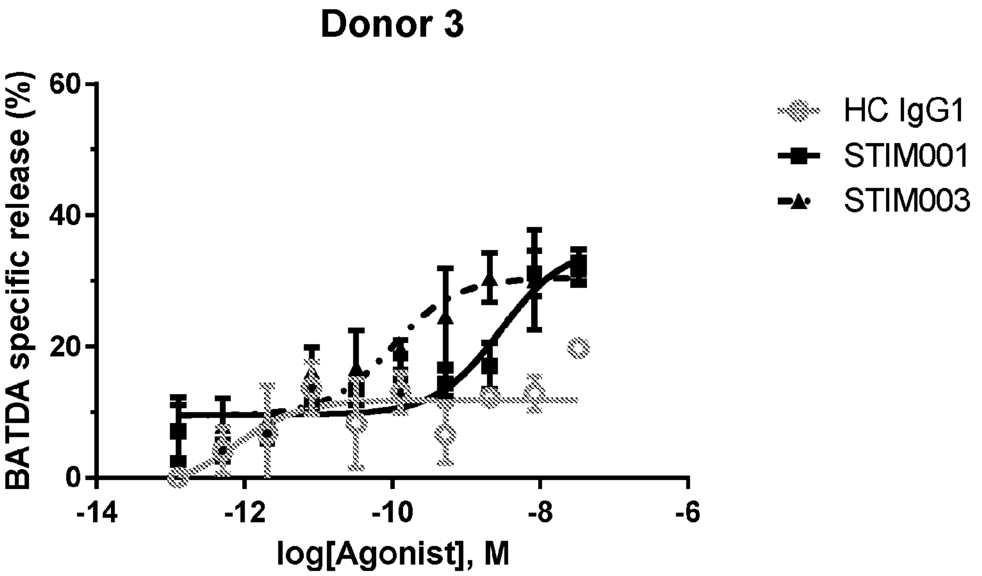
Figure 6 c and d e
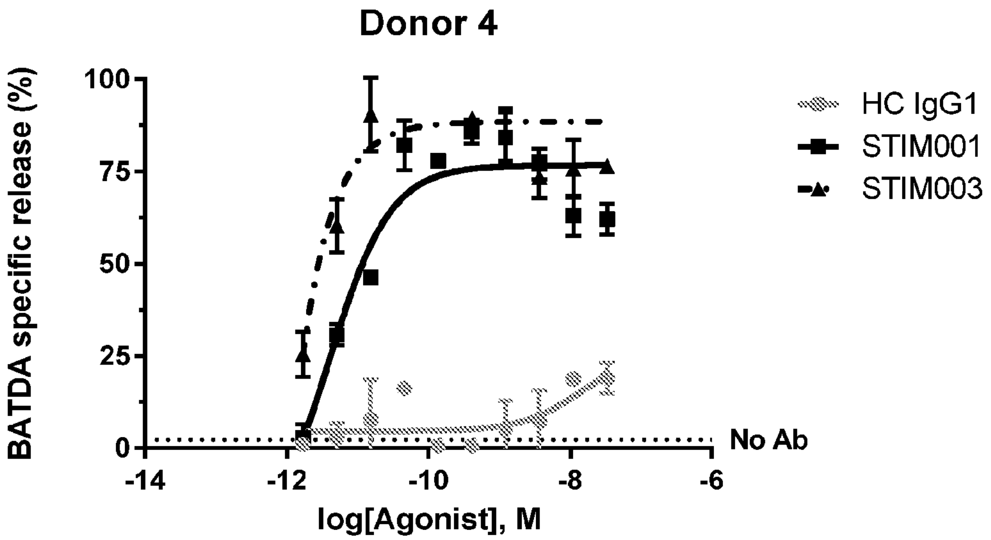
f
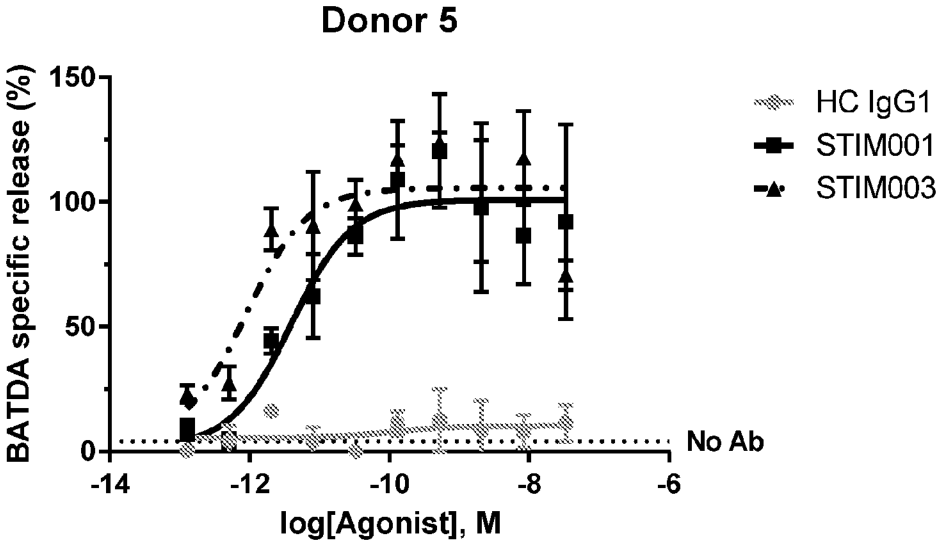
Figure 6 e and f g

CT26 efficacy study with STIM001 mIgG1

ISOTYPES

0/10

Anti-ICOS mIgG 1 (STIM001)

1/10 anti PDL1 (10F9.G2)

0/10 anti PDL1 (10F9.G2) + anti-ICOS mIgG1 (STIM001)

2/10

Dosing from days 6-18

CT26 efficacy study with STIM001 mIgG2a

Dosing between day 6 and 18

(*) Dosing time is highlighted by the shaded area
(**) Numbers in top tight indicates number of animal(s) with no signs of disease at the end of the study.

a
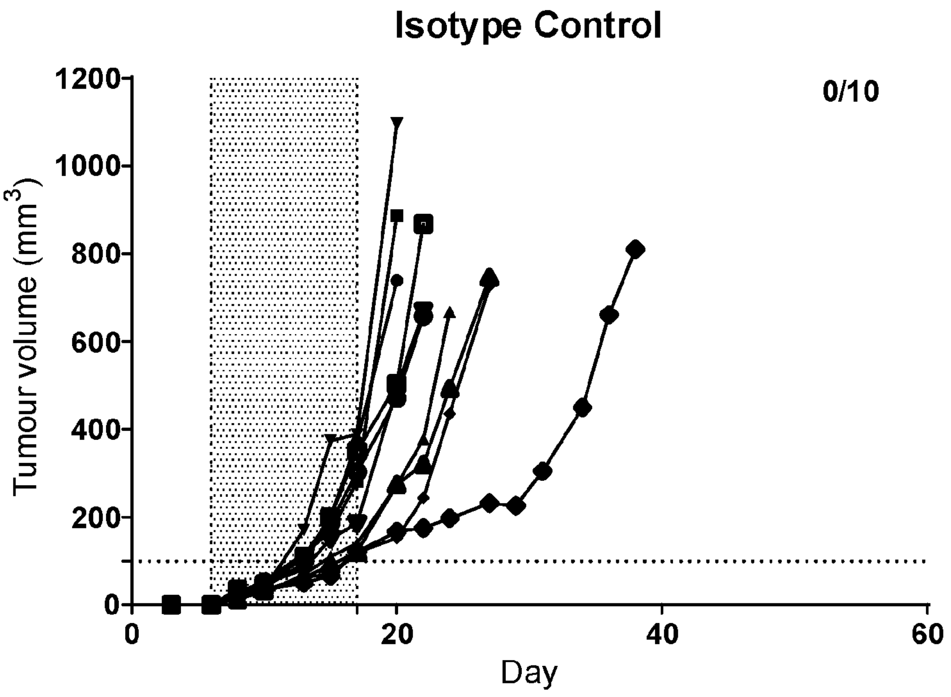
b
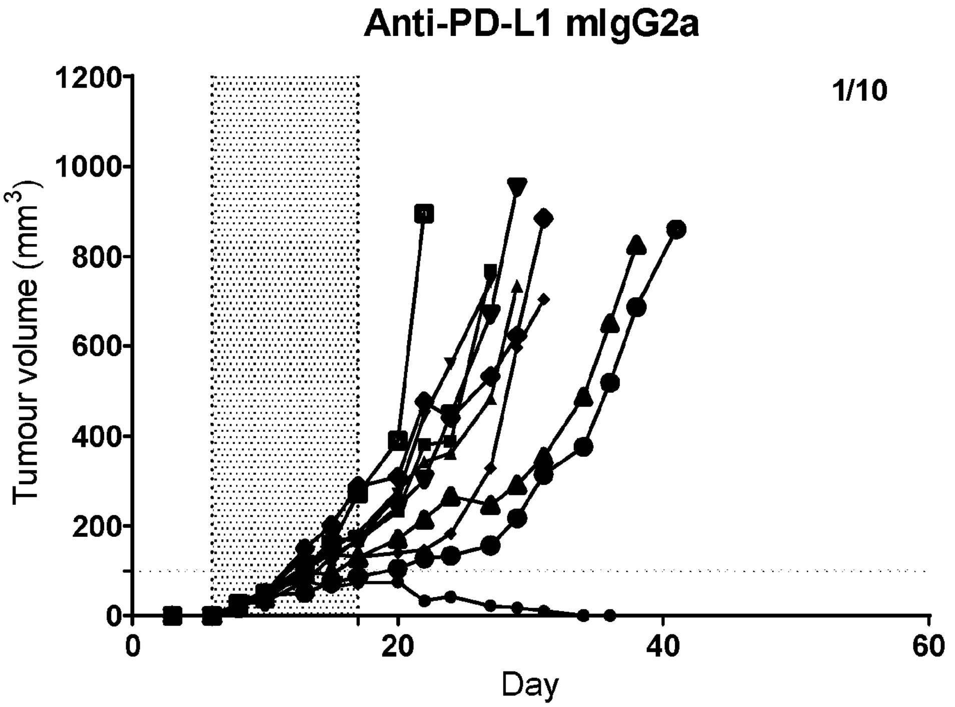
Figure 11 a and b c
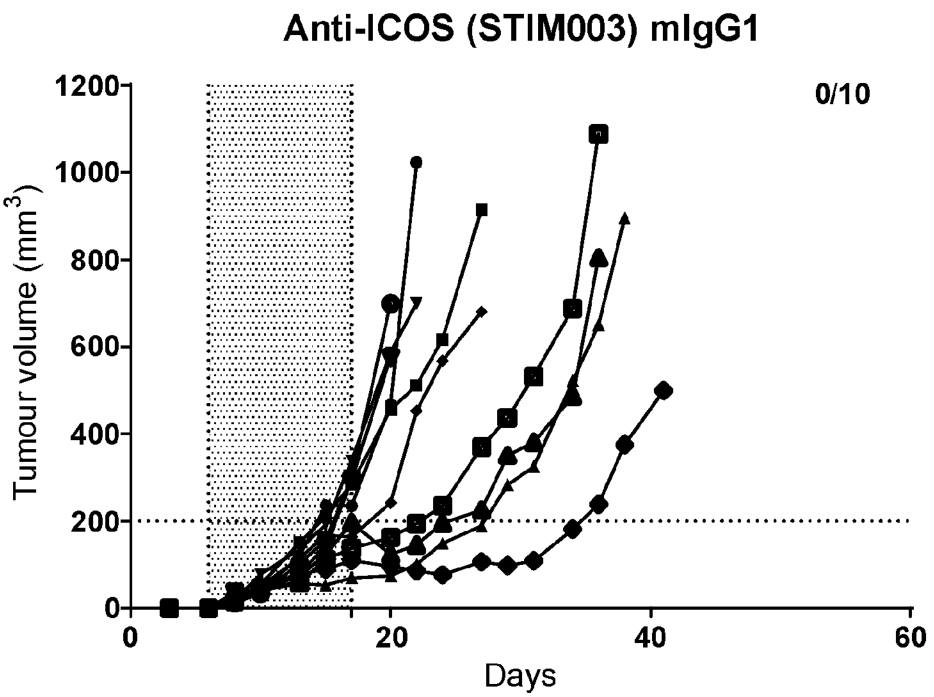
d
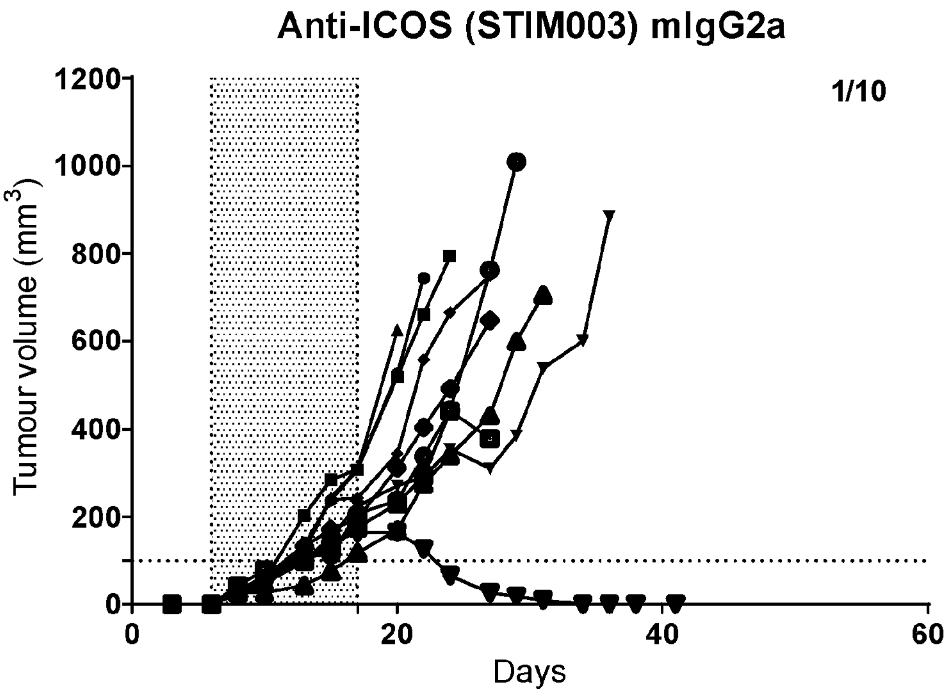
Figure 11 c and d e
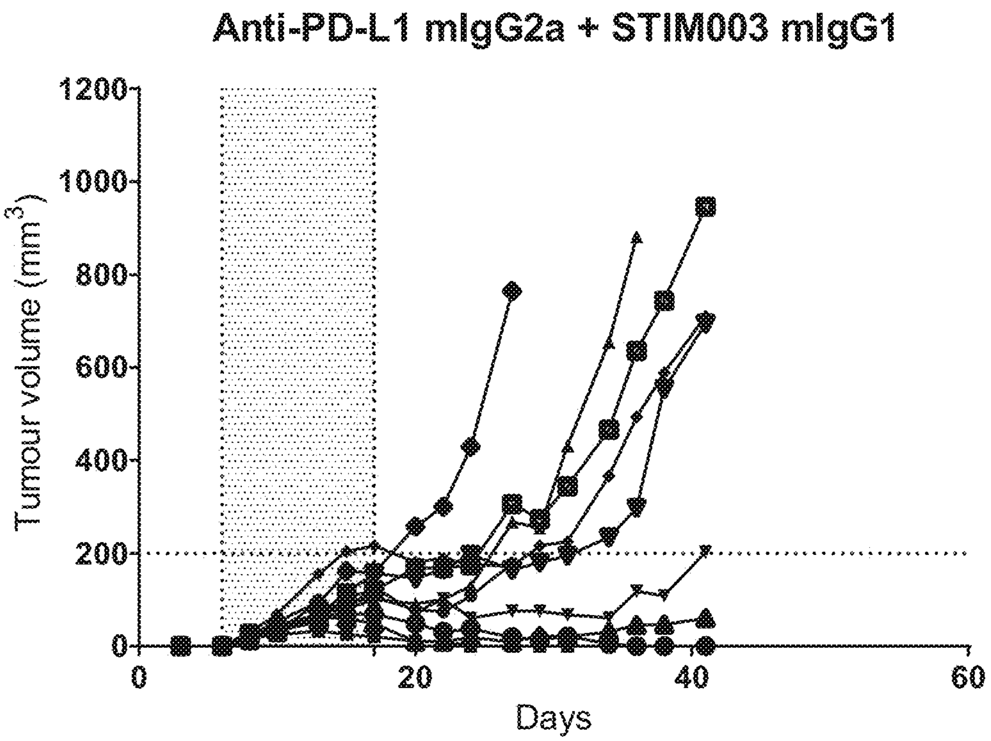
f
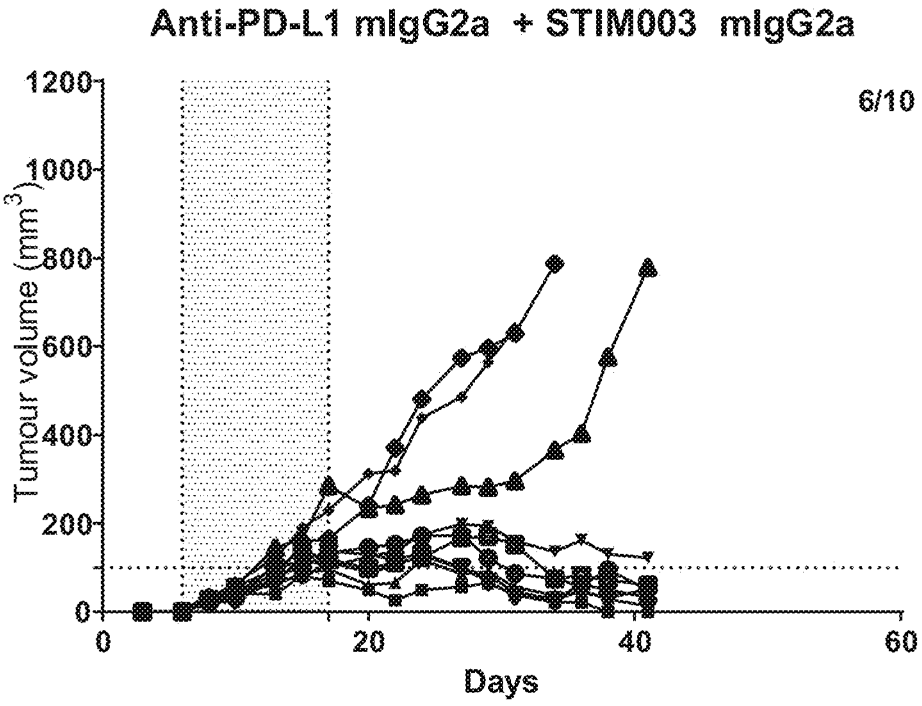
Figure 11 e and f

| | STIM001 | STIM003 |
|---|---|---|
| EC50 | 1.207e-007 | 6.953e-010 |

| | STIM001 | STIM003 |
|---|---|---|
| EC50 | 1.704e-008 | 1.463e-010 |

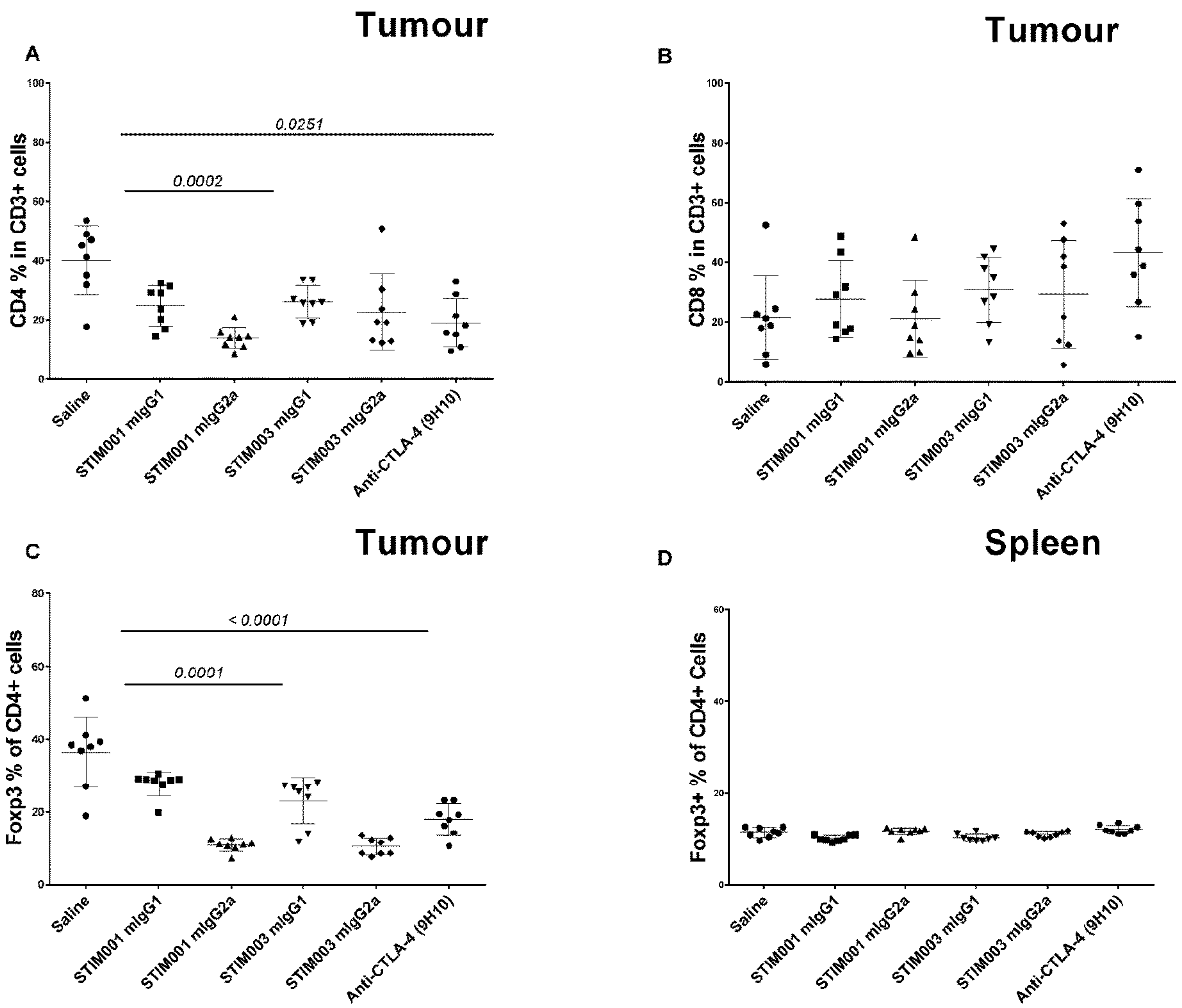
Figure 15 A-D

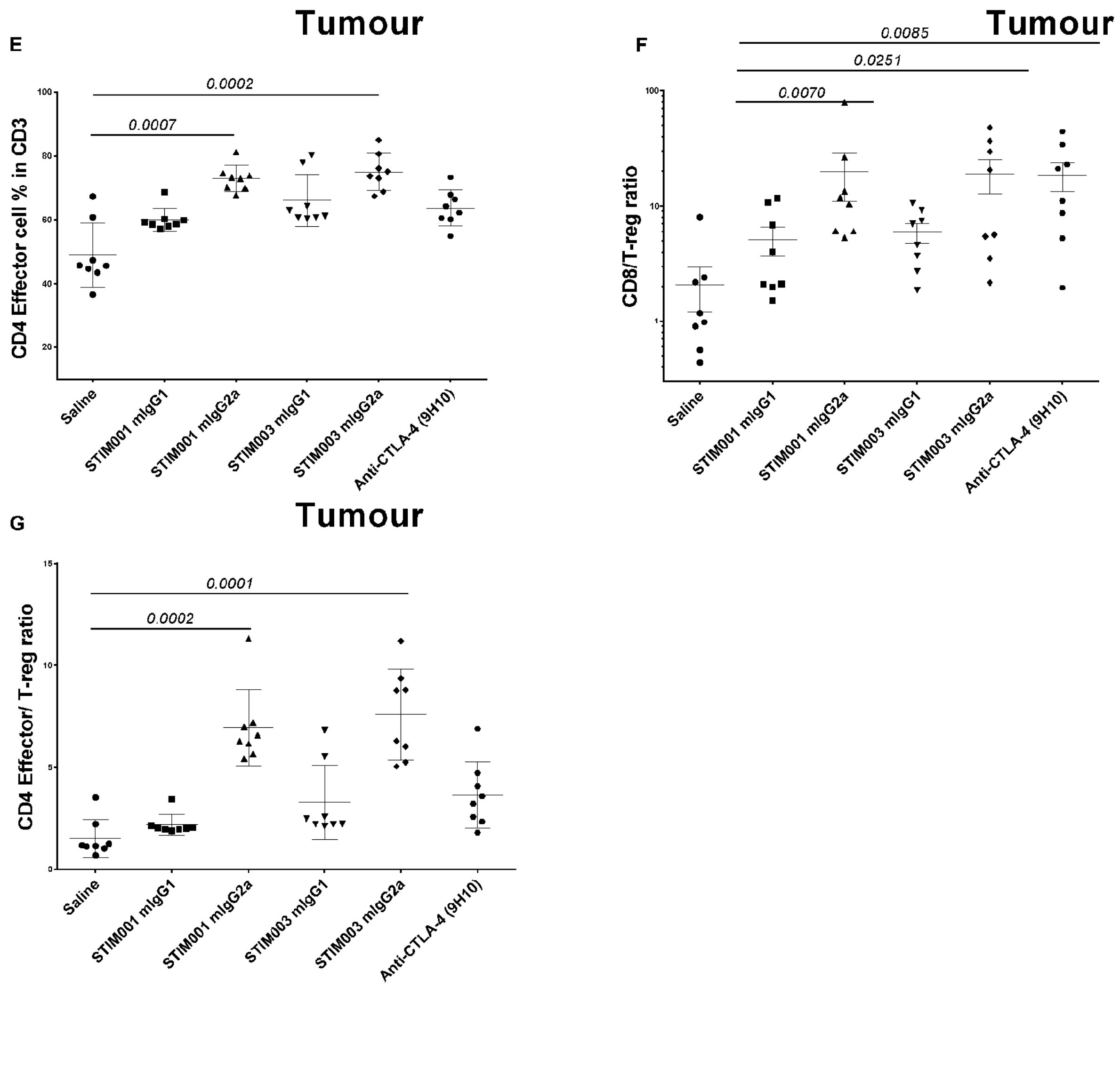
Figure 15 E-F

A
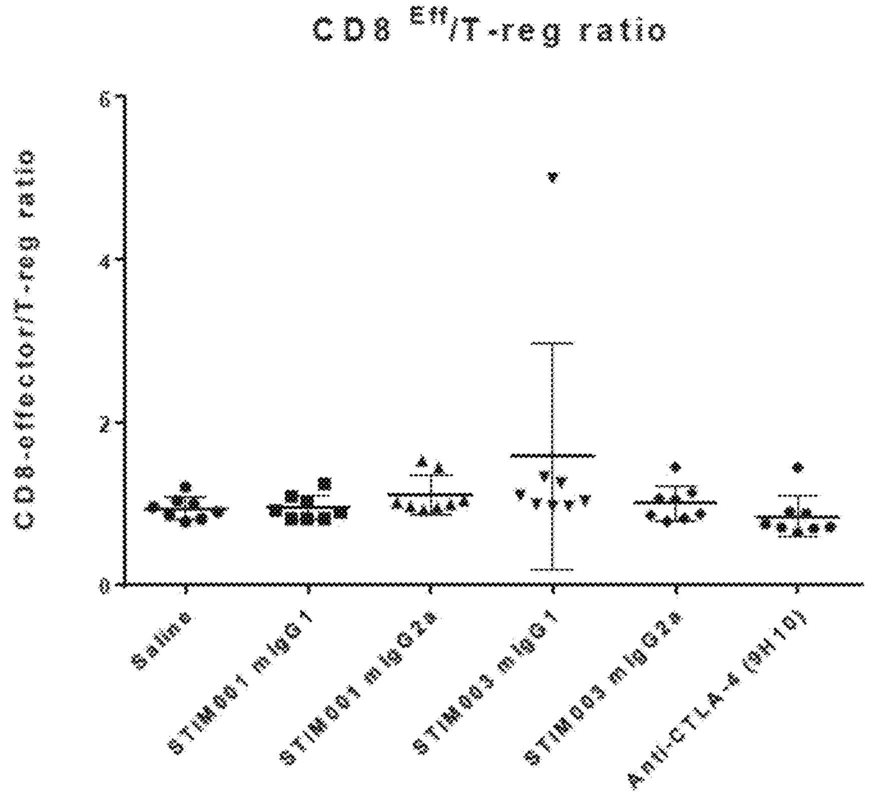
B
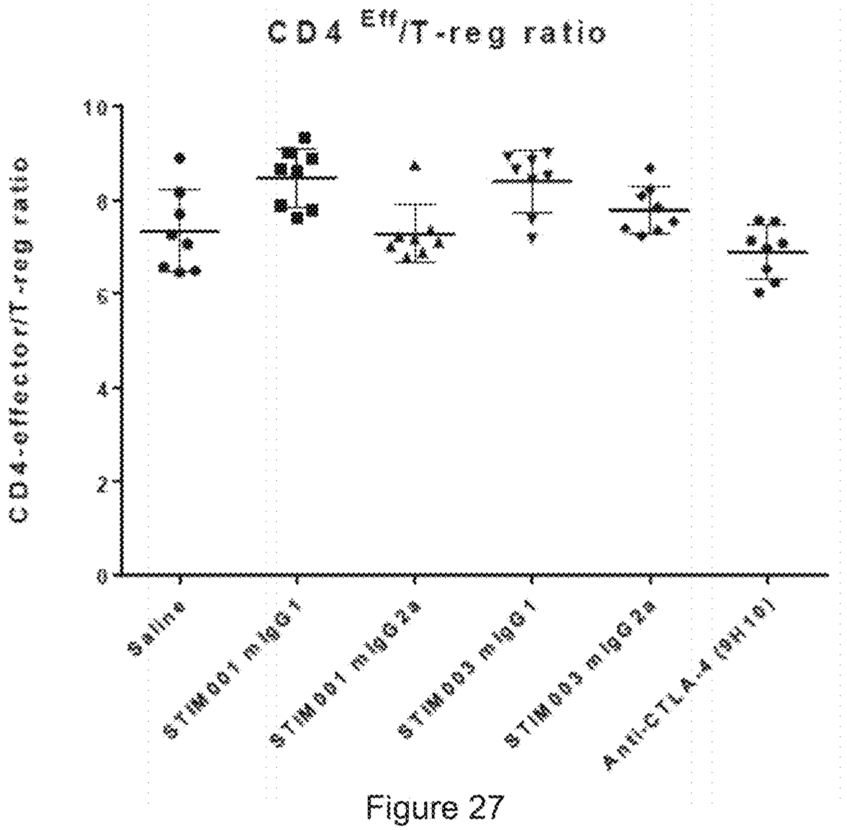
Figure 27

A
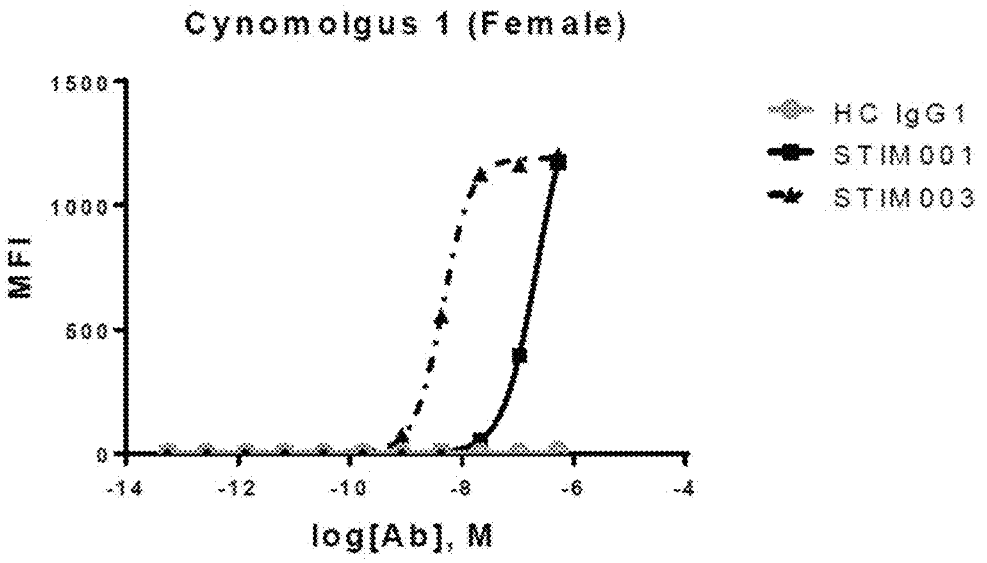
| STIM001 | STIM003 |
|---|---|
| 2.224e-007 | 4.581e-009 |
B
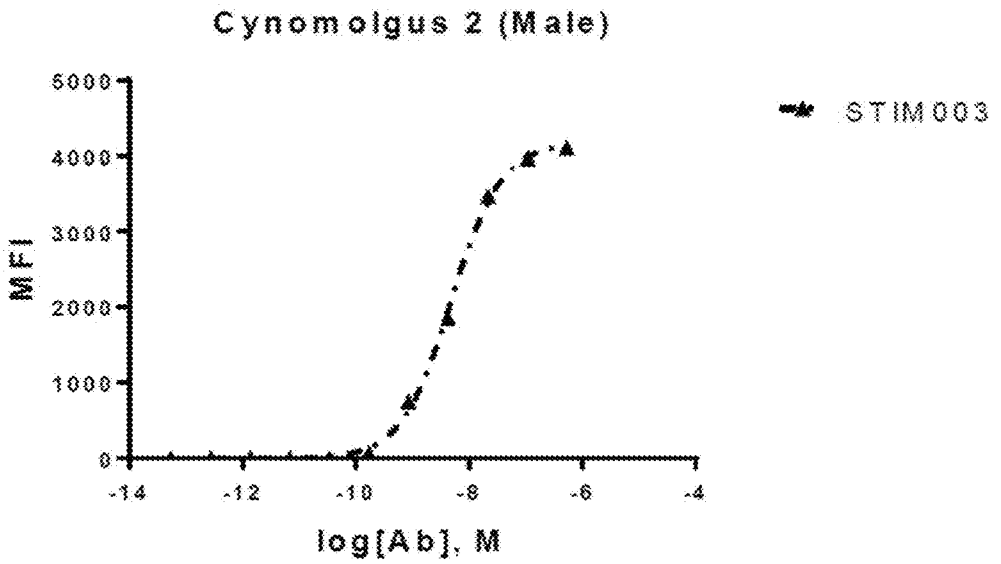
| STIM003 |
|---|
| 4.830e-009 |
Figure 28

Heavy chain

```
Positions: 1 2 3 4 5 6 7 8 9 11 12 13 14 15 16 17 18 19 20 21 22 23 24 25 26 27 28 29 30 35 36 37 38 39 40 41 42 43 44 45 46 47 48 49 50 51 52 53 54 55 56 57 58 59 62 63 64 65 66 67 68 69 70 71 72 74 75 76 77 78

STIM002    QVQLVQSGGEVKKPGASVKVSCKASGYTFTSYGFSWVRQAPGQGLEWMGWISAYNGNTNYAQKLQGRVTM
STIM002-B  ......................................................................
STIM001    ...V....A....................STF.IT.....................D.....N.....I.
CL-64912   ..............R.................V.....H.A...........G............CG.S.
CL-64841   ....................................................................S.
CL-64837   ....................................................................S.
CL-64536   ....................................................................S.
CL-61091   ....M...T..............T......T..IT...................S.D.D....F.....V
germline   ........A........................I....................................
           |------------------------|-------|----------------|-------|--------
                     FW1                CDR1        FW2          CDR2     FW3

Positions: 79 80 81 82 83 84 85 86 87 88 89 90 91 92 93 94 95 96 97 98 99 100 101 102 103 104 105 106 107 108 109 110 111 111A 111B 112B 112A 112 113 114 115 116 117 118 119 120 121 122 123 124 125 126 127 128

STIM002    TTDTSTSTAYMELRSLRSDDTAVYYCARSTYFYGSGTLYGMDVWGQGTTVTVSS
STIM002-B  ......................................................
STIM001    .............................SGH.---YY................
CL-64912   .A......................F.....SY..A...................
CL-64841   ........................F.....SY......................
CL-64837   ..............................SY......................
CL-64536   ........................F.....SY......................
CL-61091   ......N.........K............SGWP---HH................
germline   ............................--.Y....NY................
           |--------------------------|-------------|----------|
                       FW3                  CDR3         FW4
```

Light chain

```
Positions: 1 2 3 4 5 6 7 8 9 10 11 12 13 14 15 16 17 18 19 20 21 22 23 24 25 26 27 28 29 30 31 32 34 35 36 37 38 39 40 41 42 43 44 45 46 47 48 49 50 51 52 53 54 55 56 57 65 66 67 68 69 70 71 72 74 75 76 77 78 79

STIM002-B  DIVMTQSPLSLPVTPGEPASISCRSSQSLLHSDGYNCLDWYLQKPGQSPQLLIYLGSTRASGFPDRFSGS
STIM002    ....................................Y.................................
STIM001    ................................NE..Y................F...N....V.......
CL-64912   ................................N.....................................
CL-64841   ................................N.....................................
CL-64837   ................................N.....................................
CL-64536   ................................N.....................................
CL-61091   ................................N.F.YF...............F.V.N....V.......
germline   ................................N...Y....................N....V.......
           |--------------------------|-----------|-----------------|--|--------
                      FW1                  CDR1          FW2        CDR2  FW3

Positions: 80 83 84 85 86 87 88 89 90 91 92 93 94 95 96 97 98 99 100 101 102 103 104 105 106 107 108 109 114 115 116 117 118 119 120 121 122 123 124 125 126 127

STIM002-B  GSGTDFTLKISRVEAEDVGVYYCMQALQTPCSFGQGTKLEIK
STIM002    ..............................L...........
STIM001    ..........T........I.....S....LT..G...V...
CL-64912   ..........................................
CL-64841   .....S....................................
CL-64837   ..........................................
CL-64536   ..........................................
CL-61091   ...................I..........LT..G...V...
germline   .......................DDSVS.L............
           |----------------------|---------|----------|
                     FW3              CDR3       FW4
```

Figure 35

Heavy chain

```
          1 2 3 4 5 6 7 8 9 10 11 12 13 14 15 16 17 18 19 20 21 22 23 24 25 26 27 28 29 35 36 37 38 39 40 41 42 43 44 45 46 47 48 49 50 51 52 53 54 55 56 57 58 59 62 63 64 65 66 67 68 69 70 71 72 74 75 76 77 78
germline  EVQLVESGGGVVRPGGSLRLSCAASGFTFDDYGMSWVRQAPGKGLEWVSGINWNGGSTGYADSVKGRFTI
STIM003   ......................v...v.............................d.d.s.........
CL-71642  ......................................................................
CL-74570  ...........i.........................................i.dn.d...........
          |----------FW1----------|---CDR1---|------FW2------|---CDR2---|---FW3---

          79 80 81 82 83 84 85 86 87 88 89 90 91 92 93 94 95 96 97 98 99 100 101 102 103 104 105 106 107 108 109 110 111 111A 111B 112B 112A 112 113 114 115 116 117 118 119 120 121 122 123 124 125 126 127 128
germline  SRDNAKNSLYLQMNSLRAEDTALYYCARDYYGSGSYYN-YFDYWGQGTLVTVSS
STIM003   .............................f.......hvp.......i......
CL-71642  ...........................a..........vp..............
CL-74570  ..............................f.......vp..............
          |----------FW3----------|-----CDR3-----|----FW4----|
```

Light chain

```
          1 2 3 4 5 6 7 8 9 10 11 12 13 14 15 16 17 18 19 20 21 22 23 24 25 26 27 28 29 35 36 37 38 39 40 41 42 43 44 45 46 47 48 49 50 51 52 53 54 55 56 57 65 66 67 68 69 70 71 72 74 75 76 77 78 79 80 83 84 85
germline  EIVLTQSPGTLSLSPGERATLSCRASQSVSSSYLAWYQQKPGQAPRLLIYGASSRATGIPDRFSGSGSGT
STIM003   ..............................r.........r........................d....
CL-71642  -.....................................................................
CL-74570  ......................................................................
          |----------FW1----------|---CDR1---|------FW2------|CDR2|----FW3----

          86 87 88 89 90 91 92 93 94 95 96 97 98 99 100 101 102 103 104 105 106 107 108 109 114 115 116 117 118 119 120 121 122 123 124 125 126 127
germline  DFTLTISRLEPEDFAVYYCQQYGSSPFTFGPGTKVDIK
STIM003   ....s..............h..dm..............
CL-71642  ......................................
CL-74570  ...................h...n..............
          |------FW3------|---CDR3---|---FW4---|
```

Figure 36

Heavy chain

Positions: 1 2 3 4 5 6 7 8 9 11 12 13 14 15 16 17 18 19 20 21 22 23 24 25 26 27 28 29 30 31 34 35 36 37 38 39 40 41 42 43 44 45 46 47 48 49 50 51 52 53 54 55 56 57 58 59 63 64 65 66 67 68 69 70 71 72 74 75 76 77

```
germline  QITLKESGPTLVKPTQTLTLTCTFSGFSLSTSGVGVGWIRQPPGKALEWLALIYWDDDKRYSPSLKSRLT
STIM007   ...............................t....................v.................
STIM008   ....................................................v.................
```

FW1 | CDR1 | FW2 | CDR2 | FW3

Positions: 78 79 80 81 82 83 84 85 86 87 88 89 90 91 92 93 94 95 96 97 98 99 100 101 102 103 104 105 106 107 108 109 110 111 111A 111B 112A 112 113 114 115 116 117 118 119 120 121 122 123 124 125 126 127 128

```
germline  ITKDTSKNQVVLTMTNMDPVDTATYYCAHRHGSESYYYYGMDVWGQGTTVTVSS
STIM007   ...........................f.t.gy..a...h..............
STIM008   ...........................f.t.gy..a...h..............
```

FW3 | CDR3 | FW4

Light chain

Positions: 1 2 3 4 5 6 7 8 9 10 11 12 13 14 15 16 17 18 19 20 21 22 23 24 25 26 27 28 29 36 37 38 39 40 41 42 43 44 45 46 47 48 49 50 51 52 53 54 55 56 57 65 66 67 68 69 70 71 72 74 75 76 77 78 79 80 83 84 85 86

```
germline  EIVLTQSPATLSLSPGERATLSCRASQSVSSYLAWYQQKPGQAPRLLIYDASNRATGIPARFSGSGSGTD
STIM007   .............................tn...h...................................
STIM008   .............................tn...h...................................
```

FW1 | CDR1 | FW2 | CDR2 | FW3

Positions: 87 88 89 90 91 92 93 94 95 96 97 98 99 100 101 102 103 104 105 106 107 108 109 114 115 116 117 118 119 120 121 122 123 124 125 126 127

```
germline  FTLTISSLEPEDFAVYYCQQRSNWPLTFGGGTKVEIK
STIM007   ...................h.................
STIM008   .....................................
```

FW3 | CDR3 | FW4

Figure 37

A)
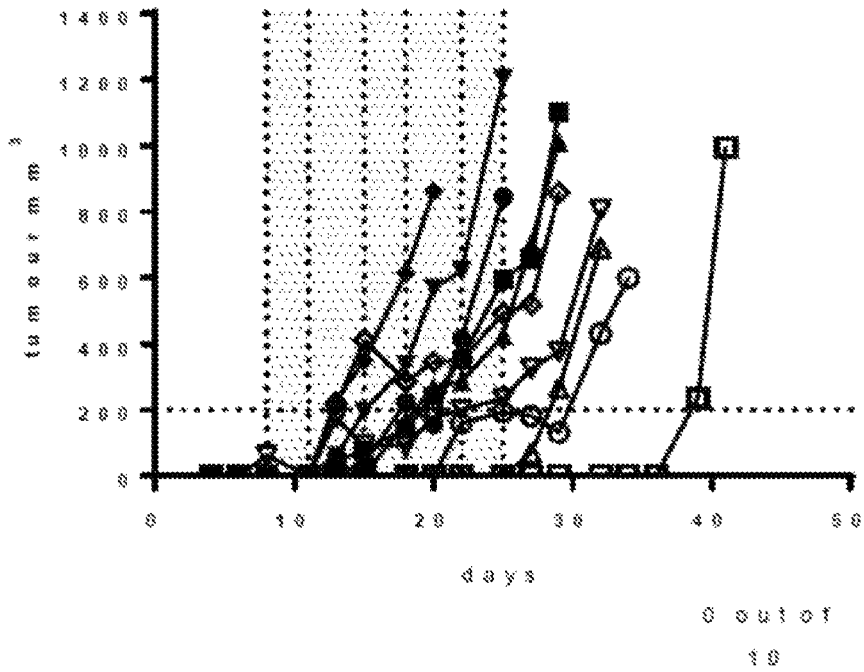
B)
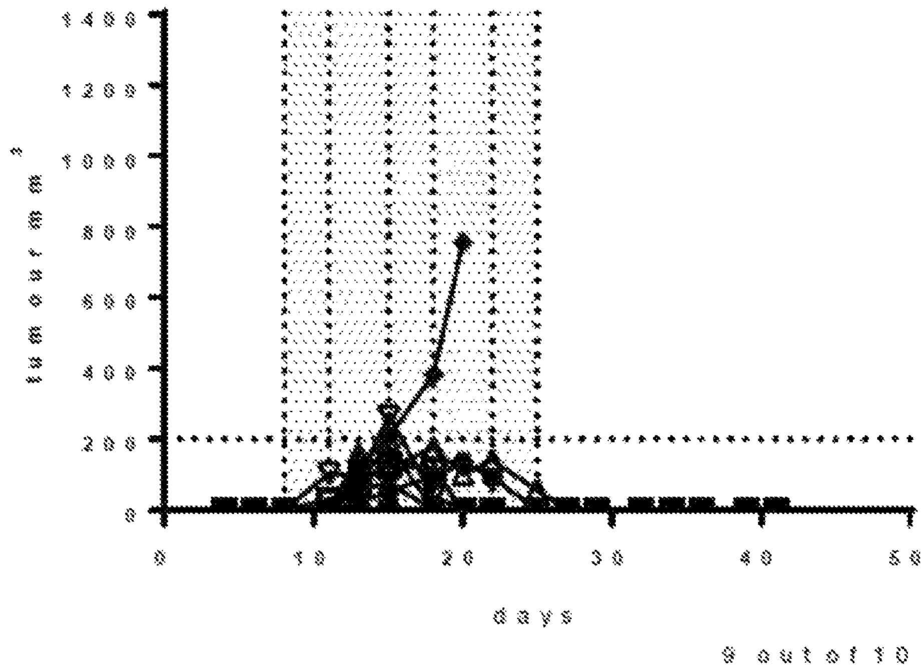
Figure 40 A and B

C)

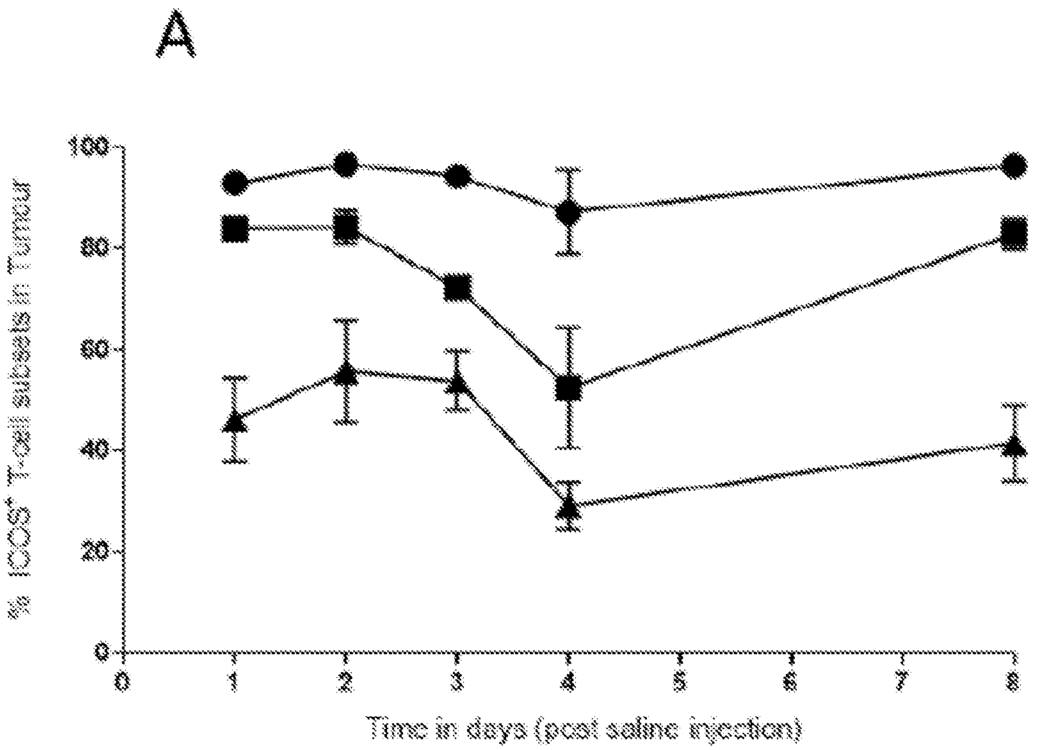
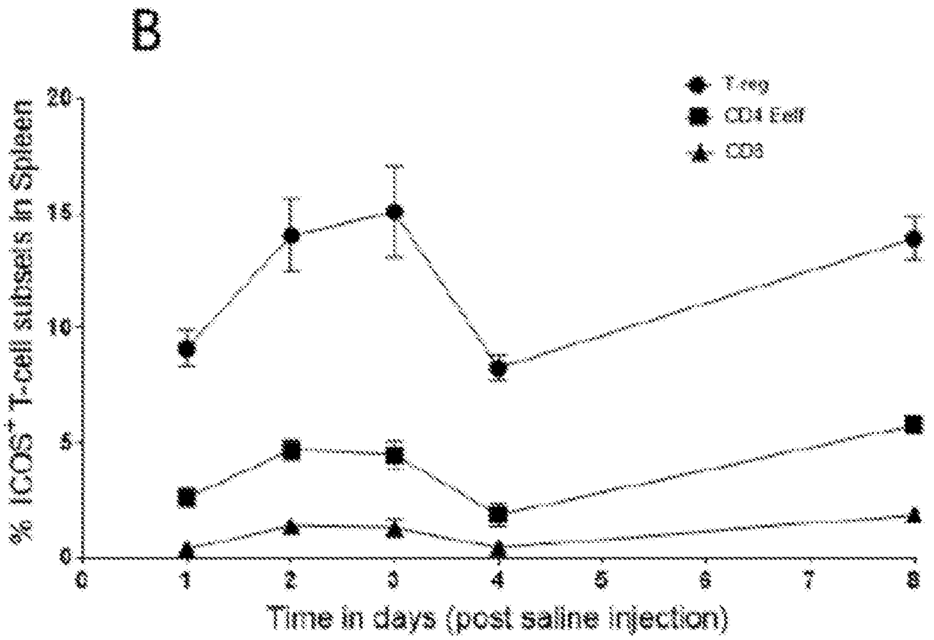
Figure 42 A and B

C
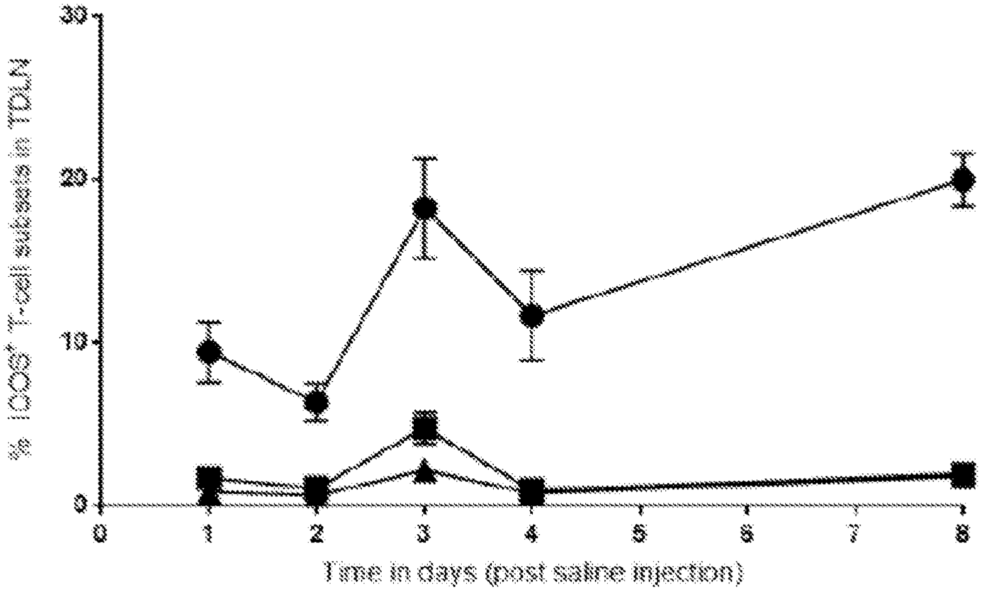
D
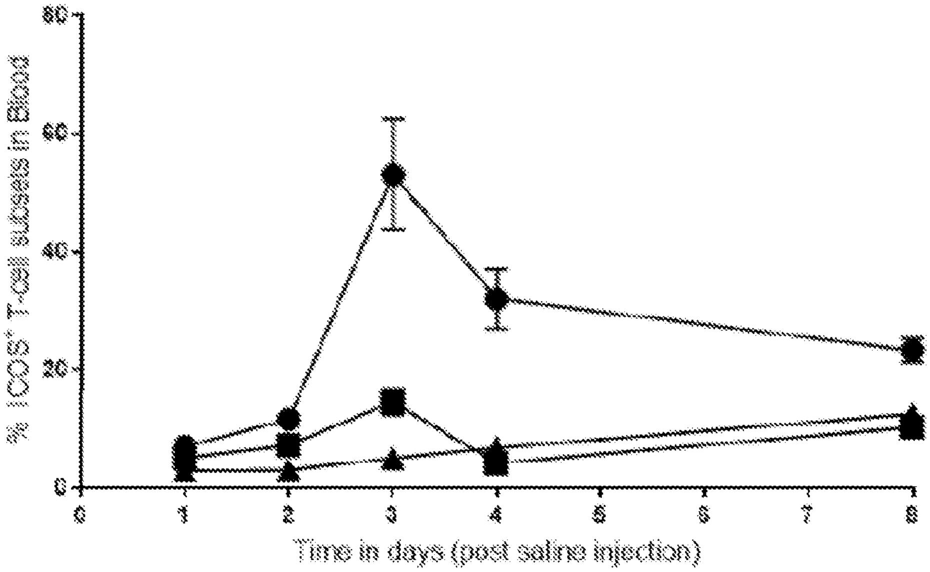
Figure 42 C and D

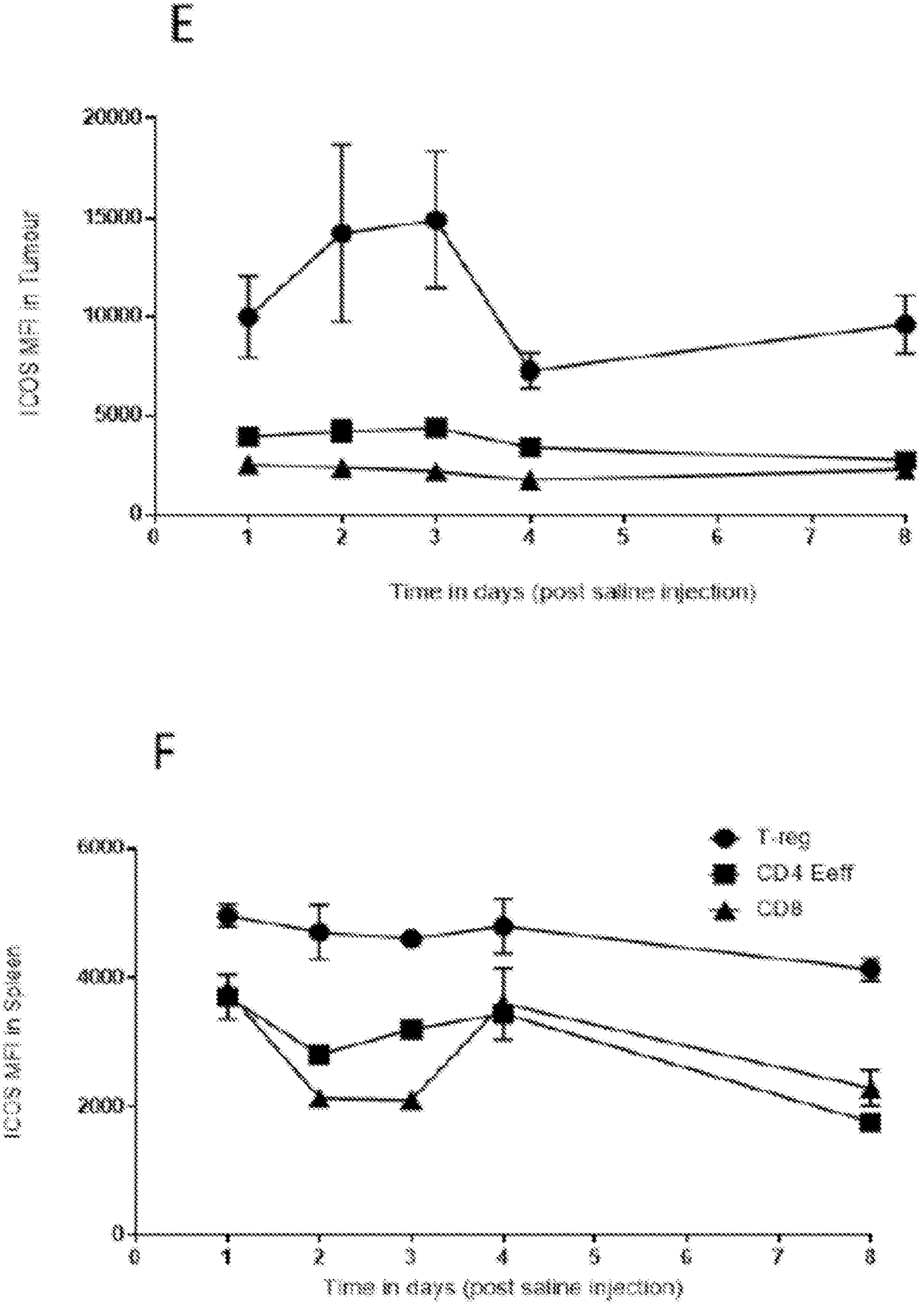
Figure 42 E and F

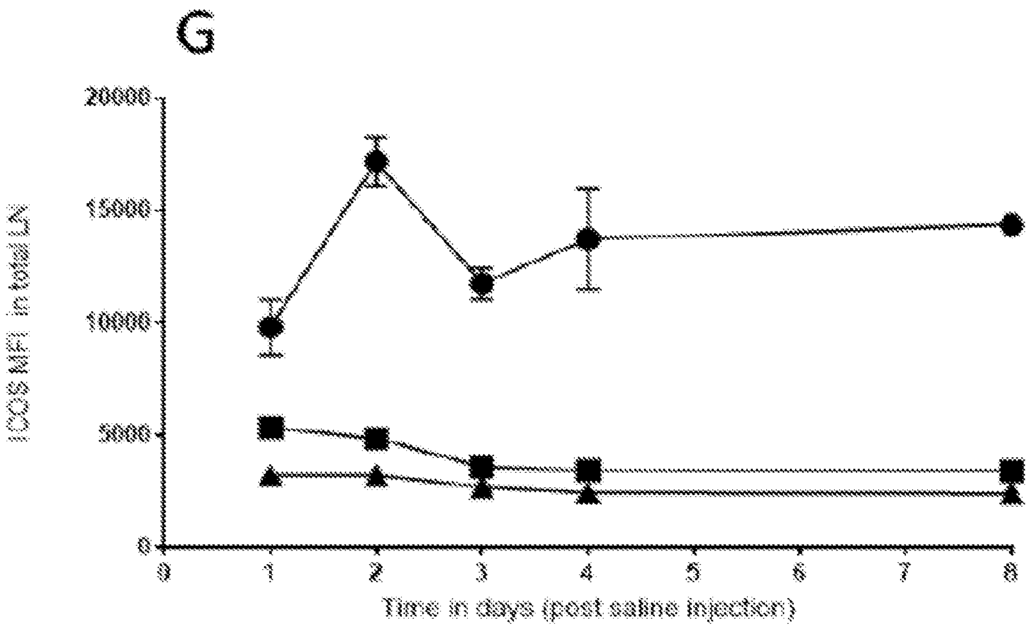
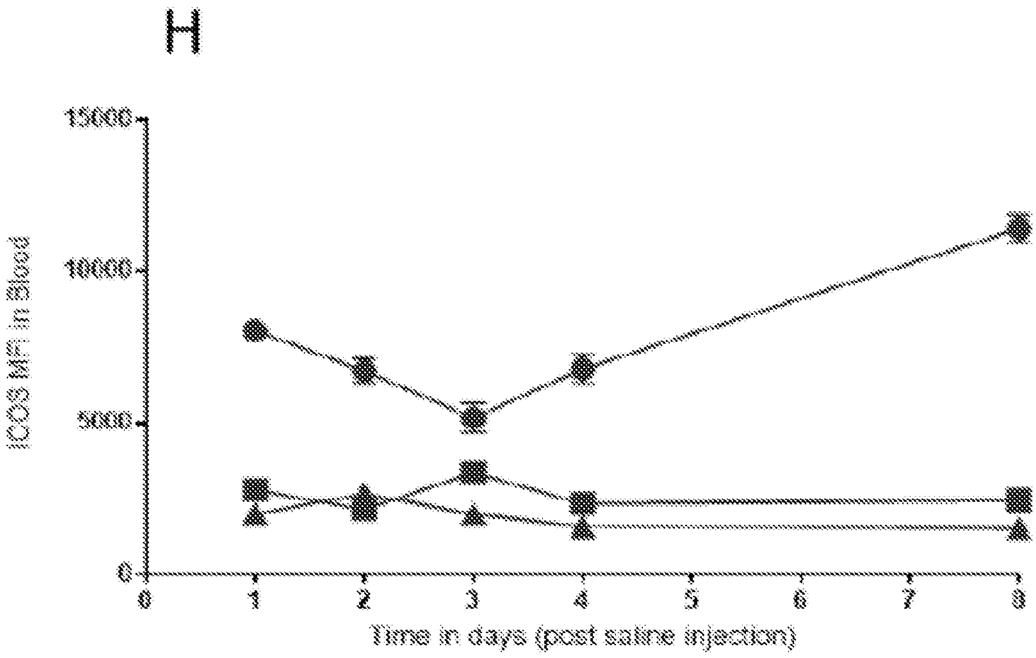
Figure 42 G and H

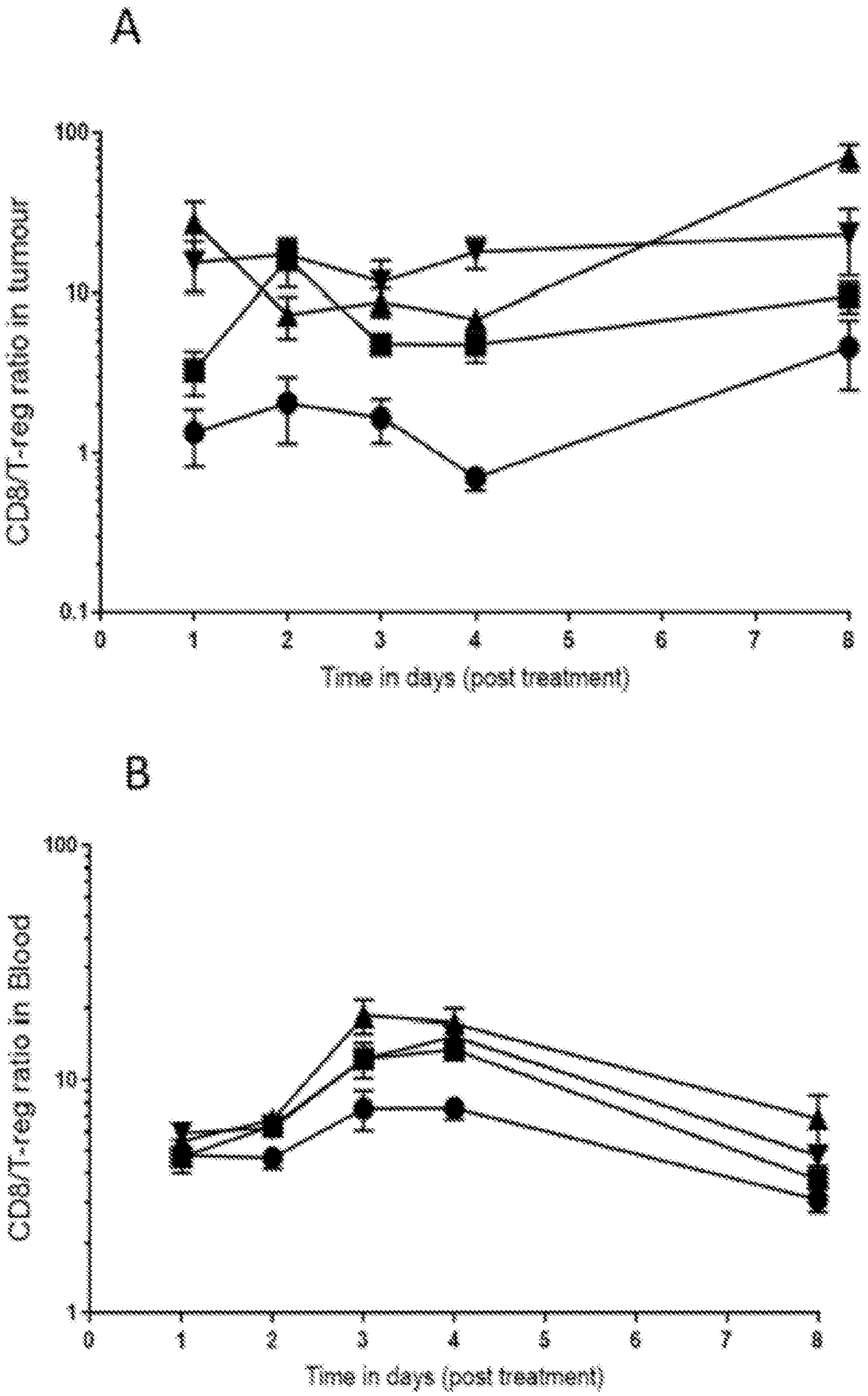
Figure 44 A and B

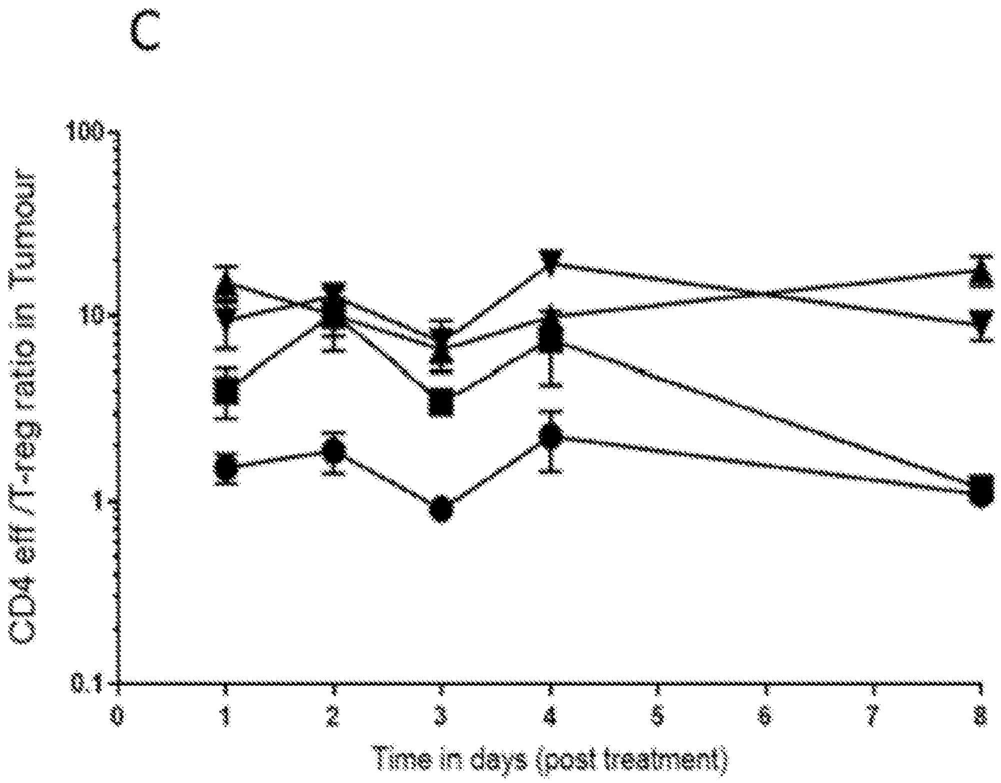
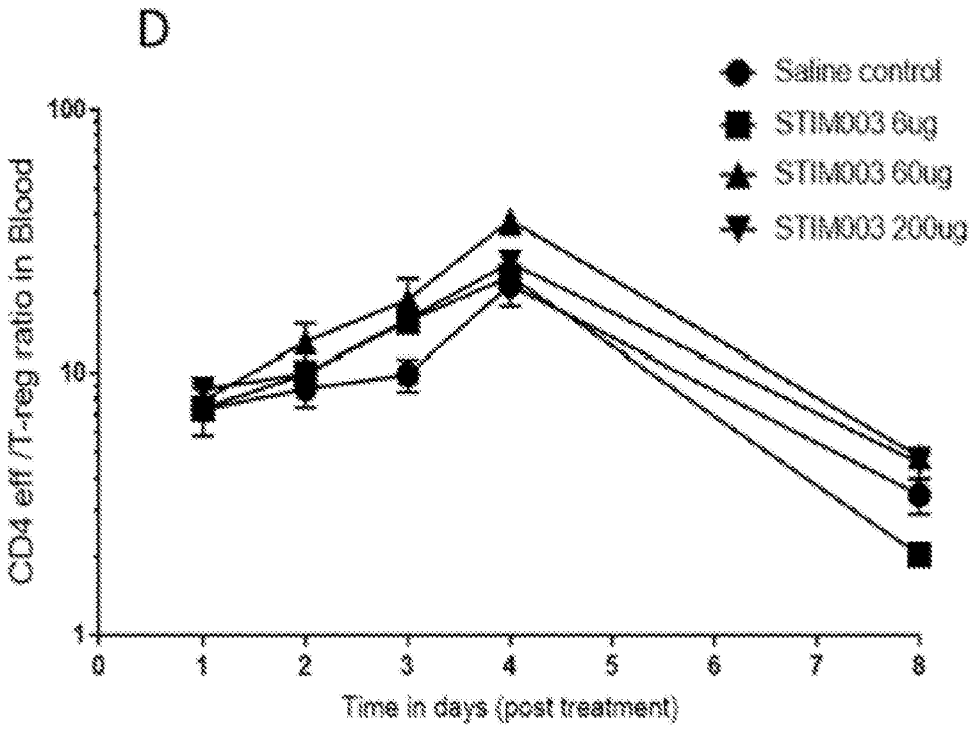
Figure 44 C and D

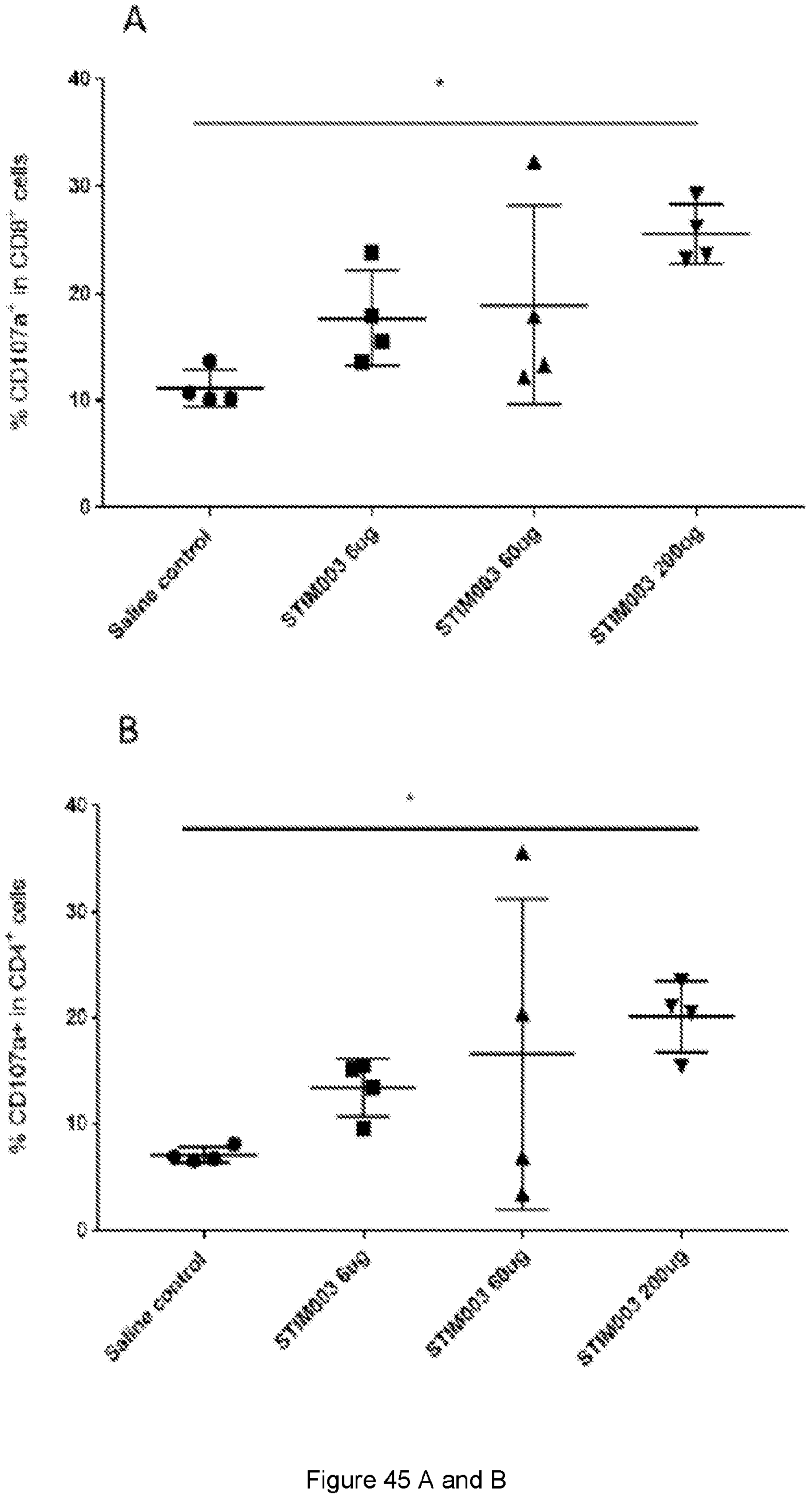
Figure 45 A and B

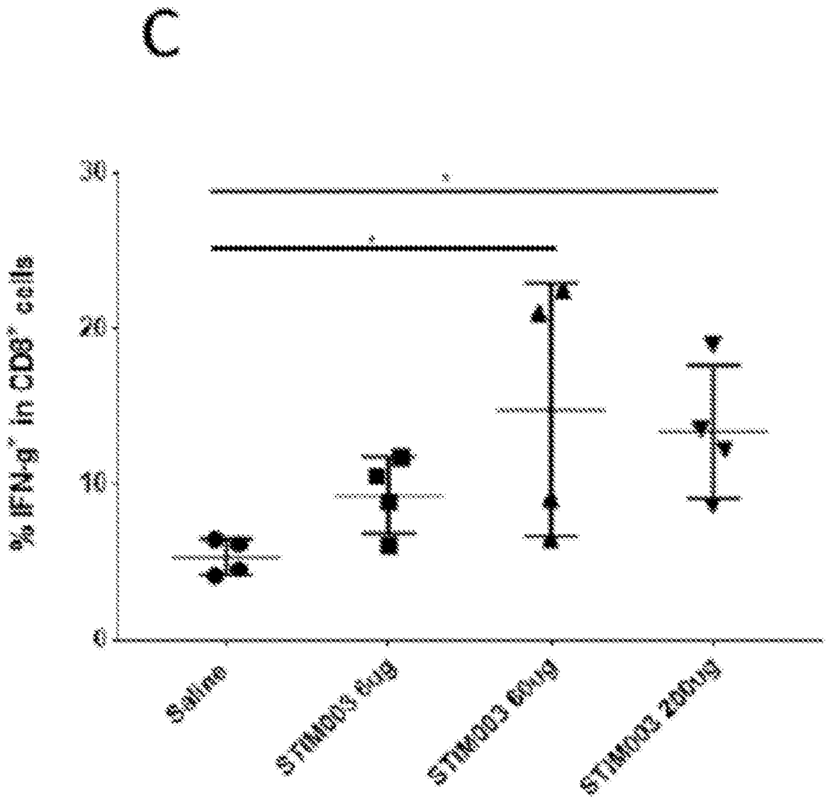
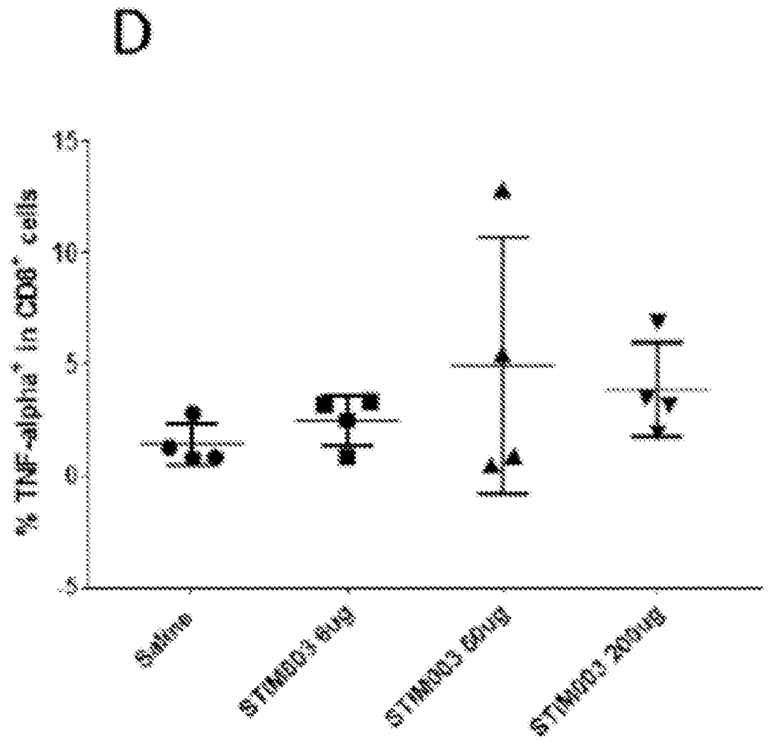
Figure 45 C and D

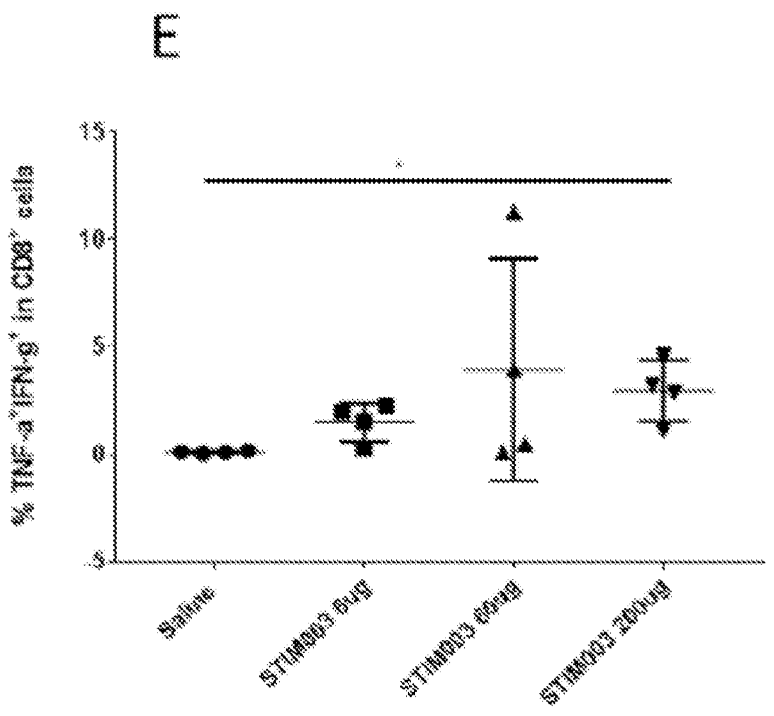
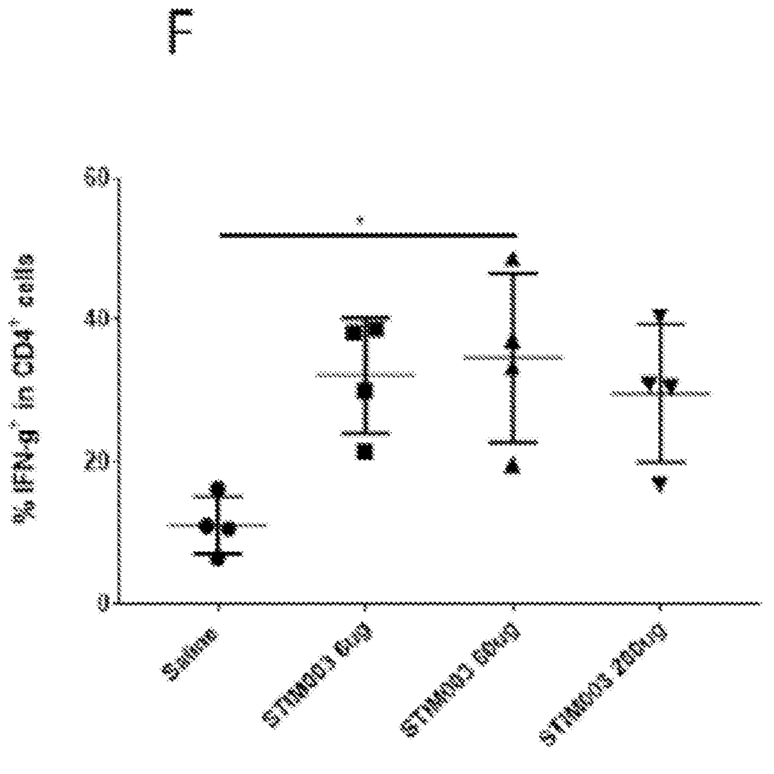
Figure 45 E and F

G
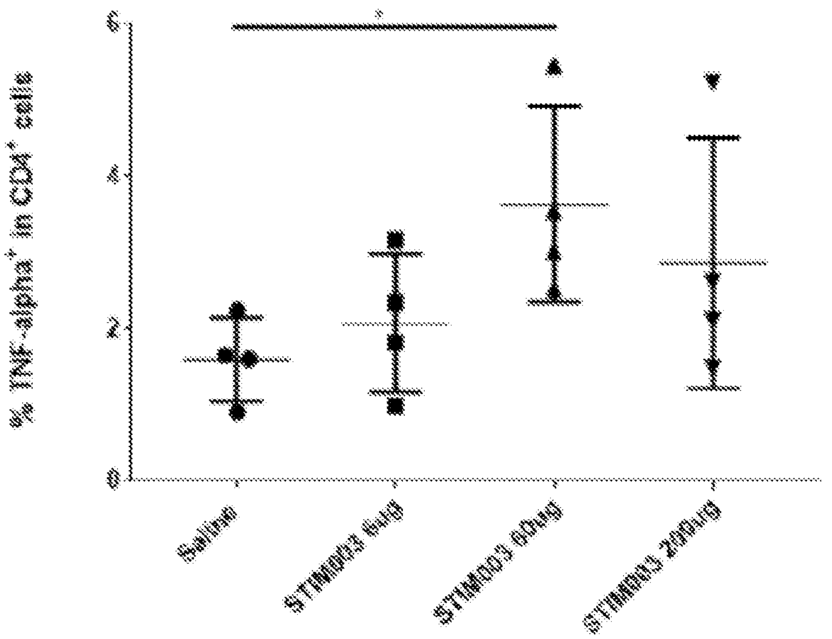
H
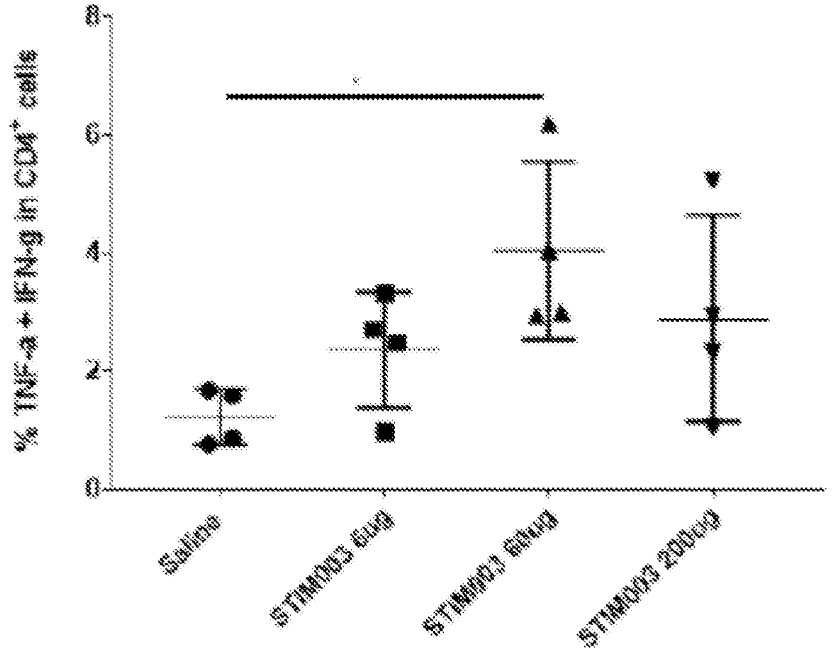
Figure 45 G and H

ANTI-ICOS ANTIBODIES

This application is a national stage filing under 35 U.S.C. § 371 of International Application No. PCT/GB2017/052352, filed on Aug. 9, 2017, which claims priority of British Patent Application No. 1613638.0, filed Aug. 9, 2016, British Patent Application No. 1615224.1, filed Sep. 7, 2016, British Patent Application No. 1615335.5, filed Sep. 9, 2016, British Patent Application No. 1620414.1, filed Dec. 1, 2016, British Patent Application No. 1621782.0, filed Dec. 20, 2016, British Patent Application No. 1702338.3, filed Feb. 13, 2017, British Patent Application No. 1702339.1, filed Feb. 13, 2017, British Patent Application No. 1703071.9, filed Feb. 24, 2017, British Patent Application No. 1709818.7, filed Jun. 20, 2017, International Application No. PCT/GB2017/051794, filed Jun. 20, 2017, Taiwanese Patent Application No. 106120563, filed Jun. 20, 2017, International Application No. PCT/GB2017/051795, filed Jun. 20, 2017, Taiwanese Patent Application No. 106120562, filed Jun. 20, 2017, International Application No. PCT/GB2017/051796, filed Jun. 20, 2017, and Taiwanese Patent Application No. 106120564, filed Jun. 20, 2017. The contents of these applications are each incorporated herein by reference.

SEQUENCE LISTING

The instant application contains a Sequence Listing which has been submitted electronically in ASCII format and is hereby incorporated by reference in its entirety. Said ASCII copy, created on Jul. 2, 2021, is named 718531_SA9-616US_ST25.txt and is 610,804 bytes in size.

FIELD OF THE INVENTION

This invention relates to compositions for stimulating the mammalian immune response, especially the T cell response. The invention also relates to medical use of such compositions in immuno-oncology, including anti-tumour therapy by promotion of anti-tumour T cell response in a patient, as well as to use of the compositions in other diseases and conditions where it is of therapeutic benefit to modulate the balance between effector T cells and regulatory T cells in favour of effector T cell activity, for example through stimulation of effector T cells and/or through depletion of regulatory T cells.

BACKGROUND

ICOS (Inducible T cell Co-Stimulator) is a member of the CD28 gene family involved in regulating immune responses, in particular humoral immune responses, first identified in 1999 [1]. It is a 55 kDa transmembrane protein, existing as a disulphide linked homodimer with two differentially glycosylated subunits. ICOS is exclusively expressed on T lymphocytes, and is found on a variety of T cell subsets. It is present at low levels on naïve T lymphocytes but its expression is rapidly induced upon immune activation, being upregulated in response to pro-inflammatory stimuli such as on engagement of TCR and co-stimulation with CD28 [2, 3]. ICOS plays a role in the late phase of T cell activation, memory T cell formation and importantly in the regulation of humoral responses through T cell dependent B cell responses [4, 5]. Intracellularly, ICOS binds PI3K and activates the kinases phophoinositide-dependent kinase 1 (PDK1) and protein kinase B (PKB). Activation of ICOS prevents cell death and upregulates cellular metabolism. In the absence of ICOS (ICOS knock-out) or in the presence of anti-ICOS neutralising antibodies there would be a suppression of pro-inflammatory responses.

ICOS binds to ICOS ligand (ICOSL) expressed on B-cells and antigen presenting cells (APC) [6, 7]. As a co-stimulatory molecule it serves to regulate TCR mediated immune responses and antibody responses to antigen. The expression of ICOS on T regulatory cells may be important, as it has been suggested that this cell type plays a negative role in immunosurveillance of cancer cells—there is emerging evidence for this in ovarian cancer [8]. Importantly, ICOS expression has been reported to be higher on intratumoural regulatory T cells (TRegs) compared with CD4+ and CD8+ effector cells that are present in the tumour microenvironment. Depletion of TRegs using antibodies with Fc-mediated cellular effector function has demonstrated strong anti-tumour efficacy in a pre-clinical model [9]. Mounting evidence implicates ICOS in an anti-tumour effect in both animal models as well as patients treated with immune-checkpoint inhibitors. In mice deficient in ICOS or ICOSL the anti-tumor effect of anti-CTLA4 therapy is diminished [10] while in normal mice ICOS ligand increases the effectiveness of anti-CTLA4 treatment in melanoma and prostate cancer [11]. Furthermore, in humans a retrospective study of advanced melanoma patients showed increased levels of ICOS following ipilimumab (anti-CTLA4) treatment [12]. In addition, ICOS expression is upregulated in bladder cancer patients treated with anti-CTLA4 [13]. It has also been observed that in cancer patients treated with anti-CTLA4 therapy the bulk of tumour specific IFNγ producing CD4 T-cells are ICOS positive while sustained elevation of ICOS positive CD4 T cells correlates with survival [12, 13, 14].

WO2016/120789 described anti-ICOS antibodies and proposed their use for activating T cells and for treating cancer, infectious disease and/or sepsis. A number of murine anti-ICOS antibodies were generated, of which a sub-set were reported to be agonists of the human ICOS receptor. The antibody "422.2" was selected as the lead anti-ICOS antibody and was humanised to produce a human "IgG4PE" antibody designated "H2L5". H2L5 was reported to have an affinity of 1.34 nM for human ICOS and 0.95 nM for cynomolgus ICOS, to induce cytokine production in T cells, and to upregulate T cell activation markers in conjunction with CD3 stimulation. However, mice bearing implanted human melanoma cells were reported to show only minimal tumour growth delay or increase in survival when treated with H2L5 hIgG4PE, compared with control treated group. The antibody also failed to produce significant further inhibition of tumour growth in combination experiments with ipilimumab (anti-CTLA-4) or pembrolizumab (anti-PD-1), compared with ipilimumab or pembrolizumab monotherapy. Finally, In mice bearing implanted colon cancer cells (CT26), low doses of a mouse cross reactive surrogate of H2L5 in combination with a mouse surrogate of ipilimumab or pembrolizumab only mildly improved overall survival compared with anti-CTL4 and anti-PD1 therapy alone. A similar lack of strong therapeutic benefit was shown in mice bearing implanted EMT6 cells.

WO2016/154177 described further examples of anti-ICOS antibodies. These antibodies were reported to be agonists of CD4+ T cells, including effector CD8+ T cells (TEff), and to deplete T regulator cells (TRegs). Selective effects of the antibodies on TEff vs TReg cells were described, whereby the antibodies could preferentially deplete TRegs while having minimal effect on TEffs that express a lower level of ICOS. The anti-ICOS antibodies were proposed for use in treating cancer, and combination therapy with anti-PD-1 or anti-PD-L1 antibodies was described.

SUMMARY OF THE INVENTION

An antibody to ICOS that acts to increase effector T cell activity represents a therapeutic approach in immunooncology and in other medical contexts where a CD8+ T cell response is beneficial, including various diseases and conditions and in vaccination regimens. In many diseases and conditions involving an immune component, a balance exists between effector T cells (TEff) which exert the CD8+ T cell immune response, and regulatory T cells (TReg) which suppress that immune response by downregulating TEffs. The present invention relates to antibodies that modulate this TEff/TReg balance in favour of effector T cell activity. Antibodies that trigger the depletion of ICOS highly positive regulatory T cells would relieve the suppression of TEffs, and thus have a net effect of promoting the effector T cell response. An additional or complementary mechanism for an anti-ICOS antibody is via agonistic activity at the ICOS receptor level, to stimulate the effector T cell response.

The relative expression of ICOS on effector T cells (TEff) compared with regulatory T cells (TReg), and the relative activities of these cell populations, will influence the overall effect of an anti-ICOS antibody in vivo. An envisaged mode of action combines agonism of effector T cells with depletion of ICOS positive regulatory T cells. Differential and even opposing effects on these two different T cell populations may be achievable due to their different levels of ICOS expression. Dual-engineering of the variable and constant regions respectively of an anti-ICOS antibody can provide a molecule that exerts a net positive effect on effector T cell response by affecting the CD8/TReg ratio. An antigen-binding domain of an agonist antibody, which activates the ICOS receptor, may be combined with an antibody constant (Fc) region that promotes downregulation and/or clearance of highly expressing cells to which the antibody is bound. An effector positive constant region may be used to recruit cellular effector functions against the target cells (TRegs), e.g., to promote antibody-dependent cell-mediated cytotoxicity (ADCC) or antibody dependent cell phagocytosis (ADCP). The antibody may thus act both to promote effector T cell activation and to downregulate immunosuppressive T Regulatory cells. Since ICOS is more highly expressed on TRegs than on TEffs, a therapeutic balance may be achieved whereby Teff function is promoted while TRegs are depleted, resulting in a net increase in the T cell immune response (e.g, anti-tumour response or other therapeutically beneficial T cell response).

Several pre-clinical and clinical studies have shown a strong positive correlation between high effector T-cell to T-reg cell ratio in the tumour microenvironment (TME) and overall survival. In ovarian cancer patients the ratio of CD8:T-reg cells has been reported to be an indicator of good clinical outcome [15]. A similar observation was made in metastatic melanoma patients after receiving ipilumumab [16]. In pre-clinical studies, it has also been shown that high effector cell:T-reg ratio in TME is associated with anti-tumour response [43].

This invention provides antibodies that bind human ICOS. The antibodies target the ICOS extracellular domain and thereby bind to T cells expressing ICOS. Examples are provided of antibodies that have been designed to have an agonistic effect on ICOS, thus enhancing the function of effector T cells, as indicated by an ability to increase IFNγ expression and secretion. As noted, anti-ICOS antibodies may also be engineered to deplete cells to which they bind, which should have the effect of preferentially downregulating regulatory T cells, lifting the suppressive effect of these cells on the effector T cell response and thus promoting the effector T cell response overall. Regardless of their mechanism of action, it is demonstrated empirically that anti-ICOS antibodies according to the present invention do stimulate T cell response and have anti-tumour effects in vivo, as shown in the Examples. Through selection of appropriate antibody formats such as those including constant regions with a desired level of Fc effector function, or absence of such effector function where appropriate, the anti-ICOS antibodies may be tailored for use in a variety of medical contexts including treatment of diseases and conditions in which an effector T cell response is beneficial and/or where suppression of regulatory T cells is desired.

Exemplary antibodies include STIM001, STIM002, STIM002-B, STIM003, STIM004, STIM005, STIM006, STIM007, STIM008 and STIM009, the sequences of which are set out herein.

An antibody according to the invention may be one that competes for binding to human ICOS with an antibody (e.g., human IgG1, or an scFv) comprising the heavy and light chain complementarity determining regions (CDRs) of STIM001, STIM002, STIM002-B, STIM003, STIM004, STIM005, STIM006, STIM007, STIM008 or STIM009, optionally an antibody comprising the VH and VL domains of STIM001, STIM002, STIM002-B, STIM003, STIM004, STIM005, STIM006, STIM007, STIM008 or STIM009.

An antibody according to the present invention may comprise one or more CDRs of any of STIM001, STIM002, STIM002-B, STIM003, STIM004, STIM005, STIM006, STIM007, STIM008 and STIM009 (e.g., all 6 CDRs of any such antibody, or a set of HCDRs and/or LCDRs) or variants thereof as described herein.

The antibody may comprise an antibody VH domain comprising CDRs HCDR1, HCDR2 and HCDR3 and an antibody VL domain comprising CDRs LCDR1, LCDR2 and LCDR3, wherein the HCDR3 is an HCDR3 of an antibody selected from STIM001, STIM002, STIM002-B, STIM003, STIM004, STIM005, STIM006, STIM007, STIM008 and STIM009 or comprises that HCDR3 with 1, 2, 3, 4 or 5 amino acid alterations. The HCDR2 may be the HCDR2 of the selected antibody or it may comprise that HCDR2 with 1, 2, 3, 4 or 5 amino acid alterations. The HCDR1 may be the HCDR1 of the selected antibody or it may comprise that HCDR1 with 1, 2, 3, 4 or 5 amino acid alterations.

The antibody may comprise an antibody VL domain comprising CDRs HCDR1, HCDR2 and HCDR3 and an antibody VL domain comprising CDRs LCDR1, LCDR2 and LCDR3, wherein the LCDR3 is an LCDR3 of an antibody selected from STIM001, STIM002, STIM002-B, STIM003, STIM004, STIM005, STIM006, STIM007, STIM008 and STIM009 or comprises that LCDR3 with 1, 2, 3, 4 or 5 amino acid alterations. The LCDR2 may be the LCDR2 of the selected antibody or it may comprise that LCDR2 with 1, 2, 3, 4 or 5 amino acid alterations. The LCDR1 may be the LCDR1 of the selected antibody or it may comprise that LCDR1 with 1, 2, 3, 4 or 5 amino acid alterations.

An antibody may comprise:

an antibody VH domain comprising complementarity determining regions HCDR1, HCDR2 and HCDR3, and an antibody VL domain comprising complementarity determining regions LCDR1, LCDR2 and LCDR3, wherein the heavy chain complementarity determining regions are those of STIM001, STIM002, STIM002-B, STIM003, STIM004, STIM005, STIM006, STIM007, STIM008 or STIM009 or comprise the STIM001, STIM002, STIM002-B, STIM003, STIM004 or STIM005, STIM006, STIM007, STIM008 or STIM009 heavy chain complementarity determining regions with 1, 2, 3, 4 or 5 amino acid alterations; and/or wherein the light chain complementarity determining regions are those of antibody STIM001, STIM002, STIM002-B, STIM003, STIM004, STIM005, STIM006, STIM007, STIM008 or STIM009, or comprise the STIM001, STIM002, STIM002-B, STIM003, STIM004, STIM005, STIM006, STIM007, STIM008 or STIM009 light chain complementarity determining regions with 1, 2, 3, 4 or 5 amino acid alterations.

An antibody may comprise a VH domain comprising a set of heavy chain complementarity determining regions (HCDRs) HCDR1, HCDR2 and HCDR3, wherein HCDR1 is the HCDR1 of STIM003, HCDR2 is the HCDR2 of STIM003, HCDR3 is the HCDR3 of STIM003, or comprising that set of HCDRs with 1, 2, 3, 4, 5 or 6 amino acid alterations.

An antibody may comprise a VL domain comprising a set of light chain complementarity determining regions (LCDRs) LCDR1, LCDR2 and LCDR3, wherein LCDR1 is the LCDR1 of STIM003, LCDR2 is the LCDR2 of STIM003, LCDR3 is the LCDR3 of STIM003, or comprising that set of LCDRs with 1, 2, 3 or 4 amino acid alterations.

Amino acid alterations (e.g., substitutions) may be at any residue position in the CDRs. Examples of amino acid alterations are those illustrated in FIG. 35, FIG. 36 and FIG. 37, which show alignments of variant sequences of anti-ICOS antibodies. Thus, an amino acid alteration in a STIM003 CDR may be a substitution of the residue present at the corresponding position in antibody CL-74570 or antibody CL-71642 as indicated in FIG. 36.

Example amino acid alterations in STIM003 CDRs are substitutions at the following residue positions, defined according to IMGT:

In HCDR1, substitution at IMGT position 28, optionally a conservative substitution, e.g., V28F.

In HCDR2, substitution at IMGT position 59, 63 and/or 64. Optionally the substitution at position 59 is N591, the substitution at position 63 is G63D and/or the substitution at position 64 is D64N and/or D64S.

In HCDR3, substitution at IMGT position 106, 108, 109 and/or 112. Optionally the substitution at position 106 is R106A, the substitution at position 108 is F108Y, the substitution at position 109 is Y109F and/or the substitution at position 112 is H112N.

In LCDR1, substitution at position 36, e.g., R36S.

In LCDR3, substitution at position 105, 108 and/or 109. Optionally the substitution at position 105 is H105Q, the substitution at position 108 is D108G and/or the substitution at position 109 is M109N or M109S.

Antibodies of the invention may comprise VH and/or VL domain framework regions corresponding to human germline gene segment sequences. For example, it may comprise one or more framework regions of STIM001, STIM002, STIM002-B, STIM003, STIM004, STIM005, STIM006, STIM007, STIM008 or STIM009. The framework region or framework regions may be a FR1, FR2, FR3 and/or FR4.

As described in Example 12, Table E12-1 shows the human germline V, D and J gene segments that generated the VH domains of these antibodies through recombination and Table E12-2 shows the human germline V and J gene segments that generated the VL domains of these antibodies through recombination. Antibody VH and VL domains of the present invention may be based on these V(D)J segments.

An antibody of the invention may comprise an antibody VH domain which (i) is derived from recombination of a human heavy chain V gene segment, a human heavy chain D gene segment and a human heavy chain J gene segment, wherein the V segment is IGHV1-18 (e.g., V1-18*01), IGVH3-20 (e.g. V3-20*d01), IGVH3-11 (e.g, V3-11*01) or IGVH2-5 (e.g., V2-5*10);

the D gene segment is IGHD6-19 (e.g., IGHD6-19*01), IGHD3-10 (e.g., IGHD3-10*01) or IGHD3-9 (e.g., IGHD3-9*01); and/or the J gene segment is IGHJ6 (e.g., IGHJ6*02), IGHJ4 (e.g., IGHJ4*02) or IGHJ3 (e.g., IGHJ3*02), or (ii) comprises framework regions FR1, FR2, FR3 and FR4, wherein FR1 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, FR2 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, FR3 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, and/or FR4 aligns with human germline J gene segment IGJH6 (e.g., JH6*02), IGJH4 (e.g., JH4*02) or IGJH3 (e.g., JH3*02), optionally with 1, 2, 3, 4 or 5 amino acid alterations.

FR1, FR2 and FR3 of the VH domain typically align with the same germline V gene segment. Thus, for example, the antibody may comprise a VH domain derived from recombination of human heavy chain V gene segment IGHV3-20 (e.g., VH3-20*d01), a human heavy chain D gene segment and a human heavy chain J gene segment IGJH4 (e.g., JH4*02). An antibody may comprise VH domain framework regions FR1, FR2, FR3 and FR4, wherein FR1, FR2 and FR3 each align with human germline V gene segment IGHV3-20 (e.g., IGVH3-20*d01) with up to 1, 2, 3, 4 or 5 amino acid alterations, and a FR4 that aligns with human germline J gene segment IGHJ4 (e.g., IGHJ4*02) with up to 1, 2, 3, 4 or 5 amino acid alterations. Alignment may be exact, but in some cases one or more residues can be mutated from germline, so there may be amino acid substitutions present, or in rarer cases deletions or insertions.

An antibody of the invention may comprise an antibody VL domain which (i) is derived from recombination of a human light chain V gene segment and a human light chain J gene segment, wherein the V segment is IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), and/or the J gene segment is IGKJ4 (e.g., IGKJ4*01), IGKJ2 (e.g., IGKJ2*04), IGLJ3 (e.g., IGKJ3*01) or IGKJ1 (e.g., IGKJ1*01); or (ii) comprises framework regions FR1, FR2, FR3 and FR4, wherein FR1 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, FR2 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, FR3 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, and/or FR4 aligns with human germline J gene segment IGKJ4 (e.g., IGKJ4*01), IGKJ2 (e.g., IGKJ2*04), IGKJ3 (e.g., IGKJ3*01) or IGKJ1 (e.g., IGKJ1*01), optionally with 1, 2, 3, 4 or 5 amino acid alterations.

FR1, FR2 and FR3 of the VL domain typically align with the same germline V gene segment. Thus, for example, the antibody may comprise a VL domain derived from recombination of human light chain V gene segment IGKV3-20 (e.g., IGKV3-20*01) and human light chain J gene segment IGKJ3 (e.g., IGKJ3*01). An antibody may comprise VL domain framework regions FR1, FR2, FR3 and FR4, wherein FR1, FR2 and FR3 each align with human germline V gene segment IGKV3-20 (e.g., IGKV3-20*01) with up to 1, 2, 3, 4 or 5 amino acid alterations, and a FR4 that aligns with human germline J gene segment IGKJ3 (e.g., IGKJ3*01) with up to 1, 2, 3, 4 or 5 amino acid alterations. Alignment may be exact, but in some cases one or more residues can be mutated from germline, so there may be amino acid substitutions present, or in rarer cases deletions or insertions.

An antibody according to the invention may comprise an antibody VH domain which is the VH domain of STIM001, STIM002, STIM002-B, STIM003, STIM004 or STIM005, STIM006, STIM007, STIM008 or STIM009, or which has an amino acid sequence at least 90% identical to the antibody VH domain sequence of STIM001, STIM002, STIM002-B, STIM003, STIM004, STIM005, STIM006, STIM007, STIM008 or STIM009. The amino acid sequence identity may be at least 95%.

The antibody may comprise an antibody VL domain which is the VL domain of STIM001, STIM002, STIM002-B, STIM003, STIM004 or STIM005, STIM006, STIM007, STIM008 or STIM009, or which has an amino acid sequence at least 90% identical to the antibody VL domain sequence of STIM001, STIM002, STIM002-B, STIM003, STIM004, STIM005, STIM006, STIM007, STIM008 or STIM009. The amino acid sequence identity may be at least 95%.

An antibody VH domain having the HCDRs of STIM001, STIM002, STIM002-B, STIM003, STIM004, STIM005, STIM006, STIM007, STIM008 or STIM009, or having a variant of those CDRs, may be paired with an antibody VL domain having the LCDRs of the same antibody, or having a variant of those CDRs. Similarly, the VH domain of any of STIM001, STIM002, STIM002-B, STIM003, STIM004, STIM005, STIM006, STIM007, STIM008 or STIM009, or a variant of that VH domain, may be paired with a VL domain of the same antibody, or a VL domain variant of the same antibody.

For instance, the antibody may comprise the antibody STIM001 VH domain and the STIM001 VL domain. In another example, the antibody may comprise the antibody STIM002 VH domain and the STIM002 VL domain. In another example, the antibody may comprise the antibody STIM003 VH domain and the STIM003 VL domain.

Antibodies may include constant regions, optionally human heavy and/or light chain constant regions. An exemplary isotype is IgG, e.g., human IgG1.

Further aspects of the invention include nucleic acid molecules encoding sequences of the antibodies described herein, host cells containing such nucleic acids, and methods of producing the antibodies by culturing the host cells and expressing and optionally isolating or purifying the antibodies. The expressed antibody is thereby obtained. VH and VL domains of antibodies described herein may similarly be produced and are aspects of the present invention. Pharmaceutical compositions comprising the antibodies are also provided.

Other aspects of the invention relate to ICOS knock out non-human animals and their use for generating antibodies to human ICOS. In an ICOS knock out animal, ICOS is not expressed, for example because the gene encoding ICOS has been inactivated or deleted from the animal's genome. Such animals are useful for generating species cross-reactive antibodies, which recognise both human ICOS and ICOS from the non-human species. The normal process of immune tolerance means that lymphocytes that recognise "self" antigens are deleted or inactivated to prevent autoimmune reactions in the body, whereas the absence of the endogenous ICOS antigen in the non-human knock out animal means that the animal's immune system should not be tolerised to that antigen and therefore can mount an immune response against ICOS when injected as recombinant protein or using cell lines or vesicles expressing ICOS. The immune repertoire of the knock out animal should contain lymphocytes able to recognise the ICOS protein from that animal species. A non-human test animal (e.g., a mouse) immunised with human ICOS may thus generate antibodies that bind both human ICOS and the test animal ICOS (e.g., mouse ICOS).

This has at least two advantages. First, a species cross-reactive antibody can be used for pre-clinical testing in the non-human test animal before being taken forward into development in human clinical trials. Second, a knock out animal's immune system may be able to recognise a greater number of possible epitopes on a human ICOS molecule compared with those recognised by an ICOS-expressing animal, so that the immune repertoire of the knock out animal may contain a greater functional diversity of antibodies. Since there is similarity between the sequences of homologous ICOS molecules from different species, the immune system of a non-human animal may ordinarily be tolerised to those regions of the human ICOS protein that match those of the non-human animal ICOS, whereas this tolerisation does not occur in a knock out animal.

The ability to use an ICOS knock out animal, and its advantage for generating cross-reactive antibodies, is shown in the Examples. It is particularly surprising that an ICOS knock out animal could be successfully immunised to produce an antibody response, because ICOS itself is involved in the immune system biology such as formation and maintenance of the germinal centers and contributes to the generation of an immune response through its role on T follicular helper cells which are ICOS+ve cells [37]. With this in mind, an ICOS knock out animal might be predicted to generate a poor antibody response at best. Surprisingly, strong titres were obtained in ICOS knock out mice, and highly functional antibodies were isolated from among the antibody repertoire, including desirable cross-reactive antibodies.

Exemplary embodiments of the invention are set out in the appended claims.

BRIEF DESCRIPTION OF THE DRAWINGS

Certain aspects and embodiments of the invention will now be described in more detail with reference to the accompanying drawings.

FIG. 11: Graphs showing the CT26 tumour volumes over time of animals treated with anti-ICOS or anti-PDL1 monotherapies or combination therapies. Each treatment group is represented by a "spider plot" showing the tumour size of individual animals (n=10 per group). For each group, the number of animals with tumour size below 100 mm^3 (stable/cured of their disease) is indicated on the top right of the respective graphs. Dosing was performed on days 6, 8, 10, 13, 15 and 17. Dosing time is indicated by the shaded area. (a) Isotype control; (b) Anti-PDL1 mIgG2a AbW; (c) Anti ICOS STIM003 mIgG1; (d) Anti ICOS STIM003 mIgG2a; (e) Anti-PDL1 mIgG2a AbW+STIM003 mIgG1; (f) Anti-PDL1 mIgG2a AbW+STIM003 mIgG2a. STIM003 mIgG2 significantly inhibits CT26 tumour growth when combined with anti-PDL1 (AbW) mIgG2a.

FIG. 15: STIM001 and STIM003 showed isotype-dependent effects on the T cell compartment at the tumour site. A total of 1×10E5 CT-26 tumour cells were implanted subcutaneously in Balb/c female mice. At day 13 and day 15 post implantation animals were dosed with antibodies or saline intraperitoneally (n=10/each group). On day 16 post implantation spleen and tumours were harvest from tumour bearing animals (n=8/each group), dissociated and stained for FACS analysis. A, percentage of CD3 cells that are positive for CD4 cells. B, percentage of CD3 cells that are positive for CD8 cells. C, percentage of CD4 cells that are Foxp3+ & CD25+. D, percentage of CD4 cells in spleen that are positive for Foxp3+ & CD25+. E, percentage of CD4 effector cells in total CD4 cells. F, ratio of CD8 effector to T-Reg cells. G, ratio of CD4 effector to T-Reg cells. Statistical analysis were performed using GraphPad Prism, all the Antibody treated groups were compared with saline treated group, P values were noted when significant ($p<0.05$). Values denote means+SD (n=8 mice/group). For F: Values denote mean+SEM.

FIG. 27: (A) CD8 effector:Treg ratio and (B) CD4:TReg ratio in spleen of CT26 tumour bearing animals.

FIG. 28: Surface staining of AF647-conjugated STIM001, STIM003 and hIgG1 hybrid control (HC IgG1) on activated Mauritian cynomolgus pan T cells. Data from assays using different donor sources of T cells are shown in A and B respectively. EC50 values are indicated in the table.

FIG. 35: STIM002 VH (top) and VL (bottom) domain amino acid sequences, showing residues that differ in the corresponding sequences of STIM001, STIM002B and related antibodies CL-61091, CL-64536, CL-64837, CL-64841 and CL-64912 and/or in the human germline. Sequence numbering is according to IMGT.

FIG. 36: STIM003 VH (top) and VL (bottom) domain amino acid sequences, showing residues that differ in the corresponding sequences of related antibodies CL-71642 and CL-74570 and/or in the human germline. Sequence numbering is according to IMGT. The VL domain of antibody CL-71642 obtained from sequencing is shown here without the N terminal residue. From the alignment it can be seen that the full VH domain sequence would comprise an N terminal glutamic acid.

FIG. 37: STIM007 VH (top) and VL (bottom) domain amino acid sequences, showing residues that differ in the corresponding sequences of STIM008 and/or in the human germline. Sequence numbering is according to IMGT.

FIG. 42: ICOS expression on major T cells subsets (T-reg [CD4+/FoxP3+], CD4 Eff [CD4+/FoxP3−]cells and CD8+) from CT26 tumour bearing animals (n=4 per time point) dosed with saline. Immune cells phenotyping were conducted on day 1, 2, 3, 4 and 8 post treatment and stained for ICOS expression in all the tissues at all time points. A-D showing the percentage of ICOS positive cells at all the time points in four different tissues. E-H show the ICOS dMFI (relative expression) all the time points in all the four different tissues. See Example 24.

FIG. 44: Increase in CD8:T-reg and CD4 eff:T-reg ratio in response to STIM003 mIgG2a. CT-26 tumour bearing animals received a single dose (6, 60 or 200 μg) of STIM003 mIgG2a on day 12 post tumour cell implantation. Tissues (n=4 per time point) were harvested for FACS analysis on day 1, 2, 3, 4 and 8 post treatment and T eff to T-reg ratios were calculated. (A) & (B), CD8:T-reg ratio in tumour and blood, (C) & (D) CD4-eff:T-reg ratio in tumour and blood. See Example 24.

FIG. 45: STIM003 treatment correlates with increased degranulation and Th1 cytokine production by TILs. On day 8 post treatment TILs were isolated and FACS analysis were performed to detect CD107a expression on CD4 and CD8 T cells (A-B). In parallel, cells from dissociated tumours were rested for 4 hrs in the presence of Brefeldin-A, cells were stained for T cells markers and permeabilised for intracellular staining to detect IFN-γ and TNF-α (C—H). See Example 24.

DETAILED DESCRIPTION

ICOS

Figure 1A:
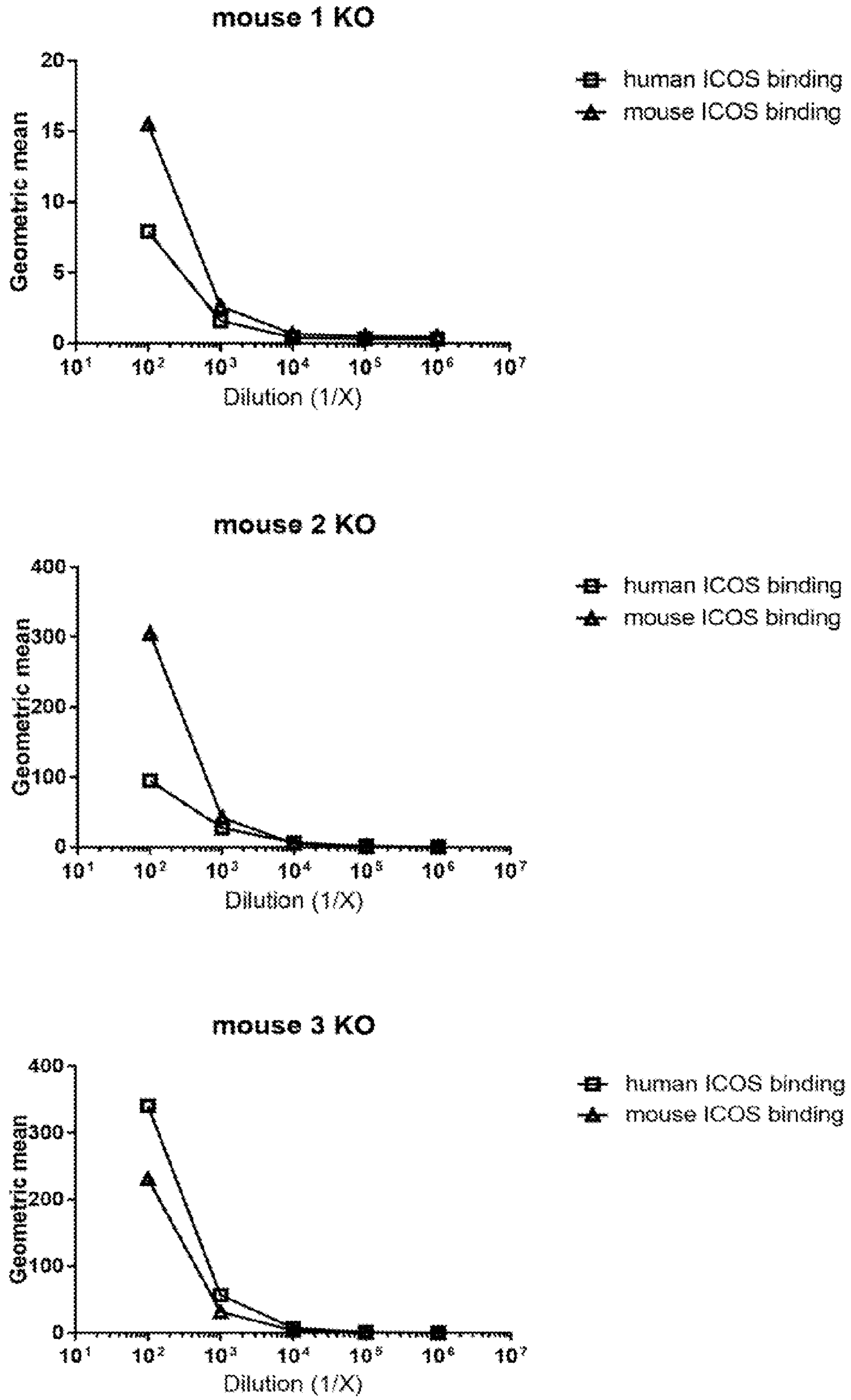
FIG. 1: Determination of serum titres of ICOS KO and wild type Kymouse against both human and mouse ICOS expressed on CHO cells by flow cytometry. Data illustrate ability of immunoglobulin in sera of (a) ICOS KO mice (KO) or (b) wild type non-ICOS KO mice (HK or HL), each immunised with human ICOS expressing MEF cells and human ICOS protein, to bind human ICOS (human ICOS binding) or mouse ICOS (mouse ICOS binding) expressed on CHO cells. Geometric mean is a measure of fluorescent intensity of immunoglobulin binding to cells as determined by flow cytometry.

Antibodies according to the present invention bind the extracellular domain of human ICOS. Thus, the antibodies bind ICOS-expressing T lymphocytes. "ICOS" or "the ICOS receptor" referred to herein may be human ICOS, unless the context dictates otherwise. Sequences of human, cynomolgus and mouse ICOS are shown in the appended sequence listing, and are available from NCBI as human NCBI ID: NP_036224.1, mouse NCBI ID: NP_059508.2 and cynomolgus GenBank ID: EHH55098.1.

Cross-Reactivity

Antibodies according to the present invention are preferably cross-reactive, and may for example bind the extracellular domain of mouse ICOS as well as human ICOS. The antibodies may bind other non-human ICOS, including ICOS of primates such as cynomolgus. An anti-ICOS antibody intended for therapeutic use in humans must bind human ICOS, whereas binding to ICOS of other species would not have direct therapeutic relevance in the human clinical context. Nevertheless, the data herein indicate that antibodies that bind both human and mouse ICOS have properties that render them particularly suitable as agonist and depleting molecules. This may result from one or more particular epitopes being targeted by the cross-reactive antibodies. Regardless of the underlying theory, however, cross-reactive antibodies are of high value and are excellent candidates as therapeutic molecules for pre-clinical and clinical studies.

As explained in the experimental Examples, the STIM antibodies described here were generated using Kymouse™ technology where the mouse had been engineered to lack expression of mouse ICOS (an ICOS knock-out). ICOS knock-out transgenic animals and their use for generating cross-reactive antibodies are further aspects of the present invention.

One way to quantify the extent of species cross-reactivity of an antibody is as the fold-difference in its affinity for antigen or one species compared with antigen of another species, e.g., fold difference in affinity for human ICOS vs mouse ICOS. Affinity may be quantified as $K_D$, referring to the equilibrium dissociation constant of the antibody-antigen reaction as determined by SPR with the antibody in Fab format as described elsewhere herein. A species cross-reactive anti-ICOS antibody may have a fold-difference in affinity for binding human and mouse ICOS that is 30-fold or less, 25-fold or less, 20-fold or less, 15-fold or less, 10-fold or less or 5-fold or less. To put it another way, the $K_D$ of binding the extracellular domain of human ICOS may be within 30-fold, 25-fold, 20-fold, 15-fold, 10-fold or 5-fold of the $K_D$ of binding the extracellular domain of mouse ICOS. Antibodies can also be considered cross-reactive if the $K_D$ for binding antigen of both species meets a threshold value, e.g., if the $K_D$ of binding human ICOS and the $K_D$ of binding mouse ICOS are both 10 mM or less, preferably 5 mM or less, more preferably 1 mM or less. The $K_D$ may be 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

An alternative measure of cross-reactivity for binding human ICOS and mouse ICOS is the ability of an antibody to neutralise ICOS ligand binding to ICOS receptor, such as in an HTRF assay (see Example 8). Examples of species cross-reactive antibodies are provided herein, including STIM001, STIM002, STIM002-B, STIM003, STIM005 and STIM006, each of which was confirmed as neutralising binding of human B7-H2 (ICOS ligand) to human ICOS and neutralising binding of mouse B7-H2 to mouse ICOS in an HTRF assay. Any of these antibodies or their variants may be selected when an antibody cross-reactive for human and mouse ICOS is desired. A species cross-reactive anti-ICOS antibody may have an IC50 for inhibiting binding of human ICOS to human ICOS receptor that is within 25-fold, 20-fold, 15-fold, 10-fold or 5-fold of the IC50 for inhibiting mouse ICOS to mouse ICOS receptor as determined in an HTRF assay. Antibodies can also be considered cross-reactive if the IC50 for inhibiting binding of human ICOS to human ICOS receptor and the IC50 for inhibiting binding of mouse ICOS to mouse ICOS receptor are both 1 mM or less, preferably 0.5 mM or less, e.g., 30 nM or less, 20 nM or less, 10 nM or less. The IC50s may be 5 nM or less, 4 nM or less, 3 nM or less or 2 nM or less. In some cases the IC50s will be at least 0.1 nM, at least 0.5 nM or at least 1 nM.

Specificity

Antibodies according to the present invention are preferably specific for ICOS. That is, the antibody binds its epitope on the target protein, ICOS (human ICOS, and preferably mouse and/or cynomolgus ICOS as noted above), but does not show significant binding to molecules that do not present that epitope, including other molecules in the CD28 gene family. An antibody according to the present invention preferably does not bind human CD28. The antibody preferably also does not bind mouse or cynomolgus CD28.

CD28 co-stimulates T cell responses when engaged by its ligands CD80 and CD86 on professional antigen presenting cells in the context of antigen recognition via the TCR. For various in vivo uses of the antibodies described herein, the avoidance of binding to CD28 is considered advantageous. Non-binding of the anti-ICOS antibody to CD28 should allow CD28 to interact with its native ligands and to generate appropriate co-stimulatory signal for T cell activation. Additionally, non-binding of the anti-ICOS antibody to CD28 avoids the risk of superagonism. Over-stimulation of CD28 can induce proliferation in resting T cells without the normal requirement for recognition of a cognate antigen via the TCR, potentially leading to runaway activation of T cells and consequent cytokine-release syndrome, especially in human subjects. The non-recognition of CD28 by antibodies according to the present invention therefore represents an advantage in terms of their safe clinical use in humans.

As discussed elsewhere herein, the present invention extends to multispecific antibodies (e.g., bispecifics). A multispecific (e.g., bispecific) antibody may comprise (i) an antibody antigen binding site for ICOS and (ii) a further antigen binding site (optionally an antibody antigen binding site, as described herein) which recognises another antigen (e.g., PD-L1). Specific binding of individual antigen binding sites may be determined. Thus, antibodies that specifically bind ICOS include antibodies comprising an antigen binding site that specifically binds ICOS, wherein optionally the antigen binding site for ICOS is comprised within an antigen-binding molecule that further includes one or more additional binding sites for one or more other antigens, e.g., a bispecific antibody that binds ICOS and PD-L1.

Affinity

The affinity of binding of an antibody to ICOS may be determined. Affinity of an antibody for its antigen may be quantified in terms of the equilibrium dissociation constant $K_D$, the ratio Ka/Kd of the association or on-rate (Ka) and the dissociation or off-rate (kd) of the antibody-antigen interaction. Kd, Ka and Kd for antibody-antigen binding can be measured using surface plasmon resonance (SPR).

An antibody according to the present invention may bind the EC domain of human ICOS with a $K_D$ of 10 mM or less, preferably 5 mM or less, more preferably 1 mM or less. The $K_D$ may be 50 nM or less, 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less. The $K_D$ may be at least 0.001 nM, for example at least 0.01 nM or at least 0.1 nM.

Quantification of affinity may be performed using SPR with the antibody in Fab format. A suitable protocol is as follows:

1. Coupling anti-human (or other antibody constant region species-matched) IgG to a biosensor chip (e.g., GLM chip) such as by primary amine coupling;
2. Exposing the anti-human IgG (or other matched species antibody) to a test antibody, e.g., in Fab format, to capture test antibody on the chip;
3. Passing the test antigen over the chip's capture surface at a range of concentrations, e.g., at 5000 nM, 1000 nM, 200 nM, 40 nM, 8 nM and 2 nM, and at 0 nM (i.e., buffer alone); and
4. Determining the affinity of binding of test antibody to test antigen using SPR at 25° C. Buffer may be at pH 7.6, 150 mM NaCl, 0.05% detergent (e.g., P20) and 3 mM EDTA. Buffer may optionally contain 10 mM HEPES. HBS-EP can be used as running buffer. HBS-EP is available from Teknova Inc (California; catalogue number H8022).

Regeneration of the capture surface can be carried out with 10 mM glycine at pH 1.7. This removes the captured antibody and allows the surface to be used for another interaction. The binding data can be fitted to 1:1 model inherent using standard techniques, e.g., using a model inherent to the ProteOn XPR36™ analysis software.

A variety of SPR instruments are known, such as Biacore™, ProteOn XPR36™ (Bio-Rad®), and KinExA® (Sapidyne Instruments, Inc). Worked examples of SPR are found in Example 7.

As described, affinity may be determined by SPR with the antibody in Fab format, with the antigen coupled to the chip surface and the test antibody passed over the chip in Fab format in solution, to determine affinity of the monomeric antibody-antigen interaction. Affinity can be determined at any desired pH, e.g., pH 5.5 or pH 7.6, and any desired temperature e.g., 25° C. or 37° C. As reported in Example 7, antibodies according to the present invention bound human ICOS with an apparent affinity of less than 2 nM, as determined by SPR using the antibody in monovalent (Fab) format.

Other ways to measure binding of an antibody to ICOS include fluorescence activated cell sorting (FACS), e.g., using cells (e.g., CHO cells) with exogenous surface expression of ICOS or activated primary T cells expressing endogenous levels of ICOS. Antibody binding to ICOS-expressing cells as measured by FACS indicates that the antibody is able to bind the extracellular (EC) domain of ICOS.

ICOS Receptor Agonism

The ICOS ligand (ICOSL, also known as B7-H2) is a cell surface expressed molecule that binds to the ICOS receptor [17]. This intercellular ligand-receptor interaction promotes multimerisation of ICOS on the T cell surface, activating the receptor and stimulating downstream signalling in the T cell. In effector T cells, this receptor activation stimulates the effector T cell response.

Anti-ICOS antibodies may act as agonists of ICOS, mimicking and even surpassing this stimulatory effect of the native ICOS ligand on the receptor. Such agonism may result from ability of the antibody to promote multimerisation of ICOS on the T cell. One mechanism for this is where the antibodies form intercellular bridges between ICOS on the T cell surface and receptors on an adjacent cell (e.g., B cell, antigen-presenting cell, or other immune cell), such as Fc receptors. Another mechanism is where antibodies having multiple (e.g., two) antigen-binding sites (e.g., two VH-VL domain pairs) bridge multiple ICOS receptor molecules and so promote multimerisation. A combination of these mechanisms may occur.

Agonism can be tested for in in vitro T cell activation assays, using antibody in soluble form (e.g., in immunoglobulin format or other antibody format comprising two spatially separated antigen-binding sites, e.g., two VH-VL pairs), either including or excluding a cross-linking agent, or using antibody bound to a solid surface to provide a tethered array of antigen-binding sites. Agonism assays may use a human ICOS positive T lymphocyte cell line such as MJ cells (ATCC CRL-8294) as the target T cell for activation in such assays. One or more measures of T cell activation can be determined for a test antibody and compared with a reference molecule or a negative control to determine whether there is a statistically significant ($p<0.05$) difference in T cell activation effected by the test antibody compared with the reference molecule or the control. One suitable measure of T cell activation is production of cytokines, e.g., IFNγ, TNFα or IL-2. The skilled person will include suitable controls as appropriate, standardising assay conditions between test antibody and control. A suitable negative control is an antibody in the same format (e.g., isotype control) that does not bind ICOS, e.g., an antibody specific for an antigen that is not present in the assay system. A significant difference is observed for test antibody relative to a cognate isotype control within the dynamic range of the assay is indicative that the antibody acts as an agonist of the ICOS receptor in that assay.

An agonist antibody may be defined as one which, when tested in a T cell activation assay:

has a significantly lower EC50 for induction of IFNγ production compared with control antibody;

induces significantly higher maximal IFNγ production compared with control antibody;

has a significantly lower EC50 for induction of IFNγ production compared with ICOSL-Fc;

induces significantly higher maximal IFNγ production compared with ICOSL-Fc;

has a significantly lower EC50 for induction of IFNγ production compared with reference antibody C398.4A; and/or induces significantly higher maximal IFNγ production compared with reference antibody C398.4A.

In vitro T cell assays include the bead-bound assay of Example 13, the plate-bound assay of Example 14 and the soluble form assay of Example 15.

A significantly lower or significantly higher value may for example be up to 0.5-fold different, up to 0.75-fold different, up to 2-fold different, up to 3-fold different, up to 4-fold different or up to 5-fold different, compared with the reference or control value.

Thus, in one example, an antibody according to the present invention has a significantly lower, e.g., at least 2-fold lower, EC50 for induction of IFNγ in an MJ cell activation assay using the antibody in bead-bound format, compared with control.

The bead-bound assay uses the antibody (and, for control or reference experiments, the control antibody, reference antibody or ICOSL-Fc) bound to the surface of beads. Magnetic beads may be used, and various kinds are commercially available, e.g., Tosyl-activated DYNABEADS M-450 (DYNAL Inc, 5 Delaware Drive, Lake Success, N.Y. 11042 Prod No. 140.03, 140.04). Beads may be coated as described in Example 13, or generally by dissolving the coating material in carbonate buffer (pH 9.6, 0.2 M) or other method known in the art. Use of beads conveniently allows the quantity of protein bound to the bead surface to be determined with a good degree of accuracy. Standard Fc-protein quantification methods can be used for coupled protein quantification on beads. Any suitable method can be used, with reference to a relevant standard within the dynamic range of the assay. DELFIA is exemplified in Example 13, but ELISA or other methods could be used.

Agonism activity of an antibody can also be measured in primary human T lymphocytes ex vivo. The ability of an antibody to induce expression of IFNγ in such T cells is indicative of ICOS agonism. Described herein are two T cell activation assays using primary cells—see Example 2, T cell activation assay 1 and T cell activation assay 2. Preferably, an antibody will show significant ($p<0.05$) induction of IFNγ at 5 μg/ml compared with control antibody in T cell activation assay 1 and/or T cell activation assay 2. As noted above, an anti-ICOS antibody may stimulate T cell activation to a greater degree than ICOS-L or C398.4 in such an assay. Thus, the antibody may show significantly ($p<0.05$) greater induction of IFNγ at 5 μg/ml compared with the control or reference antibody in T cell activation assay 1 or 2. TNFα or IL-2 induction may be measured as an alternative assay readout.

Agonism of an anti-ICOS antibody may contribute to its ability to change the balance between populations of TReg and TEff cells in vivo, e.g., in a site of pathology such as a tumour microenvironment, in favour of TEff cells. The ability of an antibody to enhance tumour cell killing by activated ICOS-positive effector T cells may be determined, as discussed elsewhere herein.

T Cell Dependent Killing

Effector T cell function can be determined in a biologically relevant context using an in vitro co-culture assay where tumour cells are incubated with relevant immune cells to trigger immune cell-dependent killing, in which the effect of an anti-ICOS antibody on tumour cell killing by TEffs is observed.

The ability of an antibody to enhance tumour cell killing by activated ICOS-positive effector T cells may be determined. An anti-ICOS antibody may stimulate significantly greater ($p<0.05$) tumour cell killing compared with a control antibody. An anti-ICOS antibody may stimulate similar or greater tumour cell killing in such an assay as compared with a reference molecule such as the ICOS ligand or the C398.4 antibody. A similar degree of tumour cell killing can be represented as the assay readout for the test antibody being less than two-fold different from that for the reference molecule.

ICOS Ligand-Receptor Neutralisation Potency

An antibody according to the present invention may be one which inhibits binding of ICOS to its ligand ICOSL.

The degree to which an antibody inhibits binding of the ICOS receptor to its ligand is referred to as its ligand-receptor neutralising potency. Potency is normally expressed as an IC50 value, in pM unless otherwise stated. In ligand-binding studies, IC50 is the concentration that reduces receptor binding by 50% of maximal specific binding level. IC50 may be calculated by plotting % specific receptor binding as a function of the log of the antibody concentration, and using a software program such as Prism (GraphPad) to fit a sigmoidal function to the data to generate IC50 values. Neutralising potency may be determined in an HTRF assay. A detailed working example of an HTRF assay for ligand-receptor neutralising potency is set out in Example 8.

An IC50 value may represent the mean of a plurality of measurements. Thus, for example, IC50 values may be obtained from the results of triplicate experiments, and a mean IC50 value can then be calculated.

An antibody may have an IC50 of 1 mM or less in a ligand-receptor neutralisation assay, e.g., 0.5 mM or less. The IC50 may be, 30 nM or less, 20 nM or less, 10 nM or less, 5 nM or less, 4 nM or less, 3 nM or less or 2 nM or less. The IC50 may be at least 0.1 nM, at least 0.5 nM or at least 1 nM.

Antibodies

As described in more detail in the Examples, we isolated and characterised antibodies of particular interest, designated STIM001, STIM002, STIM002-B, STIM003, STIM004, STIM005, STIM006, STIM007, STIM008 and STIM009. In various aspects of the invention, unless context dictates otherwise, antibodies may be selected from any of these antibodies, or from the sub-set of STIM001, STIM002, STIM003, STIM004 and STIM005. Sequences of each of these antibodies are provided in the appended sequence listing, wherein for each antibody the following sequences are shown: nucleotide sequence encoding VH domain; amino acid sequence of VH domain; VH CDR1 amino acid sequence, VH CDR2 amino acid sequence; VH CDR3 amino acid sequence; nucleotide sequence encoding VL domain; amino acid sequence of VL domain; VL CDR1 amino acid sequence; VL CDR2 amino acid sequence; and VL CDR3 amino acid sequence, respectively. The present invention encompasses anti-ICOS antibodies having the VH and/or VL domain sequences of all antibodies shown in the appended sequence listing and/or in the drawings, as well as antibodies comprising the HCDRs and/or LCDRs of those antibodies, and optionally having the full heavy chain and/or full light chain amino acid sequence.

STIM001 has a heavy chain variable region ($V_H$) amino acid sequence of Seq ID No:366, comprising the CDRH1 amino acid sequence of Seq ID No:363, the CDRH2 amino acid sequence of Seq ID No:364, and the CDRH3 amino acid sequence of Seq ID No:365. The heavy chain nucleic acid sequence of the $V_H$ domain is Seq ID No:367. STIM001 has a light chain variable region ($V_L$) amino acid sequence of Seq ID No:373, comprising the CDRL1 amino acid sequence of Seq ID No:370, the CDRL2 amino acid sequence of Seq ID No:371, and the CDRL3 amino acid sequence of Seq ID No:372. The light chain nucleic acid sequence of the $V_L$ domain is Seq ID No:374. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:368 (heavy chain nucleic acid sequence Seq ID No:369). A full length light chain amino acid sequence is Seq ID No:375 (light chain nucleic acid sequence Seq ID No:376).

STIM002 has a heavy chain variable region ($V_H$) amino acid sequence of Seq ID No:380, comprising the CDRH1 amino acid sequence of Seq ID No:377, the CDRH2 amino acid sequence of Seq ID No:378, and the CDRH3 amino acid sequence of Seq ID No:379. The heavy chain nucleic acid sequence of the $V_H$ domain is Seq ID No:381. STIM002 has a light chain variable region ($V_L$) amino acid sequence of Seq ID No:387, comprising the CDRL1 amino acid sequence of Seq ID No:384, the CDRL2 amino acid sequence of Seq ID No:385, and the CDRL3 amino acid sequence of Seq ID No:386. The light chain nucleic acid sequence of the $V_L$ domain is Seq ID No:388 or Seq ID No:519. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:382 (heavy chain nucleic acid sequence Seq ID No:383). A full length light chain amino acid sequence is Seq ID No:389 (light chain nucleic acid sequence Seq ID No:390 or Seq ID NO:520).

STIM002-B has a heavy chain variable region ($V_H$) amino acid sequence of Seq ID No:394, comprising the CDRH1 amino acid sequence of Seq ID No:391, the CDRH2 amino acid sequence of Seq ID No:392, and the CDRH3 amino acid sequence of Seq ID No:393. The heavy chain nucleic acid sequence of the $V_H$ domain is Seq ID No:395. STIM002-B has a light chain variable region ($V_L$) amino acid sequence of Seq ID No:401, comprising the CDRL1 amino acid sequence of Seq ID No:398, the CDRL2 amino acid sequence of Seq ID No:399, and the CDRL3 amino acid sequence of Seq ID No:400. The light chain nucleic acid sequence of the $V_L$ domain is Seq ID No:402. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:396 (heavy chain nucleic acid sequence Seq ID No:397). A full length light chain amino acid sequence is Seq ID No:403 (light chain nucleic acid sequence Seq ID No:404).

STIM003 has a heavy chain variable region ($V_H$) amino acid sequence of Seq ID No:408, comprising the CDRH1 amino acid sequence of Seq ID No:405, the CDRH2 amino acid sequence of Seq ID No:406, and the CDRH3 amino acid sequence of Seq ID No:407. The heavy chain nucleic acid sequence of the $V_H$ domain is Seq ID No:409 or Seq ID No:521. STIM003 has a light chain variable region ($V_L$) amino acid sequence of Seq ID No:415, comprising the CDRL1 amino acid sequence of Seq ID No:412, the CDRL2 amino acid sequence of Seq ID No:413, and the CDRL3 amino acid sequence of Seq ID No:414. The light chain nucleic acid sequence of the $V_L$ domain is Seq ID No:4416. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:410 (heavy chain nucleic acid sequence Seq ID No:411 or Seq ID No:522). A full length light chain amino acid sequence is Seq ID No:417 (light chain nucleic acid sequence Seq ID No:418).

STIM004 has a heavy chain variable region ($V_H$) amino acid sequence of Seq ID No:422, comprising the CDRH1 amino acid sequence of Seq ID No:419, the CDRH2 amino acid sequence of Seq ID No:420, and the CDRH3 amino acid sequence of Seq ID No:421. The heavy chain nucleic acid sequence of the $V_H$ domain is Seq ID No:423. STIM004 has a light chain variable region ($V_L$) amino acid sequence of Seq ID No:429, comprising the CDRL1 amino acid sequence of Seq ID No:426, the CDRL2 amino acid sequence of Seq ID No:427, and the CDRL3 amino acid sequence of Seq ID No:428. The light chain nucleic acid sequence of the $V_L$ domain is Seq ID No:430 or Seq ID No:431. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:424 (heavy chain nucleic acid sequence Seq ID No:425). A full length light chain amino acid sequence is Seq ID No:432 (light chain nucleic acid sequence Seq ID No:433 or Seq ID no: 434).

STIM005 has a heavy chain variable region ($V_H$) amino acid sequence of Seq ID No:438, comprising the CDRH1 amino acid sequence of Seq ID No:435, the CDRH2 amino acid sequence of Seq ID No:436, and the CDRH3 amino acid sequence of Seq ID No:437. The heavy chain nucleic acid sequence of the $V_H$ domain is Seq ID No:439. STIM005 has a light chain variable region ($V_L$) amino acid sequence of Seq ID No:445, comprising the CDRL1 amino acid sequence of Seq ID No:442, the CDRL2 amino acid sequence of Seq ID No:443, and the CDRL3 amino acid sequence of Seq ID No:444. The light chain nucleic acid sequence of the $V_L$ domain is Seq ID No:446. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:440 (heavy chain nucleic acid sequence Seq ID No:441). A full length light chain amino acid sequence is Seq ID No:447 (light chain nucleic acid sequence Seq ID No:448).

STIM006 has a heavy chain variable region ($V_H$) amino acid sequence of Seq ID No:452, comprising the CDRH1 amino acid sequence of Seq ID No:449, the CDRH2 amino acid sequence of Seq ID No:450, and the CDRH3 amino acid sequence of Seq ID No:451. The heavy chain nucleic acid sequence of the $V_H$ domain is Seq ID No:453. STIM006 has a light chain variable region ($V_L$) amino acid sequence of Seq ID No:459, comprising the CDRL1 amino acid sequence of Seq ID No:456, the CDRL2 amino acid sequence of Seq ID No:457, and the CDRL3 amino acid sequence of Seq ID No:458. The light chain nucleic acid sequence of the $V_L$ domain is Seq ID No:460. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:454 (heavy chain nucleic acid sequence Seq ID No:455). A full length light chain amino acid sequence is Seq ID No:461 (light chain nucleic acid sequence Seq ID No:462).

STIM007 has a heavy chain variable region ($V_H$) amino acid sequence of Seq ID No:466, comprising the CDRH1 amino acid sequence of Seq ID No:463, the CDRH2 amino acid sequence of Seq ID No:464, and the CDRH3 amino acid sequence of Seq ID No:465. The heavy chain nucleic acid sequence of the $V_H$ domain is Seq ID No:467. STIM007 has a light chain variable region ($V_L$) amino acid sequence of Seq ID No:473, comprising the CDRL1 amino acid sequence of Seq ID No:470, the CDRL2 amino acid sequence of Seq ID No:471, and the CDRL3 amino acid sequence of Seq ID No:472. The light chain nucleic acid sequence of the $V_L$ domain is Seq ID No:474. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:468 (heavy chain nucleic acid sequence Seq ID No:469). A full length light chain amino acid sequence is Seq ID No:475 (light chain nucleic acid sequence Seq ID No:476).

STIM008 has a heavy chain variable region ($V_H$) amino acid sequence of Seq ID No:480, comprising the CDRH1 amino acid sequence of Seq ID No:477, the CDRH2 amino acid sequence of Seq ID No:478, and the CDRH3 amino acid sequence of Seq ID No:479. The heavy chain nucleic acid sequence of the $V_H$ domain is Seq ID No:481. STIM008 has a light chain variable region ($V_L$) amino acid sequence of Seq ID No:487, comprising the CDRL1 amino acid sequence of Seq ID No:484, the CDRL2 amino acid sequence of Seq ID No:485, and the CDRL3 amino acid sequence of Seq ID No:486. The light chain nucleic acid sequence of the $V_L$ domain is Seq ID No:488. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:482 (heavy chain nucleic acid sequence Seq ID No:483). A full length light chain amino acid sequence is Seq ID No:489 (light chain nucleic acid sequence Seq ID No:490).

STIM009 has a heavy chain variable region ($V_H$) amino acid sequence of Seq ID No:494, comprising the CDRH1 amino acid sequence of Seq ID No:491, the CDRH2 amino acid sequence of Seq ID No:492, and the CDRH3 amino acid sequence of Seq ID No:493. The heavy chain nucleic acid sequence of the $V_H$ domain is Seq ID No:495. STIM009 has a light chain variable region ($V_L$) amino acid sequence of Seq ID No:501, comprising the CDRL1 amino acid sequence of Seq ID No:498, the CDRL2 amino acid sequence of Seq ID No:499, and the CDRL3 amino acid sequence of Seq ID No:500. The light chain nucleic acid sequence of the $V_L$ domain is Seq ID No:502. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:496 (heavy chain nucleic acid sequence Seq ID No:497). A full length light chain amino acid sequence is Seq ID No:503 (light chain nucleic acid sequence Seq ID No:504).

Antibodies according to the present invention are immunoglobulins or molecules comprising immunoglobulin domains, whether natural or partly or wholly synthetically produced. Antibodies may be IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanised using routine technology. The term antibody covers any polypeptide or protein comprising an antibody antigen-binding site. An antigen-binding site (paratope) is the part of an antibody that binds to and is complementary to the epitope of its target antigen (ICOS).

The term "epitope" refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The antigen binding site is a polypeptide or domain that comprises one or more CDRs of an antibody and is capable of binding the antigen. For example, the polypeptide comprises a CDR3 (e.g., HCDR3). For example the polypeptide comprises CDRs 1 and 2 (e.g., HCDR1 and 2) or CDRs 1-3 of a variable domain of an antibody (e.g., HCDRs1-3).

An antibody antigen-binding site may be provided by one or more antibody variable domains. In an example, the antibody binding site is provided by a single variable domain, e.g., a heavy chain variable domain (VH domain) or a light chain variable domain (VL domain). In another example, the binding site comprises a VH/VL pair or two or more of such pairs. Thus, an antibody antigen-binding site may comprise a VH and a VL.

The antibody may be a whole immunoglobulin, including constant regions, or may be an antibody fragment. An antibody fragment is a portion of an intact antibody, for example comprising the antigen binding and/or variable region of the intact antibody. Examples of antibody fragments include:

(i) a Fab fragment, a monovalent fragment consisting of the VL, VH, CL and CH1 domains; (ii) a F(ab')2 fragment, a bivalent fragment including two Fab fragments linked by a disulfide bridge at the hinge region;
(iii) an Fd fragment consisting of the VH and CH1 domains;
(iv) an Fv fragment consisting of the VL and VH domains of a single arm of an antibody,
(v) a dAb fragment (Ward et al., (1989) Nature 341:544-546; which is incorporated by reference herein in its entirety), which consists of a VH or VL domain; and
(vi) an isolated complementarity determining region (CDR) that retains specific antigen-binding functionality.

Further examples of antibodies are H2 antibodies that comprise a dimer of a heavy chain (5'-VH-(optional hinge)-CH2-CH3-3') and are devoid of a light chain.

Single-chain antibodies (e.g., scFv) are a commonly used fragment. Multispecific antibodies may be formed from antibody fragments. An antibody of the invention may employ any such format, as appropriate.

Optionally, the antibody immunoglobulin domains may be fused or conjugated to additional polypeptide sequences and/or to labels, tags, toxins or other molecules. Antibody immunoglobulin domains may be fused or conjugated to one or more different antigen binding regions, providing a molecule that is able to bind a second antigen in addition to ICOS. An antibody of the present invention may be a multispecific antibody, e.g., a bispecific antibody, comprising (i) an antibody antigen binding site for ICOS and (ii) a further antigen binding site (optionally an antibody antigen binding site, as described herein) which recognises another antigen (e.g., PD-L1).

An antibody normally comprises an antibody VH and/or VL domain. Isolated VH and VL domains of antibodies are also part of the invention. The antibody variable domains are the portions of the light and heavy chains of antibodies that include amino acid sequences of complementarity determining regions (CDRs; ie., CDR1, CDR2, and CDR3), and framework regions (FRs). Thus, within each of the VH and VL domains are CDRs and FRs. A VH domain comprises a set of HCDRs, and a VL domain comprises a set of LCDRs. VH refers to the variable domain of the heavy chain. VL refers to the variable domain of the light chain. Each VH and VL is typically composed of three CDRs and four FRs, arranged from amino-terminus to carboxy-terminus in the following order: FR1, CDR1, FR2, CDR2, FR3, CDR3, FR4. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature. An antibody may comprise an antibody VH domain comprising a VH CDR1, CDR2 and CDR3 and a framework. It may alternatively or also comprise an antibody VL domain comprising a VL CDR1, CDR2 and CDR3 and a framework. Examples of antibody VH and VL domains and CDRs according to the present invention are as listed in the appended sequence listing that forms part of the present disclosure. The CDRs shown in the sequence listing are defined according to the IMGT system [18]. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

An antibody the invention may comprise one or more CDRs as described herein, e.g. a CDR3, and optionally also a CDR1 and CDR2 to form a set of CDRs. The CDR or set of CDRs may be a CDR or set of CDRs of any of STIM001, STIM002, STIM002-B, STIM003, STIM004, STIM005, STIM006, STIM007, STIM008 and STIM009, or may be a variant thereof as described herein.

The invention provides antibodies comprising an HCDR1, HCDR2 and/or HCDR3 of any of antibodies STIM001, STIM002, STIM002-B, STIM003, STIM004, STIM005, STIM006, STIM007, STIM008 and STIM009 and/or an LCDR1, LCDR2 and/or LCDR3 of any of these antibodies, e.g. a set of CDRs. The antibody may comprise a set of VH CDRs of one of these antibodies. Optionally it may also comprise a set of VL CDRs of one of these antibodies, and the VL CDRs may be from the same or a different antibody as the VH CDRs.

A VH domain comprising a disclosed set of HCDRs, and/or a VL domain comprising a disclosed set of LCDRs, are also provided by the invention.

Typically, a VH domain is paired with a VL domain to provide an antibody antigen-binding site, although as discussed further below a VH or VL domain alone may be used to bind antigen. The STIM003 VH domain may be paired with the STIM003 VL domain, so that an antibody antigen-binding site is formed comprising both the STIM003 VH and VL domains. Analogous embodiments are provided for the other VH and VL domains disclosed herein. In other embodiments, the STIM003 VH is paired with a VL domain other than the STIM003 VL. Light-chain promiscuity is well established in the art. Again, analogous embodiments are provided by the invention for the other VH and VL domains disclosed herein.

Thus, the VH of any of antibodies STIM001, STIM002, STIM003, STIM004 and STIM005 may be paired with the VL of any of antibodies STIM001, STIM002, STIM003, STIM004 and STIM005. Further, the VH of any of antibodies STIM001, STIM002, STIM002-B, STIM003, STIM004, STIM005, STIM006, STIM007, STIM008 and STIM009 may be paired with the VL of any of antibodies STIM001, STIM002, STIM002-B, STIM003, STIM004, STIM005, STIM006, STIM007, STIM008 or STIM009.

An antibody may comprise one or more CDRs, e.g. a set of CDRs, within an antibody framework. The framework regions may be of human germline gene segment sequences. Thus, the antibody may be a human antibody having a VH domain comprising a set of HCDRs in a human germline framework. Normally the antibody also has a VL domain comprising a set of LCDRs, e.g. in a human germline framework. An antibody "gene segment", e.g., a VH gene segment, D gene segment, or JH gene segment refers to oligonucleotide having a nucleic acid sequence from which that portion of an antibody is derived, e.g., a VH gene segment is an oligonucleotide comprising a nucleic acid sequence that corresponds to a polypeptide VH domain from FR1 to part of CDR3. Human V, D and J gene segments recombine to generate the VH domain, and human V and J segments recombine to generate the VL domain. The D domain or region refers to the diversity domain or region of an antibody chain. J domain or region refers to the joining domain or region of an antibody chain. Somatic hypermutation may result in an antibody VH or VL domain having framework regions that do not exactly match or align with the corresponding gene segments, but sequence alignment can be used to identify the closest gene segments and thus identify from which particular combination of gene segments a particular VH or VL domain is derived. When aligning antibody sequences with gene segments, the antibody amino acid sequence may be aligned with the amino acid sequence encoded by the gene segment, or the antibody nucleotide sequence may be aligned directly with the nucleotide sequence of the gene segment.

Alignments of STIM antibody VH and VL domain sequences against related antibodies and against human germline sequences are shown in FIG. 35, FIG. 36 and FIG. 37.

An antibody of the invention may be a human antibody or a chimaeric antibody comprising human variable regions and non-human (e.g., mouse) constant regions. The antibody of the invention for example has human variable regions, and optionally also has human constant regions.

Thus, antibodies optionally include constant regions or parts thereof, e.g., human antibody constant regions or parts thereof. For example, a VL domain may be attached at its C-terminal end to antibody light chain kappa or lambda constant domains. Similarly, an antibody VH domain may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4.

Examples of human heavy chain constant regions are shown in Table S1.

Constant regions of antibodies of the invention may alternatively be non-human constant regions. For example, when antibodies are generated in transgenic animals (examples of which are described elsewhere herein), chimaeric antibodies may be produced comprising human variable regions and non-human (host animal) constant regions. Some transgenic animals generate fully human antibodies. Others have been engineered to generate antibodies comprising chimaeric heavy chains and fully human light chains. Where antibodies comprise one or more non-human constant regions, these may be replaced with human constant regions to provide antibodies more suitable for administration to humans as therapeutic compositions, as their immunogenicity is thereby reduced.

Digestion of antibodies with the enzyme papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognised by Fc receptors (FcR) found on certain types of cells. Digestion of antibodies with the enzyme pepsin, results in the a F(ab')2 fragment in which the two arms of the antibody molecule remain linked and comprise two-antigen binding sites. The F(ab')2 fragment has the ability to crosslink antigen.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognise and bind antigen, although at a lower affinity than the entire binding site.

Antibodies disclosed herein may be modified to increase or decrease serum half-life. In one embodiment, one or more of the following mutations: T252L, T254S or T256F are introduced to increase biological half-life of the antibody. Biological half-life can also be increased by altering the heavy chain constant region $CH_1$ domain or CL region to contain a salvage receptor binding epitope taken from two loops of a $CH_2$ domain of an Fc region of an IgG, as described in U.S. Pat. Nos. 5,869,046 and 6,121,022, the modifications described therein are incorporated herein by reference. In another embodiment, the Fc hinge region of an antibody or antigen-binding fragment of the invention is mutated to decrease the biological half-life of the antibody or fragment. One or more amino acid mutations are introduced into the $CH_2$—$CH_3$ domain interface region of the Fc-hinge fragment such that the antibody or fragment has impaired Staphylococcyl protein A (SpA) binding relative to native Fc-hinge domain SpA binding. Other methods of increasing serum half-life are known to those skilled in the art. Thus, in one embodiment, the antibody or fragment is PEGylated. In another embodiment, the antibody or fragment is fused to an albumin-biding domain, e.g. an albumin binding single domain antibody (dAb). In another embodiment, the antibody or fragment is PASylated (i.e. genetic fusion of polypeptide sequences composed of PAS (XL-Protein GmbH) which forms uncharged random coil structures with large hydrodynamic volume). In another embodiment, the antibody or fragment is XTENylated®/rPEGylated (i.e. genetic fusion of non-exact repeat peptide sequence (Amunix, Versartis) to the therapeutic peptide). In another embodiment, the antibody or fragment is ELPylated (i.e. genetic fusion to ELP repeat sequence (PhaseBio)). These various half-life extending fusions are described in more detail in Strohl, BioDrugs (2015) 29:215-239, which fusions, e.g. in Tables 2 and 6, are incorporated herein by reference.

The antibody may have a modified constant region which increases stability. Thus, in one embodiment, the heavy chain constant region comprises a Ser228Pro mutation. In another embodiment, the antibodies and fragments disclosed herein comprise a heavy chain hinge region that has been modified to alter the number of cysteine residues. This modification can be used to facilitate assembly of the light and heavy chains or to increase or decrease the stability of the antibody.

Fc Effector Functions, ADCC, ADCP and CDC

As discussed above, anti-ICOS antibodies can be provided in various isotypes and with different constant regions. Examples of human IgG antibody heavy chain constant region sequences are shown in Table S1. The Fc region of the antibody primarily determines its effector function in terms of Fc binding, antibody-dependent cell-mediated cytotoxicity (ADCC) activity, complement dependent cytotoxicity (CDC) activity and antibody-dependent cell phagocytosis (ADCP) activity. These "cellular effector functions", as distinct from effector T cell function, involve recruitment of cells bearing Fc receptors to the site of the target cells, resulting in killing of the antibody-bound cell. In addition to ADCC and CDC, the ADCP mechanism [19] represents a means of depleting antibody-bound T cells, and thus targeting high ICOS expressing TRegs for deletion.

Cellular effector functions ADCC, ADCP and/or CDC may also be exhibited by antibodies lacking Fc regions. Antibodies may comprise multiple different antigen-binding sites, one directed to ICOS and another directed to a target molecule where engagement of that target molecule induces ADCC, ADCP and/or CDC, e.g., an antibody comprising two scFv regions joined by a linker, where one scFv can engage an effector cell.

An antibody according to the present invention may be one that exhibits ADCC, ADCP and/or CDC. Alternatively, an antibody according to the present invention may lack ADCC, ADCP and/or CDC activity. In either case, an antibody according to the present invention may comprise, or may optionally lack, an Fc region that binds to one or more types of Fc receptor. Use of different antibody formats, and the presence or absence of FcR binding and cellular effector functions, allow the antibody to be tailored for use in particular therapeutic purposes as discussed elsewhere herein.

A suitable antibody format for some therapeutic applications employs a wild-type human IgG1 constant region. A constant region may be an effector-enabled IgG1 constant region, optionally having ADCC and/or CDC and/or ADCP activity. A suitable wild type human IgG1 constant region sequence is SEQ ID NO: 340 (IGHG1*01). Further examples of human IgG1 constant regions are shown in Table S1.

For testing of candidate therapeutic antibodies in mouse models of human disease, an effector positive mouse constant region, such as mouse IgG2a (mIgG2a), may be included instead of an effector positive human constant region.

A constant region may be engineered for enhanced ADCC and/or CDC and/or ADCP.

The potency of Fc-mediated effects may be enhanced by engineering the Fc domain by various established techniques. Such methods increase the affinity for certain Fc-receptors, thus creating potential diverse profiles of activation enhancement. This can achieved by modification of one or several amino acid residues [20]. Human IgG1 constant regions containing specific mutations or altered glycosylation on residue Asn297 (e.g., N297Q, EU index numbering) have been shown to enhance binding to Fc receptors. Example mutations are one or more of the residues selected from 239, 332 and 330 for human IgG1 constant regions (or the equivalent positions in other IgG isotypes). An antibody may thus comprise a human IgG1 constant region having one or more mutations independently selected from N297Q, S239D, 1332E and A330L (EU index numbering). A triple mutation (M252Y/S254T/T256E) may be used to enhance binding to FcRn, and other mutations affecting FcRn binding are discussed in Table 2 of [21], any of which may be employed in the present invention.

Increased affinity for Fc receptors can also be achieved by altering the natural glycosylation profile of the Fc domain by, for example, generating under fucosylated or de-fucosylated variants [22]. Non-fucosylated antibodies harbour a tri-mannosyl core structure of complex-type N-glycans of Fc without fucose residue. These glycoengineered antibodies that lack core fucose residue from the Fc N-glycans may exhibit stronger ADCC than fucosylated equivalents due to enhancement of FcγRIIIa binding capacity. For example, to increase ADCC, residues in the hinge region can be altered to increase binding to Fc-gamma RIII [23]. Thus, an antibody may comprise a human IgG heavy chain constant region that is a variant of a wild-type human IgG heavy chain constant region, wherein the variant human IgG heavy chain constant region binds to human Fcγ receptors selected from the group consisting of FcγRIIB and FcγRIIA with higher affinity than the wild type human IgG heavy chain constant region binds to the human Fcγ receptors. The antibody may comprise a human IgG heavy chain constant region that is a variant of a wild type human IgG heavy chain constant region, wherein the variant human IgG heavy chain constant region binds to human FcγRIIB with higher affinity than the wild type human IgG heavy chain constant region binds to human FcγRIIB. The variant human IgG heavy chain constant region can be a variant human IgG1, a variant human IgG2, or a variant human IgG4 heavy chain constant region. In one embodiment, the variant human IgG heavy chain constant region comprises one or more amino acid mutations selected from G236D, P238D, S239D, S267E, L328F, and L328E (EU index numbering system). In another embodiment, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F (EU index numbering system). The enhancement of CDC may be achieved by amino acid changes that increase affinity for C1q, the first component of the classic complement activation cascade [24]. Another approach is to create a chimeric Fc domain created from human IgG1 and human IgG3 segments that exploit the higher affinity of IgG3 for C1q [25]. Antibodies of the present invention may comprise mutated amino acids at residues 329, 331 and/or 322 to alter the C1q binding and/or reduced or abolished CDC activity. In another embodiment, the antibodies or antibody fragments disclosed herein may contain Fc regions with modifications at residues 231 and 239, whereby the amino acids are replaced to alter the ability of the antibody to fix complement. In one embodiment, the antibody or fragment has a constant region comprising one or more mutations selected from E345K, E430G, R344D and D356R, in particular a double mutation comprising R344D and D356R (EU index numbering system).

WO2008/137915 described anti-ICOS antibodies with modified Fc regions having enhanced effector function. The antibodies were reported to mediate enhanced ADCC activity as compared to the level of ADCC activity mediated by a parent antibody comprising the VH and VK domains and a wild type Fc region. Antibodies according to the present invention may employ such variant Fc regions having effector function as described therein.

ADCC activity of an antibody may be determined in an assay as described herein. ADCC activity of an anti-ICOS antibody may be determined in vitro using an ICOS positive T cell line as described in Example 10. ADCC activity of an anti-PD-L1 antibody may be determined in vitro in an ADCC assay using PD-L1 expressing cells.

For certain applications (such as in the context of vaccination) it may be preferred to use antibodies without Fc effector function. Antibodies may be provided without a constant region, or without an Fc region—examples of such antibody formats are described elsewhere herein. Alternatively, an antibody may have a constant region which is effector null. An antibody may have a heavy chain constant region that does not bind Fcγ receptors, for example the constant region may comprise a Leu235Glu mutation (i.e., where the wild type leucine residue is mutated to a glutamic acid residue). Another optional mutation for a heavy chain constant region is Ser228Pro, which increases stability. A heavy chain constant region may be an IgG4 comprising both the Leu235Glu mutation and the Ser228Pro mutation. This "IgG4-PE" heavy chain constant region is effector null.

An alternative effector null human constant region is a disabled IgG1. A disabled IgG1 heavy chain constant region may contain alanine at position 235 and/or 237 (EU index numbering), e.g., it may be a IgG1*01 sequence comprising the L235A and/or G237A mutations ("LAGA").

A variant human IgG heavy chain constant region may comprise one or more amino acid mutations that reduce the affinity of the IgG for human FcγRIIIA, human FcγRIIA, or human FcγRI. In one embodiment, the FcγRIIB is expressed on a cell selected from the group consisting of macrophages, monocytes, B-cells, dendritic cells, endothelial cells, and activated T-cells. In one embodiment, the variant human IgG heavy chain constant region comprises one or more of the following amino acid mutations G236A, S239D, F243L, T256A, K290A, R292P, S298A, Y300L, V305I, A330L, I332E, E333A, K334A, A339T, and P396L (EU index numbering system). In one embodiment, the variant human IgG heavy chain constant region comprises a set of amino acid mutations selected from the group consisting of: S239D; T256A; K290A; S298A; I332E; E333A; K334A; A339T; S239D and I332E; S239D, A330L, and I332E; S298A, E333A, and K334A; G236A, S239D, and I332E; and F243L, R292P, Y300L, V305I, and P396L (EU index numbering system). In one embodiment, the variant human IgG heavy chain constant region comprises a S239D, A330L, or I332E amino acid mutations (EU index numbering system). In one embodiment, the variant human IgG heavy chain constant region comprises an S239D and I332E amino acid mutations (EU index numbering system). In one embodiment, the variant human IgG heavy chain constant region is a variant human IgG1 heavy chain constant region comprising the S239D and I332E amino acid mutations (EU index numbering system). In one embodiment, the antibody or fragment comprises an afucosylated Fc region. In another embodiment, the antibody or fragment thereof is defucosylated. In another embodiment, the antibody or fragment is under fucosylated.

An antibody may have a heavy chain constant region that binds one or more types of Fc receptor but does not induce cellular effector functions, i.e., does not mediate ADCC, CDC or ADCP activity. Such a constant region may be unable to bind the particular Fc receptor(s) responsible for triggering ADCC, CDC or ADCP activity.

Generating and Modifying Antibodies

Methods for identifying and preparing antibodies are well known. Antibodies may be generated using transgenic mice (eg, the Kymouse™, Velocimouse®, Omnimouse®, Xenomouse®, HuMab Mouse® or MeMo Mouse®), rats (e.g., the Omnirat®), camelids, sharks, rabbits, chickens or other non-human animals immunised with ICOS or a fragment thereof or a synthetic peptide comprising an ICOS sequence motif of interest, followed optionally by humanisation of the constant regions and/or variable regions to produce human or humanised antibodies. In an example, display technologies can be used, such as yeast, phage or ribosome display, as will be apparent to the skilled person. Standard affinity maturation, e.g., using a display technology, can be performed in a further step after isolation of an antibody lead from a transgenic animal, phage display library or other library. Representative examples of suitable technologies are described in US20120093818 (Amgen, Inc), which is incorporated by reference herein in its entirety, eg, the methods set out in paragraphs [0309] to [0346].

Immunisation of an ICOS knock out non-human animal with human ICOS antigen facilitates the generation of antibodies that recognise both human and non-human ICOS. As described herein and illustrated in the Examples, an ICOS knock out mouse can be immunised with cells expressing human ICOS to stimulate production of antibodies to human and mouse ICOS in the mouse, which can be recovered and tested for binding to human ICOS and to mouse ICOS. Cross-reactive antibodies can thus be selected, which may be screened for other desirable properties as described herein. Methods of generating antibodies to an antigen (e.g., a human antigen), through immunisation of animals with the antigen where expression of the endogenous antigen (e.g, endogenous mouse antigen) has been knocked-out in the animal, may be performed in animals capable of generating antibodies comprising human variable domains. The genomes of such animals can be engineered to comprise a human or humanised immunoglobulin locus encoding human variable region gene segments, and optionally an endogenous constant region or a human constant region. Recombination of the human variable region gene segments generates human antibodies, which may have either a non-human or human constant region. Non-human constant regions may subsequently be replaced by human constant regions where the antibody is intended for in vivo use in humans. Such methods and knock-out transgenic animals are described in WO2013/061078.

Generally, a Kymouse™, VELOCIMMUNE® or other mouse or rat (optionally an ICOS knock out mouse or rat, as noted) can be challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimaeric antibodies or the variable domains of the light and heavy chains may be isolated directly from antigen-specific lymphocytes.

Initially, high affinity chimaeric antibodies are isolated having a human variable region and a mouse constant region. The antibodies are characterised and selected for desirable characteristics, including affinity, selectivity, agonism, T-cell dependent killing, neutralising potency, epitope, etc. The mouse constant regions are optionally replaced with a desired human constant region to generate the fully human antibody of the invention, for example wild-type or modified IgG1 or IgG4 (for example, SEQ ID NO: 751, 752, 753 in US2011/0065902 (which is incorporated by reference herein in its entirety). While the constant region selected may vary according to specific use, high affinity antigen-binding and target specificity characteristics reside in the variable region.

Thus, in a further aspect, the present invention provides a transgenic non-human mammal having a genome comprising a human or humanised immunoglobulin locus, wherein the mammal does not express ICOS. The mammal may for instance be a knock-out mouse or rat, or other laboratory animal species. Transgenic mice such as the Kymouse™ contain human heavy and light chain immunoglobulin loci inserted at the corresponding endogenous mouse immunoglobulin loci. A transgenic mammal according to the present invention may be one that contains such targeted insertions, or it may contain human heavy and light chain immunoglobulin loci or immunoglobulin genes that are randomly inserted in its genome, inserted at a locus other than the endogenous Ig locus, or provided on an additional chromosome or chromosomal fragment.

Further aspects of the invention are the use of such non-human mammals for producing antibodies to ICOS, and methods of producing antibodies or antibody heavy and/or light chain variable domains in such mammals.

A method of producing an antibody that binds the extracellular domain of human and non-human ICOS may comprise providing a transgenic non-human mammal having a genome comprising a human or humanised immunoglobulin locus, wherein the mammal does not express ICOS, and (a) immunising the mammal with human ICOS antigen (e.g., with cells expressing human ICOS or with purified recombinant ICOS protein);

(b) isolating antibodies generated by the mammal;

(c) testing the antibodies for ability to bind human ICOS and non-human ICOS; and (d) selecting one or more antibodies that binds both human and non-human ICOS.

Testing for ability to bind human ICOS and non-human ICOS may be done using surface plasmon resonance, HTRF, FACS or any other method described herein. Optionally, binding affinities for human and mouse ICOS are determined. The affinity, or fold-difference in affinity, of binding to human ICOS and mouse ICOS may be determined, and antibodies displaying species cross-reactivity may thus be selected (affinity thresholds and fold-differences that may be used as selection criteria are exemplified elsewhere herein). Neutralising potency, or fold difference in neutralising potency, of the antibody for inhibiting human and mouse ICOS ligand binding to the human and mouse ICOS receptor respectively may also or alternatively be determined as a way to screen for cross-reactive antibodies, e.g., in an HTRF assay. Again, possible thresholds and fold-differences that may be used as selection criteria are exemplified elsewhere herein.

The method may comprise testing the antibodies for ability to bind non-human ICOS from the same species or from a different species as the immunised mammal. Thus, where the transgenic mammal is a mouse (e.g., a Kymouse™), antibodies may be tested for ability to bind mouse ICOS. Where the transgenic mammal is a rat, antibodies may be tested for ability to bind rat ICOS. However, it may be equally useful to determine cross-reactivity of an isolated antibody for non-human ICOS of another species. Thus, antibodies generated in goats may be tested for binding to rat or mouse ICOS. Optionally, binding to goat ICOS may be determined instead or additionally.

In other embodiments, the transgenic non-human mammal may be immunised with non-human ICOS, optionally ICOS of the same mammalian species (e.g., an ICOS knock-out mouse may be immunised with mouse ICOS) instead of human ICOS. Affinity of isolated antibodies for binding to human ICOS and non-human ICOS is then determined in the same way, and antibodies that bind both human and non-human ICOS are selected.

Nucleic acid encoding an antibody heavy chain variable domain and/or an antibody light chain variable domain of a selected antibody may be isolated. Such nucleic acid may encode the full antibody heavy chain and/or light chain, or the variable domain(s) without associated constant region(s). As noted, encoding nucleotide sequences may be obtained directly from antibody-producing cells of a mouse, or B cells may be immortalised or fused to generate hybridomas expressing the antibody, and encoding nucleic acid obtained from such cells. Optionally, nucleic acid encoding the variable domain(s) is then conjugated to a nucleotide sequence encoding a human heavy chain constant region and/or human light chain constant region, to provide nucleic acid encoding a human antibody heavy chain and/or human antibody light chain, e.g., encoding an antibody comprising both the heavy and light chain. As described elsewhere herein, this step is particularly useful where the immunised mammal produces chimaeric antibodies with non-human constant regions, which are preferably replaced with human constant regions to generate an antibody that will be less immunogenic when administered to humans as a medicament. Provision of particular human isotype constant regions is also significant for determining the effector function of the antibody, and a number of suitable heavy chain constant regions are discussed herein.

Other alterations to nucleic acid encoding the antibody heavy and/or light chain variable domain may be performed, such as mutation of residues and generation of variants, as described herein.

The isolated (optionally mutated) nucleic acid may be introduced into host cells, e.g., CHO cells as discussed. Host cells are then cultured under conditions for expression of the antibody, or of the antibody heavy and/or light chain variable domain, in any desired antibody format. Some possible antibody formats are described herein, e.g., whole immunoglobulins, antigen-binding fragments, and other designs.

Variable domain amino acid sequence variants of any of the VH and VL domains or CDRs whose sequences are specifically disclosed herein may be employed in accordance with the present invention, as discussed.

There are many reasons why it may be desirable to create variants, which include optimising the antibody sequence for large-scale manufacturing, facilitating purification, enhancing stability or improving suitability for inclusion in a desired pharmaceutical formulation.

Protein engineering work can be performed at one or more target residues in the antibody sequence, e.g., to substituting one amino acid with an alternative amino acid (optionally, generating variants containing all naturally occurring amino acids at this position, with the possible exception of Cys and Met), and monitoring the impact on function and expression to determine the best substitution. It is in some instances undesirable to substitute a residue with Cys or Met, or to introduce these residues into a sequence, as to do so may generate difficulties in manufacturing—for instance through the formation of new intramolecular or intermolecular cysteine-cysteine bonds. Where a lead candidate has been selected and is being optimised for manufacturing and clinical development, it will generally be desirable to change its antigen-binding properties as little as possible, or at least to retain the affinity and potency of the parent molecule. However, variants may also be generated in order to modulate key antibody characteristics such as affinity, cross-reactivity or neutralising potency.

An antibody may comprise a set of H and/or L CDRs of any of the disclosed antibodies with one or more amino acid mutations within the disclosed set of H and/or L CDRs. The mutation may be an amino acid substitution, deletion or insertion. Thus for example there may be one or more amino acid substitutions within the disclosed set of H and/or L CDRs. For example, there may be up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3. An antibody may comprise the set of HCDRs, LCDRs or a set of 6 (H and L) CDRs shown for any STIM antibody herein or may comprise that set of CDRs with one or two conservative substitutions.

One or more amino acid mutations may optionally be made in framework regions of an antibody VH or VL domain disclosed herein. For example, one or more residues that differ from the corresponding human germline segment sequence may be reverted to germline. Human germline gene segment sequences corresponding to VH and VL domains of example anti-ICOS antibodies are indicated in Table E12-1, Table E12-2 and Table E12-3, and alignments of antibody VH and VL domains to corresponding germline sequences are shown in the drawings.

An antibody may comprise a VH domain that has at least 60, 70, 80, 85, 90, 95, 98 or 99% amino acid sequence identity with a VH domain of any of the antibodies shown in the appended sequence listing, and/or comprising a VL domain that has at least 60, 70, 80, 85, 90, 95, 98 or 99% amino acid sequence identity with a VL domain of any of those antibodies. Algorithms that can be used to calculate % identity of two amino acid sequences include e.g. BLAST, FASTA, or the Smith-Waterman algorithm, e.g. employing default parameters. Particular variants may include one or more amino acid sequence alterations (addition, deletion, substitution and/or insertion of an amino acid residue).

Alterations may be made in one or more framework regions and/or one or more CDRs. Variants are optionally provided by CDR mutagenesis. The alterations normally do not result in loss of function, so an antibody comprising a thus-altered amino acid sequence may retain an ability to bind ICOS. It may retain the same quantitative binding ability as an antibody in which the alteration is not made, e.g. as measured in an assay described herein. The antibody comprising a thus-altered amino acid sequence may have an improved ability to bind ICOS.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring.

The term "variant" as used herein refers to a peptide or nucleic acid that differs from a parent polypeptide or nucleic acid by one or more amino acid or nucleic acid deletions, substitutions or additions, yet retains one or more specific functions or biological activities of the parent molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects use include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties (e.g., acidic, basic, positively or negatively charged, polar or nonpolar, etc.). Conservative amino acid substitutions include replacement of a leucine with an isoleucine or valine, an aspartate with a glutamate, or a threonine with a serine. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

One can select the amino acid that will substitute an existing amino acid based on the location of the existing amino acid, including its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The invention includes methods of producing antibodies containing VH and/or VL domain variants of the antibody VH and/or VL domains shown in the appended sequence listing. Such antibodies may be produced by a method comprising (i) providing, by way of addition, deletion, substitution or insertion of one or more amino acids in the amino acid sequence of a parent antibody VH domain, an antibody VH domain that is an amino acid sequence variant of the parent antibody VH domain, wherein the parent antibody VH domain is the VH domain of any of antibodies STIM001, STIM002, STIM002-B, STIM003, STIM004, STIM005, STIM006, STIM007, STIM008 and STIM009 or a VH domain comprising the heavy chain complementarity determining regions of any of those antibodies, (ii) optionally combining the VH domain thus provided with a VL domain, to provide a VH/VL combination, and (iii) testing the VH domain or VH/VL domain combination thus provided to identify an antibody with one or more desired characteristics.

Desired characteristics include binding to human ICOS, binding to mouse ICOS, and binding to other non-human ICOS such as cynomolgus ICOS. Antibodies with comparable or higher affinity for human and/or mouse ICOS may be identified. Other desired characteristics include increasing effector T cell function indirectly, via depletion of immunosuppressive TRegs, or directly, via ICOS signalling activation on T effector cells. Identifying an antibody with a desired characteristic may comprise identifying an antibody with a functional attribute described herein, such as its affinity, cross-reactivity, specificity, ICOS receptor agonism, neutralising potency and/or promotion of T cell dependent killing, any of which may be determined in assays as described herein.

When VL domains are included in the method, the VL domain may be a VL domain of any of STIM001, STIM002, STIM002-B, STIM003, STIM004, STIM005, STIM006, STIM007, STIM008 or STIM009, or may be a variant provided by way of addition, deletion, substitution or insertion of one or more amino acids in the amino acid sequence of a parent VL domain, wherein the parent VL domain is the VL domain of any of STIM001, STIM002, STIM002-B, STIM003, STIM004, STIM005, STIM006, STIM007, STIM008 and STIM009 or a VL domain comprising the light chain complementarity determining regions of any of those antibodies.

Methods of generating variant antibodies may optionally comprise producing copies of the antibody or VH/VL domain combination. Methods may further comprise expressing the resultant antibody. It is possible to produce nucleotide sequences corresponding to a desired antibody VH and/or VL domain, optionally in one or more expression vectors. Suitable methods of expression, including recombinant expression in host cells, are set out in detail herein.

Encoding Nucleic Acids and Methods of Expression

Isolated nucleic acid may be provided, encoding antibodies according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above. Exemplary nucleotide sequences are included in the sequence listing. Reference to a nucleotide sequence as set out herein encompasses a DNA molecule with the specified sequence, and encompasses a RNA molecule with the specified sequence in which U is substituted for T, unless context requires otherwise.

The present invention also provides a recombinant host cell that comprises one or more nucleic acids encoding the antibody. Methods of producing the encoded antibody may comprise expression from the nucleic acid, e.g., by culturing recombinant host cells containing the nucleic acid. The antibody may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is *E. coli*. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney cells, human embryonic retina cells and many others.

Vectors may contain appropriate regulatory sequences, including promoter sequences, terminator sequences, polyadenylation sequences, enhancer sequences, marker genes and other sequences as appropriate. Nucleic acid encoding an antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using nucleic acid described herein in an expression system in order to express an antibody.

Therapeutic Use

An antibody described herein may be used in a method of treatment of the human or animal body by therapy. The antibodies find use in increasing effector T cell response, which is of benefit for a range of diseases or conditions, including treating cancers or solid tumours and in the context of vaccination. Increased Teff response may be achieved using an antibody that modulates the balance or ratio between Teffs and Tregs in favour of Teff activity.

Anti-ICOS antibodies may be used for depleting regulatory T cells and/or increasing effector T cell response in a patient, and may be administered to a patient to treat a disease or condition amenable to therapy by depleting regulatory T cells and/or increasing effector T cell response.

An antibody of the present invention, or a composition comprising such an antibody molecule or its encoding nucleic acid, may be used or provided for use in any such method. Use of the antibody, or of a composition comprising it or its encoding nucleic acid, for the manufacture of a medicament for use in any such method is also envisaged. The method typically comprises administering the antibody or composition to a mammal. Suitable formulations and methods of administration are described elsewhere herein.

One envisaged therapeutic use of the antibodies is treatment of cancer. The cancer may be a solid tumour, e.g., renal cell cancer (optionally renal cell carcinoma, e.g., clear cell renal cell carcinoma), head and neck cancer, melanoma (optionally malignant melanoma), non-small cell lung cancer (e.g., adenocarcinoma), bladder cancer, ovarian cancer, cervical cancer, gastric cancer, liver cancer, pancreatic cancer, breast cancer, testicular germ cell carcinoma, or the metastases of a solid tumour such as those listed, or it may be a liquid haematological tumour e.g., lymphoma (such as Hodgkin's lymphoma or Non-Hodgkin's lymphoma, e.g., diffuse large B-cell lymphoma, DLBCL) or leukaemia (e.g., acute myeloid leukaemia). An anti-ICOS antibody may enhance tumour clearance in melanoma, head and neck cancer and non-small cell lung cancer and other cancers with a moderate to high mutational load [26]. By enhancing patients' immune response to their neoplastic lesions, immunotherapy using an anti-ICOS antibody offers the prospect of durable cures or long-term remissions, potentially even in the context of late stage disease.

Cancers are a diverse group of diseases, but anti-ICOS antibodies offer the possibility of treating a range of different cancers by exploiting the patient's own immune system, which has the potential to kill any cancer cell through recognition of mutant or overexpressed epitopes that distinguish cancer cells from normal tissue. By modulating the Teff/Treg balance, anti-ICOS antibodies can enable and/or promote immune recognition and killing of cancer cells. While anti-ICOS antibodies are therefore useful therapeutic agents for a wide variety of cancers, there are particular categories of cancers for which anti-ICOS therapy is especially suited and/or where anti-ICOS therapy can be effective when other therapeutic agents are not.

One such group is cancer that is positive for expression of ICOS ligand. Cancer cells may acquire expression of ICOS ligand, as has been described for melanoma [27]. Expression of ICOS ligand may provide the cells with a selective advantage as the surface-expressed ligand binds ICOS on Tregs, promoting the expansion and activation of the Tregs and thereby suppressing the immune response against the cancer. Cancer cells expressing ICOS ligand may depend for their survival on this suppression of the immune system by Tregs, and would thus be vulnerable to treatment with anti-ICOS antibodies that target the Tregs. This applies also to cancers derived from cells that naturally express ICOS ligand. Continued expression of ICOS ligand by these cells again provides a survival advantage through immune suppression. A cancer expressing ICOS ligand may be derived from antigen-presenting cells such as B cells, dendritic cells and monocytes and may be a liquid haematological tumour such as those mentioned herein. Interestingly it has been shown that these types of cancer are also high in ICOS and FOXP3 expression (TCGA data)—see Example 25. Example 20 herein demonstrates efficacy of exemplary anti-ICOS antibodies in treating tumours derived from cancerous B cells (A20 syngeneic cells) that express ICOS ligand.

Accordingly, anti-ICOS antibodies can be used in methods of treating cancers that are positive for expression of ICOS ligand. Further, a cancer to be treated with anti-ICOS antibody according to the present invention may be one that is positive for expression of ICOS and/or FOXP3, and optionally also expresses ICOS ligand.

Patients may undergo testing to determine whether their cancer is positive for expression of the protein of interest (e.g., ICOS ligand, ICOS and/or FOXP3), for example by taking a test sample (e.g., tumour biopsy) from the patient and determining expression of the protein of interest. Patients whose cancer has been characterised as positive for expression of one, two or all such proteins of interest are selected for treatment with anti-ICOS antibody. As discussed elsewhere herein, anti-ICOS antibody may be used as a monotherapy or in combination with one or more other therapeutic agents.

Anti-ICOS antibodies also offer hope to patients whose cancers are refractory to treatment with antibodies or other drugs directed to immune checkpoint molecules such as CTLA-4, PD-1, PD-L1, CD137, GITR or CD73. These immunotherapies are effective against some cancers but in some cases a cancer may not respond, or it may become unresponsive to continued treatment with the antibody. In common with antibodies to immune checkpoint inhibitors, anti-ICOS antibodies modulate the patient's immune system—nevertheless an anti-ICOS antibody may succeed where such other antibodies fail. It is shown herein that animals carrying A20 B cell lymphomas could be treated with anti-ICOS antibodies to reduce growth of the tumour, shrink the tumour and indeed clear the tumour from the body, whereas treatment with an anti-PD-L1 antibody was no better than control. The A20 cell line has also been reported to be resistant to anti-CTLA-4 [28].

Accordingly, anti-ICOS antibodies can be used in methods of treating cancers that are refractory to treatment with one or more immunotherapies, such as (any or all of) an anti-CTLA-4 antibody, anti-PD1 antibody, anti-PD-L1 antibody, anti-CD137 antibody, anti-GITR antibody, or anti-CD73 antibody. A cancer may be characterised as being refractory to treatment with an antibody or other drug if treatment with that antibody or drug does not significantly reduce growth of the cancer, e.g., if a tumour continues to grow or does not reduce in size or if after a response period the tumour re-initiates its growth. Non-response to a therapeutic agent may be determined ex vivo by testing a sample (e.g., tumour biopsy sample) for cancer cell killing or growth inhibition, and/or in the clinical setting by observing (e.g., using an imaging technology, including MRI) that a patient treated with the therapy is not responding to treatment. Patients whose cancer has been characterised as refractory to treatment with such an immunotherapy are selected for treatment with anti-ICOS antibody.

Further, anti-ICOS antibodies may be used to treat B-cell derived cancer that is resistant to treatment with an anti-CD20 antibody. Anti-ICOS antibodies represent a treatment for cancers that fail to respond to, or become resistant to, therapy with anti-CD20 antibodies like rituximab. Anti-ICOS antibody may be used as a second-line (or further, or additional) treatment for such cancers. The anti-CD20 antibody resistant cancer may be a B cell cancer, e.g., B cell lymphoma, such as diffuse large B cell lymphoma. Resistance of a cancer to anti-CD20 may be determined ex vivo by testing a sample (e.g., tumour biopsy sample) for cancer cell killing or growth inhibition by anti-CD20 antibody, and/or in the clinical setting by observing that a patient treated with the anti-CD20 antibody is not responding to treatment. Alternatively, or additionally, the cancer (e.g., a tumour biopsy sample) may be tested to assess expression of CD20, where an absence or low level of CD20 expression indicates loss of sensitivity to anti-CD20 antibody.

Samples obtained from patients may thus be tested to determine surface expression of a protein of interest, for example ICOS ligand, ICOS, FOXP3 and/or a target receptor to which another therapeutic agent (e.g., anti-receptor antibody) is directed. The target receptor may be CD20 (to which anti-CD20 antibody therapy such as rituximab is directed), or another receptor such as PD1, EGFR, HER2 or HER3. Surface expression of ICOS ligand, ICOS, FOXP3 and/or lack or loss of surface expression of the target receptor is an indication that the cancer is susceptible to anti-ICOS antibody therapy. Anti-ICOS antibodies can be provided for administration to a patient whose cancer is characterised by surface expression of ICOS ligand, ICOS, FOXP3 and/or lack or loss of surface expression of a target receptor, optionally where the patient has been previously treated with anti-CTLA4, anti-PD1, anti-PD-L1 or with an antibody to the target receptor and has not responded or has stopped responding to treatment with that antibody, as measured for example by continued or renewed cancer cell growth, e.g., increase in tumour size.

Any suitable method may be employed to determine whether cancer cells test positive for surface expression of a protein such as ICOS ligand, CD20 or other target receptors mentioned herein. A typical method is immunohistochemistry, where a sample of the cells (e.g., a tumour biopsy sample) is contacted with an antibody for the protein of interest, and binding of antibody is detected using a labelled reagent—typically a second antibody that recognises the Fc region of the first antibody and carries a detectable label such as a fluorescent marker. A sample may be declared to test positive where at least 5% of cells are labelled, as visualised by cell staining or other detection of the label. Optionally a higher cut-off such as 10% or 25% may be used. The antibody will generally be used in excess. Reagent antibodies to the molecules of interest are available or may be generated by straightforward methods. To test for ICOS ligand, the antibody MAB1651 is currently available from R&D systems as a mouse IgG that recognises human ICOS ligand. To test for CD20 expression, rituximab may be used. Detection of mRNA levels of the ICOS ligand or target receptor of interest is an alternative technique [27].

A further indication that a tumour will respond to treatment with anti-ICOS antibody is the presence of Tregs in the tumour microenvironment. Activated Tregs are characterised by ICOS-high and Foxp3-high surface expression. The presence of Tregs in a tumour, especially in elevated numbers, provides a further basis on which a patient may be selected for treatment with anti-ICOS antibody. Tregs may be detected in a tumour biopsy sample ex vivo, for example by immunohistochemistry (assaying for co-expression of both Foxp3 and ICOS, using antibodies to the target protein followed by detection of labels, as described above) or by single cell dispersion of the sample for use in FACS with labelled antibodies to ICOS and Foxp3. FACS methods are exemplified in Example 17 and Example 18.

The anti-ICOS antibodies may be used for treating cancers associated with infectious agents, such as virally-induced cancers. In this category are head and neck squamous cell carcinoma, cervical cancer, Merkel cell carcinoma and many others. Viruses associated with cancer include HBV, HCV, HPV (cervical cancer, oropharyngeal cancer), and EBV (Burkitts lymphomas, gastric cancer, Hodgkin's lymphoma, other EBV positive B cell lymphomas, nasopharyngeal carcinoma and post transplant lymphoproliferative disease). The International Agency for Research on Cancer (Monograph 100B) identified the following major cancer sites associated with infectious agents:

Stomach/Gastric: *Heliobacter pylori*

Liver: Hepatitis B virus, hepatitis C virus (HCV), *Opisthorchis viverrini, Clonorchis sinensis*

Cervix uteri: Human papillomavirus (HPV) with or without HIV

Anogenital (penile, vulva, vagina, anus): HPV with or without HIV

Nasopharynx: Epstein-Barr virus (EBV)

Oropharynx: HPV with or without tobacco or alcohol consumption

Kaposi's sarcoma: Human herpes virus type 8 with or without HIV

Non-Hodgkin lymphoma: *H. pylori*, EBV with or without HIV, HCV, human T-cell lymphotropic virus type 1

Hodgkin's lymphoma: EBV with or without HIV

Bladder: *Schistosoma haematobium.*

Antibodies according to the present invention may be used for treating cancer associated with or induced by any of these infectious agents, such as the cancers specified above.

Stimulation of effector T cell response can also contribute to immunity against infectious disease and/or to recovery from infectious disease in a patient. Thus, an anti-ICOS antibody may be used for treating infectious disease by administering the antibody to a patient.

Infectious diseases include those caused by pathogens, e.g., bacterial, fungal, viral or protozoal pathogens, and treatment may be to promote immune response in a patient against the pathogen infection. An example of a bacterial pathogen is tuberculosis. Examples of viral pathogens are hepatitis B and HIV. Examples of protozoal pathogens are *Plasmodium* species, which cause malaria, such as *P. falciparum.*

The antibody may be used for treating infections, e.g., infection by any pathogen mentioned herein. Infection may be persistent or chronic infection. Infection may be localised or systemic. Extended contact between a pathogen and the immune system may lead to exhaustion of the immune system or development of tolerance (manifested for example through increased levels of Tregs, and tipping of the Treg:Teff balance in favour of Tregs) and/or to immune evasion by the pathogen, through evolution and modification of displayed pathogen antigens. These features reflect similar processes that are believed to occur in cancer. Anti-ICOS antibodies present a therapeutic approach to treating infection by a pathogen, e.g., chronic infection, through modulation of the Treg:Teff ratio in favour of Teff and/or other effects described herein.

Treatment may be of patients who have been diagnosed as having an infectious disease or an infection. Alternatively, treatment may be preventative, and administered to a patient to guard against contracting a disease, e.g., as a vaccine, as described elsewhere herein.

It has also been proposed that an immune response, particularly an IFNγ-dependent systemic immune response, could be beneficial for treatment of Alzheimer's disease and other CNS pathologies that share a neuroinflammatory component as part [29]. WO2015/136541 proposed treatment of Alzheimer's disease using an anti-PD-1 antibody. Anti-ICOS antibodies may be used in the treatment of Alzheimer's disease or other neurodegenerative diseases, optionally in combination with one or more other immunomodulators (e.g., antibody to PD-1).

Combination Therapy

Treatment with an immunomodulatory antibody such as anti-CTLA4, anti-PD1 or anti-PDL1, especially one with Fc effector function, may create an environment in which further depletion of ICOS highly expressing immune-suppressive cells is beneficial. It may be advantageous to combine an anti-ICOS antibody with such an immunomodulator to enhance its therapeutic effects.

A patient who has been treated with an immunomodulatory antibody (e.g., anti-PDL-1, anti-PD-1, anti-CTLA-4) may particularly benefit from treatment with an anti-ICOS antibody. One reason for this is that an immunomodulatory antibody may increase the number of ICOS-positive Tregs (e.g., intratumoural Tregs) in the patient. This effect is also observed with certain other therapeutic agents, such as recombinant IL-2. Anti-ICOS antibody may reduce and/or reverse a surge or rise in ICOS+ Tregs (e.g., intratumoural Tregs) resulting from treatment of the patient with another therapeutic agent. A patient selected for treatment with an anti-ICOS antibody may thus be one who has already received treatment with a first therapeutic agent, the first therapeutic agent being an antibody (e.g., immunomodulator antibody) or other agent (e.g., IL-2) that increases the number of ICOS+ Tregs in the patient.

Immunomodulators with which an anti-ICOS antibody may be combined include antibodies to any of: PDL1 (e.g., avelumab), PD-1 (e.g., pembrolizumab or nivolumab) or CTLA-4 (e.g., ipilimumab or tremelimumab). An anti-ICOS antibody may be combined with pidilizumab. In other embodiments, an anti-ICOS antibody is not administered in combination with anti-CTLA-4 antibody, and/or optionally is administered in combination with a therapeutic antibody that is not an anti-CTLA-4 antibody.

For example, an anti-ICOS antibody may be used in combination therapy with an anti-PDL1 antibody. Preferably, the anti-ICOS antibody is one that mediates ADCC, ADCP and/or CDC. Preferably, the anti-PDL1 antibody is one that mediates ADCC, ADCP and/or CDC. An example of such combination therapy is administration of an anti-ICOS antibody with an anti-PDL1 antibody wherein both antibodies have effector positive constant regions. Thus, the anti-ICOS antibody and the anti-PDL1 antibody may both be able to mediate ADCC, CDC and/or ADCP. Fc effector function and selection of constant regions is described in detail elsewhere herein, but as one example an anti-ICOS human IgG1 may be combined with an anti-PD-L1 human IgG1. The anti-ICOS antibody and/or the anti-PD-L1 antibody may comprise a wild type human IgG1 constant region. Alternatively, the effector positive constant region of an antibody may be one that is engineered for enhanced effector function, e.g., enhanced CDC, ADCC and/or ADCP. Example antibody constant regions, including wild type human IgG1 sequences and mutations that alter effector function, are discussed in detail elsewhere herein.

Anti-PDL1 antibodies with which an anti-ICOS antibody may be combined include:

- Anti-PDL1 antibody that inhibits binding of PD-1 to PDL1 and/or inhibits PDL1, optionally as effector positive human IgG1;
- Anti-PD-1 antibody that inhibits binding of PD-1 to PDL1 and/or PDL2;
- Avelumab, a human IgG1 antibody which inhibits PD-1 binding to PDL-1. See WO2013/079174;
- Durvalumab (or "MED14736"), a variant human IgG1 antibody having mutations L234A, L235A and 331. See WO2011/066389;
- Atezolizumab, a variant human IgG1 antibody having mutations N297A, D356E and L358M. See US2010/0203056;
- BMS-936559, a human IgG4 antibody comprising mutation S228P. See WO2007/005874.

Numerous further examples of anti-PD-L1 antibodies are disclosed herein and others are known in the art. Characterisation data for many of the anti-PD-L1 antibodies mentioned here has been published in U.S. Pat. Nos. 9,567,399 and 9,617,338, both incorporated by reference herein. Example anti-PD-L1 antibodies have VH and/or VL domains comprising the HCDRs and/or LCDRs of any of 1D05, 84G09, 1D05 HC mutant 1, 1D05 HC mutant 2, 1D05 HC mutant 3, 1D05 HC mutant 4, 1D05 LC mutant 1, 1D05 LC mutant 2, 1D05 LC mutant 3, 411B08, 411C04, 411D07, 385F01, 386H03, 389A03, 413D08, 413G05, 413F09, 414B06 or 416E01 as set out in U.S. Pat. No. 9,567,399 or 9,617,338. The antibody may comprise the VH and VL domain of any of these antibodies, and may optionally comprise a heavy and/or light chain having the heavy and/or light chain amino acid sequence of any of these antibodies. VH and VL domains of these anti-PD-L1 antibodies are further described elsewhere herein.

Further example anti-PD-L1 antibodies have VH and/or VL domains comprising the HCDRs and/or LCDRs of KN-035, CA-170, FAZ-053, M7824, ABBV-368, LY-3300054, GNS-1480, YW243.55.S70, REGN3504, or of an anti-PD-L1 antibody disclosed in any of WO2017/034916, WO2017/020291, WO2017/020858, WO2017/020801, WO2016/111645, WO2016/197367, WO2016/061142, WO2016/149201, WO2016/000619, WO2016/160792, WO2016/022630, WO2016/007235, WO2015/179654, WO2015/173267, WO2015/181342, WO2015/109124, WO2015/112805, WO2015/061668, WO2014/159562, WO2014/165082, WO2014/100079, WO2014/055897, WO2013/181634, WO2013/173223, WO2013/079174, WO2012/145493, WO2011/066389, WO2010/077634, WO2010/036959, WO2010/089411 and WO2007/005874. The antibody may comprise the VH and VL domain of any of these antibodies, and may optionally comprise a heavy and/or light chain having the heavy and/or light chain amino acid sequence of any of these antibodies. The anti-ICOS antibody which is used in combination therapy with anti-PD-L1 may be an antibody of the present invention as disclosed herein. Alternatively, the anti-ICOS antibody may comprise the CDRs of, or a VH and/or VL domain of, an anti-ICOS antibody disclosed in any of the following publications:

WO2016154177, US2016304610—for example any of antibodies 7F12, 37A10, 35A9, 36E10, 16G10, 37A10S713, 37A10S714, 37A10S715, 37A10S716, 37A10S717, 37A10S718, 16G10S71, 16G10S72, 16G10S73, 16G10S83, 35A9S79, 35A9S710, or 35A9S89;

WO16120789, US2016215059—for example the antibody known as 422.2 and/or H2L5;

WO14033327, EP2892928, US2015239978—for example the antibody known as 314-8 and/or produced from hybridoma CNCM I-4180;

WO12131004, EP2691419, U.S. Pat. No. 9,376,493, US20160264666—example the antibody Icos145-1 and/or antibody produced by hybridoma CNCM I-4179;

WO10056804—for example the antibody JMAb 136 or "136";

WO9915553, EP1017723B1, U.S. Pat. Nos. 7,259,247, 7,132,099, 7,125,551, 7,306,800, 7,722,872, WO05103086, EP1740617, U.S. Pat. Nos. 8,318,905, 8,916,155—for example the antibody MIC-944 or 9F3;

WO983821, U.S. Pat. No. 7,932,358B2, US2002156242, EP0984023, EP1502920, U.S. Pat. Nos. 7,030,225, 7,045, 615, 7,279,560, 7,226,909, 7,196,175, 7,932,358, 8,389,690, WO02070010, EP1286668, EP1374901, U.S. Pat. Nos. 7,438,905, 7,438,905, WO0187981, EP1158004, U.S. Pat. Nos. 6,803,039, 7,166,283, 7,988,965, WO0115732, EP1125585, U.S. Pat. Nos. 7,465,445, 7,998,478—for example any JMAb antibody, e.g., any of JMAb-124, JMAb-126, JMAb-127, JMAb-128, JMAb-135, JMAb-136, JMAb-137, JMAb-138, JMAb-139, JMAb-140, JMAb-141, e.g., JMAb136;

WO2014/089113—for example antibody 17G9;

WO12174338;

US2016145344;

WO11020024, EP2464661, US2016002336, US2016024211, U.S. Pat. No. 8,840,889;

U.S. Pat. No. 8,497,244.

The anti-ICOS antibody optionally comprises the CDRs of 37A10S713 as disclosed in WO2016154177. It may comprise the VH and VL domains of 37A10S713, and may optionally have the antibody heavy and light chains of 37A10S713.

Combination of an anti-ICOS antibody with an immunomodulator may provide an increased therapeutic effect compared with monotherapy, and may allow therapeutic benefit to be achieved with a lower dose of the immunomodulator(s). Thus, for example, an antibody (e.g., anti-PD-L1 antibody, optionally ipilimumab) that is used in combination with anti-ICOS antibody may be dosed at 3 mg/kg rather than a more usual dose of 10 mg/kg. The administration regimen of the anti-PD-L1 or other antibody may involve intravenous administration over a 90 minute period every 3 weeks for a total of 4 doses.

An anti-ICOS antibody may be used to increase the sensitivity of a tumour to treatment with an anti-PD-L1 antibody, which may be recognised as a reduction in the dose at which the anti-PD-L1 antibody exerts a therapeutic benefit. Thus, anti-ICOS antibody may be administered to a patient to reduce the dose of anti-PD-L1 antibody effective to treat cancer or a tumour in the patient. Administration of anti-ICOS antibody may reduce the recommended or required dosage of anti-PD-L1 antibody administration to that patient to, for example, 75%, 50%, 25%, 20%, 10% or less, compared with the dosage when anti-PD-L1 antibody is administered without anti-ICOS. The patient may be treated by administration of anti-ICOS antibody and anti-PD-L1 antibody in a combination therapy as described herein.

The benefit of combining anti-PD-L1 with anti-ICOS may extend to a reduction in dosage of each agent when compared with its use as a monotherapy. Anti-PD-L1 antibody may be used to reduce the dose at which anti-ICOS antibody exerts a therapeutic benefit, and thus may be administered to a patient to reduce the dose of anti-ICOS antibody effective to treat cancer or a tumour in the patient. Thus, an anti-PD-L1 antibody may reduce the recommended or required dosage of anti-ICOS antibody administration to that patient to, for example, 75%, 50%, 25%, 20%, 10% or less, compared with the dosage when anti-ICOS antibody is administered without anti-PD-L1. The patient may be treated by administration of anti-ICOS antibody and anti-PD-L1 antibody in a combination therapy as described herein.

As discussed in Example 22 herein, treatment with anti-PD-L1 antibody, especially antibody with effector positive Fc, appears not to increase the expression of ICOS on Teff cells. This is advantageous when administering such antibodies in combination with effector positive anti-ICOS antibodies, where an increase in ICOS expression on Teffs would undesirably render these cells more sensitive to depletion by the anti-ICOS antibody. In a combination with anti-PD-L1, anti-ICOS therapy may thus exploit a differential expression of ICOS on Teffs compared with Tregs, preferentially targeting the ICOS-high Tregs for depletion. This in turn relieves the suppression of TEffs and has a net effect of promoting the effector T cell response in a patient. The effect of targeting immune checkpoint molecules on expression of ICOS on T cells has also been studied previously—see Figure S6C in ref. [30] (supplementary materials), where treatment with CTLA-4 antibody and/or anti-PD-1 antibody was reported to increase the percentage of CD4+ Tregs expressing ICOS. The effect of a therapeutic agent on ICOS expression in Tregs and Teffs may be a factor in selection of appropriate agents for use in combination with anti-ICOS antibodies, noting that effect of the anti-ICOS antibody may be enhanced under conditions where there is high differential expression of ICOS on Tregs versus Teffs.

As described herein, a single dose of anti-ICOS antibody may be sufficient to provide therapeutic effect, especially in combination with other therapeutic agents such as anti-PD-L1 antibody. In tumour therapy, the underlying rationale for this single dose benefit may be that the anti-ICOS antibody mediates its effect, at least in part, by resetting or altering the microenvironment of the tumour sufficiently to render the tumour more sensitive to immune attack and/or to the effects of other immunomodulators such as those mentioned. Tumour microenviroment resetting is triggered through for example depletion of ICOS positive tumour infiltrating T-regs. So, for example, a patient may be treated with a single dose of an anti-ICOS antibody followed by one or multiple doses of anti-PD-L1 antibody. Over a period of treatment, for example six months or a year, the anti-ICOS antibody may be administered in a single dose while other agents, e.g., anti-PD-L1 antibody, are optionally administered multiple times over that treatment period, preferably with at least one such dose being administered subsequent to treatment with the anti-ICOS antibody.

Further examples of combination therapy include combination of anti-ICOS antibody with:

an antagonist of an adenosine A2A receptor (“A2AR inhibitor”);

a CD137 agonist (e.g., agonist antibody);

an antagonist of the enzyme indoleamine-2,3 dioxygenase, which catalyses the breakdown of tryptophan (“IDO inhibitor”). IDO is an immune checkpoint, activated in dendritic cells and macrophages, which contributes to immune suppression/tolerance.

Anti-ICOS antibodies may be used in combination therapy with IL-2 (e.g., recombinant IL-2 such as aldesleukin). The IL-2 may be administered at high dose (HD). Typical HD IL-2 therapy involves bolus infusion of over 500,000 IU/kg, e.g., bolus infusions of 600,000 or 720,000 IU/kg, per cycle of therapy, where 10-15 such bolus infusions are given at intervals of between 5-10 hours, e.g., up to 15 bolus infusions every 8 hours, and repeating the therapy cycle approximately every 14 to 21 days for up to 6 to 8 cycles. HD IL-2 therapy has been successful in treating tumours, especially melanoma (e.g., metastatic melanoma)

and renal cell carcinoma, but its use is limited to the high toxicity of IL-2 which can cause severe adverse effects.

Treatment with high dose IL-2 has been shown to increase the population of ICOS-positive Tregs in cancer patients [31]. This increase in ICOS+ TRegs following the first cycle of HD IL-2 therapy was reported to correlate with worse clinical outcome—the higher the number of ICOS+ Tregs, the worse the prognosis. An IL-2 variant F42K has been proposed as an alternative therapy to avoid this undesirable increase in ICOS+ Treg cells [32]. However, another approach would be to exploit the increase in ICOS+ T regs by using an antibody in accordance with the present invention as a second-line therapeutic agent.

It may be beneficial to combine IL-2 therapy with anti-ICOS antibodies, capitalising on the ability of anti-ICOS antibodies to target TRegs that highly express ICOS, inhibiting these cells and improving the prognosis for patients undergoing IL-2 therapy. Concomitant administration of IL-2 and anti-ICOS antibody may increase the response rate while avoiding or reducing adverse events in the treated patient population. The combination may permit IL-2 to be used at lower dose compared with IL-2 monotherapy, reducing the risk or level of adverse events arising from the IL-2 therapy, while retaining or enhancing clinical benefit (e.g., reduction of tumour growth, clearance of solid tumour and/or reduction of metastasis). In this way, addition of anti-ICOS can improve treatment of patients who are receiving IL-2, whether high-dose (HD) or low-dose (LD) IL-2.

Accordingly, one aspect of the invention provides a method of treating a patient by administering an anti-ICOS antibody to the patient, wherein the patient is also treated with IL-2, e.g., HD IL-2. Another aspect of the invention is an anti-ICOS antibody for use in treating a patient, wherein the patient is also treated with IL-2, e.g., HD IL-2. The anti-ICOS antibody may be used as a second-line therapy. Thus, the patient may be one who has been treated with IL-2, e.g., having received at least one cycle of HD IL-2 therapy, and who has an increased level of ICOS+ Tregs. Assays may be performed on samples of cancer cells, e.g., tumour biopsy samples, using immunohistochemistry or FACS as described elsewhere herein to detect cells positive for ICOS, Foxp3, ICOSL and optionally one or more further markers of interest. Methods may comprise determining that the patient has an increased level of ICOS+ Tregs (e.g., in peripheral blood, or in a tumour biopsy) following IL-2 treatment, where an increased level is indicative that the patient would benefit from treatment with the anti-ICOS antibody. The increase in Tregs may be relative to control (untreated) individuals or to the patient prior to IL-2 therapy. Such patients with elevated Tregs represent a group who may not benefit from continued IL-2 treatment alone, but for whom a combination of anti-ICOS antibody and IL-2 therapy, or treatment with anti-ICOS antibody alone, offers therapeutic benefit. Thus, following a positive determination that the patient has an increased level of ICOS+ Tregs, anti-ICOS antibody and/or further IL-2 therapy may be administered. Treatment with the anti-ICOS antibody may selectively target and deplete the ICOS+ Tregs relative to other T cell populations in such patients. This provides a therapeutic effect by relieving the immunosuppression mediated by these cells and thereby enhancing activity of Teffs against the target cells, e.g., tumour cells or infected cells.

Combination therapy with anti-ICOS antibodies and IL-2 may be used for any therapeutic indication described herein, and particularly for treating a tumour, e.g., melanoma such as metastatic melanoma, or renal cell carcinoma. Thus, in one example, the patient treated with an anti-ICOS antibody is one who presents with metastatic melanoma and has been treated with IL-2, e.g., HD IL-2 therapy or LD IL-2 therapy.

In general, where an anti-ICOS antibody is administered to a patient who has received treatment with a first therapeutic agent (e.g., immunomodulator antibody) or other agent (e.g., IL-2), the anti-ICOS antibody may be administered after a minimum period of, for example, 24 hours, 48 hours, 72 hours, 1 week or 2 weeks following administration of the first therapeutic agent. The anti-ICOS antibody may be administered within 2, 3, 4 or 5 weeks after administration of the first therapeutic agent. This does not exclude additional administrations of either agent at any time, although it may be desirable to minimise the number of treatments administered, for ease of compliance for patients and to reduce costs. Rather, the relative timing of the administrations will be selected to optimise their combined effect, the first therapeutic agent creating an immunological environment (e.g., elevated ICOS+ Tregs, or antigen release as discussed below) in which the effect of the anti-ICOS antibody is especially advantageous. Thus, sequential administration of the first therapeutic agent and then the anti-ICOS antibody may allow time for the first agent to act, creating in vivo conditions in which the anti-ICOS antibody can exhibit its enhanced effect. Various administration regimens, including simultaneous or sequential combination treatments, are described herein and can be utilised as appropriate. Where the first therapeutic agent is one that increases the number of ICOS+ Tregs in the patient, the treatment regimen for the patient may comprise determining that the patient has an increased number of ICOS+ Tregs, and then administering the anti-ICOS antibody.

As noted, use of anti-ICOS antibodies in combination therapy may provide advantages of reducing the effective dose of the therapeutic agents and/or countering adverse effects of therapeutic agents that increase ICOS+ Tregs in patients. Yet further therapeutic benefits may be achieved through selecting a first therapeutic agent that causes release of antigens from target cells through "immunological cell death", and administering the first therapeutic agent in combination with an anti-ICOS antibody. As noted, administration of the anti-ICOS antibody may sequentially follow administration of the first therapeutic agent, administration of the two agents being separated by a certain time window as discussed above.

Immunological cell death is a recognised mode of cell death, contrasting with apoptosis. It is characterised by release of ATP and HMGB1 from the cell and exposure of calreticulin on the plasma membrane [33, 34].

Immunological cell death in a target tissue or in target cells promotes engulfment of the cell by an antigen-presenting cell, resulting in display of antigens from the target cell, which in turn induces antigen-specific Teff cells. Anti-ICOS antibody may increase the magnitude and/or duration of the Teff response by acting as an agonist of ICOS on the Teff cells. In addition, where the anti-ICOS antibody is Fc effector function enabled (e.g., a human IgG1 antibody), the anti-ICOS antibody may cause depletion of antigen-specific Tregs. Thus, through a combination of either or both of these effects, the balance between Teff and Treg cells is modulated in favour of enhancing Teff activity. Combination of an anti-ICOS antibody with a treatment that induces immunological cell death in a target tissue or cell type, such as in a tumour or in cancer cells, thereby promotes an immune response in the patient against the target tissue or cells, representing a form of vaccination in which the vaccine antigen is generated in vivo.

Accordingly, one aspect of the invention is a method of treating cancer in a patient by in vivo vaccination of the patient against their cancer cells. Another aspect of the invention is an anti-ICOS antibody for use in such a method. Anti-ICOS antibodies may be used in a method comprising:

treating the patient with a therapy that causes immunological cell death of the cancer cells, resulting in presentation of antigen to antigen-specific effector T cells, and administering an anti-ICOS antibody to the patient, wherein the anti-ICOS antibody enhances the antigen-specific effector T cell response against the cancer cells.

Treatments that induce immunological cell death include radiation (e.g., ionising irradiation of cells using UVC light or γ rays), chemotherapeutic agents (e.g., oxaliplatin, anthracyclines such as doxorubicin, idarubicin or mitoxantrone, BK channel agonists such as phloretin or pimaric acid, bortezomib, cardiac glycosides, cyclophosphamide, GADD34/PP1 inhibitors with mitomycin, PDT with hypericin, polyinosinic-polycytidylic acid, 5-fluorouracil, gemcitabine, gefitnib, erlotinib, or thapsigargin with cisplatin) and antibodies to tumour-associated antigens. The tumour-associated antigen can be any antigen that is over-expressed by tumour cells relative to non-tumour cells of the same tissue, e.g., HER2, CD20, EGFR. Suitable antibodies include herceptin (anti-HER2), rituximab (anti-CD20), or cetuximab (anti-EGFR).

Thus, it is advantageous to combine an anti-ICOS antibody with one or more such treatments. Optionally, the anti-ICOS antibody is adminstered to a patient who has already received such treatment. The anti-ICOS antibody may be administered after a period of, for example, 24 hours, 48 hours, 72 hours, 1 week or 2 weeks following the treatment that induces immunological cell death, e.g., between 24 to 72 hours after the treatment. The anti-ICOS antibody may be administered within 2, 3, 4 or 5 weeks after the treatment. Other regimens for combination therapy are discussed elsewhere herein.

While "in vivo vaccination" has been described above, it is also possible to treat tumour cells to induce immunological cell death ex vivo, after which the cells may be reintroduced to the patient. Rather than administering the agent or treatment that induces immunological cell death directly to the patient, the treated tumour cells are administered to the patient. Treatment of the patient may be in accordance with administration regimens described above.

As already noted, a single dose of an anti-ICOS antibody may be sufficient to provide therapeutic benefit. Thus, in the methods of treatment described herein, the anti-ICOS antibody is optionally administered as a single dose. A single dose of anti-ICOS antibody may deplete Tregs in a patient, with consequent beneficial effects in diseases such as cancer. It has previously been reported that transient ablation of Tregs has anti-tumour effects, including reducing tumour progression, treating established tumours and metastases and extending survival, and that it can enhance the therapeutic effect of tumour irradiation [35]. Administration of a single dose of anti-ICOS may provide such Treg depletion, and may be used to enhance the effects of other therapeutic approaches used in combination, such as radiotherapy.

Antibodies to PD-L1

An antibody to PD-L1 for use in combination with an anti-ICOS antibody, whether as a separate therapeutic agent or in a multispecific antibody as described herein, may comprise the antigen-binding site of any anti-PD-L1 antibody. Numerous examples of anti-PD-L1 antibodies are disclosed herein and others are known in the art. Characterisation data for many of the anti-PD-L1 antibodies mentioned here has been published in U.S. Pat. Nos. 9,567,399 and 9,617,338, both incorporated by reference herein.

1D05 has a heavy chain variable region ($V_H$) amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No: 526, Seq ID No:528, Seq ID No: 530, Seq ID No: 532 or Seq ID No: 534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36). A full length light chain amino acid sequence is Seq ID No:45 (light chain nucleic acid sequence Seq ID No:46).

84G09 has a heavy chain variable ($V_H$) region amino acid sequence of Seq ID No:13, comprising the CDRH1 amino acid sequence of Seq ID No:7 (IMGT) or Seq ID No:10 (Kabat), the CDRH2 amino acid sequence of Seq ID No:8 (IMGT) or Seq ID No:11 (Kabat), and the CDRH3 amino acid sequence of Seq ID No:9 (IMGT) or Seq ID No:12 (Kabat). The heavy chain nucleic acid sequence of the $V_H$ domain is Seq ID No:14. 84G09 has a light chain variable region ($V_L$) amino acid sequence of Seq ID No:23, comprising the CDRL1 amino acid sequence of Seq ID No:17 (IMGT) or Seq ID No:20 (Kabat), the CDRL2 amino acid sequence of Seq ID No:18 (IMGT) or Seq ID No:21 (Kabat), and the CDRL3 amino acid sequence of Seq ID No:19 (IMGT) or Seq ID No:22 (Kabat). The light chain nucleic acid sequence of the $V_L$ domain is Seq ID No:24. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:15 (heavy chain nucleic acid sequence Seq ID No:16). A full length light chain amino acid sequence is Seq ID No:25 (light chain nucleic acid sequence Seq ID No:26).

1D05 HC mutant 1 has a heavy chain variable ($V_H$) region amino acid sequence of Seq ID No:47, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 1 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 2 has a heavy chain variable ($V_H$) region amino acid sequence of Seq ID No:48, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 2 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 3 has a heavy chain variable ($V_H$) region amino acid sequence of Seq ID No:49, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 3 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 HC mutant 4 has a heavy chain variable ($V_H$) region amino acid sequence of Seq ID No:342, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). 1D05 HC mutant 4 has a light chain variable region ($V_L$) amino acid sequence of Seq ID No:43, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length light chain amino acid sequence is Seq ID No:45 (light chain nucleic acid sequence Seq ID No:46).

1D05 LC mutant 1 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 1 has a light chain variable region ($V_L$) amino acid sequence of Seq ID No:50, comprising the CDRL1 amino acid sequence of Seq ID No:37 (IMGT) or Seq ID No:40 (Kabat), and the CDRL3 amino acid sequence of Seq ID No:39 (IMGT) or Seq ID No:42 (Kabat). The CDRL2 sequence of 1D05 LC Mutant 1 is as defined by the Kabat or IMGT systems from the $V_L$ sequence of Seq ID No:50. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36).

1D05 LC mutant 2 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 2 has a light chain variable region ($V_L$) amino acid sequence of Seq ID No:51, comprising the CDRL1 amino acid sequence of Seq ID No:37 (IMGT) or Seq ID No:40 (Kabat), the CDRL2 amino acid sequence of Seq ID No:38 (IMGT) or Seq ID No:41 (Kabat), and the CDRL3 amino acid sequence of Seq ID No:39 (IMGT) or Seq ID No:42 (Kabat). The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36).

1D05 LC mutant 3 has a heavy chain variable ($V_H$) region amino acid sequence of Seq ID No:33, comprising the CDRH1 amino acid sequence of Seq ID No:27 (IMGT) or Seq ID No:30 (Kabat), the CDRH2 amino acid sequence of Seq ID No:28 (IMGT) or Seq ID No:31 (Kabat), and the CDRH3 amino acid sequence of Seq ID No:29 (IMGT) or Seq ID No:32 (Kabat). The heavy chain nucleic acid sequence of the $V_H$ domain is Seq ID No:34. 1D05 LC mutant 3 has a light chain variable region ($V_L$) amino acid sequence of Seq ID No:298, comprising the CDRL1 amino acid sequence of Seq ID No:37 (IMGT) or Seq ID No:40 (Kabat), and the CDRL3 amino acid sequence of Seq ID No:39 (IMGT) or Seq ID No:42 (Kabat). The CDRL2 sequence of 1D05 LC Mutant 3 is as defined by the Kabat or IMGT systems from the $V_L$ sequence of Seq ID No:298. The light chain nucleic acid sequence of the $V_L$ domain is Seq ID No:44. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205 or Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:35 (heavy chain nucleic acid sequence Seq ID No:36). A full length light chain amino acid sequence is Seq ID No:45 (light chain nucleic acid sequence Seq ID No:46).

411B08 has a heavy chain variable ($V_H$) region amino acid sequence of Seq ID No:58, comprising the CDRH1 amino acid sequence of Seq ID No:52 (IMGT) or Seq ID No:55 (Kabat), the CDRH2 amino acid sequence of Seq ID No:53 (IMGT) or Seq ID No:56 (Kabat), and the CDRH3 amino acid sequence of Seq ID No:54 (IMGT) or Seq ID No:57 (Kabat). The heavy chain nucleic acid sequence of the $V_H$ domain is Seq ID No:59. 411B08 has a light chain variable region ($V_L$) amino acid sequence of Seq ID No:68, comprising the CDRL1 amino acid sequence of Seq ID No:62 (IMGT) or Seq ID No:65 (Kabat), the CDRL2 amino acid sequence of Seq ID No:63 (IMGT) or Seq ID No:66 (Kabat), and the CDRL3 amino acid sequence of Seq ID No:64 (IMGT) or Seq ID No:67 (Kabat). The light chain nucleic acid sequence of the $V_L$ domain is Seq ID No:69. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:60 (heavy chain nucleic acid sequence Seq ID No:61). A full length light chain amino acid sequence is Seq ID No:70 (light chain nucleic acid sequence Seq ID No:71).

411C04 has a heavy chain variable ($V_H$) region amino acid sequence of Seq ID No:78, comprising the CDRH1 amino acid sequence of Seq ID No:72 (IMGT) or Seq ID No:75 (Kabat), the CDRH2 amino acid sequence of Seq ID No:73 (IMGT) or Seq ID No:76 (Kabat), and the CDRH3 amino acid sequence of Seq ID No:74 (IMGT) or Seq ID No:77 (Kabat). The heavy chain nucleic acid sequence of the $V_H$ domain is Seq ID No:79. 411C04 has a light chain variable region ($V_L$) amino acid sequence of Seq ID No:88, comprising the CDRL1 amino acid sequence of Seq ID No:82 (IMGT) or Seq ID No:85 (Kabat), the CDRL2 amino acid sequence of Seq ID No:83 (IMGT) or Seq ID No:86 (Kabat), and the CDRL3 amino acid sequence of Seq ID No:84 (IMGT) or Seq ID No:87 (Kabat). The light chain nucleic acid sequence of the $V_L$ domain is Seq ID No:89. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:80 (heavy chain nucleic acid sequence Seq ID No:81). A full length light chain amino acid sequence is Seq ID No:90 (light chain nucleic acid sequence Seq ID No:91).

411D07 has a heavy chain variable ($V_H$) region amino acid sequence of Seq ID No:98, comprising the CDRH1 amino acid sequence of Seq ID No:92 (IMGT) or Seq ID No:95 (Kabat), the CDRH2 amino acid sequence of Seq ID No:93 (IMGT) or Seq ID No:96 (Kabat), and the CDRH3 amino acid sequence of Seq ID No:94 (IMGT) or Seq ID No:97 (Kabat). The heavy chain nucleic acid sequence of the $V_H$ domain is Seq ID No:99. 411D07 has a light chain variable region ($V_L$) amino acid sequence of Seq ID No:108, comprising the CDRL1 amino acid sequence of Seq ID No:102 (IMGT) or Seq ID No:105 (Kabat), the CDRL2 amino acid sequence of Seq ID No:103 (IMGT) or Seq ID No:106 (Kabat), and the CDRL3 amino acid sequence of Seq ID No:104 (IMGT) or Seq ID No:107 (Kabat). The light chain nucleic acid sequence of the $V_L$ domain is Seq ID No:109. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:100 (heavy chain nucleic acid sequence Seq ID No:101). A full length light chain amino acid sequence is Seq ID No: 110 (light chain nucleic acid sequence Seq ID No:111).

385F01 has a heavy chain variable ($V_H$) region amino acid sequence of Seq ID No:118, comprising the CDRH1 amino acid sequence of Seq ID No:112 (IMGT) or Seq ID No:115 (Kabat), the CDRH2 amino acid sequence of Seq ID No:113 (IMGT) or Seq ID No:116 (Kabat), and the CDRH3 amino acid sequence of Seq ID No:114 (IMGT) or Seq ID No:117 (Kabat). The heavy chain nucleic acid sequence of the $V_H$ domain is Seq ID No:119. 385F01 has a light chain variable region ($V_L$) amino acid sequence of Seq ID No:128, comprising the CDRL1 amino acid sequence of Seq ID No:122 (IMGT) or Seq ID No:125 (Kabat), the CDRL2 amino acid sequence of Seq ID No:123 (IMGT) or Seq ID No:126 (Kabat), and the CDRL3 amino acid sequence of Seq ID No:124 (IMGT) or Seq ID No:127 (Kabat). The light chain nucleic acid sequence of the $V_L$ domain is Seq ID No:129. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:120 (heavy chain nucleic acid sequence Seq ID No:121). A full length light chain amino acid sequence is Seq ID No:130 (light chain nucleic acid sequence Seq ID No:131).

386H03 has a heavy chain variable ($V_H$) region amino acid sequence of Seq ID No:158, comprising the CDRH1 amino acid sequence of Seq ID No:152 (IMGT) or Seq ID No:155 (Kabat), the CDRH2 amino acid sequence of Seq ID No:153 (IMGT) or Seq ID No:156 (Kabat), and the CDRH3 amino acid sequence of Seq ID No:154 (IMGT) or Seq ID No:157 (Kabat). The heavy chain nucleic acid sequence of the $V_H$ domain is Seq ID No:159. 386H03 has a light chain variable region ($V_L$) amino acid sequence of Seq ID No:168, comprising the CDRL1 amino acid sequence of Seq ID No:162 (IMGT) or Seq ID No:165 (Kabat), the CDRL2 amino acid sequence of Seq ID No:163 (IMGT) or Seq ID No:166 (Kabat), and the CDRL3 amino acid sequence of Seq ID No:164 (IMGT) or Seq ID No:167 (Kabat). The light chain nucleic acid sequence of the $V_L$ domain is Seq ID No:169. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:160 (heavy chain nucleic acid sequence Seq ID No:161). A full length light chain amino acid sequence is Seq ID No:170 (light chain nucleic acid sequence Seq ID No:171).

389A03 has a heavy chain variable ($V_H$) region amino acid sequence of Seq ID No:178, comprising the CDRH1 amino acid sequence of Seq ID No:172 (IMGT) or Seq ID No:175 (Kabat), the CDRH2 amino acid sequence of Seq ID No:173 (IMGT) or Seq ID No:176 (Kabat), and the CDRH3 amino acid sequence of Seq ID No:174 (IMGT) or Seq ID No:177 (Kabat). The heavy chain nucleic acid sequence of the $V_H$ domain is Seq ID No:179. 389A03 has a light chain variable region ($V_L$) amino acid sequence of Seq ID No:188, comprising the CDRL1 amino acid sequence of Seq ID No:182 (IMGT) or Seq ID No:185 (Kabat), the CDRL2 amino acid sequence of Seq ID No:183 (IMGT) or Seq ID No:186 (Kabat), and the CDRL3 amino acid sequence of Seq ID No:184 (IMGT) or Seq ID No:187 (Kabat). The light chain nucleic acid sequence of the $V_L$ domain is Seq ID No:189. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:180 (heavy chain nucleic acid sequence Seq ID No:181). A full length light chain amino acid sequence is Seq ID No:190 (light chain nucleic acid sequence Seq ID No:191).

413D08 has a heavy chain variable ($V_H$) region amino acid sequence of Seq ID No:138, comprising the CDRH1 amino acid sequence of Seq ID No:132 (IMGT) or Seq ID No:135 (Kabat), the CDRH2 amino acid sequence of Seq ID No:133 (IMGT) or Seq ID No:136 (Kabat), and the CDRH3 amino acid sequence of Seq ID No:134 (IMGT) or Seq ID No:137 (Kabat). The heavy chain nucleic acid sequence of the $V_H$ domain is Seq ID No:139. 413D08 has a light chain variable region ($V_L$) amino acid sequence of Seq ID No:148, comprising the CDRL1 amino acid sequence of Seq ID No:142 (IMGT) or Seq ID No:145 (Kabat), the CDRL2 amino acid sequence of Seq ID No:143 (IMGT) or Seq ID No:146 (Kabat), and the CDRL3 amino acid sequence of Seq ID No:144 (IMGT) or Seq ID No:147 (Kabat). The light chain nucleic acid sequence of the $V_L$ domain is Seq ID No:149. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No: 140 (heavy chain nucleic acid sequence Seq ID No:141). A full length light chain amino acid sequence is Seq ID No:150 (light chain nucleic acid sequence Seq ID No:151).

413G05 has a heavy chain variable ($V_H$) region amino acid sequence of Seq ID No:244, comprising the CDRH1 amino acid sequence of Seq ID No:238 (IMGT) or Seq ID No:241 (Kabat), the CDRH2 amino acid sequence of Seq ID No:239 (IMGT) or Seq ID No:242 (Kabat), and the CDRH3 amino acid sequence of Seq ID No:240 (IMGT) or Seq ID No:243 (Kabat). The heavy chain nucleic acid sequence of the $V_H$ domain is Seq ID No:245. 413G05 has a light chain variable region ($V_L$) amino acid sequence of Seq ID No:254, comprising the CDRL1 amino acid sequence of Seq ID No:248 (IMGT) or Seq ID No:251 (Kabat), the CDRL2 amino acid sequence of Seq ID No:249 (IMGT) or Seq ID No:252 (Kabat), and the CDRL3 amino acid sequence of Seq ID No:250 (IMGT) or Seq ID No:253 (Kabat). The light chain nucleic acid sequence of the $V_L$ domain is Seq ID No:255. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:246 (heavy chain nucleic acid sequence Seq ID No:247). A full length light chain amino acid sequence is Seq ID No:256 (light chain nucleic acid sequence Seq ID No:257).

413F09 has a heavy chain variable ($V_H$) region amino acid sequence of Seq ID No:264, comprising the CDRH1 amino acid sequence of Seq ID No:258 (IMGT) or Seq ID No:261 (Kabat), the CDRH2 amino acid sequence of Seq ID No:259 (IMGT) or Seq ID No:262 (Kabat), and the CDRH3 amino acid sequence of Seq ID No:260 (IMGT) or Seq ID No:263 (Kabat). The heavy chain nucleic acid sequence of the $V_H$ domain is Seq ID No:265. 413F09 has a light chain variable region ($V_L$) amino acid sequence of Seq ID No:274, comprising the CDRL1 amino acid sequence of Seq ID No:268 (IMGT) or Seq ID No:271 (Kabat), the CDRL2 amino acid sequence of Seq ID No:269 (IMGT) or Seq ID No:272 (Kabat), and the CDRL3 amino acid sequence of Seq ID No:270 (IMGT) or Seq ID No:273 (Kabat). The light chain nucleic acid sequence of the $V_L$ domain is Seq ID No:275. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:266 (heavy chain nucleic acid sequence Seq ID No:267). A full length light chain amino acid sequence is Seq ID No:276 (light chain nucleic acid sequence Seq ID No:277).

414B06 has a heavy chain variable ($V_H$) region amino acid sequence of Seq ID No:284, comprising the CDRH1 amino acid sequence of Seq ID No:278 (IMGT) or Seq ID No:281 (Kabat), the CDRH2 amino acid sequence of Seq ID No:279 (IMGT) or Seq ID No:282 (Kabat), and the CDRH3 amino acid sequence of Seq ID No:280 (IMGT) or Seq ID No:283 (Kabat). The heavy chain nucleic acid sequence of the $V_H$ domain is Seq ID No:285. 414B06 has a light chain variable region ($V_L$) amino acid sequence of Seq ID No:294, comprising the CDRL1 amino acid sequence of Seq ID No:288 (IMGT) or Seq ID No:291(Kabat), the CDRL2 amino acid sequence of Seq ID No:289 (IMGT) or Seq ID No:292 (Kabat), and the CDRL3 amino acid sequence of Seq ID No:290 (IMGT) or Seq ID No:293 (Kabat). The light chain nucleic acid sequence of the $V_L$ domain is Seq ID No:295. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:286 (heavy chain nucleic acid sequence Seq ID No:287). A full length light chain amino acid sequence is Seq ID No:296 (light chain nucleic acid sequence Seq ID No:297).

416E01 has a heavy chain variable region ($V_H$) amino acid sequence of Seq ID No:349, comprising the CDRH1 amino acid sequence of Seq ID No:343 (IMGT) or Seq ID No:346 (Kabat), the CDRH2 amino acid sequence of Seq ID No:344 (IMGT) or Seq ID No:347 (Kabat), and the CDRH3 amino acid sequence of Seq ID No:345 (IMGT) or Seq ID No:348 (Kabat). The heavy chain nucleic acid sequence of the $V_H$ domain is Seq ID No:350. 416E01 has a light chain variable region ($V_L$) amino acid sequence of Seq ID No:359, comprising the CDRL1 amino acid sequence of Seq ID No:353 (IMGT) or Seq ID No:356 (Kabat), the CDRL2 amino acid sequence of Seq ID No:354 (IMGT) or Seq ID No:357 (Kabat), and the CDRL3 amino acid sequence of Seq ID No:355 (IMGT) or Seq ID No:358 (Kabat). The light chain nucleic acid sequence of the $V_L$ domain is Seq ID No:360. The $V_H$ domain may be combined with any of the heavy chain constant region sequences described herein, e.g. Seq ID No:193, Seq ID No:195, Seq ID No:197, Seq ID No:199, Seq ID No:201, Seq ID No:203, Seq ID No:205, Seq ID No:340, Seq ID No:524, Seq ID No:526, Seq ID No:528, Seq ID No:530, Seq ID No:532 or Seq ID No:534. The $V_L$ domain may be combined with any of the light chain constant region sequences described herein, e.g. Seq ID Nos:207, 209, 211, 213, 215, 217, 219, 221, 223, 225, 227, 229, 231, 233, 235, 237, 536 and 538. A full length heavy chain amino acid sequence is Seq ID No:351 (heavy chain nucleic acid sequence Seq ID No:352). A full length light chain amino acid sequence is Seq ID No:361 (light chain nucleic acid sequence Seq ID No:362).

Antibody-Drug Conjugates

Anti-ICOS antibodies can be used as carriers of cytotoxic agents, to target Tregs. As reported in Example 18, Tregs located in the tumour microenvironment (TME) strongly express ICOS. ICOS is more strongly expressed on intratumoural Tregs than on intratumoural Teffs or peripheral Tregs. Thus, anti-ICOS antibodies labelled with a toxic drug or pro-drug may preferentially target Tregs in the TME to deliver the toxic payload, selectively inhibiting those cells. Such targeting of cytotoxic agents provides an additional route to removing the immune suppressive effect of Tregs, thereby altering the Treg:Teff balance in favour of Teff activity and may be used as an alternative to, or in combination with, any one or more of the other therapeutic approaches discussed herein (e.g., Fc effector-mediated inhibition of Tregs, agonism of effector T cells).

Accordingly, the invention provides an anti-ICOS antibody that is conjugated to a cytotoxic drug or pro-drug. In the case of a pro-drug, the pro-drug is activatable in the TME or other target site of therapeutic activity to generate the cytotoxic agent. Activation may be in response to a trigger such as photoactivation, e.g., using near-infrared light to activate a photoabsorber conjugate [36]. Spatially-selective activation of a pro-drug further enhances the cytotoxic effect of the antibody-drug conjugate, combining with the high ICOS expression on intratumoural Tregs to provide a cytotoxic effect that is highly selective for these cells.

For use in an antibody-drug conjugate, the cytotoxic drug or pro-drug is preferably non-immunogenic and non-toxic (dormant or inactive) during circulation of the antibody-drug conjugate in the blood. Preferably the cytotoxic drug (or the pro-drug, when activated) is potent—e.g., two to four molecules of the drug may be sufficient to kill the target cell. A photoactivatable pro-drug is silicapthalocyanine dye (IRDye 700 DX), which induces lethal damage to the cell membrane after near-infrared light exposure. Cytotoxic drugs include anti-mitotic agents such as monomethyl auristatin E and microtubule inhibitors such as maytansine derivatives, e.g., mertansine, DM1, emtansine.

Conjugation of the drug (or pro-drug) to the antibody will usually be via a linker. The linker may be a cleavable linker, e.g., disulphide, hydrazone or peptide link. Cathepsin-cleavable linkers may be used, so that the drug is released by cathepsin in tumour cells. Alternatively, non-cleavable linkers can be used, e.g., thioether linkage. Additional attachment groups and/or spacers may also be included.

The antibody in the antibody-drug conjugate may be an antibody fragment, such as Fab'2 or other antigen-binding fragment as described herein, as the small size of such fragments may assist penetration to the tissue site (e.g., solid tumour).

An anti-ICOS antibody according to the present invention may be provided as an immunocytokine. Anti-ICOS antibodies may also be administered with immunocytokines in combination therapy. A number of examples of antibodies are described herein for use in combination therapy with anti-ICOS, and any of these (e.g., an anti-PD-L1 antibody) may be provided as immunocytokines for use in the present invention. An immunocytokine comprises an antibody molecule conjugated to a cytokine, such as IL-2. Anti-ICOS: IL-2 conjugates and anti-PD-L1:1 L-2 conjugates are thus further aspects of the present invention.

An IL-2 cytokine may have activity at the high (any) affinity IL-2 receptor and/or the intermediate affinity (αβ) IL-2 receptor. IL-2 as used in an immunocytokine may be human wild type IL-2 or a variant IL-2 cytokine having one or more amino acid deletions, substitutions or additions, e.g., IL-2 having a 1 to 10 amino acid deletion at the N-terminus. Other IL-2 variants include mutations R38A or R38Q.

An example anti-PD-L1 immunocytokine comprises an immunoglobulin heavy chain and an immunoglobulin light chain, wherein the heavy chain comprises in N- to C-terminal direction:

a) A $V_H$ domain comprising CDRH1, CDRH2 and CDRH3; and b) A heavy chain constant region;

and wherein the light chain comprises in N- to C-terminal direction:

c) A $V_L$ domain comprising CDRL1, CDRL2 and CDRL3;

d) A light chain constant region, (CL);

e) Optionally, a linker, (L); and f) An IL-2 cytokine;

wherein the $V_H$ domain and $V_L$ domain are comprised by an antigen-binding site that specifically binds to human PD-L1; and wherein the immunocytokine comprises a $V_H$ domain which comprises a CDRH3 comprising the motif $X_1GSGX_2YGX_3X_4FD$ (SEQ ID NO: 609), wherein $X_1$, $X_2$ and $X_3$ are independently any amino acid, and $X_4$ is either present or absent, and if present, may be any amino acid.

The VH and VL domain may be the VH and VL domain of any anti-PD-L1 antibody mentioned herein, e.g., the 1D05 VH and VL domains.

The IL-2 may be human wild type or variant IL-2.

Vaccination

Anti-ICOS antibodies may be provided in vaccine compositions or co-administered with vaccines preparations. ICOS is involved in T follicular helper cell formation and the germinal centre reaction [37]. Agonist ICOS antibodies thus have potential clinical utility as molecular adjuvants to enhance vaccine efficacy. The antibodies may be used to increase protective efficacy of numerous vaccines, such as those against hepatitis B, malaria, HIV.

In the context of vaccination, the anti-ICOS antibody will generally be one that lacks Fc effector function, and thus does not mediate ADCC, CDC or ADCP. The antibody may be provided in a format lacking an Fc region, or having an effector null constant region. Optionally, an anti-ICOS antibody may have a heavy chain constant region that binds one or more types of Fc receptor but does not induce ADCC, CDC or ADCP activity, or that exhibits lower ADCC, CDC and ADCP activity compared with wild type human IgG1. Such a constant region may be unable to bind, or may bind with lower affinity, the particular Fc receptor(s) responsible for triggering ADCC, CDC or ADCP activity. Alternatively, where cellular effector functions are acceptable or desirable in the context of the vaccination, the anti-ICOS antibody may comprise a heavy chain constant region that is Fc effector function positive. Any of IgG1, IgG4 and IgG4.PE formats may for instance be used for anti-ICOS antibodies in vaccination regimens, and other examples of suitable isotypes and antibody constant regions are set out in more detail elsewhere herein.

Formulations and Administration

Antibodies may be monoclonal or polyclonal, but are preferably provided as monoclonal antibodies for therapeutic use. They may be provided as part of a mixture of other antibodies, optionally including antibodies of different binding specificity.

Antibodies according to the invention, and encoding nucleic acid, will usually be provided in isolated form. Thus, the antibodies, VH and/or VL domains, and nucleic acids may be provided purified from their natural environment or their production environment. Isolated antibodies and isolated nucleic acid will be free or substantially free of material with which they are naturally associated, such as other polypeptides or nucleic acids with which they are found in vivo, or the environment in which they are prepared (e.g., cell culture) when such preparation is by recombinant DNA technology in vitro. Optionally an isolated antibody or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

Antibodies or nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. Antibodies may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern. In some applications, modification to remove undesirable glycosylation sites may be useful, or e.g., removal of a fucose moiety to increase ADCC function [38]. In other applications, modification of galactosylation can be made in order to modify CDC.

Typically, an isolated product constitutes at least about 5%, at least about 10%, at least about 25%, or at least about 50% of a given sample. An antibody may be substantially free from proteins or polypeptides or other contaminants that are found in its natural or production environment that would interfere with its therapeutic, diagnostic, prophylactic, research or other use.

An antibody may have been identified, separated and/or recovered from a component of its production environment (eg, naturally or recombinantly). The isolated antibody may be free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated antibody or its encoding nucleic acid will be prepared by at least one purification step.

The invention provides therapeutic compositions comprising the antibodies described herein. Therapeutic compositions comprising nucleic acid encoding such antibodies are also provided. Encoding nucleic acids are described in more detail elsewhere herein and include DNA and RNA, e.g., mRNA. In therapeutic methods described herein, use of nucleic acid encoding the antibody, and/or of cells containing such nucleic acid, may be used as alternatives (or in addition) to compositions comprising the antibody itself. Cells containing nucleic acid encoding the antibody, optionally wherein the nucleic acid is stably integrated into the genome, thus represent medicaments for therapeutic use in a patient. Nucleic acid encoding the anti-ICOS antibody may be introduced into human B lymphocytes, optionally B lymphocytes derived from the intended patient and modified ex vivo. Optionally, memory B cells are used. Administration of cells containing the encoding nucleic acid to the patient provides a reservoir of cells capable of expressing the anti-ICOS antibody, which may provide therapeutic benefit over a longer term compared with administration of isolated nucleic acid or isolated antibody.

Compositions may contain suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTINT™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Compositions may comprise the antibody or nucleic acid in combination with medical injection buffer and/or with adjuvant.

Antibodies, or their encoding nucleic acids, may be formulated for the desired route of administration to a patient, e.g., in liquid (optionally aqueous solution) for injection. Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes. Formulating antibodies for subcutaneous administration typically requires concentrating them into a smaller volume compared with intravenous preparations. The high potency of antibodies according to the present invention may lend them to use at sufficiently low doses to make subcutaneous formulation practical, representing an advantage compared with less potent anti-ICOS antibodies.

The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule. A pharmaceutical composition of the present invention can be delivered subcutaneously or intravenously with a standard needle and syringe. It is envisaged that treatment will not be restricted to use in the clinic. Therefore, subcutaneous injection using a needle-free device is also advantageous. With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms.

The antibody, nucleic acid, or composition comprising it, may be contained in a medical container such as a phial, syringe, IV container or an injection device. In an example, the antibody, nucleic acid or composition is in vitro, and may be in a sterile container. In an example, a kit is provided comprising the antibody, packaging and instructions for use in a therapeutic method as described herein.

One aspect of the invention is a composition comprising an antibody or nucleic acid of the invention and one or more pharmaceutically acceptable excipients, examples of which are listed above. “Pharmaceutically acceptable” refers to approved or approvable by a regulatory agency of the USA Federal or a state government or listed in the U.S. Pharmacopeia or other generally recognized pharmacopeia for use in animals, including humans. A pharmaceutically acceptable carrier, excipient, or adjuvant can be administered to a patient, together with an agent, e.g., any antibody or antibody chain described herein, and does not destroy the pharmacological activity thereof and is nontoxic when administered in doses sufficient to deliver a therapeutic amount of the agent.

In some embodiments, an anti-ICOS antibody will be the sole active ingredient in a composition according to the present invention. Thus, a composition may consist of the antibody or it may consist of the antibody with one or more pharmaceutically acceptable excipients. However, compositions according to the present invention optionally include one or more additional active ingredients. Detailed description of agents with which the anti-ICOS antibodies may be combined is provided elsewhere herein. Optionally, compositions contain multiple antibodies (or encoding nucleic acids) in a combined preparation, e.g., a single formulation comprising the anti-ICOS antibody and one or more other antibodies. Other therapeutic agents that it may be desirable to administer with antibodies or nucleic acids according to the present invention include analgaesic agents. Any such agent or combination of agents may be administered in combination with, or provided in compositions with antibodies or nucleic acids according to the present invention, whether as a combined or separate preparation. The antibody or nucleic acid according to the present invention may be administered separately and sequentially, or concurrently and optionally as a combined preparation, with another therapeutic agent or agents such as those mentioned.

Anti-ICOS antibodies for use in a particular therapeutic indication may be combined with the accepted standard of care. Thus, for anti-cancer treatment, the antibody therapy may be employed in a treatment regimen that also includes chemotherapy, surgery and/or radiation therapy for example. Radiotherapy may be single dose or in fractionated doses, either delivered to affected tissues directly or to the whole body.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

Antibodies, and their encoding nucleic acids, can be used as therapeutic agents. Patients herein are generally mammals, typically humans. An antibody or nucleic acid may be administered to a mammal, e.g., by any route of administration mentioned herein.

Administration is normally in a “therapeutically effective amount”, this being an amount that produces the desired effect for which it is administered, sufficient to show benefit to a patient. The exact amount will depend on the purpose of the treatment, and will be ascertainable by one skilled in the art using known techniques (see, for example, Lloyd (1999) The Art, Science and Technology of Pharmaceutical Compounding). Prescription of treatment, e.g. decisions on dosage etc, is within the responsibility of general practitioners and other medical doctors and may depend on the severity of the symptoms and/or progression of a disease being treated. A therapeutically effective amount or suitable dose of antibody or nucleic acid can be determined by comparing its in vitro activity and in vivo activity in an animal model. Methods for extrapolation of effective dosages in mice and other test animals to humans are known.

As indicated by the in vivo studies described in the Examples herein, anti-ICOS antibody may be effective at a range of doses. Pharmacodynamic studies are reported in Example 24.

Anti-ICOS antibodies may be administered in an amount in one of the following ranges per dose:

- about 10 μg/kg body weight to about 100 mg/kg body weight,
- about 50 μg/kg body weight to about 5 mg/kg body weight,
- about 100 μg/kg body weight to about 10 mg/kg body weight,
- about 100 μg/kg body weight to about 20 mg/kg body weight,
- about 0.5 mg/kg body weight to about 20 mg/kg body weight, or
- about 5 mg/kg body weight or lower, for example less than 4, less than 3, less than 2, or less than 1 mg/kg of the antibody.

An optimal therapeutic dose may be between 0.1 and 0.5 mg/kg in a human, for example about 0.1 mg/kg, 0.15 mg/kg, 0.2 mg/kg, 0.25 mg/kg, 0.3 mg/kg, 0.35 mg/kg, 0.4 mg/kg, 0.45 mg/kg or 0.5 mg/kg. For fixed dosing in adult humans, a suitable dose may be between 8 and 50 mg, or between 8 and 25 mg, e.g., 15 mg or 20 mg.

In methods of treatment described herein, one or more doses may be administered. In some cases, a single dose may be effective to achieve a long-term benefit. Thus, the method may comprise administering a single dose of the antibody, its encoding nucleic acid, or the composition. Alternatively, multiple doses may be administered, usually sequentially and separated by a period of days, weeks or months. Anti-ICOS antibody may be repeatedly administered to a patient at intervals of 4 to 6 weeks, e.g., every 4 weeks, every 5 weeks, or every 6 weeks. Optionally, the anti-ICOS antibody may be administered to a patient once a month, or less frequently, e.g., every two months or every three months. Accordingly, a method of treating a patient may comprise administering a single dose of the anti-ICOS antibody to the patient, and not repeating the administration for at least one month, at least two months, at least three months, and optionally not repeating the administration for at least 12 months.

As discussed in Example 11c, comparable therapeutic effects may be obtained using either one or multiple doses of anti-ICOS antibody, which may be a result of a single dose of antibody being effective to reset the tumour microenvironment. Physicians can tailor the administration regimen of the anti-ICOS antibody to the disease and the patient undergoing therapy, taking into account the disease status and any other therapeutic agents or therapeutic measures (e.g., surgery, radiotherapy etc) with which the anti-ICOS antibody is being combined. In some embodiments, an effective dose of an anti-ICOS antibody is administered more frequently than once a month, such as, for example, once every three weeks, once every two weeks, or once every week. Treatment with anti-ICOS antibody may include multiple doses administered over a period of at least a month, at least six months, or at least a year.

As used herein, the terms “treat,” “treatment,” “treating,” or “amelioration” refer to therapeutic treatments, wherein the object is to reverse, alleviate, ameliorate, inhibit, slow down or stop the progression or severity of a condition associated with a disease or disorder. The term “treating” includes reducing or alleviating at least one adverse effect or symptom of a condition, disease or disorder. Treatment is generally “effective” if one or more symptoms or clinical markers are reduced. Alternatively, treatment is “effective” if the progression of a disease is reduced or halted. That is, “treatment” includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilised (i.e., not worsening) state of disease, delay or slowing of disease progression, amelioration or palliation of the disease state, remission (whether partial or total), and/or decreased mortality, whether detectable or undetectable. The term “treatment” of a disease also includes providing relief from the symptoms or side-effects of the disease (including palliative treatment). For treatment to be effective a complete cure is not contemplated. The method can in certain aspects include cure as well. In the context of the invention, treatment may be preventative treatment.

T Cell Therapy

WO2011/097477 described use of anti-ICOS antibodies for generating and expanding T cells, by contacting a population of T cells with a first agent that provides a primary activation signal (e.g., an anti-CD3 antibody) and a second agent that activates ICOS (e.g., an anti-ICOS antibody), optionally in the presence of a Th17 polarising agent such as IL-1β, IL-6, neutralising anti-IFNγ and/or anti-IL-4. Anti-ICOS antibodies described herein may be used in such methods to provide T cell populations. Populations of cultured expanded T cells having therapeutic activity (e.g., anti-tumour activity) may be generated. As described in WO2011/097477, such T cells may be used therapeutically in methods of treating patients by immunotherapy.

Morphological Assay for Anti-ICOS Antibodies as Therapeutic Candidates

It was observed that when candidate therapeutic anti-ICOS antibodies were coupled to a solid surface and brought into contact with ICOS-expressing T cells, they were able to induce morphological change in the cells. On addition of ICOS+ T cells to wells that were internally coated with anti-ICOS antibodies, cells were seen to change from their initial rounded shape, adopting a spindle-shape, spreading and adhering to the antibody-coated surface. This morphological change was not observed with control antibody. Moreover, the effect was found to be dose-dependent, with faster and/or more pronounced shape change occurring as the concentration of antibody on the surface increased. The shape change provides a surrogate indicator of T cell binding to ICOS, and/or of agonism by anti-ICOS antibody. The assay may be used to identify an antibody that promotes multimerisation of ICOS on the T cell surface. Such antibodies represent therapeutic candidate agonist antibodies. Conveniently, the visual indicator provided by this assay is a simple method of screening antibodies or cells, particularly in large numbers. The assay may be automated to run in a high-throughput system.

Accordingly, one aspect of the invention is an assay for selecting an antibody that binds ICOS, optionally for selecting an ICOS agonist antibody, the assay comprising:

providing an array of antibodies immobilised (attached or adhered) to a substrate in a test well;

adding ICOS-expressing cells (e.g., activated primary T cells, or MJ cells) to the test well;

observing morphology of the cells;

detecting shape change in the cells from rounded to flattened against the substrate within the well; wherein the shape change indicates that the antibody is an antibody that binds ICOS, optionally an ICOS agonist antibody, and selecting the antibody from the test well.

The assay may be run with multiple test wells, each containing a different antibody for testing, optionally in parallel, e.g., in a 96 well plate format. The substrate is preferably an inner surface of the well. Thus, a two-dimensional surface is provided against which flattening of the cells may be observed. For example, the bottom and/or wall of a well may be coated with antibody. Tethering of antibody to the substrate may be via a constant region of the antibody.

A negative control may be included, such an antibody known not to bind ICOS, preferably an antibody that does not bind an antigen on the surface of the ICOS-expressing cells to be used. The assay may comprise quantifying the degree of morphological change and, where multiple antibodies are tested, selecting an antibody that induces greater morphological change than one or more other test antibodies.

Selection of antibody may comprise expressing nucleic acid encoding the antibody present in the test well of interest, or expressing an antibody comprising the CDRs or antigen binding domain of that antibody. The antibody may optionally be reformatted, for example to provide an antibody comprising the antigen binding domain of the selected antibody, e.g., an antibody fragment, or an antibody comprising a different constant region. A selected antibody is preferably provided with a human IgG1 constant region or other constant region as described herein. A selected antibody may further be formulated in a composition comprising one or more additional ingredients—suitable pharmaceutical formations are discussed elsewhere herein.

Clauses

Embodiments of the invention are set out in the following numbered clauses, which are part of the description.

Clause 1. An isolated antibody that binds the extracellular domain of human and/or mouse ICOS, wherein the antibody comprises a VH domain comprising an amino acid sequence having at least 95% sequence identity to the STIM003 VH domain SEQ ID NO: 408 and a VL domain comprising an amino acid sequence having at least 95% sequence identity to the STIM003 VL domain SEQ ID NO: 415.

Clause 2. An antibody according to clause 1, wherein the VH domain comprises a set of heavy chain complementarity determining regions (HCDRs) HCDR1, HCDR2 and HCDR3, wherein HCDR1 is the STIM003 HCDR1 having amino acid sequence SEQ ID NO: 405, HCDR2 is the STIM003 HCDR2 having amino acid sequence SEQ ID NO: 406, HCDR3 is the STIM003 HCDR3 having amino acid sequence SEQ ID NO: 407.

Clause 3. An antibody according to clause 1 or clause 2, wherein the VL domain comprises a set of light chain complementarity determining regions (LCDRs) LCDR1, LCDR2 and LCDR3, wherein LCDR1 is the STIM003 LCDR1 having amino acid sequence SEQ ID NO: 412, LCDR2 is the STIM003 LCDR2 having amino acid sequence SEQ ID NO: 413, LCDR3 is the STIM003 LCDR3 having amino acid sequence SEQ ID NO: 414.

Clause 4. An antibody according to clause 1, wherein the VH domain amino acid sequence is SEQ ID NO: 408 and/or wherein the VL domain amino acid sequence is SEQ ID NO: 415.

Clause 5. An isolated antibody that binds the extracellular domain of human and/or mouse ICOS, comprising an antibody VH domain comprising complementarity determining regions (CDRs) HCDR1, HCDR2 and HCDR3, and an antibody VL domain comprising complementarity determining regions LCDR1, LCDR2 and LCDR3, wherein HCDR1 is the HCDR1 of STIM001, STIM002, STIM002-B, STIM003, STIM004, STIM005, STIM006, STIM007, STIM008 or STIM009, or comprises that HCDR1 with 1, 2, 3, 4 or 5 amino acid alterations, HCDR2 is the HCDR2 of STIM001, STIM002, STIM002-B, STIM003, STIM004, STIM005, STIM006, STIM007, STIM008 or STIM009, or comprises that HCDR2 with 1, 2, 3, 4 or 5 amino acid alterations, and/or HCDR3 is the HCDR3 of STIM001, STIM002, STIM002-B, STIM003, STIM004, STIM005, STIM006, STIM007, STIM008 or STIM009 or comprises that HCDR3 with 1, 2, 3, 4 or 5 amino acid alterations.

Clause 6. An antibody according to clause 5, wherein the antibody heavy chain CDRs are those of STIM001, STIM002, STIM002-B, STIM003, STIM004, STIM005, STIM006, STIM007, STIM008 or STIM009 or comprise the STIM001, STIM002, STIM002-B, STIM003, STIM004, STIM005, STIM006, STIM007, STIM008 or STIM009 heavy chain CDRs with 1, 2, 3, 4 or 5 amino acid alterations.

Clause 7. An antibody according to clause 6, wherein the antibody VH domain has the heavy chain CDRs of STIM003.

Clause 8. An isolated antibody that binds the extracellular domain of human and/or mouse ICOS, comprising an antibody VH domain comprising complementarity determining regions HCDR1, HCDR2 and HCDR3, and an antibody VL domain comprising complementarity determining regions LCDR1, LCDR2 and LCDR3, wherein LCDR1 is the LCDR1 of STIM001, STIM002, STIM002-B, STIM003, STIM004 STIM005, STIM006, STIM007, STIM008 or STIM009, or comprises that LCDR1 with 1, 2, 3, 4 or 5 amino acid alterations, LCDR2 is the LCDR2 of STIM001, STIM002, STIM002-B, STIM003, STIM004, STIM005, STIM006, STIM007, STIM008 or STIM009, or comprises that LCDR2 with 1, 2, 3, 4 or 5 amino acid alterations, and/or LCDR3 is the LCDR3 of STIM001, STIM002, STIM002-B, STIM003, STIM004, STIM005, STIM006, STIM007, STIM008 or STIM009 or comprises that LCDR3 with 1, 2, 3, 4 or 5 amino acid alterations.

Clause 9. An antibody according to any of clauses 5 to 8, wherein the antibody light chain CDRs are those of STIM001, STIM002, STIM002-B, STIM003, STIM004, STIM005, STIM006, STIM007, STIM008 or STIM009, or comprise the STIM001, STIM002, STIM002-B, STIM003, STIM004, STIM005, STIM006, STIM007, STIM008 or STIM009 light chain CDRs with 1, 2, 3, 4 or 5 amino acid alterations.

Clause 10. An antibody according to clause 9, wherein the antibody VL domain has the light chain CDRs of STIM003.

Clause 11. An antibody according to any of clauses 5 to 10, comprising VH and/or VL domain framework regions of human germline gene segment sequences.

Clause 12. An antibody according to any of clauses 5 to 11, comprising a VH domain which (i) is derived from recombination of a human heavy chain V gene segment, a human heavy chain D gene segment and a human heavy chain J gene segment, wherein the V segment is IGHV1-18 (e.g., V1-18*01), IGVH3-20 (e.g. V3-20*d01), IGVH3-11 (e.g, V3-11*01) or IGVH2-5 (e.g., V2-5*10);

the D gene segment is IGHD6-19 (e.g., IGHD6-19*01), IGHD3-10 (e.g., IGHD3-10*01) or IGHD3-9 (e.g., IGHD3-9*01); and/or the J gene segment is IGHJ6 (e.g., IGHJ6*02), IGHJ4 (e.g., IGHJ4*02) or IGHJ3 (e.g., IGHJ3*02), or (ii) comprises framework regions FR1, FR2, FR3 and FR4, wherein FR1 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, FR2 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, FR3 aligns with human germline V gene segment IGHV1-18 (e.g., V1-18*01), IGVH3-20 (e.g. V3-20*d01), IGVH3-11 (e.g, V3-11*01) or IGVH2-5 (e.g., V2-5*10), optionally with 1, 2, 3, 4 or 5 amino acid alterations, and/or FR4 aligns with human germline J gene segment IGJH6 (e.g., JH6*02), IGJH4 (e.g., JH4*02) or IGJH3 (e.g., JH3*02), optionally with 1, 2, 3, 4 or 5 amino acid alterations.

Clause 13. An antibody according to any of clauses 5 to 12, comprising an antibody VL domain which (i) is derived from recombination of a human light chain V gene segment and a human light chain J gene segment, wherein the V segment is IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), and/or the J gene segment is IGKJ4 (e.g., IGKJ4*01), IGKJ2 (e.g., IGKJ2*04), IGLJ3 (e.g., IGKJ3*01) or IGKJ1 (e.g., IGKJ1*01); or (ii) comprises framework regions FR1, FR2, FR3 and FR4, wherein FR1 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, FR2 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, FR3 aligns with human germline V gene segment IGKV2-28 (e.g., IGKV2-28*01), IGKV3-20 (e.g., IGKV3-20*01), IGKV1D-39 (e.g., IGKV1D-39*01) or IGKV3-11 (e.g., IGKV3-11*01), optionally with 1, 2, 3, 4 or 5 amino acid alterations, and/or FR4 aligns with human germline J gene segment IGKJ4 (e.g., IGKJ4*01), IGKJ2 (e.g., IGKJ2*04), IGKJ3 (e.g., IGKJ3*01) or IGKJ1 (e.g., IGKJ1*01), optionally with 1, 2, 3, 4 or 5 amino acid alterations.

Clause 14. An antibody according to any of clauses 5 to 13, comprising an antibody VH domain which is the VH domain of STIM001, STIM002, STIM002-B, STIM003, STIM004, STIM005, STIM006, STIM007, STIM008 or STIM009, or which has an amino acid sequence at least 90% identical to the antibody VH domain sequence of STIM001, STIM002, STIM002-B, STIM003, STIM004, STIM005, STIM006, STIM007, STIM008 or STIM009.

Clause 15. An antibody according to any of clauses 5 to 14, comprising an antibody VL domain which is the VL domain of STIM001, STIM002, STIM002-B, STIM003, STIM004, STIM005, STIM006, STIM007, STIM008 or STIM009, or which has an amino acid sequence at least 90% identical to the antibody VL domain sequence of STIM001, STIM002, STIM002-B, STIM003, STIM004, STIM005, STIM006, STIM007, STIM008 or STIM009.

Clause 16. An antibody according to clause 15, comprising an antibody VH domain which is selected from the VH domain of STIM001, STIM002, STIM002-B, STIM003, STIM004, STIM005, STIM006, STIM007, STIM008 or STIM009, or which has an amino acid sequence at least 90% identical to the antibody VH domain sequence of STIM001, STIM002, STIM002-B, STIM003, STIM004, STIM005, STIM006, STIM007, STIM008 or STIM009, and an antibody VL domain which is the VL domain of said selected antibody, or which has an amino acid sequence at least 90% identical to the antibody VL domain sequence of said selected antibody.

Clause 17. An antibody according to clause 16, comprising the STIM003 VH domain and the STIM003 VL domain.

Clause 18. An antibody according to any of the preceding clauses, comprising an antibody constant region.

Clause 19. An antibody according to clause 18, wherein the constant region comprises a human heavy and/or light chain constant region.

Clause 20. An antibody according to clause 18 or clause 19, wherein the constant region is Fc effector positive.

Clause 21. An antibody according to clause 20, comprising an Fc region that has enhanced ADCC, ADCP and/or CDC function compared with a native human Fc region.

Clause 22. An antibody according to any of clauses 18 to 21, wherein the antibody is an IgG1.

Clause 23. An antibody according to clause 21 or clause 22, wherein the antibody is afucosylated.

Clause 24. An antibody according to any of the preceding clauses which is conjugated to a cytotoxic drug or pro-drug.

Clause 25. An antibody according to any of the preceding clauses, which is a multispecific antibody.

Clause 26. An isolated antibody that binds the extracellular domain of human and mouse ICOS with an affinity ($K_D$) of less than 50 nM as determined by surface plasmon resonance.

Clause 27. An antibody according to clause 26, wherein the antibody binds the extracellular domain of human and mouse ICOS with an affinity ($K_D$) of less than 5 nM as determined by surface plasmon resonance.

Clause 28. An antibody according to clause 26 or clause 27, wherein the $K_D$ of binding the extracellular domain of human ICOS is within 10-fold of the $K_D$ of binding the extracellular domain of mouse ICOS.

Clause 29. A composition comprising an isolated antibody according to any of the preceding clauses and a pharmaceutically acceptable excipient.

Clause 30. A composition comprising isolated nucleic acid encoding an antibody according to any of clauses 1 to 28 and a pharmaceutically acceptable excipient.

Clause 31. A method of modulating the balance of regulatory T cells (Tregs) to effector T cells (Teffs) to increase Teff response in a patient, comprising administering an antibody according to any of clauses 1 to 28 or composition according to clause 29 to the patient.

Clause 32. A method of treating a disease or condition amenable to therapy by depleting regulatory T cells (Tregs) and/or increasing effector T cell (Teff) response in a patient, the method comprising administering an antibody according to any of clauses 1 to 28 or a composition according to clause 29 to the patient.

Clause 33. An antibody according to any of clauses 1 to 28, or a composition according to clause 29, for use in a method of treatment of the human body by therapy.

Clause 34. An antibody or composition for use according to clause 33, for use in modulating the balance of regulatory T cells (Tregs) to effector T cells (Teffs) to increase effector T cell response in a patient.

Clause 35. An antibody or composition for use according to clause 33, for use in treating a disease or condition amenable to therapy by depleting regulatory T cells (Tregs) and/or increasing effector T cell (Teff) response in a patient.

Clause 36. A method according to clause 32, or an antibody or a composition for use according to clause 35, wherein the disease is a cancer or a solid tumour.

Clause 37. An antibody according to any of clauses 1 to 28 or a composition according to clause 29, for use in a method of treating cancer in a human patient.

Clause 38. A method of treating cancer in a human patient, comprising administering an antibody according to any of clauses 1 to 28 or a composition according to clause 29 to the patient.

Clause 39. A method or an antibody or composition for use according to any of clauses 36 to 38, wherein the cancer is renal cell cancer, head and neck cancer, melanoma, non small cell lung cancer or diffuse large B-cell lymphoma.

Clause 40. A method or an antibody or composition for use according to any of clauses 31 to 39, wherein the method comprises administering the antibody and another therapeutic agent and/or radiation therapy to the patient.

Clause 41. A method or an antibody or composition for use according to clause 40, wherein the therapeutic agent is an anti-PD-L1 antibody.

Clause 42. A method or an antibody or composition for use according to clause 41, wherein the anti-PD-L1 antibody comprises a VH domain having amino acid sequence SEQ ID NO: 299 and a VL domain having amino acid sequence SEQ ID NO: 300.

Clause 43. A method or an antibody or composition for use according to clause 41 or clause 42, wherein the therapeutic agent is an anti-PD-L1 IL-2 immunocytokine.

Clause 44. A method or an antibody or composition for use according to clause 43, wherein the anti-PD-L1 antibody is an immunocytokine comprising human wild type or variant IL-2.

Clause 45. A method or an antibody or composition for use according to clause 44, wherein the anti-ICOS antibody and the anti-PDL1 antibody are each able to mediate ADCC, ADCP and/or CDC.

Clause 46. A method or an antibody or composition for use according to any of clauses 41 to 45, wherein the anti-ICOS antibody is a human IgG1 antibody and the anti-PDL1 antibody is a human IgG1 antibody.

Clause 47. A method or an antibody or composition for use according to clause 40, wherein the therapeutic agent is an anti-PD-1 antibody.

Clause 48. A method or an antibody or composition for use according to clause 40, wherein the other therapeutic agent is IL-2.

Clause 49. A method or an antibody or composition for use according to any of clauses 40 to 48, wherein the method comprises administering the anti-ICOS antibody after administering the other therapeutic agent and/or radiation therapy.

Clause 50. A method or an antibody or composition for use according to any of clauses 31 to 49, wherein the anti-ICOS antibody is conjugated to a pro-drug, and wherein the method or use comprises administering the anti-ICOS antibody to a patient and selectively activating the pro-drug at a target tissue site.

Clause 51. A method or an antibody or composition for use according to clause 50, wherein the patient has a solid tumour and the method comprises selectively activating the pro-drug in the tumour.

Clause 52. A method or an antibody or composition for use according to clause 50 or clause 51, comprising selectively activating the pro-drug through photoactivation.

Clause 53. Combination of anti-ICOS human IgG1 antibody and anti-PDL1 human IgG1 antibody for use in a method of treating cancer in a patient.

Clause 54. A method of treating cancer in a patient, comprising administering an anti-ICOS human IgG1 antibody and an anti-PD-L1 human IgG1 antibody to the patient.

Clause 55. Anti-ICOS antibody for use in a method of treating cancer in a patient, the method comprising administering the anti-ICOS antibody and the anti-PD-L1 antibody to the patient, wherein a single dose of the anti-ICOS antibody is administered.

Clause 56. Anti-ICOS antibody for use according to clause 55, wherein the anti-ICOS antibody is a human IgG1 antibody and the anti-PD-L1 antibody is a human IgG1 antibody.

Clause 57. Combination according to clause 53, method according to clause 54 or anti-ICOS antibody for use according to clause 55 or clause 56, wherein the cancer is renal cell cancer, head and neck cancer, melanoma, non small cell lung cancer or diffuse large B-cell lymphoma.

Clause 58. A method or an antibody, composition or combination for use according to any of clauses 41 to 46 or 53 to 54, the method comprising administering the anti-ICOS antibody and the anti-PD-L1 antibody to the patient, wherein a single dose of the anti-ICOS antibody is administered.

Clause 59. A method or an antibody, composition or combination for use according to clause 58, wherein the method comprises administering a single dose of the anti-ICOS antibody followed by multiple doses of the anti-PD-L1 antibody.

Clause 60. A method or an antibody, composition or combination for use according to any of clauses 41 to 46 or 53 to 54, wherein the anti-ICOS antibody and the anti-PDL1 antibody are provided in separate compositions for administration.

Clause 61. A method or an antibody, composition or combination for use according to any of clauses 41 to 46 or 53 to 60, wherein the anti-ICOS antibody and/or the anti-PD- L1 antibody comprises a human IgG1 constant region comprising amino acid sequence SEQ ID NO: 340.

Clause 62. Anti-ICOS antibody for use in a method of treating a patient, the method comprising administering the anti-ICOS antibody to a patient who has an increased level of ICOS-positive regulatory T cells following treatment with another therapeutic agent.

Clause 63. A method of treating a patient, the method comprising administering an anti-ICOS antibody to a patient who has an increased level of ICOS-positive regulatory T cells following treatment with another therapeutic agent.

Clause 64. An anti-ICOS antibody for use according to clause 62, or a method according to clause 63, wherein the method comprises administering a therapeutic agent to the patient, determining that the patient has an increased level of ICOS-positive regulatory T cells following the treatment with said agent, and administering an anti-ICOS antibody to the patient to reduce the level of regulatory T cells.

Clause 65. An anti-ICOS antibody for use or a method according to any of clauses 62 to 64, wherein the therapeutic agent is IL-2 or an immunomodulatory antibody (e.g., anti-PDL-1, anti-PD-1 or anti-CTLA-4).

Clause 66. An anti-ICOS antibody for use or a method according to any of clauses 62 to 65, wherein the method comprises treating a tumour, e.g., melanoma, such as metastatic melanoma.

Clause 67. Anti-ICOS antibody for use in a method of treating cancer in a patient by in vivo vaccination of the patient against their cancer cells, the method comprising

- treating the patient with a therapy that causes immunological cell death of the cancer cells, resulting in presentation of antigen to antigen-specific effector T cells, and
- administering an anti-ICOS antibody to the patient, wherein the anti-ICOS antibody enhances the antigen-specific effector T cell response.

Clause 68. A method of treating cancer in a patient by in vivo vaccination of the patient against their cancer cells, the method comprising

- treating the patient with a therapy that causes immunological cell death of the cancer cells, resulting in presentation of antigen to antigen-specific effector T cells, and
- administering an anti-ICOS antibody to the patient, wherein the anti-ICOS antibody enhances the antigen-specific effector T cell response.

Clause 69. A method of treating cancer in a patient by in vivo vaccination of the patient against their cancer cells, the method comprising administering an anti-ICOS antibody to the patient, wherein

- the patient is one who has been previously treated with a therapy that causes immunological cell death of the cancer cells, resulting in presentation of antigen to antigen-specific effector T cells, and wherein
- the anti-ICOS antibody enhances the antigen-specific effector T cell response.

Clause 70. Anti-ICOS antibody for use or a method according to any of clauses 67 to 69, wherein the therapy that causes immunological cell death is radiation of the cancer cells, administration of a chemotherapeutic agent and/or administration of an antibody directed to a tumour-associated antigen.

Clause 71. Anti-ICOS antibody for use or a method according to clause 70, wherein the chemotherapeutic agent is oxaliplatin.

Clause 72. Anti-ICOS antibody for use or a method according to clause 70, wherein the tumour-associated antigen is HER2 or CD20.

Clause 73. Anti-ICOS antibody for use in a method of treating a cancer in a patient, wherein the cancer is or has been characterised as being positive for expression of ICOS ligand and/or FOXP3.

Clause 74. A method of treating a cancer in a patient, wherein the cancer is or has been characterised as being positive for expression of ICOS ligand and/or FOXP3, the method comprising administering an anti-ICOS antibody to the patient.

Clause 75. Anti-ICOS antibody for use according to clause 73, or a method according to clause 74, wherein the method comprises:

- testing a sample from a patient to determine that the cancer expresses ICOS ligand and/or FOXP3;
- selecting the patient for treatment with the anti-ICOS antibody; and
- administering the anti-ICOS antibody to the patient.

Clause 76. Anti-ICOS antibody for use according to clause 73, or a method according to clause 74, wherein the method comprises administering an anti-ICOS antibody to a patient from whom a test sample has indicated that the cancer is positive for expression of ICOS ligand and/or FOXP3.

Clause 77. Anti-ICOS antibody for use or a method according to clause 75 or clause 76, wherein the sample is biopsy sample of a solid tumour.

Clause 78. Anti-ICOS antibody for use in a method of treating a cancer in a patient, wherein the cancer is or has been characterised as being refractory to treatment with an immunooncology drug, e.g., anti-CTLA-4 antibody, anti-PD1 antibody, anti-PD-L1 antibody, anti-CD137 antibody or anti-GITR antibody.

Clause 79. A method of treating a cancer in a patient, wherein the cancer is or has been characterised as being refractory to treatment with an immunooncology drug, e.g., anti-CTLA-4 antibody, anti-PD1 antibody, anti-PD-L1 antibody, anti-CD137 antibody or anti-GITR antibody, the method comprising administering an anti-ICOS antibody to the patient.

Clause 80. Anti-ICOS antibody for use according to clause 78 or a method according to clause 79, wherein the method comprises:

- treating the patient with the immunooncology drug;
- determining that the cancer is not responsive to the drug;
- selecting the patient for treatment with the anti-ICOS antibody; and
- administering the anti-ICOS antibody to the patient.

Clause 81. Anti-ICOS antibody for use according to clause 78, or a method according to clause 79, wherein the method comprises administering an anti-ICOS antibody to a patient whose cancer was not responsive to prior treatment with the immunooncology drug.

Clause 82. Anti-ICOS antibody for use or a method according to any of clauses 73 to 81, wherein the cancer is a tumour derived from cells that have acquired ability to express ICOS ligand.

Clause 83. Anti-ICOS antibody for use or a method according to clause 82, wherein the cancer is melanoma.

Clause 84. Anti-ICOS antibody for use or a method according to any of clauses 73 to 81, wherein the cancer is derived from an antigen-presenting cell, such as a B lymphocyte (e.g., B cell lymphoma, such as diffuse large B cell lymphoma) or a T lymphocyte.

Clause 85. Anti-ICOS antibody for use or a method according to any of clauses 73 to 81, wherein the cancer is resistant to treatment with an anti-CD20 antibody.

Clause 86. Anti-ICOS antibody for use or a method according to clause 85, wherein the cancer is B cell lymphoma.

Clause 87. Anti-ICOS antibody for use or a method according to clause 86, wherein the anti-CD20 antibody is rituximab.

Clause 88. Anti-ICOS antibody for use or a method according to any of clauses 85 to 87, wherein the method comprises treating the patient with the anti-CD20 antibody;

determining that the cancer is not responsive to the anti-CD20 antibody;

testing a sample from a patient to determine that the cancer expresses ICOS ligand;

selecting the patient for treatment with the anti-ICOS antibody; and administering the anti-ICOS antibody to the patient.

Clause 89. Anti-ICOS antibody for use or a method according to any of clauses 85 to 87, wherein the method comprises administering an anti-ICOS antibody to a patient whose cancer was not responsive to prior treatment with anti-CD20 antibody.

Clause 90. Anti-ICOS antibody for use or a method according to any of clauses 67 to 89, wherein the cancer is a solid tumour.

Clause 91. Anti-ICOS antibody for use or a method according to any of clauses 67 to 89, wherein the cancer is a haemotological liquid tumour.

Clause 92. Anti-ICOS antibody for use or a method according to clause 90 or 91, wherein the tumour is high in regulatory T cells.

Clause 93. Anti-ICOS antibody for use or a method according to any of clauses 53 to 92, wherein the anti-ICOS antibody is as defined in any of clauses 1 to 28 or is provided in a composition according to clause 29.

Clause 94. A transgenic non-human mammal having a genome comprising a human or humanised immunoglobulin locus encoding human variable region gene segments, wherein the mammal does not express ICOS.

Clause 95. A method of producing an antibody that binds the extracellular domain of human and non-human ICOS, comprising (a) immunising a mammal according to clause 94 with human ICOS antigen;

(b) isolating antibodies generated by the mammal;

(c) testing the antibodies for ability to bind human ICOS and non-human ICOS; and (d) selecting one or more antibodies that binds both human and non-human ICOS.

Clause 96. A method according to clause 95, comprising immunising the mammal with cells expressing human ICOS.

Clause 97. A method according to clause 95 or clause 96, comprising (c) testing the antibodies for ability to bind human ICOS and non-human ICOS using surface plasmon resonance and determining binding affinities; and (d) selecting one or more antibodies for which the $K_D$ of binding to human ICOS is less than 50 nM and the $K_D$ of binding to non-human ICOS is less than 500 nM.

Clause 98. A method according to clause 97, comprising (d) selecting one or more antibodies for which the $K_D$ of binding to human ICOS is less than 10 nM and the $K_D$ of binding to non-human ICOS is less than 100 nM.

Clause 99. A method according to any of clauses 95 to 98, comprising (c) testing the antibodies for ability to bind human ICOS and non-human ICOS using surface plasmon resonance and determining binding affinities; and (d) selecting one or more antibodies for which the $K_D$ of binding to human ICOS is within 10-fold of the $K_D$ of binding to non-human ICOS.

Clause 100. A method according to clause 99, comprising (d) selecting one or more antibodies for which the $K_D$ of binding to human ICOS is within 5-fold of the $K_D$ of binding to non-human ICOS.

Clause 101. A method according to any of clauses 95 to 100, comprising testing the antibodies for ability to bind non-human ICOS from the same species as the mammal.

Clause 102. A method according to any of clauses 95 to 101, comprising testing the antibodies for ability to bind non-human ICOS from a different species as the mammal.

Clause 103. A method according to any of clauses 95 to 102, wherein the mammal is a mouse or a rat.

Clause 104. A method according to any of clauses 95 to 103, wherein the non-human ICOS is mouse ICOS or rat ICOS.

Clause 105. A method according to any of clauses 95 to 104, wherein the human or humanised immunoglobulin locus comprises human variable region gene segments upstream of an endogenous constant region.

Clause 106. A method according to clause 105, comprising (a) immunising a mammal according to clause 94 with human ICOS antigen, wherein the mammal is a mouse;

(b) isolating antibodies generated by the mouse;

(c) testing the antibodies for ability to bind human ICOS and mouse ICOS; and (d) selecting one or more antibodies that binds both human and mouse ICOS.

Clause 107. A method according to any of clauses 95 to 106, comprising isolating nucleic acid encoding an antibody heavy chain variable domain and/or an antibody light chain variable domain.

Clause 108. A method according to any of clauses 95 to 107, wherein the mammal generates antibodies through recombination of human variable region gene segments and an endogenous constant region.

Clause 109. A method according to clause 107 or clause 108, comprising conjugating the nucleic acid encoding the heavy and/or light chain variable domain to a nucleotide sequence encoding a human heavy chain constant region and/or human light chain constant region respectively.

Clause 110. A method according to any of clauses 107 to 109, comprising introducing the nucleic acid into a host cell.

Clause 111. A method according to clause 110, comprising culturing the host cell under conditions for expression of the antibody, or of the antibody heavy and/or light chain variable domain.

Clause 112. An antibody, or antibody heavy and/or light chain variable domain, produced by the method according to any of clauses 95 to 111.

Clause 113. A method of selecting an antibody that binds ICOS, optionally for selecting an ICOS agonist antibody, the assay comprising:

providing an array of antibodies immobilised (attached or adhered) to a substrate in a test well;

adding ICOS-expressing cells (e.g., activated primary T cells, or MJ cells) to the test well;

observing morphology of the cells;

detecting shape change in the cells from rounded to flattened against the substrate within the well; wherein the shape change indicates that the antibody is an antibody that binds ICOS, optionally an ICOS agonist antibody;

selecting the antibody from the test well;
expressing nucleic acid encoding the CDRs of the selected antibody; and
formulating the antibody into a composition comprising one or more additional components.

Various further aspects and embodiments of the present invention will be apparent to those skilled in the art in view of the present disclosure. All documents mentioned in this specification, including published US counterparts of any patents or patent applications referred to, are incorporated herein by reference in their entirety.

EXPERIMENTAL EXAMPLES

The following Examples describe the generation, characterisation and performance of anti-ICOS antibodies. Antibodies were generated using the Kymouse™, a transgenic mouse platform capable of generating antibodies with human variable domains. Antibodies from the Kymouse™ have human variable domains, generated from human V (D) and J segments, and mouse constant domains. The endogenous mouse variable genes have been silenced and make up a very small portion of the repertoire (less than 0.5% of all heavy chain variable regions are of mouse origin). The Kymouse™ system is described in Lee et al 2014 [39], WO2011/004192, WO2011/158009 and WO2013/061098. This project employed the Kymouse™ HK strain, in which the heavy chain locus and light chain kappa locus are humanised.

ICOS knock-out Kymouse™ were immunised with either ICOS protein or a combination of alternating boosts of protein and cells expressing human and mouse ICOS.

Hits which bound to human ICOS were identified. The primary selection criteria for the screen was binding to human cell expressed ICOS (CHO cells) and binding to ICOS protein (HTRF). Binding to mouse ICOS protein and mouse cell expressed ICOS (CHO cells) was also assessed and taken into consideration when selecting primary screen hits. Using these criteria hits were progressed to a secondary screen. In the secondary screen hits were confirmed by determining binding to human and mouse ICOS expressed on CHO cells by flow cytometry.

From a large number of antibodies screened, a small panel were identified which bind to human/cynomolgus and mouse ICOS as determined by surface plasmon resonance and flow cytometry. These antibodies included STIM001, STIM002 and its variant STIM002-B, STIM003, STIM004 and STIM005. An additional four antibodies STIM006, STIM007, STIM008 and STIM009 were also selected, showing less cross-reactivity with mouse ICOS but demonstrating agonism of the human ICOS receptor. The data presented here indicate the ability of anti-ICOS antibodies to act as agonists of the ICOS receptor in an ICOS positive CD4+ cell line and also in a primary T cell-based assay, show cell-killing ability in an ADCC assay and an ability to promote an anti-tumour immune response in vivo.

Example 1: Generation of ICOS Knock-Out Mouse

An ICOS knock-out Kymouse™ line was generated by homologous recombination in Kymouse™ HK ES cells. In brief, a 3.5 kb targeting vector encoding a puromycin selection was targeted into ES cells. Successful targeting resulted in the replacement of a small region (72 bp) of the mouse ICOS locus with the puromycin cassette, disrupting the signal peptide/start codon of the gene. Positive ES clones were expanded and microinjected into mouse blastocysts and resulting chimaeras bred in order to ultimately generate animals homozygous for both the humanised heavy and kappa immunoglobulin loci and the modified, functionally-null, ICOS locus.

Example 2: Antigen and Cell-Line Preparation

Generation of Stably Transfected MEF and CHO-S Cells Expressing Human or Mouse ICOS Full length DNA sequences encoding human and mouse ICOS were codon optimised for mammalian expression, ordered as synthetic string DNA and cloned into an expression vector under the control of the CMV promoter and flanked by 3' and 5' piggyBac specific terminal repeat sequences facilitating stable integration into the cell genome (see [40]). The expression vector contained a puromycin selection cassette to facilitate stable cell line generation. For generation of human ICOS expressing and mouse ICOS expressing cell lines respectively, the human or mouse ICOS expression plasmid was co-transfected with a plasmid encoding piggyBac transposase into a mouse embryonic fibroblast (MEF) cell line and CHO-S cells using the FreeStyle Max transfection reagent (Invitrogen) according to manufacturer instructions. MEF cells were generated from embryos obtained from a 129S5 crossed to C57BL6 female mouse. Twenty four hours after transfection, the media was supplemented with puromycin and grown for at least two weeks to select stable cell lines. Cell culture medium was replaced every 3-4 days. Expression of human or mouse ICOS protein was assessed by flow cytometry using anti-human or anti-mouse ICOS-PE conjugated antibodies (eBioscience) respectively. Complete MEF media was made up of Dulbecco's Modified Eagle's Medium (Gibco) supplemented with 10% v/v fetal bovine serum (Gibco). Complete CHO-S media was made up of CD-CHO media supplemented with 8 mM Glutamax (Gibco). CHO-S cells are the CHO-3E7 cell line included with the pTT5 system available from the National Research Council of Canada, but other CHO cell lines could be employed.

Preparation of MEF Cells for Mouse Immunisations

Cell culture medium was removed and cells washed once with 1×PBS. Cells were treated for 5 minutes with trypsin to loosen cells from tissue culture surface. Cells were collected and the trypsin neutralized by the addition of complete media containing 10% v/v fetal bovine serum (FCS). Cells were then centrifuged at 300 g for 10 minutes and washed with 25 ml of 1×PBS. Cells were counted and resuspended at the appropriate concentration in 1×PBS.

Cloning and Expression of Recombinant Proteins

Synthetic DNA encoding the extracellular domains of human ICOS (NCBI ID: NP_036224.1), mouse ICOS (NCBI ID: NP_059508.2) and cynomolgus ICOS (GenBank ID: EHH55098.1) were cloned into either a pREP4 (Invitrogen) or a pTT5 (National Research Council Of Canada) expression plasmid using standard molecular biology techniques. The constructs also contained either a human Fc, a mouse Fc or a FLAG His peptide motif to aid purification and detection. These were added to the DNA constructs by overlap extension. All constructs were sequenced prior to expression to ensure their correct sequence composition.

Example 3: Immunisation

ICOS knock out HK Kymice™ (see Example 1), Kymouse™ wild type HK strain and Kymouse™ wild type HL strain were immunised according to the regimens shown in Table E3. Kymouse™ wild type HK and HL strains express wild type mouse ICOS. In the HK strain the immunoglobulin heavy chain locus and light chain kappa locus are humanised, and in the HL strain the immunoglobulin heavy chain locus and light chain lambda locus are humanised.

TABLE E3

Immunisation regimens for Kymouse ™ strains

| Regime | Mouse | Prime | Boost 1 | Boost 2 | Boost 3 | Final Boost |
|---|---|---|---|---|---|---|
| KM103 | ICOS KO | mICOS Fc | hICOS MEF | mICOS Fc | hICOS MEF | mICOS Fc |
| KM103 | ICOS KO | mICOS Fc | hICOS Fc | mICOS Fc | hICOS Fc | N/A |
| KM111 | ICOS KO | mICOS Fc + hICOS Fc | mICOS MEF + hICOS MEF | mICOS Fc + hICOS Fc | mICOS MEF + hICOS MEF | mICOS Fc + hICOS Fc |
| KM111 | ICOS KO | hICOS Fc | hICOS MEF | hICOS Fc | hICOS MEF | hICOS Fc |
| KM111 | ICOS KO | mICOS Fc | mICOS MEF | mICOS Fc | mICOS MEF | mICOS Fc |
| KM111 | HK and HL | hICOS Fc | hICOS MEF | hICOS Fc | hICOS MEF | hICOS Fc |
| KM135 | ICOS KO | mICOS Fc 1 prime and 6 boosts (RIMMS) | | | | |
| KM135 | ICOS KO | hICOS Fc 1 prime and 6 boosts (RIMMS) | | | | |

Key to table:
mICOS Fc = mouse ICOS protein with human Fc
hICOS Fc = human ICOS protein with human Fc
mICOS MEF = mouse ICOS expressed on MEF cells
hICOS MEF = human ICOS expressed on MEF cells
mICOS Fc + hICOS Fc = mouse ICOS protein with human Fc + human ICOS protein with human Fc administered simultaneously
mICOS MEF + hICOS MEF = mouse ICOS expressed on MEF cells + human ICOS expressed on MEF cells administered simultaneously
ICOS KO = ICOS knockout HK Kymouse
HK and HL = wild type Kymouse HK and HL genotype
RIMMS is a modified sub-cutaneous immunisation procedure (rapid immunisation at multiple sites); modified after Kilpatrick et al. [41]). Immunisation regimens KM103 and KM111 were prime-rest-boost by intraperitoneal (i.p.) administration. Sigma Adjuvant System was used for all immunisations and rest intervals were usually between 2 and 3 weeks. Final boosts were administered by intravenously in absence of adjuvant.

Sera from serial or terminal blood samples were analysed for the presence of specific antibodies by flow cytometry and the titre data was used (where possible) to select mice to be used for B cell sorting.

Example 4: Comparison of Serum Titres Between ICOS KO and Wild Type Mice

Figure 1B:
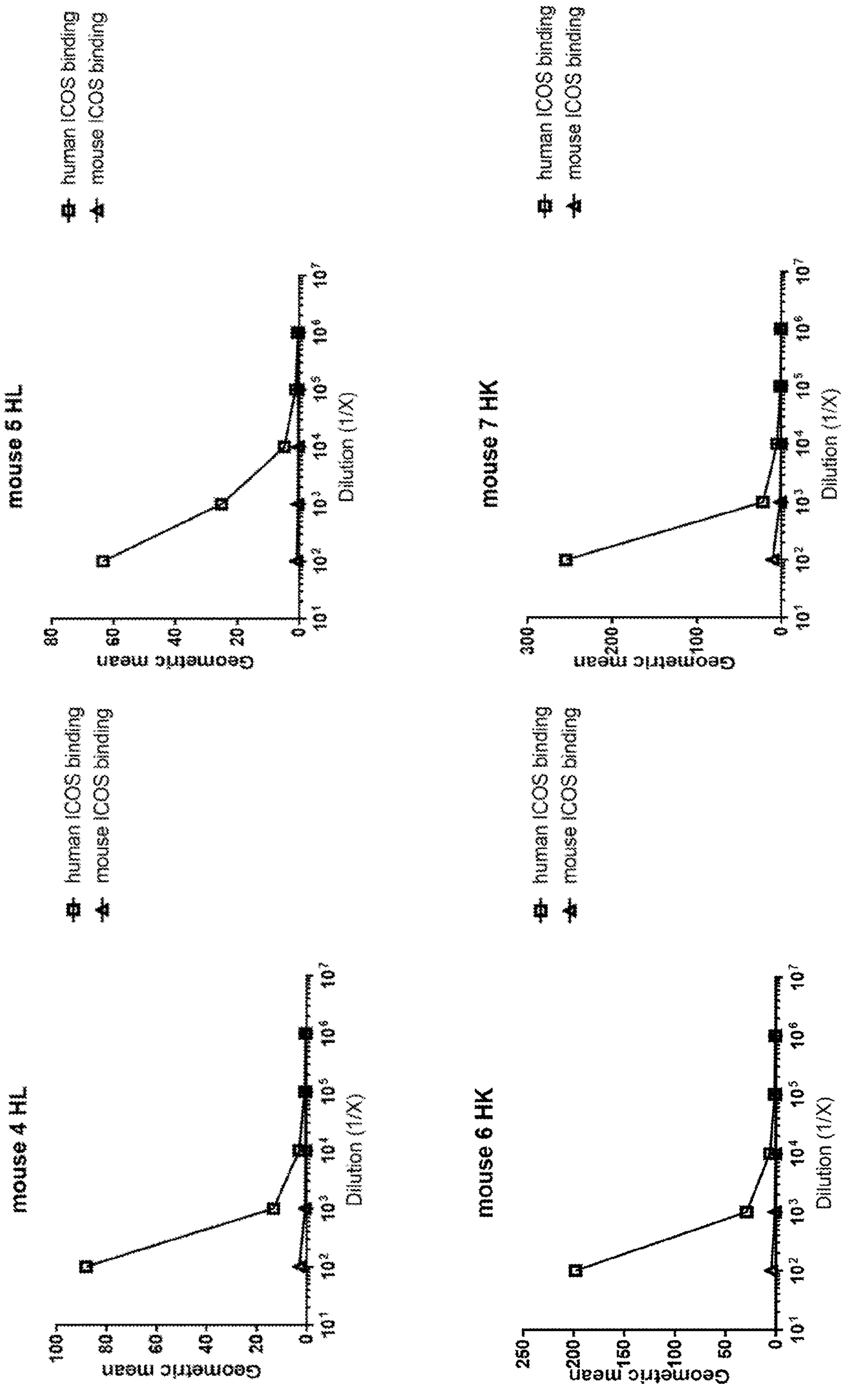

Serum titres of immunised ICOS KO and immunised wild type Kymouse were determined using flow cytometry. In ICOS KO mice, immunisation with human ICOS antigen induced a serum immunoglobulin response with Ig binding to both human and mouse ICOS expressed on CHO cells (FIG. 1*a*). Conversely, in the wild type Kymouse (expressing mouse ICOS), immunisation with the same human ICOS antigen produced sera that showed markedly reduced binding to mouse ICOS compared with binding of the same serum to human ICOS (FIG. 1*b*).

Method

CHO-S cells expressing human ICOS or mouse ICOS (see Example 2) or untransfected CHO-S cells (referred to as wild type (WT)), suspended in FACS buffer (PBS+1% w/v BSA+0.1% w/v sodium azide) were distributed to a 96-well, V-bottom plate (Greiner) at a density of $10^5$ cells per well. A titration of mouse serum was prepared, diluting samples in FACS buffer. 50 μL/well of this titration was then added to the cell plate. To determine the change in activity level due to immunisation, serum from each animal prior to immunisation was diluted to 1/100 in FACS buffer and 50 μL/well added to the cells. Cells were incubated at 4° C. for 1 hour. Cells were washed twice with 150 μL PBS, centrifuging after each wash step and aspirating supernatant (centrifuged at 300×g for 3 minutes). To detect antibody binding, APC goat-anti-mouse IgG (Jackson ImmunoResearch) was diluted 1/500 in FACS buffer and 50 μL was added to the cells. In some instances AF647 goat-anti-mouse IgG (Jackson ImmunoResearch) was used. Cells were incubated 1 hour at 4° C. in the dark, then washed twice with 150 μL PBS as above. To fix cells, 100 μL 2% v/v paraformaldehyde was added and cells incubated for 30 minutes at 4° C. Cells were then pelleted by centrifugation at 300×g and the plates resuspended in 50 μL of FACS buffer. Fluorescent signal intensity (geometric mean) was measured by flow cytometry using a BD FACS Array instrument.

Example 5: Sorting of Antigen-Specific B Cells by FACS

B-cells expressing anti-ICOS antibodies were recovered from immunised mice, using techniques substantially as described in Example 1 of WO2015/040401. In brief, splenocytes and/or lymph node cells isolated from the immunisation regimes were stained with an antibody cocktail containing markers for the selection of cells of interest (CD19), whereas unwanted cells were excluded from the final sorted population (IgM, IgD, 7AAD). CD19+B-cells were further labelled with fluorescently-tagged human ICOS ECD-Fc dimers and fluorescently-tagged mouse ICOS ECD-Fc to detect B-cells producing anti-ICOS antibodies. Fluorescent labelling of human and mouse ICOS was with AlexaFluor647 and AlexaFluor488, respectively—see Example 6. Cells binding human ICOS, or both human and mouse ICOS were selected. These cells were single cell sorted by FACS into lysis buffer. V-region sequences were recovered using RT-PCR and two further rounds of PCR, then bridged to mouse IgG1 constant region and expressed in HEK293 cells. Supernatants from HEK293 cells were screened for the presence of ICOS binding and functional antibodies. This method is hereafter referred to as BCT.

Example 6: Screening of Antibodies from BCT

HTRF Screening of BCT Supernatants for Binding to Recombinant Human and Mouse ICOS-Fc Supernatants collected from BCT in Example 5 were screened for the ability of secreted antibodies to bind to human ICOS Fc and mouse ICOS Fc expressed as recombinant proteins. Binding of secreted antibodies to recombinant human and mouse ICOS were identified by HTRF® (Homogeneous Time-Resolved Fluorescence, Cisbio) assay format using FluoProbes®647H (Innova Biosciences) labelled ICOS (referred to herein as 647 hICOS or 647 mICOS for human ICOS and mouse ICOS labelled with FluoProbes®647H respectively). 5 μL BCT supernatant was transferred to a white 384-well, low-volume, non-binding surface polystyrene plate (Greiner). 5 μL of 20 nM 647 hICOS or 647 mICOS diluted in HTRF assay buffer was added to all wells. For human ICOS binding assay the reference antibody was diluted in BCT media (Gibco #A14351-01) to 120 nM and 5 μL added to plate. For negative control wells for human ICOS binding assay, 5 μL of mouse IgG1 (Sigma M9269 in some instances referred to as CM7) diluted to 120 nM in BCT media. In the case of mouse ICOS binding assay the reference antibody was diluted in BCT media (Gibco #A14351-01) to 120 nM and 5 μL added to plate. A rat IgG2b isotype control (R&D systems) was added to negative control wells (R&D Systems) diluted in BCT media to 120 nM and 5 μL added to plate. Binding of secreted antibodies to human ICOS was detected by addition of 10 μL of goat anti-mouse IgG (Southern Biotech) directly labelled with Europium cryptate (Cisbio) diluted 1/2000 in HTRF assay buffer. In the case of the mouse ICOS binding assay 5 μL of mouse anti-Rat IgG2B-UBLB (Southern Biotech) was added to positive and negative control wells, and 5 μL of HTRF assay buffer added to all other wells of plate. Then 5 μL of goat anti-mouse IgG (Southern Biotech) directly labelled with Europium cryptate (Cisbio) diluted 1/1000 in HTRF assay buffer was added to detect binding. The plate was left to incubate in the dark for 2 hours prior to reading time resolved fluorescence at 620 nm and 665 nm emission wavelengths, 100 flashes, using an EnVision plate reader (Perkin Elmer).

Data were analysed by calculating 665/620 ratio and percent effect for each sample according to equation 2 and equation 1 respectively.

For KM103 and KM11-B1, primary hits were selected based on greater than or equal to 5 percent effect for binding to human and mouse ICOS. For KM135 primary hits were selected based on greater than or equal to 10 percent effect for binding to human and mouse ICOS. For KM111-B2 primary hits were defined as greater than or equal to 4 percent effect for binding to human and greater than or equal to 3 percent effect for binding to mouse ICOS.

Equation 1

Calculation of Percentage Effect from PrimaryScreen Envision cell binding and HTRF Using well ratio value (equation 3) or 665/620 nm ratio (see equation 2) (HTRF) Percent effect =

$$\frac{(\text{sample well} - \text{non-specific binding}) \times 100}{(\text{total binding} - \text{non-specific binding})}$$

Non-specific binding = values from wells containing isotype control mouse IgG1

Total Binding = values from wells containing reference antibody

Equation 2

Calculation of 665/620 ratio $$665/620\ \text{ratio} = (\text{sample } 665/620\ \text{nm value}) \times 10{,}000$$

-continued

Equation 3

Calculation of 647/FITC ratio

Data were first normalised for cell number by dividing mAb channel (647) by FITC (cell stain) channel to give "well ratio value":

$$\text{Well Ratio Value} = \frac{647\ \text{Channel}}{FITC\ \text{Channel}}$$

Screening of BCT Supernatants for Binding to Cell-Expressed Human and Mouse ICOS Supernatants collected from BCT in Example 5 were screened for the ability of secreted antibodies to bind to human or mouse ICOS expressed on the surface of CHO-S cells. To determine CHO-S human and mouse ICOS binding, cells were plated in black-walled, clear-bottom tissue culture treated 384-well plates (Perkin Elmer) at $4\times10^4$/well in F12 media (Gibco) supplemented with 10% FBS (Gibco) and cultured overnight. Culture media was removed from 384-well assay plates. At least 50 μL of BCT supernatant or 50 μL reference antibody at 2 μg/mL in BCT media or isotype IgG1 control antibody (referred to in some instances as Cm7, Sigma M9269), at a final concentration of 2 μg/mL) diluted in BCT media were added to each well. Plates were incubated for 1 hour at 4° C. Supernatant was aspirated and 50 μL of goat anti-Mouse 647 (Jackson immunoresearch) at 5 μg/ml with vibrant green DNA stain (Life Technologies) diluted 1 in 500 in secondary antibody buffer (1×PBS+1% BSA+0.1% Sodium Azide) was added to detect antibody binding and visualise cells. Plates were incubated for 1 hr at 4 degrees. Supernatant was aspirated and 25 μL of 4% v/v paraformaldehyde added and plates were incubated for 15 minutes at room temperature. Plates were washed twice with 100 μL PBS and then the wash buffer was completely removed. Fluorescence intensity was measured using Envision plate reader (Perkin Elmer) measuring FITC (excitation 494 nm, emission 520 nm) and alexafluor 647 (excitation 650 nm, emission 668 nm). Assay signal was determined as described in equation 3 and percent effect as in equation 1. Total binding was defined using reference antibody at a final assay concentration of 2 μg/mL. Non-specific binding was defined using mouse IgG1 isotype control (Sigma) at a final assay concentration of 2 μg/mL. Criteria for hit selection were based on assay signal and percent effect.

For KM103, KM111-B1 and KM135, primary hits were selected based on greater than or equal to 10 percent effect. For KM111-B2, primary hits were selected based on greater than or equal to 4 percent effect.

Summary of Primary Screening Results

TABLE E6

Summary of number of BCT supernatants screened from immunisations, and number of supernatants meeting primary screening selection criteria for binding to human and mouse ICOS.

| Experiment ID | Supernatants screened | Primary hits selected |
|---|---|---|
| KM103 | 1232 | 40 |
| KM111-B1 | 1056 | 198 |
| KM111-B2 | 1056 | 136 |
| KM135 | 704 | 31 |

FACS Screening for Binding to Cell Expressed Human and Mouse ICOS

BCT supernatants and HEK293 expressed antibodies from Example 5 were tested for ability to bind to CHO-S cells expressing human or mouse ICOS.

CHO-S cells expressing human or mouse ICOS (see Example 2), were diluted in FACS buffer (PBS 1% BSA 0.1% sodium azide) and were distributed to a 96-well, V-bottom plate (Greiner) at a density of $1\times10^5$ cells per well. Cells were washed with 150 μL PBS and centrifuged at 300 g for 3 minutes. For supernatant screening, supernatant was aspirated and 150 μL PBS added. This wash step was repeated. 30 μL BCT undiluted supernatant or 50 μL of reference antibody or control antibody diluted to 5 μg/ml in BCT media was added to the washed cells. Cells were incubated at 4° C. for 60 minutes. 150 μL FACS buffer was added and cells washed as described above. To detect antibody binding, 50 μL of goat anti-mouse APC (Jackson ImmunoResearch) diluted to 2 μg/ml in FACS buffer was added to cells. Cells were incubated 4° C. for 60 minutes. Cells were washed twice with 150 μL FACS buffer, centrifuging at 300 g for 3 minutes after each wash step and aspirating supernatant. Cells were fixed by addition of 25 μL 4% paraformaldehyde for 20 minutes at room temperature. Cells were washed once as above and resuspended in FACS buffer for analysis. APC signal intensity (geometric mean) was measured by flow cytometry using a BD FACS Array instrument. Data were plotted as geometric mean values without further calculation.

A small sub-set of antibodies were selected as meeting more stringent species cross-reactivity criteria in this further screening compared with the primary screening. In brief:

From KM103, 4 antibodies were selected by taking the average geomean of the hybrid control binding to hICOS, mICOS and WT CHO cells and identifying mouse and human binders that were >4 fold above. These 4 antibodies were designated STIM001, STIM002-B, STIM007 and STIM009.

From KM111-81, 4 antibodies were selected by taking the average of geomean of the negative control (Armenian hamster: clone HTK888) binding to hICOS, mICOS and WT CHO cells and identifying mouse and human binders that were >10 fold above.

From KM111-82, 4 antibodies were selected by taking the average of geomean of the negative control (Armenian hamster: clone HTK888) binding to hICOS, mICOS and WT CHO cells and identifying mouse and human binders that were >4 fold above. These 4 antibodies included STIM003, STIM004 and STIM005.

From KM135, no cross-reactive antibodies were identified. Due to a technical failure of the FACS secondary screening method, screening was also carried out using SPR and HTRF, but no antibodies were found to meet the desired cross-reactivity level.

In conclusion, from the various multiple immunisation regimens described in Example 3, upward of 4000 BCT supernatants (from the ICOS KO mice only) were screened for binding to human ICOS and mouse ICOS, and a small panel of candidates, including STIM001, STIM002-B, STIM003, STIM004, STIM005, STIM007 and STIM009, were identified as having the most promising characteristics for further development. These were taken forward for more detailed characterisation.

Separately, two antibodies STIM006 and STIM008, which did not meet the species cross-reactivity criteria, were also chosen for further characterisation on the basis of their ability to bind human ICOS.

Example 7: Affinity Determination by Surface Plasmon Resonance (SPR)

Fab affinities of the ICOS leads were generated by SPR using the ProteOn XPR3 6 (BioRad). An anti-human IgG capture surface was created on a GLC biosensor chip by primary amine coupling, immobilising three anti-human IgG antibodies (Jackson Labs 109-005-008, 109-006-008 and 309-006-008). The human Fc tagged human ICOS (hICOS) and mouse ICOS (mICOS) were captured individually on the anti-human IgG surface and the purified Fabs were used as analytes at 5000 nM, 1000 nM, 200 nM, 40 nM and 8 nM, except for STIM003 which was used at 1000 nM, 200 nM, 40 nM, 8 nM and 2 nM. Binding sensorgrams were double referenced using a buffer injection (i.e. 0 nM), and the data was fitted to the 1:1 model inherent to the ProteOn XPR36 analysis software. The assay was run at 25° C. and using HBS-EP as running buffer.

TABLE E7-1

Affinity and kinetic data for selected antibodies as measured by SPR.

| Sample Ab | Ligand | ka | kd | KD (nM) |
|---|---|---|---|---|
| STIM006 | hICOS | 6.67E+05 | 9.20E−03 | 13.8 |
| STIM003 | hICOS | 6.56E+05 | 8.62E−04 | 1.3 |
| STIM001 | hICOS | 2.54E+04 | 1.12E−03 | 44.0 |
| STIM002 | hICOS | 3.20E+04 | 3.43E−02 | 1070.0 |
| STIM006 | mICOS | 1.57E+03 | 5.00E−04 | 318.0 |
| STIM003 | mICOS | 1.29E+06 | 5.03E−04 | 0.4 |
| STIM001 | mICOS | 5.66E+04 | 2.30E−02 | 407.0 |
| STIM002 | mICOS | weak | weak | weak |

In addition, a comparison was performed of antibody: antigen binding affinity at different pH values. As before, the dimeric human ICOS protein, presented as the extracellular domain of ICOS fused to a human Fc region, was captured on the anti-human Fc capture surface created using the 3 antibody cocktail, immobilised on the GLC biosensor chip by primary amine coupling. SPR analysis of recombinantly expressed anti-ICOS Fabs was carried out on the ProteOn XPR36 Array system (Biorad). The Fab fragments were used as analyte to generate binding sensorgrams, which were double referenced with a buffer injection (i.e., 0 nM). The subsequent referenced sensorgrams were fitted to the 1:1 model inherent to the ProteOn analysis software. Table E7-2 presents affinity and kinetic data for the antibodies, all run at 3TC unless stated, using either HBS-EP at pH 7.4/7.6 or pH 5.5 as indicated. Data were fitted to the 1:1 model. Note that data for STIM002 fitted poorly to the 1:1 model at both pH 7.4 and 5.5—the affinity for this antibody may therefore be lower than indicated in the table.

TABLE E7-2

Relative affinity of STIM001, STIM002, STIM002-B and STIM003 Fabs against recombinant human ICOS, at 37° C. except where stated.

| Antibody (Fab) | pH | ka | kd | KD (nM) |
|---|---|---|---|---|
| STIM001 | 7.4 | 5.08E+04 | 3.23E−03 | 63.5 |
| | 5.5 | 4.90E+04 | 3.58E−03 | 73.1 |
| | 7.6 | 8.29E+04 | 3.54E−03 | 42.6 |
| | 5.5 | 6.77E+04 | 5.41E−03 | 80.3 |
| | 7.6 (25° C.) | 2.54E+04 | 1.12E−03 | 44 |
| STIM002 | 7.4 | 3.72E+04 | 8.31E−03 | 223 |
| | 5.5 | 8.79E+04 | 3.67E−03 | 4.17 |
| STIM002-B | 7.4 | 8.28E+04 | 3.46E−03 | 41.8 |
| | 5.5 | 8.64E+04 | 2.30E−03 | 26.6 |

TABLE E7-2-continued

Relative affinity of STIM001, STIM002, STIM002-B and STIM003 Fabs against recombinant human ICOS, at 37° C. except where stated.

| Antibody (Fab) | pH | ka | kd | KD (nM) |
|---|---|---|---|---|
| STIM003 | 7.4 | 1.49E+06 | 2.54E−03 | 1.71 |
| | 5.5 | 1.55E+06 | 1.58E−03 | 1.02 |
| | 7.6 | 1.87E+06 | 3.70E−03 | 1.98 |
| | 5.5 | 1.71E+06 | 1.94E−03 | 1.15 |
| | 7.6 (25° C.) | 6.65E+06 | 0.862E−03 | 1.31 |

Comparison of the affinity data at different pH values indicated that the antibodies retain binding to their target across a physiological pH range. The tumour microenvironment may be relatively acidic compared with blood, thus maintenance of affinity at low pH is a potential advantage in vivo to improve intra-tumoural T-reg depletion.

Example 8: Neutralisation of ICOS Ligand Binding to ICOS Receptor Assayed by HTRF Selected anti-ICOS antibodies were further assessed for their ability to neutralise ICOS ligand (B7-H2) binding to ICOS, using homogenous time resolved fluorescence (HTRF). Human IgG1 and human IgG4.PE (null-effector) isotypes of the mAbs were assessed in:

- HTRF assay for neutralisation of human B7-H2 binding to human ICOS; and
- HTRF assay for neutralisation of mouse B7-H2 binding to mouse ICOS.

Anti-ICOS antibody C398.4A (hamster IgG in each case) was included for comparison.

A number of antibodies were found to have high neutralising potency for human and/or mouse ICOS receptor-ligand binding, and the results indicated that some of these antibodies showed good cross-reactivity. The antibody isotype had no significant effect, differences in results between the IgG1 and IgG4.PE assays being within experimental error.

IgG1

In the human IgG1 assays, antibody C398.4A produced an IC50 of 1.2±0.30 nM for the neutralisation of human ICOS ligand and an IC50 of 0.14±0.01 nM for the neutralisation of mouse ICOS ligand.

IgG1 mAbs STIM001, STIM002, STIM003 and STIM005 produced similar IC50 to C398.4A using the human ICOS ligand neutralisation system and were also cross-reactive, neutralising binding of mouse ICOS ligand to the mouse ICOS receptor.

Two additional cross-reactive mAbs, STIM002-B and STIM004, showed weaker human and mouse ICOS ligand neutralisation.

STIM006, STIM007, STIM008 and STIM009 showed neutralisation of human ICOS ligand but did not demonstrate significant cross-reactivity in the mouse ICOS ligand neutralisation system. Neutralising IC50 values for mouse B7-H2 ligand could not be calculated for these antibodies.

TABLE E8-1

Figure 2:
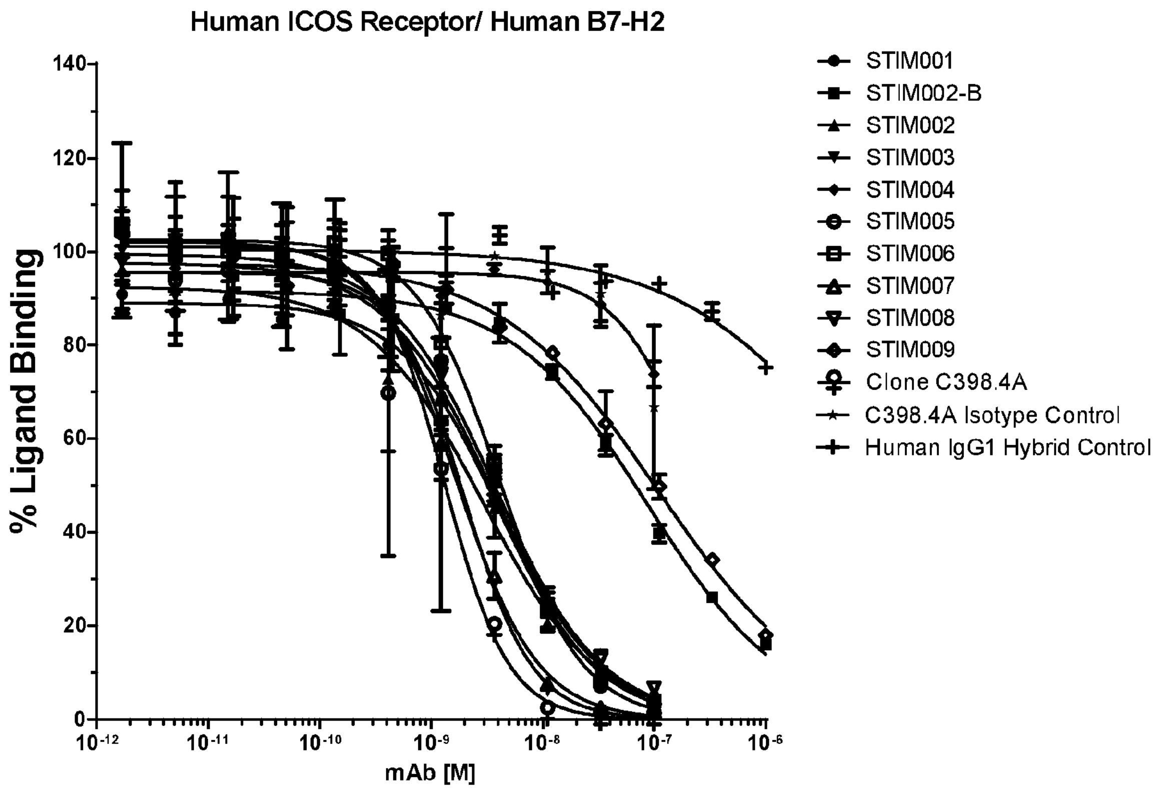
FIG. 2: Human ICOS-ligand neutralisation HTRF with human ICOS receptor. Neutralisation profiles of STIM001 to STIM009 anti-ICOS mAbs in human IgG1 format compared to C398.4A and respective isotype controls. Data representative of four experiments.

IC50 values for human IgG1 isotype mAb for neutralisation of human ICOS Receptor binding to human B7-H2. See also FIG. 2.

| | Mean IC50 (nM) | SD (nM) (n = 4) |
|---|---|---|
| STIM001 | 2.2 | 1.3 |
| STIM002 | 1.9 | 0.8 |
| STIM002-B | 3.6 | 3.5 |
| STIM003 | 1.3 | 0.5 |
| STIM004 | 233 | 123 |
| STIM005 | 2.5 | 0.8 |
| STIM006 | 2.2 | 1.5 |
| STIM007 | 1.1 | 0.5 |
| STIM008 | 1.6 | 1.4 |
| STIM009 | 30.5 | 53 |
| C398.4A | 1.2 | 0.3 |

TABLE E8-2

Figure 3:
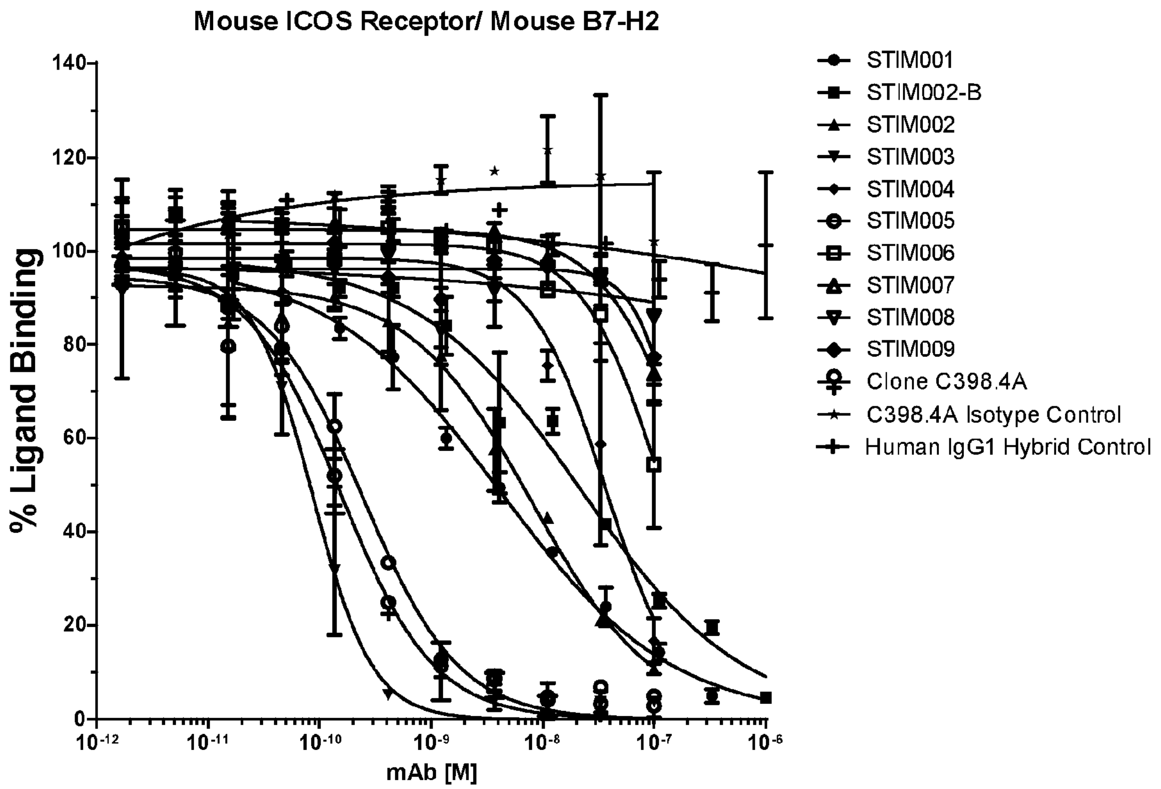
FIG. 3: Mouse ICOS-Ligand neutralisation HTRF with mouse ICOS receptor. Neutralisation profiles of STIM001 to STIM009 anti-ICOS mAbs in human IgG1 format compared to C398.4A and respective isotype controls. Data representative of three experiments.

IC50 values for human IgG1 isotype mAb for neutralisation of mouse ICOS Receptor binding to mouse B7-H2. See also FIG. 3.

| | Mean IC50 (nM) | SD (nM) (n = 3) |
|---|---|---|
| STIM001 | 6.5 | 2.5 |
| STIM002 | 6.9 | 2.1 |
| STIM002-B | 30 | 11.4 |
| STIM003 | 0.1 | 0 |
| STIM004 | 22.1 | 15.4 |
| STIM005 | 0.3 | 0.2 |
| C398.4A | 0.1 | 0 |

IgG4.PE

As expected, IgG4.PE mAbs produced similar results to the IgG1 isotypes.

STIM001, STIM003 and STIM005 showed similar IC50 values to C398.4A using the human ICOS ligand neutralisation system. These mAbs were also cross-reactive at neutralising mouse ICOS ligand. STIM002-B and STIM004 produced weaker IC50 values for human ICOS B7-H2 neutralisation and mouse B7-H2 ligand. STIM007, STIM008 and STIM009 showed neutralisation of human ICOS ligand binding to human ICOS receptor but neutralising IC50 values for mouse B7-H2 ligand could not be calculated in these assays.

IgG4.PE isotypes of STIM006 and STIM002 were not assayed.

TABLE E8-3

Figure 4:
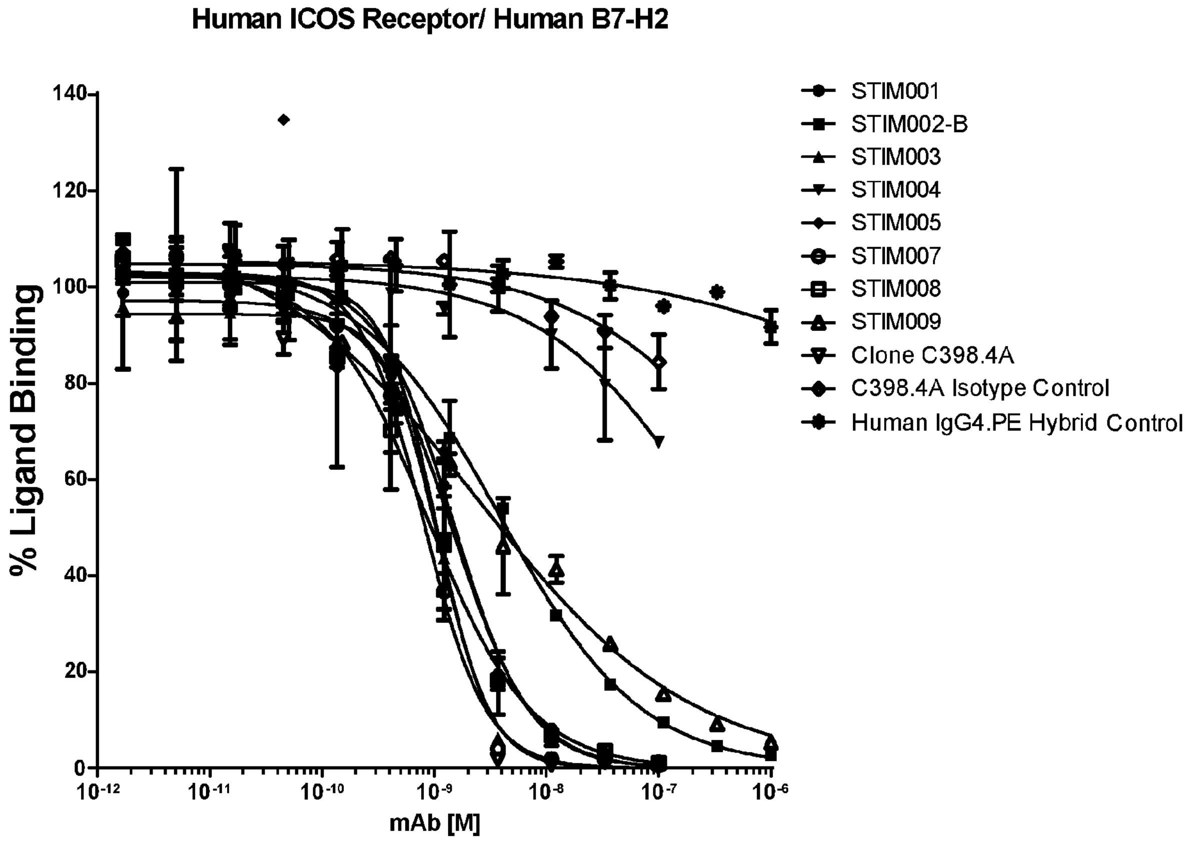
FIG. 4: Human ICOS-Ligand direct neutralisation HTRF with human ICOS receptor. Neutralisation profiles of STIM001 to STIM009 anti-ICOS mAbs in human IgG4.PE format compared to C398.4A and respective isotype controls. Data representative of four experiments.

IC50 values for human IgG4.PE isotype mAb for neutralisation of human ICOS Receptor binding to human B7-H2. See also FIG. 4.

| | Mean IC50 (nM) | SD (nM) (n = 4 unless otherwise stated) |
|---|---|---|
| STIM001 | 1.3 | 0.2 |
| STIM002-B | 3.4 | 1.8 |
| STIM003 | 1.2 | 0.3 |
| STIM004 | 161 | 152 (n = 3) |
| STIM005 | 1.6 | 0.2 |
| STIM006 | 0.8 | (n = 1) |
| STIM007 | 0.8 | 0.1 |
| STIM008 | 0.8 | 0.1 |
| STIM009 | 4.6 | 2.2 |
| C398.4A | 2.8 | 3.8 |

TABLE E8-4

Figure 5:
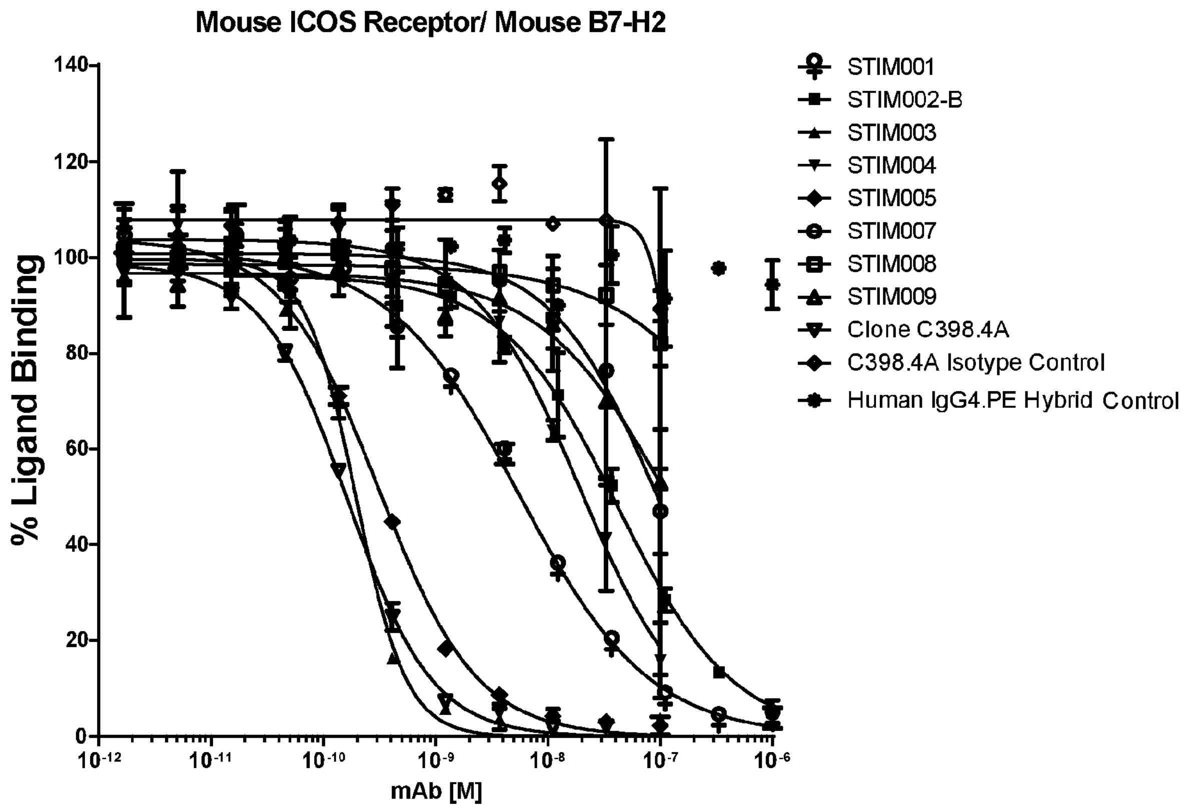
FIG. 5: Mouse ICOS-Ligand neutralisation HTRF with mouse ICOS receptor. Neutralisation profiles of STIM001 to STIM009 anti-ICOS mAbs in human IgG4.PE format compared to C398.4A and respective isotype controls. Data representative of four experiments.

IC50 values for human IgG4.PE isotype mAb for neutralisation of mouse ICOS Receptor binding to mouse B7-H2. See also FIG. 5.

| | Mean IC50 (nM) | SD (nM) (n = 3) |
|---|---|---|
| STIM001 | 4.7 | 2.1 |
| STIM002-B | 43.9 | 25.7 |
| STIM003 | 0.2 | 0.1 |
| STIM004 | 30 | 14 |
| STIM005 | 0.3 | 0.1 |
| C398.4A | 0.2 | 0.1 |

Materials and Methods

Test antibodies and isotype controls were diluted in assay buffer (0.53 M Potassium Fluoride (KF), 0.1% Bovine Serum Albumin (BSA) in 1×PBS) from a starting working concentration of up to 4 μM, 1 μM final to 0.002 nM, 5.64e-4 nM final over 11 point titration, 1 in 3 dilutions. Titrations of 5 μl of antibody were added to 384w white walled assay plate (Greiner Bio-One). Positive control wells received 5 μl of assay buffer only.

5 μl of ICOS receptor (human ICOS-mFc, 20 nM, 5 nM final or mouse ICOS-mFc 4 nM, 1 nM final (Chimerigen)) was added to required wells. Plate was incubated for 1 hr at room temperature (RT). After incubation, 5 μl of either mouse or human ICOS ligand, (B7-H2, R&D Systems) conjugated to Alexa 647 (Innova Bioscience) was diluted to either 32 nM (8 nM final) for human B7-H2 or 30 nM, 7.5 nM final for mouse B7-H2 and added to all wells of assay plate except negative control wells which instead received 5 μl of assay buffer.

Finally, 5 μl of anti-mouse IgG donor mAb (Southern Biotech) labelled with europium cryptate (Cis Bio), 40 nM, 10 nM final was added to each well and the assay was left in the dark at RT to incubate for a further 2 hours. After incubation, assay was read on Envision plate reader (Perkin Elmer) using a standard HTRF protocol. 620 nm and 665 nm channel values were exported to Microsoft Excel (Microsoft) and % Delta-F and % Neutralisation calculations performed. Titration curves and IC50 values [M] were plotted using Graphpad (Prism). IC50 values were calculated by first transforming the data using equation X=Log (X). The transformed data was then fitted using nonlinear regression, using fitting algorithm, log (inhibitor) vs. response—variable slope (four parameters).

% Delta-$F$ Calculation:

665/620 nm ratio for ratio metric data reduction.

$$\%\ \text{Delta}\ F = \frac{(665/620\ \text{nm Well Signal Ratio} - \text{Signal Negative Control})}{(\text{Signal Negative Control})} * 100$$

Signal Negative control = average of minimum signal ratio.

% Neutralisation:

$$\%\ \text{Max (neutralisation)} = \frac{(\%\ \text{Delta-}F\ \text{of sample well} - \text{Negative Control})}{(\text{Positive Control} - \text{Negative Control})} * 100$$

Example 9a: T-Cell Activation

STIM001 and STIM003 agonistic potential on cytokine production was tested in plate-bound and soluble format in a human primary T-cell activation assay where anti-CD3 and anti-CD28 Abs were added concurrently to the anti-ICOS Ab to induce ICOS expression on effector T-cells. Effect of the ICOS co-stimulation on the level of IFNγ produced by these activated T-cells were assessed using ELISA at 72 hrs post-activation.

Materials and Methods

T-Cell Activation Assay 1:

Isolation of Mononuclear Cells from Human Peripheral Blood (PBMC):

Leukocyte cones were collected from healthy donors and their content was diluted up to 50 ml with phosphate buffered saline (PBS, from Gibco) and layered into 2 centrifuge tubes on top of 15 mL Ficoll-Paque (from GE Healthcare). PBMC were separated by density gradient centrifugation (400 g for 40 min without brake), transferred to a clean centrifuge tube and then washed with 50 mL PBS, twice by centrifuging at 300 g for 5 min and twice by centrifuging at 200 g for 5 min. PBMC were then resuspended in R10 media (RPMI+10% heat-inactivated Fetal Bovine Serum, both from Gibco) and their cell count and viability assess with EVE™ Automated Cell Counter (from NanoEnTek).

ICOS Antibodies (Abs) Preparation and Dilutions:

STIM001 and STIM003 were tested in 3 formats: plate-bound, soluble or soluble plus $F(ab')_2$ Fragments (109-006-170 from Jackson Immuno Research) which crosslink the anti-ICOS Abs.

For plate-bound format: the anti-ICOS Abs and their isotype control were serially diluted 1:3 in PBS to give final antibody concentrations ranging from 45 to 0.19 μg/mL. 100 μL of diluted antibodies were coated in duplicate into a 96-well, high-binding, flat-bottom plate (Corning EIA/RIA plate) overnight at 4° C. Plate was then washed with PBS and 125 μl of R10 were added to each well.

For soluble format: The anti-ICOS Abs and their isotype control were serially diluted 1:3 in R10 media to give an 2× Ab stock concentrations ranging from 90 to 0.38 μg/mL. 125 μl of diluted Abs were pipetted in duplicate into a 96-well, flat-bottom plate.

For crosslinked soluble format: The anti-ICOS Abs and their isotype control were mixed with $F(ab')_2$ Fragments at 1M to 1M ratio. Abs/$F(ab')_2$ Fragments mixes were then 1:3 serially diluted in R10 media to give an 2× Ab concentrations ranging from 90 to 0.38 μg/mL for ICOS and from 60 to 0.24 μg/ml for $F(ab')_2$ Fragments. 125 μl of diluted Abs were pipetted in duplicate into a 96-well, flat-bottom plate.

T-Cell Isolation, Cultures and IFN-γ Quantification:

T-cell were negatively isolated from PBMC using the EasySep Human T Cell Isolation Kit (from Stemcell Technologies) and resuspended at $2\times10^6$/mL in R10 media supplemented with 40 μl/ml of Dynabeads Human T-Activator CD3/CD28 (from Life Technologies).

125 μl of T-cell suspension were added to Ab-containing plates to give a final cell concentration of $1\times10^6$ cells/ml and cultured for 72 hrs at 37° C. and 5% $CO_2$. Cell free supernatants were then collected and kept at −20° C. until analysis of secreted IFNγ by ELISA (duoset kit from R&D).

This experiment was repeated on T-cells isolated from 6 independent donors and 2 technical replicates were included for each assay condition.

T-Cell Activation Assay 2 (STIM-REST-STIM Assay):

STIM001 and STIM003 agonist potential on cytokine release were also tested plate-bound in a human T-cell assay where T-cells were prestimulated by anti-CD3 and anti-CD28 Abs for 3-days to induce ICOS expression before being rested for 3-days to reduce their activation levels.

ICOS expression was confirmed by FACS staining after stimulation (Day 3) and resting (Day 6). These stimulated rested T-cells were then cultured with STIM001 or STIM003 in presence or absence of CD3 Ab to assess the requirement of TCR engagement. Effects of the ICOS co-stimulation were assessed after 72 hrs on the levels of IFNγ, TNFα and IL-2 present in the culture.

ICOS Abs Dilutions and Coating:

Anti-human CD3 (clone UCHT1 from eBioscience) was diluted in PBS to a 2× Ab concentration of 10 μg/mL. 50 μl of PBS or 50 μl of diluted CD3 Ab were pipetted into a 96-well, high-binding, flat-bottom plate. STIM001, STIM003 and their isotype control were 1:2 serially diluted in PBS to give final 2× antibody concentrations ranging from 20 to 0.62 μg/mL. 50 μL of diluted anti-ICOS Ab were added to wells containing either PBS (no TCR engagement) or diluted CD3 Ab (TCR engagement). Plates were coated overnight at 4° C.

T-Cell Isolation, Cultures and IFN-γ Quantification:

PBMC from leukocyte cones were obtained as described in T-cell activation assay 1. T-cell were negatively isolated from this PBMC using the EasySep Human T Cell Isolation Kit (from Stemcell Technologies). T-cells were resuspended at $1\times10^6$/ml in R10 media supplemented with 20 μl/mL of Dynabeads Human T-Activator CD3/CD28 (from Life Technologies) and cultured for 3-days at 37° C. and 5% $CO_2$ (Stimulation). At day 3 dynabeads were removed from the culture. T-cells were then washed (300 g for 5 min), counted and resuspended at 1.5×106/ml in R10 media and culture at 37° C. and 5% $CO_2$ for 3-more days (Resting phase).

At day 6 stimulated rested T-cells were then washed (300 g for 5 min), counted and resuspended at $1\times10^6$/mL in R10 media and 250 μl of T-cell suspension were added to ICOS Ab-coated plates and cultured for 72 hrs at 37° C. and 5% $CO_2$. Cell free supernatants were then collected and kept at −20° C. until analysis of secreted cytokines on the MSD platform. This experiment was repeated with T-cells isolated from 5 independent donors and 3 technical replicates were included for each assay condition.

Results

Both STIM001 and STIM003 tested positive for inducing IFNγ expression therefore demonstrating agonism in both assays.

Example 9b: T Cell Activation Assay 1 Data

T cell activation assay 1 was performed as described in Example 9a, using T cells isolated from 8 independent donors, testing each of STIM001 and STIM003 in human IgG1 format. Hamster anti-ICOS antibody C398.4A and a hamster antibody isotype control were included for comparison. 2 technical replicates were included for each assay condition.

Figure 16:
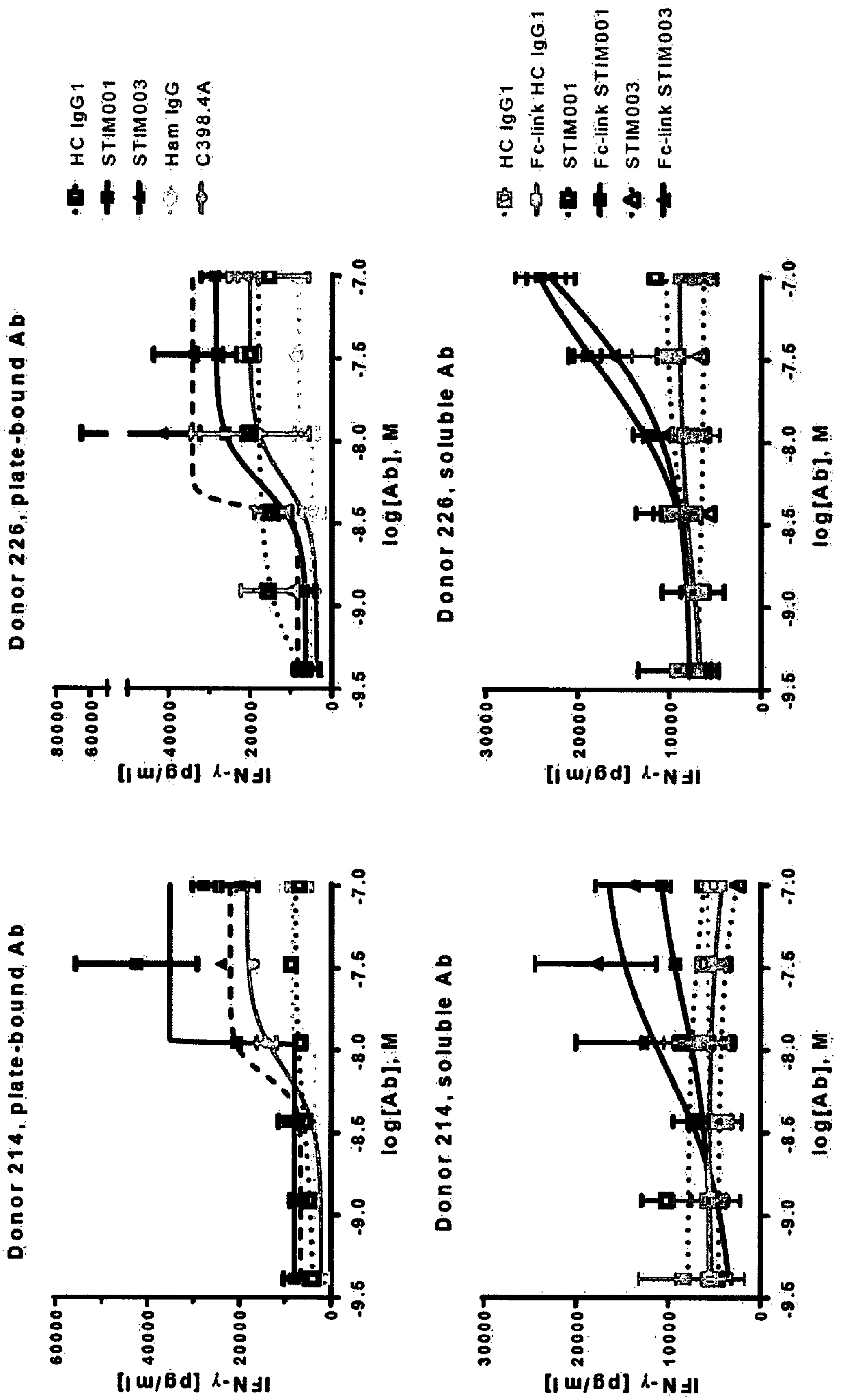
FIG. 16: Example data from concentration-dependent study of STIM001 (hIgG1) and STIM003 (hIgG1) agonist effect on isolated human T-cells co-stimulated with anti-CD3/anti-CD28 dynabeads for 3-days in T cell activation assay 1 (see Example 9b). IFN-γ production was used as an indicator of the agonistic effect. STIM001 (hIgG1) and STIM003 (hIgG1) were tested in plate-bound, soluble or crosslinked soluble (Fc-linked Ab) formats and compared with a hybrid isotype control (HC hIgG1). Included for comparison in the plate-bound assay was hamster antibody C398.4A and its isotype control (hamster IgG). Upper panel shows data from plate-bound antibodies. Lower panel shows data from IgG1 antibodies in soluble and cross-linked forms. Left and right panels respectively use T cells from two independent human donors.
Figure 17:
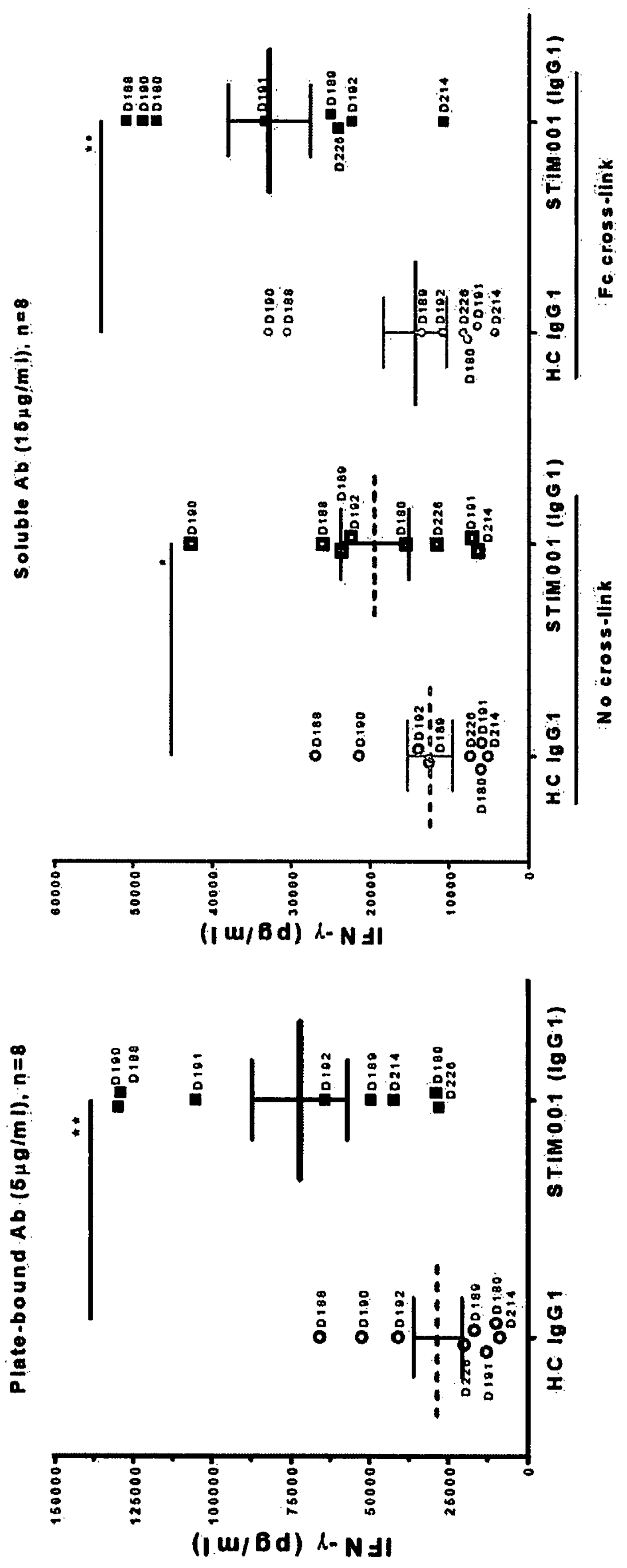
FIG. 17: Example data set for STIM001 in T cell activation assay 1 (see Example 9). Data indicate levels of IFN-γ induced by STIM001 (hIgG1) or its hybrid isotype control (HC IgG1) at one given dose for T cells from 8 independent human donors. Plate-bound antibody (FIG. 17*a*) was used at 5 μg/ml. Soluble antibody (FIG. 17*b*) was used at 15 μg/ml. Each dot represents one donor, identified by number (D214 for example). Significance was assessed using Wilcoxon statistic test: *, $p<0.05$ and **, $p<0.01$.
Figure 18:
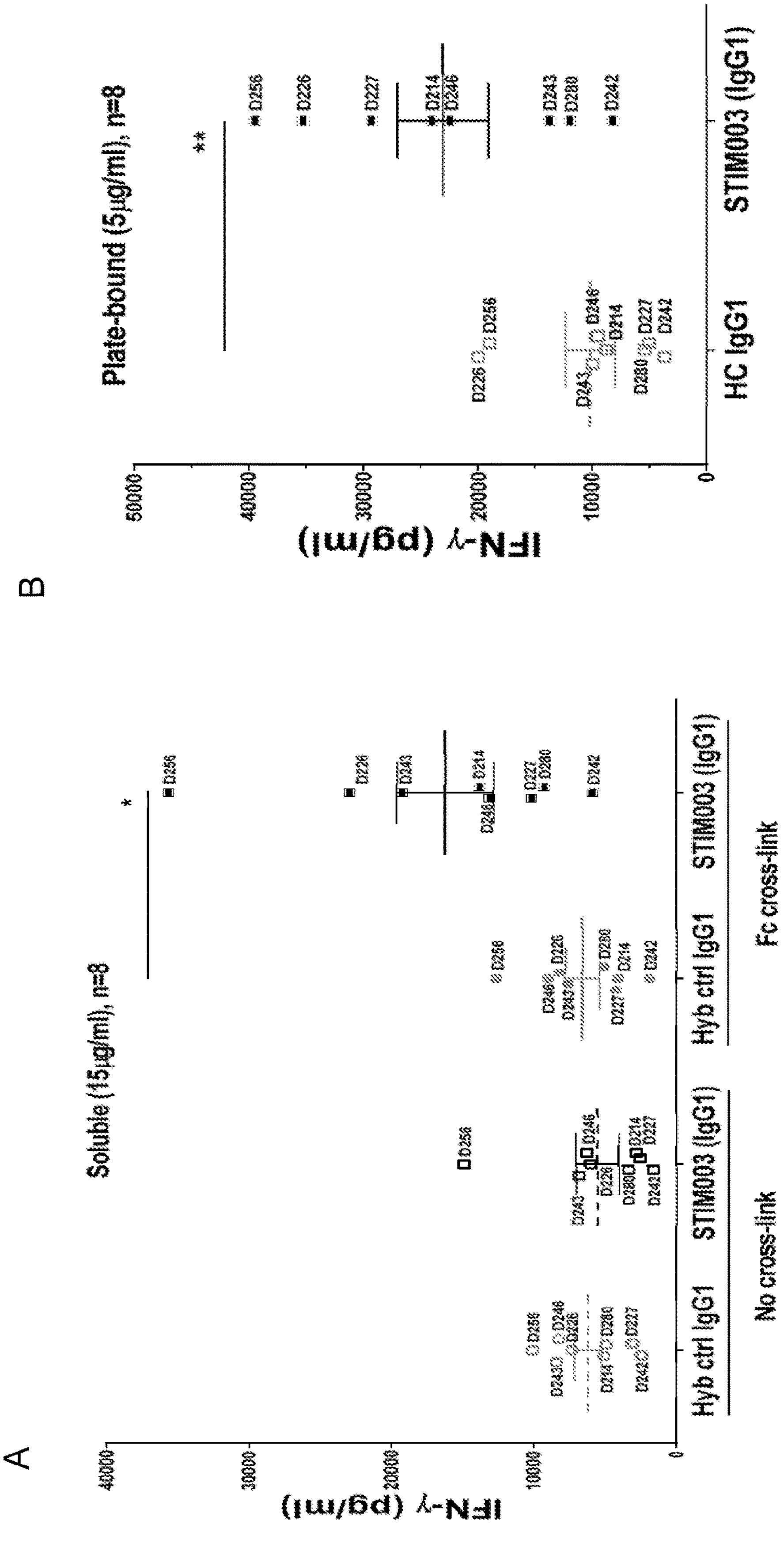
FIG. 18: Example data set for STIM003 in T cell activation assay 1 (see Example 9). Data indicate levels of IFN-γ induced by STIM003 (hIgG1) or its hybrid isotype control (HC hIgG1) at one given dose for T cells from 8 independent human healthy donors. Soluble antibody (FIG. 18*a*) was used at 15 μg/ml. Plate-bound antibody (FIG. 18*b*) was used at 5 μg/ml. Each dot represents one donor, identified by number (D214 for example). Significance was assessed using Wilcoxon statistic test: *, $p<0.05$ and **, $p<0.01$.

Results are shown in FIG. 16, FIG. 17 and FIG. 18. As noted before, both STIM001 and STIM003 tested positive for inducing IFNγ expression therefore demonstrating an agonistic effect on human primary T cells.

Cross-linked antibodies acted as agonists of T cell activation, as indicated by the strong enhancement of IFNγ induction in the presence of the Fc-linking $F(ab')_2$ fragments, compared with either soluble antibody or with control. IFNγ expression in the T cells increased with increasing concentration of cross-linked STIM001 or STIM003 (FIG. 16, lower panels). Agonism was also observed for both STIM001 and STIM003 in plate-bound form and, more weakly, for the hamster antibody C398.4A, as indicated by the increase in IFNγ expression observed in the T cells with increasing concentration of antibody (FIG. 16, top panels).

Magnitude of the IFNγ response varied between T cells obtained from different donors, but STIM001 consistently produced an increase in IFNγ expression in T cells compared with IFNγ expression observed with control antibody (HC IgG1). When considering data from assays with T cells from all 8 donors, it is seen that treatment of T cells with STIM001 significantly increased IFNγ expression compared with treatment with isotype control antibody, in plate-bound form, soluble form and cross-linked form (FIG. 17). STIM001 thus behaved as an agonist of T cell activation in all three formats.

Similar effects were observed with STIM003 (FIG. 18). Levels of IFNγ induced by STIM003 hIgG1 were compared with levels of IFNγ induced by its isotype control (HC IgG1) at a given dose of antibody in the assay, for 8 independent donors. Despite the variability between donors, the mean increase in IFNγ level induced by STIM003 was significant when compared against HC IgG1. It is proposed that STIM001, and the other STIM antibodies described here, have the potential to similarly promote T cell activation in vivo. As discussed previously, agonism of activated ICOS-expressing T cells may be mediated by the anti-ICOS antibody binding to and inducing multimerisation of the ICOS receptor on the T cell surface. Example 9c: T cell activation assay 2 data T cell activation assay 2 was performed as described in Example 9a.

In the absence of TCR engagement (no anti-CD3 antibody), levels of cytokines produced from the primary T cells were low and no increase was induced by STIM001 (hIgG1), STIM003 (hIgG1) or antibody C398.4A even at the highest concentration of 10 μg/ml. In contrast, when the anti-ICOS antibodies were added to T cells in combination with the anti-CD3 antibody, each of STIM001 (hIgG1), STIM003 (hIgG1) and C398.4A showed a dose-dependent trend to increase expression of IFNγ, TNFα and, to a lesser degree, IL-2.

Figure 19:
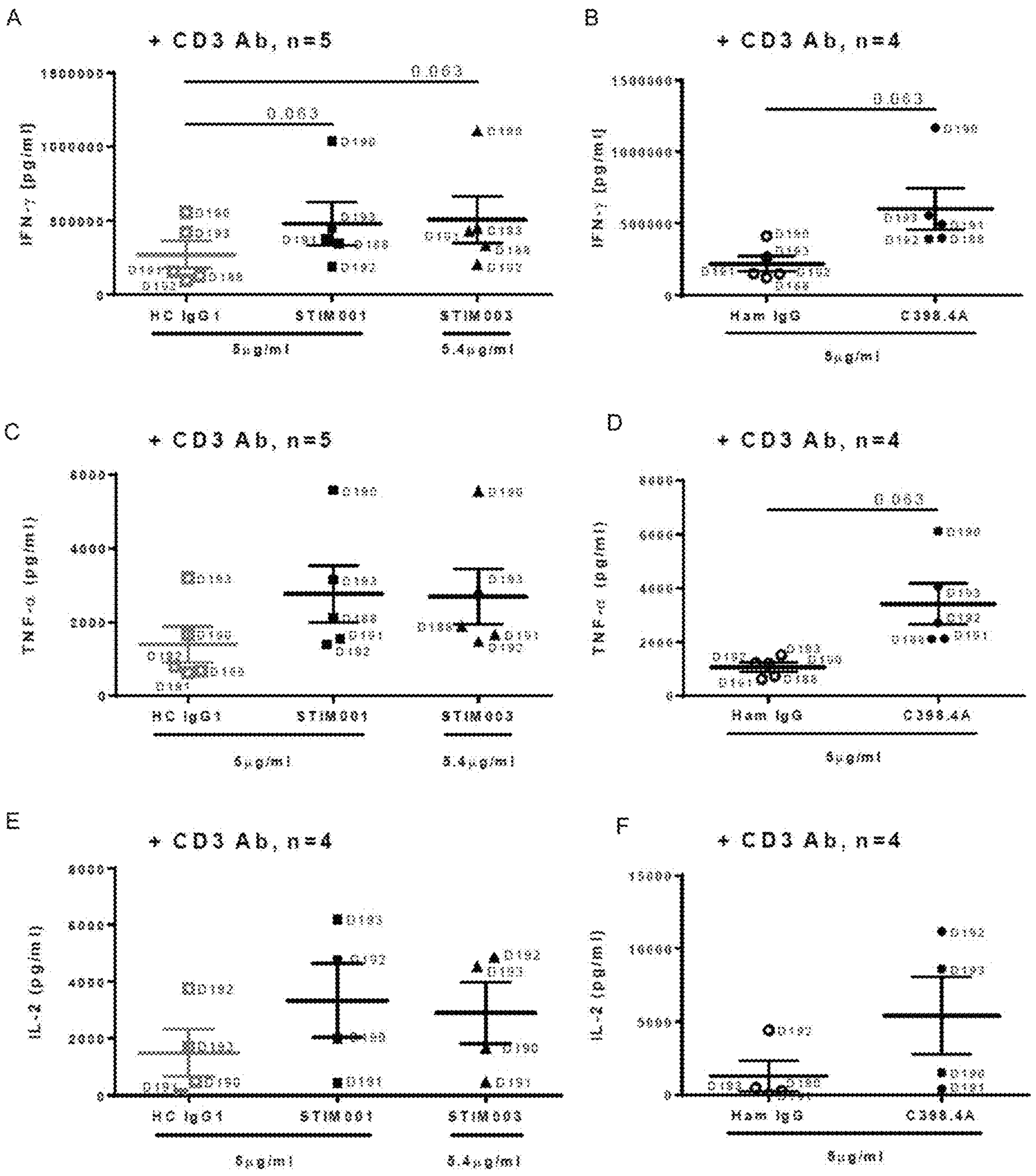
FIG. 19: Example data from T cell activation assay 2 (see Example 9c). Study of STIM001 (hIgG1) and STIM003 (hIgG1) agonist effect on isolated human T-cells stimulated with anti-CD3/anti-CD28 dynabeads for 3-days, then rested in medium for 3-days and finally re-stimulated with plate-bound STIM001, STIM003 or C398.4A Ab+/−CD3 Ab. Data comparing levels of IFN-γ (A, B), TNF-α (C, D) and IL-2 (E, F) induced by STIM001, STIM003 vs their hybrid control IgG1 (A, C, E) or C398.4A vs its hamster IgG control (B, D, F) at one given dose and in combination with CD3 Ab (TCR engagement). Each dot represents an independent donor identifiable by its number (D190 for example). Statistical significance between the Abs and their isotype control was assessed using Wilcoxon statistic test and p value indicated. Note that STIM003 concentration was slightly different to those of HC IgG1 (5.4 vs 5 μg/ml).

Data from primary T cells treated with anti-ICOS antibodies under conditions of TCR engagement are shown in FIG. 19. Although marked increases in cytokine expression were observed for each of STIM001, STIM003 and C389.4A relative to their respective isotype controls, the difference did not reach statistical significance in this assay. Further replicates of the assay with responsive primary T cells from more donors would be expected to generate statistically significant results.

Example 10a: ADCC Assay

STIM001 and STIM003 potential to kill via ADCC was tested in the Delfia BATDA cytotoxicity assay (Perkin Elmer) using human primary NK cells as effector and ICOS high MJ cell line (ATCC, CRL-8294) as target cells. MJ cells are human CD4 T-lymphocyte cells that express high levels of ICOS protein.

This method is based on loading target cells with an acetoxymethyl ester of fluorescence enhancing ligand (BATDA) which quickly penetrates the cell membrane. Within the cell the ester bonds are hydrolysed to form a hydrophilic ligand (TDA) which no longer passes the membrane. After cytolysis the ligand is released and can be detected by addition of Europium which forms with the BATDA a highly fluorescent and stable chelate (EuTDA). The measured signal correlates directly with the amount of lysed cells.

Materials and Methods

Target Cell Labelling:

According to the manufacturer's instructions, MJ cells were resuspended at $1\times10^6$/mL in assay media (RPMI+10% ultra-low IgG FBS, from Gibco) and loaded with 5 μl/mL of Delfia BATDA reagent (Perkin Elmer) for 30 min at 37° C. MJ cells were then washed 3 times with 50 mL PBS (300 g for 5 min) and resuspended at $8\times10^5$/ml in assay media supplemented with 2 mM Probenecid (from Life technologies) to reduce BATDA spontaneous release from the cells.

ICOS Ab Dilution:

STIM001, STIM003 and their isotype control were 1:4 serially diluted in assay media +2 mM Probenecid to give final 4× antibody concentrations across a range down to 80 pg/mL.

NK-Cell Isolation and Culture:

PBMC from leukocyte cones were obtained as described in T-cell activation assay 1. NK-cell were negatively isolated from this PBMC using the EasySep Human NK Cell Isolation Kit (from Stemcell Technologies) and resuspended at $4\times10^6$/ml in R10 media +2 mM Probenecid. NK cell purity was checked to be above 90% by staining for CD3−/CD56+.

50 μl of diluted Ab, 50 μl of BATDA loaded MJ cells, 50 μl of NK cells and 50 μl of assay media+2 mM Probenecid (final volume of 200 μl/well) were added in each well to give a final Ab concentration across a range down to 20 pg/mL and an effector: target ratio of 5:1. Wells containing MJ cells only or MJ cells+delfia lysis buffer (Perkin Elmer) are used to determine spontaneous and 100% BATDA release.

The assay was run at 37° C., 5% $CO_2$ for 2 hrs before transferring 50 μl of cell-free supernatant into a DELFIA Microtitration Plates (Perkin Elmer). 200 μl of Delfia Europium solution (Perkin Elmer) was added to the supernatants and incubated for 15 min at Room Temperature. Fluorescent signal was then quantified with EnVision Multilabel Reader (PerkinElmer).

Specific release induced by STIM001 and STIM003 was calculated according to the kit instructions. This experiment was repeated with NK-cells from independent donors and 3 technical replicates were included for each assay condition.

Results

Anti-ICOS antibodies STIM001 (hIgG1) and STIM003 (hIgG1) kill ICOS positive human MJ cells in a primary NK dependent ADCC assay (2 hour time point). See also FIG. 6*a*. Sub-Nanomolar EC50 were achieved in this assay for both molecules tested.

TABLE E10-1

EC50 (Molar unit) of STIM001 in the NK primary cells ADCC assay from 2 donors (2 hour time point).

| EC50 | Donor 1 | Donor 2 |
|---|---|---|
| STIM001 | 1.21e−10 | 5.29e−10 |

Example 10b: ADCC Assay with MJ Target Cells

The experiment was performed according to the Materials and Methods set out in Example 10a. STIM001, STIM003 and isotype control were 1:4 serially diluted in assay media+2 mM Probenecid to give final 4× antibody concentrations ranging from 40 μg/mL to 80 pg/mL. 50 μl of diluted Ab, 50 μl of BATDA loaded MJ cells, 50 μl of NK cells and 50 μl of assay media+2 mM Probenecid (final volume of 200 μl/well) were added in each well to give a final Ab concentration ranging from 10 μg/mL to 20 pg/mL and an effector: target ratio of 5:1.

Figure 6:
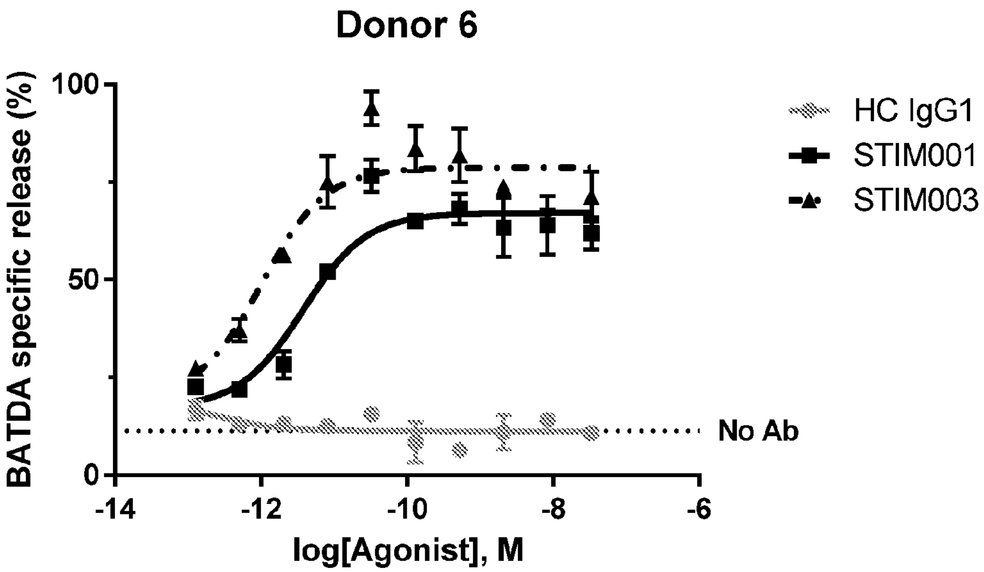
FIG. 6*a*: Concentration-dependent study of STIM001-mediated ADCC on MJ cells by using freshly isolated NK cells as effector cells. The effector cells and target cells (effector:target ratio of 5:1) were incubated together with antibody for 2 hours. BATDA releasing from lysed target cells was measured as described in the manufacturer kit instruction. HC is the hybrid isotype control.
FIG. 6*b, c, d*: Concentration-dependent study of STIM001 and STIM003-mediated ADCC on MJ cells with freshly isolated NK cells as effector cells. The effector cells and target cells (effector:target ratio of 5:1) were incubated together with antibody for 2 hours. BATDA releasing from lysed target cells was measured as described in the manufacturer kit instruction. HC is the hybrid isotype control.
FIG. 6*e, f, g*: Concentration-dependent study of STIM001 (hIgG1) and STIM003 (hIgG1)-mediated ADCC on ICOS-transfected CCRF-CEM cells with freshly isolated NK cells as effector cells. The effector cells and target cells (effector: target ratio of 5:1) were incubated together with antibody for 4 hours. BATDA releasing from lysed target cells was measured as described in the manufacturer kit instruction. HC is the hybrid isotype control.

Results are shown in FIG. 6 (*b-d*) and in the table below. STIM001 (hIgG1) and STIM003 (hIgG1) killed ICOS positive human MJ cells in the primary NK dependent ADCC assay, measured at the two hour time point.

TABLE E10-2

EC50 (Molar unit) of STIM001 and STIM003 in the NK primary cell ADCC assay from 3 donors (2 hour time point).

| EC50 | Donor 1 | Donor 2 | Donor 3 |
|---|---|---|---|
| STIM001 | 1.21e−10 (0.121 nM) | 5.29e−10 (0.529 nM) | 2.92e−09 (2.92 nM) |
| STIM003 | 2.33e−12 (2.33 pM) | 3.58-e−11 (35.8 pM) | 1.01e−10 (0.101 nM) |

Example 10c: ADCC Assay with ICOS-Transfected CCRF-CEM Target Cells

STIM001 and STIM003 hIgG1 potential to kill via ADCC was further tested in the Delfia BATDA cytotoxicity assay (Perkin Elmer) using human primary NK cells as effector and ICOS-transfected CCRF-CEM cells (ATCC, CRL-119) as target cells. CCRF-CEM is a human T lymphoblast line, originating from peripheral blood from a patient with acute lymphoblastic leukaemia. Antibody-mediated killing of CCRF-CEM cells was confirmed for both STIM001 and STIM003 in this assay.

Materials and Methods

Materials and Methods were as set out in Example 10a, but using CCRF-CEM cells obtained from ATCC (ATCC CCL-119) rather than MJ cells as the target cells, and using an incubation time of 4 hours.

CCRF-CEM cells were transfected with ICOS. A synthetic string DNA encoding full length human ICOS (with signal peptide, as shown in the appended sequence listing), codon-optimised for mammalian expression, was cloned into an expression vector under control of the CMV promoter and flanked by 3' and 5' piggyBac specific terminal repeat sequences facilitating stable integration into the cell genome (see [40]). The expression vector contained a puromycin selection cassette to facilitate stable cell line generation. The human ICOS expression plasmid was co-transfected with a plasmid encoding piggyBac transposase into CEM CCRF cells by electroporation. 24 hours after transfection, the media was supplemented with puromycin and grown for at least two weeks to select stable cell lines, with media being exchanged every 3-4 days. The expression of human ICOS was assessed by flow cytometry using an anti-human ICOS-PE conjugated antibody (eBioscience). Complete CEM media was made up of Advanced RPMI Medium containing 10% (v/v) FBS and 2 mM Glutamax.

STIM001 (hIgG1), STIM003 (hIgG1) and an isotype control antibody (HC IgG1) were serially diluted in assay media to give final 4× antibody concentrations ranging from 20 μg/mL to 80 pg/mL.

50 μl of diluted Ab, 50 μl of BATDA loaded ICOS-transfected CEM cells, 50 μl of NK cells and 50 μl of assay media (final volume of 200 μl/well) were added in each well to give a final Ab concentration ranging from 5 μg/mL to 20 pg/mL and an effector: target ratio of 5:1.

Results

STIM001 (hIgG1) and STIM003 (hIgG1) killed ICOS-transfected CCRF-CEM cells in the primary NK dependent ADCC assay, measured at the four hour time point. Results are shown in FIG. 6 (*e-g*) and in the table below.

TABLE E10-3

EC50 (Molar unit) of STIM001 and STIM003 in the NK primary cell ADCC assay from 3 donors (4 hour time point).

| EC50 | Donor 4 | Donor 5 | Donor 6 |
|---|---|---|---|
| STIM001 | 3.92e−12 (3.92 pM) | 3.95e−12 (3.95 pM) | 3.75e−12 (3.75 pM) |
| STIM003 | Approx 3 pM* | 8.95e−13 (0.895 pM) | 1.03e−12 (1.03 pM) |

*Value estimated from incomplete curve.

Example 11a: CT26 Syngeneic Model

Improved anti-tumour in vivo efficacy was shown in a CT26 syngeneic model by combining anti-ICOS (STIM001 mIgG2a, effector enable) with anti-PDL1 (10F9G2).

Materials and Methods

Efficacy studies were performed in Balb/c mice using the sub-cutaneous CT26 colon carcinoma model (ATCC, CRL-2638). This model is poorly sensitive to PD1/PDL1 blockade and only tumour growth delay (no stable disease or cure) is usually observed in response to 10F9.G2 (anti-PDL1) and RMT1-14 (anti-PD1) monotherapies. Therefore this model constitutes a relevant model for looking at anti-PD1, anti-PDL1 intrinsic resistance for combination studies. All in vivo experiments were performed in accordance with the UK Animal (Scientific Procedures) Act 1986 and the EU Directive 86/609, under a UK Home Office Project Licence and approved by the Babraham Institute Animal Welfare and Ethical Review Body.

Balb/c mice were supplied by Charles River UK at 6-8 weeks of age and >18 g and housed under specific pathogen-free conditions. A total of $1\times10^5$ CT26 cells (passage number below P20) were subcutaneously injected into the left flanks of mice. Unless stated otherwise, treatment were initiated at day 6 post tumour cells injection. The CT26 cells were passaged in vitro by using Accutase (Sigma), washed twice in PBS and resuspended in RPMI supplemented with 10% fetal calf serum. Cell viability was confirmed to be above 90% at the time of tumour cell injection.

For in vivo studies STIM001 anti-ICOS agonist (cross reactive to mouse ICOS protein) was reformatted as mouse IgG1 and mouse IgG2a to test the as effector function null and as effector function enable, respectively. The Anti-PDL1 was sourced from Biolegend (Cat. no: 124325). The hybrid controls were generated in Kymab (mIgG2a isotype) or from commercial source (hamster isotype HTK888, Biolegend (Part No92257, Lot B215504)). All antibodies were dosed intraperitoneal (IP) at 10 mg/kg (1 mg/ml in 0.9% saline) three times a week from day 6 (dosing for 2 weeks day 6-18) as monotherapies or by combining anti-PDL1 with anti-ICOS antibodies. Animal weight and tumour volume were measured 3 times per week from the day of tumour cell injection. Tumour volume was calculated by use of the modified ellipsoid formula ½(Length×Width2). Mice were kept on studies until their tumour reached an average diameter of 12 $mm^3$ or, in rare case, when incidence of tumour ulceration was observed (welfare). The experiment was stopped at day 50. The human endpoint survival statistics were calculated using the Kaplan-Meier method with Prism. This approach was used to determine if specific treatments were associated with improved survival.

TABLE E11-1

Treatment groups

| Groups | Number of animals | Treatments (T.I.W, IP from day 6) |
|---|---|---|
| 1 | 10 | 10 mg/kg mIgG2a and 10 mg/kg IgG isotype Control (HTK888) |
| 2 | 10 | 10 mg/kg Anti-ICOS STIM001 mIgG1 |
| 3 | 10 | 10 mg/kg Anti-ICOS STIM001 mIgG2a |
| 4 | 10 | 10 mg/kg Anti-PD-L1 (10F9.G2) |
| 5 | 10 | 10 mg/kg anti-PD-L1 plus 10 mg/kg Anti-ICOS STIM001 mIgG1 |
| 6 | 10 | 10 mg/kg anti-PD-L1 plus 10 mg/kg Anti-ICOS STIM001 mIgG2a |

Results

Figure 7:
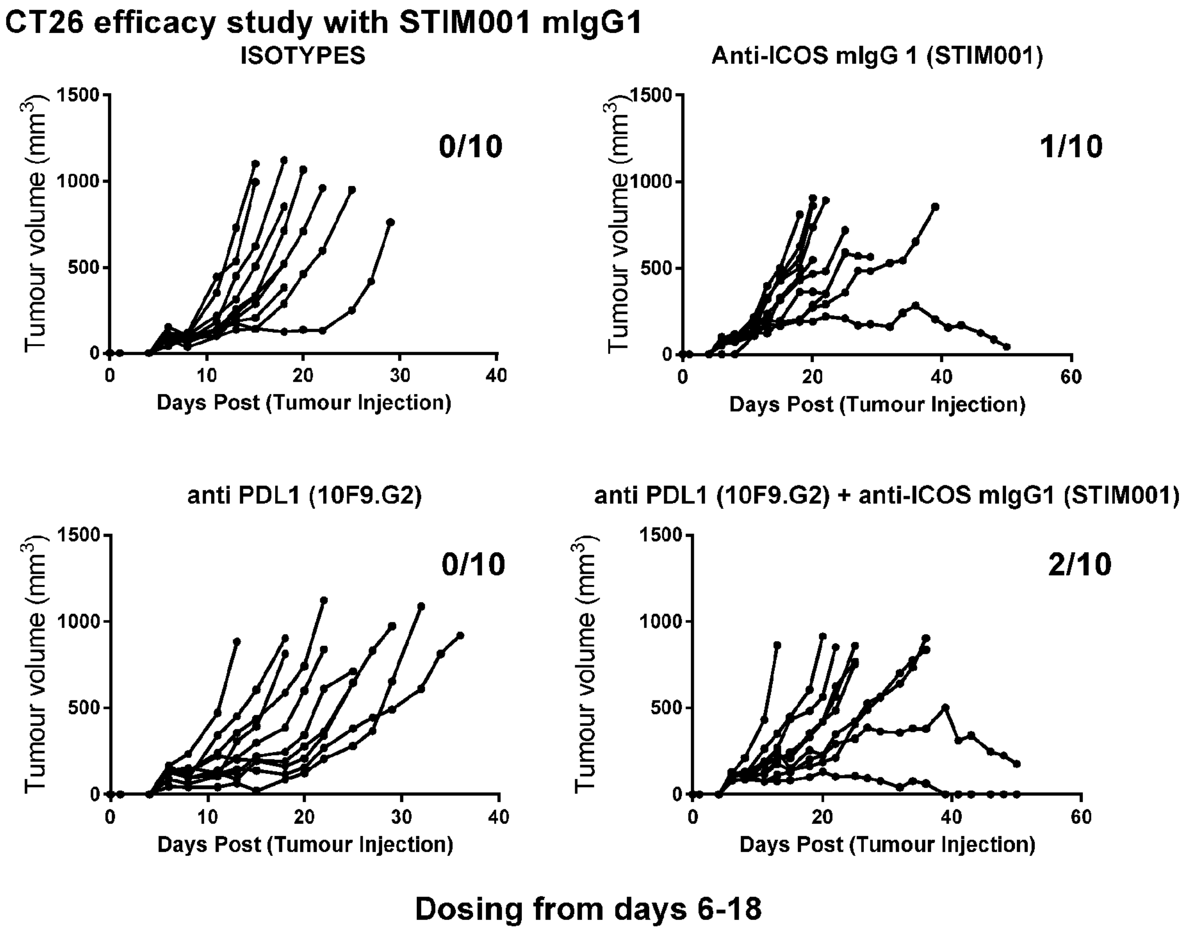
FIG. 7, FIG. 8, FIG. 9: Anti-ICOS antibody inhibits CT26 tumour growth and improved survival when dosed as monotherapy or in combination with anti-PDL1. The STIM001 mIgG2a is more potent than the mIgG1 format. The number of animals cured or with stable disease is indicated on each graph.
Figure 8:
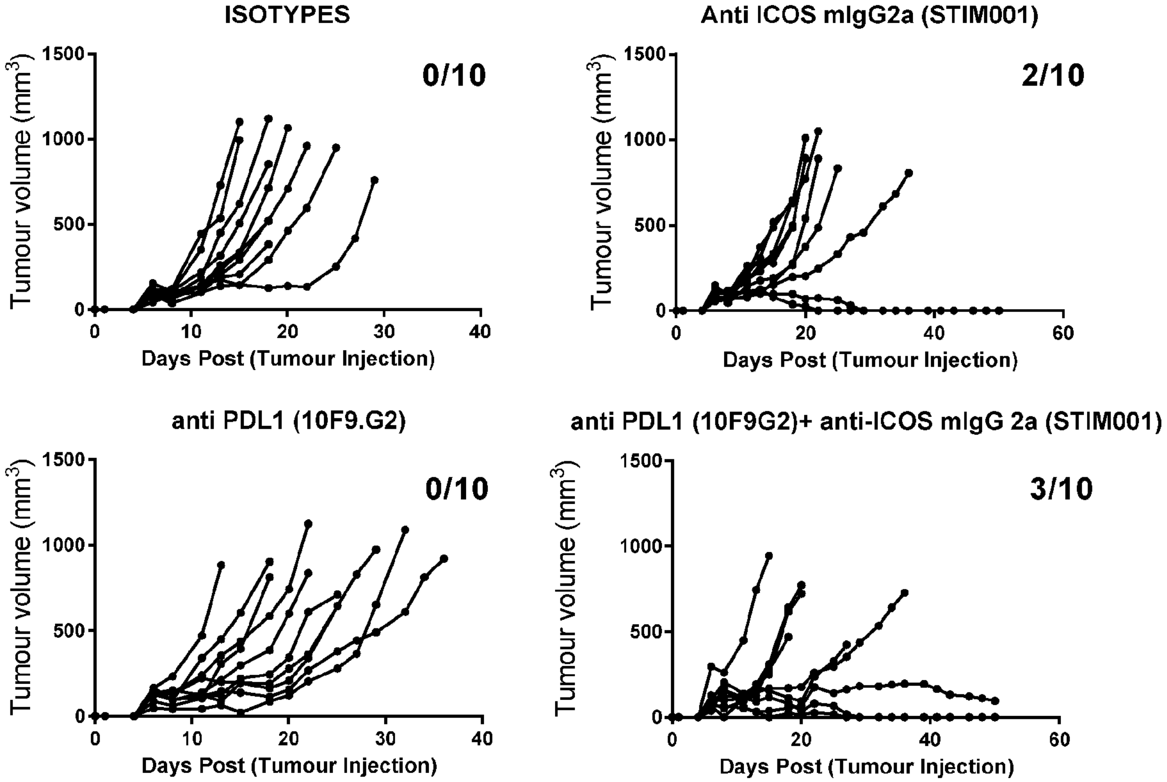
Figure 9:
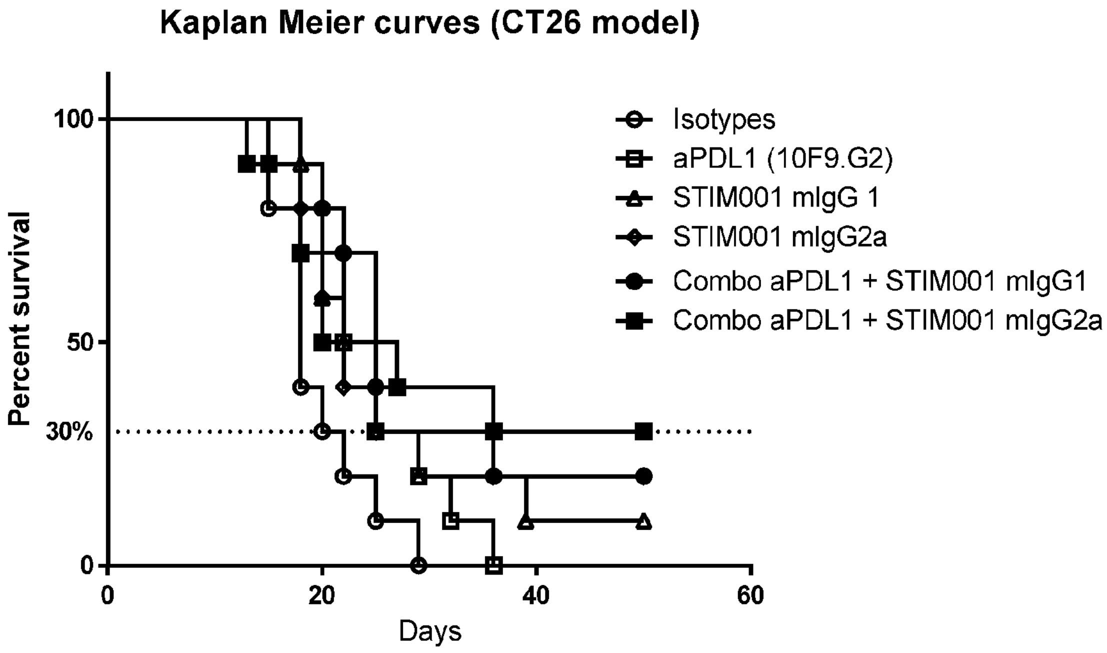

As shown in FIG. 7, FIG. 8 and FIG. 9, ICOS agonists can delay disease progression and cure a proportion of animals from the CT-26 subcutaneous tumours either as a monotherapy or in combination with anti-PDL1. Anti-PDL1 monotherapy induced tumour growth delay but no stable disease or curative potential was observed. The combination was more effective at treating the tumours than the anti-ICOS monotherapies. This study also highlighted that STIM001 in the mouse IgG2a format (effector function enable) was more potent than the mouse IgG1 (effector null) format at triggering an anti-tumour response in this model.

Example 11b: Strong Anti-Tumour Efficacy In Vivo in CT26 Syngeneic Model for Combination of Anti-ICOS mIgG2a with Anti-PDL1 mIgG2a An in vivo combination study was performed with STIM001 with a mouse cross reactive anti-human PDL1 antibody designated AbW. For this in vivo work, STIM001 was reformatted as mouse IgG1 and mouse IgG2a to compare its efficacy with low effector function or as effector function enabled molecule, respectively. The anti-PDL1 AbW was generated in the same formats (mouse IgG1 and mouse IgG2A).

The efficacy studies were performed in Balb/c mice using the sub-cutaneous CT26 colon carcinoma model (ATCC, CRL-2638). Balb/c mice were supplied by Charles River UK at 6-8 weeks of age and >18 g and housed under specific pathogen-free conditions. A total of 1×10E5 CT26 cells (passage number below P20) were subcutaneously injected into the right flanks of mice. Unless stated otherwise, treatment were initiated at day 6 post tumour cells injection. The CT26 cells were passaged in vitro by using TrypLE™ Express Enzyme (Thermofisher), washed twice in PBS and resuspended in RPMI supplemented with 10% foetal calf serum. Cell viability was confirmed to be above 90% at the time of tumour cell injection.

STIM001 and anti-PDL1 antibodies were dosed concurrently in combinations intraperitoneal (IP) at 200 μg each (1 mg/ml in 0.9% saline) three times a week from day 6 (dosing for 2 weeks between day 6-17) post tumour cell implantation. Tumour growth was monitored and compared to tumours of animals treated with a mixture of isotype control antibodies (mIgG1 and mIgG2A). Animal weight and tumour volume were measured 3 times a week from the day of tumour cell injection. Tumour volume was calculated by use of the modified ellipsoid formula ½(Length×Width2). Mice were kept on studies until their tumour reached an average diameter of 12 mm3 or, in rare case, when incidence of tumour ulceration was observed (welfare). The experiment was stopped at day 60. The human endpoint survival statistics were calculated using the Kaplan-Meier method with Prism. This approach was used to determine if specific treatments were associated with improved survival.

TABLE E11-2

Treatment groups for STIM001 2 × 2 combinations

| Group | Number of animals | Treatment regimen (3 time a week for 2 weeks) |
|---|---|---|
| 1 | 10 | mIgG2a + mIgG1 isotypes 200 μg each |
| 2 | 10 | Anti-ICOS mIgG1 STIM001 + Anti-PD-L1 mIGg1 (AbW) 200 μg each |
| 3 | 10 | Anti-ICOS mIgG2a STIM001 + Anti-PD-L1 mIGg2a (AbW) 200 μg each |
| 4 | 10 | Anti-ICOS mIgG2a STIM001 + Anti-PD-L1 mIGg1 (AbW) 200 μg each |
| 5 | 10 | Anti-ICOS mIgG1 STIM001 + Anti-PD-L1 mIGg2a (AbW) 200 μg each |

Figure 10:
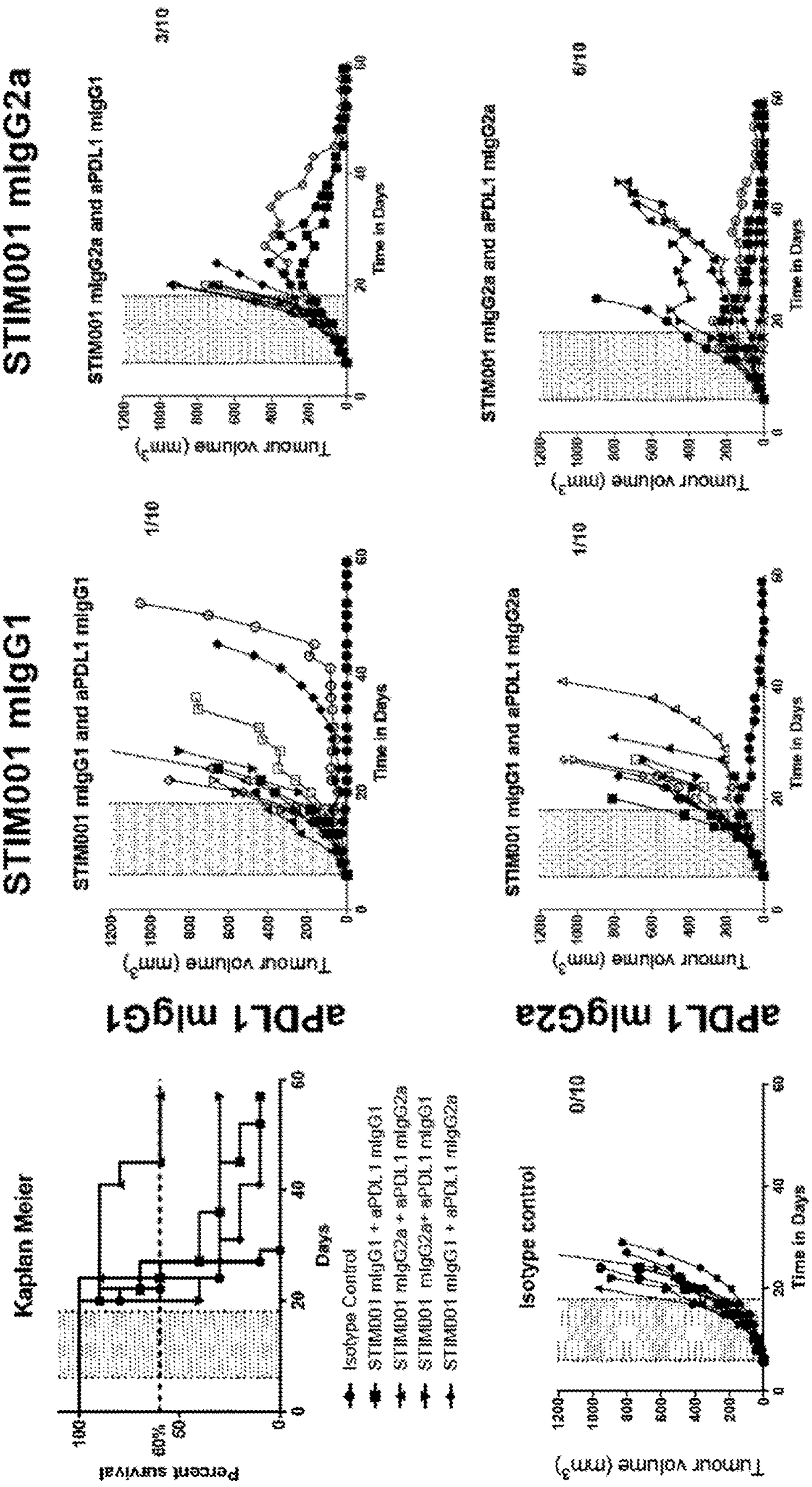
FIG. 10: 2×2 combinations CT26 in vivo efficacy study. Each treatment groups is represented by a "spider plot" showing the tumour size of individual animals (n=10 per groups). When combined with anti-PDL1 antibodies, STIM001 delays tumour growth and improves the survival of treated animals. The efficacy observed in the presence of STIM001 mIgG2a is superior to that of STIM001 mIgG1. Finally, STIM001 mIgG2a in combination with anti-PDL1 mIgG2a was the most potent combination to trigger the anti-tumour response resulting in 60% of the animals cured of the disease. For each group, the number of animals cured of their disease is indicated on the top right of the respective graphs. Dosing was on days 6, 8, 10, 13, 15 and 17.

Results are shown in FIG. 10. All antibody combinations delayed tumour growth and extended the survival (time to reach human endpoint) of treated animals when compared to isotype control-treated animals. Interestingly, when combined with anti-PDL1 (independently of its format, mIgG1 or mIgG2a), STIM001 mIgG2a antibody was more effective at inhibiting tumour growth than STIM001 in the mIgG1 format. These data suggest the advantage of an anti-ICOS antibody having effector function to maximize anti-tumour efficacy. Notably, STIM001 mIgG2a in combination with aPD-L1 mIgG2a demonstrated the strongest anti-tumour efficacy and improved survival (90% of animals to show response and 60% were cured from the disease at day 60).

Similarly, STIM003 mIgG1 and mIgG2a were tested as monotherapy or in combination with anti-PDL1 (AbW) mIgG2a in the same CT26 tumour models. STIM003 and anti-PDL1 antibodies were dosed in animals as monotherapy or in combination by intraperitoneal injection (IP) of 200 μg of antibodies each (1 mg/ml in 0.9% saline) three times a week from day 6 (dosing for 2 weeks between day 6-17) post tumour cell implantation. In this experiment tumour sizes were monitored for 41 days. The human endpoint survival statistics were calculated using the Kaplan-Meier method with Prism. This approach was used to determine if specific treatments were associated with improved survival.

TABLE E11-3

Treatment groups for STIM003 combination with anti-PDL1 AbW IgG2a

| Group | Number of animals | Treatment regimen (3 times a week for 2 weeks from day 6) |
|---|---|---|
| 1 | 10 | mIgG2a + mIgG1 isotypes control 200 μg each |
| 2 | 10 | Anti-PD-L1 mIgG2a (AbW) 200 μg |
| 3 | 10 | STIM003 mIgG1 200 μg |
| 4 | 10 | STIM003 mIgG2a 200 μg |
| 5 | 10 | STIM003 mIgG1 + Anti-PD-L1 mIGg2a (AbW) 200 μg each |
| 6 | 10 | STIM003 mIgG2a + Anti-PD-L1 mIGg2a (AbW) 200 μg each |

Results are shown in FIG. 11. Monotherapies using aPDL1 (AbW) and STIM003 mIgG2a demonstrated mild anti-tumour activity (one animal was cured of the disease in each group). Combinations of STIM003 mIgG1 or mIgG2a with aPDL1 (AbW) mIgG2a showed strong anti-tumour efficacy. Interestingly, by day 41, when combined with aPDL1 mIgG2a, STIM003 mIgG2a was more potent at inhibiting tumour growth than STIM003 mIgG1 (60% vs 30% of animals cured of the disease, respectively). The data further highlighted the advantage of an effector format for anti-ICOS antibodies to maximize anti-tumour efficacy.

Altogether, these data demonstrate that combination of an anti-ICOS antibody STIM001 or STIM003 with anti-PDL1 results in the strongest anti-tumour response when both antibodies have an effector enabled function. Suitable corresponding human antibody isotypes would include human IgG1, optionally with further enhanced effector function e.g., afucosylated IgG1.

Figure 29:
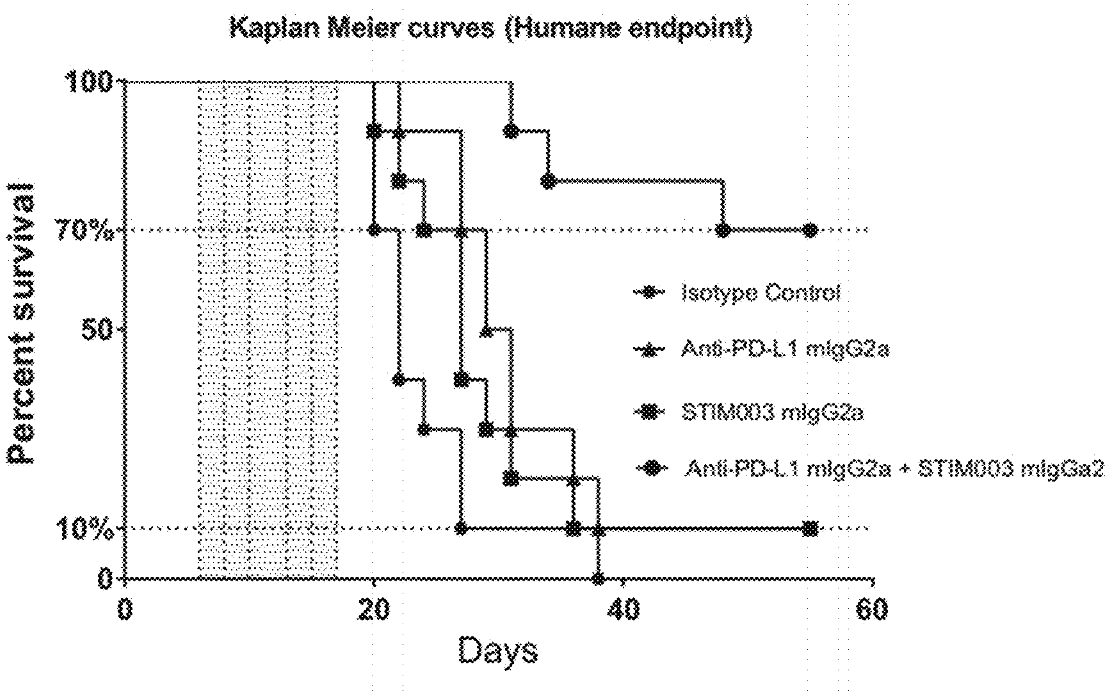
FIG. 29: Kaplan Meier curves for CT26 Balb/C model. Shading shows dosing window. LogRank $p<0.0001$.

Kaplan Meier curves for mice treated with the combination of anti-PDL1 mIgG2a and STIM003 mIgG2a and for each agent individually are shown in FIG. 29.

Example 11c: Single Dose of STIM003 Antibody Resets the Tumour Microenvironment (TME) and Results in Strong Anti-Tumour Efficacy in Combination with Continuous Anti-PD-L1 Dosing This study compared single vs multiple dosing of STIM003 mIgG2A together with multiple dosing of anti-PDL1 antibody (AbW). The data indicate that a single dose of anti-ICOS antibody could alter the tumour microenvironment so as to allow an anti-PD-L1 antibody to exert a greater effect. This can be envisaged as a "resetting" of the TME by the anti-ICOS antibody.

As before, these efficacy studies were performed in Balb/c mice using the sub-cutaneous CT26 colon carcinoma model (ATCC, CRL-2638). Balb/c mice were supplied by Charles River UK at 6-8 weeks of age and >18 g and housed under specific pathogen-free conditions. A total of 1×10E5 CT26 cells (passage number below P20) were subcutaneously injected into the right flanks of mice. Unless stated otherwise, treatments were initiated at day 6 post tumour cells injection. The CT26 cells were passaged in vitro by using TrypLE™ Express Enzyme (Thermofisher), washed twice in PBS and resuspended in RPMI supplemented with 10% foetal calf serum. Cell viability was confirmed to be above 90% at the time of tumour cell injection.

Treatment groups are shown in Table E11-4. STIM003 and anti-PDL1 antibodies were dosed intraperitoneal (IP) at 10 mg/kg (1 mg/ml in 0.9% saline). Treatments were initiated from day 6 post tumour cell implantation. Tumour growth was monitored and compared with tumours of animals treated with saline. Animal weight and tumour volume were measured 3 times a week from the day of tumour cell injection. Tumour volume was calculated by use of the modified ellipsoid formula ½(Length×Width2). Mice were kept on studies until their tumour reached an average diameter of 12 $mm^3$ or, in rare case, when incidence of tumour ulceration was observed (welfare). The experiment was stopped at day 55.

Figure 34:
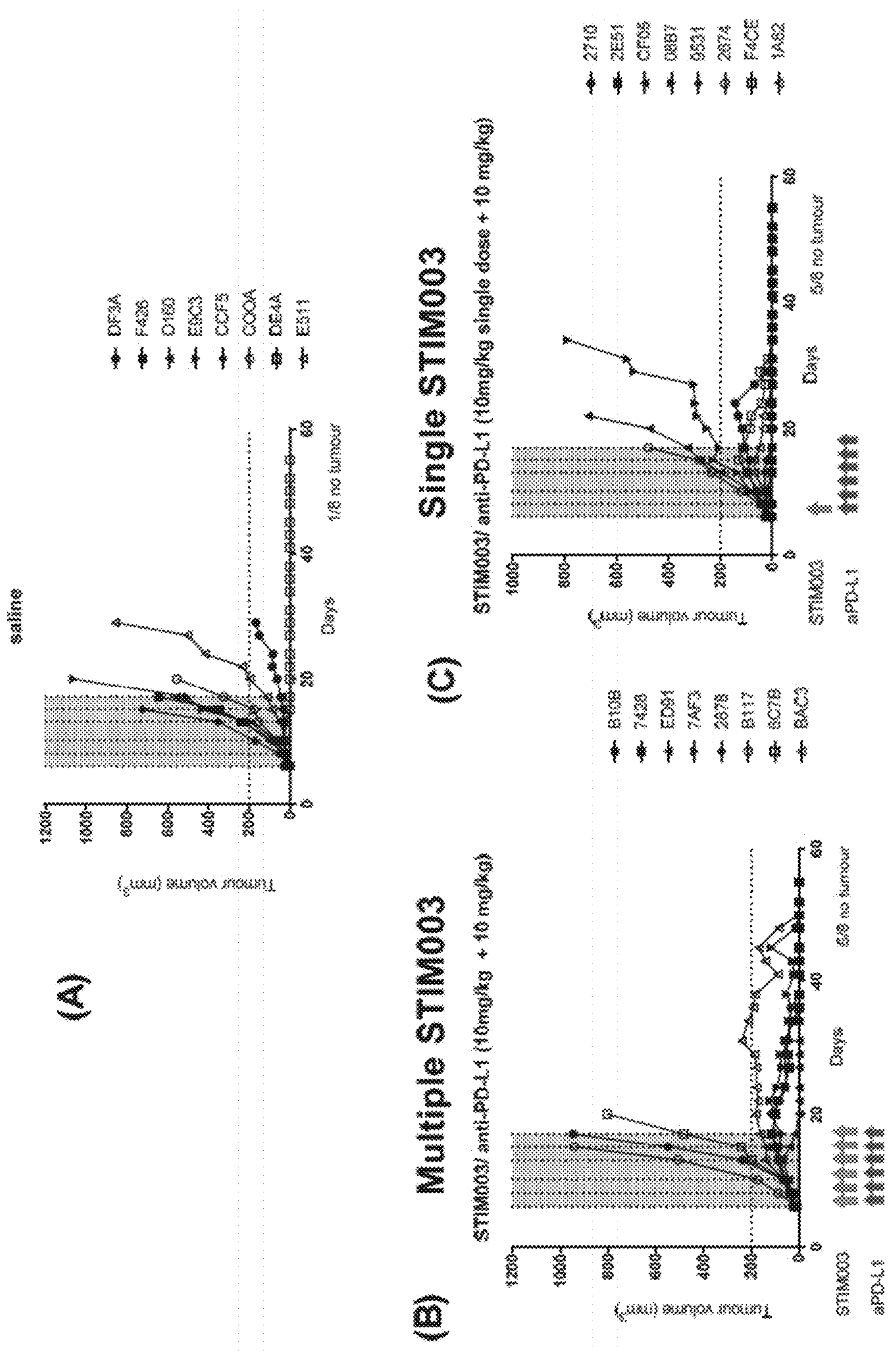
FIG. 34: Data from CT26 in vivo efficacy study described in Example 11c using combination of anti-PD-L1 mIgG2a antibody with single vs multiple doses of STIM003 mIgG2a. Each treatment group is represented by a "spider plot" showing the tumour size of individual animals (n=8 per group). For each group, the number of animals cured of their disease is indicated on the bottom right of the respective graph. Dosing days for each antibody are indicated by arrows below the respective graphs.

Data are shown in FIG. 34. Concurrent dosing of STIM003 and anti-PDL1 for 6 doses from day 6 resulted in a strong anti-tumour efficacy in the CT26 model with 5/8 animals being tumour free at the end of the study (day 55). Interestingly, similar anti-tumour efficacy was achieved with a single dose of STIM003 followed by multiple dose of anti-PDL1 as monotherapy. When combined with anti-PD-L1 mIgG2a, similar overall efficacy was observed between dosing STIM003 once (C) vs dosing 6 times (B). When compared with saline treated group (A) where only one animal had a spontaneous tumour rejection (rare in this model), the groups treated with combined drugs had full tumour rejection in 62.5% of the animals by the end of the experiment (day 55). The data suggest that the STIM003 antibody could be used to reset the tumour microenvironment and that the antibody allows immune-checkpoint resistant tumours to become sensitive to anti-PDL1. As previously shown (Example 11b), the CT26 tumour cell line is not strongly responsive to anti-PDL1 monotherapy. It appears that STIM003 causes changes that facilitate anti-tumour activity of the anti-PDL1 therapy.

Example 12: Antibody Sequence Analysis

Framework regions of antibodies STIM001, STIM002, STIM002-B, STIM003, STIM004, STIM005, STIM006, STIM007, STIM008 and STIM009 were compared with human germline gene segments to identify the closest match. See Table E12-1 and Table E12-2.

TABLE E12-1

Heavy chain germline gene segments of anti-ICOS Abs

| Heavy chain | V | D | J |
|---|---|---|---|
| STIM001 | IGHV1-18*01 | IGHD6-19*01 | IGHJ6*02 |
| STIM002 | IGHV1-18*01 | IGHD3-10*01 | IGHJ6*02 |
| STIM002-B | IGHV1-18*01 | IGHD3-10*01 | IGHJ6*02 |
| STIM003 | IGHV3-20*d01 | IGHD3-10*01 | IGHJ4*02 |
| STIM004 | IGHV3-20*d01 | IGHD3-10*01 | IGHJ4*02 |
| STIM005 | IGHV1-18*01 | IGHD3-9*01 | IGHJ3*02 |
| STIM006 | IGHV3-11*01 | IGHD3-10*01 | IGHJ6*02 |
| STIM007 | IGHV2-5*10 | IGHD3-10*01 | IGHJ6*02 |
| STIM008 | IGHV2-5*10 | IGHD3-10*01 | IGHJ6*02 |
| STIM009 | IGHV3-11*01 | IGHD3-9*01 | IGHJ6*02 |

TABLE E12-2

Kappa light chain germline gene segments of anti-ICOS Abs

| Light chain | V | J |
|---|---|---|
| STIM001 | IGKV2-28*01 | IGKJ4*01 |
| STIM002 | IGKV2-28*01 | IGKJ2*04 |
| STIM002-B | IGKV2-28*01 | IGKJ2*04 |
| STIM003 | IGKV3-20*01 | IGKJ3*01 |
| STIM004 | IGKV3-20*01 | IGKJ3*01 |
| STIM005 | IGKV1D-39*01 | IGKJ1*01 |
| STIM006 | IGKV2-28*01 | IGKJ2*04 |
| STIM007 | IGKV3-11*01 | IGKJ4*01 |
| STIM008 | IGKV3-11*01 | IGKJ4*01 |
| STIM009 | IGKV2-28*01 | IGKJ1*01 |

Additional antibody sequences were obtained by next generation sequencing of PCR-amplified antibody DNA from further ICOS-specific cells that were sorted from the immunised mice as described in Example 3. This identified a number of antibodies that could be grouped into clusters with STIM001, STIM002 or STIM003 based their heavy and light chain v and j gene segments and CDR3 length. CL-61091 clustered with STIM001; CL-64536, CL-64837, CL-64841 and CL-64912 clustered with STIM002; and CL-71642 and CL-74570 clustered with STIM003. Sequence alignments of the antibody VH and VL domains are shown in FIGS. 35 to 37.

TABLE E12-3

Antibodies clustered by sequence.

| ANTIBODIES | VH_V_ GENE | VH_J_GENE | VH_CDR3_NT_LENGTH |
|---|---|---|---|
| STIM001, CL-61091 | 1-18 | 6 | 42 |
| STIM002, CL-64536, CL-64837,CL-64841, CL-64912 | 1-18 | 6 | 51 |
| STIM003, CL-71642, CL-74570 | 3-20 | 4 | 51 |
| STI M 004 | 3-20 | 4 | 51 |
| STI M 005 | 1-18 | 3 | 51 |
| STI M 006 | 3-11 | 6 | 63 |
| STIM007, STIM008 | 2-5 | 6 | 48 |
| STI M 009 | 3-11 | 6 | 60 |
| **ANTIBODIES** | **VL_V_GENE** | **VL_J_GENE** | **VL_CDR3_NT_LENGTH** |
| STIM001, CL-61091 | 2-28 | 4 | 27 |
| STIM002, CL-64536, CL-64837,CL-64841, CL-64912 | 2-28 | 2 | 27 |
| STIM003, CL-71642, CL-74570 | 3-20 | 3 | 27 |
| STI M 004 | 3-20 | 3 | 24 |
| STI M 005 | 1D-39 | 1 | 24 |
| STI M 006 | 2-28 | 2 | 30 |
| STIM007, STIM008 | 3-11 | 4 | 27 |
| STI M 009 | 2-28 | 1 | 27 |

Example 13: Agonism of ICOS-Expressing MJ Cells by Bead-Bound Antibody

Antibodies STIM001, STIM002 and STIM003, the anti-ICOS antibody C398.4A, and ICOS ligand (ICOSL-Fc), were each covalently coupled to beads and assessed for their ability to induce expression of the cytokine IFN-γ from MJ cells grown in culture. Human IgG1 and Clone C398.4A isotype controls coupled to beads were assessed in parallel.

Figure 12:
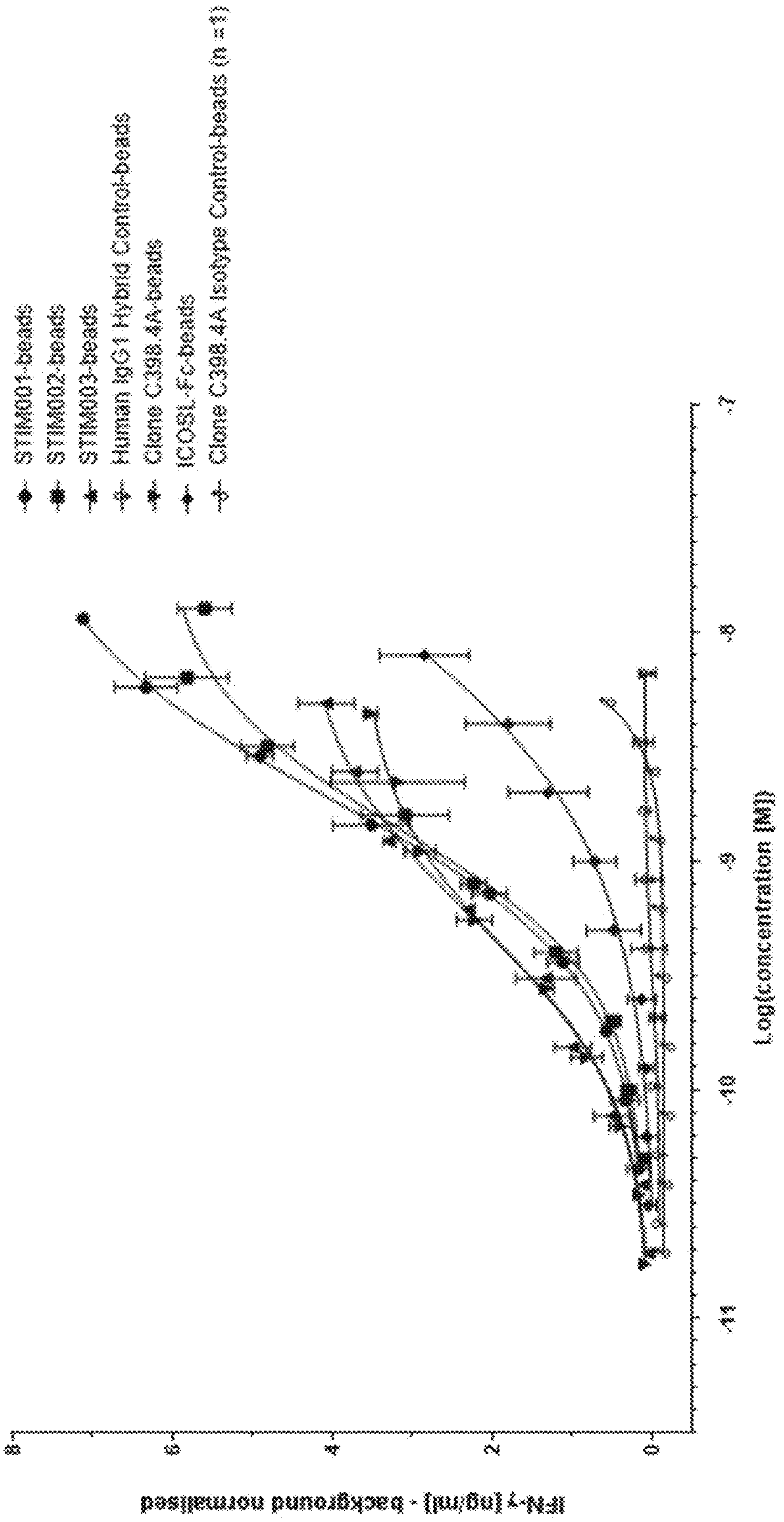
FIG. 12: MJ cell in vitro activation assay—bead bound. Stimulation profiles of STIM001, STIM002 and STIM003 anti-ICOS mAbs bound to beads compared with anti-ICOS C398.4A and respective isotype controls. Data represent the average of two experiments (n=1 in the case of C398.4A isotype control beads).

Data are shown in FIG. 12 and Table E13 below.

Each of the anti-ICOS antibodies demonstrated agonism in this assay, stimulating MJ cells as determined by IFN-γ quantification significantly above that observed by their cognate isotype controls within the dynamic range of the assay.

STIM003 and Clone C398.4A produced lower top asymptote values (95% CI: 3.79 to 5.13 and 3.07 to 4.22, respectively) but more potent Log EC50 values (95% CI: −9.40 to −9.11 and −9.56 to −9.23, respectively) compared with STIM001 (Top 95% CI: 7.21 to 8.88 and Log EC50 95% CI: −8.82 to −8.63) and STIM002 (Top 95% CI: 5.38 to 6.95 and Log EC50 95% CI: −9.00 to −8.74). Because incomplete curves (Top out of dynamic range of assay) were produced for ICOSL-Fc and Clone C398.4A isotype control, the fitted Top and Log EC50 values were not treated as reliable. Human IgG1 Hybrid Control produced a complete curve, however the area under the curve was not significantly different from 0 and it was therefore not deemed to be an agonist.

Stock protein samples were quantified spectrometrically and beads were counted on a cell counter. Dilution series of protein samples and beads were then incubated in the plates at 50 μl/well for 1 hr at RT before washing again three times with DPBS+0.1% Tween. 50 μl/well of either biotinylated anti-armenian hamster antibody or anti-human IgG—europium in DPBS+0.1% BSA were added and incubated for 1 hr at RT. In the case of addition of biotinylated anti-Armenian hamster antibody C398.4A another incubation step with 50 μl/well of streptavidin-europium (Perkin Elmer) diluted 1:500 in Assay buffer (Perkin Elmer) were added and incubated for 1 hr at RT. The wells were washed three times with 200 μl/well of TBS+0.1% Tween before developing the assay by adding 50 μl/well of Delfia enhancement solution (Perkin Elmer), incubating for 10 mins at RT and measuring the fluorescence emitted at 615 nm on the EnVision Multilabel Plate Reader. The quantity of protein on the beads was determined by extrapolating values from the signals obtained from known concentrations of uncoupled protein samples.

MJ Cell In Vitro Activation Assay—Bead Bound

MJ [G11] cell line (ATCC CRL-8294) was grown in IMDM (Gibco or ATCC) supplemented with 20% heat inactivated FBS. Cells were counted and 15000 cells/well (50 μl/well) of cell suspension was added to 96-well clear flat bottom polystyrene sterile TC-treated microplates. Beads were counted and serial 1:2 dilutions ranging from 1.5×10^6 beads/well to approximately 5860 beads/well (50 μl/well) were added to the cells in duplicate or in triplicate.

TABLE E13

Summary table of bead bound MJ cell in vitro activation assay.

| Best-fit values 95% CI | STIM001-beads | STIM002-beads | STIM003-beads | Human IgG1 Hybrid Control-beads | Clone C398.4A-beads | Clone C398.4A IC-beads | ICOSL-Fc-beads |
|---|---|---|---|---|---|---|---|
| Bottom | −0.24 to 0.36 | −0.38 to 0.56 | −0.39 to 0.34 | −0.26 to 0.06 | −0.37 to 0.42 | −0.20 to −0.09 | −0.62 to 0.49 |
| Top | 7.21 to 8.88 | 5.38 to 6.95 | 3.79 to 5.13 | −0.04 to 0.20 | 3.07 to 4.22 | NA | −45.66 to 65.37 |
| LogEC50 | −8.82 to −8.63 | −9.00 to −8.74 | −9.40 to −9.11 | −10.43 to −8.60 | −9.56 to −9.23 | NA | −12.80 to −2.37 |
| HillSlope | 0.89 to 1.38 | 0.82 to 1.85 | 0.69 to 1.56 | −3.47 to 6.61 | 0.64 to 1.90 | NA | −0.38 to 1.88 |

NA—not applicable.

MJ Cell Activation Assay Materials and Methods—Bead-Bound

Coupling Proteins of Interest to Magnetic Particles

Anti-ICOS antibodies, control antibodies, and ICOSL-Fc, were coupled to beads as follows.

Dynabeads M-450 Tosylactivated (Invitrogen; approximately 2×10^8 beads/sample) were incubated with 100 μg of each protein sample overnight at room temperature with agitation. Beads were washed three times with DPBS (Gibco) and incubated with 1M Tris-HCl, pH 8.0 (UltraPure™, Gibco) for 1 hr at room temperature with agitation to block the uncoupled reactive sites. Beads were washed again three times with DPBS and finally resuspended in 0.5 ml of DPBS/sample.

The quantity of each protein of interest on the beads was then determined as follows. Black flat bottom, high binding ELISA plates (Greiner) were coated with Anti-human IgG (Southern Biotech) or Anti-Armenian Hamster IgG (Jackson ImmunoResearch) capture antibody at 4 μg/ml in DPBS, 50 μl/well, overnight at 4° C. Wells were then washed three times with DPBS+0.1% Tween, 200 μl/well and blocked with 200 μl/well of DPBS+1% BSA for 1 hr at RT. Wells were washed again three times with DPBS+0.1% Tween.

To account for background several wells of the plate contained MJ cells only (100 μl/well). The cells and beads were co-cultured in the plates for 3 days at 37° C. and 5% $CO_2$ after which supernatants were harvested by centrifugation and collected for IFN-γ content determination.

Measuring IFN-γ Levels

The IFN-γ content in each well was determined using a modification of the Human IFN-gamma DuoSet ELISA kit (R&D systems). Capture antibody (50 μl/well) was coated overnight at 4 μg/ml in DPBS on black flat bottom, high binding plates (Greiner). The wells were washed three times with 200 μl/well of DPBS+0.1% Tween. The wells were blocked with 200 μl/well of 1% BSA in DPBS (w/v), washed three times with 200 μl/well of DPBS+0.1% Tween and then 50 μl/well of either the IFN-γ standard solutions in RPMI or neat cell supernatant were added to each well and incubated for 1 hr at RT. The wells were washed three times with 200 μl/well of DPBS+0.1% Tween before adding 50 μl/well of biotinylated detection antibody at 200 ng/ml in DPBS+0.1% BSA and incubated for 1 hr at RT. The wells were washed three times with 200 μl/well of DPBS+0.1% Tween before adding 50 μl/well of streptavidin-europium (Perkin Elmer) diluted 1:500 in Assay buffer (Perkin Elmer) and incubated for 1 hr at RT. The wells were washed three times with 200 μl/well of TBS+0.1% Tween before developing the assay by adding 50 μl/well of Delfia enhancement solution (Perkin Elmer) and incubating for 10 mins at RT and measuring the fluorescence emitted at 615 nm on the EnVision Multilabel Plate Reader.

Data Analysis

IFN-γ values for each well were interpolated from the standard curve and the average background levels from cell-only wells were subtracted. The background corrected values were then used in GraphPad prism to fit a 4-parameter log-logistic concentration response curve.

Example 14: Agonism of ICOS-Expressing MJ Cells by Plate-Bound Antibody

An alternative assay for agonism of ICOS-expressing T cells uses antibodies in a plate-bound format.

MJ Cell Activation Assay Materials and Methods—Plate-Bound

Antibody coating: 96-well, sterile, flat, high binding plates (Costar) were coated overnight at 4° C. with 100 μl/well of serial 1:2 dilutions of proteins of interest (anti-ICOS antibodies, control antibodies, and ICOSL-Fc) in DPBS (Gibco) ranging from 10 μg/ml to 0.02 μg/ml of in duplicate or in triplicate. To account for background several wells of the plate were coated with DPBS only. Plates were then washed three times with 200 μl/well of DPBS before the addition of cells.

Cell stimulation: MJ [G11] cell line (ATCC CRL-8294) was grown in IMDM (Gibco or ATCC) supplemented with 20% heat inactivated FBS. The cells were counted and 15000 cells/well (100 μl/well) of cell suspension were added to the protein coated plates. Cells were cultured in the plates for 3 days at 37° C. and 5% $CO_2$. Cells were separated from the media by centrifugation and the supernatants collected for IFN-γ content determination.

Measurement of IFNγ levels and data analysis was as described in Example 13.

Results

Figure 13:
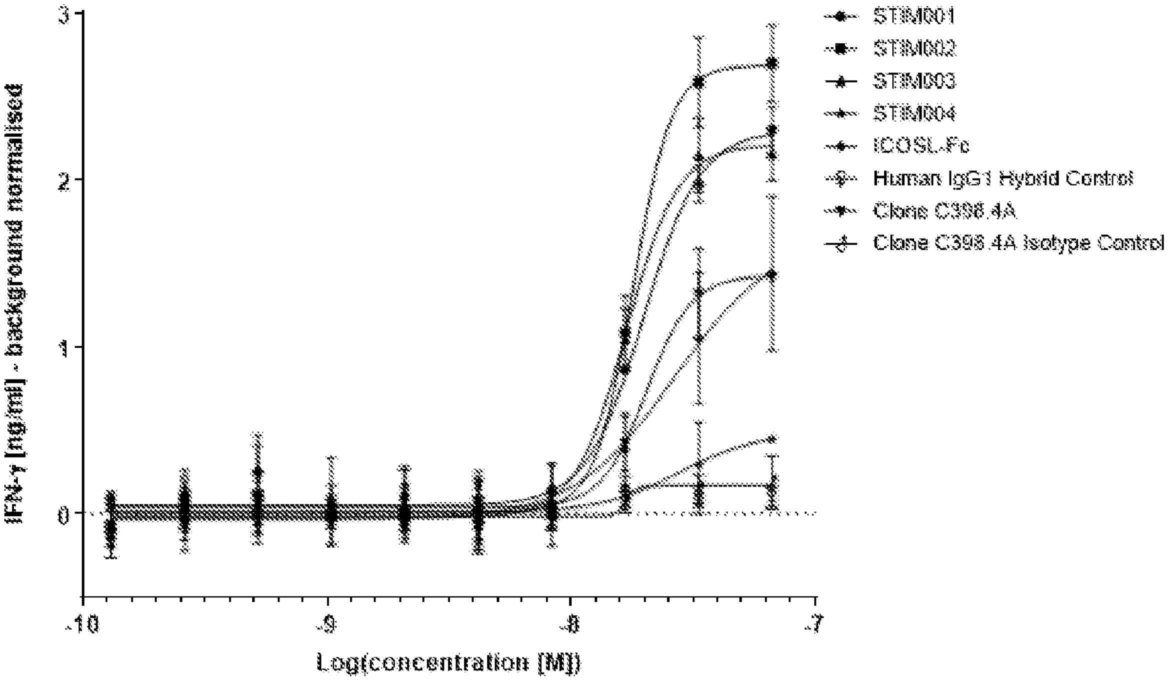
FIG. 13: MJ cell in vitro activation assay—plate bound. Stimulation profiles of plate-bound STIM001, STIM002, STIM003 and STIM004 anti-ICOS mAbs compared with anti-ICOS C398.4A and respective isotype controls. Data represent the average of two experiments.

Results are shown in FIG. 13 and in Table E14-1 below. In summary, STIM001, STIM002 and STIM003 all showed potent agonism as measured by IFN-γ secretion with similar Log EC50 values (Log EC50 95% CI: −7.76 to −7.64, −7.79 to −7.70 and −7.82 to −7.73, respectively) and Top values (Top 95% CI: 2.06 to 2.54, 2.44 to 2.93 and 2.01 to 2.41, respectively). Clone C398.4A exhibited a similar Log EC50 value (Log EC50 95% CI: −7.78 to −7.60) but lower Top value (Top 95% CI: 1.22 to 1.63) than STIM001 to STIM003. STIM004 also showed agonism in this assay, but was less potent, reaching a moderate Top value (Top 95% CI: 0.16 to 0.82) with a similar Log EC50 value (Log EC50 95% CI: −7.91 to −7.21). STIM001, STIM002 and STIM003 were stronger agonists than ICOSL-Fc (Log EC50 95% CI: −7.85 to −7.31 and Top 95% CI: 0.87 to 2.45).

Example 15: Agonism of ICOS-Expressing MJ Cells by Antibody in Soluble Form

In contrast to the assays described in Example 13 and Example 14, which used antibody arrayed on a solid surface, this assay determines whether antibody in soluble form acts as agonist of ICOS-expressing T cells.

MJ Cell Activation Assay Materials and Methods—Soluble

MJ [G11] cell line (ATCC CRL-8294) was grown in IMDM (Gibco or ATCC) supplemented with 20% heat inactivated FBS. Cells were counted and 15000 cells/well (50 μl/well) of cell suspension was added to 96-well clear flat bottom polystyrene sterile TC-treated microplates. Serial 1:2 dilutions of proteins of interest ranging from 10 μg/ml to 0.01953125 μg/ml either alone or with the addition of a cross-linking reagent (AffiniPure F(ab')2 Fragment Goat Anti-Human IgG, Fc Fragment Specific; Jackson ImmunoResearch) were added to the cells in duplicate or in triplicate (50 μl/well). To account for background several wells of the plate contained MJ cells only (100 μl/well). The cells and beads were co-cultured in the plates for 3 days at 37° C. and 5% $CO_2$ after which supernatants were harvested by centrifugation and collected for IFN-γ content determination.

Measurement of IFNγ levels and data analysis was as described in Example 13.

Results

STIM001 and STIM002 both showed significant soluble agonism as measured by IFN-γ secretion compared to Human IgG4.PE hybrid control. MAb cross-linking via Goat Anti-Human IgG Fc F(ab')2 Fragment increased secreted IFN-γ levels even more.

Example 16: Binding of Antibody to Activated T Cells

A. Human ICOS

Ability of anti-ICOS antibodies to recognise the ICOS extracellular domain in its native context on the surface of activated primary human T cells is confirmed in this assay.

Pan T-cells (CD3 cells) were isolated and cultured for 3 days with CD3/CD28 dynabeads (Thermofisher) to induce ICOS expression on their surface. Surface staining of STIM001, STIM003 and the hIgG1 hybrid control (HC IgG1) was determined by two methods, namely detection following direct binding of pre-labelled antibodies (antibodies directly conjugated with AF647) or indirectly via the use of a secondary AF647-Goat anti-human Fc antibody. Stained cells were ran on the Attune and staining intensity was presented as Mean of fluorescence intensity (MFI). EC50 was determined using GraphPad Prism.

Figure 14:
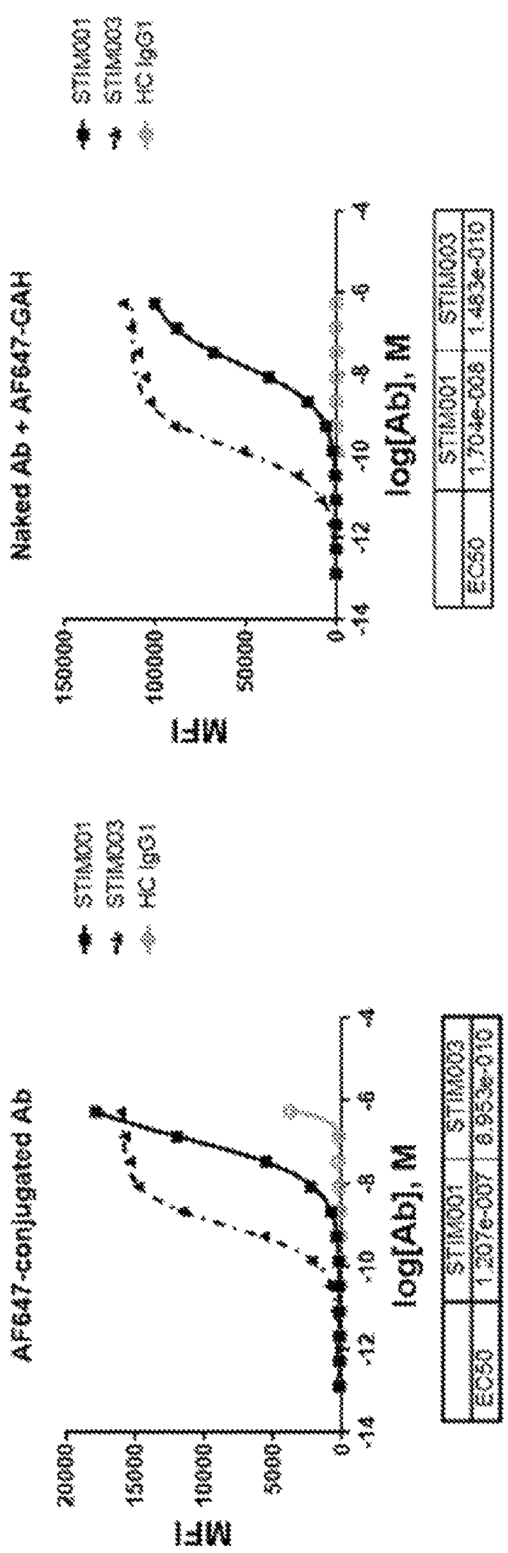
FIG. 14: FACS analysis of STIM001 and STIM003 hIgG1 binding to activated T cells. (a) shows a representative experiment of the dose response of pre-labelled antibodies binding to activated T cells, whereas (b) shows the binding following the dose response of naked antibodies followed by the detection with a secondary labelled antibody. Tables indicate relevant EC50 (M) as determined using GraphPad Prism.

Results are shown in FIG. 14. Once activated, pan CD3 T cells were clearly stained by both STIM001 and STIM003

TABLE E14-1

Summary of plate-bound MJ cell in vitro activation assay.

| Best-fit values 95% CI | STIM001 | STIM002 | STIM003 | STIM004 | IgG1 | Clone C398.4A | ICOSL-Fc | Clone C398.4A IC |
|---|---|---|---|---|---|---|---|---|
| Bottom | −0.03 to 0.13 | −0.08 to 0.11 | −0.10 to 0.07 | −0.06 to 0.07 | NA | −0.03 to 0.11 | −0.16 to 0.09 | −0.07 to 0.04 |
| Top | 2.06 to 2.54 | 2.44 to 2.93 | 2.01 to 2.41 | 0.16 to 0.82 | NA | 1.22 to 1.63 | 0.87 to 2.45 | 0.05 to 0.29 |
| LogEC50 | −7.76 to −7.64 | −7.79 to −7.70 | −7.82 to −7.73 | −7.91 to −7.21 | NA | −7.78 to −7.60 | −7.85 to −7.31 | NA |
| HillSlope | 2.06 to 5.38 | 0.16 to 10.88 | 1.77 to 6.5 | −1.46 to 6.77 | NA | 1.24 to 8.20 | 0.26 to 3.97 | NA |

IgG1 = Human IgG1 hybrid control antibody.

hIgG1. Notably, the saturation of STIM003 binding to activated T cells occurred at a lower concentration than that of STIM001, suggesting higher affinity of STIM003 to human ICOS. The EC50 of STIM003 was roughly 100× lower than that of STIM001 (0.148 nM vs 17 nM for the indirect binding assay).

B. ICOS from Non-Human Primates

Ability of anti-ICOS antibodies to recognise the ICOS extracellular domain in its native context on the surface of activated primary T cells from non-human primates (NHP) is confirmed in this assay.

PBMC from whole blood of 2 Mauritian cynomolgus macaques (Wickham Laboratories) were isolated by gradient centrifugation and cultured for 3 days with CD2/CD3/CD28 MACSiBeads (Miltenyi) to induce ICOS expression on their surface. Surface staining of STIM001, STIM003 and the hIgG1 hybrid control (HC IgG1) was determined following direct binding of AF647 pre-labelled antibodies (from 80 μg to 8 pg/ml). Cells were also labelled with V450-CD3 to assess staining on T-cell subsets. Stained cells were run on Attune (Thermofisher) and staining intensity was presented as mean fluorescence intensity (MFI). EC50 was determined using GraphPad Prism.

Results are shown in FIG. 28. Once activated, T cells were clearly stained by both STIM001 and STIM003 hIgG1. As was observed with binding to human T cells, saturation of STIM003 binding to activated NHP T cells occurred at lower concentration than that of STIM001, indicating that STIM0003 has the higher affinity of these two antibodies ICOS. EC50 values for binding to NHP ICOS were similar to those obtained for binding to human ICOS.

TABLE E16

| EC50 (Molar) calculated for antibody binding to ICOS on activated NHP T cells | | | |
|---|---|---|---|
| Pan T-cells | EC50 | Cynomolgus donor 1 | Cynomolgus donor 2 |
| NHP | STIM001 | 2.224e−7 | not tested |
| | STIM003 | 4.581e−9 | 4.830e−9 |
| Human | STIM001 | 2.209e−7 | 1.207e−7 |
| | STIM003 | 2.293e−9 | 8.953e−10 |

Example 17: Analysis of T Cell Sub-Populations Among Tumour Infiltrating Lymphocytes and Peripheral T Cells A pharmacodynamics study revealed that anti-ICOS antibodies STIM001 and STIM003 in mIgG2a isotype significantly deplete TRegs, increase the percentage of CD4+ effector cells and increase the CD4+ effector/TReg ratio as well as the CD8+/TReg ratio within the tumour microenvironment (TME).

The increased CD8+/TReg ratio and increased number of CD4+ effector cells within the TME may collectively contribute to the CT26 tumour clearance observed when these anti-ICOS antibodies were co-injected with anti-PDL1 antibody in the STIM001 & STIM003 efficacy study (Example 11).

Method

The pharmacodynamics study was performed in female Balb/c mice bearing CT-26 mouse colon carcinoma cells (ATCC, CRL-2638). Balb/c mice were supplied by Charles River UK at 6-8 weeks of age and >18 g and housed under specific pathogen-free conditions. A total of 1×10E5 CT-26 tumour cells (passage number: P8) were subcutaneously injected in the right flank. All CT-26 tumour bearing animals were assigned to 6 groups (Table E17-1) and individual mice were dosed twice (on Day 13 & Day 15 post tumour cell implantation) with 200 μg of antibody or saline. CD3+ T-cells from the CT-26 tumour bearing animals were analysed by FACS on day 16 post tumour cell implantation.

TABLE E17-1

| Treatment groups | | |
|---|---|---|
| Group | Number of animals | Treatment regimen (Day 13 and Day 15 post tumour cell implantation) |
| 1 | 10 | Saline |
| 2 | 10 | Anti-ICOS (STIM001) mIgG1 200 μg each |
| 3 | 10 | Anti-ICOS (STIM001) mIgG2a 200 μg each |
| 4 | 10 | Anti-ICOS (STIM003) mIgG1 200 μg each |
| 5 | 10 | Anti-ICOS (STIM003) mIgG2a 200 μg each |
| 6 | 10 | Anti-CTLA-4 (9H10) 200 μg each |

Results

Animals treated with STIM001 & STIM003 in the mIgG2a isotype showed a lower percentage of CD4+ CD3+ CD45+ cells at the tumour site when compared with saline treated group (FIG. 15A), whereas STIM001 or STIM003 treatments had very marginal effect of the percentage of CD8+ CD3+ CD45+ cells at the tumour site (FIG. 15B). The decrease in CD4+ T cells could be attributed to a profound decrease in the percentages of T-Regulatory cells in all the groups treated with STIM001 and STIM003 antibodies. Notably, animals treated with STIM001 and STIM003 in the mIgG2a isotype showed a dramatic reduction in T-Regs (CD4+ Foxp3+ CD25+) within the TME, whereas STIM001 & STIM003 in the mIgG1 isotype had only a modest effect on T-Reg content in TME. In addition, animals treated with STIM001 & STIM003 in the mIgG2a isotype had reduced T-Reg in the TME when compared with the animals treated with a commercial anti-CTLA-4 (9H10, Biolegend Cat#106208) antibody which is known to deplete T-Reg [42], but this result did not reach statistical significance (FIG. 15C). The effect of STIM001 and STIM003 either in mIgG1 or mIgG2a isotypes on T-Reg compartment was more specific with tumour infiltrating lymphocytes (TILs). T-reg depletion was not observed in the periphery (as previously described for anti-CTLA4 [43]) (FIG. 15D). The changes in T-Reg contents also resulted in a significant increase in the percentage of intra-tumoural CD4-effector cells (CD4+Foxp3− CD25−) (FIG. 15E), similarly the ratio of CD4 effector/T-Reg and CD8/T-Reg ratio in the animals treated with STIM001 & STIM003 in the mIgG2a was also significantly increased within TME (FIG. 15F & FIG. 15G).

Example 18: Effect of Anti-ICOS Antibody on Level of ICOS-Expressing T Cells in CT26 Tumour and Spleen Analysis was performed to quantify the percentage of immune cells within the tumour compared with the spleen, by analysis of total immune cells in the tumour and spleen tissues, following treatment with anti-ICOS antibody STIM001 or STIM003. STIM001 and STIM003 mIgG2a each caused a significant reduction in Treg within the tumour, but not in the spleen, indicating a tumour-selective effect. This depletion was selective for Tregs compared with other T cell subtypes. The results presented here assist in understanding the effects of the STIM antibodies on the immune contexture, and confirm that anti-ICOS antibodies with effector-function-enabled Fc regions can strongly deplete TRegs.

Materials and Methods

Mice bearing CT26 tumours were dosed twice with STIM001, STIM003, or anti-CTLA4 antibody (9H10). The anti-CTLA4 antibody was included as a positive control for Treg depletion, as anti-CTLA4 antibody had been previously shown to selectively reduce Tregs in tumours [43].

The immune contexture within the tumours and the spleen of treated animals was analysed by FACS following tissue disaggregation.

Details of FACS antibodies used in this study are shown in Table E18. All FACS antibodies were used at a concentration recommended by the supplier. FACS data were acquired using Attune NxT flow cytometer and data were analysed using FlowJo software.

TABLE E18

FACS antibodies.

| Marker | Supplier | Cat. number | Lot number | Fluorophore |
|---|---|---|---|---|
| Live/dead | Life technologies | L-34959 | 1784156 | Fixable Yellow |
| CD45 | E-bioscience | 45-0451-82 | E08336-1636 | PerCp-Cy5.5 |
| CD3 | E-bioscience | 48-0032-82 | 4278794 | eFlour 450 |
| CD4 | E-bioscience | 11-0042-86 | E0084-1633 | FITC |
| CD8 | E-bioscience | 12-0081-85 | E01039-1635 | PE |
| Foxp3 | E-bioscience | 17-5773-82 | 4291991 | APC |
| CD25 | E-bioscience | 47-0251-82 | 4277960 | APC eF 780 |
| ICOS | E-bioscience | 25-9942-82 | E17665-103 | PE-CY7 |
| Fc/Block | E-bioscience | 16-0161-86 | E06357-1633 | — |

Results

Figure 20:
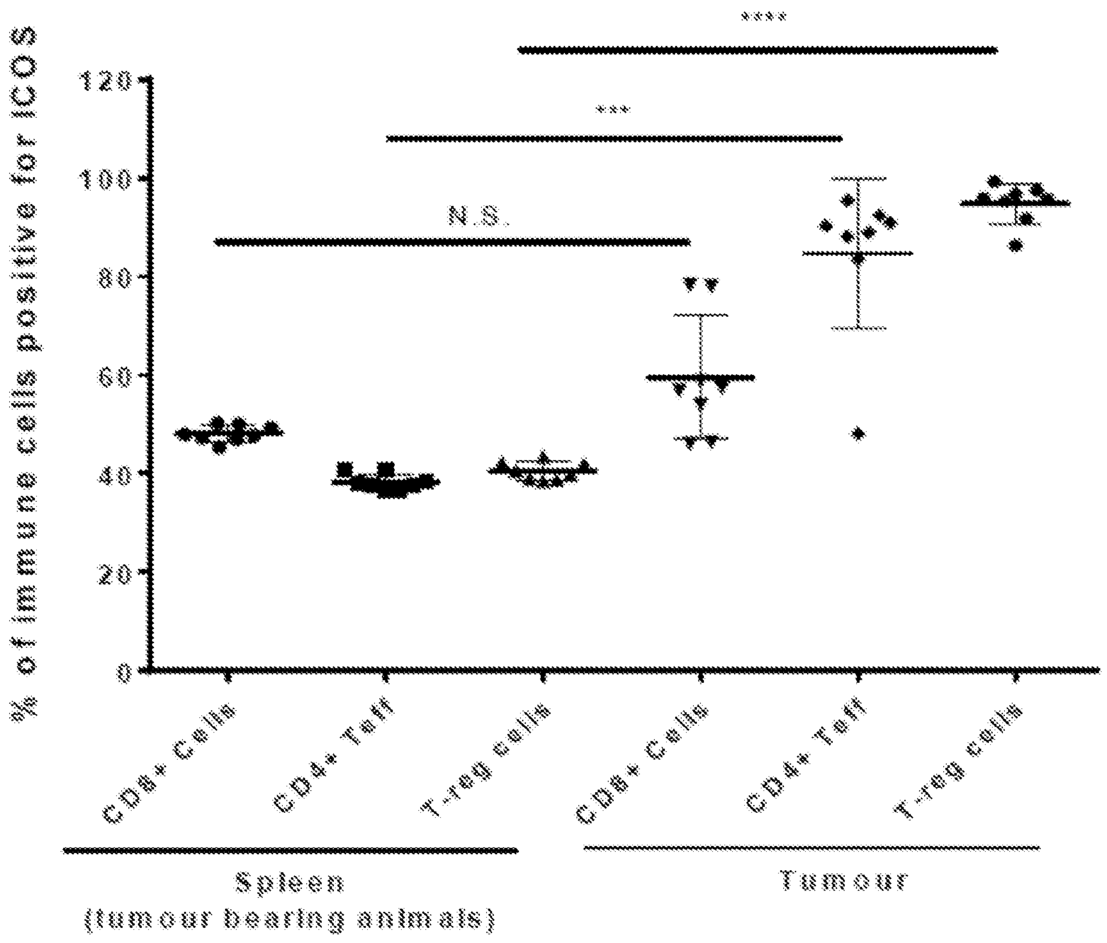
FIG. 20: Graph showing the percentage of immune cells (CD8 T-Effector, CD4 T-Effector and CD4/FoxP3 TReg cells) in the CT26 tumours and in the spleen of tumour bearing animals that are expressing ICOS on their surface. Values denote mean±SD (n=8). P values were calculated using nonparametric Dunn's multiple comparisons test. NS=not significant; *=$p<0.001$; **=$p<0.0001$.

ICOS expression was determined in the CT26 tumours and in the spleen of tumour-bearing animals. We observed an increased percentage of tumour infiltrating immune cells expressing ICOS protein (FIG. 20), indicating that immune cells in the tumours are more often positive for ICOS expression than immune cells in the periphery. TRegs in the tumour of untreated animals were nearly all (>90%) positive for ICOS expression, whereas CD8+ effector T cells in the tumour were not (approx. 60%). Comparing T cell subpopulations (again in untreated mice) in tumour with those in spleen, a significantly higher ($p<0.0001$) percentage of intratumoural Tregs were positive for ICOS compared with Tregs in spleen, and a significantly higher ($p<0.001$) percentage of intratumoural CD4+ Teff cells were positive for ICOS compared with CD4+ Teff cells in spleen.

Figure 21:
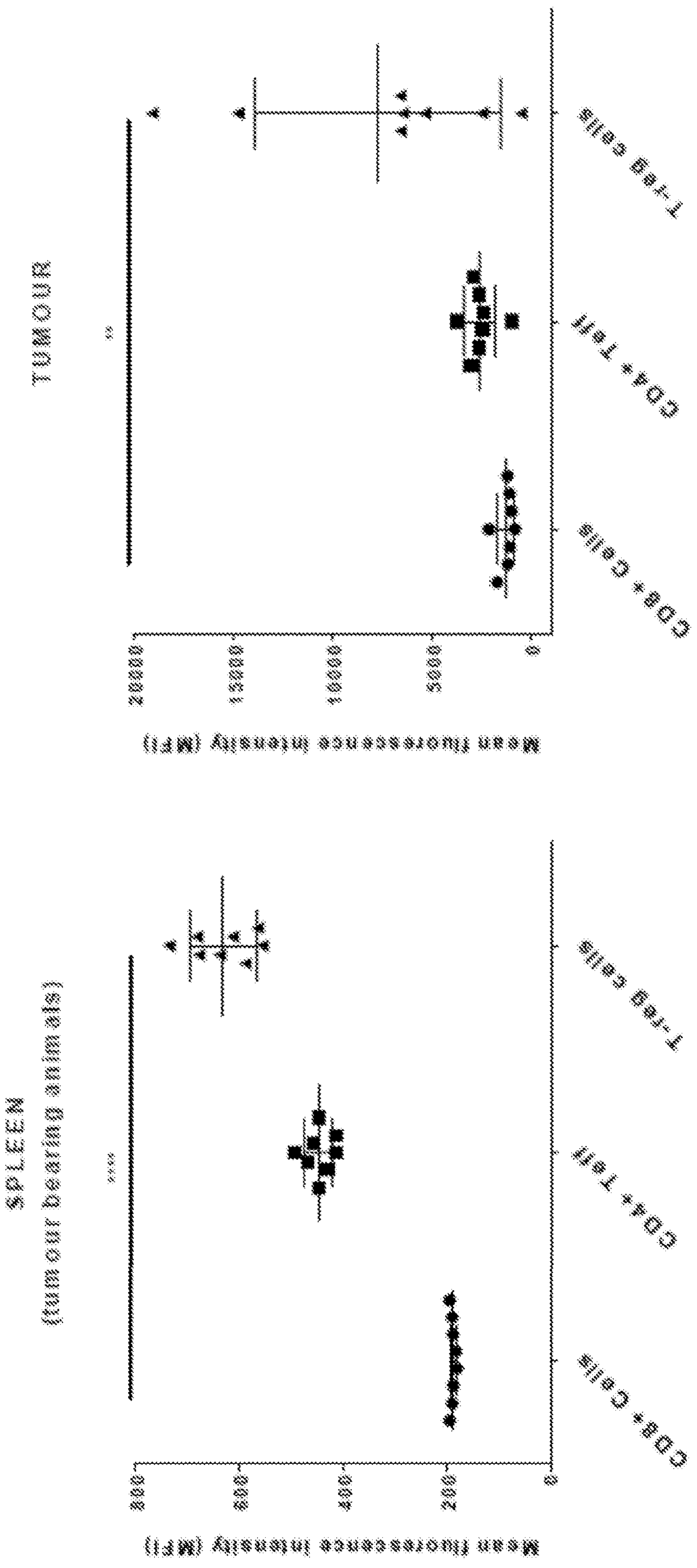
FIG. 21: Relative expression of ICOS on the surface of immune cells—CD8 T effector, CD4 T effector and CD4/FoxP3 TRegs—as determined by the mean fluorescence intensity (MFI). Values denote mean±SD (n=8). P values were calculated using nonparametric Dunn's multiple comparisons test. **=$p<0.0001$, =$p<0.01$. Note the difference in the fluorescence intensity between spleen (low) and tumours (high).

Also in the mice before treatment, the level of ICOS expression was much higher on immune cells in the microenvironment of CT26 tumours, when compared with immune cells in the spleen (FIG. 21). ICOS expression was increased on the surface of all immune cell subsets analysed (CD8 T-Effector, CD4 T-Effector and CD4/FoxP3 TReg cells) in the tumour microenvironment. Note that although immune cells in the tumours and the spleen are both expressing ICOS, immune cells in the tumour are expressing significantly more ICOS (indicated by higher MFI, FIG. 21) than cells in the spleen (indicated by lower MFI, FIG. 21). Importantly, TRegs in the tumour are expressing the highest levels of ICOS, as previously reported [11].

Figure 22:
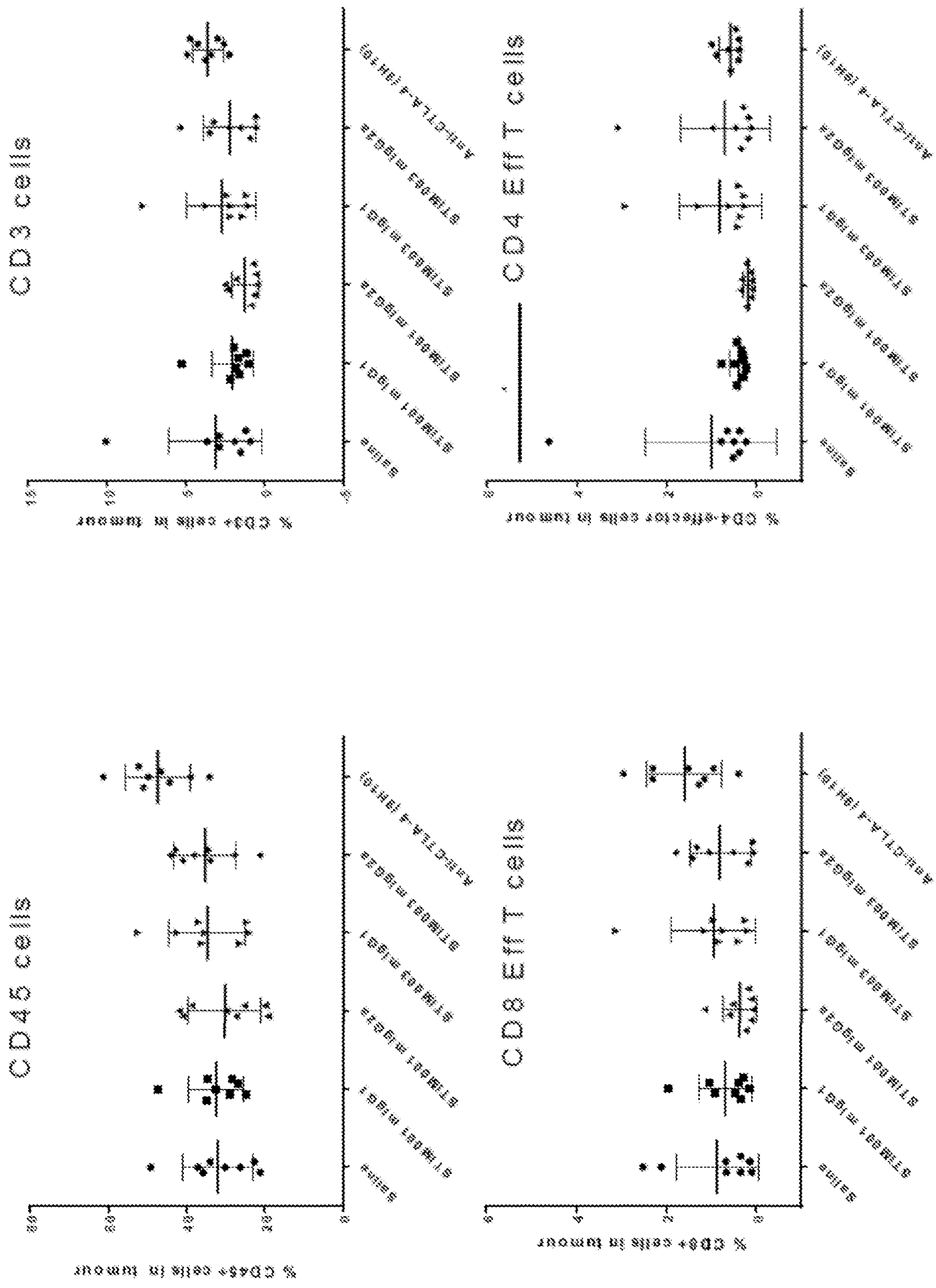
FIG. 22: Effect of STIM001 and STIM003 on the percentage of different immune cells in the microenvironment of CT26 tumours. *=$p<0.05$.

CT26 tumour bearing animals were treated with 2 doses of antibody STIM001 or STIM003 and with an anti-CTLA-4 antibody. The STIM antibodies did not affect the overall percentage of CD45 positive cells (a marker for immune cells) in the tumours, when used in either mIgG1 or mIgG2 format. Nor did treatment with these antibodies significantly affect the percentage of CD8 effector T cells in CT26 tumours (FIG. 22). Treatment with STIM001 in mIgG2a isotype led to a significant ($p<0.05$) depletion of CD4+ effector T cells, but none of STIM001 mIgG1, STIM003 mIgG1 and STIM003 mIgG2a affected the percentage of CD4+ effector T cells.

Anti-CTLA-4 treatment produced a notable (albeit not statistically significant) increase in CD45+ cells and CD8+ effector T cells in the TME, but did not affect CD4+ effector T cells (FIG. 22).

Figure 23:
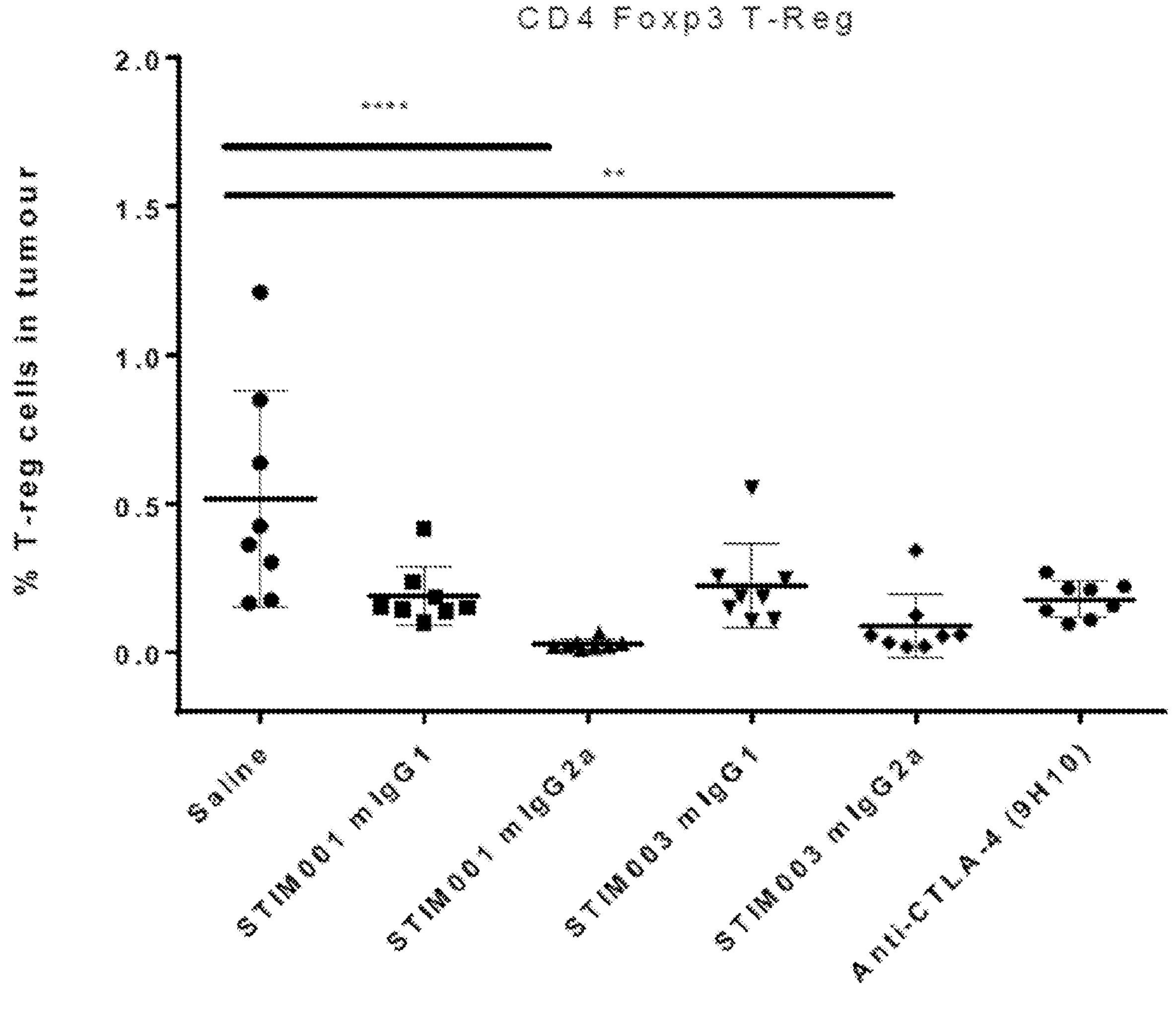
FIG. 23: Effect of antibodies STIM001 and STIM003 on the percentage of regulatory T cells (CD4+/FoxP3+ cells) in the microenvironment of CT26 tumours. =$p<0.05$, **=$p<0.0001$. Values denote mean±SD (n=8). P values were calculated using nonparametric Dunn's multiple comparisons test.

The STIM antibodies significantly affected regulatory T cells in the tumour. As shown in FIG. 23, STIM001 mIgG2a and STIM003 mIgG2a significantly and selectively depleted TRegs (which are high for ICOS expression) in the tumour microenvironment. Interestingly, the anti-CTLA4 antibody which, despite being included as a positive control for TReg depletion in this experiment, was less effective than the STIM mIgG2a antibodies at depleting TRegs.

Figure 24:
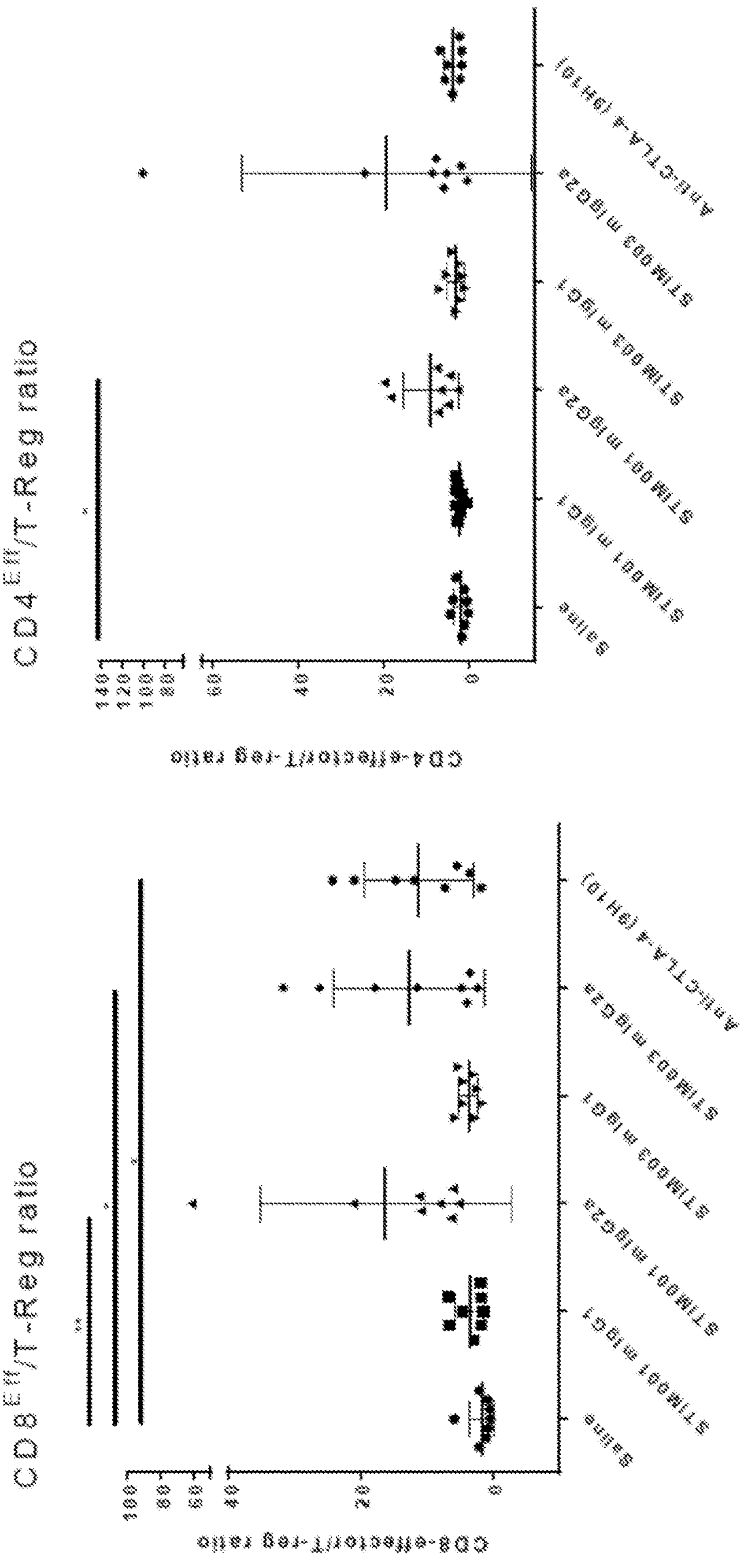
FIG. 24: STIM001 and STIM003 mIgG2 significantly increase the CD8 effector T cell to TReg ratio and the CD4 effector T cells to TReg ratio in CT26 tumours. The ratio was determined by dividing the percentage of effector cells in the tumour by the percentage of regulatory T cells in the tumour.

This selective depletion of TRegs resulted in an increase in the ratio CD8 effector T cells to TRegs in the tumour, and an increase in the ratio of CD4 effector T cells to TRegs in the tumour, both of which should favour an anti-tumour immune response. Ratio data are shown in FIG. 24.

Figure 25:
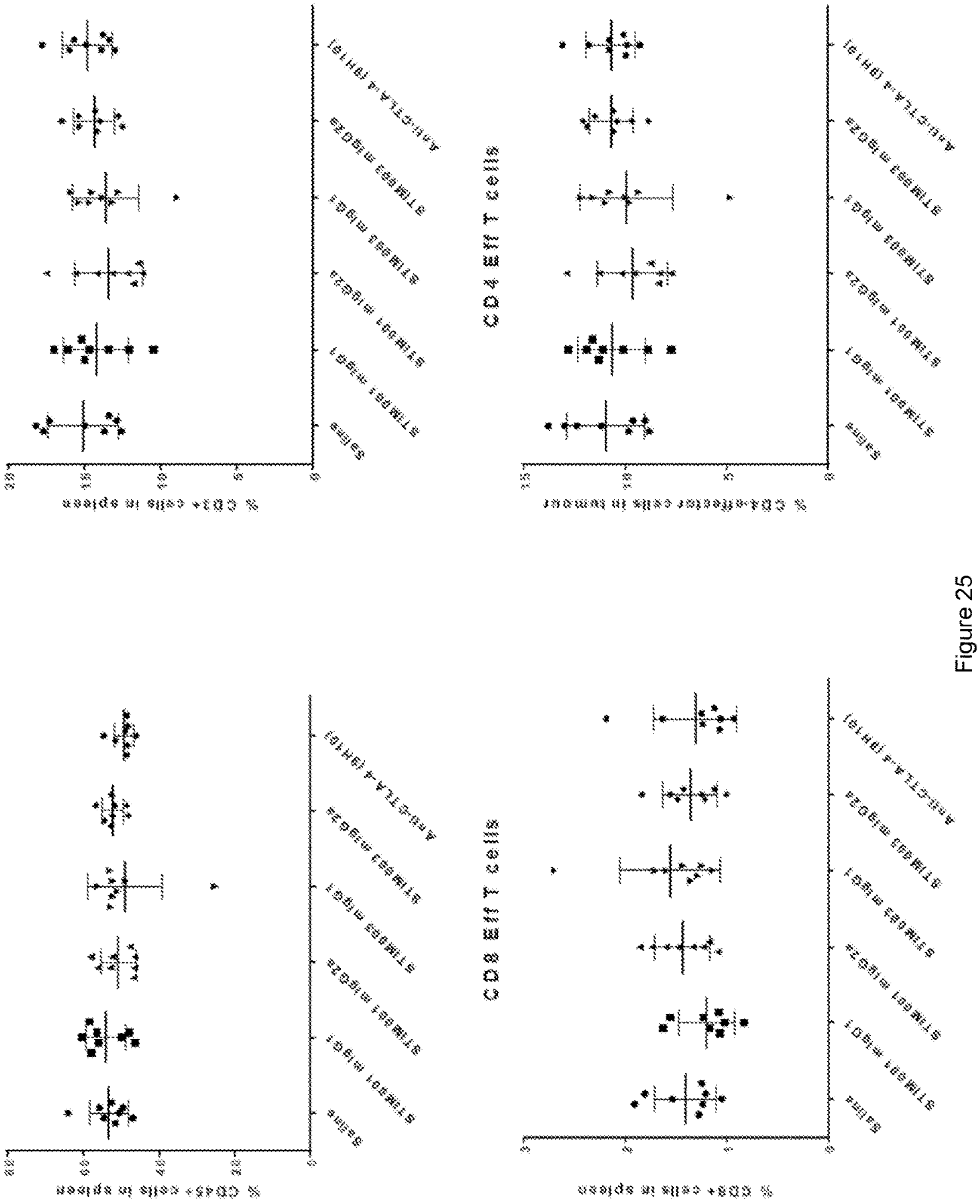
FIG. 25: Effect of antibodies on percentage of immune cells in the spleen of CT26 tumour bearing animals.
Figure 26:
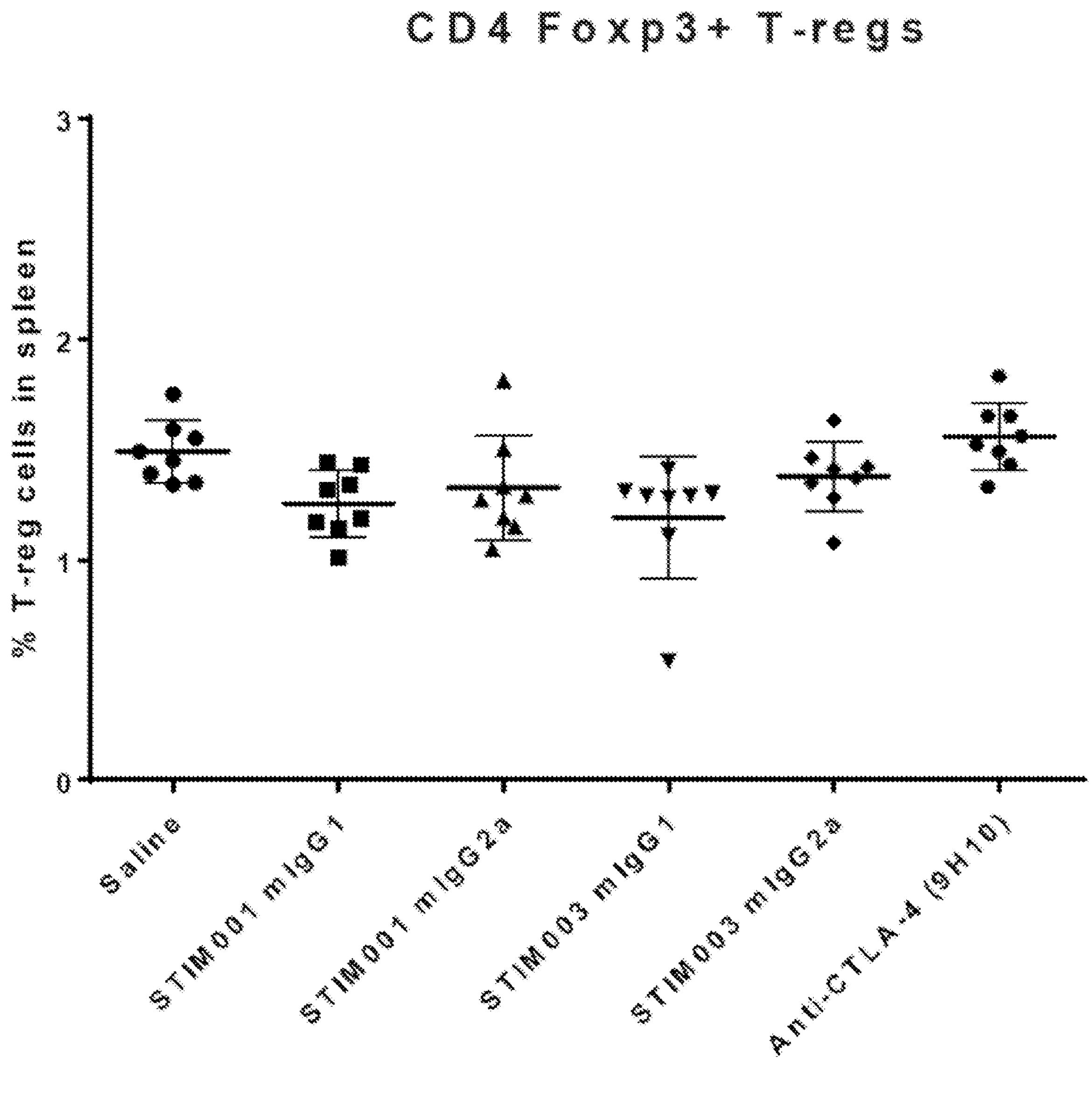
FIG. 26: Effect of antibodies on percentage of regulatory T cells (CD4+/FoxP3+ cells) in the spleen of CT26 tumour bearing animals.

In contrast to the depletion of intratumoural Tregs by STIM001 mIgG2a and STIM003 mIgG2a, no such effect was observed on Tregs in spleen (FIG. 25, FIG. 26, FIG. 27). This indicates that the effects of the anti-ICOS antibodies on depletion of Tregs depletion was not systemic in all the tissues. Such selectivity could be advantageous for therapeutic anti-ICOS antibodies in treating tumours in patients, as preferential depletion of Tregs in the tumour microenvironment could selectively relieve suppression of anti-tumour effector T cells, while minimising side effects at other sites in the body. The anti-ICOS antibodies may thus promote an anti-tumour response in the immune system with a low risk of undesirable activation of a wider T cell response that could cause treatment-limiting autoimmune adverse events.

Example 19: Antibody Stability

STIM003 human IgG1 was tested for stability during storage, freeze/thawing and purification, and was found to maintain its stability under all tested conditions. % aggregation was determined by HPLC.

There was no significant change in the percentage of monomer (>99%) after 3 months storage at 4° C. in buffer (10 mM sodium phosphate, 40 mM sodium chloride, pH 7.0).

On thermal denaturation testing, all samples (n=15) had the same Tm (no significant difference between aliquots) and had comparable thermal denaturation curves.

There was no significant change in Tm (≈70.3° C.), the percentage of monomer or the profile on SDS-PAGE after 3 cycles of freeze and thaw.

There was no significant change in Tm (≈70.3° C.), the percentage of monomer or the profile on SDS-PAGE after 7 days' storage at room temperature.

There was 90% recovery post protein A purification.

Example 20: Monotherapeutic Efficacy of Anti-ICOS Ab Against A20 Tumour Growth in Mouse Anti-ICOS antibodies STIM001 mIgG2a and STIM003 mIgG2a each showed strong anti-tumour efficacy when used as monotherapies in vivo in a mouse A20 syngeneic model.

Materials and Methods

The efficacy study was performed in BALB/c mice using the sub-cutaneous A20 reticulum cell sarcoma model (ATCC, TIB-208). The A20 cell line is a BALB/c B cell lymphoma line derived from a spontaneous reticulum cell neoplasm found in an old BALB/cAnN mouse. This cell line has been reported to be positive for ICOSL.

BALB/c mice were supplied by Charles River UK>18 gram and housed under specific pathogen-free conditions. A total of 5x10e5 A20 cells (passage number below P20) were subcutaneously injected into the right flanks of mice. The A20 cells were passaged in vitro washed twice in PBS and re-suspended in RPMI supplemented with 10% foetal calf serum. Cell viability was confirmed to be above 85% at the time of tumour cell injection. Unless stated otherwise, antibody or isotype administration was initiated from day 8 post tumour cells injection.

STIM001 and STIM003 anti-ICOS antibodies were generated in mouse IgG2a isotype format. The mouse cross reactive anti-PD-L1 antibody (AbW) was also generated in the same isotype format (mouse IgG2a). STIM001, STIM003 and anti-PD-L1 antibodies were dosed intraperitoneally (IP) at 200 µg of each antibody twice a week starting from day 8 (dosing for 3 weeks between day 8-29) post tumour cell implantation. Animal weights and tumour volume were measured 3 times a week from the day of tumour cell injection. Tumour volume was calculated by use of the modified ellipsoid formula ½(Length×Width2). Mice were kept on study until their tumour reached an average diameter of 12 mm. The experiment was stopped at day 43 post tumour cell implantation. Tumour growth was monitored and compared with tumours of animals treated with isotype control (mIgG2a) antibody. Treatment groups are shown in Table E20 below.

TABLE E20

Treatment groups for A20 study.

| Group | Number of animals | Treatment regimen (twice per week for 3 weeks 7 doses) |
|---|---|---|
| 1 | 8 | mIgG2a isotype control 200 µg/mouse/each dose |
| 2 | 8 | Anti-PD-L1 mIGg2a (AbW) 200 µg/mouse/each dose |
| 3 | 8 | Anti-ICOS mIgG2a STIM001 200 µg/mouse each dose |
| 4 | 8 | Anti-ICOS mIgG2a STIM003 200 µg/mouse/each dose |

Results

Figure 30:
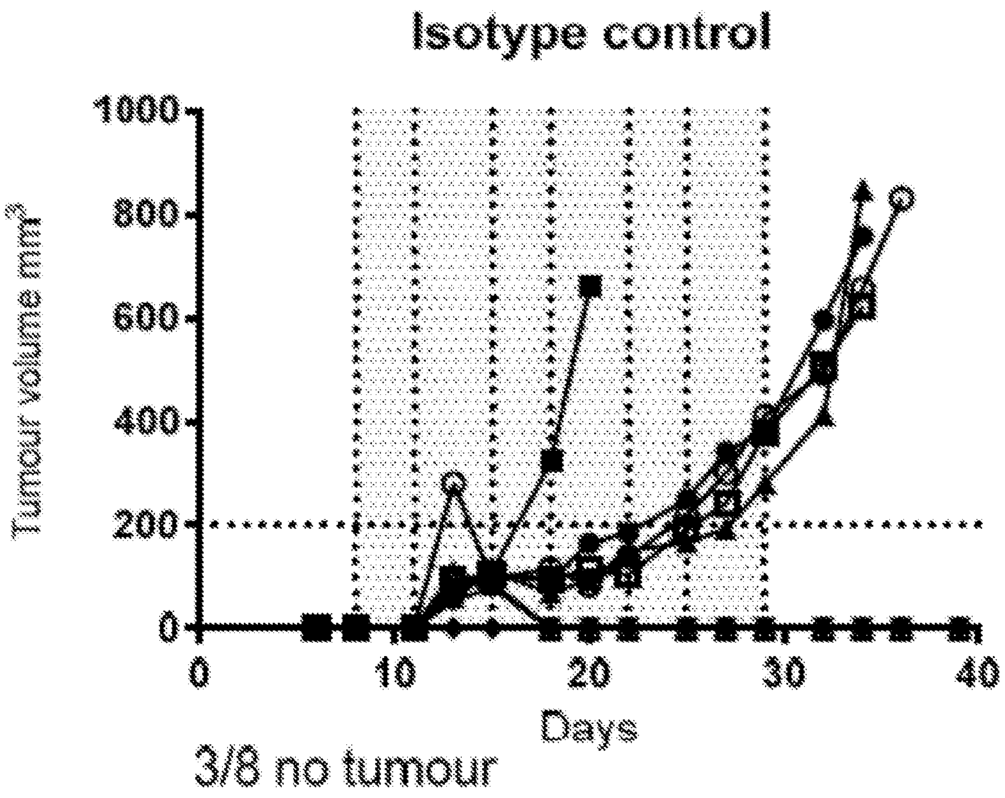
FIG. 30, FIG. 31, FIG. 32, FIG. 33: Graphs showing volumes of A20 tumours over time in mice for the study described in Example 20. Each treatment group is represented by a spider plot showing tumour size in individual animals, n=8 per group. For each group, the number of animals with no sign of tumour (indicating cured of disease) is indicated on the bottom left of the graph. Dosing was performed on days 8, 11, 15, 18, 22, 25 and 29 post tumour cell implantation and the dosing time is indicated by the grey shaded area. Compared with the control group (FIG. 30) and the anti-PD-L1 treatment group (FIG. 31), the STIM001 mIgG2a (FIG. 32) and STIM003 mIgG2a (FIG. 33) treatment groups showed significant inhibition of A20 tumour growth.
Figure 31:
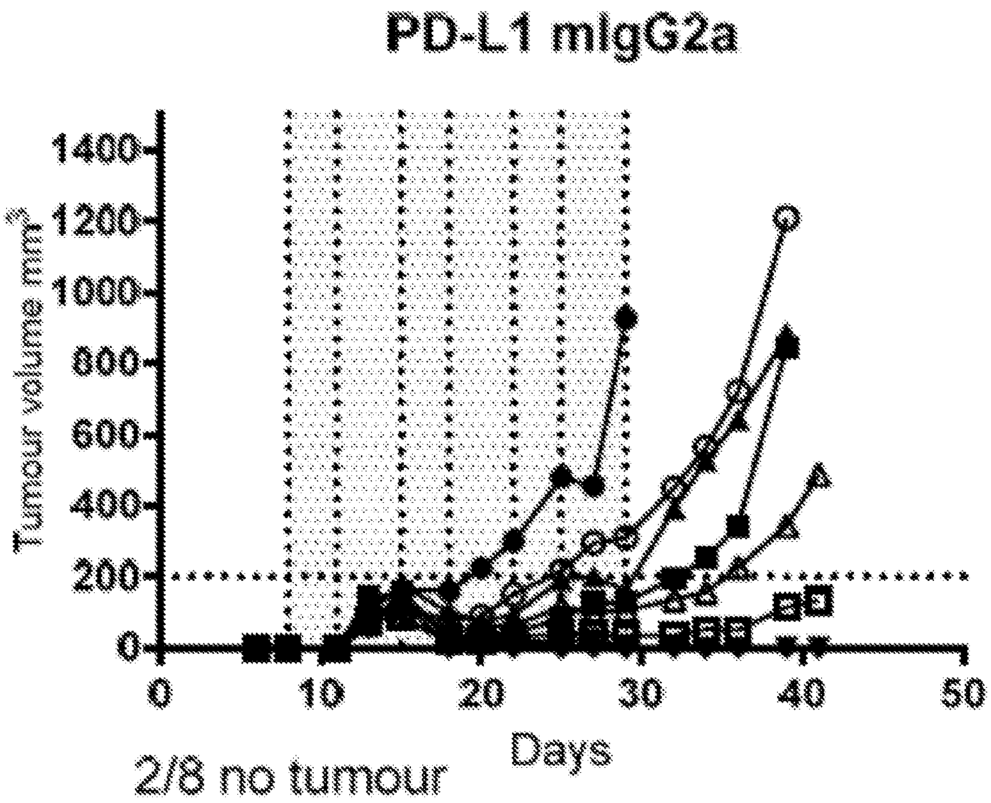
Figure 32:
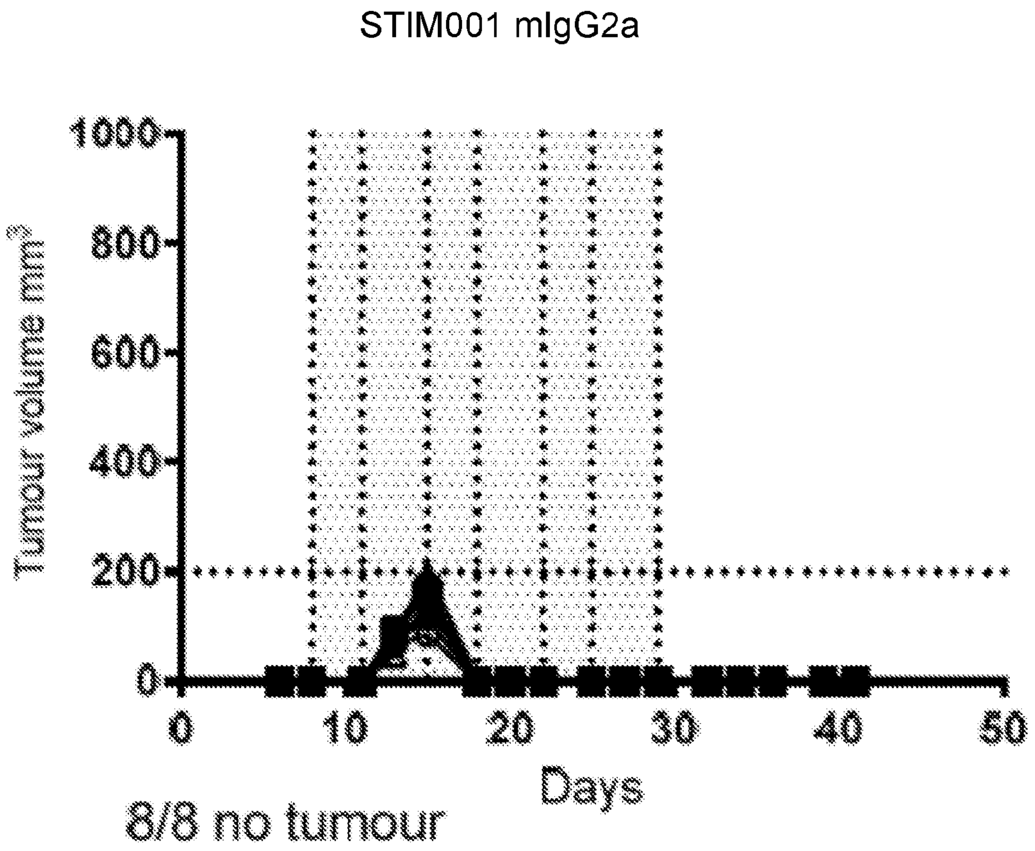
Figure 33:
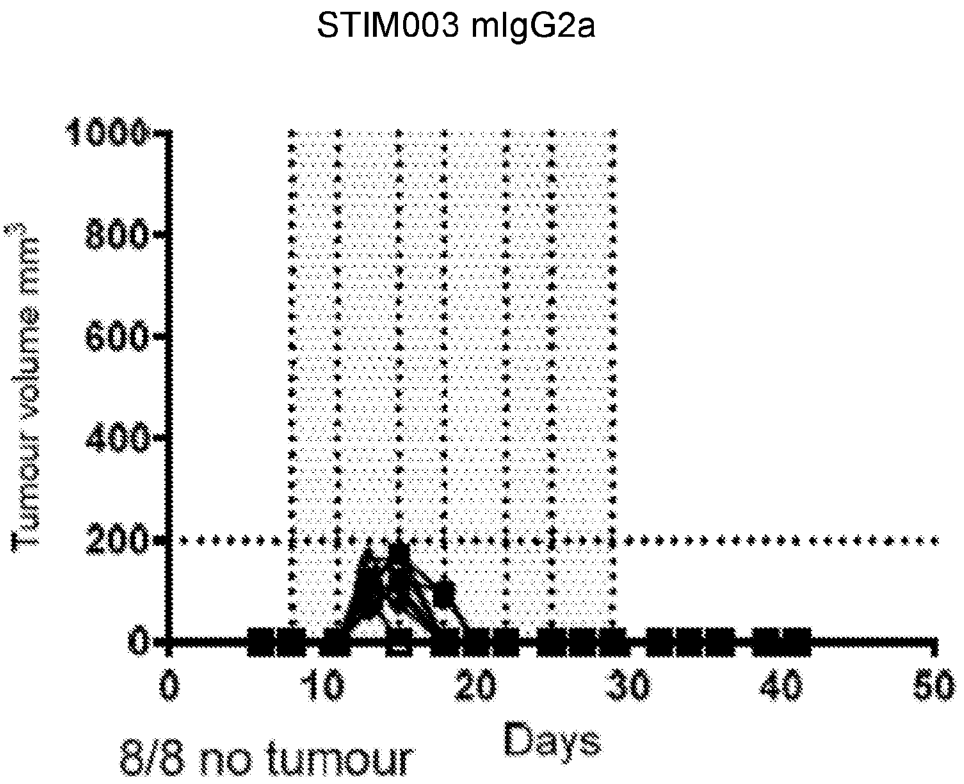

Monotherapy administration of either STIM001 or STIM003 (mIgG2a) in the A20 tumour model produced a complete anti-tumour response (FIG. 32, FIG. 33). All the animals administered with either STIM001 or STIM003 were cured of the disease. This contrasts with the results in the isotype control and PD-L1 mIgG2a groups (FIG. 30, FIG. 31). In rare cases, regression of tumours was observed for some animals in the isotype control (spontaneous regression) and anti-PDL-1 groups, but treatment with anti-ICOS antibody produced significantly greater efficacy. At the end of the study, 3 of 8 control animals and 2 of 8 anti-PDL-1 treated animals had no tumour. However, all animals treated with either STIM001 or STIM003 were tumour free at the end of the study (8 of 8 mice in both groups), representing 100% cure using the anti-ICOS antibodies.

Example 21: Strong Anti-Tumour Efficacy In Vivo in the J558 Myeloma Syngeneic Model for Combination of Anti-ICOS Antibody and Anti-PD-L1 Antibody Anti-ICOS antibody STIM003 mIgG2a and anti-PD-L1 antibody AbW mIgG2a were administered individually and in combination in the J558 tumour model. This is a syngeneic mouse model of myeloma. The anti-ICOS antibody was found to inhibit tumour growth when dosed as monotherapy or in combination with anti-PD-L1.

Materials & Methods

Anti-tumour efficacy studies were performed in Balb/c mice using the sub-cutaneous J558 plasmacytoma:myeloma cell line (ATCC, TIB-6). Balb/c mice were supplied by Charles River UK at 6-8 weeks of age and >18 g and housed under specific pathogen-free conditions. A total of $5\times10^6$ cells (passage number below P15) were subcutaneously injected (in 100 µl) into the right flanks of mice. Unless stated otherwise, on day 11 post tumour cells injection, the animals were randomised based on tumour size and treatments were initiated. The J558 cells were passaged in vitro by using TrypLE™ Express Enzyme (Thermofisher), washed twice in PBS and resuspended in DMEM supplemented with 10% foetal calf serum. Cell viability was confirmed to be above 90% at the time of tumour cell injection.

Treatment was initiated when the tumours reached an average volume of ~140 mm^3. Animals were then allocated to 4 groups with similar average tumour size (see Table E-21 for the dosing groups). Both antibodies, which are mouse cross-reactive, were dosed IP from day 11 (post tumour cell implantation) twice a week for 3 weeks (FIG. 38) unless the animals had to be removed from study due to welfare (rare) or tumour size. As a control, a group of animals (n=10) was dosed at the same time using a saline solution. For the combination group, both STIM003 and anti-PDL1 antibodies were dosed concurrently IP at 60 µg and 200 µg respectively (in 0.9% saline). Tumour growth was monitored over 37 days and compared to tumours of animals treated with saline. Animal weight and tumour volume were measured 3 time a week from the day of tumour cell injection. Tumour volume was calculated by use of the modified ellipsoid formula ½(Length×Width$^2$). Mice were kept on studies until their tumour reached an average diameter of 12 mm$^3$ or, in rare cases, when incidence of tumour ulceration was observed (welfare).

TABLE E21

Treatment groups for J558 efficacy study.

| Groups | Number of animals | Treatment regimen twice per week from day 11 |
|---|---|---|
| 1 | 10 | Saline |
| 2 | 8 | Anti-PD-L1 mIgG2a 200 µg (AbW) |
| 3 | 8 | Anti-ICOS STIM003 mIgG2a/anti-PD-L1 mIgG2a (AbW) combination 60 µg/200 µg (respectively) |
| 4 | 8 | Anti-ICOS STIM003 mIgG2a 60 µg |

Results

Figure 38:
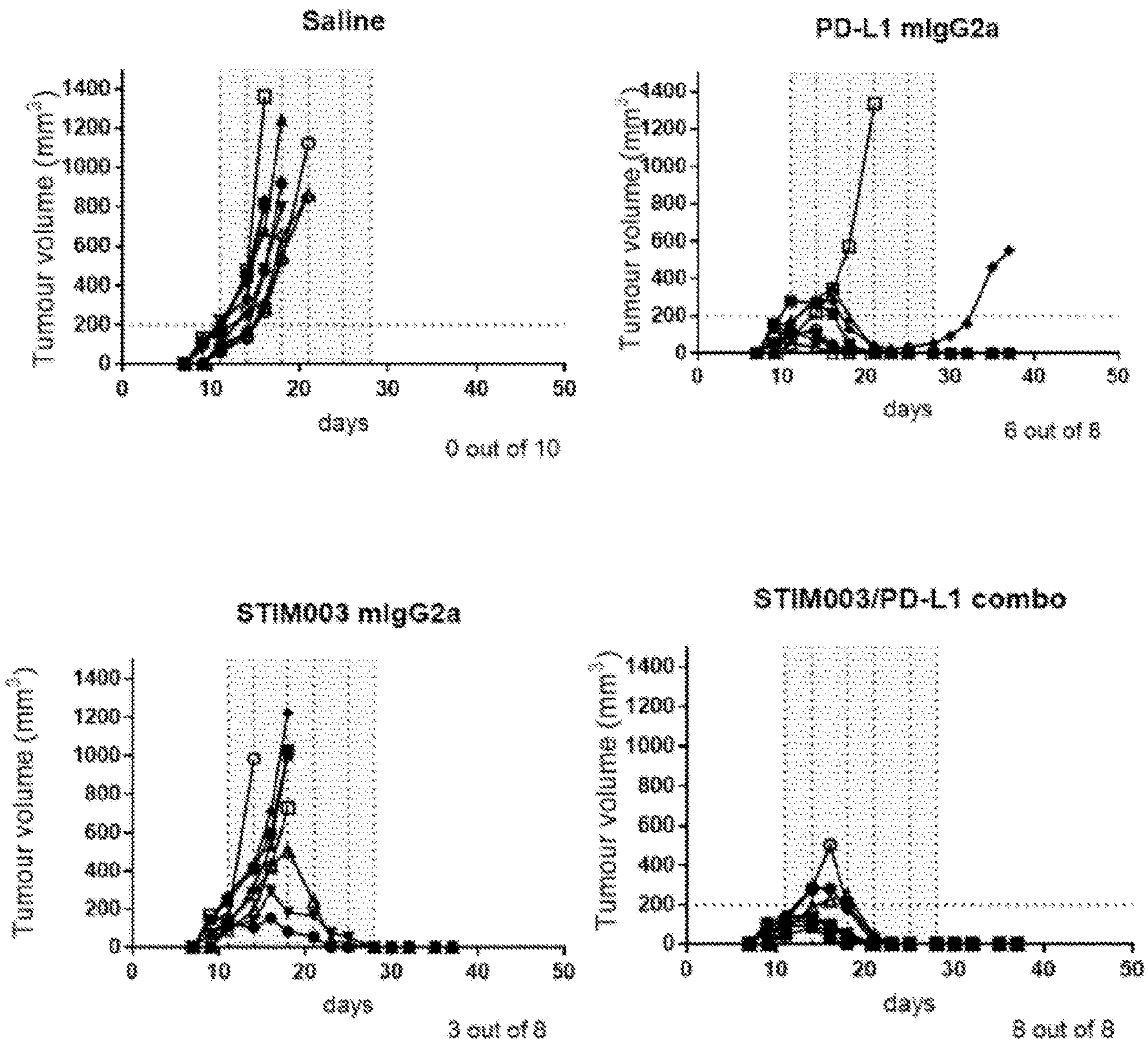
FIG. 38: Effect of STIM003 (anti-ICOS) and AbW (anti-PD-L1) mIgG2a antibodies in the J558 syngeneic model. Each treatment group is represented by a "spider plot" showing the tumour size of individual animals (n=10 or n=8 per group). STIM003 monotherapy demonstrated some efficacy with 3 of 8 animals cured from their disease. Similarly anti-PDL1 was effective in this model with 6 out of 8 animals cured from their disease by day 37. When combined with anti-PDL1 antibodies, STIM003 mIgG2 fully inhibited tumour growth and improved the survival of treated animals. For each group, the number of animals cured of their disease is indicated on the bottom right of the respective graph. Dosing days are indicated by dotted lines (day 11, 15, 18, 22, 25 and 29).

J558 syngeneic tumours were highly aggressive and all the animals in the saline control group (n=10) had to be removed from studies by day 21 due to tumour size. The anti-STIM003 mIgG2a and the anti-PDL1 mIgG2a both demonstrated good efficacy as monotherapies in this model with 37.5% and 75% of the animals cured of disease, respectively. Importantly, combination of the two antibodies resulted in 100% of the animals having rejected the plasmacytoma tumours by day 37. Data are shown in FIG. 38.

Example 22: Administration of Anti-PD1 Increases ICOS Expression on TILs Significantly More than Anti-PD-L1 Antibody A pharmacodynamic study was performed in animals harbouring established CT26 tumours to evaluate the effect of treatment with anti-PD-L1 or anti-PD-1 antibodies on ICOS expression on subsets of tumour infiltrating lymphocytes (TILs). The following antibodies were compared:

anti-PD-L1 AbW mIgG1 [limited effector function]
anti-PD-L1 AbW mIgG2a [with effector function]
anti-PD-L1 10F9.G2 rat IgG2b [with effector function]
anti-PD1 antibody RMT1-14 rat IgG2a [effector null].

Tumours of treated mice were isolated, dissociated to single cells and stained for CD45, CD3, CD4, CD8, FOXP3 and ICOS.

Materials & Methods

Rat anti-PD-1 RMP1-14 IgG2a (BioXCell; Catalog number: BE0146), rat anti-PD-L1 10F9.G2 IgG2b (Bio-Legend; Catalog number: 124325) and anti-PD-L1 AbW mIgG1 and mIgG2a were tested in the CT26 tumour model by dosing i.p. with 130 μg on days 13 and 15 post tumour cell implantation. On day 16, animals were culled and the mouse tumours were harvested for FACS analysis. Tumours were dissociated using a mouse tumour dissociation kit (Miltenyi Biotec) and homogenised. The resulting cell suspensions were clarified through 70 μM filters, pelleted and resuspended in FACS buffer at 2 million cells/well in a 96 well plate. The cell suspensions were incubated with anti-16/32 mAb (eBioscience) and stained with FACS antibodies specific for CD3 (17A2), CD45 (30-F11), CD4 (RM4-5), CD8 (53-6.7) and ICOS (7E.17G9) all obtained from eBioscience Ltd. Cells were also stained with LiveDead Yellow fixable viability dye (Life technologies). For the Foxp3 intracellular staining, samples were fixed, permeabilised, and stained with antibody specific for Foxp3 (eBioscience, FJK-16s). The samples were resuspended in PBS and data acquired on the Attune flow cytometer (Invitrogen) and analysed using FlowJo V10 software (Treestar).

Results

Figure 39A:
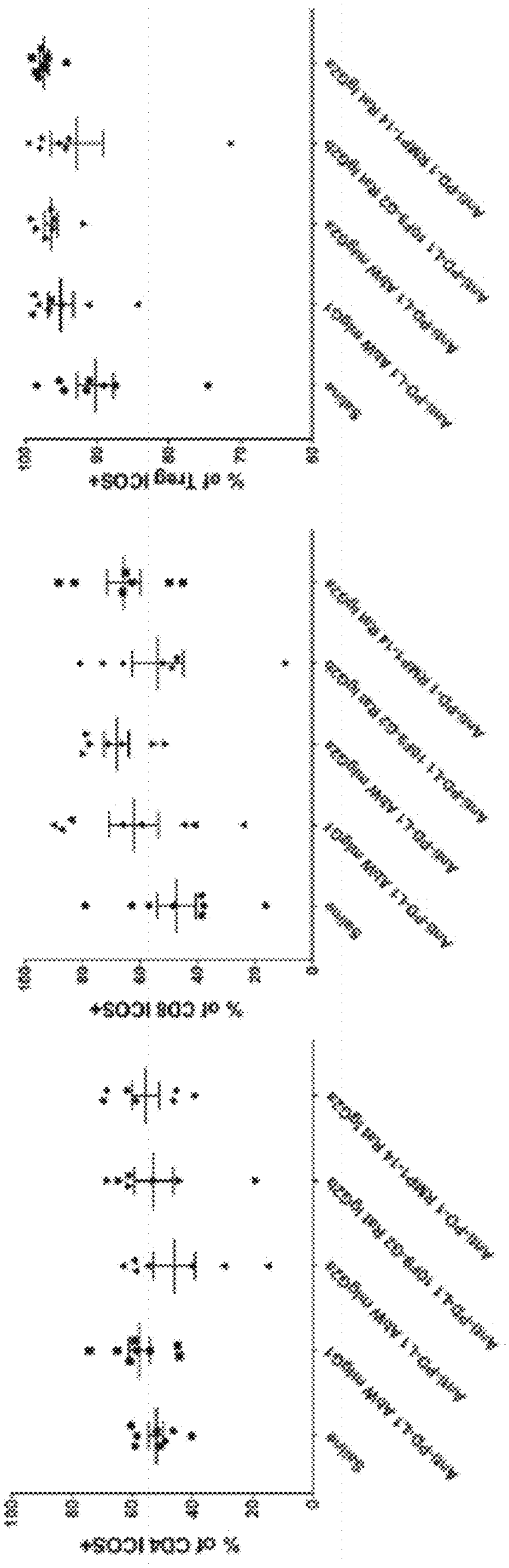
FIG. 39: Quantification of ICOS expression (percentage of positive cells and relative expression/dMFI) on the different TILS cell subtypes in the tumour tissue. (A) The % of immune cell subtypes that are positive for ICOS expression and (B) the ICOS dMFI (relative ICOS expression on ICOS positive cell) of immune cell subtypes of animals treated with saline or anti-PD-L1 or anti-PD-1 surrogate antibodies. The mice were implanted with 100 μl of $1\times10^6$ viable cells/ml on day 0 (n=7 or n=8). The animals were dosed i.p with 130 ug of antibody on day 13 and day 15. The tissue samples were isolated and analysed on day 16. CD4+/FOXP3+ cells were only included for the TReg population (right end side graphs) and were excluded from the "effector" CD4 cells (left end side graphs) which are all Foxp3 negative. See Example 22.
Figure 39B:
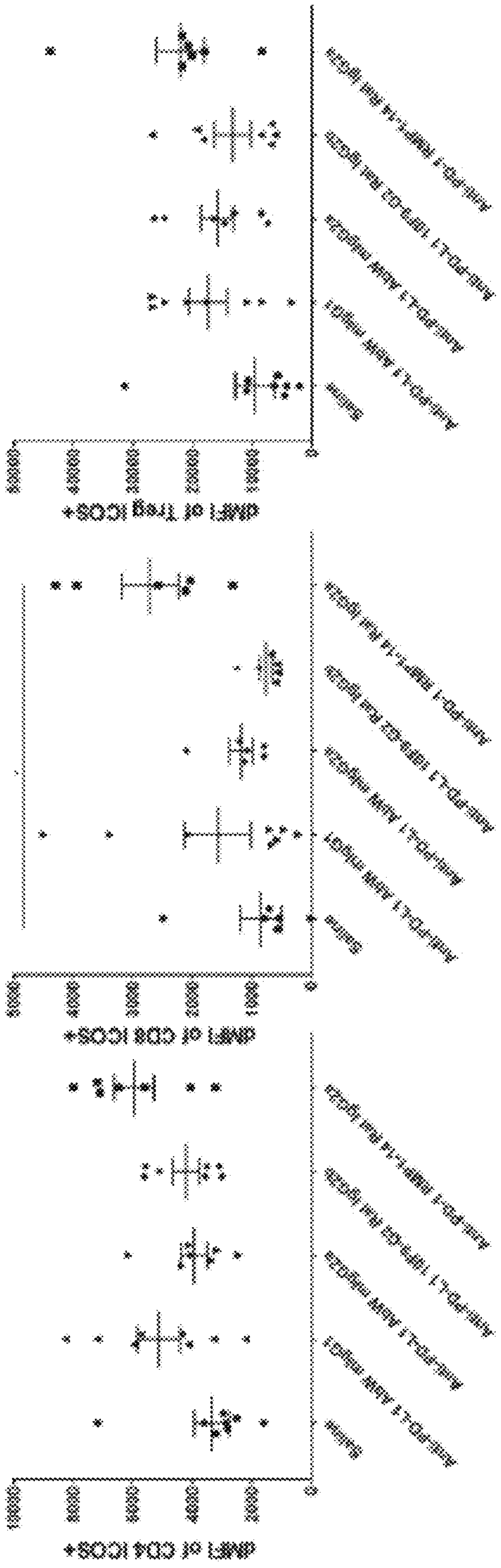

Treatment with anti-PD1 and anti-PD-L1 antibodies only resulted in a marginal increase in the percentage on CD8 cells and T Regs expressing ICOS at the measured timepoint. However, in response to anti-PD1 rat IgG2a, a clear and significant (over the saline treated group) increase in ICOS expression (increased dMFI) was observed on the surface of ICOS+ve CD8 cells. ICOS expression was also noted to be upregulated on CD4 effector and CD4 T Reg cells although this did not reach statistical significance. This anti-PD1 antibody induced a marked increase in ICOS expression on CD8 effector cells that was barely seen with the anti-PD-L1 mIgG2a. Similarly, when comparing the different formats of anti-PD-L1 antibodies, in some of the animals treated it was observed that the antibody having the lowest effector function (mIgG1) was associated with higher ICOS expression on effector CD8 and CD4 cells when compared with antibody having effector function (mIgG2a and ratIgG2b), which rarely showed this. See FIG. 39.

An increase in ICOS expression on effector CD8/CD4 T cells may have the effect of rendering these cells more sensitive to depletion by anti-ICOS antibody (e.g., on treatment of mice with STIM003 mIgG2a). An antibody that exhibits lower ICOS induction in effector CD8 and CD4 T cells may be preferable for use in combination with anti-ICOS antibody. The data from this study indicate that anti-PD-L1 effector positive antibody may be especially suitable for combination with anti-ICOS effector positive antibody, reflecting the anti-tumour efficacy observed when combining anti-PDL1 mIgG2a with STIM003 mIgG2a reported in other Examples herein.

Example 23: Strong Anti-Tumour Efficacy of Single Dose Anti-ICOS Antibody Monotherapy In Vivo in a B Cell Lymphoma Syngeneic Model This experiment confirms the anti-tumour efficacy of STIM003 mIgG2a as monotherapy. Strong anti-tumour efficacy was demonstrated after short exposure of STIM003 mIgG2a.

Materials & Methods

Efficacy studies were performed in BALB/c mice using the sub-cutaneous A20 Reticulum Cell Sarcoma model (ATCC number CRL-TIB-208). BALB/c mice were supplied by Charles River UK at 6-8 weeks of age and >18 g and housed under specific pathogen-free conditions. A total of 5×10E5 A20 cells (passage number below P20) were subcutaneously injected into the right flanks of mice. Treatments were initiated at day 8 post tumour cells injection as shown in the table below. The A20 cells were passaged in vitro by using TrypLE™ Express Enzyme (Thermofisher), washed twice in PBS and resuspended in RPMI supplemented with 10% foetal calf serum. Cell viability was confirmed to be above 85% at the time of tumour cell injection. STIM003 mIgG2a was used either as a single dose (SD) of 60 μg (equivalent to 3 mg/kg for a 20 g animal) or as multiple doses (MD, twice a week for 3 weeks) of 60 μg. Anti-tumour efficacy observed in response to the two schedules was compared to that of animals "treated" with saline (MD, twice a week for 3 weeks). The antibodies were dosed intraperitoneal (IP) as 1 mg/ml in 0.9% saline. Animal weight and tumour volume were measured 3 times a week from the day of tumour cell injection. Tumour volume was calculated by use of the modified ellipsoid formula ½(Length×Width$^2$). Mice were kept on study until their tumour reached an average diameter of 12 mm or, rarely, when incidence of tumour ulceration was observed (welfare).

TABLE E23-1

Treatment groups.

| Group | Number of animals | Treatment regimen (IP injection) |
|---|---|---|
| 1 | 10 | Saline (multiple dose from day 8, twice a week for 3 weeks) |
| 2 | 10 | STIM003 mIgG2 A (multiple dose from day 8, twice a week for 3 weeks) |
| 3 | 10 | STIM003 mIgG2 A (Single dose on day 8) |

Results

Figure 40C:
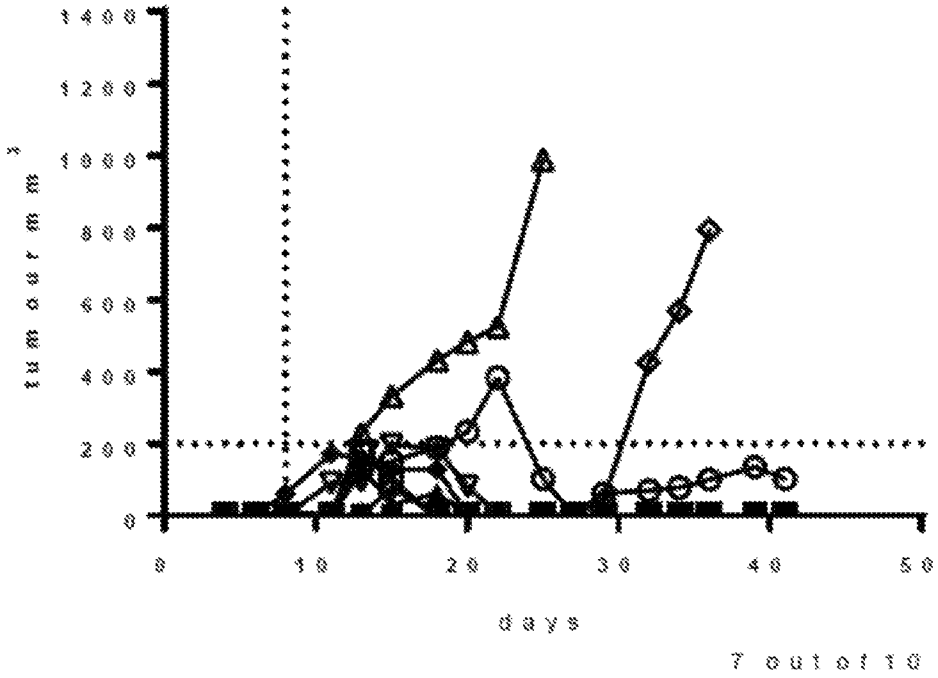
FIG. 40: Data from A20 in vivo efficacy study. Each treatment group is represented by a "spider plot" showing the tumour size of individual animals (n=10 per group). For each group, the number of animals cured of their disease is indicated on the respective graph. For the multiple dose, dosing was on days 8, 11, 15, 18, 22 and 25, indicated by dotted lines. For the single dose, animals received injection IP only on day 8. (A) Saline; (B) STIM003 mIgG2a multiple dose; (C) STIM003 mIgG2a single dose. See Example 23.

Both multiple and single dose of STIM003 mIgG2a resulted in strong and significant monotherapy anti-tumour efficacy as shown by the number of animals with no signs of tumour growth at endpoint (Day 41). SD resulted in 7 our 10 animals cured from the disease whereas the multiple dose cured 9 out of 10 animals injected with A20 B cell lymphoblast. All animals in the saline treated group had to be removed from the study by day 40 due to tumour size. See FIG. 40.

Humane endpoint survival statistics were calculated from the Kaplan-Meier curves (FIG. 41) using GraphPad Prism V7.0. This approach was used to determine if the treatments were associated with improved survival. The Hazard Ratio (Mantel-Haenszel) values and their associated P values (Log-Rank Mantel-Cox) are shown in the table below.

TABLE E23-1

Figure 41:
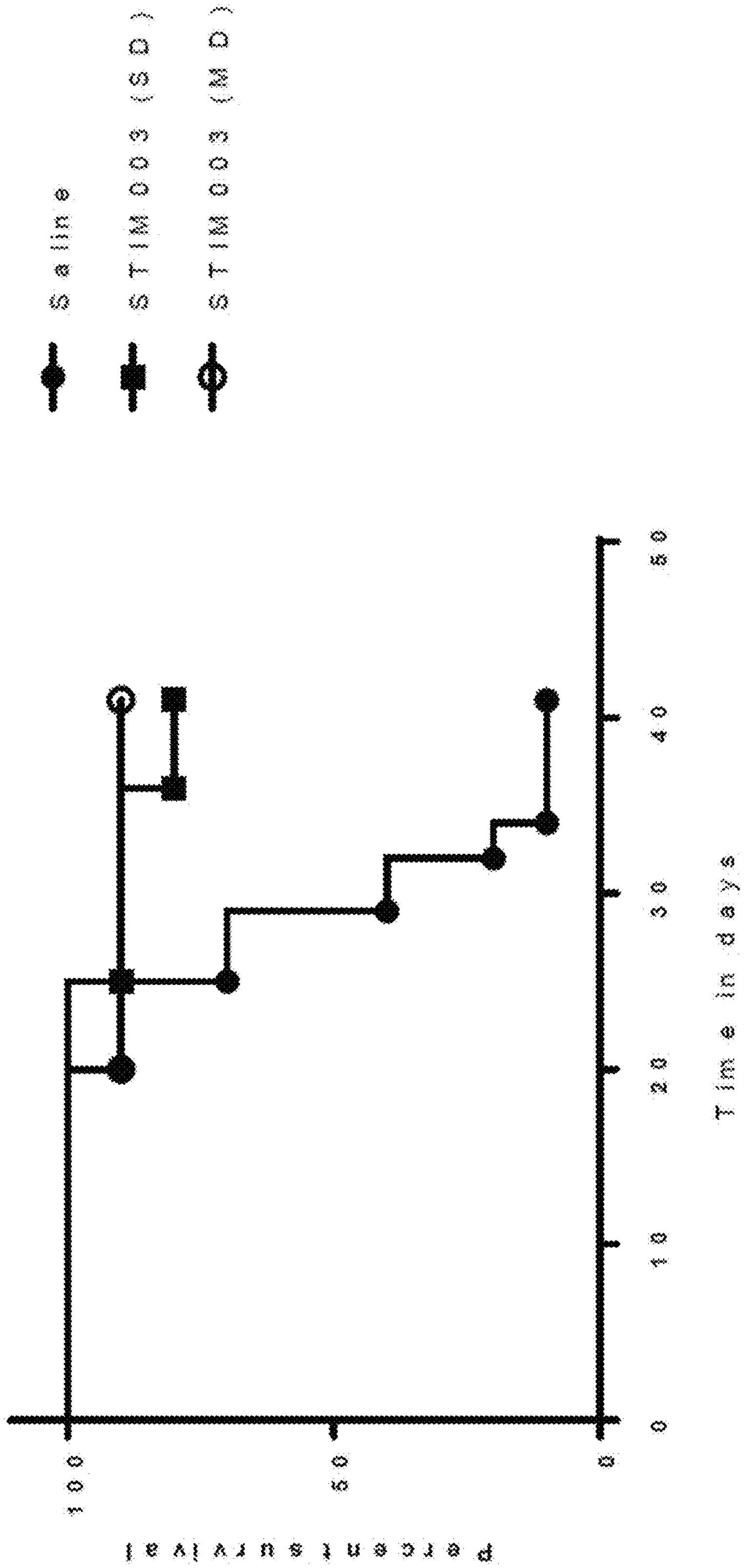
FIG. 41: Kaplan-Meier curves for study reported in Example 23 with STIM003 mIgG2a 60 μg fixed dose. SD=single dose, day 8. MD=multiple doses BIW from day 8.

Hazard Ratio (Mantel-Haenszel) values and their associated P values (Log-Rank Mantel-Cox) corresponding to FIG. 41 Kaplan-Meier curves.

| Hazard Ratio (Mantel-Haenszel) | MD vs Saline | SD vs Saline | MD vs SD |
|---|---|---|---|
| Ratio (and its reciprocal) | 0.09995 | 0.1076 | 0.5314 |
| 95% CI of ratio | 0.02604 to 0.3837 | 0.02856 to 0.4052 | 0.05522 to 5.115 |
| P Value | 0.0008 | 0.001 | 0.5842 |

Example 24: Time and Dose Dependent Effects of Anti-ICOS Antibody in CT-26 Tumour Bearing Animals This Example presents the results of a pharmacodynamic study evaluating the effects of anti-ICOS antibody on immune cells in mice bearing CT-26 tumours. T and B cell subtypes from different tissues were analysed by FACS after a single dose of STIM003 mIgG2a.

Methods

CT-26 tumour bearing animals were dosed i.p. with either saline or STIM003 at 200 μg, 60 μg or 6 μg on day 12 post tumour cell implantation. Tumour tissues, blood, tumour draining lymph node (TDLN) and spleen were harvested on day 1, 2, 3, 4, and day 8 post treatment. The tumours were dissociated to make single cell suspension using mouse tumour dissociation kit (Miltenyi Biotec). Spleen tissue was dissociated using gentle MACS dissociation, red blood cells were lysed using RBC lysis buffer. Tumour draining lymph nodes were mechanically disaggregated to make single cells suspensions. The resulting cell suspensions were clarified through either 70 μM or 40 μM filters depending on the tissue, cells were then washed twice in RMPI complete media and finally resuspended in ice cold FACS buffer. Total blood was collected into plasma tubes and red blood cells were lysed using RBC lysis buffer, cells were washed twice in RMPI complete media and finally resuspended in ice cold FACS buffer. The single cell suspension from all the tissues were distributed into 96 deep well plates for FACS analysis. Cells were stained with Live Dead Fixable Yellow viability dye (Life technologies). The cell suspensions were incubated with anti-CD16/CD32 mAb (eBioscience) and stained with FACS antibodies specific for CD3 (17A2), CD45 (30-F11), CD4 (RM4-5), CD8 (53-6.7), CD25 (PC61.5), ICOSL (HK5.3), B220 (RA3-6B2), Ki-67 (SolA15), CD107a (eBio1D4B), IFN-γ (XMG1.2), TNF-α (MP6-XT22), Foxp3 (FJK-16s) and ICOS (7E.17G9) all obtained from eBioscience Ltd. For cytokine readout by FACS, single cells suspensions from the tumours were plated in 24 well plate for 4 hours in the presence of Brefeldin-A. For the intracellular staining, samples were fixed, permeabilised, and stained with specific antibodies. The samples were finally resuspended in PBS and data acquired on the Attune flow cytometer (Invitrogen) and analysed using FlowJo V10 software (Treestar).

Results are presented and discussed below.

ICOS Expression is High on Intra-Tumoral T-Regs in the CT26 Model

When the percentage of tumour infiltrating lymphocytes (TILs) expressing ICOS was compared to the percentage of immune cells in the spleen, blood, and TDLN, we demonstrated that more immune cells in the microenvironment of CT-26 tumours expressed ICOS vs other tissues. More importantly, the percentage of ICOS positive T-reg cells in all the tissues and at all the time points was higher than the percentage of CD4 or CD8 effector T cells positive for ICOS. Importantly, the dMFI (relative expression) for ICOS also followed the similar ranking in expression with intra-tumoural T-reg being highly positive for ICOS expression vs other TILs subtypes. Interestingly, there was no striking change in the percentage of $ICOS^+$ TILs within the time frame of this experiment. Similar results were also seen in spleen and TDLN. On the other hand, in the blood, ICOS expression is relatively stable on T effector cells but increased on T-regs during the course of the experiment. Altogether the data demonstrated that more cells expressed ICOS in the tumour microenvironment and these positive cells also expressed more ICOS molecules on their surface. More importantly, T regs in TILs are highly positive for ICOS. See FIG. 42.

Figure 43:
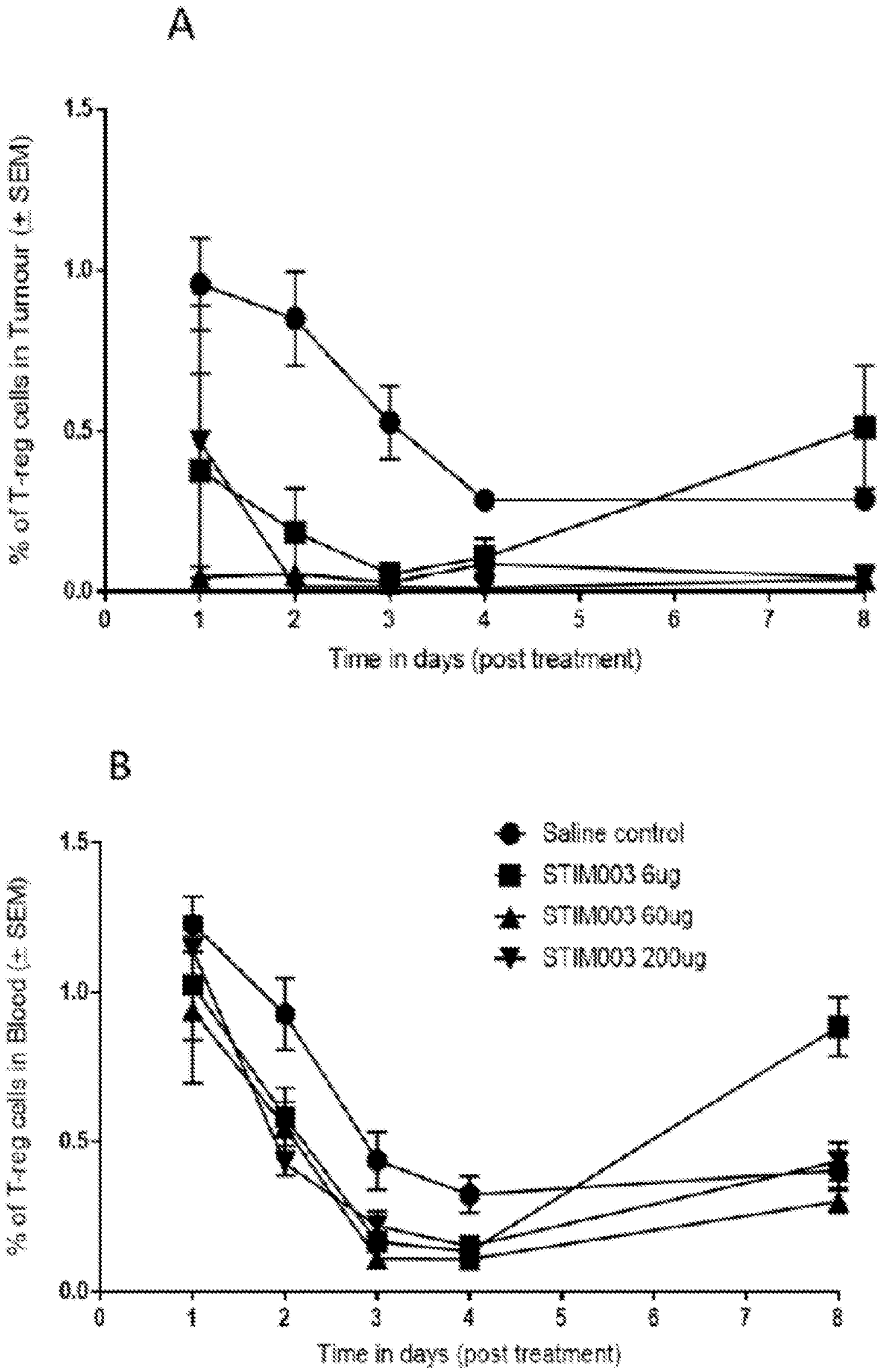
FIG. 43: FACS analysis demonstrating T-reg depletion in the TME in response to STIM003 mIgG2a antibody. CT-26 tumour bearing animals were treated with a single dose (6, 60 or 200 μg) of STIM003 on day 12 post tumour cell implantation. Tissues (n=4 per time point) where harvested for FACS analysis on day 1, 2, 3, 4 and 8 post treatment. The percentage of T-reg cells ($CD4^+CD25^+Foxp3^+$) in total tumour (A) and the percentage of T-reg cells in the blood (B) are shown at the different time points. See Example 24.

Strong Depletion of Intra-Tumoural T-Reg Cells in Response to ST/M003 Administration In response to the STIM003 mIgG2a antibody, there was strong and rapid depletion of T-reg cells (CD4+CD25+Foxp3) in TME. As T-regs have high ICOS expression compared with the other T cells subsets, it is expected that an anti-ICOS antibody with effector function would preferentially deplete these cells. At the lower dose of STIM003 (6 μg corresponding to a 0.3 mg/kg for a 20 g animal) there was a continuous depletion of T-reg and by day 3 most of the T-reg were depleted from TME. Interestingly, by day 8, T-reg cells repopulate the TME then reach a level slightly above that observed in the saline treated animals. The repopulation of T-reg cells at lower dose can be attributed to the increase in the proliferating CD4 T cells in TME as evidenced by an observed increase in Ki-67+ CD4 T-cells. At a dose higher than 6 μg there was a long-term depletion of T-reg cells in TME as shown by full T Reg depletion until the last time point analysed in this study (day 8). Whereas in the blood there was a transient depletion of T-reg cells at all doses. Importantly, by day 8, all the treated animals had similar (or higher for the 6 μg dose) level of T-reg cells in the blood when compared to the saline treated animals. Data are shown in FIG. 43. Notably, and similarly to data previously published for depleting CTLA-4 antibodies, there was no significant change in the percentage of T-reg cells in the spleen or TDLN tissues, suggesting that T-reg cells may be protected from depletion in these organs.

In summary, strong depletion of T-reg cells in TME was achieved in CT-26 model at a dose as low as 6 μg per animal. However, a dose of 60 μg resulted in long term depletion up to 8 days post STIM003 mIgG2a injection. This was not improved by using higher dose (200 μg).

STIM003 mIgG2a Increased CD8:T Reg and CD4:T Reg Ratios

Effects of STIM003 on T-eff:T-reg ratios are shown in FIG. 44.

STIM003 mIgG2a increased the CD8:T-reg ratio as well as the CD4 eff:T-reg ratio. Although all the treatment doses were associated with an increase in T-eff to T-reg ratio, the intermediate dose of 60 μg (the equivalent of 3 mg/kg for a 20 g animals) was associated with the highest ratio by day 8 post treatment.

Interestingly, at the 6 μg dose, the ratios were high until day 4 but by day 8 post treatment they were matching that of the saline treated animals. This can be explained by the repopulation of TRegs observed for this dose by day 8 post treatment. On the other hand, at a dose of 60 or 200 μg, the Teff to T-reg ratios remained high at all time points. This is explained by a long term depeletion of Tregs at these doses. Notably, at higher dose (200 μg), despite the long term Treg depletion there was only a moderate improvement in the ratio by day 8. This can be explained by some depletion of $ICOS^{INT}$ effector cells at high concentration of STIM003.

Altogether, the data demonstrated TReg depletion and increased Effector:T reg ratio at all doses tested. However, an optimal dose of 60 μg (~3 mg/kg) achieved both a long-term depletion of T-reg, as well as the highest T-eff to T-reg ratios which would be associated with the most favourable immune context to initiate an anti-tumour immune response. Interestingly a similar pattern was observed in the blood, with the intermediate dose of 60 μg associated with the highest T-eff to T-reg ratio. Importantly, in the blood, improvement of the ratio was observed at an earlier time point (between day 3 and day 4).

Activation of Effector Cells in Response to STIM003

Surface expression of CD107a on the tumour infiltrating T effector cells was previously identified as a reliable marker for cells that have been activated and exert cytotoxic activity [44]. In the present study employed this marker to confirm that STIM003, in addition to depleting T-regs, can stimulate the cytotoxic activity of effector T cells in the TME. Interestingly, on day 8 post treatment, there was an increase in surface expression of CD107a on both the CD4 and CD8 effector T cell compartments at all doses of STIM003. Furthermore, this upregulation of CD107a expression on the surface on both CD4 and CD8 T cells appeared to plateau when animals were dosed at 60 μg as no improvement was seen at 200 μg dosing.

To further demonstrate activation of effector cells in the TME, the cytokine release by CD4 and CD8 TILs was analysed by FACS. As expected and consistent with the in-vitro agonism data presented in earlier Examples herein, STIM003 mIgG2a at all doses promoted pro-inflammatory cytokine IFN-γ and TNF-α production by effector CD4 and CD8 T cells. The induction of pro-inflammatory cytokine production appeared to be high at the optimum dose of 60 μg. Indeed, 60 μg of STIM003 significantly increased cytokine production by CD4 T cells. A similar trend was seen for the proinflammatory cytokine IFN-γ and TNF-α production by effector CD8 T cells in TME. Data are shown in FIG. 45.

In summary, STIM003 at all the doses resulted in T cells activation in the TME as shown by (1) the presence of the degranulation marker CD107a on their surface and (2) by the production of Th1 cytokines (IFNγ and TNFα) by T cells. This indicates that STIM003 strongly affects the immune context in the TME and plays the dual role of depleting Treg cells and stimulate the killing activity of T effector cells.

Human Dose Estimations

Based on the pre-clinical efficacy data seen in mice, initial predictions can be made of the clinical dose appropriate for human patients, based on corresponding biological surface area (BSA) [45].

For example, taking the optimal anti-ICOS IgG dose in mouse to be 3 mg/kg (60 μg), and following the methods of ref. [45], the corresponding dose for a human is 0.25 mg/kg.

Using the Mosteller formulae, for an individual of 60 kg and 1.70 m the BSA 1.68 $m^2$. Multiplying the dose in mg/kg by a factor of 35.7 (60/1.68) gives a fixed dose of 15 mg. For an individual of 80 kg the corresponding fixed dose would be 20 mg.

Doses may be optimised for human therapy in clinical trials to determine safe and effective treatment regimens.

Example 25: Bioinformatic Analysis of Data from Tumour Samples

One target group of cancers according to the present invention is those cancers that are associated with a relatively high level of ICOS+ immunosuppressive Tregs.

To identify cancer types associated with a high content of Tregs, transcriptome data was obtained from The Cancer Genome Atlas (TCGA) public dataset and analysed for ICOS and FOXP3 expression levels. TOGA is a large-scale study that has catalogued genomic and transcriptomic data accumulated for many different types of cancers, and includes mutations, copy number variation, mRNA and miRNA gene expression, and DNA methylation along with substantial sample metadata.

Gene Set enrichment analysis (GSEA) was conducted as follows. Gene expression RNA seq data collected as part of the TOGA consortium was downloaded from the UCSC Xena Functional Genomics Browser as log 2(normalized_count+1). Non-tumour tissue samples were removed from the dataset, leaving data for 20530 genes from 9732 samples. An algorithm from [46] and its implementation in [47] that calculates enrichment scores for genes within a specified gene set was used to transpose gene level counts to gene set scores for each sample. The gene set of interest was defined as containing both ICOS and FOXP3. Samples were grouped by primary disease and the ssGSEA scores for each group were compared across the 33 primary disease groups. The disease groups that showed the highest median scores were found to be lymphoid neoplasm diffuse large b-cell lymphoma, thymoma, head and neck squamous cell carcinoma, although diffuse large b-cell lymphoma showed a multimodal distribution of scores with a subset scoring highly and the rest scoring below the group median.

In rank order of highest to lowest ssGSEA score for ICOS and FOXP3 expression, the top 15 cancer types were:

| | |
|---|---|
| DLBC (n = 48) | lymphoid neoplasm diffuse large b-cell lymphoma |
| THYM (n = 120) | thymoma |
| HNSC (n = 522) | head and neck squamous cell carcinoma |
| TGCT (n = 156) | testicular germ cell tumour |
| STAD (n = 415) | stomach adenocarcinoma |
| SKCM (n = 473) | skin cutaneous melanoma |
| CESC (n = 305) | cervical squamous cell carcinoma and endocervical adenocarcinoma |
| LUAD (n = 517) | lung adenocarcinoma |
| LAML (n = 173) | acute myeloid leukemia |
| ESCA (n = 185) | esophageal carcinoma |
| LUSC (n = 502) | lung squamous cell carcinoma |
| READ (n = 95) | rectum adenocarcinoma |
| COAD (n = 288) | colon adenocarcinoma |
| BRCA (n = 1104) | breast invasive carcinoma |
| LIHC (n = 373) | liver hepatocellular carcinoma |

In which n is the number of patient samples for that cancer type in TCGA dataset. Anti-ICOS antibodies described herein may be used for treatment of these and other cancers.

Cancers that are associated with a relatively high level of ICOS+ immunosuppressive Tregs and which further express PD-L1 may respond especially well to treatment with a combination of anti-ICOS antibody and anti-PD-L1 antibody. Appropriate treatment regiments and antibodies for this purpose have already been detailed in the foregoing description.

Using the TCGA dataset as before, enrichment scores for ICOS and FOXP3 were correlated with expression levels of PD-L1 using Spearman's rank correlation and grouped by primary disease indication. P-values were calculated for each group and a p-value of 0.05 (with Bonferroni's multiple comparison correction) was taken as statistically significant. The disease groups with the highest correlations between ICOS/FOXP3 and PD-L1 expression were:

| | |
|---|---|
| TGCT (n = 156) | testicular germ cell tumour |
| COAD (n = 288) | colon adenocarcinoma |
| READ (n = 95) | rectum adenocarcinoma |
| BLCA (n = 407) | bladder urothelial carcinoma |
| OV (n = 308) | ovarian serous cystadenocarcinoma |
| BRCA (n = 1104) | breast invasive carcinoma |
| SKCM (n = 473) | skin cutaneous melanoma |
| CESC (n = 305) | cervical squamous cell carcinoma and endocervical adenocarcinoma |
| STAD (n = 415) | stomach adenocarcinoma |
| LUAD (n = 517) | lung adenocarcinoma |

Patients may be selected for treatment following an assay determining that their cancer is associated with ICOS+ immunosuppressive Tregs and expression of PD-L1. For cancer types in which, as above, there is a high correlation score, it may suffice to determine that one of ICOS+ immunosuppressive Tregs and expression of PD-L1 is present (e.g., above a threshold value). PD-L1 immunohistochemistry assays may be used in this context.

Example 26: Assessment of Further Anti-ICOS Antibodies

CL-74570 and CL-61091 antibody sequences identified in Example 12 were synthesised and expressed in IgG1 format in HEK cells.

Functional characterisation of these antibodies was performed using an HTRF assay similar to that described in Example 6, with modifications to adapt the assay to use of purified IgG1 rather than BCT supernatant. 5 μL of supernatant containing human IgG1 antibodies expressed from HEK cells was used in place of the BCT supernatant, and the total volume made up to 20 μl per well using HTRF buffer as before. A human IgG1 antibody was used as a negative control. Both antibodies exhibited greater than 5% effect for binding to human and mouse ICOS as calculated using Equation 1 and were therefore confirmed to test positive in this assay.

Ability of these antibodies to bind human and mouse ICOS expressed on the surface of CHO-S cells was further confirmed using a Mirrorball assay. In this assay, 5 μl supernatant containing the anti-ICOS IgG1 was transferred to each well of 384 mirrorball black plates (Corning). Binding of anti-ICOS antibodies was detected by adding 10 μl of goat anti-human 488 (Jackson Immunoresearch) diluted in assay buffer (PBS+1% BSA+0.1% Sodium Azide) at a concentration of 0.8 mg/ml to all wells.

For positive control wells, 5 μL reference antibody diluted in assay media to 2.2 μg/mL was added to the plates. For negative control wells, 5 μl of Hybrid control IgG1 diluted in assay media to 2.2 μg/mL was added to the plates. 10 μM of DRAQS (Thermoscientific) was added to $0.4\times10^6$/ml cells resuspended in assay buffer and 5 μl was added to all wells. Plates were incubated for 2 hr at 4 degrees.

Fluorescence intensity was measured using Mirrorball plate reader (TTP Labtech), measuring Alexafluor 488 (excitation 493 nm, emission 519 nm) from a population of 500-700 single cells. Assay signal was measured as Median (FL2) Mean Intensity.

Total binding was defined using reference antibody at an assay concentration of 2.2 μg/mL. Non-specific binding was defined using Hybrid control hIgG1 at an assay concentration of 2.22 μg/mL. Both antibodies exhibited greater than 1 percent effect and were therefore confirmed to test positive in this assay.

$$\text{Percent effect} = \frac{(\text{sample well} - \text{non-specific binding})}{(\text{total binding} - \text{non-specific binding})} \times 100$$

Each of CL-74570 and CL-61091 also demonstrated binding to human and mouse ICOS expressed on CHO-S cells as determined by flow cytometry. FACS screening was performed using a method similar to that described in Example 6, with modifications to adapt the assay to use of purified IgG1 rather than BCT supernatant. Both antibodies exhibited binding>10 fold above the average of geomean of the negative control binding to hICOS, mICOS and WT CHO cells.

TABLE E26-1

Functional characterisation of CL-74570 and CL-61091.

| Primary Screen | | | | Secondary screen | | |
|---|---|---|---|---|---|---|
| HTRF (Protein) | | Mirrorball (ICOS CHO Cell) | | FACS | | |
| Human | Mouse | Human | Mouse | | | |
| 1:100 dil Percent Effect [%] | 1:100 dil Percent Effect [%] | 1:100 dil Percent Effect [%] | 1:100 dil Percent Effect [%] | Human ICOS CHO (1:10 dil) % Binding-APC | Mouse ICOS CHO (1:10 dil) % Binding-APC | Clone ID |
| 94.42 | 60.86 | 107.02 | 127.03 | 122.97 | 96.41 | CL-74570 |
| 83.43 | 76.65 | 54.14 | 113.10 | 19.08 | 62.94 | CL-61091 |

REFERENCES

1 Hutloff A, et al. ICOS is an inducible T-cell co-stimulator structurally and functionally related to CD28. Nature. 1999 Jan. 21; 397(6716):263-6.

2 Beier K C, et al. Induction, binding specificity and function of human ICOS. Eur J Immunol. 2000 December; 30(12):3707-17.

3 Coyle A J, et al. The CD28-related molecule ICOS is required for effective T cell-dependent immune responses. Immunity. 2000 July; 13(1):95-105.

4 Dong C, et al. ICOS co-stimulatory receptor is essential for T-cell activation and function. Nature. 2001 Jan. 4; 409 (6816):97-101.

5 Mak T W, et al. Costimulation through the inducible costimulator ligand is essential for both T helper and B cell functions in T cell-dependent B cell responses. Nat Immunol. 2003 August; 4(8):765-72.

6 Swallow M M, Wallin J J, Sha W C. B7h, a novel costimulatory homolog of B7.1 and B7.2, is induced by TNFalpha. Immunity. 1999 October; 11(4):423-32.

7 Wang S, et al. Costimulation of T cells by B7-H2, a B7-like molecule that binds ICOS. Blood. 2000 Oct. 15; 96(8):2808-13.

8 Conrad C, Gilliet M. Plasmacytoid dendritic cells and regulatory T cells in the tumor microenvironment: A dangerous liaison. Oncoimmunology. 2013 May 1; 2(5): e2388.

9 Simpson et al., Fc-dependent depletion of tumor-infiltrating regulatory T cells co-defines the efficacy of anti-CTLA-4 therapy against melanoma. J. Exp. Med. 210(9): 1695-1710 2013

10 Fu T, He Q, Sharma P. The ICOS/ICOSL pathway is required for optimal antitumor responses mediated by anti-CTLA-4 therapy. Cancer Res. 2011 Aug. 15; 71(16): 5445-54.

11 Fan X, Quezada S A, Sepulveda M A, Sharma P, Allison J P. Engagement of the ICOS pathway markedly enhances efficacy of CTLA-4 blockade in cancer immunotherapy. J Exp Med. 2014 Apr. 7; 211(4):715-25.

12 Carthon, B. C., et al. Preoperative CTLA-4 blockade: Tolerability and immune monitoring in the setting of a presurgical clinical trial. Clin. Cancer Res. 16:2861-2871.

13 Liakou C I, et al. CTLA-4 blockade increases IFN-gamma-producing CD4+ICOShi cells to shift the ratio of effector to regulatory T cells in cancer patients. Proc Natl Acad Sci USA. 2008 Sep. 30; 105(39):14987-92.

14 Vonderheide, R. H., et al. 2010. Tremelimumab in combination with exemestane in patients with advanced breast cancer and treatment-associated modulation of inducible costimulator expression on patient T cells. Clin. Cancer Res. 16:3485-3494.

15 Preston C C, et al., The ratios of CD8+ T cells to CD4+CD25+ FOXP3+ and FOXP3− T cells correlate with poor clinical outcome in human serous ovarian cancer. PLoS One Nov. 14; 8(11):e80063.

16 Hodi F S, et al., Immunologic and clinical effects of antibody blockade of cytotoxic T lymphocyte-associated antigen 4 in previously vaccinated cancer patients. PNAS 2008 Feb. 26; 105(8):3005-10

17 Chattopadhyay et al., Structural Basis of Inducible Costimulatory Ligand Function: Determination of the Cell Surface Oligomeric State and Functional Mapping of the Receptor Binding Site of the Protein, J. Immunol. 177(6):3920-3929 2006

18 Lefranc M P, IMGT unique numbering for immunoglobulin and T cell receptor variable domains and Ig superfamily V-like domains, Dev Comp Immunol. 27(1):55-77 2003

19 Gül et al., "Antibody-Dependent Phagocytosis of Tumor Cells by Macrophages: A Potent Effector Mechanism of Monoclonal Antibody Therapy of Cancer", Cancer Res., 75(23), Dec. 1, 2015

20 Lazar et al., 2006, Proc. Natl. Acad. Sci. U.S.A., March 14; 103(11):4005-10

21 Dall et al., Immunol 2002; 169:5171-5180

22 Natsume et al., 2009, Drug Des. Devel. Ther., 3:7-16 or by Zhou Q., Biotechnol. Bioeng., 2008, February 15, 99(3):652-65)

23 Shields et al., 2001, J. Biol. Chem., March 2; 276(9): 6591-604)

24 Idusogie et al., J. Immunol., 2001, 166:2571-2575

25 Natsume et al., 2008, Cancer Res., 68: 3863-3872

26 Alexandrov L B, et al. Signatures of mutational processes in human cancer. Nature. 2013 Aug. 22; 500(7463):415-21

27 Martin-Orozco et al., Melanoma Cells Express ICOS Ligand to Promote the Activation and Expansion of T-Regulatory Cells, Cancer Research 70(23):9581-9590 2010

28 Houot et al., Therapeutic effect of CD137 immunomodulation in lymphoma and its enhancement by Treg depletion, Blood 114:3431-3438 2009

29 Baruch K. et al. PD-1 immune checkpoint blockade reduces pathology and improves memory in mouse models of Alzheimer's disease. Nat Med 22(2):137-137 2016

30 Curran et al., PD01 and CTLA-4 combination blockade expands infiltrating T cells and reduces regulatory T and myeloid cells within B16 melanoma tumours, PNAS 107(9):4275-4280 2010

31 Sim et al., IL-2 therapy promotes suppressive ICOS+ Treg expansion in melanoma patients, J Clin Invest 2014

32 Sim et al., IL-2 variant circumvents ICOS+ regulatory T cell expansion and promotes NK cell activation, Cancer Immunol Res 2016

33 Kroemer et al. Immunologic Cell Death in Cancer Therapy, Ann Rev Immunol. 31:51-72 2013

34 Galluzzi, Zitvogel & Kroemer Canc. Imm. Res. 4:895-902 2016

35 Bos et al., Transient regulatory T cell ablation deters oncogene-driven breast cancer and enhances radiotherapy, J Exp Med 210(11):2434-2446 2013

36 Sato et al., Spatially selective depletion of tumor-associated regulatory T cells with near-infrared photoimmunotherapy, Science Translational Medicine 8(352) 2016

37 Crotty S. T follicular helper cell differentiation, function, and roles in disease. Immunity. 2014 Oct. 16; 41(4):529-42.

38 Shields et al. (2002) JBC 277:26733

39 Lee et al, Nature Biotechnology, 32:6-363, 2014

40 Yusa K, Zhou L, Li M A, Bradley A, Craig N L. A hyperactive piggyBac transposase for mammalian applications, Proc Natl Acad Sci USA. 2011 Jan. 25

41 Kilpatrick et al., Rapid development of affinity matured monoclonal antibodies using RIMMS; Hybridoma; 16(4): 381-9 Aug. 1997

42 Simpson, T. R. et al., Fc-dependent depletion of tumor-infiltrating regulatory T cells co-defines the efficacy of anti-CTLA-4 therapy against melanoma. The Journal of experimental medicine, 210(9):1695-710 2013
43 Selby, M. J. et al., Anti-CTLA-4 antibodies of IgG2a isotype enhance antitumor activity through reduction of intratumoral regulatory T cells. Cancer immunology research, 1(1):32-42 2013.
44 Rubio V., et al. Ex vivo identification, isolation and analysis of tumor-cytolytic T cells. Nat Med. 2003 November; 9(11):1377-82.
45 Nair & Jacob., A simple practice guide for dose conversion between animals and human. J Basic Clin Pharma 2016; 7:27-31
46 D. A. Barbie, et al., "Systematic RNA interference reveals that oncogenic KRAS-driven cancers require TBK1.," Nature, vol. 462, no. 7269, pp. 108-12, 2009
47 S. Hanzelmann, R. Castelo, and J. Guinney, "GSVA: gene set variation analysis for microarray and RNA-Seq data," BMC Bioinformatics, vol. 14, no. 1, p. 7, 2013

| Sequences |
|---|

Antibody STIM001
VH domain nucleotide sequence: SEQ ID NO: 367
CAGGTTCAGGTGGTGCAGTCTGGAGCTGAGGTGAAGAAGCCTGGGGCCTCAGTGAAGGTCTCCTGCAAGGCTTCTGG
TTACACCTTTTCCACCTTTGGTATCACCTGGGTGCGACAGGCCCCTGGACAAGGGCTTGAATGGATGGGATGGATCA
GCGCTTACAATGGTGACACAAACTATGCACAGAATCTCCAGGGCAGAGTCATCATGACCACAGACACATCCACGAGC
ACAGCCTACATGGAGCTGAGGAGCCTGAGATCTGACGACACGGCCGTTTATTACTGTGCGAGGAGCAGTGGCCACTA
CTACTACTACGGTATGGACGTCTGGGGCCAAGGGACCACGGTCACCGTCTCCTCA VH domain amino acid sequence: SEQ ID NO: 366
QVQVVQSGAEVKKPGASVKVSCKASGYTFSTFGITWVRQAPGQGLEWMGWISAYNGDTNYAQNLQGRVIMTTDTSTS
TAYMELRSLRSDDTAVYYCARSSGHYYYYGMDVWGQGTTVTVSS VH CDR1 amino acid sequence: GYTFSTFG SEQ ID NO: 363

VH CDR2 amino acid sequence: ISAYNGDT SEQ ID NO: 364

VH CDR3 amino acid sequence: ARSSGHYYYYGMDV SEQ ID NO: 365

VL domain nucleotide sequence: SEQ ID NO: 374
GATATTGTGATGACTCAGTCTCCACTCTCCCTGCCCGTCACCCCTGGAGAGCCGGCCTCCATCTCCTGCAGGTCTAG
TCAGAGCCTCCTGCATAGTAATGAATACAACTATTTGGATTGGTACCTGCAGAAGCCAGGGCAGTCTCCACAGCTCC
TGATCTTTTTGGGTTCTAATCGGGCCTCCGGGGTCCCTGACAGGTTCAGTGGCAGTGGATCAGGCACAGATTTTACA
CTGAAAATCACCAGAGTGGAGGCTGAGGATGTTGGAATTTATTACTGCATGCAATCTCTACAAACTCCGCTCACTTT
CGGCGGAGGGACCAAGGTGGAGATCAAA VL domain amino acid sequence: SEQ ID NO: 373
DIVMTQSPLSLPVTPGEPASISCRSSQSLLHSNEYNYLDWYLQKPGQSPQLLIFLGSNRASGVPDRFSGSGSGTDFT
LKITRVEAEDVGIYYCMQSLQTPLTFGGGTKVEIK VL CDR1 amino acid sequence: QSLLHSNEYNY SEQ ID NO: 370

VL CDR2 amino acid sequence: LGS SEQ ID NO: 371

VL CDR3 amino acid sequence: MQSLQTPLT SEQ ID NO: 372

Antibody STIM002
VH domain nucleotide sequence: SEQ ID NO: 381
CAGGTTCAACTGGTGCAGTCTGGAGGTGAGGTGAAGAAGCCTGGGGCCTCAGTGAAGGTCTCCTGCAAGGCTTCTGG
TTACACCTTTACCAGCTATGGTTTCAGCTGGGTGCGACAGGCCCCTGGACAAGGACTAGAGTGGATGGGATGGATCA
GCGCTTACAATGGTAACACAAACTATGCACAGAAGCTCCAGGGCAGAGTCACCATGACCACAGACACATCCACGAGC
ACAGCCTACATGGAGCTGAGGAGCTTGAGATCTGACGACACGGCCGTGTATTACTGTGCGAGATCTACGTATTTCTA
TGGTTCGGGGACCCTCTACGGTATGGACGTCTGGGGCCAAGGGACCACGGTCACCGTCTCCTCA VH domain amino acid sequence: SEQ ID NO: 380
QVQLVQSGGEVKKPGASVKVSCKASGYTFTSYGFSWVRQAPGQGLEWMGWISAYNGNTNYAQKLQGRVTMTTDTSTS
TAYMELRSLRSDDTAVYYCARSTYFYGSGTLYGMDVWGQGTTVTVSS VH CDR1 amino acid sequence: GYTFTSYG SEQ ID NO: 377

VH CDR2 amino acid sequence: ISAYNGNT SEQ ID NO: 378

VH CDR3 amino acid sequence: ARSTYFYGSGTLYGMDV SEQ ID NO: 379

VL domain nucleotide sequence: 388
GATATTGTGATGACTCAGTCTCCACTCTCCCTGCCCGTCACCCCTGGAGAGCCGGCCTCCATCTCCTGCAGGTCTAG
TCAGAGCCTCCTGCATAGTGATGGATACAACTGTTTGGATTGGTACCTGCAGAAGCCAGGGCAGTCTCCACAGCTCC
TGATCTATTTGGGTTCTACTCGGGCCTCCGGGTTCCCTGACAGGTTCAGTGGCAGTGGATCAGGCACAGATTTTACA
CTGAAAATCAGCAGAGTGGAGGCTGAGGATGTTGGGGTTTATTACTGCATGCAAGCTCTACAAACTCCGTGCAGTTT
TGGCCAGGGGACCAAGCTGGAGATCAAA Corrected STIM002 VL domain nucleotide sequence: SEQ ID NO: 519
GATATTGTGATGACTCAGTCTCCACTCTCCCTGCCCGTCACCCCTGGAGAGCCGGCCTCCATCTCCTGCAGGTCTAG
TCAGAGCCTCCTGCATAGTGATGGATACAACTATTTGGATTGGTACCTGCAGAAGCCAGGGCAGTCTCCACAGCTCC
TGATCTATTTGGGTTCTACTCGGGCCTCCGGGTTCCCTGACAGGTTCAGTGGCAGTGGATCAGGCACAGATTTTACA
CTGAAAATCAGCAGAGTGGAGGCTGAGGATGTTGGGGTTTATTACTGCATGCAAGCTCTACAAACTCCGCTCAGTTT
TGGCCAGGGGACCAAGCTGGAGATCAAA -continued

| Sequences |
|---|
| VL domain amino acid sequence: SEQ ID NO: 387<br>DIVMTQSPLSLPVTPGEPASISCRSSQSLLHSDGYNYLDWYLQKPGQSPQLLIYLGSTRASGFPDRFSGSGSGTDFT<br>LKISRVEAEDVGVYYCMQALQTPLSFGQGTKLEIK |
| VL CDR1 amino acid sequence: QSLLHSDGYNY SEQ ID NO: 384 |
| VL CDR2 amino acid sequence: LGS SEQ ID NO: 385 |
| VL CDR3 amino acid sequence: MQALQTPLS SEQ ID NO: 386 |
| Antibody STIM002-B<br>VH domain nucleotide sequence: SEQ ID NO: 395<br>CAGGTTCAACTGGTGCAGTCTGGAGGTGAGGTGAAGAAGCCTGGGGCCTCAGTGAAGGTCTCCTGCAAGGCTTCTGG<br>TTACACCTTTACCAGCTATGGTTTCAGCTGGGTGCGACAGGCCCCTGGACAAGGACTAGAGTGGATGGGATGGATCA<br>GCGCTTACAATGGTAACACAAACTATGCACAGAAGCTCCAGGGCAGAGTCACCATGACCACAGACACATCCACGAGC<br>ACAGCCTACATGGAGCTGAGGAGCTTGAGATCTGACGACACGGCCGTGTATTACTGTGCGAGATCTACGTATTTCTA<br>TGGTTCGGGGACCCTCTACGGTATGGACGTCTGGGGCCAAGGGACCACGGTCACCGTCTCCTCA |
| VH domain amino acid sequence: SEQ ID NO: 394<br>QVQLVQSGGEVKKPGASVKVSCKASGYTFTSYGFSWVRQAPGQGLEWMGWISAYNGNTNYAQKLQGRVTMTTDTSTS<br>TAYMELRSLRSDDTAVYYCARSTYFYGSGTLYGMDVWGQGTTVTVSS |
| VH CDR1 amino acid sequence: GYTFTSYG SEQ ID NO: 391 |
| VH CDR2 amino acid sequence: ISAYNGNT SEQ ID NO: 392 |
| VH CDR3 amino acid sequence: ARSTYFYGSGTLYGMDV SEQ ID NO: 393 |
| VL domain nucleotide sequence: SEQ ID NO: 402<br>GATATTGTGATGACTCAGTCTCCACTCTCCCTGCCCGTCACCCCTGGAGAGCCGGCCTCCATCTCCTGCAGGTCTAG<br>TCAGAGCCTCCTGCATAGTGATGGATACAACTGTTTGGATTGGTACCTGCAGAAGCCAGGGCAGTCTCCACAGCTCC<br>TGATCTATTTGGGTTCTACTCGGGCCTCCGGGTTCCCTGACAGGTTCAGTGGCAGTGGATCAGGCACAGATTTTACA<br>CTGAAAATCAGCAGAGTGGAGGCTGAGGATGTTGGGGTTTATTACTGCATGCAAGCTCTACAAACTCCGTGCAGTTT<br>TGGCCAGGGGACCAAGCTGGAGATCAAA |
| VL domain amino acid sequence: SEQ ID NO: 401<br>DIVMTQSPLSLPVTPGEPASISCRSSQSLLHSDGYNCLDWYLQKPGQSPQLLIYLGSTRASGFPDRFSGSGSGTDFT<br>LKISRVEAEDVGVYYCMQALQTPCSFGQGTKLEIK |
| VL CDR1 amino acid sequence: QSLLHSDGYNC SEQ ID NO: 398 |
| VL CDR2 amino acid sequence: LGS SEQ ID NO: 399 |
| VL CDR3 amino acid sequence: MQALQTPCS SEQ ID NO: 400 |
| Antibody STIM003<br>VH domain nucleotide sequence: SEQ ID NO: 409<br>GAGGTGCAGCTGGTGGAGTCTGGGGGAGGTGTGGTACGGCCTGGGGGGTCCCTGAGACTCTCCTGTGTAGCCTCTGG<br>AGTCACCTTTGATGATTATGGCATGAGCTGGGTCCGCCAAGCTCCAGGGAAGGGGCTGGARTGGGTCTCTGGTATTA<br>ATTGGAATGGTGGCGACACAGATTATTCAGACTCTGTGAAGGGCCGATTCACCATCTCCAGAGACAACGCCAAGAAC<br>TCCCTGTATCTACAAATGAATAGTCTGAGAGCCGAGGACACGGCCTTGTATTACTGTGCGAGGGATTTCTATGGTTC<br>GGGGAGTTATTATCACGTTCCTTTTGACTACTGGGGCCAGGGAATCCTGGTCACCGTCTCCTCA |
| Corrected STIM003 VH domain nucleotide sequence: SEQ ID NO: 521<br>GAGGTGCAGCTGGTGGAGTCTGGGGGAGGTGTGGTACGGCCTGGGGGGTCCCTGAGACTCTCCTGTGTAGCCTCTGG<br>AGTCACCTTTGATGATTATGGCATGAGCTGGGTCCGCCAAGCTCCAGGGAAGGGGCTGGAGTGGGTCTCTGGTATTA<br>ATTGGAATGGTGGCGACACAGATTATTCAGACTCTGTGAAGGGCCGATTCACCATCTCCAGAGACAACGCCAAGAAC<br>TCCCTGTATCTACAAATGAATAGTCTGAGAGCCGAGGACACGGCCTTGTATTACTGTGCGAGGGATTTCTATGGTTC<br>GGGGAGTTATTATCACGTTCCTTTTGACTACTGGGGCCAGGGAATCCTGGTCACCGTCTCCTCA |
| VH domain amino acid sequence: SEQ ID NO: 408<br>EVQLVESGGGVVRPGGSLRLSCVASGVTFDDYGMSWVRQAPGKGLEWVSGINWNGGDTDYSDSVKGRFTISRDNAKN<br>SLYLQMNSLRAEDTALYYCARDFYGSGSYYHVPFDYWGQGILVTVSS |
| VH CDR1 amino acid sequence: GVTFDDYG SEQ ID NO: 405 |
| VH CDR2 amino acid sequence: INWNGGDT SEQ ID NO: 406 |
| VH CDR3 amino acid sequence: ARDFYGSGSYYHVPFDY SEQ ID NO: 407 |
| VL domain nucleotide sequence: SEQ ID NO: 416<br>GAAATTGTGTTGACGCAGTCTCCAGGGACCCTGTCTTTGTCTCCAGGGGAAAGAGCCACCCTCTCCTGCAGGGCCAG<br>TCAGAGTGTTAGCAGAAGCTACTTAGCCTGGTACCAGCAGAAACGTGGCCAGGCTCCCAGGCTCCTCATCTATGGTG<br>CATCCAGCAGGGCCACTGGCATCCCAGACAGGTTCAGTGGCGATGGGTCTGGGACAGACTTCACTCTCTCCATCAGC<br>AGACTGGAGCCTGAAGATTTTGCAGTGTATTACTGTCACCAGTATGATATGTCACCATTCACTTTCGGCCCTGGGAC<br>CAAAGTGGATATCAAA |

-continued

| Sequences |
| --- |
| VL domain amino acid sequence: SEQ ID NO: 415<br>EIVLTQSPGTLSLSPGERATLSCRASQSVSRSYLAWYQQKRGQAPRLLIYGASSRATGIPDRFSGDGSGTDFTLSIS<br>RLEPEDFAVYYCHQYDMSPFTFGPGTKVDIK |
| VL CDR1 amino acid sequence: QSVSRSY SEQ ID NO: 412 |
| VL CDR2 amino acid sequence: GAS SEQ ID NO: 413 |
| VL CDR3 amino acid sequence: HQYDMSPFT SEQ ID NO: 414 |
| Antibody STIM004<br>VH domain nucleotide sequence:<br>GAGGTGCAGCTGGTGGAGTCTGGGGGAGGTGTGGTACGGCCTGGGGGGTCCCTGAGACTCTCCTGTGCAGCCTCTGG<br>ACTCACCTTTGATGATTATGGCATGAGCTGGGTCCGCCAAGTTCCAGGGAAGGGGCTGGAGTGGGTCTCTGGTATTA<br>ATTGGAATGGTGATAACACAGATTATGCAGACTCTGTGAAGGGCCGATTCACCATCTCCAGAGACAACGCCAAGAAC<br>TCCCTGTATCTGCAAATGAACAGTCTGAGAGCCGAGGACACGGCCTTGTATTACTGTGCGAGGGATTACTATGGTTC<br>GGGGAGTTATTATAACGTTCCTTTTGACTACTGGGGCCAGGGAACCCTGGTCACCGTCTCCTGA SEQ ID NO:<br>423 |
| VH domain amino acid sequence:<br>EVQLVESGGGVVRPGGSLRLSCAASGLTFDDYGMSWVRQVPGKGLEWVSGINWNGDNTDYADSVKGRFTISRDNAKN<br>SLYLQMNSLRAEDTALYYCARDYYGSGSYYNVPFDYWGQGTLVTVSS SEQ ID NO: 422 |
| VH CDR1 amino acid sequence: GLTFDDYG SEQ ID NO: 419 |
| VH CDR2 amino acid sequence: INWNGDNT SEQ ID NO: 420 |
| VH CDR3 amino acid sequence: ARDYYGSGSYYNVPFDY SEQ ID NO: 421 |
| VL domain nucleotide sequence: SEQ ID NO: 431<br>GAAATTGTGTTGACGCAGTCTCCAGGCACCCTGTCTTTGTCTCCAGGGGAAAGAGCCACCCTCTCCTGCAGGGCCAG<br>TCAGAGTGTTAGCAGCAGCTACTTAGCCTGGTACCAGCAGAAACCTGGCCAGGCTCCCAGGCTCCTCATATATGGTG<br>CATCCAGCAGGGCCACTGGCATCCCAGACAGGTTCAGTGGCAGTGGGTCTGGGACAGACTTCACTCTCACCATCAGA<br>AGACTGGAGCCTGAAGATTTTGCAGTGTATTACTGTCAGCAGTATGGTAGTTCACCATTCACTTCGGCCCTGGGACC<br>AAAGTGGATATCAAA |
| VL domain amino acid sequence as encoded by the above VL domain nucleotide<br>sequence. |
| Corrected VL domain nucleotide sequence: SEQ ID NO: 430<br>GAAATTGTGTTGACGCAGTCTCCAGGCACCCTGTCTTTGTCTCCAGGGGAAAGAGCCACCCTCTCCTGCAGGGCCAG<br>TCAGAGTGTTAGCAGCAGCTACTTAGCCTGGTACCAGCAGAAACCTGGCCAGGCTCCCAGGCTCCTCATATATGGTG<br>CATCCAGCAGGGCCACTGGCATCCCAGACAGGTTCAGTGGCAGTGGGTCTGGGACAGACTTCACTCTCACCATCAGA<br>AGACTGGAGCCTGAAGATTTTGCAGTGTATTACTGTCAGCAGTATGGTAGTTCACCATTCTTCGGCCCTGGGACCAA<br>AGTGGATATCAAA |
| Corrected VL domain amino acid sequence: SEQ ID NO: 432<br>EIVLTQSPGTLSLSPGERATLSCRASQSVSSSYLAWYQQKPGQAPRLLIYGASSRATGIPDRFSGSGSGTDFTLTIR<br>RLEPEDFAVYYCQQYGSSPFFGPGTKVDIK |
| VL CDR1 amino acid sequence: QSVSSSY SEQ ID NO: 426 |
| VL CDR2 amino acid sequence: GAS SEQ ID NO: 427 |
| VL CDR3 amino acid sequence: QQYGSSPF SEQ ID NO: 428 |
| Antibody STIM005<br>VH domain nucleotide sequence: SEQ ID NO: 439<br>CAGGTTCAGTTGGTGCAGTCTGGAGCTGAGGTGAAGAAGCCTGGGGCCTCAGTGAAGGTCTCCTGCAAGGCTTCTGG<br>TTACACCTTTAATAGTTATGGTATCATCTGGGTGCGACAGGCCCCTGGACAAGGGCTTGAGTGGATGGGATGGATCA<br>GCGTTCACAATGGTAACACAAACTGTGCACAGAAGCTCCAGGGTAGAGTCACCATGACCACAGACACATCCACGAGC<br>ACAGCCTACATGGAGCTGAGGAGCCTGAGAACTGACGACACGGCCGTGTATTACTGTGCGAGAGCGGGTTACGATAT<br>TTTGACTGATTTTTCCGATGCTTTTGATATCTGGGGCCACGGGACAATGGTCACCGTCTCTTCA |
| VH domain amino acid sequence: SEQ ID NO: 438<br>QVQLVQSGAEVKKPGASVKVSCKASGYTFNSYGIIWVRQAPGQGLEWMGWISVHNGNTNCAQKLQGRVTMTTDTSTS<br>TAYMELRSLRTDDTAVYYCARAGYDILTDFSDAFDIWGHGTMVTVSS |
| VH CDR1 amino acid sequence: GYTFNSYG SEQ ID NO: 435 |
| VH CDR2 amino acid sequence: ISVHNGNT SEQ ID NO: 436 |
| VH CDR3 amino acid sequence: ARAGYDILTDFSDAFDI SEQ ID NO: 437 |

-continued

| Sequences |
|---|
| VL domain nucleotide sequence: SEQ ID NO: 446<br>GACATCCAGATGACCCAGTCTCCATCCTCCCTGTCTGCATCTGTAGGAGACAGAGTCACCATCACTTGCCGGGCAAG<br>TCAGAACATTAATAACTTTTTAAATTGGTATCAGCAGAAAGAAGGGAAAGGCCCTAAGCTCCTGATCTATGCAGCAT<br>CCAGTTTGCAAAGAGGGATACCATCAACGTTCAGTGGCAGTGGATCTGGGACAGACTTCACTCTCACCATCAGCAGT<br>CTGCAACCTGAAGATTTTGCAACTTACATCTGTCAACAGAGCTACGGTATCCCGTGGGTCGGCCAAGGGACCAAGGT<br>GGAAATCAAA |
| VL domain amino acid sequence: SEQ ID NO: 445<br>DIQMTQPSSLSASVGDRVTITCRASQNINNFLNWYQQKEGKGPKLLIYAASSLQRGIPSTFSGSGSGTDFTLTISS<br>LQPEDFATYICQQSYGIPWVGQGTKVEIK |
| VL CDR1 amino acid sequence: QNINNF SEQ ID NO: 442 |
| VL CDR2 amino acid sequence: ASS SEQ ID NO: 443 |
| VL CDR3 amino acid sequence: QQSYGIPW SEQ ID NO: 444 |
| Antibody STIM006<br>VH domain nucleotide sequence: SEQ ID NO: 453<br>CAGGTGCAGCTGGTGGAGTCTGGGGGAGGCTTGGTCAAGCCTGGAGGGTCCCTGAGACTCTCCTGTGCAGCCTCTGG<br>ATTCACCTTCAGTGACTACTTCATGAGCTGGATCCGCCAGGCGCCAGGGAAGGGGCTGGAGTGGATTTCATACATTA<br>GTTCTAGTGGTAGTACCATATACTACGCAGACTCTGTGAGGGGCCGATTCACCATCTCCAGGGACAACGCCAAGTAC<br>TCACTGTATCTGCAAATGAACAGCCTGAGATCCGAGGACACGGCCGTGTATTACTGTGCGAGAGATCACTACGATGG<br>TTCGGGGATTTATCCCCTCTACTACTATTACGGTTTGGACGTCTGGGGCCAGGGGACCACGGTCACCGTCTCCTCA |
| VH domain amino acid sequence: SEQ ID NO: 454<br>QVQLVESGGGLVKPGGSLRLSCAASGFTESDYFMSWIRQAPGKGLEWISYISSSGSTIYYADSVRGRFTISRDNAKY<br>SLYLQMNSLRSEDTAVYYCARDHYDGSGIYPLYYYYGLDVWGQGTTVTVSS |
| VH CDR1 amino acid sequence: GFTFSDYF SEQ ID NO: 449 |
| VH CDR2 amino acid sequence: ISSSGSTI SEQ ID NO: 450 |
| VH CDR3 amino acid sequence: ARDHYDGSGIYPLYYYYGLDV SEQ ID NO: 451 |
| VL domain nucleotide sequence: SEQ ID NO: 460<br>ATTGTGATGACTCAGTCTCCACTCTCCCTACCCGTCACCCCTGGAGAGCCGGCCTCCATCTCCTGCAGGTCTAGTCA<br>GAGCCTCCTGCATAGTAATGGATACAACTATTTGGATTATTACCTGCAGAAGCCAGGGCAGTCTCCACAGCTCCTGA<br>TCTATTTGGGTTCTTATCGGGCCTCCGGGGTCCCTGACAGGTTCAGTGGCAGTGGATCAGGCACAGATTTTACACTG<br>AAAATCAGCAGAGTGGAGGCTGAGGATGTTGGGGTTTATTACTGCATGCAAGCTCTACAAACTCCTCGCAGTTTTGG<br>CCAGGGGACCACGCTGGAGATCAAA |
| VL domain amino acid sequence: SEQ ID NO: 459<br>IVMTQSPLSLPVTPGEPASISCRSSQSLLHSNGYNYLDYYLQKPGQSPQLLIYLGSYRASGVPDRFSGSGSGTDFTL<br>KISRVEAEDVGVYYCMQALQTPRSFGQGTTLEIK |
| VL CDR1 amino acid sequence: QSLLHSNGYNY SEQ ID NO: 456 |
| VL CDR2 amino acid sequence: LGS SEQ ID NO: 457 |
| VL CDR3 amino acid sequence: MQALQTPRS SEQ ID NO: 458 |
| Antibody STIM007<br>VH domain nucleotide sequence: SEQ ID NO: 467<br>CAGATCACCTTGAAGGAGTCTGGTCCTACGCTGGTGAAACCCACACAGACCCTCACGCTGACCTGCACCTTCTCTGG<br>GTTCTCACTCAGCACTACTGGAGTGGGTGTGGGCTGGATCCGTCAGCCCCCAGGAAAGGCCCTGGAGTGGCTTGCAG<br>TCATTTATTGGGATGATGATAAGCGCTACAGCCCATCTCTGAAGAGCAGACTCACCATCACCAAGGACACCTCCAAA<br>AACCAGGTGGTCCTTACAATGACCAACATGGACCCTGTGGACACAGCCACATATTTCTGTACACACGGATATGGTTC<br>GGCGAGTTATTACCACTACGGTATGGACGTCTGGGGCCAAGGGACCACGGTCACCGTCTCCTCA |
| VH domain amino acid sequence: SEQ ID NO: 466<br>QITLKESGPTLVKPTQTLTLTCTFSGFSLSTTGVGVGWIRQPPGKALEWLAVIYWDDDKRYSPSLKSRLTITKDTSK<br>NQVVLTMTNMDPVDTATYFCTHGYGSASYYHYGMDVWGQGTTVTVSS |
| VH CDR1 amino acid sequence: GFSLSTTGVG SEQ ID NO: 463 |
| VH CDR2 amino acid sequence: IYWDDDK SEQ ID NO: 464 |
| VH CDR3 amino acid sequence: THGYGSASYYHYGMDV SEQ ID NO: 465 |
| VL domain nucleotide sequence: SEQ ID NO: 474<br>GAAATTGTATTGACACAGTCTCCAGCCACCCTGTCTTTGTCTCCAGGGGAAAGAGCCACCCTCTCCTGCAGGGCCAG<br>TCAGAGTGTTACCAACTACTTAGCCTGGCACCAACAGAAACCTGGCCAGGCTCCCAGGCTCCTCATCTATGATGCAT<br>CCAACAGGGCCACTGGCATCCCAGCCAGGTTCAGTGGCAGTGGGTCTGGGACAGACTTCACTCTCACCATCAGCAGC<br>CTAGAGCCTGAAGATTTTGCAGTTTATTACTGTCAGCACCGTAGCAACTGGCCTCTCACTTTCGGCGGAGGGACCAA<br>GGTGGAGATCAAAC |

-continued

| Sequences |
|---|

VL domain amino acid sequence: SEQ ID NO: 473
EIVLTQSPATLSLSPGERATLSCRASQSVTNYLAWHQQKPGQAPRLLIYDASNRATGIPARFSGSGSGTDFTLTISS
LEPEDFAVYYCQHRSNWPLTFGGGTKVEIK VL CDR1 amino acid sequence: QSVTNY SEQ ID NO: 470

VL CDR2 amino acid sequence: DAS SEQ ID NO: 471

VL CDR3 amino acid sequence: QHRSNWPLT SEQ ID NO: 472

Antibody STIMV08
VH domain nucleotide sequence: SEQ ID NO: 481
CAGATCACCTTGAAGGAGTCTGGTCCTACGCTGGTGAAACCCACACAGACCCTCACGCTGACCTGCACCTTCTCTGG
GTTCTCACTCAGCACTAGTGGAGTGGGTGTGGGCTGGATCCGTCAGCCCCCAGGAAAGGCCCTGGAGTGGCTTGCAG
TCATTTATTGGGATGATGATAAGCGCTACAGCCCATCTCTGAAGAGCAGGCTCACCATCACCAAGGACACCTCCAAA
AACCAGGTGGTCCTTACAATGACCAACATGGACCCTGTGGACACAGCCACATATTTCTGTACACACGGATATGGTTC
GGCGAGTTATTACCACTACGGTATGGACGTCTGGGGCCAAGGGACCACGGTCACCGTCTCCTCA VH domain amino acid sequence: SEQ ID NO: 480
QITLKESGPTLVKPTQTLTLTCTFSGFSLSTSGVGVGWIRQPPGKALEWLAVIYWDDDKRYSPSLKSRLTITKDTSK
NQVVLTMTNMDPVDTATYFCTHGYGSASYYHYGMDVWGQGTTVTVSS VH CDR1 amino acid sequence: GFSLSTSGVG SEQ ID NO: 477

VH CDR2 amino acid sequence: IYWDDDK SEQ ID NO: 478

VH CDR3 amino acid sequence: THGYGSASYYHYGMDV SEQ ID NO: 479

VL domain nucleotide sequence: SEQ ID NO: 488
GAAATTGTGTTGACACAGTCTCCAGCCACCCTGTCTTTGTCTCCAGGGGAAAGAGCCACCCTCTCCTGCAGGGCCAG
TCAGAGTGTTACCAACTACTTAGCCTGGCACCAACAGAAACCTGGCCAGGCTCCCAGGCTCCTCATCTATGATGCAT
CCAACAGGGCCACTGGCATCCCAGCCAGGTTCAGTGGCAGTGGGTCTGGGACAGACTTCACTCTCACCATCAGCAGC
CTAGAGCCTGAAGATTTTGCAGTTTATTACTGTCAGCAGCGTAGCAACTGGCCTCTCACTTTCGGCGGAGGGACCAA
GGTGGAGATCAAA VL domain amino acid sequence: SEQ ID NO: 489
EIVLTQSPATLSLSPGERATLSCRASQSVTNYLAWHQQKPGQAPRLLIYDASNRATGIPARFSGSGSGTDFTLTISS
LEPEDFAVYYCQQRSNWPLTFGGGTKVEIK VL CDR1 amino acid sequence: QSVTNY SEQ ID NO: 484

VL CDR2 amino acid sequence: DAS SEQ ID NO: 485

VL CDR3 amino acid sequence: QQRSNWPLT SEQ ID NO: 486

Antibody STIM009
VH domain nucleotide sequence: SEQ ID NO: 495
CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGATCCGCCAGGCTCCAGGGAAGGGGCTGGAGTGGGTTTCATACATTA
GTAGTAGTGGTAGTACCATATACTACGCAGACTCTGTGAAGGGCCGATTCACCATCTCCAGGGACAACGCCAAGAAC
TCACTGTATCTGCAAATTAACAGCCTGAGAGCCGAGGACACGGCCGTGTATTACTGTGCGAGAGATTTTTACGATAT
TTTGACTGATAGTCCGTACTTCTACTACGGTGTGGACGTCTGGGGCCAAGGGACCACGGTCACCGTCTCCTCA VH domain amino acid sequence: SEQ ID NO: 494
QVQLVESGGGLVKPGGSLRLSCAASGFTFSDYYMSWIRQAPGKGLEWVSYISSSGSTIYYADSVKGRFTISRDNAKN
SLYLQINSLRAEDTAVYYCARDFYDILTDSPYFYYGVDVWGQGTTVTVSS VH CDR1 amino acid sequence: GFTFSDYY SEQ ID NO: 491

VH CDR2 amino acid sequence: ISSSGSTI SEQ ID NO: 492

VH CDR3 amino acid sequence: ARDFYDILTDSPYFYYGVDV SEQ ID NO: 493

VL domain nucleotide sequence: SEQ ID NO: 502
GATATTGTGATGACTCAGTCTCCACTCTCCCTGCCCGTCACCCCTGGAGAGCCGGCCTCCATCTCCTGCAGGTCTAG
TCAGAGCCTCCTGCATAGTAATGGATACAACTATTTGGATTGGTACCTGCAGAAGCCAGGGCAGTCTCCACAGCTCC
TGATCTATTTGGGTTCTAATCGGGCCTCCGGGGTCCCTGACAGGTTCAGTGGCAGTGGATCAGGCACAGATTTTACA
CTGAAAATCAGCAGAGTGGAGGCTGAGGATGTTGGGGTTTATTACTGCATGCAAGCTCTACAAACTCCTCGGACGTT
CGGCCAAGGGACCAAGGTGGAAATCAAA VL domain amino acid sequence: SEQ ID NO: 501
DIVMTQSPLSLPVTPGEPASISCRSSQSLLHSNGYNYLDWYLQKPGQSPQLLIYLGSNRASGVPDRFSGSGSGTDFT
LKISRVEAEDVGVYYCMQALQTPRTFGQGTKVEIK -continued

| Sequences |
|---|
| VL CDR1 amino acid sequence: QSLLHSNGYNY SEQ ID NO: 498 |
| VL CDR2 amino acid sequence: LGS SEQ ID NO: 499 |
| VL CDR3 amino acid sequence: MQALQTPRT SEQ ID NO: 500 |

TABLE S1

SEQ ID NOS: 1-342

| SEQ ID NO: | Name | Description | Sequence |
|---|---|---|---|
| 1 | Human PD-L1 | NCBI number: NP_054862.1 (ECD highlighted in BOLD, cytoplasmic domain underlined) | MRIFAVFIFMTYWHLLNA**FTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERT**HLVILGAILLCLGVALTFIFRLRKGRMMDVKKCGIQDTNSKKQSDTHLEET |
| 2 | Cyno PD-L1 | NCBI number: XP_014973154.1 (ECD highlighted in BOLD) | MGWSCIILFLVATATGVHSM**FTVTVPKDLYVVEYGSNMTIECKFPVEKQLDLTSLIVYWEMEDKNIIQFVHGEEDLKVQHSNYRQRAQLLKDQLSLGNAALRITDVKLQDAGVYRCMISYGGADYKRITVKVNAPYNKINQRILVVDPVTSEHELTCQAEGYPKAEVIWTSSDHQVLSGKTTTTNSKREEKLLNVTSTLRINTTANEIFYCIFRRLDPEENHTAELVIPELPLALPPNERT** |
| 3 | Human PD-L1 His | Human PD-L1 ECD with C-terminal His tag | MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERT**HHHHHH** |
| 4 | Human PD-L1 Fc | Human PD-L1 ECD with C-term Fc fusion (in bold) | MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERTIEGREPKSCDKTHTCPPCPAPELLGGPSVFLFPPKPKDTLMISRTPEV**TCVVVDVSHEDPEVKFNWYVDGVEVBNAKTKPREEQYNSTYRVVSVLTVLHQDWLNGKEYKCKVSNKALPAPIEKTISKAKGQPREPQVYTLPPSRDELTKNQVSLTQLVKGFYPSDIAVEWESNGQPENNYKTTPPVLDSDGSFFLYSKLTVDKSRWQQGNVFSCSWBEALHNHYTQKSLSLSPGK** |
| 5 | Cyno PD-L1 FLAG | Cynomolgus PD-L1 ECD with N-term FLAG tag | MGWSCIILFLVATATGVHSMFTVTVPKDLYVVEYGSNMTIECKFPVEKQLDLTSLIVYWEMEDKNIIQFVHGEEDLKVQHSNYRQRAQLLKDQLSLGNAALRITDVKLQDAGVYRCMISYGGADYKRITVKVNAPYNKINQRILVVDPVTSEHELTCQAEGYPKAEVIWTSSDHQVLSGKTTTTNSKREEKLLNVTSTLRINTTANEIFYCIFRRLDPEENHTAELVIPELPLALPPNERT**DYKDDDDK** |
| 6 | Human PD-1 Fc | Human PD-1 full length sequence derived from cDNA as human Fc fusion | MGWSCIILFLVATATGVHSLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQ**KLENLYFQGIEGRMDEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDQSFFLYSKLTVDKSRWQQGNVFSCSVMHEALHNHYTQKSLSLSP** |
| 7 | 84G09 - CDRH1 (IMGT) | Amino acid sequence of CDRH1 of 84G09 using IMGT | GFTFDDYA |
| 8 | 84G09 - CDRH2 (IMGT) | Amino acid sequence of CDRH2 of 84G09 using IMGT | ISWKSNII |
| 9 | 84G09 - CDRH3 (IMGT) | Amino acid sequence of CDRH3 of 84G09 using IMGT | ARDITGSGSYGWFDP |

TABLE S1-continued

SEQ ID NOS: 1-342

| SEQ ID NO: | Name | Description | Sequence |
|---|---|---|---|
| 10 | 84G09 - CDRH1 (Kabat) | Amino acid sequence of CDRH1 of 84G09 using Kabat | DYAMH |
| 11 | 84G09 - CDRH2 (Kabat) | Amino acid sequence of CDRH2 of 84G09 using Kabat | GISWKSNIIGYADSVKG |
| 12 | 84G09 - CDRH3 (Kabat) | Amino acid sequence of CDRH3 of 84G09 using Kabat | DITGSGSYGWFDP |
| 13 | 84G09 - Heavy chain variable region | Amino acid sequence of $V_H$ of 84G09 (mutations from germline are shown in bold letters) | EVQLVESGGGLVQPGRSLRLSCAASGFTFDDYAMHWVRQTPGKGLEWV<br>SGISW**KSNI**IGYADSVKGRFTISRDNAKNSLYLQMNSLRAEDTALYYC<br>ARDITGSGSYGWFDPWGQGTLVTVSS |
| 14 | 84G09 - Heavy chain variable region | Nucleic acid sequence of $V_H$ of 84G09 | CAaGAAAAAGCTTGCCGCCACCATGGAGTTTGGGCTGAGCTGGATTTT<br>CCTTTTGGCTATTTTAAAAGGTGTCCAGTGTGAAGTACAATTGGTGGA<br>GTCCGGGGGAGGCTTGGTACAGCCTGGCAGGTCCCTGAGACTCTCCTG<br>TGCAGCCTCTGGATTCACCTTTGATGATTATGCCATGCACTGGGTCCG<br>ACAAACTCCAGGGAAGGGCCTGGAGTGGGTCTCAGGTATAAGTTGGAA<br>GAGTAATATCATAGGCTATGCGGACTCTGTGAAGGGCCGATTCACCAT<br>CTCCAGAGACAACGCCAAGAACTCCCTGTATCTGCAAATGAACAGTCT<br>GAGAGCTGAGGACACGGCCTTGTATTATTGTGCAAGAGATATAACGGG<br>TTCGGGGAGTTATGGCTGGTTCGACCCCTGGGGCCAGGGAACCCTGGT<br>CACCGTCTCCTCAGCCAAAACGACACCCCCATCTGTCTATCCACTGGC<br>CCCTGAATCTGCTAAAACTCAGCCTCCG |
| 15 | 84G09 - full heavy chain sequence | Amino acid sequence of 84G09 heavy chain (mutations from germline are shown in bold letters) | EVQLVESGGGLVQPGRSLRLSCAASGFTFDDYAMHWVRQTPGKGLEWV<br>SGISWKSNIIGYADSVKGRFTISRDNAKNSLYLQMNSLRAEDTALYYC<br>ARDITGSGSYGWFDPWGQGTLVTVSSASTKGPSVFPLAPCSRSTSEST<br>AALGCLVKDYFPEPVTVSWNSGALTSGVHTFPAVLQSSGLYSLSSVVT<br>VPSSSLGTKTYTCNVDHKPSNTKVDKRVESKYGPPCPPCPAPEFEGGP<br>SVFLFPPKPKDTLMISRTPEVTCVVVDVSQEDPEVQFNWYVDGVEVHN<br>AKTKPREEQFNSTYRVVSVLTVLHQDWLNGKEYKCKVSNKGLPSSIEK<br>TISKAKGQPREPQVYTLPPSQEEMTKNQVSLTCLVKGFYPSDIAVEWE<br>SNGQPENNYKTTPPVLDSDGSFFLYSRLTVDKSRWQEGNVFSCSVMHE<br>ALHNHYTQKSLSLSLGK |
| 16 | 84G09 - full heavy chain sequence | Nucleic acid sequence of 84G09 heavy chain | GAAGTGCAGCTGGTGGAATCTGGCGGCGGACTGGTGCAGCCTGGCAGA<br>TCCCTGAGACTGTCTTGTGCCGCCTCCGGCTTCACCTTCGACGACTAC<br>GCTATGCACTGGGTGCGACAGACCCCTGGCAAGGGCCTGGAATGGGTG<br>TCCGGCATCTCCTGGAAGTCCAACATCATCGGCTACGCCGACTCCGTG<br>AAGGGCCGGTTCACCATCTCCCGGGACAACGCCAAGAACTCCCTGTAC<br>CTGCAGATGAACAGCCTGCGGGCCGAGGACACCGCCCTGTACTACTGC<br>GCCAGAGACATCACCGGCTCCGGCTCCTACGGATGGTTCGATCCTTGG<br>GGCCAGGGCACCCTCGTGACCGTGTCCTCTGCCAGCACCAAGGGCCCC<br>TCTGTGTTCCCTCTGGCCCCTTCCAGCAAGTCCACCTCTGGCGGAACA<br>GCCGCTCTGGGCTGCCTCGTGAAGGACTACTTCCCCGAGCCTGTGACC<br>GTGTCCTGGAACTCTGGCGCTCTGACCAGCGGAGTGCACACCTTCCCT<br>GCTGTGCTGCAGTCCTCCGGCCTGTACTCCCTGTCCTCCGTCGTGACC<br>GTGCCTTCCAGCTCTCTGGGCACCCAGACCTACATCTGCAACGTGAAC<br>CACAAGCCCTCCAACACCAAGGTGGACAAGAAGGTGGAACCCAAGTCC<br>TGCGACAAGACCCACACCTGTCCCCCTTGTCCTGCCCCTGAACTGCTG<br>GGCGGACCTTCCGTGTTCCTGTTCCCCCCAAAGCCCAAGGACACCCTG<br>ATGATCTCCCGGACCCCCGAAGTGACCTGCGTGGTGGTGGATGTGTCC<br>CACGAGGACCCTGAAGTGAAGTTCAATTGGTACGTGGACGGCGTGGAA<br>GTGCACAACGCCAAGACCAAGCCTAGAGAGGAACAGTACAACTCCACC<br>TACCGGGTGGTGTCCGTGCTGACCGTGCTGCACCAGGATTGGCTGAAC<br>GGCAAAGAGTACAAGTGCAAGGTGTCCAACAAGGCCCTGCCTGCCCCC<br>ATCGAAAAGACCATCTCCAAGGCCAAGGGCCAGCCCCGGGAACCCCAG<br>GTGTACACACTGCCCCCTAGCAGGGACGAGCTGACCAAGAACCAGGTG<br>TCCCTGACCTGTCTCGTGAAAGGCTTCTACCCCTCCGATATCGCCGTG<br>GAATGGGAGTCCAACGGCCAGCCTGAGAACAACTACAAGACCACCCCC<br>CCTGTGCTGGACTCCGACGGCTCATTCTTCCTGTACAGCAAGCTGACA<br>GTGGACAAGTCCCGGTGGCAGCAGGGCAACGTGTTCTCCTGCTCCGTG<br>ATGCACGAGGCCCTGCACAACCACTACACCCAGAAGTCCCTGTCCCTG<br>AGCCCCGGCAAG |

TABLE S1-continued

SEQ ID NOS: 1-342

| SEQ ID NO: | Name | Description | Sequence |
|---|---|---|---|
| 17 | 84G09 - CDRL1 (IMGT) | Amino acid sequence of CDRL1 of 84G09 using IMGT | QSISSY |
| 18 | 84G09 - CDRL2 (IMGT) | Amino acid sequence of CDRL2 of 84G09 using IMGT | VAS |
| 19 | 84G09 - CDRL3 (IMGT) | Amino acid sequence of CDRL3 of 84G09 using IMGT | QQSYSNPIT |
| 20 | 84G09 - CDRL1 (Kabat) | Amino acid sequence of CDRL1 of 84G09 using Kabat | RASQSISSYLN |
| 21 | 84G09 - CDRL2 (Kabat) | Amino acid sequence of CDRL2 of 84G09 using Kabat | VASSLQS |
| 22 | 84G09 - CDRL3 (Kabat) | Amino acid sequence of CDRL3 of 84G09 using Kabat | QQSYSNPIT |
| 23 | 84G09 - Light chain variable region | Amino acid sequence of $V_L$ of 84G09 | DIQMTQSPSSLSASVGDRVTITCRASQSISSYLNWYQQKPGKAPKPLI YVASSLQSGVPSSFSGSGSGTDFTLTISSLQPEDFATYYCQQSYSNPI TFGQGTRLEIK |
| 24 | 84G09 - Light chain variable region | Nucleic acid sequence of $V_L$ of 84G09 | GACATCCAGATGACCCAGTCTCCATCCTCCCTGTCTGCATCTGTAGGA GACAGAGTCACCATCACTTGCCGGGCAAGTCAGAGCATTAGCAGCTAT TTAAATTGGTATCAGCAGAAACCAGGGAAAGCCCCTAAGCCCCTGATC TATGTTGCATCCAGTTTGCAAAGTGGGGTCCCATCAAGTTTCAGTGGC AGTGGATCTGGGACAGATTTCACTCTCACCATCAGCAGTCTGCAACCT GAAGATTTTGCAACTTACTACTGTCAACAGAGTTACAGTAATCCGATC ACCTTCGGCCAAGGGACACGACTGGAGATCAAA |
| 25 | 84G09 - full light chain sequence | Amino acid sequence of 84G09 light chain | DIQMTQSPSSLSASVGDRVTITCRASQSISSYLNWYQQKPGKAPKPLI YVASSLQSGVPSSFSGSGSGTDFTLTISSLQPEDFATYYCQQSYSNPI TFGQGTRLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 26 | 84G09 - full light chain sequence | Nucleic acid sequence of 84G09 light chain | GACATCCAGATGACCCAGTCTCCATCCTCCCTGTCTGCATCTGTAGGA GACAGAGTCACCATCACTTGCCGGGCAAGTCAGAGCATTAGCAGCTAT TTAAATTGGTATCAGCAGAAACCAGGGAAAGCCCCTAAGCCCCTGATC TATGTTGCATCCAGTTTGCAAAGTGGGGTCCCATCAAGTTTCAGTGGC AGTGGATCTGGGACAGATTTCACTCTCACCATCAGCAGTCTGCAACCT GAAGATTTTGCAACTTACTACTGTCAACAGAGTTACAGTAATCCGATC ACCTTCGGCCAAGGGACACGACTGGAGATCAAACGTACGGTGGCCGCT CCCTCCGTGTTCATCTTCCCACCTTCCGACGAGCAGCTGAAGTCCGGC ACCGCTTCTGTCGTGTGCCTGCTGAACAACTTCTACCCCCGCGAGGCC AAGGTGCAGTGGAAGGTGGACAACGCCCTGCAGTCCGGCAACTCCCAG GAATCCGTGACCGAGCAGGACTCCAAGGACAGCACCTACTCCCTGTCC TCCACCCTGACCCTGTCCAAGGCCGACTACGAGAAGCACAAGGTGTAC GCCTGCGAAGTGACCCACCAGGGCCTGTCTAGCCCCGTGACCAAGTCT TTCAACCGGGGCGAGTGT |
| 27 | 1D05 - CDRH1 (TMGT) | Amino acid sequence of CDRH1 of 1D05 using IMGT | GFTFDDYA |
| 28 | 1D05 - CDRH2 (IMGT) | Amino acid sequence of CDRH2 of 1D05 using IMGT | ISWIRTGI |
| 29 | 1D05 - CDRH3 (IMGT) | Amino acid sequence of CDRH3 of 1D05 using IMGT | AKDMKGSGTYGGWFDT |
| 30 | 1D05 - CDRH1 (Kabat) | Amino acid sequence of CDRH1 of 1D05 using Kabat | DYAMH |

TABLE S1-continued

SEQ ID NOS: 1-342

| SEQ ID NO: | Name | Description | Sequence |
|---|---|---|---|
| 31 | 1D05 - CDRH2 (Kabat) | Amino acid sequence of CDRH2 of 1D05 using Kabat | GISWIRTGIGYADSVKG |
| 32 | 1D05 - CDRH3 (Kabat) | Amino acid sequence of CDRH3 of 1D05 using Kabat | DMKGSGTYGGWFDT |
| 33 | 1D05 - Heavy chain variable region | Amino acid sequence of $V_H$ of 1D05 (mutations from germline are shown in bold letters) | EVQLVESGGGLVQPGRSLRLSCAASGFTFDDYAMHWVRQ**V**PGKGLEWV SGIS**WIRTG**IGYADSVKGRFTI**FR**DNAKNSLYLQMNSLRAEDTALYYC AKDMKGSGTYGGWFDTWGQGTLVTVSS |
| 34 | 1D05 - Heavy chain variable region | Nucleic acid sequence of $V_H$ of 1D05 | AAGCTTGCCGCCACCATGGAGTTTGGGCTGAGCTGGATTTTCCTTTTG GCTATTTTAAAAGGTGTCCAGTGTGAAGTGCAGCTGGTGGAGTCTGGG GGAGGCTTGGTGCAGCCTGGCAGGTCCCTGAGACTCTCCTGTGCAGCC TCTGGATTCACCTTTGATGATTATGCCATGCACTGGGTCCGGCAAGTT CCAGGGAAGGGCCTGGAATGGGTCTCAGGCATTAGTTGGATTCGTACT GGCATAGGCTATGCGGACTCTGTGAAGGGCCGATTCACCATTTTCAGA GACAACGCCAAGAATTCCCTGTATCTGCAAATGAACAGTCTGAGAGCT GAGGACACGGCCTTGTATTACTGTGCAAAAGATATGAAGGGTTCGGGG ACTTATGGGGGGTGGTTCGACACCTGGGGCCAGGGAACCCTGGTCACC GTCTCCTCAGCCAAAACAACAGCCCCATCGGTCTATCCACTGGCCCCT GC |
| 35 | 1D05 - full heavy chain sequence | Amino acid sequence of 1D05 heavy chain | EVQLVESGGGLVQPGRSLRLSCAASGFTFDDYAMHWVRQVPGKGLEWV SGISWIRTGIGYADSVKGRFTIFRDNAKNSLYLQMNSLRAEDTALYYC AKDMKGSGTYGGWFDTWGQGTLVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAPEFEGG PSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMH EALHNHYTQKSLSLSLGK |
| 36 | 1D05 - full heavy chain sequence | Nucleic acid sequence of 1D05 heavy chain | GAAGTGCAGCTGGTGGAATCTGGCGGCGGACTGGTGCAGCCTGGCAGA TCCCTGAGACTGTCTTGTGCCGCCTCCGGCTTCACCTTCGACGACTAC GCTATGCACTGGGTGCGACAGGTGCCAGGCAAGGGCCTGGAATGGGTG TCCGGCATCTCTTGGATCCGGACCGGCATCGGCTACGCCGACTCTGTG AAGGGCCGGTTCACCATCTTCCGGGACAACGCCAAGAACTCCCTGTAC CTGCAGATGAACAGCCTGCGGGCCGAGGACACCGCCCTGTACTACTGC GCCAAGGACATGAAGGGCTCCGGCACCTACGGCGGATGGTTCGATACT TGGGGCCAGGGCACCCTCGTGACCGTGTCCTCTGCCAGCACCAAGGGC CCCTCTGTGTTCCCTCTGGCCCCTTCCAGCAAGTCCACCTCTGGCGGA ACAGCCGCTCTGGGCTGCCTCGTGAAGGACTACTTCCCCGAGCCTGTG ACCGTGTCCTGGAACTCTGGCGCTCTGACCAGCGGAGTGCACACCTTC CCTGCTGTGCTGCAGTCCTCCGGCCTGTACTCCCTGTCCTCCGTCGTG ACCGTGCCTTCCAGCTCTCTGGGCACCCAGACCTACATCTGCAACGTG AACCACAAGCCCTCCAACACCAAGGTGGACAAGAAGGTGGAACCCAAG TCCTGCGACAAGACCCACACCTGTCCCCCTTGTCCTGCCCCTGAACTG CTGGGCGGACCTTCCGTGTTCCTGTTCCCCCCAAAGCCCAAGGACACC CTGATGATCTCCCGGACCCCCGAAGTGACCTGCGTGGTGGTGGATGTG TCCCACGAGGACCCTGAAGTGAAGTTCAATTGGTACGTGGACGGCGTG GAAGTGCACAACGCCAAGACCAAGCCTAGAGAGGAACAGTACAACTCC ACCTACCGGGTGGTGTCCGTGCTGACCGTGCTGCACCAGGATTGGCTG AACGGCAAAGAGTACAAGTGCAAGGTGTCCAACAAGGCCCTGCCTGCC CCCATCGAAAAGACCATCTCCAAGGCCAAGGGCCAGCCCCGGGAACCC CAGGTGTACACACTGCCCCCTAGCAGGGACGAGCTGACCAAGAACCAG GTGTCCCTGACCTGTCTCGTGAAAGGCTTCTACCCCTCCGATATCGCC GTGGAATGGGAGTCCAACGGCCAGCCTGAGAACAACTACAAGACCACC CCCCCTGTGCTGGACTCCGACGGCTCATTCTTCCTGTACAGCAAGCTG ACAGTGGACAAGTCCCGGTGGCAGCAGGGCAACGTGTTCTCCTGCTCC GTGATGCACGAGGCCCTGCACAACCACTACACCCAGAAGTCCCTGTCC CTGAGCCCCGGCAAG |
| 37 | 1D05 - CDRL1 (IMGT) | Amino acid sequence of CDRL1 of 1D05 using IMGT | QSISSY |
| 38 | 1D05 - CDRL2 (IMGT) | Amino acid sequence of CDRL2 of 1D05 using IMGT | VAS |

TABLE S1-continued

SEQ ID NOS: 1-342

| SEQ ID NO: | Name | Description | Sequence |
|---|---|---|---|
| 39 | 1D05 - CDRL3 (IMGT) | Amino acid sequence of CDRL3 of 1D05 using IMGT | QQSYSTPIT |
| 40 | 1D05 - CDRL1 (Kabat) | Amino acid sequence of CDRL1 of 1D05 using Kabat | RASQSISSYLN |
| 41 | 1D05 - CDRL2 (Kabat) | Amino acid sequence of CDRL2 of 1D05 using Kabat | VASSLQS |
| 42 | 1D05 - CDRL3 (Kabat) | Amino acid sequence of CDRL3 of 1D05 using Kabat | QQSYSTPIT |
| 43 | 1D05 - Light chain variable region | Amino acid sequence of $V_L$ of 1D05(mutations from germline are shown in bold letters) | DIQMTQSPSSLSASVGDRVTITCRASQSISSYLNWYQQKPGKAPKLLI<br>YVASSLQSGVPSRFSGSGSGTDFTLTISSLQPEDFATYYCQQSYSTPI<br>TFGQGTRLEIK |
| 44 | 1D05 - Light chain variable region | Nucleic acid sequence of $V_L$ of 1D05 | AAAGCTTGCCGCCACCATGAGGCTCCCTGCTCAGCTTCTGGGGCTCCT<br>GCTACTCTGGCTCCGAGGTGCCAGATGTGACATCCAGATGACCCAGTC<br>TCCATCCTCCCTGTCTGCATCTGTAGGAGACAGAGTCACCATCACTTG<br>CCGGGCAAGTCAGAGCATTAGCAGCTATTTAAATTGGTATCAGCAGAA<br>ACCAGGGAAAGCCCCTAAACTCCTGATCTATGTTGCATCCAGTTTGCA<br>AAGTGGGGTCCCATCAAGGTTCAGTGGCAGTGGATCTGGGACAGATTT<br>CACTCTCACTATCAGCAGTCTGCAACCTGAAGATTTTGCAACTTACTA<br>CTGTCAACAGAGTTACAGTACCCCGATCACCTTCGGCCAAGGGACACG<br>TCTGGAGATCAAACGTACGGATGCTGCACCAACT |
| 45 | 1D05 - full light chain sequence | Amino acid sequence of 1D05 light chain | DIQMTQSPSSLSASVGDRVTITCRASQSISSYLNWYQQKPGKAPKLLI<br>YVASSLQSGVPSRFSGSGSGTDFTLTISSLQPEDFATYYCQQSYSTPI<br>TFGQGTRLEIKRTVAAPSVFIFPPSDEQLKSGTASVVCLLNNFYPREA<br>KVQWKVDNALQSGNSQESVTEQDSKDSTYSLSSTLTLSKADYEKHKVY<br>ACEVTHQGLSSPVTKSFNRGEC |
| 46 | 1D05 - full light chain sequence | Nucleic acid sequence of 1D05 light chain | GACATCCAGATGACCCAGTCCCCCTCCAGCCTGTCTGCTTCCGTGGGC<br>GACAGAGTGACCATCACCTGTCGGGCCTCCCAGTCCATCTCCTCCTAC<br>CTGAACTGGTATCAGCAGAAGCCCGGCAAGGCCCCCAAGCTGCTGATC<br>TACGTGGCCAGCTCTCTGCAGTCCGGCGTGCCCTCTAGATTCTCCGGC<br>TCTGGCTCTGGCACCGACTTTACCCTGACCATCAGCTCCCTGCAGCCC<br>GAGGACTTCGCCACCTACTACTGCCAGCAGTCCTACTCCACCCCTATC<br>ACCTTCGGCCAGGGCACCCGGCTGGAAATCAAACGTACGGTGGCCGCT<br>CCCTCCGTGTTCATCTTCCCACCTTCCGACGAGCAGCTGAAGTCCGGC<br>ACCGCTTCTGTCGTGTGCCTGCTGAACAACTTCTACCCCCGCGAGGCC<br>AAGGTGCAGTGGAAGGTGGACAACGCCCTGCAGTCCGGCAACTCCCAG<br>GAATCCGTGACCGAGCAGGACTCCAAGGACAGCACCTACTCCCTGTCC<br>TCCACCCTGACCCTGTCCAAGGCCGACTACGAGAAGCACAAGGTGTAC<br>GCCTGCGAAGTGACCCACCAGGGCCTGTCTAGCCCCGTGACCAAGTCT<br>TTCAACCGGGGCGAGTGT |
| 47 | Mutated 1D05 - HC mutant 1 | Amino acid sequence of 1D05 heavy chain with V to A back-mutation in framework region to germline highlighted with IgG1 disabled (LAGA) constant region | EVQLVESGGGLVQPGRSLRLSCAASGFTFDDYAMHWVRQ**A**PGKGLEWV<br>SGISWIRTGIGYADSVKGRFTIFRDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPE**LAGA**<br>PSVFLFPPKPKDTLMISRTPEVTCVVVDVSQEDPEVQFNWYVDGVEVH<br>NAKTKPREEQFNSTYRVVSVLTVLHQDWLNGKEYKCKVSNKGLPSSIE<br>KTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMH<br>EALHNHYTQKSLSLSLGK |
| 48 | Mutated 1D05 - HC mutant 2 | Amino acid sequence of 1D05 heavy chain with F to S back-mutation in framework region to germline highlighted with IgG1 disabled (LAGA) constant region | EVQLVESGGGLVQPGRSLRLSCAASGFTFDDYAMHWVRQVPGKGLEWV<br>SGISWIRTGIGYADSVKGRFTI**S**RDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPE**LAGA**<br>PSVFLFPPKPKDTLMISRTPEVTCVVVDVSQEDPEVQFNWYVDGVEVH<br>NAKTKPREEQFNSTYRVVSVLTVLHQDWLNGKEYKCKVSNKGLPSSIE<br>KTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMH<br>EALHNHYTQKSLSLSLGK |

TABLE S1-continued

SEQ ID NOS: 1-342

| SEQ ID NO: | Name | Description | Sequence |
|---|---|---|---|
| 49 | Mutated 1D05 - HC mutant 3 | Amino acid sequence of 1D05 heavy chain with ELLG to -PVA back-mutation in constant region to germline highlighted | EVQLVESGGGLVQPGRSLRLSCAASGFTFDDYAMHWVRQVPGKGLEWV SGISWIRTGIGYADSVKGRFTIFRDNAKNSLYLQMNSLRAEDTALYYC AKDMKGSGTYGGWFDTWGQGTLVTVSSASTKGPSVFPLAPCSRSTSES TAALGCLVKDYFPEPVTVSWNSGALTSGVHTFPAVLQSSGLYSLSSVV TVPSSSLGTKTYTCNVDHKPSNTKVDKRVESKYGPPCPPCPAP- **PVA**GPSVFLFPPKPKDTLMISRTPEVTCVVVDVSQEDPEVQFNWYVDG VEVHNAKTKPREEQFNSTYRVVSVLTVLHQDWLNGKEYKCKVSNKGLP SSIEKTISKAKGQPREPQVYTLPPSQEEMTKNQVSLTCLVKGFYPSDI AVEWESNGQPENNYKTTPPVLDSDGSFFLYSRLTVDKSRWQEGNVFSC SVMHEALHNHYTQKSLSLSLGK |
| 50 | Mutated 1D05 - LC mutant 1 | Amino acid sequence of 1D05 kappa light chain with V to A back-mutation in CDRL2 to germline highlighted | DIQMTQSPSSLSASVGDRVTITCRASQSISSYLNWYQQKPGKAPKLLI Y**A**ASSLQSGVPSRFSGSGSGTDFTLTISSLQPEDFATYYCQQSYSTPI TFGQGTRLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 51 | Mutated 1D05 - LC mutant 2 | Amino acid sequence of 1D05 kappa light chain with L to F back-mutation in framework to germline highlighted | DIQMTQSPSSLSASVGDRVTITCRASQSISSYLNWYQQKPGKAPKL**F**I YVASSLQSGVPSRFSGSGSGTDFTLTISSLQPEDFATYYCQQSYSTPI TFGQGTRLEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 52 | 411B08 - CDRH1 (IMGT) | Amino acid sequence of CDRH1 of 411B08 using IMGT | GFTFSSYW |
| 53 | 411B08 - CDRH2 (IMGT) | Amino acid sequence of CDRH2 of 411B08 using IMGT | IKEDGSEK |
| 54 | 411B08 - CDRH3 (IMGT) | Amino acid sequence of CDRH3 of 411B08 using IMGT | ARNRLYSDFLDN |
| 55 | 411B08 - CDRH1 (Kabat) | Amino acid sequence of CDRH1 of 411B08 using Kabat | SYWMS |
| 56 | 411B08 - CDRH2 (Kabat) | Amino acid sequence of CDRH2 of 411B08 using Kabat | NIKEDGSEKYYVDSVKG |
| 57 | 411B08 - CDRH3 (Kabat) | Amino acid sequence of CDRH3 of 411B08 using Kabat | NRLYSDFLDN |
| 58 | 411B08 - Heavy chain variable region | Amino acid sequence of $V_H$ of 411B08 | EVQLVESGGGLVQPGGSLRLSCAASGFTFSSYWMSWVRQAPGKGLEWV ANIKEDGSEKYYVDSVKGRFTISRDNAENSLYLQMNSLRAEDTSVYYC ARNRLYSDFLDNWGQGTLVTVSS |
| 59 | 411B08 - Heavy chain variable region | Nucleic acid sequence of $V_H$ of 411B08 | GAGGTGCAGCTGGTGGAGTCTGGGGGAGGCTTGGTCCAGCCTGGGGGG TCCCTGAGACTCTCCTGTGCAGCCTCTGGATTCACGTTTAGTAGCTAT TGGATGAGTTGGGTCCGCCAGGCTCCAGGGAAGGGGCTGGAGTGGGTG GCCAACATCAAAGAAGATGGAAGTGAGAAATACTATGTCGACTCTGTG AAGGGCCGATTCACCATCTCCAGAGACAACGCCAAGAACTCACTGTAT CTGCAAATGAACAGCCTGAGAGCCGAGGACACGTCTGTGTATTACTGT GCGAGAAATCGACTCTACAGTGACTTCCTTGACAACTGGGGCCAGGGA ACCCTGGTCACCGTCTCCTCAG |

TABLE S1-continued

SEQ ID NOS: 1-342

| SEQ ID NO: | Name | Description | Sequence |
|---|---|---|---|
| 60 | 411B08 - full heavy chain sequence | Amino acid sequence of 411B08 heavy chain | EVQLVESGGGLVQPGGSLRLSCAASGFTFSSYWMSWVRQAPGKGLEWVANIKEDGSEKYYVDSVKGRFTISRDNAKNSLYLQMNSLRAEDTSVYYCARNRLYSDFLDNWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 61 | 411B08 - full heavy chain sequence | Nucleic acid sequence of 411B08 heavy chain | GAGGTGCAGCTGGTGGAGTCTGGGGGAGGCTTGGTCCAGCCTGGGGGGTCCCTGAGACTCTCCTGTGCAGCCTCTGGATTCACGTTTAGTAGCTATTGGATGAGTTGGGTCCGCCAGGCTCCAGGGAAGGGGCTGGAGTGGGTGGCCAACATCAAAGAAGATGGAAGTGAGAAATACTATGTCGACTCTGTGAAGGGCCGATTCACCATCTCCAGAGACAACGCCAAGAACTCACTGTATCTGCAAATGAACAGCCTGAGAGCCGAGGACACGTCTGTGTATTACTGTGCGAGAAATCGACTCTACAGTGACTTCCTTGACAACTGGGGCCAGGGAACCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 62 | 411B08 - CDRL1 (IMGT) | Amino acid sequence of CDRL1 of 411B08 using IMGT | QGVSSW |
| 63 | 411B08 - CDRL2 (IMGT) | Amino acid sequence of CDRL2 of 411B08 using IMGT | GAS |
| 64 | 411B08 - CDRL3 (IMGT) | Amino acid sequence of CDRL3 of 411B08 using IMGT | QQANSIPFT |
| 65 | 411B08 - CDRL1 (Kabat) | Amino acid sequence of CDRL1 of 411B08 using Kabat | RASQGVSSWLA |
| 66 | 411B08 - CDRL2 (Kabat) | Amino acid sequence of CDRL2 of 411B08 using Kabat | GASSLQS |
| 67 | 411B08 - CDRL3 (Kabat) | Amino acid sequence of CDRL3 of 411B08 using Kabat | QQANSIPFT |
| 68 | 411B08 - Light chain variable region | Amino acid sequence of $V_L$ of 411B08 | DIQMTQSPSSVSASVGDRVTITCRASQGVSSWLAWYQQKSGKAPKLLIYGASSLQSGVPSRFSGSGSGTEFILTISSLQPEDFATYYCQQANSIPFTFGPGTKVDIK |

TABLE S1-continued

| SEQ ID NO: | Name | Description | Sequence |
|---|---|---|---|
| | | SEQ ID NOS: 1-342 | |
| 69 | 411B08 - Light chain variable region | Nucleic acid sequence of $V_L$ of 411B08 | GACATCCAGATGACCCAGTCTCCATCTTCCGTGTCTGCATCTGTCGGAGACAGAGTCACCATCACTTGTCGGGCGAGTCAGGGTGTTAGCAGCTGGTTAGCCTGGTATCAGCAGAAATCAGGGAAAGCCCCTAAGCTCCTGATCTATGGTGCATCCAGTTTGCAAAGTGGGGTCCCATCAAGATTCAGCGGCAGTGGATCTGGGACAGAGTTCATTCTCACCATCAGCAGCCTGCAGCCTGAAGATTTTGCAACTTACTATTGTCAACAGGCTAACAGTATCCCATTCACTTTCGGCCCTGGGACCAAAGTGGATATCAAAC |
| 70 | 411B08 - full light chain sequence | Amino acid sequence of 411B08 light chain | DIQMTQSPSSVSASVGDRVTITCRASQGVSSWLAWYQQKSGKAPKLLIYGASSLQSGVPSRFSGSGSGTEFILTISSLQPEDFATYYCQQANSIPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 71 | 411B08 - full light chain sequence | Nucleic acid sequence of 411B08 light chain | GACATCCAGATGACCCAGTCTCCATCTTCCGTGTCTGCATCTGTCGGAGACAGAGTCACCATCACTTGTCGGGCGAGTCAGGGTGTTAGCAGCTGGTTAGCCTGGTATCAGCAGAAATCAGGGAAAGCCCCTAAGCTCCTGATCTATGGTGCATCCAGTTTGCAAAGTGGGGTCCCATCAAGATTCAGCGGCAGTGGATCTGGGACAGAGTTCATTCTCACCATCAGCAGCCTGCAGCCTGAAGATTTTGCAACTTACTATTGTCAACAGGCTAACAGTATCCCATTCACTTTCGGCCCTGGGACCAAAGTGGATATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 72 | 411C04 - CDRH1 (IMGT) | Amino acid sequence of CDRH1 of 411C04 using IMGT | GFTFSSYW |
| 73 | 411C04 - CDRH2 (IMGT) | Amino acid sequence of CDRH2 of 411C04 using IMGT | IKEDGSEK |
| 74 | 411C04 - CDRH3 (IMGT) | Amino acid sequence of CDRH3 of 411C04 using IMGT | ARVRLYSDFLDY |
| 75 | 411C04 - CDRH1 (Kabat) | Amino acid sequence of CDRH1 of 411C04 using Kabat | SYWMS |
| 76 | 411C04 - CDRH2 (Kabat) | Amino acid sequence of CDRH2 of 411C04 using Kabat | NIKEDGSEKYYVDSLKG |
| 77 | 411C04 - CDRH3 (Kabat) | Amino acid sequence of CDRH3 of 411C04 using Kabat | VRLYSDFLDY |
| 78 | 411C04 - Heavy chain variable region | Amino acid sequence of $V_H$ of 411C04 | EVQLVDSGGGLVQPGGSLRLSCAASGFTFSSYWMSWVRQAPGKGLEWVANIKEDGSEKYYVDSLKGRFTISRDNAKNSLYLQMNSLRAEDTSVYYCARVRLYSDFLDYWGQGTLVTVSS |
| 79 | 411C04 - Heavy chain variable region | Nucleic acid sequence of $V_H$ of 411C04 | GAGGTGCAGCTGGTGGACTCTGGGGGAGGCTTGGTCCAGCCTGGGGGGTCCCTGAGACTCTCCTGTGCAGCCTCTGGATTCACGTTTAGTAGCTATTGGATGAGTTGGGTCCGCCAGGCTCCAGGAAAGGGGCTGGAGTGGGTGGCCAACATAAAAGAAGATGGAAGTGAGAAATACTATGTAGACTCTTTGAAGGGCCGATTCACCATCTCCAGAGACAACGCCAAGAACTCACTGTATCTGCAAATGAACAGCCTGAGAGCCGAGGACACGTCTGTGTATTACTGTGCGAGAGTTCGACTCTACAGTGACTTCCTTGACTACTGGGGCCAGGGAACCCTGGTCACCGTCTCCTCAG |

TABLE S1-continued

SEQ ID NOS: 1-342

| SEQ ID NO: | Name | Description | Sequence |
|---|---|---|---|
| 80 | 411C04 - full heavy chain sequence | Amino acid sequence of 411C04 heavy chain | EVQLVDSGGGLVQPGGSLRLSCAASGFTFSSYWMSWVRQAPGKGLEWV<br>ANIKEDGSEKYYVDSLKGRFTISRDNAKNSLYLQMNSLRAEDTSVYYC<br>ARVRLYSDFLDYWGQGTLVTVSSASTKGPSVFPLAPSSKSTSGGTAAL<br>GCLVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHE<br>ALHNHYTQKSLSLSPGK |
| 81 | 411C04 - full heavy chain sequence | Nucleic acid sequence of 411C04 heavy chain | GAGGTGCAGCTGGTGGACTCTGGGGGAGGCTTGGTCCAGCCTGGGGGG<br>TCCCTGAGACTCTCCTGTGCAGCCTCTGGATTCACGTTTAGTAGCTAT<br>TGGATGAGTTGGGTCCGCCAGGCTCCAGGAAAGGGGCTGGAGTGGGTG<br>GCCAACATAAAAGAAGATGGAAGTGAGAAATACTATGTAGACTCTTTG<br>AAGGGCCGATTCACCATCTCCAGAGACAACGCCAAGAACTCACTGTAT<br>CTGCAAATGAACAGCCTGAGAGCCGAGGACACGTCTGTGTATTACTGT<br>GCGAGAGTTCGACTCTACAGTGACTTCCTTGACTACTGGGGCCAGGGA<br>ACCCTGGTCACCGTCTCCTCAGCCAGCACCAAGGGCCCCTCTGTGTTC<br>CCTCTGGCCCCTTCCAGCAAGTCCACCTCTGGCGGAACAGCCGCTCTG<br>GGCTGCCTCGTGAAGGACTACTTCCCCGAGCCTGTGACCGTGTCCTGG<br>AACTCTGGCGCTCTGACCAGCGGAGTGCACACCTTCCCTGCTGTGCTG<br>CAGTCCTCCGGCCTGTACTCCCTGTCCTCCGTCGTGACCGTGCCTTCC<br>AGCTCTCTGGGCACCCAGACCTACATCTGCAACGTGAACCACAAGCCC<br>TCCAACACCAAGGTGGACAAGAAGGTGGAACCCAAGTCCTGCGACAAG<br>ACCCACACCTGTCCCCCTTGTCCTGCCCCTGAACTGCTGGGCGGACCT<br>TCCGTGTTCCTGTTCCCCCCAAAGCCCAAGGACACCCTGATGATCTCC<br>CGGACCCCCGAAGTGACCTGCGTGGTGGTGGATGTGTCCCACGAGGAC<br>CCTGAAGTGAAGTTCAATTGGTACGTGGACGGCGTGGAAGTGCACAAC<br>GCCAAGACCAAGCCTAGAGAGGAACAGTACAACTCCACCTACCGGGTG<br>GTGTCCGTGCTGACCGTGCTGCACCAGGATTGGCTGAACGGCAAAGAG<br>TACAAGTGCAAGGTGTCCAACAAGGCCCTGCCTGCCCCCATCGAAAAG<br>ACCATCTCCAAGGCCAAGGGCCAGCCCCGGGAACCCCAGGTGTACACA<br>CTGCCCCCTAGCAGGGACGAGCTGACCAAGAACCAGGTGTCCCTGACC<br>TGTCTCGTGAAAGGCTTCTACCCCTCCGATATCGCCGTGGAATGGGAG<br>TCCAACGGCCAGCCTGAGAACAACTACAAGACCACCCCCCCTGTGCTG<br>GACTCCGACGGCTCATTCTTCCTGTACAGCAAGCTGACAGTGGACAAG<br>TCCCGGTGGCAGCAGGGCAACGTGTTCTCCTGCTCCGTGATGCACGAG<br>GCCCTGCACAACCACTACACCCAGAAGTCCCTGTCCCTGAGCCCCGGC<br>APG |
| 82 | 411C04 - CDRL1 (IMGT) | Amino acid sequence of CDRL1 of 411C04 using IMGT | QGVSSW |
| 83 | 411C04 - CDRL2 (IMGT) | Amino acid sequence of CDRL2 of 411C04 using IMGT | GAS |
| 84 | 411C04 - CDRL3 (IMGT) | Amino acid sequence of CDRL3 of 411C04 using IMGT | QQANSIPFT |
| 85 | 411C04 - CDRL1 (Kabat) | Amino acid sequence of CDRL1 of 411C04 using Kabat | RASQGVSSWLA |
| 86 | 411C04 - CDRL2 (Kabat) | Amino acid sequence of CDRL2 of 411C04 using Kabat | GASSLQS |
| 87 | 411C04 - CDRL3 (Kabat) | Amino acid sequence of CDRL3 of 411C04 using Kabat | QQANSIPFT |
| 88 | 411C04 - Light chain variable region | Amino acid sequence of $V_L$ of 411C04 | DIQMTQSPSSVSASVGDRVTITCRASQGVSSWLAWYQQKSGKAPKLLI<br>YGASSLQSGVPSRFSGSGSGTEFILSISSLQPEDFATYYCQQANSIPF<br>TFGPGTKVDIK |

TABLE S1-continued

SEQ ID NOS: 1-342

| SEQ ID NO: | Name | Description | Sequence |
|---|---|---|---|
| 89 | 411C04 - Light chain variable region | Nucleic acid sequence of $V_L$ of 411C04 | GACATCCAGATGACCCAGTCTCCATCTTCCGTGTCTGCATCTGTCGGAGACAGAGTCACCATCACTTGTCGGGCGAGTCAGGGTGTTAGCAGTTGGTTAGCCTGGTATCAGCAGAAATCAGGGAAAGCCCCTAAGCTCCTGATCTATGGTGCCTCCAGTTTGCAAAGTGGGGTCCCATCAAGATTCAGCGGCAGTGGATCTGGGACAGAGTTCATTCTCAGCATCAGCAGCCTGCAGCCTGAAGATTTTGCAACTTACTATTGTCAACAGGCTAACAGTATCCCATTCACTTTCGGCCCTGGGACCAAAGTGGATATCAAAC |
| 90 | 411C04 - full light chain sequence | Amino acid sequence of 411C04 light chain | DIQMTQSPSSVSASVGDRVTITCRASQGVSSWLAWYQQKSGKAPKLLIYGASSLQSGVPSRFSGSGSGTEFILSISSLQPEDFATYYCQQANSIPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 91 | 411C04 - full light chain sequence | Nucleic acid sequence of 411C04 light chain | GACATCCAGATGACCCAGTCTCCATCTTCCGTGTCTGCATCTGTCGGAGACAGAGTCACCATCACTTGTCGGGCGAGTCAGGGTGTTAGCAGTTGGTTAGCCTGGTATCAGCAGAAATCAGGGAAAGCCCCTAAGCTCCTGATCTATGGTGCCTCCAGTTTGCAAAGTGGGGTCCCATCAAGATTCAGCGGCAGTGGATCTGGGACAGAGTTCATTCTCAGCATCAGCAGCCTGCAGCCTGAAGATTTTGCAACTTACTATTGTCAACAGGCTAACAGTATCCCATTCACTTTCGGCCCTGGGACCAAAGTGGATATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 92 | 411D07 - CDRH1 (IMGT) | Amino acid sequence of CDRH1 of 411D07 using IMGT | GGSIISSDW |
| 93 | 411D07 - CDRH2 (IMGT) | Amino acid sequence of CDRH2 of 411D07 using IMGT | IFHSGRT |
| 94 | 411D07 - CDRH3 (IMGT) | Amino acid sequence of CDRH3 of 411D07 using IMGT | ARDGSGSY |
| 95 | 411D07 - CDRH1 (Kabat) | Amino acid sequence of CDRH1 of 411D07 using Kabat | SSDWWN |
| 96 | 411D07 - CDRH2 (Kabat) | Amino acid sequence of CDRH2 of 411D07 using Kabat | EIFHSGRTNYNPSLKS |
| 97 | 411D07 - CDRH3 (Kabat) | Amino acid sequence of CDRH3 of 411D07 using Kabat | DGSGSY |
| 98 | 411D07 - Heavy chain variable region | Amino acid sequence of $V_H$ of 411D07 | QVQLQESGPGLVKPSGTLSLTCIVSGGSIISSDWWNWVRQPPGKGLEWIGEIFHSGRTNYNPSLKSRVTISIDKSKNQFSLRLSSVTAADTAVYYCARDGSGSYWGQGTLVTVSS |
| 99 | 411D07 - Heavy chain variable region | Nucleic acid sequence of $V_H$ of 411D07 | CAGGTGCAGCTGCAGGAGTCGGGCCCAGGACTGGTGAAGCCTTCGGGGACCCTGTCCCTCACCTGCATTGTCTCTGGTGGCTCCATCATCAGTAGTGACTGGTGGAATTGGGTCCGCCAGCCCCCAGGGAAGGGGCTGGAGTGGATTGGAGAAATCTTTCATAGTGGGAGGACCAACTACAACCCGTCCCTCAAGAGTCGAGTCACCATATCAATAGACAAGTCCAAGAATCAGTTCTCCCTGAGGCTGAGCTCTGTGACCGCCGCGGACACGGCCGTGTATTACTGTGCGAGAGATGGTTCGGGGAGTTACTGGGGCCAGGGAACCCTGGTCACCGTCTCCTCAG |

TABLE S1-continued

SEQ ID NOS: 1-342

| SEQ ID NO: Name | Description | Sequence |
|---|---|---|
| 100 411D07 - full heavy chain sequence | Amino acid sequence of 411D07 heavy chain | QVQLQESGPGLVKPSGTLSLTCIVSGGSIISSDWWNWVRQPPGKGLEW IGEIFHSGRTNYNPSLKSRVTISIDKSKNQFSLRLSSVTAADTAVYYC ARDGSGSYWGQGTLVTVSSASTKGPSVFPLAPSSKSTSGGTAALGCLV KDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHN HYTQKSLSLSPGK |
| 101 411D07 - full heavy chain sequence | Nucleic acid sequence of 411D07 heavy chain | CAGGTGCAGCTGCAGGAGTCGGGCCCAGGACTGGTGAAGCCTTCGGGG ACCCTGTCCCTCACCTGCATTGTCTCTGGTGGCTCCATCATCAGTAGT GACTGGTGGAATTGGGTCCGCCAGCCCCCAGGGAAGGGGCTGGAGTGG ATTGGAGAAATCTTTCATAGTGGGAGGACCAACTACAACCCGTCCCTC AAGAGTCGAGTCACCATATCAATAGACAAGTCCAAGAATCAGTTCTCC CTGAGGCTGAGCTCTGTGACCGCCGCGGACACGGCCGTGTATTACTGT GCGAGAGATGGTTCGGGGAGTTACTGGGGCCAGGGAACCCTGGTCACC GTCTCCTCAGCCAGCACCAAGGGCCCCTCTGTGTTCCCTCTGGCCCCT TCCAGCAAGTCCACCTCTGGCGGAACAGCCGCTCTGGGCTGCCTCGTG AAGGACTACTTCCCCGAGCCTGTGACCGTGTCCTGGAACTCTGGCGCT CTGACCAGCGGAGTGCACACCTTCCCTGCTGTGCTGCAGTCCTCCGGC CTGTACTCCCTGTCCTCCGTCGTGACCGTGCCTTCCAGCTCTCTGGGC ACCCAGACCTACATCTGCAACGTGAACCACAAGCCCTCCAACACCAAG GTGGACAAGAAGGTGGAACCCAAGTCCTGCGACAAGACCCACACCTGT CCCCCTTGTCCTGCCCCTGAACTGCTGGGCGGACCTTCCGTGTTCCTG TTCCCCCCAAAGCCCAAGGACACCCTGATGATCTCCCGGACCCCCGAA GTGACCTGCGTGGTGGTGGATGTGTCCCACGAGGACCCTGAAGTGAAG TTCAATTGGTACGTGGACGGCGTGGAAGTGCACAACGCCAAGACCAAG CCTAGAGAGGAACAGTACAACTCCACCTACCGGGTGGTGTCCGTGCTG ACCGTGCTGCACCAGGATTGGCTGAACGGCAAAGAGTACAAGTGCAAG GTGTCCAACAAGGCCCTGCCTGCCCCCATCGAAAAGACCATCTCCAAG GCCAAGGGCCAGCCCCGGGAACCCCAGGTGTACACACTGCCCCCTAGC AGGGACGAGCTGACCAAGAACCAGGTGTCCCTGACCTGTCTCGTGAAA GGCTTCTACCCCTCCGATATCGCCGTGGAATGGGAGTCCAACGGCCAG CCTGAGAACAACTACAAGACCACCCCCCCTGTGCTGGACTCCGACGGC TCATTCTTCCTGTACAGCAAGCTGACAGTGGACAAGTCCCGGTGGCAG CAGGGCAACGTGTTCTCCTGCTCCGTGATGCACGAGGCCCTGCACAAC CACTACACCCAGAAGTCCCTGTCCCTGAGCCCCGGCAAG |
| 102 411D07 - CDRL1 (IMGT) | Amino acid sequence of CDRL1 of 411D07 using IMGT | QSVLYSSNNKNY |
| 103 411D07 - CDRL2 (IMGT) | Amino acid sequence of CDRL2 of 411D07 using IMGT | WAS |
| 104 411D07 - CDRL3 (IMGT) | Amino acid sequence of CDRL3 of 411D07 using IMGT | QQYYSNRS |
| 105 411D07 - CDRL1 (Kabat) | Amino acid sequence of CDRL1 of 411D07 using Kabat | KSSQSVLYSSNNKNYLA |
| 106 411D07 - CDRL2 (Kabat) | Amino acid sequence of CDRL2 of 411D07 using Kabat | WASTRES |
| 107 411D07 - CDRL3 (Kabat) | Amino acid sequence of CDRL3 of 411D07 using Kabat | QQYYSNRS |
| 108 411D07 - Light chain variable region | Amino acid sequence of $V_L$ of 411D07 | DIVMTQSPDSLAVSLGERATINCKSSQSVLYSSNNKNYLAWYQQKSGQ PPKLLIYWASTRESGVPDRFSGSGSGTDFTLTISSLQTEDVAVYYCQQ YYSNRSFGQGTKLEIK |

TABLE S1-continued

SEQ ID NOS: 1-342

| SEQ ID NO: | Name | Description | Sequence |
|---|---|---|---|
| 109 | 411D07 - Light chain variable region | Nucleic acid sequence of V_L of 411D07 | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAATAAGAATTACTTAGCTTGGTACCAGCAGAAATCAGGACAG CCTCCTAAGTTGCTCATTTACTGGGCATCTACCCGGGAATCCGGGGTC CCTGACCGATTCAGTGGCAGCGGGTCTGGGACAGATTTCACTCTCACC ATCAGCAGCCTGCAGACTGAAGATGTGGCAGTTTATTACTGTCAGCAA TATTATAGTAATCGCAGTTTTGGCCAGGGGACCAAGCTGGAGATCAAA C |
| 110 | 411D07 - full light chain sequence | Amino acid sequence of 411D07 light chain | DIVMTQSPDSLAVSLGERATINCKSSQSVLYSSNNKNYLAWYQQKSGQ PPKLLIYWASTRESGVPDRFSGSGSGTDFTLTISSLQTEDVAVYYCQQ YYSNRSFGQGTKLEIKRTVAAPSVFIFPPSDEQLKSGTASVVCLLNNF YPREAKVQWKVDNALQSGNSQESVTEQDSKDSTYSLSSTLTLSKADYE KHKVYACEVTHQGLSSPVTKSFNRGEC |
| 111 | 411D07 - full light chain sequence | Nucleic acid sequence of 411D07 light chain | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAATAAGAATTACTTAGCTTGGTACCAGCAGAAATCAGGACAG CCTCCTAAGTTGCTCATTTACTGGGCATCTACCCGGGAATCCGGGGTC CCTGACCGATTCAGTGGCAGCGGGTCTGGGACAGATTTCACTCTCACC ATCAGCAGCCTGCAGACTGAAGATGTGGCAGTTTATTACTGTCAGCAA TATTATAGTAATCGCAGTTTTGGCCAGGGGACCAAGCTGGAGATCAAA CGTACGGTGGCCGCTCCCTCCGTGTTCATCTTCCCACCTTCCGACGAG CAGCTGAAGTCCGGCACCGCTTCTGTCGTGTGCCTGCTGAACAACTTC TACCCCCGCGAGGCCAAGGTGCAGTGGAAGGTGGACAACGCCCTGCAG TCCGGCAACTCCCAGGAATCCGTGACCGAGCAGGACTCCAAGGACAGC ACCTACTCCCTGTCCTCCACCCTGACCCTGTCCAAGGCCGACTACGAG AAGCACAAGGTGTACGCCTGCGAAGTGACCCACCAGGGCCTGTCTAGC CCCGTGACCAAGTCTTTCAACCGGGGCGAGTGT |
| 112 | 385F01 - CDRH1 (IMGT) | Amino acid sequence of CDRH1 of 385F01 using IMGT | GFTFSSYW |
| 113 | 385F01 - CDRH2 (IMGT) | Amino acid sequence of CDRH2 of 385F01 using IMGT | IKEDGSEK |
| 114 | 385F01 - CDRH3 (IMGT) | Amino acid sequence of CDRH3 of 385F01 using IMGT | ARNRLYSDFLDN |
| 115 | 385F01 - CDRH1 of (Kabat) | Amino acid sequence of CDRH1 of 385F01 using Kabat | SYWMS |
| 116 | 385F01 - CDRH2 (Kabat) | Amino acid sequence of CDRH2 of 385F01 using Kabat | NIKEDGSEKYYVDSVKG |
| 117 | 385F01 - CDRH3 (Kabat) | Amino acid sequence of CDRH3 of 385F01 using Kabat | NRLYSDFLDN |
| 118 | 385F01 - Heavy chain variable region | Amino acid sequence of V_H of 385F01 | EVQLVESGGGLVQPGGSLRLSCAASGFTFSSYWMSWVRQAPGKGLEWV ANIKEDGSEKYYVDSVKGRFTISRDNAKNSLYLQMNSLRAEDTSVYYC ARNRLYSDFLDNWGQGTLVTVSS |
| 119 | 385F01 - Heavy chain variable region | Nucleic acid sequence of V_H of 385F01 | GAGGTGCAGCTGGTGGAGTCTGGGGGAGGCTTGGTCCAGCCTGGGGGG TCCCTGAGACTCTCCTGTGCAGCCTCTGGATTCACGTTTAGTAGCTAT TGGATGAGTTGGGTCCGCCAGGCTCCAGGGAAGGGGCTGGAGTGGGTG GCCAACATCAAAGAAGATGGAAGTGAGAAATACTATGTCGACTCTGTG AAGGGCCGATTCACCATCTCCAGAGACAACGCCAAGAACTCACTGTAT CTGCAAATGAACAGCCTGAGAGCCGAGGACACGTCTGTGTATTACTGT GCGAGAAATCGACTCTACAGTGACTTCCTTGACAACTGGGGCCAGGGA ACCCTGGTCACCGTCTCCTCAG |

TABLE S1-continued

SEQ ID NOS: 1-342

| SEQ ID NO: | Name | Description | Sequence |
|---|---|---|---|
| 120 | 385F01 - full heavy chain sequence | Amino acid sequence of 385F01 heavy chain | EVQLVESGGGLVQPGGSLRLSCAASGFTFSSYWMSWVRQAPGKGLEWVANIKEDGSEKYYVDSVKGRFTISRDNAKNSLYLQMNSLRAEDTSVYYCARNRLYSDFLDNWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 121 | 385F01 - full heavy chain sequence | Nucleic acid sequence of 385F01 heavy chain | GAGGTGCAGCTGGTGGAGTCTGGGGGAGGCTTGGTCCAGCCTGGGGGGTCCCTGAGACTCTCCTGTGCAGCCTCTGGATTCACGTTTAGTAGCTATTGGATGAGTTGGGTCCGCCAGGCTCCAGGGAAGGGGCTGGAGTGGGTGGCCAACATCAAAGAAGATGGAAGTGAGAAATACTATGTCGACTCTGTGAAGGGCCGATTCACCATCTCCAGAGACAACGCCAAGAACTCACTGTATCTGCAAATGAACAGCCTGAGAGCCGAGGACACGTCTGTGTATTACTGTGCGAGAAATCGACTCTACAGTGACTTCCTTGACAACTGGGGCCAGGGAACCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 122 | 385F01 - CDRL1 (IMGT) | Amino acid sequence of CDRL1 of 385F01 using IMGT | QGVSSW |
| 123 | 385F01 - CDRL2 (IMGT) | Amino acid sequence of CDRL2 of 385F01 using IMGT | GAS |
| 124 | 385F01 - CDRL3 (IMGT) | Amino acid sequence of CDRL3 of 385F01 using IMGT | QQANSIPFT |
| 125 | 385F01 - CDRL1 (Kabat) | Amino acid sequence of CDRL1 of 385F01 using Kabat | RASQGVSSWLA |
| 126 | 385F01 - CDRL2 (Kabat) | Amino acid sequence of CDRL2 of 385F01 using Kabat | GASSLQS |
| 127 | 385F01 - CDRL3 (Kabat) | Amino acid sequence of CDRL3 of 385F01 using Kabat | QQANSIPFT |
| 128 | 385F01 - Light chain variable region | Amino acid sequence of VL of 385F01 | DIQMTQSPSSVSASVGDRVTITCRASQGVSSWLAWYQQKSGKAPKLLIYGASSLQSGVPSRFSGSGSGTEFILTISSLQPEDFATYYCQQANSIPFTFGPGTKVDIK |

TABLE S1-continued

| SEQ ID NO: Name | Description | Sequence |
|---|---|---|
| SEQ ID NOS: 1-342 | | |
| 129385F01 - Light chain variable region | Nucleic acid sequence of $V_L$ of 385F01 | GACATCCAGATGACCCAGTCTCCATCTTCCGTGTCTGCATCTGTCGGAGACAGAGTCACCATCACTTGTCGGGCGAGTCAGGGTGTTAGCAGCTGGTTAGCCTGGTATCAGCAGAAATCAGGGAAAGCCCCTAAGCTCCTGATCTATGGTGCATCCAGTTTGCAAAGTGGGGTCCCATCAAGATTCAGCGGCAGTGGATCTGGGACAGAGTTCATTCTCACCATCAGCAGCCTGCAGCCTGAAGATTTTGCAACTTACTATTGTCAACAGGCTAACAGTATCCCATTCACTTTCGGCCCTGGGACCAAAGTGGATATCAAAC |
| 130385F01 - full light chain sequence | Amino acid sequence of 385F01 light chain | DIQMTQSPSSVSASVGDRVTITCRASQGVSSWLAWYQQKSGKAPKLLIYGASSLQSGVPSRFSGSGSGTEFILTISSLQPEDFATYYCQQANSIPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 131385F01 - full light chain sequence | Nucleic acid sequence of 385F01 light chain | GACATCCAGATGACCCAGTCTCCATCTTCCGTGTCTGCATCTGTCGGAGACAGAGTCACCATCACTTGTCGGGCGAGTCAGGGTGTTAGCAGCTGGTTAGCCTGGTATCAGCAGAAATCAGGGAAAGCCCCTAAGCTCCTGATCTATGGTGCATCCAGTTTGCAAAGTGGGGTCCCATCAAGATTCAGCGGCAGTGGATCTGGGACAGAGTTCATTCTCACCATCAGCAGCCTGCAGCCTGAAGATTTTGCAACTTACTATTGTCAACAGGCTAACAGTATCCCATTCACTTTCGGCCCTGGGACCAAAGTGGATATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 132413D08 - CDRH1 (IMGT) | Amino acid sequence of CDRH1 of 413D08 using IMGT | GFTFRIYG |
| 133413D08 - CDRH2 (IMGT) | Amino acid sequence of CDRH2 of 413D08 using IMGT | IWYDGSNK |
| 134413D08 - CDRH3 (IMGT) | Amino acid sequence of CDRH3 of 413D08 using IMGT | ARDMDYFGMDV |
| 135413D08 - CDRH1 (Kabat) | Amino acid sequence of CDRH1 of 413D08 using Kabat | IYGMH |
| 136413D08 - CDRH2 (Kabat) | Amino acid sequence of CDRH2 of 413D08 using Kabat | VIWYDGSNKYYADSVKG |
| 137413D08 - CDRH3 (Kabat) | Amino acid sequence of CDRH3 of 413D08 using Kabat | DMDYFGMDV |
| 138413D08 - Heavy chain variable region | Amino acid sequence of $V_H$ of 413D08 | QVQLVESGGGVVQPGRSLRLSCAASGFTFRIYGMHWVRQAPGKGLEWVAVIWYDGSNKYYADSVKGRFTISRDNSDNTLYLQMNSLRAEDTAVYYCARDMDYFGMDVWGQGTTVTVSS |
| 139413D08 - Heavy chain variable region | Nucleic acid sequence of $V_H$ of 413D08 | CAGGTGCAGCTGGTGGAGTCTGGGGGAGGCGTGGTCCAGCCTGGGAGGTCCCTGAGACTCTCCTGTGCAGCGTCTGGATTCACCTTCCGTATTTATGGCATGCACTGGGTCCGCCAGGCTCCAGGCAAGGGGCTGGAGTGGGTGGCAGTTATATGGTATGATGGAAGTAATAAATACTATGCTGACTCCGTGAAGGGCCGATTCACCATCTCCAGAGACAATTCCGACAACACGCTGTATCTGCAAATGAACAGCCTGAGAGCCGAGGACACGGCTGTGTATTACTGTGCGAGAGATATGGACTACTTCGGTATGGACGTCTGGGGCCAAGGGACCACGGTCACCGTCTCCTCAG |

TABLE S1-continued

SEQ ID NOS: 1-342

| SEQ ID NO: Name | Description | Sequence |
| --- | --- | --- |
| 140 413D08 - full heavy chain sequence | Amino acid sequence of 413D08 heavy chain | QVQLVESGGGVVQPGRSLRLSCAASGFTFRIYGMHWVRQAPGKGLEWV AVIWYDGSNKYYADSVKGRFTISRDNSDNTLYLQMNSLRAEDTAVYYC ARDMDYFGMDVWGQGTTVTVSSASTKGPSVFPLAPSSKSTSGGTAALG CLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEA LHNHYTQKSLSLSPGK |
| 141 413D08 - full heavy chain sequence | Nucleic acid sequence of 413D08 heavy chain | CAGGTGCAGCTGGTGGAGTCTGGGGGAGGCGTGGTCCAGCCTGGGAGG TCCCTGAGACTCTCCTGTGCAGCGTCTGGATTCACCTTCCGTATTTAT GGCATGCACTGGGTCCGCCAGGCTCCAGGCAAGGGGCTGGAGTGGGTG GCAGTTATATGGTATGATGGAAGTAATAAATACTATGCTGACTCCGTG AAGGGCCGATTCACCATCTCCAGAGACAATTCCGACAACACGCTGTAT CTGCAAATGAACAGCCTGAGAGCCGAGGACACGGCTGTGTATTACTGT GCGAGAGATATGGACTACTTCGGTATGGACGTCTGGGGCCAAGGGACC ACGGTCACCGTCTCCTCAGCCAGCACCAAGGGCCCCTCTGTGTTCCCT CTGGCCCCTTCCAGCAAGTCCACCTCTGGCGGAACAGCCGCTCTGGGC TGCCTCGTGAAGGACTACTTCCCCGAGCCTGTGACCGTGTCCTGGAAC TCTGGCGCTCTGACCAGCGGAGTGCACACCTTCCCTGCTGTGCTGCAG TCCTCCGGCCTGTACTCCCTGTCCTCCGTCGTGACCGTGCCTTCCAGC TCTCTGGGCACCCAGACCTACATCTGCAACGTGAACCACAAGCCCTCC AACACCAAGGTGGACAAGAAGGTGGAACCCAAGTCCTGCGACAAGACC CACACCTGTCCCCCTTGTCCTGCCCCTGAACTGCTGGGCGGACCTTCC GTGTTCCTGTTCCCCCCAAAGCCCAAGGACACCCTGATGATCTCCCGG ACCCCCGAAGTGACCTGCGTGGTGGTGGATGTGTCCCACGAGGACCCT GAAGTGAAGTTCAATTGGTACGTGGACGGCGTGGAAGTGCACAACGCC AAGACCAAGCCTAGAGAGGAACAGTACAACTCCACCTACCGGGTGGTG TCCGTGCTGACCGTGCTGCACCAGGATTGGCTGAACGGCAAAGAGTAC AAGTGCAAGGTGTCCAACAAGGCCCTGCCTGCCCCCATCGAAAAGACC ATCTCCAAGGCCAAGGGCCAGCCCCGGGAACCCCAGGTGTACACACTG CCCCCTAGCAGGGACGAGCTGACCAAGAACCAGGTGTCCCTGACCTGT CTCGTGAAAGGCTTCTACCCCTCCGATATCGCCGTGGAATGGGAGTCC AACGGCCAGCCTGAGAACAACTACAAGACCACCCCCCCTGTGCTGGAC TCCGACGGCTCATTCTTCCTGTACAGCAAGCTGACAGTGGACAAGTCC CGGTGGCAGCAGGGCAACGTGTTCTCCTGCTCCGTGATGCACGAGGCC CTGCACAACCACTACACCCAGAAGTCCCTGTCCCTGAGCCCCGGCAAG |
| 142 413D08 - CDRL1 (IMGT) | Amino acid sequence of CDRL1 of 413D08 using IMGT | QGIRND |
| 143 413D08 - CDRL2 (IMGT) | Amino acid sequence of CDRL2 of 413D08 using IMGT | AAS |
| 144 413D08 - CDRL3 (IMGT) | Amino acid sequence of CDRL3 of 413D08 using IMGT | LQHNSYPRT |
| 145 413D08 - CDRL1 (Kabat) | Amino acid sequence of CDRL1 of 413D08 using Kabat | RASQGIRNDLG |
| 146 413D08 - CDRL2 (Kabat) | Amino acid sequence of CDRL2 of 413D08 using Kabat | AASSLQS |
| 147 413D08 - CDRL3 (Kabat) | Amino acid sequence of CDRL3 of 413D08 using Kabat | LQHNSYPRT |
| 148 413D08 - Light chain variable region | Amino acid sequence of $V_L$ of 413D08 | DLQMTQSPSSLSASVGDRVTITCRASQGIRNDLGWYQQKPGKAPKRLI YAASSLQSGVPSRFSGSGSGTEFTLTISSLQPEDFATYYCLQHNSYPR TFGQGTKVEIK |

TABLE S1-continued

SEQ ID NOS: 1-342

| SEQ ID NO:Name | Description | Sequence |
|---|---|---|
| 149 413D08 - Light chain variable region | Nucleic acid sequence of V_L of 413D08 | GACCTCCAGATGACCCAGTCTCCATCCTCCCTGTCTGCATCTGTAGGA GACAGAGTCACCATCACTTGCCGGGCAAGTCAGGGCATTAGAAATGAT TTAGGCTGGTATCAGCAGAAACCAGGGAAAGCCCCTAAGCGCCTGATC TATGCTGCATCCAGTTTGCAAAGTGGGGTCCCATCAAGGTTCAGCGGC AGTGGATCTGGGACAGAATTCACTCTCACAATCAGCAGCCTGCAGCCT GAAGATTTTGCAACTTATTACTGTCTACAGCATAATAGTTACCCTCGG ACGTTCGGCCAAGGGACCAAGGTGGAAATCAAAC |
| 150 413D08 - full light chain sequence | Amino acid sequence of 413D08 light chain | DLQMTQSPSSLSASVGDRVTITCRASQGIRNDLGWYQQKPGKAPKRLI YAASSLQSGVPSRFSGSGSGTEFTLTISSLQPEDFATYYCLQHNSYPR TFGQGTKVEIKRTVAAPSVFIFPPSDEQLKSGTASVVCLLNNFYPREA KVQWKVDNALQSGNSQESVTEQDSKDSTYSLSSTLTLSKADYEKHKVY ACEVTHQGLSSPVTKSFNRGEC |
| 151 413D08 - full light chain sequence | Nucleic acid sequence of 413D08 light chain | GACCTCCAGATGACCCAGTCTCCATCCTCCCTGTCTGCATCTGTAGGA GACAGAGTCACCATCACTTGCCGGGCAAGTCAGGGCATTAGAAATGAT TTAGGCTGGTATCAGCAGAAACCAGGGAAAGCCCCTAAGCGCCTGATC TATGCTGCATCCAGTTTGCAAAGTGGGGTCCCATCAAGGTTCAGCGGC AGTGGATCTGGGACAGAATTCACTCTCACAATCAGCAGCCTGCAGCCT GAAGATTTTGCAACTTATTACTGTCTACAGCATAATAGTTACCCTCGG ACGTTCGGCCAAGGGACCAAGGTGGAAATCAAACGTACGGTGGCCGCT CCCTCCGTGTTCATCTTCCCACCTTCCGACGAGCAGCTGAAGTCCGGC ACCGCTTCTGTCGTGTGCCTGCTGAACAACTTCTACCCCCGCGAGGCC AAGGTGCAGTGGAAGGTGGACAACGCCCTGCAGTCCGGCAACTCCCAG GAATCCGTGACCGAGCAGGACTCCAAGGACAGCACCTACTCCCTGTCC TCCACCCTGACCCTGTCCAAGGCCGACTACGAGAAGCACAAGGTGTAC GCCTGCGAAGTGACCCACCAGGGCCTGTCTAGCCCCGTGACCAAGTCT TTCAACCGGGGCGAGTGT |
| 152 386H03 - CDRH1 (IMGT) | Amino acid sequence of CDRH1 of 386H03 using IMGT | GGSISSSDW |
| 153 386H03 - CDRH2 (IMGT) | Amino acid sequence of CDRH2 of 386H03 using IMGT | IFHSGNT |
| 154 386H03 - CDRH3 (IMGT) | Amino acid sequence of CDRH3 of 386H03 using IMGT | VRDGSGSY |
| 155 386H03 - CDRH1 (Kabat) | Amino acid sequence of CDRH1 of 386H03 using Kabat | SSDWWS |
| 156 386H03 - CDRH2 (Kabat) | Amino acid sequence of CDRH2 of 386H03 using Kabat | EIFHSGNTNYNPSLKS |
| 157 386H03 - CDRH3 (Kabat) | Amino acid sequence of CDRH3 of 386H03 using Kabat | DGSGSY |
| 158 386H03 - Heavy chain variable region | Amino acid sequence of V_H of 386H03 | QVQLQESGPGLVKPSGTLSLTCAVSGGSISSSDWWSWVRQPPGKGLEW IGEIFHSGNTNYNPSLKSRVTISVDKSKNQISLRLNSVTAADTAVYYC VRDGSGSYWGQGTLVTVSS |
| 159 386H03 - Heavy chain variable region | Nucleic acid sequence of V_H of 386H03 | CAGGTGCAGCTGCAGGAGTCGGGCCCAGGACTGGTGAAGCCTTCGGGG ACCCTGTCCCTCACCTGCGCTGTCTCTGGTGGCTCCATCAGCAGTAGT GACTGGTGGAGTTGGGTCCGCCAGCCCCCAGGGAAGGGGCTGGAGTGG ATTGGGGAAATCTTTCATAGTGGGAACACCAACTACAACCCGTCCCTC AAGAGTCGAGTCACCATATCAGTAGACAAGTCCAAGAACCAGATCTCC CTGAGGCTGAACTCTGTGACCGCCGCGGACACGGCCGTGTATTACTGT GTGAGAGATGGTTCGGGGAGTTACTGGGGCCAGGGAACCCTGGTCACC GTCTCCTCAG |

TABLE S1-continued

SEQ ID NOS: 1-342

| SEQ ID NO: Name | Description | Sequence |
|---|---|---|
| 160386H03 - full heavy chain sequence | Amino acid sequence of 386H03 heavy chain | QVQLQESGPGLVKPSGTLSLTCAVSGGSISSSDWWSWVRQPPGKGLEW IGEIFHSGNTNYNPSLKSRVTISVDKSKNQISLRLNSVTAADTAVYYC VRDGSGSYWGQGTLVTVSSASTKGPSVFPLAPSSKSTSGGTAALGCLV KDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHN HYTQKSLSLSPGK |
| 161386H03 - full heavy chain sequence | Nucleic acid sequence of 386H03 heavy chain | CAGGTGCAGCTGCAGGAGTCGGGCCCAGGACTGGTGAAGCCTTCGGGG ACCCTGTCCCTCACCTGCGCTGTCTCTGGTGGCTCCATCAGCAGTAGT GACTGGTGGAGTTGGGTCCGCCAGCCCCCAGGGAAGGGGCTGGAGTGG ATTGGGGAAATCTTTCATAGTGGGAACACCAACTACAACCCGTCCCTC AAGAGTCGAGTCACCATATCAGTAGACAAGTCCAAGAACCAGATCTCC CTGAGGCTGAACTCTGTGACCGCCGCGGACACGGCCGTGTATTACTGT GTGAGAGATGGTTCGGGGAGTTACTGGGGCCAGGGAACCCTGGTCACC GTCTCCTCAGCCAGCACCAAGGGCCCCTCTGTGTTCCCTCTGGCCCCT TCCAGCAAGTCCACCTCTGGCGGAACAGCCGCTCTGGGCTGCCTCGTG AAGGACTACTTCCCCGAGCCTGTGACCGTGTCCTGGAACTCTGGCGCT CTGACCAGCGGAGTGCACACCTTCCCTGCTGTGCTGCAGTCCTCCGGC CTGTACTCCCTGTCCTCCGTCGTGACCGTGCCTTCCAGCTCTCTGGGC ACCCAGACCTACATCTGCAACGTGAACCACAAGCCCTCCAACACCAAG GTGGACAAGAAGGTGGAACCCAAGTCCTGCGACAAGACCCACACCTGT CCCCCTTGTCCTGCCCCTGAACTGCTGGGCGGACCTTCCGTGTTCCTG TTCCCCCCAAAGCCCAAGGACACCCTGATGATCTCCCGGACCCCCGAA GTGACCTGCGTGGTGGTGGATGTGTCCCACGAGGACCCTGAAGTGAAG TTCAATTGGTACGTGGACGGCGTGGAAGTGCACAACGCCAAGACCAAG CCTAGAGAGGAACAGTACAACTCCACCTACCGGGTGGTGTCCGTGCTG ACCGTGCTGCACCAGGATTGGCTGAACGGCAAAGAGTACAAGTGCAAG GTGTCCAACAAGGCCCTGCCTGCCCCCATCGAAAAGACCATCTCCAAG GCCAAGGGCCAGCCCCGGGAACCCCAGGTGTACACACTGCCCCCTAGC AGGGACGAGCTGACCAAGAACCAGGTGTCCCTGACCTGTCTCGTGAAA GGCTTCTACCCCTCCGATATCGCCGTGGAATGGGAGTCCAACGGCCAG CCTGAGAACAACTACAAGACCACCCCCCCTGTGCTGGACTCCGACGGC TCATTCTTCCTGTACAGCAAGCTGACAGTGGACAAGTCCCGGTGGCAG CAGGGCAACGTGTTCTCCTGCTCCGTGATGCACGAGGCCCTGCACAAC CACTACACCCAGAAGTCCCTGTCCCTGAGCCCCGGCAAG |
| 162386H03 - CDRL1 (IMGT) | Amino acid sequence of CDRL1 of 386H03 using IMGT | QSVLYSSNNKNY |
| 163386H03 - CDRL2 (IMGT) | Amino acid sequence of CDRL2 of 386H03 using IMGT | WAS |
| 164386H03 - CDRL3 (IMGT) | Amino acid sequence of CDRL3 of 386H03 using IMGT | QQYYSTRS |
| 165386H03 - CDRL1 (Kabat) | Amino acid sequence of CDRL1 of 386H03 using Kabat | KSSQSVLYSSNNKNYLA |
| 166386H03 - CDRL2 (Kabat) | Amino acid sequence of CDRL2 of 386H03 using Kabat | WASTRES |
| 167386H03 - CDRL3 (Kabat) | Amino acid sequence of CDRL3 of 386H03 using Kabat | QQYYSTRS |
| 168386H03 - Light chain variable region | Amino acid sequence of $V_L$ of 386H03 | DIVMTQSPDSLAVSLGERATINCKSSQSVLYSSNNKNYLAWYQQKPGQ PPKLLIYWASTRESGVPDRFSGSGSGTDFTLTISSLQAEDVAVYYCQQ YYSTRSFGQGTKLEIK |

TABLE S1-continued

| SEQ ID NO: Name | Description | Sequence |
|---|---|---|
| 169 386H03 - Light chain variable region | Nucleic acid sequence of $V_L$ of 386H03 | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAATAAGAACTACTTAGCTTGGTACCAGCAGAAACCAGGACAG CCTCCTAAACTGCTCATTTACTGGGCATCTACCCGGGAATCCGGGGTC CCTGACCGATTCAGTGGCAGCGGGTCTGGGACAGATTTCACTCTCACC ATCAGCAGCCTGCAGGCTGAAGATGTGGCAGTTTATTACTGTCAGCAA TATTATAGTACTCGCAGTTTTGGCCAGGGGACCAAGCTGGAGATCAAAC |
| 170 386H03 - full light chain sequence | Amino acid sequence of 386H03 light chain | DIVMTQSPDSLAVSLGERATINCKSSQSVLYSSNNKNYLAWYQQKPGQ PPKLLIYWASTRESGVPDRFSGSGSGTDFTLTISSLQAEDVAVYYCQQ YYSTRSFGQGTKLEIKRTVAAPSVFIFPPSDEQLKSGTASVVCLLNNF YPREAKVQWKVDNALQSGNSQESVTEQDSKDSTYSLSSTLTLSKADYE KHKVYACEVTHQGLSSPVTKSFNRGEC |
| 171 386H03 - full light chain sequence | Nucleic acid sequence of 386H03 light chain | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAATAAGAACTACTTAGCTTGGTACCAGCAGAAACCAGGACAG CCTCCTAAACTGCTCATTTACTGGGCATCTACCCGGGAATCCGGGGTC CCTGACCGATTCAGTGGCAGCGGGTCTGGGACAGATTTCACTCTCACC ATCAGCAGCCTGCAGGCTGAAGATGTGGCAGTTTATTACTGTCAGCAA TATTATAGTACTCGCAGTTTTGGCCAGGGGACCAAGCTGGAGATCAAA CGTACGGTGGCCGCTCCCTCCGTGTTCATCTTCCCACCTTCCGACGAG CAGCTGAAGTCCGGCACCGCTTCTGTCGTGTGCCTGCTGAACAACTTC TACCCCCGCGAGGCCAAGGTGCAGTGGAAGGTGGACAACGCCCTGCAG TCCGGCAACTCCCAGGAATCCGTGACCGAGCAGGACTCCAAGGACAGC ACCTACTCCCTGTCCTCCACCCTGACCCTGTCCAAGGCCGACTACGAG AAGCACAAGGTGTACGCCTGCGAAGTGACCCACCAGGGCCTGTCTAGC CCCGTGACCAAGTCTTTCAACCGGGGCGAGTGT |
| 172 389A03 - CDRH1 (IMGT) | Amino acid sequence of CDRH1 of 389A03 using IMGT | GGSISSSSYY |
| 173 389A03 - CDRH2 (IMGT) | Amino acid sequence of CDRH2 of 389A03 using IMGT | IYSTGYT |
| 174 389A03 - CDRH3 (IMGT) | Amino acid sequence of CDRH3 of 389A03 using IMGT | AISTAAGPEYFHR |
| 175 389A03 - CDRH1 (Kabat) | Amino acid sequence of CDRH1 of 389A03 using Kabat | SSSYYCG |
| 176 389A03 - CDRH2 (Kabat) | Amino acid sequence of CDRH2 of 389A03 using Kabat | SIYSTGYTYYNPSLKS |
| 177 389A03 - CDRH3 (Kabat) | Amino acid sequence of CDRH3 of 389A03 using Kabat | STAAGPEYFHR |
| 178 389A03 - Heavy chain variable region | Amino acid sequence of $V_H$ of 389A03 | QLQESGPGLVKPSETLSLTCTVSGGSISSSSYYCGWIRQPPGKGLDWI GSIYSTGYTYYNPSLKSRVTISIDTSKNQFSCLILTSVTAADTAVYYC AISTAAGPEYFHRWGQGTLVTVSS |
| 179 389A03 - Heavy chain variable region | Nucleic acid sequence of $V_H$ of 389A03 | CAGCTGCAGGAGTCGGGCCCAGGCCTGGTGAAGCCTTCGGAGACCCTG TCCCTCACCTGCACTGTCTCTGGTGGCTCCATCAGCAGTAGTAGTTAT TACTGCGGCTGGATCCGCCAGCCCCCTGGGAAGGGGCTGGACTGGATT GGGAGTATCTATTCTACTGGGTACACCTACTACAACCCGTCCCTCAAG AGTCGAGTCACCATTTCCATAGACACGTCCAAGAACCAGTTCTCATGC CTGATACTGACCTCTGTGACCGCCGCAGACACGGCTGTGTATTACTGT GCGATAAGTACAGCAGCTGGCCCTGAATACTTCCATCGCTGGGGCCAG GGCACCCTGGTCACCGTCTCCTCAG |

TABLE S1-continued

SEQ ID NOS: 1-342

| SEQ ID NO: Name | Description | Sequence |
|---|---|---|
| 180 389A03 - full heavy chain sequence | Amino acid sequence of 389A03 heavy chain | QLQESGPGLVKPSETLSLTCTVSGGSISSSSYYCGWIRQPPGKGLDWIGSIYSTGYTYYNPSLKSRVTISIDTSKNQFSCLILTSVTAADTAVYYCAISTAAGPEYFHRWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 181 389A03 - full heavy chain sequence | Nucleic acid sequence of 389A03 heavy chain | CAGCTGCAGGAGTCGGGCCCAGGCCTGGTGAAGCCTTCGGAGACCCTGTCCCTCACCTGCACTGTCTCTGGTGGCTCCATCAGCAGTAGTAGTTATTACTGCGGCTGGATCCGCCAGCCCCCTGGGAAGGGGCTGGACTGGATTGGGAGTATCTATTCTACTGGGTACACCTACTACAACCCGTCCCTCAAGAGTCGAGTCACCATTTCCATAGACACGTCCAAGAACCAGTTCTCATGCCTGATACTGACCTCTGTGACCGCCGCAGACACGGCTGTGTATTACTGTGCGATAAGTACAGCAGCTGGCCCTGAATACTTCCATCGCTGGGGCCAGGGCACCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 182 389A03 - CDRL1 (IMGT) | Amino acid sequence of CDRL1 of 389A03 using IMGT | QSVLYSSNSKNF |
| 183 389A03 - CDRL2 (IMGT) | Amino acid sequence of CDRL2 of 389A03 using IMGT | WAS |
| 184 389A03 - CDRL3 (IMGT) | Amino acid sequence of CDRL3 of 389A03 using IMGT | QQYYSTPRT |
| 185 389A03 - CDRL1 (Kabat) | Amino acid sequence of CDRL1 of 389A03 using Kabat | KSSQSVLYSSNSKNFLA |
| 186 389A03 - CDRL2 (Kabat) | Amino acid sequence of CDRL2 of 389A03 using Kabat | WASTRGS |
| 187 389A03 - CDRL3 (Kabat) | Amino acid sequence of CDRL3 of 389A03 using Kabat | QQYYSTPRT |
| 188 389A03 - Light chain variable region | Amino acid sequence of $V_L$ of 389A03 | DIVMTQSPDSLAVSLGERATINCKSSQSVLYSSNSKNFLAWYQQKPGQPPKLFIYWASTRGSGVPDRISGSGSGTDFNLTISSLQAEDVAVYYCQQYYSTPRTFGQGTKVEIK |

TABLE S1-continued

SEQ ID NOS: 1-342

| SEQ ID NO: | Name | Description | Sequence |
|---|---|---|---|
| 189 | 389A03 - Light chain variable region | Nucleic acid sequence of $V_L$ of 389A03 | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAGTAAGAACTTCTTAGCTTGGTACCAGCAGAAACCGGGACAG CCTCCTAAGCTGTTCATTTACTGGGCATCTACCCGGGGATCCGGGGTC CCTGACCGAATCAGTGGCAGCGGGTCTGGGACAGATTTCAATCTCACC ATCAGCAGCCTGCAGGCTGAAGATGTGGCAGTTTATTACTGTCAACAA TATTATAGTACTCCTCGGACGTTCGGCCAAGGGACCAAGGTGGAGATC AAAC |
| 190 | 389A03 - full light chain sequence | Amino acid sequence of 389A03 light chain | DIVMTQSPDSLAVSLGERATINCKSSQSVLYSSNSKNFLAWYQQKPGQ PPKLFIYWASTRGSGVPDRISGSGSGTDFNLTISSLQAEDVAVYYCQQ YYSTPRTFGQGTKVEIKRTVAAPSVFIFPPSDEQLKSGTASVVCLLNN FYPREAKVQWKVDNALQSGNSQESVTEQDSKDSTYSLSSTLTLSKADY EKHKVYACEVTHQGLSSPVTKSFNRGEC |
| 191 | 389A03 - full light chain sequence | Nucleic acid sequence of 389A03 light chain | GACATCGTGATGACCCAGTCTCCAGACTCCCTGGCTGTGTCTCTGGGC GAGAGGGCCACCATCAACTGCAAGTCCAGCCAGAGTGTTTTATACAGC TCCAACAGTAAGAACTTCTTAGCTTGGTACCAGCAGAAACCGGGACAG CCTCCTAAGCTGTTCATTTACTGGGCATCTACCCGGGGATCCGGGGTC CCTGACCGAATCAGTGGCAGCGGGTCTGGGACAGATTTCAATCTCACC ATCAGCAGCCTGCAGGCTGAAGATGTGGCAGTTTATTACTGTCAACAA TATTATAGTACTCCTCGGACGTTCGGCCAAGGGACCAAGGTGGAGATC AAACGTACGGTGGCCGCTCCCTCCGTGTTCATCTTCCCACCTTCCGAC GAGCAGCTGAAGTCCGGCACCGCTTCTGTCGTGTGCCTGCTGAACAAC TTCTACCCCCGCGAGGCCAAGGTGCAGTGGAAGGTGGACAACGCCCTG CAGTCCGGCAACTCCCAGGAATCCGTGACCGAGCAGGACTCCAAGGAC AGCACCTACTCCCTGTCCTCCACCCTGACCCTGTCCAAGGCCGACTAC GAGAAGCACAAGGTGTACGCCTGCGAAGTGACCCACCAGGGCCTGTCT AGCCCCGTGACCAAGTCTTTCAACCGGGGCGAGTGT |
| 192 | Human IgG4 heavy chain constant region #1 | IGHG*01 & IGHG4*04 Heavy Chain Constant Region Nucleotide Sequence | gcttccaccaagggcccatccgtcttcccccctggcgccctgctccagg agcacctccgagagcacagccgccctgggctgcctggtcaaggactac ttccccgaaccggtgacggtgtcgtggaactcaggcgccctgaccagc ggcgtgcacaccttcccggctgtcctacagtcctcaggactctactcc ctcagcagcgtggtgaccgtgccctccagcagcttgggcacgaagacc tacacctgcaacgtagatcacaagcccagcaacaccaaggtggacaag agagttgagtccaaatatggtcccccatgcccatcatgcccagcacct gagttcctggggggaccatcagtcttcctgttccccccaaaacccaag gacactctcatgatctcccggacccctgaggtcacgtgcgtggtggtg gacgtgagccaggaagaccccgaggtccagttcaactggtacgtggat ggcgtggaggtgcataatgccaagacaaagccgcgggaggagcagttc aacagcacgtaccgtgtggtcagcgtcctcaccgtcctgcaccaggac tggctgaacggcaaggagtacaagtgcaaggtctccaacaaaggcctc ccgtcctccatcgagaaaaccatctccaaagccaaagggcagccccga gagccacaggtgtacaccctgcccccatcccaggaggagatgaccaag aaccaggtcagcctgacctgcctggtcaaaggcttctaccccagcgac atcgccgtggagtgggagagcaatgggcagccggagaacaactacaag accacgcctcccgtgctggactccgacggctccttcttcctctacagc aggctaaccgtggacaagagcaggtggcaggaggggaatgtcttctca tgctccgtgatgcatgaggctctgcacaaccactacacacagaagagc ctctccctgtctctgggtaaa |
| 193 | | Heavy Chain Constant Region Amino Acid Sequence | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPSCPAPEFLGGPSVFLFPPKPKDTLMISRTPEVTCVVV DVSQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK |

TABLE S1-continued

SEQ ID NOS: 1-342

| SEQ ID NO: | Name | Description | | Sequence |
|---|---|---|---|---|
| 194 | Human IgG4 heavy chain constant region #2 | IGHG*02 | Heavy Chain Constant Region Nucleotide Sequence | gcttccaccaagggcccatccgtcttccccctggcgccctgctccagg<br>agcacctccgagagcacagccgccctgggctgcctggtcaaggactac<br>ttccccgaaccggtgacggtgtcgtggaactcaggcgccctgaccagc<br>ggcgtgcacaccttcccggctgtcctacagtcctcaggactctactcc<br>ctcagcagcgtggtgaccgtgccctccagcagcttgggcacgaagacc<br>tacacctgcaacgtagatcacaagcccagcaacaccaaggtggacaag<br>agagttgagtccaaatatggtcccccgtgcccatcatgcccagcacct<br>gagttcctggggggaccatcagtcttcctgttccccccaaaacccaag<br>gacactctcatgatctcccggacccctgaggtcacgtgcgtggtggtg<br>gacgtgagccaggaagaccccgaggtccagttcaactggtacgtggat<br>ggcgtggaggtgcataatgccaagacaaagccgcgggaggagcagttc<br>aacagcacgtaccgtgtggtcagcgtcctcaccgtcgtgcaccaggac<br>tggctgaacggcaaggagtacaagtgcaaggtctccaacaaaggcctc<br>ccgtcctccatcgagaaaaccatctccaaagccaaagggcagccccga<br>gagccacaggtgtacaccctgcccccatcccaggaggagatgaccaag<br>aaccaggtcagcctgacctgcctggtcaaaggcttctaccccagcgac<br>atcgccgtggagtgggagagcaatgggcagccggagaacaactacaag<br>accacgcctcccgtgctggactccgacggctccttcttcctctacagc<br>aggctaaccgtggacaagagcaggtggcaggaggggaatgtcttctca<br>tgctccgtgatgcatgaggctctgcacaaccactacacgcagaagagc<br>ctctccctgtctctgggtaaa |
| 195 | | | Heavy Chain Constant Region Amino Acid Sequence | ASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVDK<br>RVESKYGPPCPSCPAPEFLGGPSVFLFPPKPKDTLMISRTPEVTCVVV<br>DVSQEDPEVQFNWYVDGVEVHNAKTKPREEQFNSTYRVVSVLTVVHQD<br>WLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYS<br>RLTVDKSRWQEGNVFSCSVMHEALHNHYTQKSLSLSLGK |
| 196 | Human IgG4 heavy chain constant region #3 | IGHG*03 | Heavy Chain Constant Region Nucleotide Sequence | gcttccaccaagggcccatccgtcttccccctggcgccctgctccagg<br>agcacctccgagagcacagccgccctgggctgcctggtcaaggactac<br>ttccccgaaccggtgacggtgtcgtggaactcaggcgccctgaccagc<br>ggcgtgcacaccttcccggctgtcctacagtcctcaggactctactcc<br>ctcagcagcgtggtgaccgtgccctccagcagcttgggcacgaagacc<br>tacacctgcaacgtagatcacaagcccagcaacaccaaggtggacaag<br>agagttgagtccaaatatggtcccccatgcccatcatgcccagcacct<br>gagttcctggggggaccatcagtcttcctgttccccccaaaacccaag<br>gacactctcatgatctcccggacccctgaggtcacgtgcgtggtggtg<br>gacgtgagccaggaagaccccgaggtccagttcaactggtacgtggat<br>ggcgtggaggtgcataatgccaagacaaagccgcgggaggagcagttc<br>aacagcacgtaccgtgtggtcagcgtcctcaccgtcctgcaccaggac<br>tggctgaacggcaaggagtacaagtgcaaggtctccaacaaaggcctc<br>ccgtcctccatcgagaaaaccatctccaaagccaaagggcagccccga<br>gagccacaggtgtacaccctgcccccatcccaggaggagatgaccaag<br>aaccaggtcagcctgacctgcctggtcaaaggcttctaccccagcgac<br>atcgccgtggagtgggagagcaatgggcagccggagaacaactacaag<br>accacgcctcccgtgctggactccgacggctccttcttcctctacagc<br>aagctcaccgtggacaagagcaggtggcaggaggggaacgtcttctca<br>tgctccgtgatgcatgaggctctgcacaaccactacacgcagaagagc<br>ctctccctgtctctgggtaaa |
| 197 | | | Heavy Chain Constant Region Amino Acid Sequence | ASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVDK<br>RVESKYGPPCPSCPAPEFLGGPSVFLFPPKPKDTLMISRTPEVTCVVV<br>DVSQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYS<br>KLTVDKSRWQEGNVFSCSVMHEALHNHYTQKSLSLSLGK |

TABLE S1-continued

SEQ ID NOS: 1-342

| SEQ ID NO: | Name | | Description | Sequence |
|---|---|---|---|---|
| 198 | IgG4 heavy chain constant region - IgG4-PE | - IgG4-PE | Heavy Chain Constant Region Nucleotide Sequence - Synthetic Version A | gcctccaccaagggcccatccgtcttccccctggcgccctgctccagg<br>agcacctccgagagcacggccgccctgggctgcctggtcaaggactac<br>ttccccgaaccagtgacggtgtcgtggaactcaggcgccctgaccagc<br>ggcgtgcacaccttcccggctgtcctacagtcctcaggactctactcc<br>ctcagcagcgtggtgaccgtgccctccagcagcttgggcacgaagacc<br>tacacctgcaacgtagatcacaagcccagcaacaccaaggtggacaag<br>agagttgagtccaaatatggtcccccatgcccaccatgcccagcgcct<br>gaatttgaggggggaccatcagtcttcctgttccccccaaaacccaag<br>gacactctcatgatctcccggacccctgaggtcacgtgcgtggtggtg<br>gacgtgagccaggaagaccccgaggtccagttcaactggtacgtggat<br>ggcgtggaggtgcataatgccaagacaaagccgcgggaggagcagttc<br>aacagcacgtaccgtgtggtcagcgtcctcaccgtcctgcaccaggac<br>tggctgaacggcaaggagtacaagtgcaaggtctccaacaaaggcctc<br>ccgtcatcgatcgagaaaaccatctccaaagccaaagggcagccccga<br>gagccacaggtgtacaccctgcccccatcccaggaggagatgaccaag<br>aaccaggtcagcctgacctgcctggtcaaaggcttctaccccagcgac<br>atcgccgtggagtgggagagcaatgggcagccggagaacaactacaag<br>accacgcctcccgtgctggactccgacggatccttcttcctctacagc<br>aggctaaccgtggacaagagcaggtggcaggaggggaatgtcttctca<br>tgctccgtgatgcatgaggctctgcacaaccactacacacagaagagc<br>ctctccctgtctctgggtaaa |
| 199 | IgG4 heavy chain constant region - IgG4-PE | | Heavy Chain Constant Region Amino Acid Sequence - Encoded by Synthetic Version A, B & C(Two residues that differ from the wild-type sequence are identified in bold) | ASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVDK<br>RVESKYGP**P**CPPCPAPEF**E**GGPSVFLFPPKPKDTLMISRTPEVTCVVV<br>DVSQEDPEVQFNWYVDGVEVHNAKTKPREEQFNSTYRVVSVLTVLHQD<br>WLNGKEYKCKVSNKGLPSSIEKTISKAKGQPREPQVYTLPPSQEEMTK<br>NQVSLTCLVKGFYPSDIAVEWESNGQPENNYKTTPPVLDSDGSFFLYS<br>RLTVDKSRWQEGNVFSCSVMHEALHNHYTQKSLSLSLGK |
| 200 | IgG4 heavy chain constant region - IgG4-PE | | Heavy Chain Constant Region Nucleotide Sequence - Synthetic Version B | Gcctccaccaagggacctagcgtgttccctctcgcccctgttccagg<br>tccacaagcgagtccaccgctgccctcggctgtctggtgaaagactac<br>tttcccgagcccgtgaccgtctcctggaatagcggagccctgacctcc<br>ggcgtgcacacatttcccgccgtgctgcagagcagcggactgtatagc<br>ctgagcagcgtggtgaccgtgcccagctccagcctcggcaccaaaacc<br>tacacctgcaacgtggaccacaagccctccaacaccaaggtggacaag<br>cgggtggagagcaagtacggcccccccttgccctccttgtcctgcccct<br>gagttcgagggaggaccctccgtgttcctgtttccccccaaacccaag<br>gacaccctgatgatctcccggacacccgaggtgacctgtgtggtcgtg<br>gacgtcagccaggaggaccccgaggtgcagttcaactggtatgtggac<br>ggcgtggaggtgcacaatgccaaaaccaagcccagggaggagcagttc<br>aattccacctacagggtggtgagcgtgctgaccgtcctgcatcaggat<br>tggctgaacggcaaggagtacaagtgcaaggtgtccaacaagggactg<br>cccagctccatcgagaagaccatcagcaaggctaagggccagccgagg<br>gagccccaggtgtataccctgcctcctagccaggaagagatgaccaag<br>aaccaagtgtccctgacctgcctggtgaagggattctacccctccgac<br>atcgccgtggagtgggagagcaatggccagcccgagaacaactacaaa<br>acaacccctcccgtgctcgatagcgacggcagcttctttctctacagc<br>cggctgacagtggacaagagcaggtggcaggagggcaacgtgttctcc<br>tgttccgtgatgcacgaggccctgcacaatcactacacccagaagagc<br>ctctccctgtccctgggcaag |

TABLE S1-continued

SEQ ID NOS: 1-342

| SEQ ID NO: | Name | Description | Sequence |
| --- | --- | --- | --- |
| 201 | IgG4 heavy chain constant region - IgG4-PE | Heavy Chain Constant Region Nucleotide Sequence - Synthetic Version C | gccagcaccaagggcccttccgtgttcccccctggccccttgcagcaggagcacctccgaatccacagctgccctgggctgtctggtgaaggactactttcccgagcccgtgaccgtgagctggaacagcggcgctctgacatccggcgtccacacctttcctgccgtcctgcagtcctccggcctctactccctgtcctccgtggtgaccgtgcctagctcctccctcggcaccaagacctacacctgtaacgtggaccacaaaccctccaacaccaaggtggacaaacgggtcgagagcaagtacggccctccctgccctccttgtcctgcccccgagttcgaaggcggacccagcgtgttcctgttccctcctaagcccaaggacaccctcatgatcagccggacacccgaggtgacctgcgtggtggtggatgtgagccaggaggaccctgaggtccagttcaactggtatgtggatggcgtggaggtgcacaacgccaagacaaagccccgggaagagcagttcaactccacctacagggtggtcagcgtgctgaccgtgctgcatcaggactggctgaacggcaaggagtacaagtgcaaggtcagcaataagggactgcccagcagcatcgagaagaccatctccaaggctaaaggccagccccgggaacctcaggtgtacaccctgcctcccagccaggaggagatgaccaagaaccaggtgagcctgacctgcctggtgaagggattctacccttccgacatcgccgtggagtgggagtccaacggccagcccgagaacaattataagaccacccctcccgtcctcgacagcgacggatccttctttctgtactccaggctgaccgtggataagtccaggtggcaggaaggcaacgtgttcagctgctccgtgatgcacgaggccctgcacaatcactacacccagaagtccctgagcctgtccctgggaaag |
| 202 | IgG4 heavy chain constant region | Heavy Chain Constant Region Nucleotide Sequence - Synthetic Version D | gcctccaccaagggcccatccgtcttcccccctggcgccctgctccaggagcacctccgagagcacggccgccctgggctgcctggtcaaggactacttccccgaaccagtgacggtgtcgtggaactcaggcgccctgaccagcggcgtgcacaccttcccggctgtcctacagtcctcaggactctactccctcagcagcgtggtgaccgtgccctccagcagcttgggcacgaagacctacacctgcaacgtagatcacaagcccagcaacaccaaggtggacaagagagttgagtccaaatatggtcccccatgcccaccatgcccagcgcctccagttgcggggggaccatcagtcttcctgttcccccccaaaacccaaggacactctcatgatctcccggacccctgaggtcacgtgcgtggtggtggacgtgagccaggaagaccccgaggtccagttcaactggtacgtggatggcgtggaggtgcataatgccaagacaaagccgcgggaggagcagttcaacagcacgtaccgtgtggtcagcgtcctcaccgtcctgcaccaggactggctgaacggcaaggagtacaagtgcaaggtctccaacaaaggcctcccgtcatcgatcgagaaaaccatctccaaagccaaagggcagccccgagagccacaggtgtacaccctgcccccatcccaggaggagatgaccaagaaccaggtcagcctgacctgcctggtcaaaggcttctaccccagcgacatcgccgtggagtgggagagcaatgggcagccggagaacaactacaagaccacgcctcccgtgctggactccgacggatccttcttcctctacagcaggctaaccgtggacaagagcaggtggcaggaggggaatgtcttctcatgctccgtgatgcatgaggctctgcacaaccactacacacagaagagcctctccctgtctctgggtaaa |
| 203 | | Heavy Chain Constant Region Amino Acid Sequence - encoded by Synthetic Version D | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPPVAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 204 | Disabled Human IgG1 heavy chain constant region | Disabled IGHG1 Heavy Chain Constant Region Nucleotide Sequence | gcctccaccaagggcccatcggtcttcccccctggcaccctcctccaagagcacctctgggggcacagcggccctgggctgcctggtcaaggactacttccccgaaccggtgacggtgtcgtggaactcaggcgccctgaccagcggcgtgcacaccttcccggctgtcctacagtcctcaggactctactccctcagcagcgtggtgaccgtgccctccagcagcttgggcacccagacctacatctgcaacgtgaatcacaagcccagcaacaccaaggtggacaagaaagtggagcccaaatcttgtgacaaaactcacacatgcccaccgtgcccagcacctgaactcgcgggggcaccgtcagtcttcctcttccccccaaaacccaaggacaccctcatgatctcccggacccctgaggtcacatgcgtggtggtggacgtgagccacgaagaccctgaggtcaagttcaactggtacgtggacggcgtggaggtgcataatgccaagacaaagccgcgggaggagcagtacaacagcacgtaccgtgtggtcagcgtcctcaccgtcctgcaccaggactggctgaatggcaaggagtacaagtgcaaggtctccaacaaagccctcccagcccccatcgagaaaaccatctccaaagccaaagggcagccccgagaaccacaggtgtacaccctgcccccatcccgggatgagctgaccaagaaccaggtcagcctgacctgcctggtcaaaggcttctatcccagcgacatcgccgtggagtgggagagcaatgggcagccggagaacaactacaagaccacgcctcccgtgctggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaa |

TABLE S1-continued

SEQ ID NOS: 1-342

| SEQ ID NO: | Name | | Description | Sequence |
|---|---|---|---|---|
| 205 | | | Heavy Chain Constant Region Amino Acid Sequence (Two residues that differ from the wild-type sequence are identified in bold) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEL**A**G**A**PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 206 | Human Cκ constant region | IGKC*01 | Cκ Light Chain Constant Region Nucleotide Sequence | cgtacggtggccgctccctccgtgttcatcttcccaccttccgacgagcagctgaagtccggcaccgcttctgtcgtgtgcctgctgaacaacttctacccccgcgaggccaaggtgcagtggaaggtggacaacgccctgcagtccggcaactcccaggaatccgtgaccgagcaggactccaaggacagcacctactccctgtcctccaccctgaccctgtccaaggccgactacgagaagcacaaggtgtacgcctgcgaagtgacccaccagggcctgtctagccccgtgaccaagtctttcaaccggggcgagtgt |
| 207 | | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 208 | Human Cκ constant region | IGKC*02 | Cκ Light Chain Constant Region Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggagagcaaggacagcacctacagcctcagcagcaccctgacgctgagcaaagcagactacgagaaacacaaagtctacgccggcgaagtcacccatcagggcctgagctcgcccgtcacaaagagcttcaacaggggagagtgt |
| 209 | | | Cκ Light Chain Constant Region Amino Acid Sequence | RTVAAPSVFIFPPSDEQLKSGTASVVCLLNNFYPREAKVQWKVDNALQSGNSQESVTEQESKDSTYSLSSTLTLSKADYEKHKVYAGEVTHQGLSSPVTKSFNRGEC |
| 210 | Human Cκ constant region | IGKC*03 | Cκ Light Chain Constant Region Nucleotide Sequence | cgaactgtggctgcaccatctgtcttcatcttcccgccatctgatgagcagttgaaatctggaactgcctctgttgtgtgcctgctgaataacttctatcccagagaggccaaagtacagcggaaggtggataacgccctccaatcgggtaactcccaggagagtgtcacagagcaggagagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgt |
| 211 | | | Cκ Light Chain Constant Region Amino Acid Sequence | RTVAAPSVFIFPPSDEQLKSGTASVVCLLNNEYPREAKVQRKVDNALQSGNSQESVTEQESKDSTYSLSSTLTLSKADYEKHKVYACEVTHQGLSSPVTKSFNRGEC |
| 212 | Human Cκ constant region | IGKC*04 | Cκ Light Chain Constant Region Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaactctacgcctgcgaagtcacccatcagggcctgagctcgcccgtcacaaagagcttcaacaggggagagtgt |
| 213 | | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC |

TABLE S1-continued

SEQ ID NOS: 1-342

| SEQ ID NO: | Name | | Description | Sequence |
|---|---|---|---|---|
| 214 | Human Cκ constant region | IGKC*05 | Cκ Light Chain Constant Region Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcaacaccctgacgctgagcaaagcagactacgagaaacacaaagtctacgcctgcgaagtcacccatcagggcctgagctcgcccgtcacaaagagcttcaacaggggagagtgc |
| 215 | | | Cκ Light Chain Constant Region Amino Acid Sequence | RTVAAPSVFIFPPSDEQLKSGTASVVCLLNNFYPREAKVQWKVDNALQSGNSQESVTEQDSKDSTYSLSNTLTLSKADYEKHKVYACEVTHQGLSSPVTKSFNRGEC |
| 216 | Human Cλ constant region | IGCλ1*01 | Cλ Light Chain Constant Region Nucleotide Sequence | cccaaggccaaccccacggtcactctgttcccgccctcctctgaggagctccaagccaacaaggccacactagtgtgtctgatcagtgacttctacccgggagctgtgacagtggcttggaaggcagatggcagccccgtcaaggcgggagtggagacgaccaaaccctccaaacagagcaacaacaagtacgcggccagcagctacctgagcctgacgcccgagcagtggaagtcccacagaagctacagctgccaggtcacgcatgaagggagcaccgtggagaagacagtggcccctacagaatgttca |
| 217 | | | Cλ Light Chain Constant Region Amino Acid Sequence | PKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| 218 | Human Cλ constant region | IGCλ1*02 | Cλ Light Chain Constant Region Nucleotide Sequence | ggtcagcccaaggccaaccccactgtcactctgttcccgccctcctctgaggagctccaagccaacaaggccacactagtgtgtctgatcagtgacttctacccgggagctgtgacagtggcctggaaggcagatggcagccccgtcaaggcgggagtggagaccaccaaaccctccaaacagagcaacaacaagtacgcggccagcagctacctgagcctgacgcccgagcagtggaagtcccacagaagctacagctgccaggtcacgcatgaagggagcaccgtggagaagacagtggcccctacagaatgttca |
| 219 | | | Cλ Light Chain Constant Region Amino Acid Sequence | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| 220 | Human Cλ constant region | IGCλ2*01 | Cλ Light Chain Constant Region Nucleotide Sequence - Version A | ggtcagcccaaggccaaccccactgtcactctgttcccgccctcctctgaggagctccaagccaacaaggccacactagtgtgtctgatcagtgacttctacccgggagctgtgacagtggcctggaaggcagatggcagccccgtcaaggcgggagtggagaccaccaaaccctccaaacagagcaacaacaagtacgcggccagcagctacctgagcctgacgcccgagcagtggaagtcccacagaagctacagctgccaggtcacgcatgaagggagcaccgtggagaagacagtggcccctacagaatgttca |
| 221 | | | Cλ Light Chain Constant Region Nucleotide Sequence - Version B | ggccagcctaaggccgctccttctgtgaccctgttcccccccatcctccgaggaactgcaggctaacaaggccaccctcgtgtgcctgatcagcgacttctaccctggcgccgtgaccgtggcctggaaggctgatagctctcctgtgaaggccggcgtggaaaccaccaccccttccaagcagtccaacaacaaatacgccgcctcctcctacctgtccctgacccctgagcagtggaagtcccaccggtcctacagctgccaagtgacccacgagggctccaccgtggaaaagaccgtggctcctaccgagtgctcc |
| 222 | | | Cλ Light Chain Constant Region Nucleotide Sequence - Version C | ggccagcctaaagctgcccccagcgtcaccctgtttcctccctccagcgaggagctccaggccaacaaggccaccctcgtgtgcctgatctccgacttctatcccggcgctgtgaccgtggcttggaaagccgactccagccctgtcaaagccggcgtggagaccaccacaccctccaagcagtccaacaacaagtacgccgcctccagctatctctccctgacccctgagcagtggaagtcccaccggtcctactcctgtcaggtgacccacgagggctccaccgtggaaaagaccgtcgcccccaccgagtgctcc |
| 223 | | | Cλ Light Chain Constant Region Amino Acid Sequence - Encoded by Version A, B & C | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |

TABLE S1-continued

SEQ ID NOS: 1-342

| SEQ ID NO: | Name | | Description | Sequence |
|---|---|---|---|---|
| 224 | Human Cλ constant region | IGCλ2*02 & IGLC2*03 | Cλ Light Chain Constant Region Nucleotide Sequence | ggtcagcccaaggctgccccctcggtcactctgttcccgccctcctct gaggagcttcaagccaacaaggccacactggtgtgtctcataagtgac ttctacccgggagccgtgacagtggcctggaaggcagatagcagcccc gtcaaggcgggagtggagaccaccacaccctccaaacaaagcaacaac aagtacgcggccagcagctatctgagcctgacgcctgagcagtggaag tcccacagaagctacagctgccaggtcacgcatgaagggagcaccgtg gagaagacagtggcccctacagaatgttca |
| 225 | | | Cλ Light Chain Constant Region Amino Acid Sequence | GQPKAAPSVTLFPPSSEELQANKATLVCLISDFYPGAVTVAWKADSSP VKAGVETTTPSKQSNNKYAASSYLSLTPEQWKSHRSYSCQVTHEGSTV EKTVAPTECS |
| 226 | Human Cλ constant region | IGCλ3*01 | Cλ Light Chain Constant Region Nucleotide Sequence | cccaaggctgccccctcggtcactctgttcccaccctcctctgaggag cttcaagccaacaaggccacactggtgtgtctcataagtgacttctac ccgggagccgtgacagttgcctggaaggcagatagcagccccgtcaag gcgggggtggagaccaccacaccctccaaacaaagcaacaacaagtac gcggccagcagctacctgagcctgacgcctgagcagtggaagtcccac aaaagctacagctgccaggtcacgcatgaagggagcaccgtggagaag acagttgcccctacggaatgttca |
| 227 | | | Cλ Light Chain Constant Region Amino Acid Sequence | PKAAPSVTLFPPSSEELQANKATLVCLISDFYPGAVTVAWKADSSPVK AGVETTTPSKQSNNKYAASSYLSLTPEQWKSHKSYSCQVTHEGSTVEK TVAPTECS |
| 228 | Human Cλ constant region | IGCλ3*02 | Cλ Light Chain Constant Region Nucleotide Sequence | ggtcagcccaaggctgccccctcggtcactctgttcccaccctcctct gaggagcttcaagccaacaaggccacactggtgtgtctcataagtgac ttctacccggggccagtgacagttgcctggaaggcagatagcagcccc gtcaaggcgggggtggagaccaccacaccctccaaacaaagcaacaac aagtacgcggccagcagctacctgagcctgacgcctgagcagtggaag tcccacaaaagctacagctgccaggtcacgcatgaagggagcaccgtg gagaagacagtggcccctacggaatgttca |
| 229 | | | Cλ Light Chain Constant Region Amino Acid Sequence | GQPKAAPSVTLFPPSSEELQANKATLVCLISDFYPGPVTVAWKADSSP VKAGVETTTPSKQSNNKYAASSYLSLTPEQWKSHKSYSCQVTHEGSTV EKTVAPTECS |
| 230 | Human Cλ constant region | IGCλ3*03 | Cλ Light Chain Constant Region Nucleotide Sequence | ggtcagcccaaggctgccccctcggtcactctgttcccaccctcctct gaggagcttcaagccaacaaggccacactggtgtgtctcataagtgac ttctacccgggagccgtgacagtggcctggaaggcagatagcagcccc gtcaaggcgggagtggagaccaccacaccctccaaacaaagcaacaac aagtacgcggccagcagctacctgagcctgacgcctgagcagtggaag tcccacaaaagctacagctgccaggtcacgcatgaagggagcaccgtg gagaagacagtggcccctacagaatgttca |
| 231 | | | Cλ Light Chain Constant Region Amino Acid Sequence | GQPKAAPSVTLFPPSSEELQANKATLVCLISDFYPGAVTVAWKADSSP VKAGVETTTPSKQSNNKYAASSYLSLTPEQWKSHKSYSCQVTHEGSTV EKTVAPTECS |
| 232 | Human Cλ constant region | IGCλ3*04 | Cλ Light Chain Constant Region Nucleotide Sequence | ggtcagcccaaggctgccccctcggtcactctgttcccgccctcctct gaggagcttcaagccaacaaggccacactggtgtgtctcataagtgac ttctacccgggagccgtgacagtggcctggaaggcagatagcagcccc gtcaaggcgggagtggagaccaccacaccctccaaacaaagcaacaac aagtacgcggccagcagctacctgagcctgacgcctgagcagtggaag tcccacagaagctacagctgccaggtcacgcatgaagggagcaccgtg gagaagacagtggcccctacagaatgttca |
| 233 | | | Cλ Light Chain Constant Region Amino Acid Sequence | GQPKAAPSVTLFPPSSEELQANKATLVCLISDFYPGAVTVAWKADSSP VKAGVETTTPSKQSNNKYAASSYLSLTPEQWKSHRSYSCQVTHEGSTV EKTVAPTECS |

TABLE S1-continued

SEQ ID NOS: 1-342

| SEQ ID NO: | Name | Description | | Sequence |
|---|---|---|---|---|
| 234 | Human Cλ constant region | IGCλ6*01 | Cλ Light Chain Constant Region Nucleotide Sequence | ggtcagcccaaggctgccccatcggtcactctgttcccgccctcctct gaggagcttcaagccaacaaggccacactggtgtgcctgatcagtgac ttctacccgggagctgtgaaagtggcctggaaggcagatggcagcccc gtcaacacgggagtggagaccaccacaccctccaaacagagcaacaac aagtacgcggccagcagctacctgagcctgacgcctgagcagtggaag tcccacagaagctacagctgccaggtcacgcatgaagggagcaccgtg gagaagacagtggcccctgcagaatgttca |
| 235 | | | Cλ Light Chain Constant Region Amino Acid Sequence | GQPKAAPSVTLFPPSSEELQANKATLVCLISDFYPGAVKVAWKADGSP VNTGVETTTPSKQSNNKYAASSYLSLTPEQWKSHRSYSCQVTHEGSTV EKTVAPAECS |
| 236 | Human Cλ constant region | IGLC7*01 & IGCλ7*02 | Cλ Light Chain Constant Region Nucleotide Sequence | ggtcagcccaaggctgccccatcggtcactctgttcccaccctcctct gaggagcttcaagccaacaaggccacactggtgtgtctcgtaagtgac ttctacccgggagccgtgacagtggcctggaaggcagatggcagcccc gtcaaggtgggagtggagaccaccaaaccctccaaacaaagcaacaac aagtatgcggccagcagctacctgagcctgacgcccgagcagtggaag tcccacagaagctacagctgccgggtcacgcatgaagggagcaccgtg gagaagacagtggcccctgcagaatgctct |
| 237 | | | Cλ Light Chain Constant Region Amino Acid Sequence | GQPKAAPSVTLFPPSSEELQANKATLVCLVSDFYPGAVTVAWKADGSP VKVGVETTKPSKQSNNKYAASSYLSLTPEQWKSHRSYSCRVTHEGSTV EKTVAPAECS |
| 238 | 413G05 - CDRH1 (IMGT) | Amino acid sequence of CDRH1 of 413G05 using IMGT | | GFTFSDYY |
| 239 | 413G05 - CDRH2 (IMGT) | Amino acid sequence of CDRH2 of 413G05 using IMGT | | ISTSGSTI |
| 240 | 413G05 - CDRH3 (IMGT) | Amino acid sequence of CDRH3 of 413G05 using IMGT | | ARGITGTNFYHYGLGV |
| 241 | 413G05 - CDRH1 (Kabat) | Amino acid sequence of CDRH1 of 413G05 using Kabat | | DYYMS |
| 242 | 413G05 - CDRH2 (Kabat) | Amino acid sequence of CDRH2 of 413G05 using Kabat | | YISTSGSTIYYADSVKG |
| 243 | 413G05 - CDRH3 (Kabat) | Amino acid sequence of CDRH3 of 413G05 using Kabat | | GITGTNFYHYGLGV |
| 244 | 413G05 - Heavy chain variable region | Amino acid sequence of $V_H$ of 413G05 | | QVQLVESGGGLVKPGGSLRLSCAASGFTFSDYYMSWIRQVPGKGLEWV SYISTSGSTIYYADSVKGRFTISRDNAKNSLYLQMNSLRAEDAAVYHC ARGITGTNFYHYGLGVWGQGTTVTVSS |
| 245 | 413G05 - Heavy chain variable region | Nucleic acid sequence of $V_H$ of 413G05 | | CAGGTGCAGCTGGTGGAGTCTGGGGGAGGCTTGGTCAAGCCTGGAGGG TCCCTGAGACTCTCCTGTGCAGCCTCTGGATTCACCTTCAGTGACTAC TACATGAGCTGGATCCGCCAGGTTCCAGGGAAGGGGCTGGAGTGGGTT TCATACATTAGTACTAGTGGTAGTACCATATACTACGCAGACTCTGTG AAGGGCCGATTCACCATCTCCAGGGACAACGCCAAGAACTCACTGTAT CTACAAATGAACAGCCTGAGAGCCGAGGACGCGGCCGTGTATCACTGT GCGAGAGGTATAACTGGAACTAACTTCTACCACTACGGTTTGGGCGTC TGGGGCCAAGGGACCACGGTCACCGTCTCCTCAG |

TABLE S1-continued

SEQ ID NOS: 1-342

| SEQ ID NO: | Name | Description | Sequence |
|---|---|---|---|
| 246 | 413G05 - full heavy chain sequence | Amino acid sequence of 413G05 heavy chain | QVQLVESGGGLVKPGGSLRLSCAASGFTFSDYYMSWIRQVPGKGLEWVSYISTSGSTIYYADSVKGRFTISRDNAKNSLYLQMNSLRAEDAAVYHCARGITGTNFYHYGLGVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 247 | 413G05 - full heavy chain sequence | Nucleic acid sequence of 413G05 heavy chain | CAGGTGCAGCTGGTGGAGTCTGGGGGAGGCTTGGTCAAGCCTGGAGGGTCCCTGAGACTCTCCTGTGCAGCCTCTGGATTCACCTTCAGTGACTACTACATGAGCTGGATCCGCCAGGTTCCAGGGAAGGGGCTGGAGTGGGTTTCATACATTAGTACTAGTGGTAGTACCATATACTACGCAGACTCTGTGAAGGGCCGATTCACCATCTCCAGGGACAACGCCAAGAACTCACTGTATCTACAAATGAACAGCCTGAGAGCCGAGGACGCGGCCGTGTATCACTGTGCGAGAGGTATAACTGGAACTAACTTCTACCACTACGGTTTGGGCGTCTGGGGCCAAGGGACCACGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 248 | 413G05 - CDRL1 (IMGT) | Amino acid sequence of CDRL1 of 413G05 using IMGT | QGINSW |
| 249 | 413G05 - CDRL2 (IMGT) | Amino acid sequence of CDRL2 of 413G05 using IMGT | AAS |
| 250 | 413G05 - CDRL3 (IMGT) | Amino acid sequence of CDRL3 of 413G05 using IMGT | QQVNSFPLT |
| 251 | 413G05 - CDRL1 (Kabat) | Amino acid sequence of CDRL1 of 413G05 using Kabat | RASQGINSWLA |
| 252 | 413G05 - CDRL2 (Kabat) | Amino acid sequence of CDRL2 of 413G05 using Kabat | AASTLQS |
| 253 | 413G05 - CDRL3 (Kabat) | Amino acid sequence of CDRL3 of 413G05 using Kabat | QQVNSFPLT |
| 254 | 413G05 - Light chain variable region | Amino acid sequence of $V_L$ of 413G05 | DIQMTQSPSSVSASVGDRVTITCRASQGINSWLAWYQQKPGKAPKLLIYAASTLQSGVPSRFSGSGSGADFTLTISSLQPEDFATYYCQQVNSFPLTFGGGTKVEIK |

TABLE S1-continued

| SEQ ID NO:Name | Description | Sequence |
|---|---|---|
| 255413G05 - Light chain variable region | Nucleic acid sequence of $V_L$ of 413G05 | GACATCCAGATGACCCAGTCTCCATCTTCCGTGTCTGCATCTGTAGGAGACAGAGTCACCATCACTTGTCGGGCGAGTCAGGGTATTAACAGCTGGTTAGCCTGGTATCAGCAGAAACCAGGGAAAGCCCCTAAGCTCCTGATCTATGCTGCATCCACTTTGCAAAGTGGGGTCCCATCAAGGTTCAGCGGCAGTGGGTCTGGGGCAGATTTCACTCTCACCATCAGCAGCCTGCAGCCTGAAGATTTTGCAACTTACTATTGTCAACAGGTTAACAGTTTCCCGCTCACTTTCGGCGGAGGGACCAAGGTGGAGATCAAAC |
| 256413G05 - full light chain sequence | Amino acid sequence of 413G05 light chain | DIQMTQSPSSVSASVGDRVTITCRASQGINSWLAWYQQKPGKAPKLLIYAASTLQSGVPSRFSGSGSGADFTLTISSLQPEDFATYYCQQVNSFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 257413G05 - full light chain sequence | Nucleic acid sequence of 413G05 light chain | GACATCCAGATGACCCAGTCTCCATCTTCCGTGTCTGCATCTGTAGGAGACAGAGTCACCATCACTTGTCGGGCGAGTCAGGGTATTAACAGCTGGTTAGCCTGGTATCAGCAGAAACCAGGGAAAGCCCCTAAGCTCCTGATCTATGCTGCATCCACTTTGCAAAGTGGGGTCCCATCAAGGTTCAGCGGCAGTGGGTCTGGGGCAGATTTCACTCTCACCATCAGCAGCCTGCAGCCTGAAGATTTTGCAACTTACTATTGTCAACAGGTTAACAGTTTCCCGCTCACTTTCGGCGGAGGGACCAAGGTGGAGATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 258413F09 - CDRH1 (IMGT) | Amino acid sequence of CDRH1 of 413F09 using IMGT | GFTFSYYA |
| 259413F09 - CDRH2 (IMGT) | Amino acid sequence of CDRH2 of 413F09 using IMGT | ISGGGGNT |
| 260413F09 - CDRH3 (IMGT) | Amino acid sequence of CDRH3 of 413F09 using IMGT | AKDRMKQLVRAYYFDY |
| 261413F09 - CDRH1 (Kabat) | Amino acid sequence of CDRH1 of 413F09 using Kabat | YYAMS |
| 262413F09 - CDRH2 (Kabat) | Amino acid sequence of CDRH2 of 413F09 using Kabat | TISGGGGNTHYADSVKG |
| 263413F09 - CDRH3 (Kabat) | Amino acid sequence of CDRH3 of 413F09 using Kabat | DRMKQLVRAYYFDY |
| 264413F09 - Heavy chain variable region | Amino acid sequence of $V_H$ of 413F09 | EVPLVESGGGLVQPGGSLRLSCAASGFTFSYYAMSWVRQAPGKGLDWVSTISGGGGNTHYADSVKGRFTISRDNSKNTLYLHMNSLRAEDTAVYYCAKDRMKQLVRAYYFDYWGQGTLVTVSS |
| 265413F09 - Heavy chain variable region | Nucleic acid sequence of $V_H$ of 413F09 | GAGGTGCCGCTGGTGGAGTCTGGGGGAGGCTTGGTACAGCCTGGGGGGTCCCTGAGACTCTCCTGTGCAGCCTCTGGATTCACGTTTAGCTACTATGCCATGAGCTGGGTCCGTCAGGCTCCAGGGAAGGGGCTGGACTGGGTCTCAACTATTAGTGGTGGTGGTGGTAACACACACTACGCAGACTCCGTGAAGGGCCGATTCACTATATCCAGAGACAATTCCAAGAACACGCTGTATCTGCACATGAACAGCCTGAGAGCCGAAGACACGGCCGTCTATTACTGTGCGAAGGATCGGATGAAACAGCTCGTCCGGGCCTACTACTTTGACTACTGGGGCCAGGGAACCCTGGTCACCGTCTCCTCAG |

TABLE S1-continued

| SEQ ID NO: Name | Description | Sequence |
|---|---|---|
| 266 413F09 - full heavy chain sequence | Amino acid sequence of 413F09 heavy chain | EVPLVESGGGLVQPGGSLRLSCAASGFTFSYYAMSWVRQAPGKGLDWVSTISGGGGNTHYADSVKGRFTISRDNSKNTLYLHMNSLRAEDTAVYYCAKDRMKQLVRAYYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 267 413F09 - full heavy chain sequence | Nucleic acid sequence of 413F09 heavy chain | GAGGTGCCGCTGGTGGAGTCTGGGGGAGGCTTGGTACAGCCTGGGGGGTCCCTGAGACTCTCCTGTGCAGCCTCTGGATTCACGTTTAGCTACTATGCCATGAGCTGGGTCCGTCAGGCTCCAGGGAAGGGGCTGGACTGGGTCTCAACTATTAGTGGTGGTGGTGGTAACACACACTACGCAGACTCCGTGAAGGGCCGATTCACTATATCCAGAGACAATTCCAAGAACACGCTGTATCTGCACATGAACAGCCTGAGAGCCGAAGACACGGCCGTCTATTACTGTGCGAAGGATCGGATGAAACAGCTCGTCCGGGCCTACTACTTTGACTACTGGGGCCAGGGAACCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 268 413F09 - CDRL1 (IMGT) | Amino acid sequence of CDRL1 of 413F09 using IMGT | QDISTY |
| 269 413F09 - CDRL2 (IMGT) | Amino acid sequence of CDRL2 of 413F09 using IMGT | GTS |
| 270 413F09 - CDRL3 (IMGT) | Amino acid sequence of CDRL3 of 413F09 using IMGT | QQLHTDPIT |
| 271 413F09 - CDRL1 (Kabat) | Amino acid sequence of CDRL1 of 413F09 using Kabat | WASQDISTYLG |
| 272 413F09 - CDRL2 (Kabat) | Amino acid sequence of CDRL2 of 413F09 using Kabat | GTSSLQS |
| 273 413F09 - CDRL3 (Kabat) | Amino acid sequence of CDRL3 of 413F09 using Kabat | QQLHTDPIT |
| 274 413F09 - Light chain variable region | Amino acid sequence of $V_L$ of 413F09 | DIQLTQSPSFLSASVGDRVTITCWASQDISTYLGWYQQKPGKAPKLLIYGTSSLQSGVPSRFSGSGSGTEFTLTISSLQPEDFATYYCQQLHTDPITFGQGTRLEIK |

TABLE S1-continued

SEQ ID NOS: 1-342

| SEQ ID NO:Name | Description | Sequence |
|---|---|---|
| 275413F09 - Light chain variable region | Nucleic acid sequence of $V_L$ of 413F09 | GACATCCAGTTGACCCAGTCTCCATCCTTCCTGTCTGCATCTGTAGGAGACAGAGTCACCATCACTTGCTGGGCCAGTCAGGACATTAGCACTTATTTAGGCTGGTATCAGCAAAAACCAGGGAAAGCCCCTAAGCTCCTGATCTATGGTACATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCAACAGCTTCATACTGACCCGATCACCTTCGGCCAAGGGACACGACTGGAGATCAAAC |
| 276413F09 - full light chain sequence | Amino acid sequence of 413F09 light chain | DIQLTQSPSFLSASVGDRVTITCWASQDISTYLGWYQQKPGKAPKLLIYGTSSLQSGVPSRFSGSGSGTEFTLTISSLQPEDFATYYCQQLHTDPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 277413F09 - full light chain sequence | Nucleic acid sequence of 413F09 light chain | GACATCCAGTTGACCCAGTCTCCATCCTTCCTGTCTGCATCTGTAGGAGACAGAGTCACCATCACTTGCTGGGCCAGTCAGGACATTAGCACTTATTTAGGCTGGTATCAGCAAAAACCAGGGAAAGCCCCTAAGCTCCTGATCTATGGTACATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCAACAGCTTCATACTGACCCGATCACCTTCGGCCAAGGGACACGACTGGAGATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 278414806 - CDRH1 (IMGT) | Amino acid sequence of CDRH1 of 414B06 using IMGT | GFTFSSYW |
| 279414B06 - CDRH2 (IMGT) | Amino acid sequence of CDRH2 of 414B06 using IMGT | IKQDGSEK |
| 280414B06 - CDRH3 (IMGT) | Amino acid sequence of CDRH3 of 414B06 using IMGT | ARVRQWSDYSDY |
| 281414B06 - CDRH1 (Kabat) | Amino acid sequence of CDRH1 of 414B06 using Kabat | SYWMN |
| 282414B06 - CDRH2 (Kabat) | Amino acid sequence of CDRH2 of 414B06 using Kabat | NIKQDGSEKYYVDSVKG |
| 283414B06 - CDRH3 (Kabat) | Amino acid sequence of CDRH3 of 414B06 using Kabat | VRQWSDYSDY |
| 284414B06 - Heavy chain variable region | Amino acid sequence of $V_H$ of 414B06 | EVHLVESGGGLVQPGGSLRLSCAASGFTFSSYWMNWVRQAPGKGLEWVANIKQDGSEKYYVDSVKGRFTVSRDNAKNSLYLQMNSLRAEDTAVYYCARVRQWSDYSDYWGQGTPVTVSS |
| 285414B06 - Heavy chain variable region | Nucleic acid sequence of $V_H$ of 414B06 | GAGGTGCACCTGGTGGAGTCTGGGGGAGGCTTGGTCCAGCCTGGGGGGTCCCTGAGACTCTCCTGTGCAGCCTCTGGATTCACCTTTAGTAGCTATTGGATGAACTGGGTCCGCCAGGCTCCAGGGAAGGGGCTGGAGTGGGTGGCCAACATAAAGCAAGATGGAAGTGAGAAATACTATGTGGACTCTGTGAAGGGCCGCTTCACCGTCTCCAGAGACAACGCCAAGAACTCACTGTATCTGCAAATGAACAGCCTGAGAGCCGAGGACACGGCTGTGTATTACTGTGCGAGAGTTCGACAATGGTCCGACTACTCTGACTACTGGGGCCAGGGAACCCCGGTCACCGTCTCCTCAG |

TABLE S1-continued

| SEQ ID NO: | Name | Description | Sequence |
|---|---|---|---|
| | | SEQ ID NOS: 1-342 | |
| 286 | 414B06 - full heavy chain sequence | Amino acid sequence of 414B06 heavy chain | EVHLVESGGGLVQPGGSLRLSCAASGFTFSSYWMNWVRQAPGKGLEWVANIKQDGSEKYYVDSVKGRFTVSRDNAKNSLYLQMNSLRAEDTAVYYCARVRQWSDYSDYWGQGTPVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 287 | 414B06 - full heavy chain sequence | Nucleic acid sequence of 414B06 heavy chain | GAGGTGCACCTGGTGGAGTCTGGGGGAGGCTTGGTCCAGCCTGGGGGGTCCCTGAGACTCTCCTGTGCAGCCTCTGGATTCACCTTTAGTAGCTATTGGATGAACTGGGTCCGCCAGGCTCCAGGGAAGGGGCTGGAGTGGGTGGCCAACATAAAGCAAGATGGAAGTGAGAAATACTATGTGGACTCTGTGAAGGGCCGCTTCACCGTCTCCAGAGACAACGCCAAGAACTCACTGTATCTGCAAATGAACAGCCTGAGAGCCGAGGACACGGCTGTGTATTACTGTGCGAGAGTTCGACAATGGTCCGACTACTCTGACTACTGGGGCCAGGGAACCCCGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAG |
| 288 | 414B06 - CDRL1 (IMGT) | Amino acid sequence of CDRL1 of 414B06 using IMGT | QGISSW |
| 289 | 414B06 - CDRL2 (IMGT) | Amino acid sequence of CDRL2 of 414B06 using IMGT | AAS |
| 290 | 414306 - CDRL3 (IMGT) | Amino acid sequence of CDRL3 of 414B06 using IMGT | QQANSFPFT |
| 291 | 414306 - CDRL1 (Kabat) | Amino acid sequence of CDRL1 of 414B06 using Kabat | RASQGISSWLA |
| 292 | 414B06 - CDRL2 (Kabat) | Amino acid sequence of CDRL2 of 414B06 using Kabat | AASSLQS |
| 293 | 414B06 - CDRL3 (Kabat) | Amino acid sequence of CDRL3 of 414B06 using Kabat | QQANSFPFT |
| 294 | 414306 - Light chain variable region | Amino acid sequence of $V_L$ of 414B06. | DIQMTQSPSSVSASVGDRVTITCRASQGISSWLAWYQQKPGKAPKLLIYAASSLQSGVPSRFSGSGSGTDFTLTISSLQPEDFATYYCQQANSFPFTFGPGTKVDIK |

TABLE S1-continued

SEQ ID NOS: 1-342

| SEQ ID NO: | Name | Description | Sequence |
|---|---|---|---|
| 295 | 414B06 - Light chain variable region | Nucleic acid sequence of $V_L$ of 414B06 | GACATCCAGATGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTATTGTCAACAGGCTAACAGTTTCCCATTCACTTTCGGCCCTGGGACCAAAGTGGATATCAAAC |
| 296 | 414B06 - full light chain sequence | Amino acid sequence of 414B06 light chain | DIQMTQSPSSVSASVGDRVTITCRASQGISSWLAWYQQKPGKAPKLLIYAASSLQSGVPSRFSGSGSGTDFTLTISSLQPEDFATYYCQQANSFPFTFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 297 | 414B06 - full light chain sequence | Nucleic acid sequence of 414B06 light chain | GACATCCAGATGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTATTGTCAACAGGCTAACAGTTTCCCATTCACTTTCGGCCCTGGGACCAAAGTGGATATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 298 | Mutated 1D05 - LC mutant 3 | Amino acid sequence of 1D05 kappa light chain with V to Y mutation in CDRL2 highlighted | DIQMTQSPSSLSASVGDRVTITCRASQSISSYLNWYQQKPGKAPKLLIY**Y**ASSLQSGVPSRFSGSGSGTDFTLTISSLQPEDFATYYCQQSYSTPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 299 | 1D05 - heavy chain disabled IgG1 Fc | Amino acid sequence of IgG1 disabled variant of 1D05 | EVQLVESGGGLVQPGRSLRLSCAASGFTFDDYAMHWVRQVPGKGLEWVSGISWIRTGIGYADSVKGRFTIFRDNAKNSLYLQMNSLRAEDTALYYCAKDMKGSGTYGGWFDTWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPE**LAGA**PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 300 | 1D05 - light chain IL-2 fusion | 1D05 Light chain sequence fused to wild-type human IL-2 sequence (IL-2 amino acid sequence is underlined and region to be varied is shown in bold) | DIQMTQSPSSLSASVGDRVTITCRASQSISSYLNWYQQKPGKAPKLLIYVASSLQSGVPSRFSGSGSGTDFTLTISSLQPEDFATYYCQQSYSTPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**APTSSSTKKTQLQLEHLLLD**LQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| 301 | Human IL-2 | Uniprot number: P60568 Full length amino acid sequence of human IL-2 (minus signal sequence) | **APTSSSTKKTQLQLEHLLLD**LQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |

TABLE S1-continued

SEQ ID NOS: 1-342

| SEQ ID NO: | Name | Description | Sequence |
|---|---|---|---|
| 302 | Control 1D05 immunocytokine HC C-terminal fusion | Heavy chain 1D05 IgG1 variant fused at the N-terminus to wild-type human IL2 sequence (control) | EVQLVESGGGLVQPGRSLRLSCAASGFTFDDYAMHWVRQVPGKGLEWVSGISWIRTGIGYADSVKGRFTIFRDNAKNSLYLQMNSLRAEDTALYYCAKDMKGSGTYGGWFDTWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPE**LAGA**PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKAPTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| 303 | IL-2 D5-9 | IL-2 IC45 (Del 5-9) N terminal IL-2 sequence | **APTSTQLQLELLLD** |
| 304 | IL-2 D1-9 | IL-2 IC46 (Del 1-9) N terminal IL-2 sequence | **TQLQLEHLLLD** |
| 305 | IL-2 D5-7 | IL-2 IC64 (Del 5-7) N terminal IL-2 sequence | **APTSKKTQLQLEHLLLD** |
| 306 | IL-2 D1 | IL-2 D1 N terminal IL-2 sequence | **PTSSSTKKTQLQLEHLLLD** |
| 307 | IL-2 D1-2 | IL-2 D1-2 N terminal IL-2 sequence | **TSSSTKKTQLQLEHLLLD** |
| 308 | IL-2 D1-3 | IL-2 D1-3 N terminal IL-2 sequence | **SSSTKKTQLQLEHLLLD** |
| 309 | IL-2 D1-4 | IL-2 D1-4 N terminal IL-2 sequence | **SSTKKTQLQLEHLLLD** |
| 310 | IL-2 D1-5 | IL-2 D1-5 N terminal IL-2 sequence | **STKKTQLQLEHLLLD** |
| 311 | IL-2 D1-6 | IL-2 D1-6 N terminal IL-2 sequence | **TKKTQLQLEHLLLD** |
| 312 | IL-2 D1-7 | IL-2 D1-7 N terminal IL-2 sequence | **KKTQLQLEHLLLD** |
| 313 | IL-2 D1-8 | IL-2 D1-8 N terminal IL-2 sequence | **KTQLQLEHLLLD** |
| 314 | IL-2 D9 | IL-2 D9 N terminal IL-2 sequence | **APTSSSTKTQLQLEHLLLD** |
| 315 | IL-2 D9-8 | IL-2 D9-8 N terminal IL-2 sequence | **APTSSSTTQLQLEHLLLD** |
| 316 | IL-2 D9-7 | IL-2 D9-7 N terminal IL-2 sequence | **APTSSSTQLQLEHLLLD** |
| 317 | IL-2 D9-6 | IL-2 D9-6 N terminal IL-2 sequence | **APTSSTQLQLEHLLLD** |

TABLE S1-continued

SEQ ID NOS: 1-342

| SEQ ID NO: | Name | Description | Sequence |
|---|---|---|---|
| 318 | IL-2 D9-4 | IL-2 D9-4 N terminal IL-2 sequence | **APTTQLQLEHLLLD** |
| 319 | IL-2 D9-3 | IL-2 D9-3 N terminal IL-2 sequence | **APTQLQLEHLLLD** |
| 320 | IL-2 D9-2 | IL-2 D9-2 N terminal IL-2 sequence | **ATQLQLEHLLLD** |
| 321 | IL-2 D2-6 | IL-2 D2-6 N terminal IL-2 sequence | **ATKKTQLQLEHLLLD** |
| 322 | IL-2 D3-7 | IL-2 D3-7 N terminal IL-2 sequence | **APKKTQLQLEHLLLD** |
| 323 | IL-2 D4-8 | IL-2 D4-8 N terminal IL-2 sequence | **APTKTQLQLEHLLLD** |
| 324 | C-terminal amino acid sequence of hIL-2 | Amino acids 21 to 133 of hIL-2 | LQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT |
| 325 | Mouse PD-L1 | Uniprot number: Q9EP73 (ECD highlighted in BOLD, and cytoplasmic domain underlined) | MRIFAGIIFTACCHLLRA**FTITAPEDLYVVEYGSNVTMECRFPVERELDLLALVVYWEKEDEQVIQFVAGEEDLKPQHSNFRGRASLPKDQLLKGNAALQITDVKLQDAGVYCCIISYGGADYKRITLEVNAPYRKINQRISVDPATSEHELICQAEGYPEAEVIWTNSDHQPVSGKRSVTTSRTEGMLLNVTSSLRVNATANDVFYCTFWRSQPGQNHTAELIIPELPATHPPQNRT**HWVLLGSILLFLIVVSTVLLFLRKQVRMLDVEKCGVEDTSSKNRNDTQFEET |
| 326 | Mouse PD-L1 ECD His | Mouse PD-L1 extracellular domain with his tag | FTITAPKDLYVVEYGSNVTMECRFPVERELDLLALVVYWEKEDEQVIQFVAGEEDLKPQHSNFRGRASLPKDQLLKGNAALQITDVKLQDAGVYCCIISYGGADYKRITLKVNAPYRKINQRISVDPATSEHELICQAEGYPEAEVIWTNSDHQPVSGKRSVTTSRTEGMLLNVTSSLRVNATANDVFYCTFWRSQPGQNHTAELIIPELPATHPPQNRT**HHHHHH** |
| 327 | Human IL-2Rα chain | Human IL-2 receptor alpha chain | ELCDDDPPEIPHATFKAMAYKEGTMLNCECKRGFRRIKSGSLYMLCTGNSSHSSWDNQCQCTSSATRNTTKQVTPQPEEQKERKTTEMQSPMQPVDQASLPGHCREPPPWENEATERIYHFVVGQMVYYQCVQGYRALHRGPAESVCKMTHGKTRWTQPQLICTGEMETSQFPGEEKPQASPEGRPESETSCLVTTTDFQIQTEMAATMETSIFTTEYQVAVAGCVFLLISVLLLSGLTWQRRQRKSRRTI |
| 328 | Human IL-2Rβ chain | Human IL-2 receptor beta chain | AVNGTSQFTCFYNSRANISCVWSQDGALQDTSCQVHAWPDRRRWNQTCELLPVSQASWACNLILGAPDSQKLTTVDIVTLRVLCREGVRWRVMAIQDFKPFENLRLMAPISLQVVHVETHRCNISWEISQASHYFERHLEFEARTLSPGHTWEEAPLLTLKQKQEWICLETLTPDTQYEFQVRVKPLQGEFTTWSPWSQPLAFRTKPAALGKDTIPWLGHLLVGLSGAFGFIILVYLLINCRNTGPWLKKVLKCNTPDPSKFFSQLSSEHGGDVQKWLSSPFPSSSFSPGGLAPEISPLEVLERDKVTQLLLQQDKVPEPASLSSNHSLTSCFTNQGYFFFHLPDALEIEACQVYFTYDPYSEEDPDEGVAGAPTGSSPQPLQPLSGEDDAYCTFPSRDDLLLFSPSLLGGPSPPSTAPGGSGAGEERMPPSLQERVPRDWDPQPLGPPTPGVPDLVDFQPPPELVLREAGEEVPDAGPREGVSFPWSRPPGQGEFRALNARLPLNTDAYLSLQELQGQDPTHLV |
| 329 | Human IL-2Rγ chain | Human IL-2 receptor common gamma chain | LNTTILTPNGNEDTTADFFLTTMPTDSLSVSTLPLPEVQCFVFNVEYMNCTWNSSSEPQPTNLTLHYWYKNSDNDKVQKCSHYLFSEEITSGCQLQKKEIHLYQTFVVQLQDPREPRRQATQMLKLQNLVIPWAPENLTLHKLSESQLELNWNNRFLNHCLEHLVQYRTDWDHSWTEQSVDYRHKFSLPSVDGQKRYTFRVRSRFNPLCGSAQHWSEWSHPIHWGSNTSKENPFLFALEAVVISVGSMGLIISLLCVYFWLERTMPRIPTLKNLEDLVTEYHGNFSAWSGVSKGLAESLQPDYSERLCLVSEIPPKGGALGEGPGASPCNQHSPYWAPPCYTLKPET |

TABLE S1-continued

SEQ ID NOS: 1-342

| SEQ ID NO: | Name | Description | Sequence |
|---|---|---|---|
| 330 | IL-7 | Human IL-7 amino acid sequence | DCDIEGKDGKQYESVLMVSIDQLLDSMKEIGSNCLNNEFNFFKRHICDANKEGMFLFRAARKLRQFLKMNSTGDFDLHLLKVSEGTTILLNCTGQVKGRKPAALGEAQPTKSLEENKSLKEQKKLNDLCFLKRLLQEIKTCWNKILMGTKEH |
| 331 | IL-15 | Human IL-15 amino acid sequence | GIHVFILGCFSAGLPKTEANWVNVISDLKKIEDLIQSMHIDATLYTESDVHPSCKVTAMKCFLLELQVISLESGDASIHDTVENLIILANNSLSSNGNVTESGCKECEELEEKNIKEFLQSFVHIVQMFINTS |
| 332 | IL-21 | Human IL-21 amino acid sequence | QGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLFRFKSLLQKMIHQHLSSRTHGSEDS |
| 333 | GM-CSF | Human GM-CSF amino acid sequence | APARSPSPSTQPWEHVNAIQEARRLLNLSRDTAAEMNETVEVISEMFDLQEPTCLQTRLELYKQGLRGSLTKLKGPLTMMASHYKQHCPPTPETSCATQIITFESFKENLKDFLLVIPFDCWEPVQE |
| 334 | IFNα | Human IFN-α amino acid sequence | CDLPQNHGLLSRNTLVLLHQMRRISPFLCLKDRRDFRFPQEMVKGSQLQKAHVMSVLHEMLQQIFSLFHTERSSAAWNMTLLDQLHTELHQQLQHLETCLLQVVGEGESAGAISSPALTLRRYFQGIRVYLKEKKYSDCAWEVVRMEIMKSLFLSTNMQERLRSKDRDLGS |
| 335 | TNFα | Extracellular portion of human TNF-α amino acid sequence | GPQREEFPRDLSLISPLAQAVRSSSRTPSDKPVAHVVANPQAEGQLQWLNRRANALLANGVELRDNQLVVPSEGLYLIYSQVLFKGQGCPSTHVLLTHTISRIAVSYQTKVNLLSAIKSPCQRETPEGAEAKPWYEPIYLGGVFQLEKGDRLSAEINRPDYLDFAESGQVYFGIIAL |
| 336 | IL-12α | Alpha chain of human IL-12 amino acid sequence | RNLPVATPDPGMFPCLHHSQNLLRAVSNMLQKARQTLEFYPCTSEEIDHEDITKDKTSTVEACLPLELTKNESCLNSRETSFITNGSCLASRKTSFMMALCLSSIYEDLKMYQVEFKTMNAKLLMDPKRQIFLDQNMLAVIDELMQALNFNSETVPQKSSLEEPDFYKTKIKLCILLHAFRIRAVTIDRVMSYLNAS |
| 337 | IL-12β | Beta chain of human IL-12 amino acid sequence | IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCS |
| 338 | CXCL9 | Human CXCL-9 amino acid sequence | TPVVRKGRCSCISTNQGTIHLQSLKDLKQFAPSPSCEKIEIIATLKNGVQTCLNPDSADVKELIKKWEKQVSQKKKQKNGKKHQKKKVLKVRKSQRSRQKKTT |
| 339 | CXCL10 | Human CXCL-10 amino acid sequence | VPLSRTVRCTCISISNQPVNPRSLEKLEIIPASQFCPRVEIIATMKKKGEKRCLNPESKAIKNLLKAVSKERSKRSP |
| 340 | Human WT IgG1 constant region | IGHG1*01 & IGHG1*02 & IGHG1*05 (IgG1) WT human IgG1 amino acid sequence | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |

TABLE S1-continued

| SEQ ID NOS: 1-342 | | | |
|---|---|---|---|
| SEQ ID NO: | Name | Description | Sequence |
| 341 | | WT human IgG1 nucleic acid sequence | GCCAGCACCAAGGGCCCCTCTGTGTTCCCTCTGGCCCCTTCCAGCAAG<br>TCCACCTCTGGCGGAACAGCCGCTCTGGGCTGCCTCGTGAAGGACTAC<br>TTCCCCGAGCCTGTGACCGTGTCCTGGAACTCTGGCGCTCTGACCAGC<br>GGAGTGCACACCTTCCCTGCTGTGCTGCAGTCCTCCGGCCTGTACTCC<br>CTGTCCTCCGTCGTGACCGTGCCTTCCAGCTCTCTGGGCACCCAGACC<br>TACATCTGCAACGTGAACCACAAGCCCTCCAACACCAAGGTGGACAAG<br>AAGGTGGAACCCAAGTCCTGCGACAAGACCCACACCTGTCCCCCTTGT<br>CCTGCCCCTGAACTGCTGGGCGGACCTTCCGTGTTCCTGTTCCCCCCA<br>AAGCCCAAGGACACCCTGATGATCTCCCGGACCCCCGAAGTGACCTGC<br>GTGGTGGTGGATGTGTCCCACGAGGACCCTGAAGTGAAGTTCAATTGG<br>TACGTGGACGGCGTGGAAGTGCACAACGCCAAGACCAAGCCTAGAGAG<br>GAACAGTACAACTCCACCTACCGGGTGGTGTCCGTGCTGACCGTGCTG<br>CACCAGGATTGGCTGAACGGCAAAGAGTACAAGTGCAAGGTGTCCAAC<br>AAGGCCCTGCCTGCCCCCATCGAAAAGACCATCTCCAAGGCCAAGGGC<br>CAGCCCCGGGAACCCCAGGTGTACACACTGCCCCCTAGCAGGGACGAG<br>CTGACCAAGAACCAGGTGTCCCTGACCTGTCTCGTGAAAGGCTTCTAC<br>CCCTCCGATATCGCCGTGGAATGGGAGTCCAACGGCCAGCCTGAGAAC<br>AACTACAAGACCACCCCCCCTGTGCTGGACTCCGACGGCTCATTCTTC<br>CTGTACAGCAAGCTGACAGTGGACAAGTCCCGGTGGCAGCAGGGCAAC<br>GTGTTCTCCTGCTCCGTGATGCACGAGGCCCTGCACAACCACTACACC<br>CAGAAGTCCCTGTCCCTGAGCCCCGGCAAGTGATGA |
| 342 | Mutated 1D05 - HC mutant 2 | Amino acid sequence of 1D05 heavy chain with V to A and F to S back-mutation in framework region to germline highlighted with IgG1 disabled (LAGA) constant region | EVQLVESGGGLVQPGRSLRLSCAASGFTFDDYAMHWVRQ**A**PGKGLEWV<br>SGISWIRTGIGYADSVKGRFTI**S**RDNAKNSLYLQMNSLRAEDTALYYC<br>AKDMKGSGTYGGWFDTWGQGTLVTVSSASTKGPSVFPLAPCSRSTSES<br>TAALGCLVKDYFPEPVTVSWNSGALTSGVHTFPAVLQSSGLYSLSSVV<br>TVPSSSLGTKTYTCNVDHKPSNTKVDKRVESKYGPPCPPCPAPE**LAGA**<br>PSVFLFPPKPKDTLMISRTPEVTCVVVDVSQEDPEVQFNWYVDGVEVH<br>NAKTKPREEQFNSTYRVVSVLTVLHQDWLNGKEYKCKVSNKGLPSSIE<br>KTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMH<br>EALHNHYTQKSLSLSLGK |

TABLE S2

| SEQ ID NOS: 343-538 | | | |
|---|---|---|---|
| SEQ ID NO: | Name | Description | Sequence |
| 343 | 416E01 - CDRH1 (IMGT) | Amino acid sequence of CDRH1 of 416E01 using IMGT | GFTFSNYA |
| 344 | 416E01 - CDRH2 (IMGT) | Amino acid sequence of CDRH2 of 416E01 using IMGT | ISFSGGTT |
| 345 | 416E01 - CDRH3 (IMGT) | Amino acid sequence of CDRH3 of 416E01 using IMGT | AKDEAPAGATFFDS |
| 346 | 416E01 - CDRH1 (Kabat) | Amino acid sequence of CDRH1 of 416E01 using Kabat | NYAMS |
| 347 | 416E01 - CDRH2 (Kabat) | Amino acid sequence of CDRH2 of 416E01 using Kabat | AISFSGGTTYYADSVKG |
| 348 | 416E01 - CDRH3 (Kabat) | Amino acid sequence of CDRH3 of 416E01 using Kabat | DEAPAGATFFDS |
| 349 | 416E01 - Heavy chain variable region | Amino acid sequence of $V_H$ of 416E01 (mutations from germline are shown in bold letters) | EVQL**A**ESGGGLVQPGGSLRLSCAASGFTFS**N**YAMSWVRQTPGKGLE<br>WVSAIS**F**SGG**T**TYYADSVKGRFTISRDNSKNTLYL**H**MNSLRA**D**DTA<br>VYYCAK**DEA**PA**GATF**FD**S**WGQGTLVTVSS |

TABLE S2-continued

SEQ ID NOS: 343-538

| SEQ ID NO: | Name | Description | Sequence |
|---|---|---|---|
| 350 | 416E01 - Heavy chain variable region | Nucleic acid sequence of $V_H$ of 416E01 | GAAGTGCAACTGGCGGAGTCTGGGGGAGGCTTGGTACAGCCGGGGGGGTCCCTGAGACTCTCCTGTGCAGCCTCTGGATTCACCTTTAGCAACTATGCCATGAGTTGGGTCCGCCAGACTCCAGGAAAGGGGCTGGAGTGGGTCTCAGCTATTAGTTTTAGTGGTGGTACTACATACTACGCTGACTCCGTGAAGGGCCGGTTCACCATCTCCAGAGACAATTCCAAGAACACGCTGTATTTGCACATGAACAGCCTGAGAGCCGATGACACGGCCGTATATTACTGTGCGAAAGATGAGGCACCAGCTGGCGCAACCTTCTTTGACTCCTGGGGCCAGGGAACGCTGGTCACCGTCTCCTCAG |
| 351 | 416E01 - full heavy chain sequence | Amino acid sequence of 416E01 heavy chain | EVQLAESGGGLVQPGGSLRLSCAASGFTFSNYAMSWVRQTPGKGLEWVSAISFSGGTTYYADSVKGRFTISRDNSKNTLYLHMNSLRADDTAVYYCAKDEAPAGATFFDSWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFEGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 352 | 416E01 - full heavy chain sequence | Nucleic acid sequence of 416E01 heavy chain | GAAGTGCAACTGGCGGAGTCTGGGGGAGGCTTGGTACAGCCGGGGGGGTCCCTGAGACTCTCCTGTGCAGCCTCTGGATTCACCTTTAGCAACTATGCCATGAGTTGGGTCCGCCAGACTCCAGGAAAGGGGCTGGAGTGGGTCTCAGCTATTAGTTTTAGTGGTGGTACTACATACTACGCTGACTCCGTGAAGGGCCGGTTCACCATCTCCAGAGACAATTCCAAGAACACGCTGTATTTGCACATGAACAGCCTGAGAGCCGATGACACGGCCGTATATTACTGTGCGAAAGATGAGGCACCAGCTGGCGCAACCTTCTTTGACTCCTGGGGCCAGGGAACGCTGGTCACCGTCTCCTCAGCCAGCACCAAGGGCCCTTCCGTGTTCCCCCTGGCCCCTTGCAGCAGGAGCACCTCCGAATCCACAGCTGCCCTGGGCTGTCTGGTGAAGGACTACTTTCCCGAGCCCGTGACCGTGAGCTGGAACAGCGGCGCTCTGACATCCGGCGTCCACACCTTTCCTGCCGTCCTGCAGTCCTCCGGCCTCTACTCCCTGTCCTCCGTGGTGACCGTGCCTAGCTCCTCCCTCGGCACCAAGACCTACACCTGTAACGTGGACCACAAACCCTCCAACACCAAGGTGGACAAACGGGTCGAGAGCAAGTACGGCCCTCCCTGCCCTCCTTGTCCTGCCCCCGAGTTCGAAGGCGGACCCAGCGTGTTCCTGTTCCCTCCTAAGCCCAAGGACACCCTCATGATCAGCCGGACACCCGAGGTGACCTGCGTGGTGGTGGATGTGAGCCAGGAGGACCCTGAGGTCCAGTTCAACTGGTATGTGGATGGCGTGGAGGTGCACAACGCCAAGACAAAGCCCCGGGAAGAGCAGTTCAACTCCACCTACAGGGTGGTCAGCGTGCTGACCGTGCTGCATCAGGACTGGCTGAACGGCAAGGAGTACAAGTGCAAGGTCAGCAATAAGGGACTGCCCAGCAGCATCGAGAAGACCATCTCCAAGGCTAAAGGCCAGCCCCGGGAACCTCAGGTGTACACCCTGCCTCCCAGCCAGGAGGAGATGACCAAGAACCAGGTGAGCCTGACCTGCCTGGTGAAGGGATTCTACCCTTCCGACATCGCCGTGGAGTGGGAGTCCAACGGCCAGCCCGAGAACAATTATAAGACCACCCCTCCCGTCCTCGACAGCGACGGATCCTTCTTTCTGTACTCCAGGCTGACCGTGGATAAGTCCAGGTGGCAGGAAGGCAACGTGTTCAGCTGCTCCGTGATGCACGAGGCCCTGCACAATCACTACACCCAGAAGTCCCTGAGCCTGTCCCTGGGAAAG |
| 353 | 416E01 - CDRL1 (IMGT) | Amino acid sequence of CDRL1 of 416E01 using IMGT | QGIRRW |
| 354 | 416E01 - CDRL2 (IMGT) | Amino acid sequence of CDRL2 of 416E01 using IMGT | GAS |
| 355 | 416E01 - CDRL3 (IMGT) | Amino acid sequence of CDRL3 of 416E01 using IMGT | QQANSFPIT |
| 356 | 416E01 - CDRL1 (Kabat) | Amino acid sequence of CDRL1 of 416E01 using Kabat | RASQGIRRWLA |
| 357 | 416E01 - CDRL2 (Kabat) | Amino acid sequence of CDRL2 of 416E01 using Kabat | GASSLQS |
| 358 | 416E01 - CDRL3 (Kabat) | Amino acid sequence of CDRL3 of 416E01 using Kabat | QQANSFPIT |

TABLE S2-continued

| SEQ ID NOS: 343-538 | | | |
|---|---|---|---|
| SEQ ID NO: | Name | Description | Sequence |
| 359 | 416E01 - Light chain variable region | Amino acid sequence of $V_L$ of 416E01 (mutations from germline are shown in bold letters) | DIQMTQSPSSVSASVGDRVTITCRASQGI**RR**WLAWYQQKPGKAPKL LI**SG**ASSLQSGVPSRFSGSGSGTDFTL**I**I**T**SLQPEDFATYYCQQAN SFPITFGQGTRLEIK |
| 360 | 416E01 - Light chain variable region | Nucleic acid sequence of $V_L$ of 416E01 | GACATCCAGATGACCCAGTCTCCATCTTCCGTGTCTGCATCTGTAG GAGACAGAGTCACCATCACTTGTCGGGCGAGTCAGGGTATTAGGAG GTGGTTAGCCTGGTATCAGCAGAAACCAGGGAAAGCCCCTAAACTC CTGATCTCTGGTGCATCCAGTTTGCAAAGTGGGGTCCCATCAAGGT TCAGCGGCAGTGGATCTGGGACAGATTTCACTCTCATCATTACCAG TCTGCAGCCTGAAGATTTTGCAACTTACTATTGTCAACAGGCTAAC AGTTTCCCGATCACCTTCGGCCAAGGGACACGACTGGAGATCAAAC |
| 361 | 416E01 - full light chain sequence | Amino acid sequence of 416E01 light chain | DIQMTQSPSSVSASVGDRVTITCRASQGIRRWLAWYQQKPGKAPKL LISGASSLQSGVPSRFSGSGSGTDFTLIITSLQPEDFATYYCQQAN SFPITFGQGTRLEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 362 | 416E01 - full light chain sequence | Nucleic acid sequence of 416E01 light chain | GACATCCAGATGACCCAGTCTCCATCTTCCGTGTCTGCATCTGTAG GAGACAGAGTCACCATCACTTGTCGGGCGAGTCAGGGTATTAGGAG GTGGTTAGCCTGGTATCAGCAGAAACCAGGGAAAGCCCCTAAACTC CTGATCTCTGGTGCATCCAGTTTGCAAAGTGGGGTCCCATCAAGGT TCAGCGGCAGTGGATCTGGGACAGATTTCACTCTCATCATTACCAG TCTGCAGCCTGAAGATTTTGCAACTTACTATTGTCAACAGGCTAAC AGTTTCCCGATCACCTTCGGCCAAGGGACACGACTGGAGATCAAAC GTACGGTGGCCGCTCCCTCCGTGTTCATCTTCCCACCTTCCGACGA GCAGCTGAAGTCCGGCACCGCTTCTGTCGTGTGCCTGCTGAACAAC TTCTACCCCCGCGAGGCCAAGGTGCAGTGGAAGGTGGACAACGCCC TGCAGTCCGGCAACTCCCAGGAATCCGTGACCGAGCAGGACTCCAA GGACAGCACCTACTCCCTGTCCTCCACCCTGACCCTGTCCAAGGCC GACTACGAGAAGCACAAGGTGTACGCCTGCGAAGTGACCCACCAGG GCCTGTCTAGCCCCGTGACCAAGTCTTTCAACCGGGGCGAGTGT |
| 363 | STIM001 - CDRH1 | Amino acid sequence of CDRH1 of STIM001 using IMGT | GYTFSTFG |
| 364 | STIM001 - CDRH2 | Amino acid sequence of CDRH2 of STIM001 using IMGT | ISAYNGDT |
| 365 | STIM001 - CDRH3 | Amino acid sequence of CDRH3 of STIM001 using IMGT | ARSSGHYYYYGMDV |
| 366 | STIM001 - Heavy chain variable region | Amino acid sequence of $V_H$ of STIM001 | QVQVVQSGAEVKKPGASVKVSCKASGYTFSTFGITWVRQAPGQGLE WMGWISAYNGDTNYAQNLQGRVIMTTDTSTSTAYMELRSLRSDDTA VYYCARSSGHYYYYGMDVWGQGTTVTVSS |
| 367 | STIM001 - Heavy chain variable region | Nucleic acid sequence of $V_H$ of STIM001 | CAGGTTCAGGTGGTGCAGTCTGGAGCTGAGGTGAAGAAGCCTGGGG CCTCAGTGAAGGTCTCCTGCAAGGCTTCTGGTTACACCTTTTCCAC CTTTGGTATCACCTGGGTGCGACAGGCCCCTGGACAAGGGCTTGAA TGGATGGGATGGATCAGCGCTTACAATGGTGACACAAACTATGCAC AGAATCTCCAGGGCAGAGTCATCATGACCACAGACACATCCACGAG CACAGCCTACATGGAGCTGAGGAGCCTGAGATCTGACGACACGGCC GTTTATTACTGTGCGAGGAGCAGTGGCCACTACTACTACTACGGTA TGGACGTCTGGGGCCAAGGGACCACGGTCACCGTCTCCTCA |
| 368 | STIM001 - full heavy chain sequence | Amino acid sequence of STIM001 heavy chain | QVQVVQSGAEVKKPGASVKVSCKASGYTFSTFGITWVRQAPGQGLE WMGWISAYNGDTNYAQNLQGRVIMTTDTSTSTAYMELRSLRSDDTA VYYCARSSGHYYYYGMDVWGQGTTVTVSSASTKGPSVFPLAPSSKS TSGGTAALGCLVKDYFPEPVTVSWNSGALTSGVHTFPAVLQSSGLY SLSSVVTVPSSSLGTQTYICNVNHKPSNTKVDKKVEPKSCDKTHTC PPCPAPELLGGPSVFLFPPKPKDTLMISRTPEVTCVVVDVSHEDPE VKFNWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVMHEALHNHYTQKSLSLSPGK |

TABLE S2-continued

SEQ ID NOS: 343-538

| SEQ ID NO: | Name | Description | Sequence |
|---|---|---|---|
| 369 | STIM001 - full heavy chain sequence | Nucleic acid sequence of STIM001 heavy chain | CAGGTTCAGGTGGTGCAGTCTGGAGCTGAGGTGAAGAAGCCTGGGG CCTCAGTGAAGGTCTCCTGCAAGGCTTCTGGTTACACCTTTTCCAC CTTTGGTATCACCTGGGTGCGACAGGCCCCTGGACAAGGGCTTGAA TGGATGGGATGGATCAGCGCTTACAATGGTGACACAAACTATGCAC AGAATCTCCAGGGCAGAGTCATCATGACCACAGACACATCCACGAG CACAGCCTACATGGAGCTGAGGAGCCTGAGATCTGACGACACGGCC GTTTATTACTGTGCGAGGAGCAGTGGCCACTACTACTACTACGGTA TGGACGTCTGGGGCCAAGGGACCACGGTCACCGTCTCCTCAGCCAG CACCAAGGGCCCCTCTGTGTTCCCTCTGGCCCCTTCCAGCAAGTCC ACCTCTGGCGGAACAGCCGCTCTGGGCTGCCTCGTGAAGGACTACT TCCCCGAGCCTGTGACCGTGTCCTGGAACTCTGGCGCTCTGACCAG CGGAGTGCACACCTTCCCTGCTGTGCTGCAGTCCTCCGGCCTGTAC TCCCTGTCCTCCGTCGTGACCGTGCCTTCCAGCTCTCTGGGCACCC AGACCTACATCTGCAACGTGAACCACAAGCCCTCCAACACCAAGGT GGACAAGAAGGTGGAACCCAAGTCCTGCGACAAGACCCACACCTGT CCCCCTTGTCCTGCCCCTGAACTGCTGGGCGGACCTTCCGTGTTCC TGTTCCCCCCAAAGCCCAAGGACACCCTGATGATCTCCCGGACCCC CGAAGTGACCTGCGTGGTGGTGGATGTGTCCCACGAGGACCCTGAA GTGAAGTTCAATTGGTACGTGGACGGCGTGGAAGTGCACAACGCCA AGACCAAGCCTAGAGAGGAACAGTACAACTCCACCTACCGGGTGGT GTCCGTGCTGACCGTGCTGCACCAGGATTGGCTGAACGGCAAAGAG TACAAGTGCAAGGTGTCCAACAAGGCCCTGCCTGCCCCCATCGAAA AGACCATCTCCAAGGCCAAGGGCCAGCCCCGGGAACCCCAGGTGTA CACACTGCCCCCTAGCAGGGACGAGCTGACCAAGAACCAGGTGTCC CTGACCTGTCTCGTGAAAGGCTTCTACCCCTCCGATATCGCCGTGG AATGGGAGTCCAACGGCCAGCCTGAGAACAACTACAAGACCACCCC CCCTGTGCTGGACTCCGACGGCTCATTCTTCCTGTACAGCAAGCTG ACAGTGGACAAGTCCCGGTGGCAGCAGGGCAACGTGTTCTCCTGCT CCGTGATGCACGAGGCCCTGCACAACCACTACACCCAGAAGTCCCT GTCCCTGAGCCCCGGCAAGTGATGA |
| 370 | STIM001 - CDRL1 | Amino acid sequence of CDRL1 of STIM001 using IMGT | QSLLHSNEYNY |
| 371 | STIM001 - CDRL2 | Amino acid sequence of CDRL2 of STIM001 using IMGT | LGS |
| 372 | STIM001 - CDRL3 | Amino acid sequence of CDRL3 of STIM001 using IMGT | MQSLQTPLT |
| 373 | STIM001 - Light chain variable region | Amino acid sequence of $V_L$ of STIM001 | DIVMTQSPLSLPVTPGEPASISCRSSQSLLHSNEYNYLDWYLQKPG QSPQLLIFLGSNRASGVPDRFSGSGSGTDFTLKITRVEAEDVGIYY CMQSLQTPLTFGGGTKVEIK |
| 374 | STIM001 - Light chain variable region | Nucleic acid sequence of $V_L$ of STIM001 | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTAATGAATACAACTATTTGGATTGGTACCTGCAGAAGCCAGGG CAGTCTCCACAGCTCCTGATCTTTTTGGGTTCTAATCGGGCCTCCG GGGTCCCTGACAGGTTCAGTGGCAGTGGATCAGGCACAGATTTTAC ACTGAAAATCACCAGAGTGGAGGCTGAGGATGTTGGAATTTATTAC TGCATGCAATCTCTACAAACTCCGCTCACTTTCGGCGGAGGGACCA AGGTGGAGATCAAA |
| 375 | STIM001 - full light chain sequence | Amino acid sequence of STIM001 light chain | DIVMTQSPLSLPVTPGEPASISCRSSQSLLHSNEYNYLDWYLQKPG QSPQLLIFLGSNRASGVPDRFSGSGSGTDFTLKITRVEAEDVGIYY CMQSLQTPLTFGGGTKVEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |

TABLE S2-continued

| SEQ ID NO: | Name | Description | Sequence |
|---|---|---|---|
| | | SEQ ID NOS: 343-538 | |
| 376 | STIM001 - full light chain sequence | Nucleic acid sequence of STIM001 light chain | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTAATGAATACAACTATTTGGATTGGTACCTGCAGAAGCCAGGG CAGTCTCCACAGCTCCTGATCTTTTTGGGTTCTAATCGGGCCTCCG GGGTCCCTGACAGGTTCAGTGGCAGTGGATCAGGCACAGATTTTAC ACTGAAAATCACCAGAGTGGAGGCTGAGGATGTTGGAATTTATTAC TGCATGCAATCTCTACAAACTCCGCTCACTTTCGGCGGAGGGACCA AGGTGGAGATCAAAcgtacggtggccgctccctccgtgttcatctt cccaccttccgacgagcagctgaagtccggcaccgcttctgtcgtg tgcctgctgaacaacttctacccccgcgaggccaaggtgcagtgga aggtggacaacgccctgcagtccggcaactcccaggaatccgtgac cgagcaggactccaaggacagcacctactccctgtcctccaccctg accctgtccaaggccgactacgagaagcacaaggtgtacgcctgcg aagtgacccaccagggcctgtctagccccgtgaccaagtctttcaa ccggggcgagtgt |
| 377 | STIM002 - CDRH1 | Amino acid sequence of CDRH1 of STIM002 using IMGT | GYTFTSYG |
| 378 | STIM002 - CDRH2 | Amino acid sequence of CDRH2 of STIM002 using IMGT | ISAYNGNT |
| 379 | STIM002 - CDRH3 | Amino acid sequence of CDRH3 of STIM002 using IMGT | ARSTYFYGSGTLYGMDV |
| 380 | STIM002 - Heavy chain variable region | Amino acid sequence of $V_H$ of STIM002 | QVQLVQSGGEVKKPGASVKVSCKASGYTFTSYGFSWVRQAPGQGLE WMGWISAYNGNTNYAQKLQGRVTMTTDTSTSTAYMELRSLRSDDTA VYYCARSTYFYGSGTLYGMDVWGQGTTVTVSS |
| 381 | STIM002 - Heavy chain variable region | Nucleic acid sequence of $V_H$ of STIM002 | CAGGTTCAACTGGTGCAGTCTGGAGGTGAGGTGAAGAAGCCTGGGG CCTCAGTGAAGGTCTCCTGCAAGGCTTCTGGTTACACCTTTACCAG CTATGGTTTCAGCTGGGTGCGACAGGCCCCTGGACAAGGACTAGAG TGGATGGGATGGATCAGCGCTTACAATGGTAACACAAACTATGCAC AGAAGCTCCAGGGCAGAGTCACCATGACCACAGACACATCCACGAG CACAGCCTACATGGAGCTGAGGAGCTTGAGATCTGACGACACGGCC GTGTATTACTGTGCGAGATCTACGTATTTCTATGGTTCGGGGACCC TCTACGGTATGGACGTCTGGGGCCAAGGGACCACGGTCACCGTCTC CTCA |
| 382 | STIM002 - full heavy chain sequence | Amino acid sequence of STIM002 heavy chain | QVQLVQSGGEVKKPGASVKVSCKASGYTFTSYGFSWVRQAPGQGLE WMGWISAYNGNTNYAQKLQGRVTMTTDTSTSTAYMELRSLRSDDTA VYYCARSTYFYGSGTLYGMDVWGQGTTVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |
| 383 | STIM002 - full heavy chain sequence | Nucleic acid sequence of STIM002 heavy chain | CAGGTTCAACTGGTGCAGTCTGGAGGTGAGGTGAAGAAGCCTGGGG CCTCAGTGAAGGTCTCCTGCAAGGCTTCTGGTTACACCTTTACCAG CTATGGTTTCAGCTGGGTGCGACAGGCCCCTGGACAAGGACTAGAG TGGATGGGATGGATCAGCGCTTACAATGGTAACACAAACTATGCAC AGAAGCTCCAGGGCAGAGTCACCATGACCACAGACACATCCACGAG CACAGCCTACATGGAGCTGAGGAGCTTGAGATCTGACGACACGGCC GTGTATTACTGTGCGAGATCTACGTATTTCTATGGTTCGGGGACCC TCTACGGTATGGACGTCTGGGGCCAAGGGACCACGGTCACCGTCTC CTCA |

TABLE S2-continued

SEQ ID NOS: 343-538

| SEQ ID NO: | Name | Description | Sequence |
|---|---|---|---|
| | | | GCCAGCACCAAGGGCCCCTCTGTGTTCCCTCTGGCCCCTTCCAGCA AGTCCACCTCTGGCGGAACAGCCGCTCTGGGCTGCCTCGTGAAGGA CTACTTCCCCGAGCCTGTGACCGTGTCCTGGAACTCTGGCGCTCTG ACCAGCGGAGTGCACACCTTCCCTGCTGTGCTGCAGTCCTCCGGCC TGTACTCCCTGTCCTCCGTCGTGACCGTGCCTTCCAGCTCTCTGGG CACCCAGACCTACATCTGCAACGTGAACCACAAGCCCTCCAACACC AAGGTGGACAAGAAGGTGGAACCCAAGTCCTGCGACAAGACCCACA CCTGTCCCCCTTGTCCTGCCCCTGAACTGCTGGGCGGACCTTCCGT GTTCCTGTTCCCCCCAAAGCCCAAGGACACCCTGATGATCTCCCGG ACCCCCGAAGTGACCTGCGTGGTGGTGGATGTGTCCCACGAGGACC CTGAAGTGAAGTTCAATTGGTACGTGGACGGCGTGGAAGTGCACAA CGCCAAGACCAAGCCTAGAGAGGAACAGTACAACTCCACCTACCGG GTGGTGTCCGTGCTGACCGTGCTGCACCAGGATTGGCTGAACGGCA AAGAGTACAAGTGCAAGGTGTCCAACAAGGCCCTGCCTGCCCCCAT CGAAAAGACCATCTCCAAGGCCAAGGGCCAGCCCCGGGAACCCCAG GTGTACACACTGCCCCCTAGCAGGGACGAGCTGACCAAGAACCAGG TGTCCCTGACCTGTCTCGTGAAAGGCTTCTACCCCTCCGATATCGC CGTGGAATGGGAGTCCAACGGCCAGCCTGAGAACAACTACAAGACC ACCCCCCCTGTGCTGGACTCCGACGGCTCATTCTTCCTGTACAGCA AGCTGACAGTGGACAAGTCCCGGTGGCAGCAGGGCAACGTGTTCTC CTGCTCCGTGATGCACGAGGCCCTGCACAACCACTACACCCAGAAG TCCCTGTCCCTGAGCCCCGGCAAGTGATGA |
| 384 | STIM002 - CDRL1 | Amino acid sequence of CDRL1 of STIM002 using IMGT | QSLLHSDGYNY |
| 385 | STIM002 - CDRL2 | Amino acid sequence of CDRL2 of STIM002 using IMGT | LGS |
| 386 | STIM002 - CDRL3 | Amino acid sequence of CDRL3 of STIM002 using IMGT | MQALQTPLS |
| 387 | STIM002 - Light chain variable region | Amino acid sequence of $V_L$ of STIM002 | DIVMTQSPLSLPVTPGEPASISCRSSQSLLHSDGYNYLDWYLQKPG QSPQLLIYLGSTRASGFPDRFSGSGSGTDFTLKISRVEAEDVGVYY CMQALQTPLSFGQGTKLEIK |
| 388 | STIM002 - Light chain variable region | Nucleic acid sequence of $V_L$ of STIM002 | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTGATGGATACAACTGTTTGGATTGGTACCTGCAGAAGCCAGGG CAGTCTCCACAGCTCCTGATCTATTTGGGTTCTACTCGGGCCTCCG GGTTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCGTGCAGTTTTGGCCAGGGGACCA AGCTGGAGATCAAA |
| 389 | STIM002 - full light chain sequence | Amino acid sequence of STIM002 light chain | DIVMTQSPLSLPVTPGEPASISCRSSQSLLHSDGYNYLDWYLQKPG QSPQLLIYLGSTRASGFPDRFSGSGSGTDFTLKISRVEAEDVGVYY CMQALQTPLSFGQGTKLEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |
| 390 | STIM002 - full light chain sequence | Nucleic acid sequence of STIM002 light chain | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTGATGGATACAACTGTTTGGATTGGTACCTGCAGAAGCCAGGG CAGTCTCCACAGCTCCTGATCTATTTGGGTTCTACTCGGGCCTCCG GGTTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCGTGCAGTTTTGGCCAGGGGACCA AGCTGGAGATCAAAcgtacggtggccgctccctccgtgttcatctt cccaccttccgacgagcagctgaagtccggcaccgcttctgtcgtg tgcctgctgaacaacttctacccccgcgaggccaaggtgcagtgga aggtggacaacgccctgcagtccggcaactcccaggaatccgtgac cgagcaggactccaaggacagcacctactccctgtcctccaccctg accctgtccaaggccgactacgagaagcacaaggtgtacgcctgcg aagtgacccaccagggcctgtctagccccgtgaccaagtctttcaa ccggggcgagtgt |

TABLE S2-continued

| SEQ ID NO: | Name | Description | Sequence |
|---|---|---|---|
| | | SEQ ID NOS: 343-538 | |
| 391 | STIM002-B - CDRH1 | Amino acid sequence of CDRH1 of STIM002-B using IMGT | GYTFTSYG |
| 392 | STIM002-B - CDRH2 | Amino acid sequence of CDRH2 of STIM002-B using IMGT | ISAYNGNT |
| 393 | STIM002-B - CDRH3 | Amino acid sequence of CDRH3 of STIM002-B using IMGT | ARSTYFYGSGTLYGMDV |
| 394 | STIM002-B - Heavy chain variable region | Amino acid sequence of $V_H$ of STIM002-B | QVQLVQSGGEVKKPGASVKVSCKASGYTFTSYGFSWVRQAPGQGLE WMGWISAYNGNTNYAQKLQGRVTMTTDTSTSTAYMELRSLRSDDTA VYYCARSTYFYGSGTLYGMDVWGQGTTVTVSS |
| 395 | STIM002-B - Heavy chain variable region | Nucleic acid sequence of $V_H$ of STIM002-B | CAGGTTCAACTGGTGCAGTCTGGAGGTGAGGTGAAGAAGCCTGGGG CCTCAGTGAAGGTCTCCTGCAAGGCTTCTGGTTACACCTTTACCAG CTATGGTTTCAGCTGGGTGCGACAGGCCCCTGGACAAGGACTAGAG TGGATGGGATGGATCAGCGCTTACAATGGTAACACAAACTATGCAC AGAAGCTCCAGGGCAGAGTCACCATGACCACAGACACATCCACGAG CACAGCCTACATGGAGCTGAGGAGCTTGAGATCTGACGACACGGCC GTGTATTACTGTGCGAGATCTACGTATTTCTATGGTTCGGGGACCC TCTACGGTATGGACGTCTGGGGCCAAGGGACCACGGTCACCGTCTC CTCA |
| 396 | STIM002-B—full heavy chain sequence | Amino acid sequence of STIM002-B heavy chain | QVQLVQSGGEVKKPGASVKVSCKASGYTFTSYGFSWVRQAPGQGLE WMGWISAYNGNTNYAQKLQGRVTMTTDTSTSTAYMELRSLRSDDTA VYYCARSTYFYGSGTLYGMDVWGQGTTVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |
| 397 | STIM002-B—full heavy chain sequence | Nucleic acid sequence of STIM002-B heavy chain | CAGGTTCAACTGGTGCAGTCTGGAGGTGAGGTGAAGAAGCCTGGGG CCTCAGTGAAGGTCTCCTGCAAGGCTTCTGGTTACACCTTTACCAG CTATGGTTTCAGCTGGGTGCGACAGGCCCCTGGACAAGGACTAGAG TGGATGGGATGGATCAGCGCTTACAATGGTAACACAAACTATGCAC AGAAGCTCCAGGGCAGAGTCACCATGACCACAGACACATCCACGAG CACAGCCTACATGGAGCTGAGGAGCTTGAGATCTGACGACACGGCC GTGTATTACTGTGCGAGATCTACGTATTTCTATGGTTCGGGGACCC TCTACGGTATGGACGTCTGGGGCCAAGGGACCACGGTCACCGTCTC CTCAGCCAGCACCAAGGGCCCCTCTGTGTTCCCTCTGGCCCCTTCC AGCAAGTCCACCTCTGGCGGAACAGCCGCTCTGGGCTGCCTCGTGA AGGACTACTTCCCCGAGCCTGTGACCGTGTCCTGGAACTCTGGCGC TCTGACCAGCGGAGTGCACACCTTCCCTGCTGTGCTGCAGTCCTCC GGCCTGTACTCCCTGTCCTCCGTCGTGACCGTGCCTTCCAGCTCTC TGGGCACCCAGACCTACATCTGCAACGTGAACCACAAGCCCTCCAA CACCAAGGTGGACAAGAAGGTGGAACCCAAGTCCTGCGACAAGACC CACACCTGTCCCCCTTGTCCTGCCCCTGAACTGCTGGGCGGACCTT CCGTGTTCCTGTTCCCCCCAAAGCCCAAGGACACCCTGATGATCTC CCGGACCCCCGAAGTGACCTGCGTGGTGGTGGATGTGTCCCACGAG GACCCTGAAGTGAAGTTCAATTGGTACGTGGACGGCGTGGAAGTGC ACAACGCCAAGACCAAGCCTAGAGAGGAACAGTACAACTCCACCTA CCGGGTGGTGTCCGTGCTGACCGTGCTGCACCAGGATTGGCTGAAC GGCAAAGAGTACAAGTGCAAGGTGTCCAACAAGGCCCTGCCTGCCC CCATCGAAAAGACCATCTCCAAGGCCAAGGGCCAGCCCCGGGAACC CCAGGTGTACACACTGCCCCCTAGCAGGGACGAGCTGACCAAGAAC CAGGTGTCCCTGACCTGTCTCGTGAAAGGCTTCTACCCCTCCGATA TCGCCGTGGAATGGGAGTCCAACGGCCAGCCTGAGAACAACTACAA GACCACCCCCCCTGTGCTGGACTCCGACGGCTCATTCTTCCTGTAC AGCAAGCTGACAGTGGACAAGTCCCGGTGGCAGCAGGGCAACGTGT TCTCCTGCTCCGTGATGCACGAGGCCCTGCACAACCACTACACCCA GAAGTCCCTGTCCCTGAGCCCCGGCAAGTGATGA |

TABLE S2-continued

SEQ ID NOS: 343-538

| SEQ ID NO: | Name | Description | Sequence |
|---|---|---|---|
| 398 | STIM002-B - CDRL1 | Amino acid sequence of CDRL1 of STIM002-B using IMGT | QSLLHSDGYNC |
| 399 | STIM002-B - CDRL2 | Amino acid sequence of CDRL2 of STIM002-B using IMGT | LGS |
| 400 | STIM002-B - CDRL3 | Amino acid sequence of CDRL3 of STIM002-B using IMGT | MQALQTPCS |
| 401 | STIM002-B - Light chain variable region | Amino acid sequence of $V_L$ of STIM002-B | DIVMTQSPLSLPVTPGEPASISCRSSQSLLHSDGYNCLDWYLQKPG QSPQLLIYLGSTRASGFPDRFSGSGSGTDFTLKISRVEAEDVGVYY CMQALQTPCSFGQGTKLEIK |
| 402 | STIM002-B - Light chain variable region | Nucleic acid sequence of VL of STIM002-B | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTGATGGATACAACTGTTTGGATTGGTACCTGCAGAAGCCAGGG CAGTCTCCACAGCTCCTGATCTATTTGGGTTCTACTCGGGCCTCCG GGTTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCGTGCAGTTTTGGCCAGGGGACCA AGCTGGAGATCAAA |
| 403 | STIM002-B—full light chain sequence | Amino acid sequence of STIM002-B light chain | DIVMTQSPLSLPVTPGEPASISCRSSQSLLHSDGYNCLDWYLQKPG QSPQLLIYLGSTRASGFPDRFSGSGSGTDFTLKISRVEAEDVGVYY CMQALQTPCSFGQGTKLEIK RTVAAPSVFIFPPSDEQLKSGTASVVCLLNNEYPREAKVQWKVDNA LQSGNSQESVTEQDSKDSTYSLSSTLTLSKADYEKHKVYACEVTHQ GLSSPVTKSFNRGEC |
| 404 | STIM002-B—full light chain sequence | Nucleic acid sequence of STIM002-B light chain | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTGATGGATACAACTGTTTGGATTGGTACCTGCAGAAGCCAGGG CAGTCTCCACAGCTCCTGATCTATTTGGGTTCTACTCGGGCCTCCG GGTTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCGTGCAGTTTTGGCCAGGGGACCA AGCTGGAGATCAAAcgtacggtggccgctccctccgtgttcatctt cccaccttccgacgagcagctgaagtccggcaccgcttctgtcgtg tgcctgctgaacaacttctacccccgcgaggccaaggtgcagtgga aggtggacaacgccctgcagtccggcaactcccaggaatccgtgac cgagcaggactccaaggacagcacctactccctgtcctccaccctg accctgtccaaggccgactacgagaagcacaaggtgtacgcctgcg aagtgacccaccagggcctgtctagccccgtgaccaagtctttcaa ccggggcgagtgt |
| 405 | STIM003 - CDRH1 | Amino acid sequence of CDRH1 of STIM003 using IMGT | GVTFDDYG |
| 406 | STIM003 - CDRH2 | Amino acid sequence of CDRH2 of STIM003 using IMGT | INWNGGDT |
| 407 | STIM003 - CDRH3 | Amino acid sequence of CDRH3 of STIM003 using IMGT | ARDFYGSGSYYHVPFDY |
| 408 | STIM003 - Heavy chain variable region | Amino acid sequence of VH of STIM003 | EVQLVESGGGVVRPGGSLRLSCVASGVTFDDYGMSWVRQAPGKGLE WVSGINWNGGDTDYSDSVKGRFTISRDNAKNSLYLQMNSLRAEDTA LYYCARDFYGSGSYYHVPFDYWGQGILVTVSS |

TABLE S2-continued

SEQ ID NOS: 343-538

| SEQ ID NO: | Name | Description | Sequence |
|---|---|---|---|
| 409 | STIM003 - Heavy chain variable region | Nucleic acid sequence of $V_H$ of STIM003 | GAGGTGCAGCTGGTGGAGTCTGGGGGAGGTGTGGTACGGCCTGGGGGGTCCCTGAGACTCTCCTGTGTAGCCTCTGGAGTCACCTTTGATGATTATGGCATGAGCTGGGTCCGCCAAGCTCCAGGGAAGGGGCTGGARTGGGTCTCTGGTATTAATTGGAATGGTGGCGACACAGATTATTCAGACTCTGTGAAGGGCCGATTCACCATCTCCAGAGACAACGCCAAGAACTCCCTGTATCTACAAATGAATAGTCTGAGAGCCGAGGACACGGCCTTGTATTACTGTGCGAGGGATTTCTATGGTTCGGGGAGTTATTATCACGTTCCTTTTGACTACTGGGGCCAGGGAATCCTGGTCACCGTCTCCTCA |
| 410 | STIM003 - full heavy chain sequence | Amino acid sequence of STIM003 heavy chain | EVQLVESGGGVVRPGGSLRLSCVASGVTFDDYGMSWVRQAPGKGLEWVSGINWNGGDTDYSDSVKGRFTISRDNAKNSLYLQMNSLRAEDTALYYCARDFYGSGSYYHVPFDYWGQGILVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 411 | STIM003 - full heavy chain sequence | Nucleic acid sequence of STIM003 heavy chain | GAGGTGCAGCTGGTGGAGTCTGGGGGAGGTGTGGTACGGCCTGGGGGGTCCCTGAGACTCTCCTGTGTAGCCTCTGGAGTCACCTTTGATGATTATGGCATGAGCTGGGTCCGCCAAGCTCCAGGGAAGGGGCTGGARTGGGTCTCTGGTATTAATTGGAATGGTGGCGACACAGATTATTCAGACTCTGTGAAGGGCCGATTCACCATCTCCAGAGACAACGCCAAGAACTCCCTGTATCTACAAATGAATAGTCTGAGAGCCGAGGACACGGCCTTGTATTACTGTGCGAGGGATTTCTATGGTTCGGGGAGTTATTATCACGTTCCTTTTGACTACTGGGGCCAGGGAATCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAGTGATGA |
| 412 | STIM003 - CDRL1 | Amino acid sequence of CDRL1 of STIM003 using IMGT | QSVSRSY |
| 413 | STIM003 - CDRL2 | Amino acid sequence of CDRL2 of STIM003 using IMGT | GAS |
| 414 | STIM003 - CDRL3 | Amino acid sequence of CDRL3 of STIM003 using IMGT | HQYDMSPFT |
| 415 | STIM003 - Light chain variable region | Amino acid sequence of $V_L$ of STIM003 | EIVLTQSPGTLSLSPGERATLSCRASQSVSRSYLAWYQQKRGQAPRLLIYGASSRATGIPDRFSGDGSGTDFTLSISRLEPEDFAVYYCHQYDMSPFTFGPGTKVDIK |

TABLE S2-continued

SEQ ID NOS: 343-538

| SEQ ID NO: | Name | Description | Sequence |
|---|---|---|---|
| 416 | STIM003 - Light chain variable region | Nucleic acid sequence of $V_L$ of STIM003 | GAAATTGTGTTGACGCAGTCTCCAGGGACCCTGTCTTTGTCTCCAG GGGAAAGAGCCACCCTCTCCTGCAGGGCCAGTCAGAGTGTTAGCAG AAGCTACTTAGCCTGGTACCAGCAGAAACGTGGCCAGGCTCCCAGG CTCCTCATCTATGGTGCATCCAGCAGGGCCACTGGCATCCCAGACA GGTTCAGTGGCGATGGGTCTGGGACAGACTTCACTCTCTCCATCAG CAGACTGGAGCCTGAAGATTTTGCAGTGTATTACTGTCACCAGTAT GATATGTCACCATTCACTTTCGGCCCTGGGACCAAAGTGGATATCA AA |
| 417 | STIM003 - full light chain sequence | Amino acid sequence of STIM003 light chain | EIVLTQSPGTLSLSPGERATLSCRASQSVSRSYLAWYQQKRGQAPR LLIYGASSRATGIPDRFSGDGSGTDFTLSISRLEPEDFAVYYCHQY DMSPFTFGPGTKVDIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 418 | STIM003 - full light chain sequence | Nucleic acid sequence of STIM003 light chain | GAAATTGTGTTGACGCAGTCTCCAGGGACCCTGTCTTTGTCTCCAG GGAAAGAGCCACCCTCTCCTGCAGGGCCAGTCAGAGTGTTAGCAG AAGCTACTTAGCCTGGTACCAGCAGAAACGTGGCCAGGCTCCCAGG CTCCTCATCTATGGTGCATCCAGCAGGGCCACTGGCATCCCAGACA GGTTCAGTGGCGATGGGTCTGGGACAGACTTCACTCTCTCCATCAG CAGACTGGAGCCTGAAGATTTTGCAGTGTATTACTGTCACCAGTAT GATATGTCACCATTCACTTTCGGCCCTGGGACCAAAGTGGATATCA AAcgtacggtggccgctccctccgtgttcatcttcccaccttccga cgagcagctgaagtccggcaccgcttctgtcgtgtgcctgctgaac aacttctacccccgcgaggccaaggtgcagtggaaggtggacaacg ccctgcagtccggcaactcccaggaatccgtgaccgagcaggactc caaggacagcacctactccctgtcctccaccctgaccctgtccaag gccgactacgagaagcacaaggtgtacgcctgcgaagtgacccacc agggcctgtctagccccgtgaccaagtctttcaaccggggcgagtgt |
| 419 | STIM004 - CDRH1 | Amino acid sequence of CDRH1 of STIM004 using IMGT | GLTFDDYG |
| 420 | STIM004 - CDRH2 | Amino acid sequence of CDRH2 of STIM004 using IMGT | INWNGDNT |
| 421 | STIM004 - CDRH3 | Amino acid sequence of CDRH3 of STIM004 using IMGT | ARDYYGSGSYYNVPFDY |
| 422 | STIM004 - Heavy chain variable region | Amino acid sequence of $V_H$ of STIM004 | EVQLVESGGGVVRPGGSLRLSCAASGLTFDDYGMSWVRQVPGKGLE WVSGINWNGDNTDYADSVKGRFTISRDNAKNSLYLQMNSLRAEDTA LYYCARDYYGSGSYYNVPFDYWGQGTLVTVSS |
| 423 | STIM004 - Heavy chain variable region | Nucleic acid sequence of $V_H$ of STIM004 | GAGGTGCAGCTGGTGGAGTCTGGGGGAGGTGTGGTACGGCCTGGGG GGTCCCTGAGACTCTCCTGTGCAGCCTCTGGACTCACCTTTGATGA TTATGGCATGAGCTGGGTCCGCCAAGTTCCAGGGAAGGGGCTGGAG TGGGTCTCTGGTATTAATTGGAATGGTGATAACACAGATTATGCAG ACTCTGTGAAGGGCCGATTCACCATCTCCAGAGACAACGCCAAGAA CTCCCTGTATCTGCAAATGAACAGTCTGAGAGCCGAGGACACGGCC TTGTATTACTGTGCGAGGGATTACTATGGTTCGGGGAGTTATTATA ACGTTCCTTTTGACTACTGGGGCCAGGGAACCCTGGTCACCGTCTC CTCA |
| 424 | STIM004 - full heavy chain sequence | Amino acid sequence of STIM004 heavy chain | EVQLVESGGGVVRPGGSLRLSCAASGLTFDDYGMSWVRQVPGKGLE WVSGINWNGDNTDYADSVKGRFTISRDNAENSLYLQMNSLRAEDTA LYYCARDYYGSGSYYNVPFDYWGQGTLVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |

TABLE S2-continued

SEQ ID NOS: 343-538

| SEQ ID NO: | Name | Description | Sequence |
| --- | --- | --- | --- |
| 425 | STIM004 - full heavy chain sequence | Nucleic acid sequence of STIM004 heavy chain | GAGGTGCAGCTGGTGGAGTCTGGGGGAGGTGTGGTACGGCCTGGGGGGTCCCTGAGACTCTCCTGTGCAGCCTCTGGACTCACCTTTGATGATTATGGCATGAGCTGGGTCCGCCAAGTTCCAGGGAAGGGGCTGGAGTGGGTCTCTGGTATTAATTGGAATGGTGATAACACAGATTATGCAGACTCTGTGAAGGGCCGATTCACCATCTCCAGAGACAACGCCAAGAACTCCCTGTATCTGCAAATGAACAGTCTGAGAGCCGAGGACACGGCCTTGTATTACTGTGCGAGGGATTACTATGGTTCGGGGAGTTATTATAACGTTCCTTTTGACTACTGGGGCCAGGGAACCCTGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACTCCACCTACCGGGTGGTGTCCGTGCTGACCGTGCTGCACCAGGATTGGCTGAACGGCAAAGAGTACAAGTGCAAGGTGTCCAACAAGGCCCTGCCTGCCCCCATCGAAAAGACCATCTCCAAGGCCAAGGGCCAGCCCCGGGAACCCCAGGTGTACACACTGCCCCCTAGCAGGGACGAGCTGACCAAGAACCAGGTGTCCCTGACCTGTCTCGTGAAAGGCTTCTACCCCTCCGATATCGCCGTGGAATGGGAGTCCAACGGCCAGCCTGAGAACAACTACAAGACCACCCCCCCTGTGCTGGACTCCGACGGCTCATTCTTCCTGTACAGCAAGCTGACAGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAGTGATGA |
| 426 | STIM004 - CDRL1 | Amino acid sequence of CDRL1 of STIM004 using IMGT | QSVSSSY |
| 427 | STIM004 - CDRL2 | Amino acid sequence of CDRL2 of STIM004 using IMGT | GAS |
| 428 | STIM004 - CDRL3 | Amino acid sequence of CDRL3 of STIM004 using IMGT | QQYGSSPF |
| 429 | STIM004 - Corrected light chain variable region | Amino acid sequence of corrected $V_L$ of STIM004 | EIVLTQSPGTLSLSPGERATLSCRASQSVSSSYLAWYQQKPGQAPRLLIYGASSRATGIPDRFSGSGSGTDFTLTIRRLEPEDFAVYYCQQYGSSPFFGPGTKVDIK |
| 430 | STIM004 - Corrected light chain variable region | Nucleic acid sequence of corrected $V_L$ of STIM004 | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCAGCTACTTAGCCTGGTACCAGCAGAAACCTGGCCAGGCTCCCAGGCTCCTCATATATGGTGCATCCAGCAGGGCCACTGGCATCCCAGACAGGTTCAGTGGCAGTGGGTCTGGGACAGACTTCACTCTCACCATCAGAAGACTGGAGCCTGAAGATTTTGCAGTGTATTACTGTCAGCAGTATGGTAGTTCACCATTCTTCGGCCCTGGGACCAAAGTGGATATCAAA |
| 431 | STIM004 - Light chain variable region | Nucleic acid sequence of $V_L$ of STIM004 | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCAGCTACTTAGCCTGGTACCAGCAGAAACCTGGCCAGGCTCCCAGGCTCCTCATATATGGTGCATCCAGCAGGGCCACTGGCATCCCAGACAGGTTCAGTGGCAGTGGGTCTGGGACAGACTTCACTCTCACCATCAGAAGACTGGAGCCTGAAGATTTTGCAGTGTATTACTGTCAGCAGTATGGTAGTTCACCATTCACTTCGGCCCTGGGACCAAAGTGGATATCAAA |
| 432 | STIM004 - full corrected light chain sequence | Amino acid sequence of STIM004 light chain | EIVLTQSPGTLSLSPGERATLSCRASQSVSSSYLAWYQQKPGQAPRLLIYGASSRATGIPDRFSGSGSGTDFTLTIRRLEPEDFAVYYCQQYGSSPFFGPGTKVDIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE S2-continued

| SEQ ID NOS: 343-538 | | | |
|---|---|---|---|
| SEQ ID NO: | Name | Description | Sequence |
| 433 | STIM004 - full corrected light chain sequence | Nucleic acid sequence of corrected STIM004 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATATATGGTGCATCCAGCAGGGCCACTGGCATCCCAGACA GGTTCAGTGGCAGTGGGTCTGGGACAGACTTCACTCTCACCATCAG AAGACTGGAGCCTGAAGATTTTGCAGTGTATTACTGTCAGCAGTAT GGTAGTTCACCATTCTTCGGCCCTGGGACCAAAGTGGATATCAAAc gtacggtggccgctccctccgtgttcatcttcccaccttccgacga gcagctgaagtccggcaccgcttctgtcgtgtgcctgctgaacaac ttctacccccgcgaggccaaggtgcagtggaaggtggacaacgccc tgcagtccggcaactcccaggaatccgtgaccgagcaggactccaa ggacagcacctactccctgtcctccaccctgaccctgtccaaggcc gactacgagaagcacaaggtgtacgcctgcgaagtgacccaccagg gcctgtctagccccgtgaccaagtctttcaaccggggcgagtgt |
| 434 | STIM004 - full light chain sequence | Nucleic acid sequence of STIM004 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATATATGGTGCATCCAGCAGGGCCACTGGCATCCCAGACA GGTTCAGTGGCAGTGGGTCTGGGACAGACTTCACTCTCACCATCAG AAGACTGGAGCCTGAAGATTTTGCAGTGTATTACTGTCAGCAGTAT GGTAGTTCACCATTCACTTCGGCCCTGGGACCAAAGTGGATATCAA Acgtacggtggccgctccctccgtgttcatcttcccaccttccgac gagcagctgaagtccggcaccgcttctgtcgtgtgcctgctgaaca acttctacccccgcgaggccaaggtgcagtggaaggtggacaacgc cctgcagtccggcaactcccaggaatccgtgaccgagcaggactcc aaggacagcacctactccctgtcctccaccctgaccctgtccaagg ccgactacgagaagcacaaggtgtacgcctgcgaagtgacccacca gggcctgtctagccccgtgaccaagtctttcaaccggggcgagtgt |
| 435 | STIM005 - CDRH1 | Amino acid sequence of CDRH1 of STIM005 using IMGT | GYTFNSYG |
| 436 | STIM005 - CDRH2 | Amino acid sequence of CDRH2 of STIM005 using IMGT | ISVHNGNT |
| 437 | STIM005 - CDRH3 | Amino acid sequence of CDRH3 of STIM005 using IMGT | ARAGYDILTDFSDAFDI |
| 438 | STIM005 - Heavy chain variable region | Amino acid sequence of $V_H$ of STIM005 | QVQLVQSGAEVKKPGASVKVSCKASGYTFNSYGIIWVRQAPGQGLE WMGWISVHNGNTNCAQKLQGRVTMTTDTSTSTAYMELRSLRTDDTA VYYCARAGYDILTDFSDAFDIWGHGTMVTVSS |
| 439 | STIM005 - Heavy chain variable region | Nucleic acid sequence of $V_H$ of STIM005 | CAGGTTCAGTTGGTGCAGTCTGGAGCTGAGGTGAAGAAGCCTGGGG CCTCAGTGAAGGTCTCCTGCAAGGCTTCTGGTTACACCTTTAATAG TTATGGTATCATCTGGGTGCGACAGGCCCCTGGACAAGGGCTTGAG TGGATGGGATGGATCAGCGTTCACAATGGTAACACAAACTGTGCAC AGAAGCTCCAGGGTAGAGTCACCATGACCACAGACACATCCACGAG CACAGCCTACATGGAGCTGAGGAGCCTGAGAACTGACGACACGGCC GTGTATTACTGTGCGAGAGCGGGTTACGATATTTTGACTGATTTTT CCGATGCTTTTGATATCTGGGGCCACGGGACAATGGTCACCGTCTC TTCA |
| 440 | STIM005 - full heavy chain sequence | Amino acid sequence of STIM005 heavy chain | QVQLVQSGAEVKKPGASVKVSCKASGYTFNSYGIIWVRQAPGQGLE WMGWISVHNGNTNCAQKLQGRVTMTTDTSTSTAYMELRSLRTDDTA VYYCARAGYDILTDFSDAFDIWGHGTMVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |

TABLE S2-continued

| SEQ ID NOS: 343-538 | | | |
|---|---|---|---|
| SEQ ID NO: | Name | Description | Sequence |
| 441 | STIM005 - full heavy chain sequence | Nucleic acid sequence of STIM005 heavy chain | CAGGTTCAGTTGGTGCAGTCTGGAGCTGAGGTGAAGAAGCCTGGGG CCTCAGTGAAGGTCTCCTGCAAGGCTTCTGGTTACACCTTTAATAG TTATGGTATCATCTGGGTGCGACAGGCCCCTGGACAAGGGCTTGAG TGGATGGGATGGATCAGCGTTCACAATGGTAACACAAACTGTGCAC AGAAGCTCCAGGGTAGAGTCACCATGACCACAGACACATCCACGAG CACAGCCTACATGGAGCTGAGGAGCCTGAGAACTGACGACACGGCC GTGTATTACTGTGCGAGAGCGGGTTACGATATTTTGACTGATTTTT CCGATGCTTTTGATATCTGGGGCCACGGGACAATGGTCACCGTCTC TTCA GCCAGCACCAAGGGCCCCTCTGTGTTCCCTCTGGCCCCTTCCAGCA AGTCCACCTCTGGCGGAACAGCCGCTCTGGGCTGCCTCGTGAAGGA CTACTTCCCCGAGCCTGTGACCGTGTCCTGGAACTCTGGCGCTCTG ACCAGCGGAGTGCACACCTTCCCTGCTGTGCTGCAGTCCTCCGGCC TGTACTCCCTGTCCTCCGTCGTGACCGTGCCTTCCAGCTCTCTGGG CACCCAGACCTACATCTGCAACGTGAACCACAAGCCCTCCAACACC AAGGTGGACAAGAAGGTGGAACCCAAGTCCTGCGACAAGACCCACA CCTGTCCCCCTTGTCCTGCCCCTGAACTGCTGGGCGGACCTTCCGT GTTCCTGTTCCCCCCAAAGCCCAAGGACACCCTGATGATCTCCCGG ACCCCCGAAGTGACCTGCGTGGTGGTGGATGTGTCCCACGAGGACC CTGAAGTGAAGTTCAATTGGTACGTGGACGGCGTGGAAGTGCACAA CGCCAAGACCAAGCCTAGAGAGGAACAGTACAACTCCACCTACCGG GTGGTGTCCGTGCTGACCGTGCTGCACCAGGATTGGCTGAACGGCA AAGAGTACAAGTGCAAGGTGTCCAACAAGGCCCTGCCTGCCCCCAT CGAAAAGACCATCTCCAAGGCCAAGGGCCAGCCCCGGGAACCCCAG GTGTACACACTGCCCCCTAGCAGGGACGAGCTGACCAAGAACCAGG TGTCCCTGACCTGTCTCGTGAAAGGCTTCTACCCCTCCGATATCGC CGTGGAATGGGAGTCCAACGGCCAGCCTGAGAACAACTACAAGACC ACCCCCCCTGTGCTGGACTCCGACGGCTCATTCTTCCTGTACAGCA AGCTGACAGTGGACAAGTCCCGGTGGCAGCAGGGCAACGTGTTCTC CTGCTCCGTGATGCACGAGGCCCTGCACAACCACTACACCCAGAAG TCCCTGTCCCTGAGCCCCGGCAAGTGATGA |
| 442 | STIM005 - CDRL1 | Amino acid sequence of CDRL1 of STIM005 using IMGT | QNINNF |
| 443 | STIM005 - CDRL2 | Amino acid sequence of CDRL2 of STIM005 using IMGT | AAS |
| 444 | STIM005 - CDRL3 | Amino acid sequence of CDRL3 of STIM005 using IMGT | QQSYGIPW |
| 445 | STIM005 - Light chain variable region | Amino acid sequence of $V_L$ of STIM005 | DIQMTQSPSSLSASVGDRVTITCRASQNINNFLNWYQQKEGKGPKL LIYAASSLQRGIPSTFSGSGSGTDFTLTISSLQPEDFATYICQQSY GIPWVGQGTKVEIK |
| 446 | STIM005 - Light chain variable region | Nucleic acid sequence of $V_L$ of STIM005 | GACATCCAGATGACCCAGTCTCCATCCTCCCTGTCTGCATCTGTAG GAGACAGAGTCACCATCACTTGCCGGGCAAGTCAGAACATTAATAA CTTTTTAAATTGGTATCAGCAGAAAGAAGGGAAAGGCCCTAAGCTC CTGATCTATGCAGCATCCAGTTTGCAAAGAGGGATACCATCAACGT TCAGTGGCAGTGGATCTGGGACAGACTTCACTCTCACCATCAGCAG TCTGCAACCTGAAGATTTTGCAACTTACATCTGTCAACAGAGCTAC GGTATCCCGTGGGTCGGCCAAGGGACCAAGGTGGAAATCAAA |
| 447 | STIM005 - full light chain sequence | Amino acid sequence of STIM005 light chain | DIQMTQSPSSLSASVGDRVTITCRASQNINNFLNWYQQKEGKGPKL LIYAASSLQRGIPSTFSGSGSGTDFTLTISSLQPEDFATYICQQSY GIPWVGQGTKVEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |

TABLE S2-continued

SEQ ID NOS: 343-538

| SEQ ID NO: | Name | Description | Sequence |
|---|---|---|---|
| 448 | STIM005 - full light chain sequence | Nucleic acid sequence of STIM005 light chain | GACATCCAGATGACCCAGTCTCCATCCTCCCTGTCTGCATCTGTAGGAGACAGAGTCACCATCACTTGCCGGGCAAGTCAGAACATTAATAACTTTTTAAATTGGTATCAGCAGAAAGAAGGGAAAGGCCCTAAGCTCCTGATCTATGCAGCATCCAGTTTGCAAAGAGGGATACCATCAACGTTCAGTGGCAGTGGATCTGGGACAGACTTCACTCTCACCATCAGCAGTCTGCAACCTGAAGATTTTGCAACTTACATCTGTCAACAGAGCTACGGTATCCCGTGGGTCGGCCAAGGGACCAAGGTGGAAATCAAAcgtacggtggccgctccctccgtgttcatcttcccaccttccgacgagcagctgaagtccggcaccgcttctgtcgtgtgcctgctgaacaacttctacccccgcgaggccaaggtgcagtggaaggtggacaacgccctgcagtccggcaactcccaggaatccgtgaccgagcaggactccaaggacagcacctactccctgtcctccaccctgaccctgtccaaggccgactacgagaagcacaaggtgtacgcctgcgaagtgacccaccagggcctgtctagccccgtgaccaagtctttcaaccggggcgagtgt |
| 449 | STIM006 - CDRH1 | Amino acid sequence of CDRH1 of STIM006 using IMGT | GFTFSDYF |
| 450 | STIM006 - CDRH2 | Amino acid sequence of CDRH2 of STIM006 using IMGT | ISSSGSTI |
| 451 | STIM006 - CDRH3 | Amino acid sequence of CDRH3 of STIM006 using IMGT | ARDHYDGSGIYPLYYYYGLDV |
| 452 | STIM006 - Heavy chain variable region | Amino acid sequence of $V_H$ of STIM006 | QVQLVESGGGLVKPGGSLRLSCAASGFTFSDYFMSWIRQAPGKGLEWISYISSSGSTIYYADSVRGRFTISRDNAKYSLYLQMNSLRSEDTAVYYCARDHYDGSGIYPLYYYYGLDVWGQGTTVTVSS |
| 453 | STIM006 - Heavy chain variable region | Nucleic acid sequence of $V_H$ of STIM006 | CAGGTGCAGCTGGTGGAGTCTGGGGGAGGCTTGGTCAAGCCTGGAGGGTCCCTGAGACTCTCCTGTGCAGCCTCTGGATTCACCTTCAGTGACTACTTCATGAGCTGGATCCGCCAGGCGCCAGGGAAGGGGCTGGAGTGGATTTCATACATTAGTTCTAGTGGTAGTACCATATACTACGCAGACTCTGTGAGGGGCCGATTCACCATCTCCAGGGACAACGCCAAGTACTCACTGTATCTGCAAATGAACAGCCTGAGATCCGAGGACACGGCCGTGTATTACTGTGCGAGAGATCACTACGATGGTTCGGGGATTTATCCCCTCTACTACTATTACGGTTTGGACGTCTGGGGCCAGGGGACCACGGTCACCGTCTCCTCA |
| 454 | STIM006 - full heavy chain sequence | Amino acid sequence of STIM006 heavy chain | QVQLVESGGGLVKPGGSLRLSCAASGFTFSDYFMSWIRQAPGKGLEWISYISSSGSTIYYADSVRGRFTISRDNAKYSLYLQMNSLRSEDTAVYYCARDHYDGSGIYPLYYYYGLDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 455 | STIM006 - full heavy chain sequence | Nucleic acid sequence of STIM006 heavy chain | CAGGTGCAGCTGGTGGAGTCTGGGGGAGGCTTGGTCAAGCCTGGAGGGTCCCTGAGACTCTCCTGTGCAGCCTCTGGATTCACCTTCAGTGACTACTTCATGAGCTGGATCCGCCAGGCGCCAGGGAAGGGGCTGGAGTGGATTTCATACATTAGTTCTAGTGGTAGTACCATATACTACGCAGACTCTGTGAGGGGCCGATTCACCATCTCCAGGGACAACGCCAAGTACTCACTGTATCTGCAAATGAACAGCCTGAGATCCGAGGACACGGCCGTGTATTACTGTGCGAGAGATCACTACGATGGTTCGGGGATTTATCCCCTCTACTACTATTACGGTTTGGACGTCTGGGGCCAGGGGACCACGGTCACCGTCTCCTCAGCCAGCACCAAGGGCCCCTCTGTGTTCCCTCTGGCCCCTTCCAGCAAGTCCACCTCTGGCGGAACAGCCGCTCTGGGCTGCCTCGTGAAGGACTACTTCCCCGAGCCTGTGACCGTGTCCTGGAACTCTGGCGCTCTGACCAGCGGAGTGCACACCTTCCCTGCTGTGCTGCAGTCCTCCGGCCTGTACTCCCTGTCCTCCGTCGTGACCGTGCCTTCCAGCTCTCTGGGCACCCAGACCTACATCTGCAACGTGAACCACAAGCCCTCCAACACCAAGGTGGACAAGAAGGTGGAACCCAAGTCCTGCGACAAGACCCACACCTGTCCCCCTTGTCCTGCCCCTGAACTGCTGGGCGGACCTTCCGTGTTCCTGTTCCCCCCAAAGCCCAAGGACACCCTGATGATCTCCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTA |

TABLE S2-continued

SEQ ID NOS: 343-538

| SEQ ID NO: | Name | Description | Sequence |
|---|---|---|---|
| | | | CAACTCCACCTACCGGGTGGTGTCCGTGCTGACCGTGCTGCACCAG GATTGGCTGAACGGCAAAGAGTACAAGTGCAAGGTGTCCAACAAGG CCCTGCCTGCCCCCATCGAAAAGACCATCTCCAAGGCCAAGGGCCA GCCCCGGGAACCCCAGGTGTACACACTGCCCCCTAGCAGGGACGAG CTGACCAAGAACCAGGTGTCCCTGACCTGTCTCGTGAAAGGCTTCT ACCCCTCCGATATCGCCGTGGAATGGGAGTCCAACGGCCAGCCTGA GAACAACTACAAGACCACCCCCCCTGTGCTGGACTCCGACGGCTCA TTCTTCCTGTACAGCAAGCTGACAGTGGACAAGTCCCGGTGGCAGC AGGGCAACGTGTTCTCCTGCTCCGTGATGCACGAGGCCCTGCACAA CCACTACACCCAGAAGTCCCTGTCCCTGAGCCCCGGCAAGTGATGA |
| 456 | STIM006 - CDRL1 | Amino acid sequence of CDRL1 of STIM006 using IMGT | QSLLHSNGYNY |
| 457 | STIM006 - CDRL2 | Amino acid sequence of CDRL2 of STIM006 using IMGT | LGS |
| 458 | STIM006 - CDRL3 | Amino acid sequence of CDRL3 of STIM006 using IMGT | MQALQTPRS |
| 459 | STIM006 - Light chain variable region | Amino acid sequence of $V_L$ of STIM006 | IVMTQSPLSLPVTPGEPASISCRSSQSLLHSNGYNYLDYYLQKPGQ SPQLLIYLGSYRASGVPDRFSGSGSGTDFTLKISRVEAEDVGVYYC MQALQTPRSFGQGTTLEIK |
| 460 | STIM006 - Light chain variable region | Nucleic acid sequence of $V_L$ of STIM006 | ATTGTGATGACTCAGTCTCCACTCTCCCTACCCGTCACCCCTGGAG AGCCGGCCTCCATCTCCTGCAGGTCTAGTCAGAGCCTCCTGCATAG TAATGGATACAACTATTTGGATTATTACCTGCAGAAGCCAGGGCAG TCTCCACAGCTCCTGATCTATTTGGGTTCTTATCGGGCCTCCGGGG TCCCTGACAGGTTCAGTGGCAGTGGATCAGGCACAGATTTTACACT GAAAATCAGCAGAGTGGAGGCTGAGGATGTTGGGGTTTATTACTGC ATGCAAGCTCTACAAACTCCTCGCAGTTTTGGCCAGGGGACCACGC TGGAGATCAAA |
| 461 | STIM006 - full light chain sequence | Amino acid sequence of STIM006 light chain | IVMTQSPLSLPVTPGEPASISCRSSQSLLHSNGYNYLDYYLQKPGQ SPQLLIYLGSYRASGVPDRFSGSGSGTDFTLKISRVEAEDVGVYYC MQALQTPRSFGQGTTLEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSFNRGEC |
| 462 | STIM006 - full light chain sequence | Nucleic acid sequence of STIM006 light chain | ATTGTGATGACTCAGTCTCCACTCTCCCTACCCGTCACCCCTGGAG AGCCGGCCTCCATCTCCTGCAGGTCTAGTCAGAGCCTCCTGCATAG TAATGGATACAACTATTTGGATTATTACCTGCAGAAGCCAGGGCAG TCTCCACAGCTCCTGATCTATTTGGGTTCTTATCGGGCCTCCGGGG TCCCTGACAGGTTCAGTGGCAGTGGATCAGGCACAGATTTTACACT GAAAATCAGCAGAGTGGAGGCTGAGGATGTTGGGGTTTATTACTGC ATGCAAGCTCTACAAACTCCTCGCAGTTTTGGCCAGGGGACCACGC TGGAGATCAAAcgtacggtggccgctccctccgtgttcatcttccc accttccgacgagcagctgaagtccggcaccgcttctgtcgtgtgc ctgctgaacaacttctacccccgcgaggccaaggtgcagtggaagg tggacaacgccctgcagtccggcaactcccaggaatccgtgaccga gcaggactccaaggacagcacctactccctgtcctccaccctgacc ctgtccaaggccgactacgagaagcacaaggtgtacgcctgcgaag tgacccaccagggcctgtctagccccgtgaccaagtctttcaaccg gggcgagtgt |
| 463 | STIM007 - CDRH1 | Amino acid sequence of CDRH1 of STIM007 using IMGT | GFSLSTTGVG |
| 464 | STIM007 - CDRH2 | Amino acid sequence of CDRH2 of STIM007 using IMGT | IYWDDDK |
| 465 | STIM007 - CDRH3 | Amino acid sequence of CDRH3 of STIM007 using IMGT | THGYGSASYYHYGMDV |

TABLE S2-continued

| SEQ ID NO: | Name | Description | Sequence |
|---|---|---|---|
| | | SEQ ID NOS: 343-538 | |
| 466 | STIM007 - Heavy chain variable region | Amino acid sequence of $V_H$ of STIM007 | QITLKESGPTLVKPTQTLTLTCTFSGFSLSTTGVGVGWIRQPPGKA LEWLAVIYWDDDKRYSPSLKSRLTITKDTSKNQVVLTMTNMDPVDT ATYFCTHGYGSASYYHYGMDVWGQGTTVTVSS |
| 467 | STIM007 - Heavy chain variable region | Nucleic acid sequence of $V_H$ of STIM007 | CAGATCACCTTGAAGGAGTCTGGTCCTACGCTGGTGAAACCCACAC AGACCCTCACGCTGACCTGCACCTTCTCTGGGTTCTCACTCAGCAC TACTGGAGTGGGTGTGGGCTGGATCCGTCAGCCCCCAGGAAAGGCC CTGGAGTGGCTTGCAGTCATTTATTGGGATGATGATAAGCGCTACA GCCCATCTCTGAAGAGCAGACTCACCATCACCAAGGACACCTCCAA AAACCAGGTGGTCCTTACAATGACCAACATGGACCCTGTGGACACA GCCACATATTTCTGTACACACGGATATGGTTCGGCGAGTTATTACC ACTACGGTATGGACGTCTGGGGCCAAGGGACCACGGTCACCGTCTC CTCA |
| 468 | STIM007 - full heavy chain sequence | Amino acid sequence of STIM007 heavy chain | QITLKESGPTLVKPTQTLTLTCTFSGFSLSTTGVGVGWIRQPPGKA LEWLAVIYWDDDKRYSPSLKSRLTITKDTSKNQVVLTMTNMDPVDT ATYFCTHGYGSASYYHYGMDVWGQGTTVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |
| 469 | STIM007 - full heavy chain sequence | Nucleic acid sequence of STIM007 heavy chain | CAGATCACCTTGAAGGAGTCTGGTCCTACGCTGGTGAAACCCACAC AGACCCTCACGCTGACCTGCACCTTCTCTGGGTTCTCACTCAGCAC TACTGGAGTGGGTGTGGGCTGGATCCGTCAGCCCCCAGGAAAGGCC CTGGAGTGGCTTGCAGTCATTTATTGGGATGATGATAAGCGCTACA GCCCATCTCTGAAGAGCAGACTCACCATCACCAAGGACACCTCCAA AAACCAGGTGGTCCTTACAATGACCAACATGGACCCTGTGGACACA GCCACATATTTCTGTACACACGGATATGGTTCGGCGAGTTATTACC ACTACGGTATGGACGTCTGGGGCCAAGGGACCACGGTCACCGTCTC CTCA GCCAGCACCAAGGGCCCCTCTGTGTTCCCTCTGGCCCCTTCCAGCA AGTCCACCTCTGGCGGAACAGCCGCTCTGGGCTGCCTCGTGAAGGA CTACTTCCCCGAGCCTGTGACCGTGTCCTGGAACTCTGGCGCTCTG ACCAGCGGAGTGCACACCTTCCCTGCTGTGCTGCAGTCCTCCGGCC TGTACTCCCTGTCCTCCGTCGTGACCGTGCCTTCCAGCTCTCTGGG CACCCAGACCTACATCTGCAACGTGAACCACAAGCCCTCCAACACC AAGGTGGACAAGAAGGTGGAACCCAAGTCCTGCGACAAGACCCACA CCTGTCCCCCTTGTCCTGCCCCTGAACTGCTGGGCGGACCTTCCGT GTTCCTGTTCCCCCCAAAGCCCAAGGACACCCTGATGATCTCCCGG ACCCCCGAAGTGACCTGCGTGGTGGTGGATGTGTCCCACGAGGACC CTGAAGTGAAGTTCAATTGGTACGTGGACGGCGTGGAAGTGCACAA CGCCAAGACCAAGCCTAGAGAGGAACAGTACAACTCCACCTACCGG GTGGTGTCCGTGCTGACCGTGCTGCACCAGGATTGGCTGAACGGCA AAGAGTACAAGTGCAAGGTGTCCAACAAGGCCCTGCCTGCCCCCAT CGAAAAGACCATCTCCAAGGCCAAGGGCCAGCCCCGGGAACCCCAG GTGTACACACTGCCCCCTAGCAGGGACGAGCTGACCAAGAACCAGG TGTCCCTGACCTGTCTCGTGAAAGGCTTCTACCCCTCCGATATCGC CGTGGAATGGGAGTCCAACGGCCAGCCTGAGAACAACTACAAGACC ACCCCCCCTGTGCTGGACTCCGACGGCTCATTCTTCCTGTACAGCA AGCTGACAGTGGACAAGTCCCGGTGGCAGCAGGGCAACGTGTTCTC CTGCTCCGTGATGCACGAGGCCCTGCACAACCACTACACCCAGAAG TCCCTGTCCCTGAGCCCCGGCAAGTGATGA |
| 470 | STIM007 - CDRL1 | Amino acid sequence of CDRL1 of STIM007 using IMGT | QSVTNY |
| 471 | STIM007 - CDRL2 | Amino acid sequence of CDRL2 of STIM007 using IMGT | DAS |
| 472 | STIM007 - CDRL3 | Amino acid sequence of CDRL3 of STIM007 using IMGT | QHRSNWPLT |

TABLE S2-continued

SEQ ID NOS: 343-538

| SEQ ID NO: | Name | Description | Sequence |
|---|---|---|---|
| 473 | STIM007 - Light chain variable region | Amino acid sequence of $V_L$ of STIM007 | EIVLTQSPATLSLSPGERATLSCRASQSVTNYLAWHQQKPGQAPRL LIYDASNRATGIPARFSGSGSGTDFTLTISSLEPEDFAVYYCQHRS NWPLTFGGGTKVEIK |
| 474 | STIM007 - Light chain variable region | Nucleic acid sequence of $V_L$ of STIM007 | GAAATTGTATTGACACAGTCTCCAGCCACCCTGTCTTTGTCTCCAG GGGAAAGAGCCACCCTCTCCTGCAGGGCCAGTCAGAGTGTTACCAA CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCTGGGACAGACTTCACTCTCACCATCAGCAG CCTAGAGCCTGAAGATTTTGCAGTTTATTACTGTCAGCACCGTAGC AACTGGCCTCTCACTTTCGGCGGAGGGACCAAGGTGGAGATCAAAC |
| 475 | STIM007 - full light chain sequence | Amino acid sequence of STIM007 light chain | EIVLTQSPATLSLSPGERATLSCRASQSVTNYLAWHQQKPGQAPRL LIYDASNRATGIPARFSGSGSGTDFTLTISSLEPEDFAVYYCQHRS NWPLTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 476 | STIM007 - full light chain sequence | Nucleic acid sequence of STIM007 light chain | GAAATTGTATTGACACAGTCTCCAGCCACCCTGTCTTTGTCTCCAG GGGAAAGAGCCACCCTCTCCTGCAGGGCCAGTCAGAGTGTTACCAA CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCTGGGACAGACTTCACTCTCACCATCAGCAG CCTAGAGCCTGAAGATTTTGCAGTTTATTACTGTCAGCACCGTAGC AACTGGCCTCTCACTTTCGGCGGAGGGACCAAGGTGGAGATCAAAC cgtacggtggccgctccctccgtgttcatcttcccaccttccgacg agcagctgaagtccggcaccgcttctgtcgtgtgcctgctgaacaa cttctacccccgcgaggccaaggtgcagtggaaggtggacaacgcc ctgcagtccggcaactcccaggaatccgtgaccgagcaggactcca aggacagcacctactccctgtcctccaccctgaccctgtccaaggc cgactacgagaagcacaaggtgtacgcctgcgaagtgacccaccag ggcctgtctagccccgtgaccaagtctttcaaccggggcgagtgt |
| 477 | STIM008 - CDRH1 | Amino acid sequence of CDRH1 of STIM008 using IMGT | GFSLSTSGVG |
| 478 | STIM008 - CDRH2 | Amino acid sequence of CDRH2 of STIM008 using IMGT | IYWDDDK |
| 479 | STIM008 - CDRH3 | Amino acid sequence of CDRH3 of STIM008 using IMGT | THGYGSASYYHYGMDV |
| 480 | STIM008 - Heavy chain variable region | Amino acid sequence of $V_H$ of STIM008 | QITLKESGPTLVKPTQTLTLTCTFSGFSLSTSGVGVGWIRQPPGKA LEWLAVIYWDDDKRYSPSLKSRLTITKDTSKNQVVLTMTNMDPVDT ATYFCTHGYGSASYYHYGMDVWGQGTTVTVSS |
| 481 | STIM008 - Heavy chain variable region | Nucleic acid sequence of $V_H$ of STIM008 | CAGATCACCTTGAAGGAGTCTGGTCCTACGCTGGTGAAACCCACAC AGACCCTCACGCTGACCTGCACCTTCTCTGGGTTCTCACTCAGCAC TAGTGGAGTGGGTGTGGGCTGGATCCGTCAGCCCCCAGGAAAGGCC CTGGAGTGGCTTGCAGTCATTTATTGGGATGATGATAAGCGCTACA GCCCATCTCTGAAGAGCAGGCTCACCATCACCAAGGACACCTCCAA AAACCAGGTGGTCCTTACAATGACCAACATGGACCCTGTGGACACA GCCACATATTTCTGTACACACGGATATGGTTCGGCGAGTTATTACC ACTACGGTATGGACGTCTGGGGCCAAGGGACCACGGTCACCGTCTC CTCA |
| 482 | STIM008 - full heavy chain sequence | Amino acid sequence of STIM008 heavy chain | QITLKESGPTLVKPTQTLTLTCTFSGFSLSTSGVGVGWIRQPPGKA LEWLAVIYWDDDKRYSPSLKSRLTITKDTSKNQVVLTMTNMDPVDT ATYFCTHGYGSASYYHYGMDVWGQGTTVTVSSASTKGPSVFPLAPS SKSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDWLN GKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPGK |

TABLE S2-continued

SEQ ID NOS: 343-538

| SEQ ID NO: | Name | Description | Sequence |
|---|---|---|---|
| 483 | STIM008 - full heavy chain sequence | Nucleic acid sequence of STIM008 heavy chain | CAGATCACCTTGAAGGAGTCTGGTCCTACGCTGGTGAAACCCACAC AGACCCTCACGCTGACCTGCACCTTCTCTGGGTTCTCACTCAGCAC TAGTGGAGTGGGTGTGGGCTGGATCCGTCAGCCCCCAGGAAAGGCC CTGGAGTGGCTTGCAGTCATTTATTGGGATGATGATAAGCGCTACA GCCCATCTCTGAAGAGCAGGCTCACCATCACCAAGGACACCTCCAA AAACCAGGTGGTCCTTACAATGACCAACATGGACCCTGTGGACACA GCCACATATTTCTGTACACACGGATATGGTTCGGCGAGTTATTACC ACTACGGTATGGACGTCTGGGGCCAAGGGACCACGGTCACCGTCTC CTCAGCCAGCACCAAGGGCCCCTCTGTGTTCCCTCTGGCCCCTTCC AGCAAGTCCACCTCTGGCGGAACAGCCGCTCTGGGCTGCCTCGTGA AGGACTACTTCCCCGAGCCTGTGACCGTGTCCTGGAACTCTGGCGC TCTGACCAGCGGAGTGCACACCTTCCCTGCTGTGCTGCAGTCCTCC GGCCTGTACTCCCTGTCCTCCGTCGTGACCGTGCCTTCCAGCTCTC TGGGCACCCAGACCTACATCTGCAACGTGAACCACAAGCCCTCCAA CACCAAGGTGGACAAGAAGGTGGAACCCAAGTCCTGCGACAAGACC CACACCTGTCCCCCTTGTCCTGCCCCTGAACTGCTGGGCGGACCTT CCGTGTTCCTGTTCCCCCCAAAGCCCAAGGACACCCTGATGATCTC CCGGACCCCCGAAGTGACCTGCGTGGTGGTGGATGTGTCCCACGAG GACCCTGAAGTGAAGTTCAATTGGTACGTGGACGGCGTGGAAGTGC ACAACGCCAAGACCAAGCCTAGAGAGGAACAGTACAACTCCACCTA CCGGGTGGTGTCCGTGCTGACCGTGCTGCACCAGGATTGGCTGAAC GGCAAAGAGTACAAGTGCAAGGTGTCCAACAAGGCCCTGCCTGCCC CCATCGAAAAGACCATCTCCAAGGCCAAGGGCCAGCCCCGGGAACC CCAGGTGTACACACTGCCCCCTAGCAGGGACGAGCTGACCAAGAAC CAGGTGTCCCTGACCTGTCTCGTGAAAGGCTTCTACCCCTCCGATA TCGCCGTGGAATGGGAGTCCAACGGCCAGCCTGAGAACAACTACAA GACCACCCCCCCTGTGCTGGACTCCGACGGCTCATTCTTCCTGTAC AGCAAGCTGACAGTGGACAAGTCCCGGTGGCAGCAGGGCAACGTGT TCTCCTGCTCCGTGATGCACGAGGCCCTGCACAACCACTACACCCA GAAGTCCCTGTCCCTGAGCCCCGGCAAGTGATGA |
| 484 | STIM008 - CDRL1 | Amino acid sequence of CDRL1 of STIM008 using IMGT | QSVTNY |
| 485 | STIM008 - CDRL2 | Amino acid sequence of CDRL2 of STIM008 using IMGT | DAS |
| 486 | STIM008 - CDRL3 | Amino acid sequence of CDRL3 of STIM008 using IMGT | QQRSNWPLT |
| 487 | STIM008 - Light chain variable region | Amino acid sequence of $V_L$ of STIM008 | EIVLTQSPATLSLSPGERATLSCRASQSVTNYLAWHQQKPGQAPRL LIYDASNRATGIPARFSGSGSGTDFTLTISSLEPEDFAVYYCQQRS NWPLTFGGGTKVEIK |
| 488 | STIM008 - Light chain variable region | Nucleic acid sequence of $V_L$ of STIM008 | GAAATTGTGTTGACACAGTCTCCAGCCACCCTGTCTTTGTCTCCAG GGGAAAGAGCCACCCTCTCCTGCAGGGCCAGTCAGAGTGTTACCAA CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCTGGGACAGACTTCACTCTCACCATCAGCAG CCTAGAGCCTGAAGATTTTGCAGTTTATTACTGTCAGCAGCGTAGC AACTGGCCTCTCACTTTCGGCGGAGGGACCAAGGTGGAGATCAAA |
| 489 | STIM008 - full light chain sequence | Amino acid sequence of STIM008 light chain | EIVLTQSPATLSLSPGERATLSCRASQSVTNYLAWHQQKPGQAPRL LIYDASNRATGIPARFSGSGSGTDFTLTISSLEPEDFAVYYCQQRS NWPLTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |

TABLE S2-continued

| SEQ ID NOS: 343-538 | | | |
|---|---|---|---|
| SEQ ID NO: | Name | Description | Sequence |
| 490 | STIM008 - full light chain sequence | Nucleic acid sequence of STIM008 light chain | GAAATTGTGTTGACACAGTCTCCAGCCACCCTGTCTTTGTCTCCAG GGGAAAGAGCCACCCTCTCCTGCAGGGCCAGTCAGAGTGTTACCAA CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCTGGGACAGACTTCACTCTCACCATCAGCAG CCTAGAGCCTGAAGATTTTGCAGTTTATTACTGTCAGCAGCGTAGC AACTGGCCTCTCACTTTCGGCGGAGGGACCAAGGTGGAGATCAAAc gtacggtggccgctccctccgtgttcatcttcccaccttccgacga gcagctgaagtccggcaccgcttctgtcgtgtgcctgctgaacaac ttctacccccgcgaggccaaggtgcagtggaaggtggacaacgccc tgcagtccggcaactcccaggaatccgtgaccgagcaggactccaa ggacagcacctactccctgtcctccaccctgaccctgtccaaggcc gactacgagaagcacaaggtgtacgcctgcgaagtgacccaccagg gcctgtctagccccgtgaccaagtctttcaaccggggcgagtgt |
| 491 | STIM009 - CDRH1 | Amino acid sequence of CDRH1 of STIM009 using IMGT | GFTFSDYY |
| 492 | STIM009 - CDRH2 | Amino acid sequence of CDRH2 of STIM009 using IMGT | ISSSGSTI |
| 493 | STIM009 - CDRH3 | Amino acid sequence of CDRH3 of STIM009 using IMGT | ARDFYDILTDSPYFYYGVDV |
| 494 | STIM009 - Heavy chain variable region | Amino acid sequence of $V_H$ of STIM009 | QVQLVESGGGLVKPGGSLRLSCAASGFTFSDYYMSWIRQAPGKGLE WVSYISSSGSTIYYADSVKGRFTISRDNAKNSLYLQINSLRAEDTA VYYCARDFYDILTDSPYFYYGVDVWGQGTTVTVSS |
| 495 | STIM009 - Heavy chain variable region | Nucleic acid sequence of $V_H$ of STIM009 | CAGGTGCAGCTGGTGGAGTCTGGGGGAGGCTTGGTCAAGCCTGGAG GGTCCCTGAGACTCTCCTGTGCAGCCTCTGGATTCACCTTCAGTGA CTACTACATGAGCTGGATCCGCCAGGCTCCAGGGAAGGGGCTGGAG TGGGTTTCATACATTAGTAGTAGTGGTAGTACCATATACTACGCAG ACTCTGTGAAGGGCCGATTCACCATCTCCAGGGACAACGCCAAGAA CTCACTGTATCTGCAAATTAACAGCCTGAGAGCCGAGGACACGGCC GTGTATTACTGTGCGAGAGATTTTTACGATATTTTGACTGATAGTC CGTACTTCTACTACGGTGTGGACGTCTGGGGCCAAGGGACCACGGT CACCGTCTCCTCA |
| 496 | STIM009 - full heavy chain sequence | Amino acid sequence of STIM009 heavy chain | QVQLVESGGGLVKPGGSLRLSCAASGFTFSDYYMSWIRQAPGKGLE WVSYISSSGSTIYYADSVKGRFTISRDNAKNSLYLQINSLRAEDTA VYYCARDFYDILTDSPYFYYGVDVWGQGTTVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 497 | STIM009 - full heavy chain sequence | Nucleic acid sequence of STIM009 heavy chain | CAGGTGCAGCTGGTGGAGTCTGGGGGAGGCTTGGTCAAGCCTGGAG GGTCCCTGAGACTCTCCTGTGCAGCCTCTGGATTCACCTTCAGTGA CTACTACATGAGCTGGATCCGCCAGGCTCCAGGGAAGGGGCTGGAG TGGGTTTCATACATTAGTAGTAGTGGTAGTACCATATACTACGCAG ACTCTGTGAAGGGCCGATTCACCATCTCCAGGGACAACGCCAAGAA CTCACTGTATCTGCAAATTAACAGCCTGAGAGCCGAGGACACGGCC GTGTATTACTGTGCGAGAGATTTTTACGATATTTTGACTGATAGTC CGTACTTCTACTACGGTGTGGACGTCTGGGGCCAAGGGACCACGGT CACCGTCTCCTCAGCCAGCACCAAGGGCCCCTCTGTGTTCCCTCTG GCCCCTTCCAGCAAGTCCACCTCTGGCGGAACAGCCGCTCTGGGCT GCCTCGTGAAGGACTACTTCCCCGAGCCTGTGACCGTGTCCTGGAA CTCTGGCGCTCTGACCAGCGGAGTGCACACCTTCCCTGCTGTGCTG CAGTCCTCCGGCCTGTACTCCCTGTCCTCCGTCGTGACCGTGCCTT CCAGCTCTCTGGGCACCCAGACCTACATCTGCAACGTGAACCACAA GCCCTCCAACACCAAGGTGGACAAGAAGGTGGAACCCAAGTCCTGC GACAAGACCCACACCTGTCCCCCTTGTCCTGCCCCTGAACTGCTGG GCGGACCTTCCGTGTTCCTGTTCCCCCCAAAGCCCAAGGACACCCT GATGATCTCCCGGACCCCCGAAGTGACCTGCGTGGTGGTGGATGTG TCCCACGAGGACCCTGAAGTGAAGTTCAATTGGTACGTGGACGGCG TGGAAGTGCACAACGCCAAGACCAAGCCTAGAGAGGAACAGTACAA |

TABLE S2-continued

SEQ ID NOS: 343-538

| SEQ ID NO: | Name | Description | Sequence |
|---|---|---|---|
| | | | CTCCACCTACCGGGTGGTGTCCGTGCTGACCGTGCTGCACCAGGAT TGGCTGAACGGCAAAGAGTACAAGTGCAAGGTGTCCAACAAGGCCC TGCCTGCCCCCATCGAAAAGACCATCTCCAAGGCCAAGGGCCAGCC CCGGGAACCCCAGGTGTACACACTGCCCCCTAGCAGGGACGAGCTG ACCAAGAACCAGGTGTCCCTGACCTGTCTCGTGAAAGGCTTCTACC CCTCCGATATCGCCGTGGAATGGGAGTCCAACGGCCAGCCTGAGAA CAACTACAAGACCACCCCCCCTGTGCTGGACTCCGACGGCTCATTC TTCCTGTACAGCAAGCTGACAGTGGACAAGTCCCGGTGGCAGCAGG GCAACGTGTTCTCCTGCTCCGTGATGCACGAGGCCCTGCACAACCA CTACACCCAGAAGTCCCTGTCCCTGAGCCCCGGCAAGTGATGA |
| 498 | STIM009 - CDRL1 | Amino acid sequence of CDRL1 of STIM009 using IMGT | QSLLHSNGYNY |
| 499 | STIM009 - CDRL2 | Amino acid sequence of CDRL2 of STIM009 using IMGT | LGS |
| 500 | STIM009 - CDRL3 | Amino acid sequence of CDRL3 of STIM009 using IMGT | MQALQTPRT |
| 501 | STIM009 - Light chain variable region | Amino acid sequence of $V_L$ of STIM009 | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQALQTPRTFGQGTKVEIK |
| 502 | STIM009 - Light chain variable region | Nucleic acid sequence of $V_L$ of STIM009 | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTAATGGATACAACTATTTGGATTGGTACCTGCAGAAGCCAGGG CAGTCTCCACAGCTCCTGATCTATTTGGGTTCTAATCGGGCCTCCG GGGTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCTCGGACGTTCGGCCAAGGGACCA AGGTGGAAATCAAA |
| 503 | STIM009 - full light chain sequence | Amino acid sequence of STIM009 light chain | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQALQTPRTFGQGTKVEIKRTVAAPSVFIFPPSDEQLKSGTASVV CLLNNFYPREAKVQWKVDNALQSGNSQESVTEQDSKDSTYSLSSTL TLSKADYEKHKVYACEVTHQGLSSPVTKSFNRGEC |
| 504 | STIM009 - full light chain sequence | Nucleic acid sequence of STIM009 light chain | GATATTGTGATGACTCAGTCTCCACTCTCCCTGCCCGTCACCCCTG GAGAGCCGGCCTCCATCTCCTGCAGGTCTAGTCAGAGCCTCCTGCA TAGTAATGGATACAACTATTTGGATTGGTACCTGCAGAAGCCAGGG CAGTCTCCACAGCTCCTGATCTATTTGGGTTCTAATCGGGCCTCCG GGGTCCCTGACAGGTTCAGTGGCAGTGGATCAGGCACAGATTTTAC ACTGAAAATCAGCAGAGTGGAGGCTGAGGATGTTGGGGTTTATTAC TGCATGCAAGCTCTACAAACTCCTCGGACGTTCGGCCAAGGGACCA AGGTGGAAATCAAAcgtacggtggccgctccctccgtgttcatctt cccaccttccgacgagcagctgaagtccggcaccgcttctgtcgtg tgcctgctgaacaacttctacccccgcgaggccaaggtgcagtgga aggtggacaacgccctgcagtccggcaactcccaggaatccgtgac cgagcaggactccaaggacagcacctactccctgtcctccaccctg accctgtccaaggccgactacgagaagcacaaggtgtacgcctgcg aagtgacccaccagggcctgtctagccccgtgaccaagtctttcaa ccggggcgagtgt |
| 505 | Human PD-L1 Flag His (KYPROT286) | Amino acid sequence of KYPROT286 with FLAG tag in bold and underlined and histidine tag in bold | FTVTVPKDLYVVEYGSNMTIECKFPVEKQLDLAALIVYWEMEDKNI IQFVHGEEDLKVQHSSYRQRARLLKDQLSLGNAALQITDVKLQDAG VYRCMISYGGADYKRITVKVNAPYNKINQRILVVDPVTSEHELTCQ AEGYPKAEVIWTSSDHQVLSGKTTTTNSKREEKLFNVTSTLRINTT TNEIFYCTFRRLDPEENHTAELVIPELPLAHPPNERTIEGR**DYKDD DDKHHHHHH** |
| 506 | Mature human ICOS | Mature amino acid sequence of human ICOS | EINGSANYEMFIFHNGGVQILCKYPDIVQQFKMQLLKGGQILCDLT KTKGSGNTVSIKSLKFCHSQLSNNSVSFFLYNLDHSHANYYFCNLS IFDPPPFKVTLTGGYLHIYESQLCCQLKFWLPIGCAAFVVVCILGC ILICWLTKKKYSSSVHDPNGEYMFMRAVNTAKKSRLTDVTL |

TABLE S2-continued

SEQ ID NOS: 343-538

| SEQ ID NO: | Name | Description | Sequence |
|---|---|---|---|
| 507 | Human ICOS extracellular domain | Amino acid sequence of human ICOS extracellular domain | EINGSANYEMFIFHNGGVQILCKYPDIVQQFKMQLLKGGQILCDLT<br>KTKGSGNTVSIKSLKFCHSQLSNNSVSFFLYNLDHSHANYYFCNLS<br>IFDPPPFKVTLTGGYLHIYESQLCCQLKF |
| 508 | Human ICOS with signal peptide | Amino acid sequence of human ICOS (signal peptide is underlined) | MKSGLWYFFLFCLRIKVLTGEINGSANYEMFIFHNGGVQILCKYPD<br>IVQQFKMQLLKGGQILCDLTKTKGSGNTVSIKSLKFCHSQLSNNSV<br>SFFLYNLDHSHANYYFCNLSIFDPPPFKVTLTGGYLHIYESQLCCQ<br>LKFWLPIGCAAFVVVCILGCILICWLTKKKYSSSVHDPNGEYMFMR<br>AVNTAKKSRLTDVTL |
| 509 | Isoform of human ICOS (Q9Y6W8-2) | Amino acid sequence of a human ICOS isoform | The sequence of this isoform differs from the canonical sequence in its cytoplasmic domain as follows: 168-199:<br>KYSSSVHDPNGEYMFMRAVNTAKKSRLTDVTLM |
| 510 | Mature mouse ICOS | Mature amino acid sequence of mouse ICOS | EINGSADHRMFSFHNGGVQISCKYPETVQQLKMRLFREREVLCELT<br>KTKGSGNAVSIKNPMLCLYHLSNNSVSFFLNNPDSSQGSYYFCSLS<br>IFDPPPFQERNLSGGYLHIYESQLCCQLKIVVQVTE |
| 511 | Mouse ICOS extracellular domain | Amino acid sequence of the extracellular domain of mouse ICOS | EINGSADHRMFSFHNGGVQISCKYPETVQQLKMRLFREREVLCELT<br>KTKGSGNAVSIKNPMLCLYHLSNNSVSFFLNNPDSSQGSYYFCSLS<br>IFDPPPFQERNLSGGYLHIYESQLCCQLK |
| 512 | Mouse ICOS with signal peptide | Amino acid sequence of mouse ICOS (signal peptide is underlined) | MGWSCIILFLVATATGVHSEINGSADHRMFSFHNGGVQISCKYPET<br>VQQLKMRLFREREVLCELTKTKGSGNAVSIKNPMLCLYHLSNNSVS<br>FFLNNPDSSQGSYYFCSLSIFDPPPFQERNLSGGYLHIYESQLCCQ<br>LKIVVQVTE |
| 513 | Cynomolgus ICOS with signal peptide | Amino acid sequence of cynomolgus ICOS (signal peptide is underlined) | MKSGLWYFFL FCLHMKVLTG EINGSANYEM FIFHNGGVQI<br>LCKYPDIVQQ<br>FKMQLLKGGQILCDLTKTKGSGNKVSIKSLKFCHSQLSNNSVSFFL<br>YNLD<br>RSHANYYFCNLSIFDPPPFKVTLTGGYLHIYESQLCCQLKFWLPIG<br>CATF<br>VVVCIFGCILICWLTKKKYSSTVHDPNGEYMFMRAVNTAKKSRLTG<br>TTP |
| 514 | Cynomolgus ICOS extracellular domain | Amino acid sequence of cynomolgus ICOS extracellular domain | EINGSANYEMFIFHNGGVQILCKYPDIVQQFKMQLLKGGQILCDLT<br>KTKG<br>SGNKVSIKSLKFCHSQLSNNSVSFFLYNLDRSHANYYFCNLSIFDP<br>PPFK VTLTGGYLHIYESQLCCQLK |
| 515 | Human ICOS ligand | Amino acid sequence of human ICOS ligand comprising extracellular domain | DTQEKEVRAMVGSDVELSCACPEGSRFDLNDVYVYWQTSESKTVVT<br>YHIPQNSSLENVDSRYRNRALMSPAGMLRGDFSLRLFNVTPQDEQK<br>FHCLVLSQSLGFQEVLSVEVTLHVAANFSVPVVSAPHSPSQDELTF<br>TCTSINGYPRPNVYWINKTDNSLLDQALQNDTVELNMRGLYDVVSV<br>LRIARTPSVNIGCCIENVLLQQNLTVGSQTGNDIGERDKITENPVS<br>TGEKNAATWS |
| 516 | Human ICOS ligand | Amino acid sequence of human ICOS ligand including signal peptide | MRLGSPGLLFLLFSSLRADTQEKEVRAMVGSDVELSCACPEGSRFD<br>LNDVYVYWQTSESKTVVTYHIPQNSSLENVDSRYRNRALMSPAGML<br>RGDFSLRLFNVTPQDEQKFHCLVLSQSLGFQEVLSVEVTLHVAANF<br>SVPVVSAPHSPSQDELTFTCTSINGYPRPNVYWINKTDNSLLDQAL<br>QNDTVELNMRGLYDVVSVLRIARTPSVNIGCCIENVLLQQNLTVGS<br>QTGNDIGERDKITENPVSTGEKNAATWSILAVLCLLVVVAVAIGWV<br>CRDRCLQHSYAGAWAVSPETELTGHV |

TABLE S2-continued

SEQ ID NOS: 343-538

| SEQ ID NO: | Name | Description | Sequence |
|---|---|---|---|
| SEQ ID NO: 610 ICOSL-Fc<br>DTQEKEVRAMVGSDVELSCACPEGSRFDLNDVYVYWQTSESKTVVTYHIPQNSSLENVDSRYRNRALMSPAGMLRGDFSLRLFNVT<br>PQDEQKFHCLVLSQSLGFQEVLSVEVTLHVAANFSVPVVSAPHSPSQDELTFTCTSINGYPRPNVYWINKTDNSLLDQALQNDTVF<br>LNMRGLYDVVSVLRIARTPSVNIGCCIENVLLQQNLTVGSQTGNDIGERDKITENPVSTGEKNAATWS**DIEGRMD**PKSCDKTHTCP<br>PCPAPELLGGPSVFLEPPKPKDTLMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSRDELTKNQVSLTCLVKGFYPSDIAVEWESNGQPENNYKTTPPVLD<br>SDGSFFLYSKLTVDKSRWQQGNVESCSVMHEALHNHYTQKSLSLSPGK<br>Linker is underlined and in bold. Sequence preceding linker is human ICOSL (B7-H2).<br>Sequence following linker is human IgG1 Fc. | | | |
| 517 | C-terminal amino acid sequence of hIL-2 | Amino acids 21 to 133 of hIL-2 with R38W mutation (bold & underlined) | LQMILNGINNYKNPKLT**A**MLTFKFYMPKKATELKHLQCL<br>EEELKPLEEVLNLAQSKNFHLRPRDLISNINVIVLELKG<br>SETTFMCEYADETATIVEFLNRWITFCQSIISTLT |
| 518 | C-terminal amino acid sequence of hIL-2 | Amino acids 21 to 133 of hIL-2 with R38Q mutation (bold & underlined) | LQMILNGINNYKNPKLT**Q**MLTFKFYMPKKATELKHLQCL<br>EEELKPLEEVLNLAQSKNFHLRPRDLISNINVIVLELKG<br>SETTFMCEYADETATIVEFLNRWITFCQSIISTLT |
| 519 | STIM002 - Corrected Light chain variable region | Nucleic acid sequence of corrected $V_L$ of STIM002 | GATATTGTGATGACTCAGTCTCCACTCTCCCTGCCCGTC<br>ACCCCTGGAGAGCCGGCCTCCATCTCCTGCAGGTCTAGT<br>CAGAGCCTCCTGCATAGTGATGGATACAACTATTTGGAT<br>TGGTACCTGCAGAAGCCAGGGCAGTCTCCACAGCTCCTG<br>ATCTATTTGGGTTCTACTCGGGCCTCCGGGTTCCCTGAC<br>AGGTTCAGTGGCAGTGGATCAGGCACAGATTTTACACTG<br>AAAATCAGCAGAGTGGAGGCTGAGGATGTTGGGGTTTAT<br>TACTGCATGCAAGCTCTACAAACTCCGCTCAGTTTTGGC<br>CAGGGGACCAAGCTGGAGATCAAA |
| 520 | STIM002 - Corrected full light chain sequence | Nucleic acid sequence of corrected STIM002 light chain | GATATTGTGATGACTCAGTCTCCACTCTCCCTGCCCGTC<br>ACCCCTGGAGAGCCGGCCTCCATCTCCTGCAGGTCTAGT<br>CAGAGCCTCCTGCATAGTGATGGATACAACTATTTGGAT<br>TGGTACCTGCAGAAGCCAGGGCAGTCTCCACAGCTCCTG<br>ATCTATTTGGGTTCTACTCGGGCCTCCGGGTTCCCTGAC<br>AGGTTCAGTGGCAGTGGATCAGGCACAGATTTTACACTG<br>AAAATCAGCAGAGTGGAGGCTGAGGATGTTGGGGTTTAT<br>TACTGCATGCAAGCTCTACAAACTCCGCTCAGTTTTGGC<br>CAGGGGACCAAGCTGGAGATCAAAcgtacggtggccgct<br>ccctccgtgttcatcttcccaccttccgacgagcagctg<br>aagtccggcaccgcttctgtcgtgtgcctgctgaacaac<br>ttctacccccgcgaggccaaggtgcagtggaaggtggac<br>aacgccctgcagtccggcaactcccaggaatccgtgacc<br>gagcaggactccaaggacagcacctactccctgtcctcc<br>accctgaccctgtccaaggccgactacgagaagcacaag<br>gtgtacgcctgcgaagtgacccaccagggcctgtctagc<br>cccgtgaccaagtctttcaaccggggcgagtgt |
| 521 | STIM003 - Corrected heavy chain variable region | Nucleic acid sequence of corrected $V_H$ of STIM003 | GAGGTGCAGCTGGTGGAGTCTGGGGGAGGTGTGGTACGG<br>CCTGGGGGGTCCCTGAGACTCTCCTGTGTAGCCTCTGGA<br>GTCACCTTTGATGATTATGGCATGAGCTGGGTCCGCCAA<br>GCTCCAGGGAAGGGGCTGGAGTGGGTCTCTGGTATTAAT<br>TGGAATGGTGGCGACACAGATTATTCAGACTCTGTGAAG<br>GGCCGATTCACCATCTCCAGAGACAACGCCAAGAACTCC<br>CTGTATCTACAAATGAATAGTCTGAGAGCCGAGGACACG<br>GCCTTGTATTACTGTGCGAGGGATTTCTATGGTTCGGGG<br>AGTTATTATCACGTTCCTTTTGACTACTGGGGCCAGGGA<br>ATCCTGGTCACCGTCTCCTCA |
| 522 | STIM003 - Corrected full heavy chain sequence | Nucleic acid sequence of corrected STIM003 heavy chain | GAGGTGCAGCTGGTGGAGTCTGGGGGAGGTGTGGTACGG<br>CCTGGGGGGTCCCTGAGACTCTCCTGTGTAGCCTCTGGA<br>GTCACCTTTGATGATTATGGCATGAGCTGGGTCCGCCAA<br>GCTCCAGGGAAGGGGCTGGAGTGGGTCTCTGGTATTAAT<br>TGGAATGGTGGCGACACAGATTATTCAGACTCTGTGAAG<br>GGCCGATTCACCATCTCCAGAGACAACGCCAAGAACTCC<br>CTGTATCTACAAATGAATAGTCTGAGAGCCGAGGACACG<br>GCCTTGTATTACTGTGCGAGGGATTTCTATGGTTCGGGG<br>AGTTATTATCACGTTCCTTTTGACTACTGGGGCCAGGGA<br>ATCCTGGTCACCGTCTCCTCAGCCAGCACCAAGGGCCCC<br>TCTGTGTTCCCTCTGGCCCCTTCCAGCAAGTCCACCTCT<br>GGCGGAACAGCCGCTCTGGGCTGCCTCGTGAAGGACTAC<br>TTCCCCGAGCCTGTGACCGTGTCCTGGAACTCTGGCGCT<br>CTGACCAGCGGAGTGCACACCTTCCCTGCTGTGCTGCAG |

TABLE S2-continued

SEQ ID NOS: 343-538

| SEQ ID NO: | Name | Description | Sequence |
|---|---|---|---|
| | | | TCCTCCGGCCTGTACTCCCTGTCCTCCGTCGTGACCGTG CCTTCCAGCTCTCTGGGCACCCAGACCTACATCTGCAAC GTGAACCACAAGCCCTCCAACACCAAGGTGGACAAGAAG GTGGAACCCAAGTCCTGCGACAAGACCCACACCTGTCCC CCTTGTCCTGCCCCTGAACTGCTGGGCGGACCTTCCGTG TTCCTGTTCCCCCCAAAGCCCAAGGACACCCTGATGATC TCCCGGACCCCCGAAGTGACCTGCGTGGTGGTGGATGTG TCCCACGAGGACCCTGAAGTGAAGTTCAATTGGTACGTG GACGGCGTGGAAGTGCACAACGCCAAGACCAAGCCTAGA GAGGAACAGTACAACTCCACCTACCGGGTGGTGTCCGTG CTGACCGTGCTGCACCAGGATTGGCTGAACGGCAAAGAG TACAAGTGCAAGGTGTCCAACAAGGCCCTGCCTGCCCCC ATCGAAAAGACCATCTCCAAGGCCAAGGGCCAGCCCCGG GAACCCCAGGTGTACACACTGCCCCCTAGCAGGGACGAG CTGACCAAGAACCAGGTGTCCCTGACCTGTCTCGTGAAA GGCTTCTACCCCTCCGATATCGCCGTGGAATGGGAGTCC AACGGCCAGCCTGAGAACAACTACAAGACCACCCCCCCT GTGCTGGACTCCGACGGCTCATTCTTCCTGTACAGCAAG CTGACAGTGGACAAGTCCCGGTGGCAGCAGGGCAACGTG TTCTCCTGCTCCGTGATGCACGAGGCCCTGCACAACCAC TACACCCAGAAGTCCCTGTCCCTGAGCCCCGGCAAGTGA TGA |
| 523 | Human IgG1 constant region IGHG1*03 | Human Heavy Chain Constant Region (IGHG1*03) Nucleotide Sequence | gcctccaccaagggcccatcggtcttccccctggcaccc tcctccaagagcacctctgggggcacagcggccctgggc tgcctggtcaaggactacttccccgaaccggtgacggtg tcgtggaactcaggcgccctgaccagcggcgtgcacacc ttcccggctgtcctacagtcctcaggactctactccctc agcagcgtggtgaccgtgccctccagcagcttgggcacc cagacctacatctgcaacgtgaatcacaagcccagcaac accaaggtggacaagagagttgagcccaaatcttgtgac aaaactcacacatgcccaccgtgcccagcacctgaactc ctggggggaccgtcagtcttcctcttccccccaaaaccc aaggacaccctcatgatctcccggacccctgaggtcaca tgcgtggtggtggacgtgagccacgaagaccctgaggtc aagttcaactggtacgtggacggcgtggaggtgcataat gccaagacaaagccgcgggaggagcagtacaacagcacg taccgtgtggtcagcgtcctcaccgtcctgcaccaggac tggctgaatggcaaggagtacaagtgcaaggtctccaac aaagccctcccagcccccatcgagaaaaccatctccaaa gccaaagggcagccccgagaaccacaggtgtacaccctg cccccatcccgggaggagatgaccaagaaccaggtcagc ctgacctgcctggtcaaaggcttctatcccagcgacatc gccgtggagtgggagagcaatgggcagccggagaacaac tacaagaccacgcctcccgtgctggactccgacggctcc ttcttcctctatagcaagctcaccgtggacaagagcagg tggcagcaggggaacgtcttctcatgctccgtgatgcat gaggctctgcacaaccactacacgcagaagagcctctcc ctgtccccgggtaaa |
| 524 | | Human Heavy Chain Constant Region (IGHG1*03) Protein Sequence | A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K R V E P K S C D K T H T C P P C P A P E L L G G P S V F L F P P K P K D T L M I S R T P E V T C V V V D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R E E M T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G K |

TABLE S2-continued

SEQ ID NOS: 343-538

| SEQ ID NO: | Name | Description | Sequence |
|---|---|---|---|
| 525 | Human IgG1 constant region IGHG1*04 | Human Heavy Chain Constant Region (IGHG1*04) Nucleotide Sequence | gcctccaccaagggcccatcggtcttccccctggcaccc tcctccaagagcacctctgggggcacagcggccctgggc tgcctggtcaaggactacttccccgaaccggtgacggtg tcgtggaactcaggcgccctgaccagcggcgtgcacacc ttcccggctgtcctacagtcctcaggactctactccctc agcagcgtggtgaccgtgccctccagcagcttgggcacc cagacctacatctgcaacgtgaatcacaagcccagcaac accaaggtggacaagaaagttgagcccaaatcttgtgac aaaactcacacatgcccaccgtgcccagcacctgaactc ctggggggaccgtcagtcttcctcttccccccaaaaccc aaggacaccctcatgatctcccggacccctgaggtcaca tgcgtggtggtggacgtgagccacgaagaccctgaggtc aagttcaactggtacgtggacggcgtggaggtgcataat gccaagacaaagccgcgggaggagcagtacaacagcacg taccgtgtggtcagcgtcctcaccgtcctgcaccaggac tggctgaatggcaaggagtacaagtgcaaggtctccaac aaagccctcccagcccccatcgagaaaaccatctccaaa gccaaagggcagccccgagaaccacaggtgtacaccctg cccccatcccgggatgagctgaccaagaaccaggtcagc ctgacctgcctggtcaaaggcttctatcccagcgacatc gccgtggagtgggagagcaatgggcagccggagaacaac tacaagaccacgcctcccgtgctggactccgacggctcc ttcttcctctacagcaagctcaccgtggacaagagcagg tggcagcaggggaacatcttctcatgctccgtgatgcat gaggctctgcacaaccactacacgcagaagagcctctcc ctgtctccgggtaaa |
| 526 | | Human Heavy Chain Constant Region (IGHG1*04) Protein Sequence | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNIFSCSVMH EALHNHYTQKSLSLSPGK |
| 527 | Human IgG2 constant region IGHG2*01 & IGHG2*03 & IGHG2*05 | Human Heavy Chain Constant Region (IGHG2*01) Nucleotide Sequence | gcctccaccaagggcccatcggtcttccccctggcgccc tgctccaggagcacctccgagagcacagccgccctgggc tgcctggtcaaggactacttccccgaaccggtgacggtg tcgtggaactcaggcgctctgaccagcggcgtgcacacc ttcccagctgtcctacagtcctcaggactctactccctc agcagcgtggtgaccgtgccctccagcaacttcggcacc cagacctacacctgcaacgtagatcacaagcccagcaac accaaggtggacaagacagttgagcgcaaatgttgtgtc gagtgcccaccgtgcccagcaccacctgtggcaggaccg tcagtcttcctcttccccccaaaacccaaggacaccctc atgatctcccggacccctgaggtcacgtgcgtggtggtg gacgtgagccacgaagaccccgaggtccagttcaactgg tacgtggacggcgtggaggtgcataatgccaagacaaag ccacgggaggagcagttcaacagcacgttccgtgtggtc agcgtcctcaccgttgtgcaccaggactggctgaacggc aaggagtacaagtgcaaggtctccaacaaaggcctccca gcccccatcgagaaaaccatctccaaaaccaaagggcag ccccgagaaccacaggtgtacaccctgcccccatcccgg gaggagatgaccaagaaccaggtcagcctgacctgcctg gtcaaaggcttctaccccagcgacatcgccgtggagtgg gagagcaatgggcagccggagaacaactacaagaccaca cctcccatgctggactccgacggctccttcttcctctac agcaagctcaccgtggacaagagcaggtggcagcagggg aacgtcttctcatgctccgtgatgcatgaggctctgcac aaccactacacgcagaagagcctctccctgtctccgggt aaa |
| 528 | | Human Heavy Chain Constant Region (IGHG2*01) Protein Sequence | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKCCVECPPCPAPPVAGP SVFLFPPKPKDTLMISRTPEVTCVVVDVSHEDPEVQFNW YVDGVEVHNAKTKPREEQFNSTFRVVSVLTVVHQDWLNG KEYKCKVSNKGLPAPIEKTISKTKGQPREPQVYTLPPSR EEMTKNQVSLTCLVKGFYPSDIAVEWESNGQPENNYKTT PPMLDSDGSFFLYSKLTVDKSRWQQGNVFSCSVMHEALH NHYTQKSLSLSPGK |

TABLE S2-continued

SEQ ID NOS: 343-538

| SEQ ID NO: | Name | Description | Sequence |
|---|---|---|---|
| 529 | Human IgG2 constant region IGHG2*02 | Human Heavy Chain Constant Region (IGHG2*02) Nucleotide Sequence | GCCTCCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCCGGCTGTCCTACAGTCCTCAGGACTCTACTCCCTCAGCAGCGTGGTGACCGTGACCTCCAGCAACTTCGGCACCCAGACCTACACCTGCAACGTAGATCACAAGCCCAGCAACACCAAGGTGGACAAGACAGTTGAGCGCAAATGTTGTGTCGAGTGCCCACCGTGCCCAGCACCACCTGTGGCAGGACCGTCAGTCTTCCTCTTCCCCCCAAAACCCAAGGACACCCTCATGATCTCCCGGACCCCTGAGGTCACGTGCGTGGTGGTGGACGTGAGCCACGAAGACCCCGAGGTCCAGTTCAACTGGTACGTGGACGGCATGGAGGTGCATAATGCCAAGACAAAGCCACGGGAGGAGCAGTTCAACAGCACGTTCCGTGTGGTCAGCGTCCTCACCGTCGTGCACCAGGACTGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTACCCCAGCGACATCGCCGTGGAGTGGGAGAGCAATGGGCAGCCGGAGAACAACTACAAGACCACACCTCCCATGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACACAGAAGAGCCTCTCCCTGTCTCCGGGTAAA |
| 530 | | Human Heavy Chain Constant Region (IGHG2*02) Protein Sequence | ASTKGPSVFPLAPCSRSTSESTAALGCLVKDYFPEPVTVSWNSGALTSGVHTFPAVLQSSGLYSLSSVVTVTSSNFGTQTYTCNVDHKPSNTKVDKTVERKCCVECPPCPAPPVAGPSVFLFPPKPKDTLMISRTPEVTCVVVDVSHEDPEVQFNWYVDGMEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 531 | Human IgG2 constant region IGHG2*04 | Human Heavy Chain Constant Region (IGHG2*04) Nucleotide Sequence | gcctccaccaagggcccatcggtcttccccctggcgccctgctccaggagcacctccgagagcacagcggccctgggctgcctggtcaaggactacttccccgaaccggtgacggtgtcgtggaactcaggcgctctgaccagcggcgtgcacaccttcccagctgtcctacagtcctcaggactctactccctcagcagcgtggtgaccgtgccctccagcagcttgggcacccagacctacacctgcaacgtagatcacaagcccagcaacaccaaggtggacaagacagttgagcgcaaatgttgtgtcgagtgcccaccgtgcccagcaccacctgtggcaggaccgtcagtcttcctcttccccccaaaacccaaggacaccctcatgatctcccggacccctgaggtcacgtgcgtggtggtggacgtgagccacgaagaccccgaggtccagttcaactggtacgtggacggcgtggaggtgcataatgccaagacaaagccacgggaggagcagttcaacagcacgttccgtgtggtcagcgtcctcaccgttgtgcaccaggactggctgaacggcaaggagtacaagtgcaaggtctccaacaaaggcctcccagcccccatcgagaaaaccatctccaaaaccaaagggcagccccgagaaccacaggtgtacaccctgcccccatcccgggaggagatgaccaagaaccaggtcagcctgacctgcctggtcaaaggcttctaccccagcgacatcgccgtggagtgggagagcaatgggcagccggagaacaactacaagaccacacctcccatgctggactccgacggctccttcttcctctacagcaagctcaccgtggacaagagcaggtggcagcaggggaacgtcttctcatgctccgtgatgcatgaggctctgcacaaccactacacgcagaagagcctctccctgtctccgggtaaa |
| 532 | | Human Heavy Chain Constant Region (IGHG2*04) Protein Sequence | ASTKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |

TABLE S2-continued

SEQ ID NOS: 343-538

| SEQ ID NO: | Name | | Description | Sequence |
|---|---|---|---|---|
| 533 | Human IgG2 constant region | IGHG2*06 | Human Heavy Chain Constant Region (IGHG2*06) Nucleotide Sequence | GCCTCCACCAAGGGCCCATCGGTCTTCCCCCTGGCGCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCCGGCTGTCCTACAGTCCTCAGGACTCTACTCCCTCAGCAGCGTGGTGACCGTGCCCTCCAGCAACTTCGGCACCCAGACCTACACCTGCAACGTAGATCACAAGCCCAGCAACACCAAGGTGGACAAGACAGTTGAGCGCAAATGTTGTGTCGAGTGCCCACCGTGCCCAGCACCACCTGTGGCAGGACCGTCAGTCTTCCTCTTCCCCCCAAAACCCAAGGACACCCTCATGATCTCCCGGACCCCTGAGGTCACGTGCGTGGTGGTG.GACGTGAGCCACGAAGACCCCGAGGTCCAGTTCAACTGGTACGTGGACGGCGTGGAGGTGCATAATGCCAAGACAAAGCCACGGGAGGAGCAGTTCAACAGCACGTTCCGTGTGGTCAGCGTCCTCACCGTCGTGCACCAGGACTGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTACCCCAGCGACATCTCCGTGGAGTGGGAGAGCAATGGGCAGCCGGAGAACAACTACAAGACCACACCTCCCATGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACACAGAAGAGCCTCTCCCTGTCTCCGGGTAAA |
| 534 | | | Human Heavy Chain Constant Region (IGHG2*06) Protein Sequence | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK |
| 535 | Human Cλ constant region | IGLC7*03 | Cλ Light Chain Constant Region (IGLC7*03) Nucleotide Sequence | GGTCAGCCCAAGGCTGCCCCCTCGGTCACTCTGTTCCCACCCTCCTCTGAGGAGCTTCAAGCCAACAAGGCCACACTGGTGTGTCTCGTAAGTGACTTCAACCCGGGAGCCGTGACAGTGGCCTGGAAGGCAGATGGCAGCCCCGTCAAGGTGGGAGTGGAGACCACCAAACCCTCCAAACAAAGCAACAACAAGTATGCGGCCAGCAGCTACCTGAGCCTGACGCCCGAGCAGTGGAAGTCCCACAGAAGCTACAGCTGCCGGGTCACGCATGAAGGGAGCACCGTGGAGAAGACAGTGGCCCCTGCAGAATGCTCT |
| 536 | | | Cλ Light Chain Constant Region (IGLC7*03) Amino Acid Sequence | GQPKAAPSVTLFPPSSEELQANKATLVCLVSDFNPGAVTVAWKADGSPVKVGVETTKPSKQSNNKYAASSYLSLTPEQWKSHRSYSCRVTHEGSTVEKTVAPAECS |

TABLE S2-continued

SEQ ID NOS: 343-538

| SEQ ID NO: | Name | | Description | Sequence |
|---|---|---|---|---|
| 537 | Human WT IgG1 constant region | IGHG1*01 & IGHG1*05 (IgG1) | WT human IgG1 nucleotide sequence #2 | gcctccaccaagggcccatcggtcttccccctggcaccc tcctccaagagcacctctgggggcacagcggccctgggc tgcctggtcaaggactacttccccgaaccggtgacggtg tcgtggaactcaggcgccctgaccagcggcgtgcacacc ttcccggctgtcctacagtcctcaggactctactccctc agcagcgtggtgaccgtgccctccagcagcttgggcacc cagacctacatctgcaacgtgaatcacaagcccagcaac accaaggtggacaagaaagttgagcccaaatcttgtgac aaaactcacacatgcccaccgtgcccagcacctgaactc ctggggggaccgtcagtcttcctcttccccccaaaaccc aaggacaccctcatgatctcccggacccctgaggtcaca tgcgtggtggtggacgtgagccacgaagaccctgaggtc aagttcaactggtacgtggacggcgtggaggtgcataat gccaagacaaagccgcgggaggagcagtacaacagcacg taccgggtggtcagcgtcctcaccgtcctgcaccaggac tggctgaatggcaaggagtacaagtgcaaggtctccaac aaagccctcccagcccccatcgagaaaaccatctccaaa gccaaagggcagccccgagaaccacaggtgtacaccctg cccccatcccgggatgagctgaccaagaaccaggtcagc ctgacctgcctggtcaaaggcttctatcccagcgacatc gccgtggagtgggagagcaatgggcagccggagaacaac tacaagaccacgcctcccgtgctggactccgacggctcc ttcttcctctacagcaagctcaccgtggacaagagcagg tggcagcaggggaacgtcttctcatgctccgtgatgcat gaggctctgcacaaccactacacgcagaagagcctctcc ctgtctccgggtaaa |
| 538 | Human Cλ constant region | IGLC2*01 | Cλ Light Chain Constant Region Amino Acid Sequence #2 - Encoded by nucleotide sequence version A & B | GQPKAAPSVTLFPPSSEELQANKATLVCLISDFYPGAVT VAWKADSSPVKAGVETTTPSKQSNNKYAASSYLSLTPEQ WKSHRSYSCQVTHEGSTVEKTVAPTECS |

TABLE S3

SEQ ID NOS: 539-562

| | | Sequence |
|---|---|---|
| | | hIgG1 FIT-Ig bispecific 1a |
| Antibody A | anti-ICOS STIM003 | |
| Antibody B | anti-PD-L1 84G09 | |
| FIT-Ig Construct #1 | SEQ ID NO: 539 | DIQMTQSPASLSASLGETVTIQCRASEDIYSGLAWFQQKPGKSPQLLIYGASS LQDGVPSRFSGSGSGTQYSLKISSMQTEDEGVYFCQQGLKYPPTFGSGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFNRG ECEVQLVESGGGLTQPGKSLKLSCEASGFTFSSFTMHWVRQSPGKGLEWVAFI RSGSGIVFYADAVRGRFTISRDNAKNLLFLQMNDLKSEDTAMYYCARRPLGHN TFDSWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPSN TKVDKKVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRWQQG NVFSCSVMHEALHNHYTQKSLSLSPGK |
| FIT-Ig Construct #2 | SEQ ID NO: 540 | EVQLVESGGGLVQPGRSLKLSCAASGFTFSDFYMAWVRQAPKKGLEWVASISY EGSSTYYGDSVMGRFTISRDNAKSTLYLQMNSLRSEDTATYYCARQREANWED WGQGVMVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVD KKV |

TABLE S3-continued

| SEQ ID NOS: 539-562 | | |
|---|---|---|
| | | Sequence |
| FIT-Ig Construct #3 | SEQ ID NO: 541 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| hIgG1 FIT-Ig bispecific 1b | | |
| Antibody A | anti-PD-L1 84G09 | |
| Antibody B | anti-ICOS STIM003 | |
| FIT-Ig Construct #1 | SEQ ID NO: 542 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| FIT-Ig Construct #2 | SEQ ID NO: 543 | EVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| FIT-Ig Construct #3 | SEQ ID NO: 544 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| hIgG1 FIT-Ig bispecific 2a | | |
| Antibody A | anti-ICOS STIM001 | |
| Antibody B | anti-PD-L1 1D05 | |
| FIT-Ig Construct #1 | SEQ ID NO: 545 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTDAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNECEVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 546 | EVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKI |
| FIT-Ig Construct #3 | SEQ ID NO: 547 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTDAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |

TABLE S3-continued

| SEQ ID NOS: 539-562 | | |
|---|---|---|
| | | Sequence |
| hIgG1 FIT-Ig bispecific 2b | | |
| Antibody A | anti-PD-L1 1D05 | |
| Antibody B | anti-ICOS STIM001 | |
| FIT-Ig Construct #1 | SEQ ID NO: 548 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTDAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNECEVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 549 | EVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKI |
| FIT-Ig Construct #3 | SEQ ID NO: 550 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTDAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| hIgG1 FIT-Ig bispecific 3a | | |
| Antibody A | anti-ICOS STIM003 | |
| Antibody B | anti-PD-L1 1D05 | |
| FIT-Ig Construct #1 | SEQ ID NO: 551 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 552 | EVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| FIT-Ig Construct #3 | SEQ ID NO: 553 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| hIgG1 FIT-Ig bispecific 3b | | |
| Antibody A | anti-PD-L1 1D05 | |
| Antibody B | anti-ICOS STIM003 | |

TABLE S3-continued

| SEQ ID NOS: 539-562 | | |
|---|---|---|
| | | Sequence |
| FIT-Ig Construct #1 | SEQ ID NO: 554 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 555 | EVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| FIT-Ig Construct #3 | SEQ ID NO: 556 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| hIgG1 FIT-Ig bispecific 4a | | |
| Antibody A | anti-ICOS STIM001 | |
| Antibody B | anti-PD-L1 84G09 | |
| FIT-Ig Construct #1 | SEQ ID NO: 557 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 558 | EVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| FIT-Ig Construct #3 | SEQ ID NO: 559 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| hIgG1 FIT-Ig bispecific 4b | | |
| Antibody A | anti-PD-L1 84G09 | |
| Antibody B | anti-ICOS STIM001 | |

TABLE S3-continued

| SEQ ID NOS: 539-562 | | |
|---|---|---|
| | | Sequence |
| FIT-Ig Construct #1 | SEQ ID NO: 560 | DIVMTQSPSSLAVSPGEKVTMTCKSSQSLYYSGVKENLLAWYQQKPGQSPKLLIYYASIRFTGVPDRFTGSGSGTDYTLTITSVQAEDMGQYFCQQGINNPLTFGDGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLVQPGRSLKLSCAASGFTFSDFYMAWVRQAPKKGLEWVASISYEGSSTYYGDSVMGRFTISRDNAKSTLYLQMNSLRSEDTATYYCARQREANWEDWGQGVMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| FIT-Ig Construct #2 | SEQ ID NO: 561 | EVQLVESGGGLTQPGKSLKLSCEASGFTFSSFTMHWVRQSPGKGLEWVAFIRSGSGIVFYADAVRGRFTISRDNAKNLLFLQMNDLKSEDTAMYYCARRPLGHNTFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| FIT-Ig Construct #3 | SEQ ID NO: 562 | DIQMTQSPASLSASLGETVTIQCRASEDIYSGLAWFQQKPGKSPQLLIYGASSLQDGVPSRFSGSGSGTQYSLKISSMQTEDEGVYFCQQGLKYPPTFGSGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE S4

Sequences of antibody heavy chain variable regions obtained from additional clones
CDRs are defined according to IMGT.

| CLONE_ID | VH_NUCLEOTIDE_SEQUENCE | VH_AMINO_ACID_SEQ | HCDR1 | HCDR2 | HCDR3 |
|---|---|---|---|---|---|
| CL-61091 | CAGGTTCAACTGATGCAGTCTGGAACTGAGGTGAAGAAGCCTGGGGCCTCAGTGAAGGTCTCCTGCAAGACTTCTGGTTACACCTTTACCACCTATGGTATCACTTGGGTGCGACAGGCCCCTGGACAAGGGCTTGAGTGGATGGGATGGATCAGCGCTTACAGTGGTGACACAGACTATGCACAGAAGTTCCAGGGCAGAGTCACCGTGACAACAGACACATCCACGAACACAGCCTACATGGAGTTGAGGAGCCTGAAATCTGACGACACGGCCGTGTATTATTGTGCGAGAAGTAGTGGCTGGCCCCACCACTACGGTATGGACGTCTGGGGCCAAGGGACCACGGTCACCGTCTCCTCAG SEQ ID NO: 563 | QVQLMQSGTEVKKPGASVKVSCKTSGYTFTTYGITWVRQAPGQGLEWMGWISAYSGDTDYAQKFQGRVTVTTDTSTNTAYMELRSLKSDDTAVYYCARSSGWPHHYGMDVWGQGTTVTVSS SEQ ID NO: 564 | GYTFTTYG SEQ ID NO: 565 | ISAYSGDT SEQ ID NO: 566 | ARSSGWPHHYGMDV SEQ ID NO: 567 |
| CL-64536 | CAGGTTCAACTGGTGCAGTCTGGAGGTGAGGTGAAAAAGCCTGGGGCCTCAGTGAAGGTCTCCTGCAAGGCTTCTGGTTACACCTTTACCAGCTATGGTTTCAGCTGGGTGCGACAGGCCCCTGGACAAGGACTAGAGTGGATGGGATGGATCAGCGCTTACAATGGTAACACAAACTATGCACAGAAGCTCCAGGGCAGAGTCTCCATGACCACAGACACATCCACGAGCACAGCCTACATGGAGCTGAGGAGCTTGAGATCTGACGACACGGCCGTGTATTTCTGTGCGCGATCTACGTCTTACTATGGTTCGGGGACCCTATACGGTATGGACGTCTGGGGCCAAGGGACCACGGTCACCGTCTCCTCAG SEQ ID NO: 568 | QVQLVQSGGEVKKPGASVKVSCKASGYTFTSYGFSWVRQAPGQGLEWMGWISAYNGNTNYAQKLQGRVSMTTDTSTSTAYMELRSLRSDDTAVYFCARSTSYYGSGTLYGMDVWGQGTTVTVSS SEQ ID NO: 569 | GYTFTSYG SEQ ID NO: 377 | ISAYNGNT SEQ ID NO: 378 | ARSTSYYGSGTLYGMDV SEQ ID NO: 570 |
| CL-64837 | CAGGTTCAACTGGTGCAGTCTGGAGGTGAGGTGAAGAAGCCTGGGGCCTCAGTGAAGGTCTCCTGCAAGGCTTCTGGTTACACCTTTACCAGCTATGGTTTCAGCTGGGTGCGACAGGCCCCTGGACAAGGACTAGAGTGGATGGGATGGATCAGCGCTTACAATGGTAACACAAACTATGCACAGAAGCTCCAGGGCAGAGTCTCCATGACCACAGACACATCCACGAGCACAGCCTACATGGAGCTGAGGAGCTTGAGATCTGACGACACGGCCGTGTATTACTGTGCGCGATCTACGTCTTACTATGGTTCGGGGACCCTCTACGGTATGGACGTCTGGGGCCAAGGGACCACGGTCACCGTCTCCTCAG SEQ ID NO: 571 | QVQLVQSGGEVKKPGASVKVSCKASGYTFTSYGFSWVRQAPGQGLEWMGWISAYNGNTNYAQKLQGRVSMTTDTSTSTAYMELRSLRSDDTAVYYCARSTSYYGSGTLYGMDVWGQGTTVTVSS SEQ ID NO: 572 | GYTFTSYG SEQ ID NO: 377 | ISAYNGNT SEQ ID NO: 378 | ARSTSYYGSGTLYGMDV SEQ ID NO: 570 |

TABLE S4-continued

Sequences of antibody heavy chain variable regions obtained from additional clones
CDRs are defined according to IMGT.

| CLONE_ID | VH_NUCLEOTIDE_SEQUENCE | VH_AMINO_ACID_SEQ | HCDR1 | HCDR2 | HCDR3 |
|---|---|---|---|---|---|
| CL-64841 | CAGGTTCAACTGGTGCAGTCTGGAGGTGAGGTGAAAAAGCCTGGGGCCTCAGTGAAGGTCTCCTGCAAGGCTTCTGGTTACACCTTTACCAGCTATGGTTTCAGCTGGGTGCGACAGGCCCCTGGACAAGGACTAGAGTGGATGGGATGGATCAGCGCTTACAATGGTAACACAAACTATGCACAGAAGCTCCAGGGCAGAGTCTCCATGACCACAGACACATCCACGAGCACAGCCTACATGGAGCTGAGGAGCTTGAGATCTGACGACACGGCCGTGTATTTCTGTGCGCGATCTACGTCTTACTATGGTTCGGGGACCCTATACGGTATGGACGTCTGGGGCCAAGGGACCACGGTCACCGTCTCCTCAG SEQ ID NO: 573 | QVQLVQSGGEVKKPGASVKVSCKASGYTFTSYGFSWVRQAPGQGLEWMGWISAYNGNTNYAQKLQGRVSMTTDTSTSTAYMELRSLRSDDTAVYFCARSTSYYGSGTLYGMDVWGQGTTVTVSS SEQ ID NO: 574 | GYTFTSYG SEQ ID NO: 377 | ISAYNGNT SEQ ID NO: 378 | ARSTSYYGSGTLYGMDV SEQ ID NO: 570 |
| CL-64912 | CAGGTTCAACTGGTGCAGTCTGGAGGTGAGGTGAAAAAGCCTCGGGCCTCAGTGAAGGTCTCCTGCAAGGCTTCTGGTTACACCTTTACCAGCTATGTGTTCAGCTGGGTGCGACATGCCGCTGGACAAGGACTAGAGTGGATGGGATGGATCAGCGGTTACAATGGTAACACAAACTATGCACAGAAGCTCCAGTGCGGAGTCTCGATGACCGCAGACACATCCACGAGCACAGCCTACATGGAGCTGAGGAGCTTGAGATCTGACGACACGGCCGTGTATTTCTGTGCGCGATCTACGTCTTACTATGGTGCGGGGACCCTATACGGTATGGACGTCTGGGGCCAAGGGACCACGGTCACCGTCTCCTCAG SEQ ID NO: 575 | QVQLVQSGGEVKKPRASVKVSCKASGYTFTSYVFSWVRHAAGQGLEWMGWISGYNGNTNYAQKLQCGVSMTADTSTSTAYMELRSLRSDDTAVYFCARSTSYYGAGTLYGMDVWGQGTTVTVSS SEQ ID NO: 576 | GYTFTSYV SEQ ID NO: 577 | ISGYNGNT SEQ ID NO: 578 | ARSTSYYGAGTLYGMDV SEQ ID NO: 579 |
| CL-71642 | GAGGTGCAGCTGGTGGAGTCTGGGGGAGGTGTGGTACGGCCTGGGGGGTCCCTGAGACTCTCCTGTGCAGCCTCTGGATTCACCTTTGATGATTATGGCATGAGCTGGGTCCGCCAAGCTCCAGGGAAGGGGCTGGAGTGGGTCTCTGGTATTAATTGGAATGGTGGTAGCACAGGTTATGCAGACTCTGTGAAGGGCCGATTCACCATCTCCAGAGACAACGCCAAGAACTCCCTGTATCTGCAAATGAACAGTCTGAGAGCCGAGGACACGGCCTTGTATTACTGTGCGGCCGATTACTATGGTTCGGGGAGTTATTATAACGTCCCCTTTGACTACTGGGGCCAGGGAACCCTGGTCACCGTCTCCTCAG SEQ ID NO: 580 | EVQLVESGGGVVRPGGSLRLSCAASGFTFDDYGMSWVRQAPGKGLEWVSGINWNGGSTGYADSVKGRFTISRDNAKNSLYLQMNSLRAEDTALYYCAADYYGSGSYYNVPFDYWGQGTLVTVSS SEQ ID NO: 581 | GFTFDDYG SEQ ID NO: 582 | INWNGGST SEQ ID NO: 583 | AADYYGSGSYYNVPFDY SEQ ID NO: 584 |
| CL-74570 | GAGGTGCAGCTGGTGGAGTCTGGGGGAGGTGTGATACGGCCTGGGGGGTCCCTGAGACTCTCCTGTGCAGCCTCTGGATTCACCTTTGATGATTATGGCATGAGCTGGGTCCGCCAAGCTCCAGGGAAGGGGCTGGAGTGGGTCTCTGGTATTAATTGGATTGGTGATAACACAGATTATGCAGACTCTGTGAAGGGCCGATTCACCATCTCCAGAGACAACGCCAAGAACTCCCTATATCTGCAAATGAACAGTCTGAGAGCCGAGGACACGGCCTTGTATTACTGTGCGAGAGATTACTTTGGTTCGGGGAGTTATTATAACGTTCCCTTTGACTACTGGGGCCAGGGAACCCTGGTCACCGTCTCCTCAG SEQ ID NO: 585 | EVQLVESGGGVIRPGGSLRLSCAASGFTFDDYGMSWVRQAPGKGLEWVSGINWIGDNTDYADSVKGRFTISRDNAKNSLYLQMNSLRAEDTALYYCARDYFGSGSYYNVPFDYWGQGTLVTVSS SEQ ID NO: 586 | GFTFDDYG SEQ ID NO: 582 | INWIGDNT SEQ ID NO: 587 | ARDYFGSGSYYNVPFDY SEQ ID NO: 588 |

TABLE S5

Sequences of antibody light chain variable regions obtained from additional clones
N terminal E and 5' nucleotide additions in CL-71642 are shown in bold.
These were not recovered in sequencing but were determined to be present
in the sequence by comparison against the related clones as shown in FIG. 36.
CDRs are defined according to IMGT.

| CLONE_ID | VL_NUCLEOTIDE_SEQUENCE | VL_AMINO_ACID_SEQ | LCDR1 | LCDR2 | LCDR3 |
|---|---|---|---|---|---|
| CL-61091 | GATATTGTGATGACTCAGTCTCCACTCTCCCTGCCCGTCACCCCTGGAGAGCCGGCCTCCATCTCCTGCAGGTCTAGTCAGAGCCTCCTGCATAGTAATGGATTCAACTATTTCGATTGGTACCTGCAGAAGCCAGGACAGTCTCCACAGCTCCTGATCTTTTTGGTTTCTAATCGGGCCTCCGGGGTCCCTGACAGGTTCAGTGGCAGTGGATCAGGCACAGATTTTACACTGAAAATCAGCAGAGTGGAGGCTGAGGATGTTGGGATTTATTACTGCATGCAAGCTCTACAAACTCCGCTCACTTTCGGCGGAGGGACCAAGGTGGAGATCAAAC SEQ ID NO: 589 | DIVMTQSPLSLPVTPGEPASISCRSSQSLLHSNGFNYFDWYLQKPGQSPQLLIFLVSNRASGVPDRFSGSGSGTDFTLKISRVEAEDVGIYYCMQALQTPLTFGGGTKVEIK SEQ ID NO: 590 | QSLLHSNGFNY SEQ ID NO: 591 | LVS SEQ ID NO: 592 | MQALQTPLT SEQ ID NO: 593 |

TABLE S5-continued

Sequences of antibody light chain variable regions obtained from additional clones
N terminal E and 5' nucleotide additions in CL-71642 are shown in bold.
These were not recovered in sequencing but were determined to be present
in the sequence by comparison against the related clones as shown in FIG. 36.
CDRs are defined according to IMGT.

| CLONE_ID | VL_NUCLEOTIDE_SEQUENCE | VL_AMINO_ACID_SEQ | LCDR1 | LCDR2 | LCDR3 |
|---|---|---|---|---|---|
| CL-64536 | GATATTGTGATGACTCAGTCTCCACTCTCCCTGCCCGTCACCCCT<br>GGAGAGCCGGCCTCCATCTCCTGCAGGTCTAGTCAGAGCCTCCTG<br>CATAGTAATGGATACAACTGTTTGGATTGGTACCTGCAGAAGCCA<br>GGGCAGTCTCCACAGCTCCTGATCTATTTGGGTTCTACTCGGGCC<br>TCCGGGTTCCCTGACAGGTTCAGTGGCAGTGGATCAGGCACAGAT<br>TTTACACTGAAAATCAGCAGAGTGGAGGCTGAGGATGTTGGGGTT<br>TATTACTGCATGCAAGCTCTACAAACTCCGTGCAGTTTTGGCCAG<br>GGGACCAAGCTGGAGATCAAAC<br>SEQ ID NO: 594 | DIVMTQSPLSLPVTPGEPA<br>SISCRSSQSLLHSNGYNCL<br>DWYLQKPGQSPQLLIYLGS<br>TRASGFPDRFSGSGSGTDF<br>TLKISRVEAEDVGVYYCMQ<br>ALQTPCSFGQGTKLEIK<br>SEQ ID NO: 595 | QSLLHSNGYNC<br>SEQ ID NO:<br>596 | LGS<br>SEQ ID<br>NO:<br>371 | MQALQTPCS<br>SEQ ID<br>NO: 400 |
| CL-64837 | GATATTGTGATGACTCAGTCTCCACTCTCCCTGCCCGTCACCCCT<br>GGAGAGCCGGCCTCCATCTCCTGCAGGTCTAGTCAGAGCCTCCTG<br>CATAGTAATGGATACAACTGTTTGGATTGGTACCTGCAGAAGCCA<br>GGGCAGTCTCCACAGCTCCTGATCTATTTGGGTTCTACTCGGGCC<br>TCCGGGTTCCCTGACAGGTTCAGTGGCAGTGGATCAGGCACAGAT<br>TTTACACTGAAAATCAGCAGAGTGGAGGCTGAGGATGTTGGGGTT<br>TATTACTGCATGCAAGCTCTACAAACTCCGTGCAGTTTTGGCCAG<br>GGGACCAAGCTGGAGATCAAAC<br>SEQ ID NO: 597 | DIVMTQSPLSLPVTPGEPA<br>SISCRSSQSLLHSNGYNCL<br>DWYLQKPGQSPQLLIYLGS<br>TRASGFPDRFSGSGSGTDF<br>TLKISRVEAEDVGVYYCMQ<br>ALQTPCSFGQGTKLEIK<br>SEQ ID NO: 598 | QSLLHSNGYNC<br>SEQ ID NO:<br>596 | LGS<br>SEQ ID<br>NO:<br>371 | MQALQTPCS<br>SEQ ID<br>NO: 400 |
| CL-64841 | GATATTGTGATGACTCAGTCTCCACTCTCCCTGCCCGTCACCCCT<br>GGAGAGCCGGCCTCCATCTCCTGCAGGTCTAGTCAGAGCCTCCTG<br>CATAGTAATGGATACAACTGTTTGGATTGGTACCTGCAGAAGCCA<br>GGGCAGTCTCCACAGCTCCTGATCTATTTGGGTTCTACTCGGGCC<br>TCCGGGTTCCCTGACAGGTTCAGTGGCAGTGGATCAGGCACAGAT<br>TCTACACTGAAAATCAGCAGAGTGGAGGCTGAGGATGTTGGGGTT<br>TATTACTGCATGCAAGCTCTACAAACTCCGTGCAGTTTTGGCCAG<br>GGGACCAAGCTGGAGATCAAAC<br>SEQ ID NO: 599 | DIVMTQSPLSLPVTPGEPA<br>SISCRSSQSLLHSNGYNCL<br>DWYLQKPGQSPQLLIYLGS<br>TRASGFPDRFSGSGSGTDS<br>TLKISRVEAEDVGVYYCMQ<br>ALQTPCSFGQGTKLEIK<br>SEQ ID NO: 600 | QSLLHSNGYNC<br>SEQ ID NO:<br>596 | LGS<br>SEQ ID<br>NO:<br>371 | MQALQTPCS<br>SEQ ID<br>NO: 400 |
| CL-64912 | GATATTGTGATGACTCAGTCTCCACTCTCCCTGCCCGTCACCCCT<br>GGAGAGCCGGCCTCCATCTCCTGCAGGTCTAGTCAGAGCCTCCTG<br>CATAGTAATGGATACAACTGTTTGGATTGGTACCTGCAGAAGCCA<br>GGGCAGTCTCCACAGCTCCTGATCTATTTGGGTTCTACTCGGGCC<br>TCCGGGTTCCCTGACAGGTTCAGTGGCAGTGGATCAGGCACAGAT<br>TTTACACTGAAAATCAGCAGAGTGGAGGCTGAGGATGTTGGGGTT<br>TATTACTGCATGCAAGCTCTACAAACTCCGTGCAGTTTTGGCCAG<br>GGGACCAAGCTGGAGATCAAAC<br>SEQ ID NO: 601 | DIVMTQSPLSLPVTPGEPA<br>SISCRSSQSLLHSNGYNCL<br>DWYLQKPGQSPQLLIYLGS<br>TRASGFPDRFSGSGSGTDF<br>TLKISRVEAEDVGVYYCMQ<br>ALQTPCSFGQGTKLEIK<br>SEQ ID NO: 602 | QSLLHSNGYNC<br>SEQ ID NO:<br>596 | LGS<br>SEQ ID<br>NO:<br>371 | MQALQTPCS<br>SEQ ID<br>NO: 400 |
| CL-71642 | **GA**AATTGTGTTGACGCAGTCTCCAGGCACCCTGTCTTTGTCTCCA<br>GGGGAAAGAGCCACCCTCTCCTGCAGGGCCAGTCAGAGTGTTAGC<br>AGCAGCTACTTAGCCTGGTACCAGCAGAAACCTGGCCAGGCTCCC<br>AGGCTCCTCATCTATGGTGCATCCAGCAGGGCCACTGGCATCCCA<br>GACAGGTTCAGTGGCAGTGGGTCTGGGACAGACTTCACTCTCACC<br>ATCAGCAGACTGGAGCCTGAAGATTTTGCAGTGTATTACTGTCAG<br>CAGTATGGTAGCTCACCTTTCACTTTCGGCCCTGGGACCAAAGTG<br>GATATCAAAC<br>SEQ ID NO: 603 | **E**IVLTQSPGTLSLSPGERA<br>TLSCRASQSVSSSYLAWYQ<br>QKPGQAPRLLIYGASSRAT<br>GIPDRFSGSGSGTDFTLTI<br>SRLEPEDFAVYYCQQYGSS<br>PFTFGPGTKVDIK<br>SEQ ID NO: 604 | QSVSSSY<br>SEQ ID NO:<br>426 | GAS<br>SEQ ID<br>NO:<br>413 | QQYGSSPFT<br>SEQ ID<br>NO: 605 |
| CL-74570 | GAAATTGTGTTGACGCAGTCTCCAGGCACCCTGTCTTTGTCTCCA<br>GGGGAAAGAGCCACCCTCTCCTGCAGGGCCAGTCAGAGTGTTAGC<br>AGCAGCTACTTAGCCTGGTACCAGCAGAAACCTGGCCAGGCTCCC<br>AGGCTCCTCATCTATGGTGCATCCAGCAGGGCCACTGGCATCCCA<br>GACAGGTTCAGTGGCAGTGGGTCTGGGACAGACTTCACTCTCACC<br>ATCAGCAGACTGGAACCTGAAGATTTTGCAGTATATTACTGTCAC<br>CAGTATGGTAATTCACCATTCACTTTCGGCCCTGGGACCAAAGTG<br>GATATCAAAC<br>SEQ ID NO: 606 | EIVLTQSPGTLSLSPGERA<br>TLSCRASQSVSSSYLAWYQ<br>QKPGQAPRLLIYGASSRAT<br>GIPDRFSGSGSGTDFTLTI<br>SRLEPEDFAVYYCHQYGNS<br>PFTFGPGTKVDIK<br>SEQ ID NO: 607 | QSVSSSY<br>SEQ ID NO:<br>426 | GAS<br>SEQ ID<br>NO:<br>413 | HQYGNSPFT<br>SEQ ID<br>NO: 608 |

What is claimed is:

1. An isolated antibody that binds the extracellular domain of human ICOS, comprising a heavy chain amino acid sequence SEQ ID NO: 410 and a light chain amino acid sequence SEQ ID NO: 417.

2. A composition comprising the isolated antibody of claim 1 and a pharmaceutically acceptable excipient.

3. The isolated antibody of claim 1, wherein the antibody comprises an Fc effector positive constant region.

4. The isolated antibody of claim 1, which is a multispecific antibody.

5. The isolated antibody of claim 1, wherein the antibody is afucosylated.

6. The isolated antibody of claim 1 which is conjugated to a cytotoxic drug or pro-drug.

7. An isolated antibody that binds the extracellular domain of human ICOS, comprising a VH domain comprising an amino acid sequence SEQ ID NO: 408 and a VL domain comprising an amino acid sequence SEQ ID NO: 415, wherein the antibody is not a multispecific antibody.

8. A composition comprising the isolated antibody of claim 7 and a pharmaceutically acceptable excipient.

9. The isolated antibody of claim 7, wherein the antibody comprises an Fc effector positive constant region.

10. The isolated antibody of claim 7, wherein the antibody is afucosylated.

11. The isolated antibody of claim 7 which is conjugated to a cytotoxic drug or pro-drug.

12. An isolated antibody that is not multispecific and does not bind PD-L1 antigen, wherein the isolated antibody binds the extracellular domain of human ICOS, comprising a VH domain comprising amino acid sequence SEQ ID NO: 408, a VL domain comprising amino acid sequence SEQ ID NO: 415, and a human IgG1 constant region.

13. A composition comprising the isolated antibody of claim 12 and a pharmaceutically acceptable excipient.

14. The isolated antibody of claim 12, wherein the antibody comprises an Fc effector positive constant region.

15. The isolated antibody of claim 12, wherein the antibody is afucosylated.

16. The isolated antibody of claim 12 which is conjugated to a cytotoxic drug or pro-drug.

17. An isolated antibody that binds the extracellular domain of human ICOS, wherein said antibody is made by the process of (i) culturing a host cell comprising one or more vectors encoding a heavy chain amino acid sequence SEQ ID NO: 410 and a light chain amino acid sequence SEQ ID NO: 417; and (ii) recovering the antibody.

18. A composition comprising the isolated antibody of claim 17 and a pharmaceutically acceptable excipient.

19. The isolated antibody of claim 17, which is a multispecific antibody.

20. The isolated antibody of claim 17, wherein the antibody is afucosylated.

21. The isolated antibody of claim 17 which is conjugated to a cytotoxic drug or pro-drug.

22. A method of treating cancer in a human patient, the method comprising administering to the patient an antibody that binds the extracellular domain of human ICOS, comprising a heavy chain amino acid sequence SEQ ID NO: 410 and a light chain amino acid sequence SEQ ID NO: 417.

23. The method of claim 22, wherein the cancer is a solid tumor or a hematological liquid tumor.

24. The method of claim 22, wherein the cancer is renal cell cancer, head and neck cancer, melanoma, non-small cell lung cancer or diffuse large B-cell lymphoma, B cell lymphoma, or a T lymphocyte.

25. The method of claim 22, wherein the cancer is head and neck cancer.

26. The method of claim 22, wherein the cancer is not responsive to prior treatment with an immunooncology drug.

27. The method of claim 22, wherein the cancer is resistant to treatment with an anti-CD20 antibody.

28. The method of claim 27, wherein the anti-CD20 antibody is rituximab.

29. A method of treating cancer in a human patient, the method comprising administering to the patient an antibody that binds the extracellular domain of human ICOS, comprising a VH domain comprising an amino acid sequence SEQ ID NO: 408 and a VL domain comprising an amino acid sequence SEQ ID NO: 415, wherein the antibody is not a multispecific antibody.

* * * * *

SEQUENCE LISTING

<160> NUMBER OF SEQ ID NOS: 610

<210> SEQ ID NO 1
<211> LENGTH: 290
<212> TYPE: PRT
<213> ORGANISM: Homo Sapiens -continued

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 241
<212> TYPE: PRT
<213> ORGANISM: Cynomologus

<400> SEQUENCE: 2

Met Gly Trp Ser Cys Ile Ile Leu Phe Leu Val Ala Thr Ala Thr Gly
1               5                   10                  15

Val His Ser Met Phe Thr Val Thr Val Pro Lys Asp Leu Tyr Val Val
            20                  25                  30

Glu Tyr Gly Ser Asn Met Thr Ile Glu Cys Lys Phe Pro Val Glu Lys
        35                  40                  45

Gln Leu Asp Leu Thr Ser Leu Ile Val Tyr Trp Glu Met Glu Asp Lys
    50                  55                  60

-continued

Asn Ile Ile Gln Phe Val His Gly Glu Glu Asp Leu Lys Val Gln His
65 70 75 80

Ser Asn Tyr Arg Gln Arg Ala Gln Leu Leu Lys Asp Gln Leu Ser Leu
85 90 95

Gly Asn Ala Ala Leu Arg Ile Thr Asp Val Lys Leu Gln Asp Ala Gly
100 105 110

Val Tyr Arg Cys Met Ile Ser Tyr Gly Gly Ala Asp Tyr Lys Arg Ile
115 120 125

Thr Val Lys Val Asn Ala Pro Tyr Asn Lys Ile Asn Gln Arg Ile Leu
130 135 140

Val Val Asp Pro Val Thr Ser Glu His Glu Leu Thr Cys Gln Ala Glu
145 150 155 160

Gly Tyr Pro Lys Ala Glu Val Ile Trp Thr Ser Ser Asp His Gln Val
165 170 175

Leu Ser Gly Lys Thr Thr Thr Thr Asn Ser Lys Arg Glu Glu Lys Leu
180 185 190

Leu Asn Val Thr Ser Thr Leu Arg Ile Asn Thr Thr Ala Asn Glu Ile
195 200 205

Phe Tyr Cys Ile Phe Arg Arg Leu Asp Pro Glu Glu Asn His Thr Ala
210 215 220

Glu Leu Val Ile Pro Glu Leu Pro Leu Ala Leu Pro Pro Asn Glu Arg
225 230 235 240

Thr

<210> SEQ ID NO 3
<211> LENGTH: 245
<212> TYPE: PRT
<213> ORGANISM: Homo Sapiens

<400> SEQUENCE: 3

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Glu Asp Leu Lys Val Gln His Ser Ser
65 70 75 80

Tyr Arg Gln Arg Ala Arg Leu Leu Lys Asp Gln Leu Ser Leu Gly Asn
85 90 95

Ala Ala Leu Gln Ile Thr Asp Val Lys Leu Gln Asp Ala Gly Val Tyr
100 105 110

Arg Cys Met Ile Ser Tyr Gly Gly Ala Asp Tyr Lys Arg Ile Thr Val
115 120 125

Lys Val Asn Ala Pro Tyr Asn Lys Ile Asn Gln Arg Ile Leu Val Val
130 135 140

Asp Pro Val Thr Ser Glu His Glu Leu Thr Cys Gln Ala Glu Gly Tyr
145 150 155 160

Pro Lys Ala Glu Val Ile Trp Thr Ser Ser Asp His Gln Val Leu Ser
165 170 175

Gly Lys Thr Thr Thr Thr Asn Ser Lys Arg Glu Glu Lys Leu Phe Asn
180 185 190

```
Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

His His His His His
                245


<210> SEQ ID NO 4
<211> LENGTH: 475
<212> TYPE: PRT
<213> ORGANISM: Homo Sapiens

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr Ile
225                 230                 235                 240

Glu Gly Arg Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
```

-continued 305 310 315 320

Glu Glu Gln Tyr Asn Ser Thr Tyr Arg Val Val Ser Val Leu Thr Val
325 330 335

Leu His Gln Asp Trp Leu Asn Gly Lys Glu Tyr Lys Cys Lys Val Ser
340 345 350

Asn Lys Ala Leu Pro Ala Pro Ile Glu Lys Thr Ile Ser Lys Ala Lys
355 360 365

Gly Gln Pro Arg Glu Pro Gln Val Tyr Thr Leu Pro Pro Ser Arg Asp
370 375 380

Glu Leu Thr Lys Asn Gln Val Ser Leu Thr Cys Leu Val Lys Gly Phe
385 390 395 400

Tyr Pro Ser Asp Ile Ala Val Glu Trp Glu Ser Asn Gly Gln Pro Glu
405 410 415

Asn Asn Tyr Lys Thr Thr Pro Pro Val Leu Asp Ser Asp Gly Ser Phe
420 425 430

Phe Leu Tyr Ser Lys Leu Thr Val Asp Lys Ser Arg Trp Gln Gln Gly
435 440 445

Asn Val Phe Ser Cys Ser Val Met His Glu Ala Leu His Asn His Tyr
450 455 460

Thr Gln Lys Ser Leu Ser Leu Ser Pro Gly Lys
465 470 475

<210> SEQ ID NO 5
<211> LENGTH: 249
<212> TYPE: PRT
<213> ORGANISM: Cynomologus

<400> SEQUENCE: 5

Met Gly Trp Ser Cys Ile Ile Leu Phe Leu Val Ala Thr Ala Thr Gly
1 5 10 15

Val His Ser Met Phe Thr Val Thr Val Pro Lys Asp Leu Tyr Val Val
20 25 30

Glu Tyr Gly Ser Asn Met Thr Ile Glu Cys Lys Phe Pro Val Glu Lys
35 40 45

Gln Leu Asp Leu Thr Ser Leu Ile Val Tyr Trp Glu Met Glu Asp Lys
50 55 60

Asn Ile Ile Gln Phe Val His Gly Glu Glu Asp Leu Lys Val Gln His
65 70 75 80

Ser Asn Tyr Arg Gln Arg Ala Gln Leu Leu Lys Asp Gln Leu Ser Leu
85 90 95

Gly Asn Ala Ala Leu Arg Ile Thr Asp Val Lys Leu Gln Asp Ala Gly
100 105 110

Val Tyr Arg Cys Met Ile Ser Tyr Gly Gly Ala Asp Tyr Lys Arg Ile
115 120 125

Thr Val Lys Val Asn Ala Pro Tyr Asn Lys Ile Asn Gln Arg Ile Leu
130 135 140

Val Val Asp Pro Val Thr Ser Glu His Glu Leu Thr Cys Gln Ala Glu
145 150 155 160

Gly Tyr Pro Lys Ala Glu Val Ile Trp Thr Ser Ser Asp His Gln Val
165 170 175

Leu Ser Gly Lys Thr Thr Thr Thr Asn Ser Lys Arg Glu Glu Lys Leu
180 185 190

Leu Asn Val Thr Ser Thr Leu Arg Ile Asn Thr Thr Ala Asn Glu Ile
195 200 205

```
Phe Tyr Cys Ile Phe Arg Arg Leu Asp Pro Glu Glu Asn His Thr Ala
    210                 215                 220

Glu Leu Val Ile Pro Glu Leu Pro Leu Ala Leu Pro Pro Asn Glu Arg
225                 230                 235                 240

Thr Asp Tyr Lys Asp Asp Asp Asp Lys
                245


<210> SEQ ID NO 6
<211> LENGTH: 405
<212> TYPE: PRT
<213> ORGANISM: Homo Sapiens

<400> SEQUENCE: 6

Met Gly Trp Ser Cys Ile Ile Leu Phe Leu Val Ala Thr Ala Thr Gly
1               5                   10                  15

Val His Ser Leu Asp Ser Pro Asp Arg Pro Trp Asn Pro Pro Thr Phe
            20                  25                  30

Ser Pro Ala Leu Leu Val Val Thr Glu Gly Asp Asn Ala Thr Phe Thr
        35                  40                  45

Cys Ser Phe Ser Asn Thr Ser Glu Ser Phe Val Leu Asn Trp Tyr Arg
    50                  55                  60

Met Ser Pro Ser Asn Gln Thr Asp Lys Leu Ala Ala Phe Pro Glu Asp
65                  70                  75                  80

Arg Ser Gln Pro Gly Gln Asp Cys Arg Phe Arg Val Thr Gln Leu Pro
                85                  90                  95

Asn Gly Arg Asp Phe His Met Ser Val Val Arg Ala Arg Arg Asn Asp
            100                 105                 110

Ser Gly Thr Tyr Leu Cys Gly Ala Ile Ser Leu Ala Pro Lys Ala Gln
        115                 120                 125

Ile Lys Glu Ser Leu Arg Ala Glu Leu Arg Val Thr Glu Arg Arg Ala
    130                 135                 140

Glu Val Pro Thr Ala His Pro Ser Pro Ser Pro Arg Pro Ala Gly Gln
145                 150                 155                 160

Lys Leu Glu Asn Leu Tyr Phe Gln Gly Ile Glu Gly Arg Met Asp Glu
                165                 170                 175

Pro Lys Ser Cys Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg
    290                 295                 300

Glu Pro Gln Val Tyr Thr Leu Pro Pro Ser Arg Asp Glu Leu Thr Lys
305                 310                 315                 320

Asn Gln Val Ser Leu Thr Cys Leu Val Lys Gly Phe Tyr Pro Ser Asp
                325                 330                 335
```

```
Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro
                405


<210> SEQ ID NO 7
<211> LENGTH: 8
<212> TYPE: PRT
<213> ORGANISM: Homo Sapiens

<400> SEQUENCE: 7

Gly Phe Thr Phe Asp Asp Tyr Ala
1               5


<210> SEQ ID NO 8
<211> LENGTH: 8
<212> TYPE: PRT
<213> ORGANISM: Homo Sapiens

<400> SEQUENCE: 8

Ile Ser Trp Lys Ser Asn Ile Ile
1               5


<210> SEQ ID NO 9
<211> LENGTH: 15
<212> TYPE: PRT
<213> ORGANISM: Homo Sapiens

<400> SEQUENCE: 9

Ala Arg Asp Ile Thr Gly Ser Gly Ser Tyr Gly Trp Phe Asp Pro
1               5                   10                  15


<210> SEQ ID NO 10
<211> LENGTH: 5
<212> TYPE: PRT
<213> ORGANISM: Homo Sapiens

<400> SEQUENCE: 10

Asp Tyr Ala Met His
1               5


<210> SEQ ID NO 11
<211> LENGTH: 17
<212> TYPE: PRT
<213> ORGANISM: Homo Sapiens

<400> SEQUENCE: 11

Gly Ile Ser Trp Lys Ser Asn Ile Ile Gly Tyr Ala Asp Ser Val Lys
1               5                   10                  15

Gly


<210> SEQ ID NO 12
<211> LENGTH: 13
<212> TYPE: PRT
<213> ORGANISM: Homo Sapiens
```

<400> SEQUENCE: 12

```
Asp Ile Thr Gly Ser Gly Ser Tyr Gly Trp Phe Asp Pro
1               5                   10
```

<210> SEQ ID NO 13
<211> LENGTH: 122
<212> TYPE: PRT
<213> ORGANISM: Homo Sapiens

<400> SEQUENCE: 13

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser
        115                 120
```

<210> SEQ ID NO 14
<211> LENGTH: 508
<212> TYPE: DNA
<213> ORGANISM: Homo Sapiens

<400> SEQUENCE: 14

```
caagaaaaag cttgccgcca ccatggagtt tgggctgagc tggattttcc ttttggctat      60

tttaaaaggt gtccagtgtg aagtacaatt ggtggagtcc gggggaggct tggtacagcc     120

tggcaggtcc ctgagactct cctgtgcagc ctctggattc acctttgatg attatgccat     180

gcactgggtc cgacaaactc cagggaaggg cctggagtgg gtctcaggta taagttggaa     240

gagtaatatc ataggctatg cggactctgt gaagggccga ttcaccatct ccagagacaa     300

cgccaagaac tccctgtatc tgcaaatgaa cagtctgaga gctgaggaca cggccttgta     360

ttattgtgca agagatataa cgggttcggg gagttatggc tggttcgacc cctggggcca     420

gggaaccctg gtcaccgtct cctcagccaa aacgacaccc ccatctgtct atccactggc     480

ccctgaatct gctaaaactc agcctccg                                        508
```

<210> SEQ ID NO 15
<211> LENGTH: 449
<212> TYPE: PRT
<213> ORGANISM: Homo Sapiens

<400> SEQUENCE: 15

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45
```

```
Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 16
<211> LENGTH: 1356
<212> TYPE: DNA
<213> ORGANISM: Homo Sapiens

<400> SEQUENCE: 16
gaagtgcagc tggtggaatc tggcggcgga ctggtgcagc ctggcagatc cctgagactg 60
tcttgtgccg cctccggctt caccttcgac gactacgcta tgcactgggt gcgacagacc 120
cctggcaagg gcctggaatg ggtgtccggc atctcctgga agtccaacat catcggctac 180
gccgactccg tgaagggccg gttcaccatc tcccgggaca acgccaagaa ctccctgtac 240
ctgcagatga acagcctgcg ggccgaggac accgccctgt actactgcgc cagagacatc 300
accggctccg gctcctacgg atggttcgat ccttggggcc agggcaccct cgtgaccgtg 360
tcctctgcca gcaccaaggg cccctctgtg ttccctctgg ccccttccag caagtccacc 420
tctggcggaa cagccgctct gggctgcctc gtgaaggact acttccccga gcctgtgacc 480
gtgtcctgga actctggcgc tctgaccagc ggagtgcaca ccttccctgc tgtgctgcag 540
tcctccggcc tgtactccct gtcctccgtc gtgaccgtgc cttccagctc tctgggcacc 600
cagacctaca tctgcaacgt gaaccacaag ccctccaaca ccaaggtgga caagaaggtg 660
gaacccaagt cctgcgacaa gacccacacc tgtccccctt gtcctgcccc tgaactgctg 720
ggcggacctt ccgtgttcct gttcccccca aagcccaagg acaccctgat gatctcccgg 780
acccccgaag tgacctgcgt ggtggtggat gtgtcccacg aggaccctga agtgaagttc 840
aattggtacg tggacggcgt ggaagtgcac aacgccaaga ccaagcctag agaggaacag 900
tacaactcca cctaccgggt ggtgtccgtg ctgaccgtgc tgcaccagga ttggctgaac 960
ggcaaagagt acaagtgcaa ggtgtccaac aaggccctgc ctgcccccat cgaaaagacc 1020
atctccaagg ccaagggcca gccccgggaa ccccaggtgt acacactgcc ccctagcagg 1080
gacgagctga ccaagaacca ggtgtccctg acctgtctcg tgaaaggctt ctacccctcc 1140
gatatcgccg tggaatggga gtccaacggc cagcctgaga acaactacaa gaccaccccc 1200
cctgtgctgg actccgacgg ctcattcttc ctgtacagca agctgacagt ggacaagtcc 1260
cggtggcagc agggcaacgt gttctcctgc tccgtgatgc acgaggccct gcacaaccac 1320
tacacccaga agtccctgtc cctgagcccc ggcaag 1356

<210> SEQ ID NO 17
<211> LENGTH: 6
<212> TYPE: PRT
<213> ORGANISM: Homo Sapiens

<400> SEQUENCE: 17

Gln Ser Ile Ser Ser Tyr
1 5

<210> SEQ ID NO 18
<211> LENGTH: 3
<212> TYPE: PRT
<213> ORGANISM: Homo Sapiens

<400> SEQUENCE: 18

Val Ala Ser
1

<210> SEQ ID NO 19
<211> LENGTH: 9
<212> TYPE: PRT

<213> ORGANISM: Homo Sapiens

<400> SEQUENCE: 19

Gln Gln Ser Tyr Ser Asn Pro Ile Thr
1               5

<210> SEQ ID NO 20
<211> LENGTH: 11
<212> TYPE: PRT
<213> ORGANISM: Homo Sapiens

<400> SEQUENCE: 20

Arg Ala Ser Gln Ser Ile Ser Ser Tyr Leu Asn
1               5                   10

<210> SEQ ID NO 21
<211> LENGTH: 7
<212> TYPE: PRT
<213> ORGANISM: Homo Sapiens

<400> SEQUENCE: 21

Val Ala Ser Ser Leu Gln Ser
1               5

<210> SEQ ID NO 22
<211> LENGTH: 9
<212> TYPE: PRT
<213> ORGANISM: Homo Sapiens

<400> SEQUENCE: 22

Gln Gln Ser Tyr Ser Asn Pro Ile Thr
1               5

<210> SEQ ID NO 23
<211> LENGTH: 107
<212> TYPE: PRT
<213> ORGANISM: Homo Sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys
            100                 105

<210> SEQ ID NO 24
<211> LENGTH: 321
<212> TYPE: DNA
<213> ORGANISM: Homo Sapiens

<400> SEQUENCE: 24
gacatccaga tgacccagtc tccatcctcc ctgtctgcat ctgtaggaga cagagtcacc     60

```
atcacttgcc gggcaagtca gagcattagc agctatttaa attggtatca gcagaaacca    120

gggaaagccc ctaagcccct gatctatgtt gcatccagtt tgcaaagtgg ggtcccatca    180

agtttcagtg gcagtggatc tgggacagat ttcactctca ccatcagcag tctgcaacct    240

gaagattttg caacttacta ctgtcaacag agttacagta atccgatcac cttcggccaa    300

gggacacgac tggagatcaa a                                              321


<210> SEQ ID NO 25
<211> LENGTH: 214
<212> TYPE: PRT
<213> ORGANISM: Homo Sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 642
<212> TYPE: DNA
<213> ORGANISM: Homo Sapiens

<400> SEQUENCE: 26

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagcccct gatctatgtt gcatccagtt tgcaaagtgg ggtcccatca    180

agtttcagtg gcagtggatc tgggacagat ttcactctca ccatcagcag tctgcaacct    240

gaagattttg caacttacta ctgtcaacag agttacagta atccgatcac cttcggccaa    300

gggacacgac tggagatcaa acgtacggtg gccgctccct ccgtgttcat cttcccacct    360
```

```
tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642
```

<210> SEQ ID NO 27
<211> LENGTH: 8
<212> TYPE: PRT
<213> ORGANISM: Homo Sapiens

<400> SEQUENCE: 27

```
Gly Phe Thr Phe Asp Asp Tyr Ala
1               5
```

<210> SEQ ID NO 28
<211> LENGTH: 8
<212> TYPE: PRT
<213> ORGANISM: Homo Sapiens

<400> SEQUENCE: 28

```
Ile Ser Trp Ile Arg Thr Gly Ile
1               5
```

<210> SEQ ID NO 29
<211> LENGTH: 16
<212> TYPE: PRT
<213> ORGANISM: Homo Sapiens

<400> SEQUENCE: 29

```
Ala Lys Asp Met Lys Gly Ser Gly Thr Tyr Gly Gly Trp Phe Asp Thr
1               5                   10                  15
```

<210> SEQ ID NO 30
<211> LENGTH: 5
<212> TYPE: PRT
<213> ORGANISM: Homo Sapiens

<400> SEQUENCE: 30

```
Asp Tyr Ala Met His
1               5
```

<210> SEQ ID NO 31
<211> LENGTH: 17
<212> TYPE: PRT
<213> ORGANISM: Homo Sapiens

<400> SEQUENCE: 31

```
Gly Ile Ser Trp Ile Arg Thr Gly Ile Gly Tyr Ala Asp Ser Val Lys
1               5                   10                  15

Gly
```

<210> SEQ ID NO 32
<211> LENGTH: 14
<212> TYPE: PRT
<213> ORGANISM: Homo Sapiens

<400> SEQUENCE: 32

```
Asp Met Lys Gly Ser Gly Thr Tyr Gly Gly Trp Phe Asp Thr
1               5                   10
```

<210> SEQ ID NO 33
<211> LENGTH: 123
<212> TYPE: PRT
<213> ORGANISM: Homo Sapiens

<400> SEQUENCE: 33

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Val Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Phe Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Met Lys Gly Ser Gly Thr Tyr Gly Gly Trp Phe Asp Thr
100 105 110

Trp Gly Gln Gly Thr Leu Val Thr Val Ser Ser
115 120

<210> SEQ ID NO 34
<211> LENGTH: 482
<212> TYPE: DNA
<213> ORGANISM: Homo Sapiens

<400> SEQUENCE: 34
aagcttgccg ccaccatgga gtttgggctg agctggattt tccttttggc tattttaaaa 60
ggtgtccagt gtgaagtgca gctggtggag tctgggggag gcttggtgca gcctggcagg 120
tccctgagac tctcctgtgc agcctctgga ttcacctttg atgattatgc catgcactgg 180
gtccggcaag ttccagggaa gggcctggaa tgggtctcag gcattagttg gattcgtact 240
ggcataggct atgcggactc tgtgaagggc cgattcacca ttttcagaga caacgccaag 300
aattccctgt atctgcaaat gaacagtctg agagctgagg acacggcctt gtattactgt 360
gcaaaagata tgaagggttc ggggacttat ggggggtggt tcgacacctg gggccaggga 420
accctggtca ccgtctcctc agccaaaaca acagccccat cggtctatcc actggcccct 480
gc 482

<210> SEQ ID NO 35
<211> LENGTH: 450
<212> TYPE: PRT
<213> ORGANISM: Homo Sapiens

<400> SEQUENCE: 35

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Val Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Phe Arg Asp Asn Ala Lys Asn Ser Leu Tyr

```
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 36
<211> LENGTH: 1359
<212> TYPE: DNA
<213> ORGANISM: Homo Sapiens

<400> SEQUENCE: 36

```
gaagtgcagc tggtggaatc tggcggcgga ctggtgcagc ctggcagatc cctgagactg     60
tcttgtgccg cctccggctt caccttcgac gactacgcta tgcactgggt gcgacaggtg    120
ccaggcaagg gcctggaatg ggtgtccggc atctcttgga tccggaccgg catcggctac    180
gccgactctg tgaagggccg gttcaccatc ttccgggaca acgccaagaa ctccctgtac    240
ctgcagatga acagcctgcg ggccgaggac accgccctgt actactgcgc caaggacatg    300
aagggctccg gcacctacgg cggatggttc gatacttggg gccagggcac cctcgtgacc    360
gtgtcctctg ccagcaccaa gggcccctct gtgttccctc tggccccttc cagcaagtcc    420
acctctggcg gaacagccgc tctgggctgc ctcgtgaagg actacttccc cgagcctgtg    480
accgtgtcct ggaactctgg cgctctgacc agcggagtgc acaccttccc tgctgtgctg    540
cagtcctccg gcctgtactc cctgtcctcc gtcgtgaccg tgccttccag ctctctgggc    600
acccagacct acatctgcaa cgtgaaccac aagccctcca acaccaaggt ggacaagaag    660
gtggaaccca agtcctgcga caagacccac acctgtcccc cttgtcctgc ccctgaactg    720
ctgggcggac cttccgtgtt cctgttcccc ccaaagccca aggacaccct gatgatctcc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaact ccacctaccg ggtggtgtcc gtgctgaccg tgctgcacca ggattggctg    960
aacggcaaag agtacaagtg caaggtgtcc aacaaggccc tgcctgcccc catcgaaaag   1020
accatctcca aggccaaggg ccagccccgg gaaccccagg tgtacacact gccccctagc   1080
agggacgagc tgaccaagaa ccaggtgtcc ctgacctgtc tcgtgaaagg cttctacccc   1140
tccgatatcg ccgtggaatg ggagtccaac ggccagcctg agaacaacta caagaccacc   1200
ccccctgtgc tggactccga cggctcattc ttcctgtaca gcaagctgac agtggacaag   1260
tcccggtggc agcagggcaa cgtgttctcc tgctccgtga tgcacgaggc cctgcacaac   1320
cactacaccc agaagtccct gtccctgagc cccggcaag                          1359
```

<210> SEQ ID NO 37
<211> LENGTH: 6
<212> TYPE: PRT
<213> ORGANISM: Homo Sapiens

<400> SEQUENCE: 37

```
Gln Ser Ile Ser Ser Tyr
1               5
```

<210> SEQ ID NO 38
<211> LENGTH: 3
<212> TYPE: PRT
<213> ORGANISM: Homo Sapiens

<400> SEQUENCE: 38

```
Val Ala Ser
1
```

<210> SEQ ID NO 39
<211> LENGTH: 9
<212> TYPE: PRT
<213> ORGANISM: Homo Sapiens

<400> SEQUENCE: 39

```
Gln Gln Ser Tyr Ser Thr Pro Ile Thr
1               5


<210> SEQ ID NO 40
<211> LENGTH: 11
<212> TYPE: PRT
<213> ORGANISM: Homo Sapiens

<400> SEQUENCE: 40

Arg Ala Ser Gln Ser Ile Ser Ser Tyr Leu Asn
1               5                   10


<210> SEQ ID NO 41
<211> LENGTH: 7
<212> TYPE: PRT
<213> ORGANISM: Homo Sapiens

<400> SEQUENCE: 41

Val Ala Ser Ser Leu Gln Ser
1               5


<210> SEQ ID NO 42
<211> LENGTH: 9
<212> TYPE: PRT
<213> ORGANISM: Homo Sapiens

<400> SEQUENCE: 42

Gln Gln Ser Tyr Ser Thr Pro Ile Thr
1               5


<210> SEQ ID NO 43
<211> LENGTH: 107
<212> TYPE: PRT
<213> ORGANISM: Homo Sapiens

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105


<210> SEQ ID NO 44
<211> LENGTH: 418
<212> TYPE: DNA
<213> ORGANISM: Homo Sapiens

<400> SEQUENCE: 44

aaagcttgcc gccaccatga ggctccctgc tcagcttctg gggctcctgc tactctggct      60

ccgaggtgcc agatgtgaca tccagatgac ccagtctcca tcctccctgt ctgcatctgt     120

aggagacaga gtcaccatca cttgccgggc aagtcagagc attagcagct atttaaattg     180
```

gtatcagcag aaaccaggga aagcccctaa actcctgatc tatgttgcat ccagtttgca 240
aagtggggtc ccatcaaggt tcagtggcag tggatctggg acagatttca ctctcactat 300
cagcagtctg caacctgaag attttgcaac ttactactgt caacagagtt acagtacccc 360
gatcaccttc ggccaaggga cacgtctgga gatcaaacgt acggatgctg caccaact 418

<210> SEQ ID NO 45
<211> LENGTH: 214
<212> TYPE: PRT
<213> ORGANISM: Homo Sapiens

<400> SEQUENCE: 45

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Ile
85 90 95

Thr Phe Gly Gln Gly Thr Arg Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 46
<211> LENGTH: 642
<212> TYPE: DNA
<213> ORGANISM: Homo Sapiens

<400> SEQUENCE: 46
gacatccaga tgacccagtc cccctccagc ctgtctgctt ccgtgggcga cagagtgacc 60
atcacctgtc gggcctccca gtccatctcc tcctacctga actggtatca gcagaagccc 120
ggcaaggccc ccaagctgct gatctacgtg gccagctctc tgcagtccgg cgtgccctct 180
agattctccg gctctggctc tggcaccgac tttaccctga ccatcagctc cctgcagccc 240
gaggacttcg ccacctacta ctgccagcag tcctactcca cccctatcac cttcggccag 300
ggcacccggc tggaaatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 47
<211> LENGTH: 450
<212> TYPE: PRT
<213> ORGANISM: Homo Sapiens

<400> SEQUENCE: 47

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Phe Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Met Lys Gly Ser Gly Thr Tyr Gly Gly Trp Phe Asp Thr
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Lys Thr Tyr Thr Cys Asn Val
195 200 205

Asp His Lys Pro Ser Asn Thr Lys Val Asp Lys Arg Val Glu Ser Lys
210 215 220

Tyr Gly Pro Pro Cys Pro Pro Cys Pro Ala Pro Glu Leu Ala Gly Ala
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser Gln Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Arg Leu Thr Val Asp
405 410 415

Lys Ser Arg Trp Gln Glu Gly Asn Val Phe Ser Cys Ser Val Met His
420 425 430

Glu Ala Leu His Asn His Tyr Thr Gln Lys Ser Leu Ser Leu Ser Leu
435 440 445

Gly Lys
450

<210> SEQ ID NO 48
<211> LENGTH: 450
<212> TYPE: PRT
<213> ORGANISM: Homo Sapiens

<400> SEQUENCE: 48

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Val Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Met Lys Gly Ser Gly Thr Tyr Gly Gly Trp Phe Asp Thr
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Lys Thr Tyr Thr Cys Asn Val
195 200 205

Asp His Lys Pro Ser Asn Thr Lys Val Asp Lys Arg Val Glu Ser Lys
210 215 220

Tyr Gly Pro Pro Cys Pro Pro Cys Pro Ala Pro Glu Leu Ala Gly Ala
225 230 235 240

Pro Ser Val Phe Leu Phe Pro Pro Lys Pro Lys Asp Thr Leu Met Ile 245 250 255

Ser Arg Thr Pro Glu Val Thr Cys Val Val Val Asp Val Ser Gln Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Arg Leu Thr Val Asp
405 410 415

Lys Ser Arg Trp Gln Glu Gly Asn Val Phe Ser Cys Ser Val Met His
420 425 430

Glu Ala Leu His Asn His Tyr Thr Gln Lys Ser Leu Ser Leu Ser Leu
435 440 445

Gly Lys
450

<210> SEQ ID NO 49
<211> LENGTH: 448
<212> TYPE: PRT
<213> ORGANISM: Homo Sapiens

<400> SEQUENCE: 49

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Val Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Phe Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Met Lys Gly Ser Gly Thr Tyr Gly Gly Trp Phe Asp Thr
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

-continued

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 50
<211> LENGTH: 214
<212> TYPE: PRT
<213> ORGANISM: Homo Sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95
```

```
Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 51
<211> LENGTH: 214
<212> TYPE: PRT
<213> ORGANISM: Homo Sapiens

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Phe Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 52
<211> LENGTH: 8
<212> TYPE: PRT
```

<213> ORGANISM: Homo Sapiens

<400> SEQUENCE: 52

Gly Phe Thr Phe Ser Ser Tyr Trp
1               5

<210> SEQ ID NO 53
<211> LENGTH: 8
<212> TYPE: PRT
<213> ORGANISM: Homo Sapiens

<400> SEQUENCE: 53

Ile Lys Glu Asp Gly Ser Glu Lys
1               5

<210> SEQ ID NO 54
<211> LENGTH: 12
<212> TYPE: PRT
<213> ORGANISM: Homo Sapiens

<400> SEQUENCE: 54

Ala Arg Asn Arg Leu Tyr Ser Asp Phe Leu Asp Asn
1               5                   10

<210> SEQ ID NO 55
<211> LENGTH: 5
<212> TYPE: PRT
<213> ORGANISM: Homo Sapiens

<400> SEQUENCE: 55

Ser Tyr Trp Met Ser
1               5

<210> SEQ ID NO 56
<211> LENGTH: 17
<212> TYPE: PRT
<213> ORGANISM: Homo Sapiens

<400> SEQUENCE: 56

Asn Ile Lys Glu Asp Gly Ser Glu Lys Tyr Tyr Val Asp Ser Val Lys
1               5                   10                  15

Gly

<210> SEQ ID NO 57
<211> LENGTH: 10
<212> TYPE: PRT
<213> ORGANISM: Homo Sapiens

<400> SEQUENCE: 57

Asn Arg Leu Tyr Ser Asp Phe Leu Asp Asn
1               5                   10

<210> SEQ ID NO 58
<211> LENGTH: 119
<212> TYPE: PRT
<213> ORGANISM: Homo Sapiens

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val 35 40 45

Ala Asn Ile Lys Glu Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ser Val Tyr Tyr Cys
85 90 95

Ala Arg Asn Arg Leu Tyr Ser Asp Phe Leu Asp Asn Trp Gly Gln Gly
100 105 110

Thr Leu Val Thr Val Ser Ser
115

<210> SEQ ID NO 59
<211> LENGTH: 358
<212> TYPE: DNA
<213> ORGANISM: Homo Sapiens

<400> SEQUENCE: 59
gaggtgcagc tggtggagtc tgggggaggc ttggtccagc ctggggggtc cctgagactc 60
tcctgtgcag cctctggatt cacgtttagt agctattgga tgagttgggt ccgccaggct 120
ccagggaagg ggctggagtg ggtggccaac atcaaagaag atggaagtga gaaatactat 180
gtcgactctg tgaagggccg attcaccatc tccagagaca acgccaagaa ctcactgtat 240
ctgcaaatga acagcctgag agccgaggac acgtctgtgt attactgtgc gagaaatcga 300
ctctacagtg acttccttga caactggggc cagggaaccc tggtcaccgt ctcctcag 358

<210> SEQ ID NO 60
<211> LENGTH: 449
<212> TYPE: PRT
<213> ORGANISM: Homo Sapiens

<400> SEQUENCE: 60

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Glu Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ser Val Tyr Tyr Cys
85 90 95

Ala Arg Asn Arg Leu Tyr Ser Asp Phe Leu Asp Asn Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser

```
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 61
<211> LENGTH: 1347
<212> TYPE: DNA
<213> ORGANISM: Homo Sapiens

<400> SEQUENCE: 61

gaggtgcagc tggtggagtc tgggggaggc ttggtccagc ctgggggggtc cctgagactc      60

tcctgtgcag cctctggatt cacgtttagt agctattgga tgagttgggt ccgccaggct     120

ccagggaagg ggctggagtg ggtggccaac atcaaagaag atggaagtga gaaatactat     180

gtcgactctg tgaagggccg attcaccatc tccagagaca acgccaagaa ctcactgtat     240

ctgcaaatga acagcctgag agccgaggac acgtctgtgt attactgtgc gagaaatcga     300

ctctacagtg acttccttga caactggggc cagggaaccc tggtcaccgt ctcctcagcc     360

agcaccaagg gcccctctgt gttccctctg gccccttcca gcaagtccac ctctggcgga     420

acagccgctc tgggctgcct cgtgaaggac tacttccccg agcctgtgac cgtgtcctgg     480

aactctggcg ctctgaccag cggagtgcac accttccctg ctgtgctgca gtcctccggc     540

ctgtactccc tgtcctccgt cgtgaccgtg ccttccagct ctctgggcac ccagacctac     600
```

```
atctgcaacg tgaaccacaa gccctccaac accaaggtgg acaagaaggt ggaacccaag    660

tcctgcgaca agacccacac ctgtccccct tgtcctgccc ctgaactgct gggcggacct    720

tccgtgttcc tgttcccccc aaagcccaag gacaccctga tgatctcccg gacccccgaa    780

gtgacctgcg tggtggtgga tgtgtcccac gaggaccctg aagtgaagtt caattggtac    840

gtggacggcg tggaagtgca caacgccaag accaagccta gagaggaaca gtacaactcc    900

acctaccggg tggtgtccgt gctgaccgtg ctgcaccagg attggctgaa cggcaaagag    960

tacaagtgca aggtgtccaa caaggccctg cctgccccca tcgaaaagac catctccaag   1020

gccaagggcc agccccggga accccaggtg tacacactgc cccctagcag ggacgagctg   1080

accaagaacc aggtgtccct gacctgtctc gtgaaaggct tctacccctc cgatatcgcc   1140

gtggaatggg agtccaacgg ccagcctgag aacaactaca agaccacccc ccctgtgctg   1200

gactccgacg gctcattctt cctgtacagc aagctgacag tggacaagtc ccggtggcag   1260

cagggcaacg tgttctcctg ctccgtgatg cacgaggccc tgcacaacca ctacacccag   1320

aagtccctgt ccctgagccc cggcaag                                       1347
```

<210> SEQ ID NO 62
<211> LENGTH: 6
<212> TYPE: PRT
<213> ORGANISM: Homo Sapiens

<400> SEQUENCE: 62

Gln Gly Val Ser Ser Trp
1               5

<210> SEQ ID NO 63
<211> LENGTH: 3
<212> TYPE: PRT
<213> ORGANISM: Homo Sapiens

<400> SEQUENCE: 63

Gly Ala Ser
1

<210> SEQ ID NO 64
<211> LENGTH: 9
<212> TYPE: PRT
<213> ORGANISM: Homo Sapiens

<400> SEQUENCE: 64

Gln Gln Ala Asn Ser Ile Pro Phe Thr
1               5

<210> SEQ ID NO 65
<211> LENGTH: 11
<212> TYPE: PRT
<213> ORGANISM: Homo Sapiens

<400> SEQUENCE: 65

Arg Ala Ser Gln Gly Val Ser Ser Trp Leu Ala
1               5                   10

<210> SEQ ID NO 66
<211> LENGTH: 7
<212> TYPE: PRT
<213> ORGANISM: Homo Sapiens

<400> SEQUENCE: 66

```
Gly Ala Ser Ser Leu Gln Ser
1               5


<210> SEQ ID NO 67
<211> LENGTH: 9
<212> TYPE: PRT
<213> ORGANISM: Homo Sapiens

<400> SEQUENCE: 67

Gln Gln Ala Asn Ser Ile Pro Phe Thr
1               5


<210> SEQ ID NO 68
<211> LENGTH: 107
<212> TYPE: PRT
<213> ORGANISM: Homo Sapiens

<400> SEQUENCE: 68

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Thr Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105


<210> SEQ ID NO 69
<211> LENGTH: 322
<212> TYPE: DNA
<213> ORGANISM: Homo Sapiens

<400> SEQUENCE: 69

gacatccaga tgacccagtc tccatcttcc gtgtctgcat ctgtcggaga cagagtcacc      60

atcacttgtc gggcgagtca gggtgttagc agctggttag cctggtatca gcagaaatca     120

gggaaagccc ctaagctcct gatctatggt gcatccagtt tgcaaagtgg ggtcccatca     180

agattcagcg gcagtggatc tgggacagag ttcattctca ccatcagcag cctgcagcct     240

gaagattttg caacttacta ttgtcaacag gctaacagta tcccattcac tttcggccct     300

gggaccaaag tggatatcaa ac                                              322


<210> SEQ ID NO 70
<211> LENGTH: 214
<212> TYPE: PRT
<213> ORGANISM: Homo Sapiens

<400> SEQUENCE: 70

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45
```

-continued

Tyr Gly Ala Ser Ser Leu Gln Ser Gly Val Pro Ser Arg Phe Ser Gly
50 55 60

Ser Gly Ser Gly Thr Glu Phe Ile Leu Thr Ile Ser Ser Leu Gln Pro
65 70 75 80

Glu Asp Phe Ala Thr Tyr Tyr Cys Gln Gln Ala Asn Ser Ile Pro Phe
85 90 95

Thr Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 71
<211> LENGTH: 642
<212> TYPE: DNA
<213> ORGANISM: Homo Sapiens

<400> SEQUENCE: 71
gacatccaga tgacccagtc tccatcttcc gtgtctgcat ctgtcggaga cagagtcacc 60
atcacttgtc gggcgagtca gggtgttagc agctggttag cctggtatca gcagaaatca 120
gggaaagccc ctaagctcct gatctatggt gcatccagtt tgcaaagtgg ggtcccatca 180
agattcagcg gcagtggatc tgggacagag ttcattctca ccatcagcag cctgcagcct 240
gaagattttg caacttacta ttgtcaacag gctaacagta tcccattcac tttcggccct 300
gggaccaaag tggatatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 72
<211> LENGTH: 8
<212> TYPE: PRT
<213> ORGANISM: Homo Sapiens

<400> SEQUENCE: 72

Gly Phe Thr Phe Ser Ser Tyr Trp
1 5

<210> SEQ ID NO 73
<211> LENGTH: 8
<212> TYPE: PRT

<213> ORGANISM: Homo Sapiens

<400> SEQUENCE: 73

Ile Lys Glu Asp Gly Ser Glu Lys
1 5

<210> SEQ ID NO 74
<211> LENGTH: 12
<212> TYPE: PRT
<213> ORGANISM: Homo Sapiens

<400> SEQUENCE: 74

Ala Arg Val Arg Leu Tyr Ser Asp Phe Leu Asp Tyr
1 5 10

<210> SEQ ID NO 75
<211> LENGTH: 5
<212> TYPE: PRT
<213> ORGANISM: Homo Sapiens

<400> SEQUENCE: 75

Ser Tyr Trp Met Ser
1 5

<210> SEQ ID NO 76
<211> LENGTH: 17
<212> TYPE: PRT
<213> ORGANISM: Homo Sapiens

<400> SEQUENCE: 76

Asn Ile Lys Glu Asp Gly Ser Glu Lys Tyr Tyr Val Asp Ser Leu Lys
1 5 10 15

Gly

<210> SEQ ID NO 77
<211> LENGTH: 10
<212> TYPE: PRT
<213> ORGANISM: Homo Sapiens

<400> SEQUENCE: 77

Val Arg Leu Tyr Ser Asp Phe Leu Asp Tyr
1 5 10

<210> SEQ ID NO 78
<211> LENGTH: 119
<212> TYPE: PRT
<213> ORGANISM: Homo Sapiens

<400> SEQUENCE: 78

Glu Val Gln Leu Val Asp Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Glu Asp Gly Ser Glu Lys Tyr Tyr Val Asp Ser Leu
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ser Val Tyr Tyr Cys
85 90 95

```
Ala Arg Val Arg Leu Tyr Ser Asp Phe Leu Asp Tyr Trp Gly Gln Gly
            100                 105                 110

Thr Leu Val Thr Val Ser Ser
        115


<210> SEQ ID NO 79
<211> LENGTH: 358
<212> TYPE: DNA
<213> ORGANISM: Homo Sapiens

<400> SEQUENCE: 79

gaggtgcagc tggtggactc tgggggaggc ttggtccagc ctggggggtc cctgagactc      60

tcctgtgcag cctctggatt cacgtttagt agctattgga tgagttgggt ccgccaggct     120

ccaggaaagg ggctggagtg ggtggccaac ataaaagaag atggaagtga gaaatactat     180

gtagactctt tgaagggccg attcaccatc tccagagaca acgccaagaa ctcactgtat     240

ctgcaaatga acagcctgag agccgaggac acgtctgtgt attactgtgc gagagttcga     300

ctctacagtg acttccttga ctactggggc cagggaaccc tggtcaccgt ctcctcag       358


<210> SEQ ID NO 80
<211> LENGTH: 449
<212> TYPE: PRT
<213> ORGANISM: Homo Sapiens

<400> SEQUENCE: 80

Glu Val Gln Leu Val Asp Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Val Arg Leu Tyr Ser Asp Phe Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 81
<211> LENGTH: 1347
<212> TYPE: DNA
<213> ORGANISM: Homo Sapiens

<400> SEQUENCE: 81

gaggtgcagc tggtggactc tgggggaggc ttggtccagc ctgggggtc cctgagactc      60

tcctgtgcag cctctggatt cacgtttagt agctattgga tgagttgggt ccgccaggct     120

ccaggaaagg ggctggagtg ggtggccaac ataaaagaag atggaagtga gaaatactat     180

gtagactctt tgaagggccg attcaccatc tccagagaca acgccaagaa ctcactgtat     240

ctgcaaatga acagcctgag agccgaggac acgtctgtgt attactgtgc gagagttcga     300

ctctacagtg acttccttga ctactggggc cagggaaccc tggtcaccgt ctcctcagcc     360

agcaccaagg gccccctctgt gttccctctg gccccttcca gcaagtccac ctctggcgga     420

acagccgctc tgggctgcct cgtgaaggac tacttccccg agcctgtgac cgtgtcctgg     480

aactctggcg ctctgaccag cggagtgcac accttccctg ctgtgctgca gtcctccggc     540

ctgtactccc tgtcctccgt cgtgaccgtg ccttccagct ctctgggcac ccagacctac     600

atctgcaacg tgaaccacaa gccctccaac accaaggtgg acaagaaggt ggaacccaag     660

tcctgcgaca agacccacac ctgtccccct tgtcctgccc ctgaactgct gggcggacct     720

tccgtgttcc tgttcccccc aaagcccaag gacaccctga tgatctcccg gacccccgaa     780

gtgacctgcg tggtggtgga tgtgtcccac gaggaccctg aagtgaagtt caattggtac     840

gtggacggcg tggaagtgca caacgccaag accaagccta gagaggaaca gtacaactcc     900
```

-continued

```
acctaccggg tggtgtccgt gctgaccgtg ctgcaccagg attggctgaa cggcaaagag    960

tacaagtgca aggtgtccaa caaggccctg cctgccccca tcgaaaagac catctccaag   1020

gccaagggcc agccccggga accccaggtg tacacactgc cccctagcag ggacgagctg   1080

accaagaacc aggtgtccct gacctgtctc gtgaaaggct tctacccctc cgatatcgcc   1140

gtggaatggg agtccaacgg ccagcctgag aacaactaca agaccacccc ccctgtgctg   1200

gactccgacg gctcattctt cctgtacagc aagctgacag tggacaagtc ccggtggcag   1260

cagggcaacg tgttctcctg ctccgtgatg cacgaggccc tgcacaacca ctacacccag   1320

aagtccctgt ccctgagccc cggcaag                                       1347


<210> SEQ ID NO 82
<211> LENGTH: 6
<212> TYPE: PRT
<213> ORGANISM: Homo Sapiens

<400> SEQUENCE: 82

Gln Gly Val Ser Ser Trp
1               5


<210> SEQ ID NO 83
<211> LENGTH: 3
<212> TYPE: PRT
<213> ORGANISM: Homo Sapiens

<400> SEQUENCE: 83

Gly Ala Ser
1


<210> SEQ ID NO 84
<211> LENGTH: 9
<212> TYPE: PRT
<213> ORGANISM: Homo Sapiens

<400> SEQUENCE: 84

Gln Gln Ala Asn Ser Ile Pro Phe Thr
1               5


<210> SEQ ID NO 85
<211> LENGTH: 11
<212> TYPE: PRT
<213> ORGANISM: Homo Sapiens

<400> SEQUENCE: 85

Arg Ala Ser Gln Gly Val Ser Ser Trp Leu Ala
1               5                   10


<210> SEQ ID NO 86
<211> LENGTH: 7
<212> TYPE: PRT
<213> ORGANISM: Homo Sapiens

<400> SEQUENCE: 86

Gly Ala Ser Ser Leu Gln Ser
1               5


<210> SEQ ID NO 87
<211> LENGTH: 9
<212> TYPE: PRT
<213> ORGANISM: Homo Sapiens

<400> SEQUENCE: 87
```

-continued

Gln Gln Ala Asn Ser Ile Pro Phe Thr
1               5

<210> SEQ ID NO 88
<211> LENGTH: 107
<212> TYPE: PRT
<213> ORGANISM: Homo Sapiens

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Ser Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys
            100                 105

<210> SEQ ID NO 89
<211> LENGTH: 322
<212> TYPE: DNA
<213> ORGANISM: Homo Sapiens

<400> SEQUENCE: 89
gacatccaga tgacccagtc tccatcttcc gtgtctgcat ctgtcggaga cagagtcacc     60
atcacttgtc gggcgagtca gggtgttagc agttggttag cctggtatca gcagaaatca    120
gggaaagccc ctaagctcct gatctatggt gcctccagtt tgcaaagtgg ggtcccatca    180
agattcagcg gcagtggatc tgggacagag ttcattctca gcatcagcag cctgcagcct    240
gaagattttg caacttacta ttgtcaacag gctaacagta tcccattcac tttcggccct    300
gggaccaaag tggatatcaa ac                                             322

<210> SEQ ID NO 90
<211> LENGTH: 214
<212> TYPE: PRT
<213> ORGANISM: Homo Sapiens

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Ser Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Ile Leu Ser Ile Ser Ser Leu Gln Pro
65                  70                  75                  80

Glu Asp Phe Ala Thr Tyr Tyr Cys Gln Gln Ala Asn Ser Ile Pro Phe
                85                  90                  95

Thr Phe Gly Pro Gly Thr Lys Val Asp Ile Lys Arg Thr Val Ala Ala

-continued

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 91
<211> LENGTH: 642
<212> TYPE: DNA
<213> ORGANISM: Homo Sapiens

<400> SEQUENCE: 91

gacatccaga tgacccagtc tccatcttcc gtgtctgcat ctgtcggaga cagagtcacc     60

atcacttgtc gggcgagtca gggtgttagc agttggttag cctggtatca gcagaaatca    120

gggaaagccc ctaagctcct gatctatggt gcctccagtt tgcaaagtgg ggtcccatca    180

agattcagcg gcagtggatc tgggacagag ttcattctca gcatcagcag cctgcagcct    240

gaagattttg caacttacta ttgtcaacag gctaacagta tcccattcac tttcggccct    300

gggaccaaag tggatatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 92
<211> LENGTH: 9
<212> TYPE: PRT
<213> ORGANISM: Homo Sapiens

<400> SEQUENCE: 92

Gly Gly Ser Ile Ile Ser Ser Asp Trp
1               5


<210> SEQ ID NO 93
<211> LENGTH: 7
<212> TYPE: PRT
<213> ORGANISM: Homo Sapiens

<400> SEQUENCE: 93

Ile Phe His Ser Gly Arg Thr
1               5


<210> SEQ ID NO 94
<211> LENGTH: 8
<212> TYPE: PRT
```

<213> ORGANISM: Homo Sapiens

<400> SEQUENCE: 94

Ala Arg Asp Gly Ser Gly Ser Tyr
1               5

<210> SEQ ID NO 95
<211> LENGTH: 6
<212> TYPE: PRT
<213> ORGANISM: Homo Sapiens

<400> SEQUENCE: 95

Ser Ser Asp Trp Trp Asn
1               5

<210> SEQ ID NO 96
<211> LENGTH: 16
<212> TYPE: PRT
<213> ORGANISM: Homo Sapiens

<400> SEQUENCE: 96

Glu Ile Phe His Ser Gly Arg Thr Asn Tyr Asn Pro Ser Leu Lys Ser
1               5                   10                  15

<210> SEQ ID NO 97
<211> LENGTH: 6
<212> TYPE: PRT
<213> ORGANISM: Homo Sapiens

<400> SEQUENCE: 97

Asp Gly Ser Gly Ser Tyr
1               5

<210> SEQ ID NO 98
<211> LENGTH: 115
<212> TYPE: PRT
<213> ORGANISM: Homo Sapiens

<400> SEQUENCE: 98

Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asp Gly Ser Gly Ser Tyr Trp Gly Gln Gly Thr Leu Val Thr
            100                 105                 110

Val Ser Ser
        115

<210> SEQ ID NO 99
<211> LENGTH: 346
<212> TYPE: DNA
<213> ORGANISM: Homo Sapiens

<400> SEQUENCE: 99

```
caggtgcagc tgcaggagtc gggcccagga ctggtgaagc cttcggggac cctgtccctc      60

acctgcattg tctctggtgg ctccatcatc agtagtgact ggtggaattg ggtccgccag     120

cccccaggga aggggctgga gtggattgga gaaatctttc atagtgggag gaccaactac     180

aacccgtccc tcaagagtcg agtcaccata tcaatagaca agtccaagaa tcagttctcc     240

ctgaggctga gctctgtgac cgccgcggac acggccgtgt attactgtgc gagagatggt     300

tcggggagtt actggggcca gggaaccctg gtcaccgtct cctcag                    346
```

<210> SEQ ID NO 100
<211> LENGTH: 445
<212> TYPE: PRT
<213> ORGANISM: Homo Sapiens

<400> SEQUENCE: 100

```
Gln Val Gln Leu Gln Glu Ser Gly Pro Gly Leu Val Lys Pro Ser Gly
1               5                   10                  15

Thr Leu Ser Leu Thr Cys Ile Val Ser Gly Gly Ser Ile Ile Ser Ser
            20                  25                  30

Asp Trp Trp Asn Trp Val Arg Gln Pro Pro Gly Lys Gly Leu Glu Trp
        35                  40                  45

Ile Gly Glu Ile Phe His Ser Gly Arg Thr Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Asp Gly Ser Gly Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

-continued 305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Asp Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 101
<211> LENGTH: 1335
<212> TYPE: DNA
<213> ORGANISM: Homo Sapiens

<400> SEQUENCE: 101
caggtgcagc tgcaggagtc gggcccagga ctggtgaagc cttcggggac cctgtccctc 60
acctgcattg tctctggtgg ctccatcatc agtagtgact ggtggaattg ggtccgccag 120
cccccaggga aggggctgga gtggattgga gaaatctttc atagtgggag gaccaactac 180
aacccgtccc tcaagagtcg agtcaccata tcaatagaca agtccaagaa tcagttctcc 240
ctgaggctga gctctgtgac cgccgcggac acggccgtgt attactgtgc gagagatggt 300
tcggggagtt actggggcca gggaaccctg gtcaccgtct cctcagccag caccaagggc 360
ccctctgtgt tccctctggc cccttccagc aagtccacct ctggcggaac agccgctctg 420
ggctgcctcg tgaaggacta cttccccgag cctgtgaccg tgtcctggaa ctctggcgct 480
ctgaccagcg gagtgcacac cttccctgct gtgctgcagt cctccggcct gtactccctg 540
tcctccgtcg tgaccgtgcc ttccagctct ctgggcaccc agacctacat ctgcaacgtg 600
aaccacaagc cctccaacac caaggtggac aagaaggtgg aacccaagtc ctgcgacaag 660
acccacacct gtcccccttg tcctgcccct gaactgctgg gcggaccttc cgtgttcctg 720
ttccccccaa agcccaagga caccctgatg atctcccgga cccccgaagt gacctgcgtg 780
gtggtggatg tgtcccacga ggaccctgaa gtgaagttca attggtacgt ggacggcgtg 840
gaagtgcaca acgccaagac caagcctaga gaggaacagt acaactccac ctaccgggtg 900
gtgtccgtgc tgaccgtgct gcaccaggat tggctgaacg gcaaagagta caagtgcaag 960
gtgtccaaca aggccctgcc tgcccccatc gaaaagacca tctccaaggc caagggccag 1020
ccccgggaac cccaggtgta cacactgccc cctagcaggg acgagctgac caagaaccag 1080
gtgtccctga cctgtctcgt gaaaggcttc taccccctccg atatcgccgt ggaatgggag 1140
tccaacggcc agcctgagaa caactacaag accacccccc ctgtgctgga ctccgacggc 1200
tcattcttcc tgtacagcaa gctgacagtg gacaagtccc ggtggcagca gggcaacgtg 1260
ttctcctgct ccgtgatgca cgaggccctg cacaaccact acacccagaa gtccctgtcc 1320
ctgagccccg gcaag 1335

<210> SEQ ID NO 102
<211> LENGTH: 12
<212> TYPE: PRT
<213> ORGANISM: Homo Sapiens

<400> SEQUENCE: 102

Gln Ser Val Leu Tyr Ser Ser Asn Asn Lys Asn Tyr
1               5                   10

<210> SEQ ID NO 103
<211> LENGTH: 3
<212> TYPE: PRT
<213> ORGANISM: Homo Sapiens

<400> SEQUENCE: 103

Trp Ala Ser
1

<210> SEQ ID NO 104
<211> LENGTH: 8
<212> TYPE: PRT
<213> ORGANISM: Homo Sapiens

<400> SEQUENCE: 104

Gln Gln Tyr Tyr Ser Asn Arg Ser
1               5

<210> SEQ ID NO 105
<211> LENGTH: 17
<212> TYPE: PRT
<213> ORGANISM: Homo Sapiens

<400> SEQUENCE: 105

Lys Ser Ser Gln Ser Val Leu Tyr Ser Ser Asn Asn Lys Asn Tyr Leu
1               5                   10                  15

Ala

<210> SEQ ID NO 106
<211> LENGTH: 7
<212> TYPE: PRT
<213> ORGANISM: Homo Sapiens

<400> SEQUENCE: 106

Trp Ala Ser Thr Arg Glu Ser
1               5

<210> SEQ ID NO 107
<211> LENGTH: 8
<212> TYPE: PRT
<213> ORGANISM: Homo Sapiens

<400> SEQUENCE: 107

Gln Gln Tyr Tyr Ser Asn Arg Ser
1               5

<210> SEQ ID NO 108
<211> LENGTH: 112
<212> TYPE: PRT
<213> ORGANISM: Homo Sapiens

<400> SEQUENCE: 108

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Gln Gln
                85                  90                  95

Tyr Tyr Ser Asn Arg Ser Phe Gly Gln Gly Thr Lys Leu Glu Ile Lys
            100                 105                 110


<210> SEQ ID NO 109
<211> LENGTH: 337
<212> TYPE: DNA
<213> ORGANISM: Homo Sapiens

<400> SEQUENCE: 109

gacatcgtga tgacccagtc tccagactcc ctggctgtgt ctctgggcga gagggccacc      60

atcaactgca agtccagcca gagtgtttta tacagctcca acaataagaa ttacttagct     120

tggtaccagc agaaatcagg acagcctcct aagttgctca tttactgggc atctacccgg     180

gaatccgggg tccctgaccg attcagtggc agcgggtctg ggacagattt cactctcacc     240

atcagcagcc tgcagactga agatgtggca gtttattact gtcagcaata ttatagtaat     300

cgcagttttg gccaggggac caagctggag atcaaac                              337


<210> SEQ ID NO 110
<211> LENGTH: 219
<212> TYPE: PRT
<213> ORGANISM: Homo Sapiens

<400> SEQUENCE: 110

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Thr Glu Asp Val Ala Val Tyr Tyr Cys Gln Gln
                85                  90                  95

Tyr Tyr Ser Asn Arg Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 111
<211> LENGTH: 657
<212> TYPE: DNA
<213> ORGANISM: Homo Sapiens

<400> SEQUENCE: 111
gacatcgtga tgacccagtc tccagactcc ctggctgtgt ctctgggcga gagggccacc 60
atcaactgca agtccagcca gagtgtttta tacagctcca acaataagaa ttacttagct 120
tggtaccagc agaaatcagg acagcctcct aagttgctca tttactgggc atctacccgg 180
gaatccgggg tccctgaccg attcagtggc agcgggtctg ggacagattt cactctcacc 240
atcagcagcc tgcagactga agatgtggca gtttattact gtcagcaata ttatagtaat 300
cgcagttttg gccaggggac caagctggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 112
<211> LENGTH: 8
<212> TYPE: PRT
<213> ORGANISM: Homo Sapiens

<400> SEQUENCE: 112

Gly Phe Thr Phe Ser Ser Tyr Trp
1 5

<210> SEQ ID NO 113
<211> LENGTH: 8
<212> TYPE: PRT
<213> ORGANISM: Homo Sapiens

<400> SEQUENCE: 113

Ile Lys Glu Asp Gly Ser Glu Lys
1 5

<210> SEQ ID NO 114
<211> LENGTH: 12
<212> TYPE: PRT
<213> ORGANISM: Homo Sapiens

<400> SEQUENCE: 114

Ala Arg Asn Arg Leu Tyr Ser Asp Phe Leu Asp Asn
1 5 10

<210> SEQ ID NO 115
<211> LENGTH: 5
<212> TYPE: PRT
<213> ORGANISM: Homo Sapiens

<400> SEQUENCE: 115

Ser Tyr Trp Met Ser
1 5

<210> SEQ ID NO 116
<211> LENGTH: 17
<212> TYPE: PRT
<213> ORGANISM: Homo Sapiens

<400> SEQUENCE: 116

Asn Ile Lys Glu Asp Gly Ser Glu Lys Tyr Tyr Val Asp Ser Val Lys
1 5 10 15

Gly

<210> SEQ ID NO 117
<211> LENGTH: 10
<212> TYPE: PRT
<213> ORGANISM: Homo Sapiens

<400> SEQUENCE: 117

Asn Arg Leu Tyr Ser Asp Phe Leu Asp Asn
1 5 10

<210> SEQ ID NO 118
<211> LENGTH: 119
<212> TYPE: PRT
<213> ORGANISM: Homo Sapiens

<400> SEQUENCE: 118

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Glu Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ser Val Tyr Tyr Cys
85 90 95

Ala Arg Asn Arg Leu Tyr Ser Asp Phe Leu Asp Asn Trp Gly Gln Gly
100 105 110

Thr Leu Val Thr Val Ser Ser
115

<210> SEQ ID NO 119
<211> LENGTH: 358
<212> TYPE: DNA
<213> ORGANISM: Homo Sapiens

<400> SEQUENCE: 119
gaggtgcagc tggtggagtc tgggggaggc ttggtccagc ctggggggtc cctgagactc 60
tcctgtgcag cctctggatt cacgtttagt agctattgga tgagttgggt ccgccaggct 120
ccagggaagg ggctggagtg ggtggccaac atcaaagaag atggaagtga gaaatactat 180
gtcgactctg tgaagggccg attcaccatc tccagagaca acgccaagaa ctcactgtat 240
ctgcaaatga acagcctgag agccgaggac acgtctgtgt attactgtgc gagaaatcga 300
ctctacagtg acttccttga caactggggc cagggaaccc tggtcaccgt ctcctcag 358

<210> SEQ ID NO 120
<211> LENGTH: 449
<212> TYPE: PRT
<213> ORGANISM: Homo Sapiens

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ser Val Tyr Tyr Cys
                85                  90                  95

Ala Arg Asn Arg Leu Tyr Ser Asp Phe Leu Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 121
<211> LENGTH: 1347
<212> TYPE: DNA
<213> ORGANISM: Homo Sapiens

<400> SEQUENCE: 121

gaggtgcagc tggtggagtc tgggggaggc ttggtccagc ctggggggtc cctgagactc     60

tcctgtgcag cctctggatt cacgtttagt agctattgga tgagttgggt ccgccaggct    120

ccagggaagg ggctggagtg ggtggccaac atcaaagaag atggaagtga gaaatactat    180

gtcgactctg tgaagggccg attcaccatc tccagagaca acgccaagaa ctcactgtat    240

ctgcaaatga acagcctgag agccgaggac acgtctgtgt attactgtgc gagaaatcga    300

ctctacagtg acttccttga caactggggc cagggaaccc tggtcaccgt ctcctcagcc    360

agcaccaagg gcccctctgt gttccctctg gccccttcca gcaagtccac ctctggcgga    420

acagccgctc tgggctgcct cgtgaaggac tacttccccg agcctgtgac cgtgtcctgg    480

aactctggcg ctctgaccag cggagtgcac accttccctg ctgtgctgca gtcctccggc    540

ctgtactccc tgtcctccgt cgtgaccgtg ccttccagct ctctgggcac ccagacctac    600

atctgcaacg tgaaccacaa gccctccaac accaaggtgg acaagaaggt ggaacccaag    660

tcctgcgaca agacccacac ctgtccccct tgtcctgccc ctgaactgct gggcggacct    720

tccgtgttcc tgttcccccc aaagcccaag gacaccctga tgatctcccg gacccccgaa    780

gtgacctgcg tggtggtgga tgtgtcccac gaggaccctg aagtgaagtt caattggtac    840

gtggacggcg tggaagtgca caacgccaag accaagccta gagaggaaca gtacaactcc    900

acctaccggg tggtgtccgt gctgaccgtg ctgcaccagg attggctgaa cggcaaagag    960

tacaagtgca aggtgtccaa caaggccctg cctgccccca tcgaaaagac catctccaag   1020

gccaagggcc agccccggga accccaggtg tacacactgc cccctagcag ggacgagctg   1080

accaagaacc aggtgtccct gacctgtctc gtgaaaggct tctacccctc cgatatcgcc   1140

gtggaatggg agtccaacgg ccagcctgag aacaactaca agaccacccc ccctgtgctg   1200

gactccgacg gctcattctt cctgtacagc aagctgacag tggacaagtc ccggtggcag   1260

cagggcaacg tgttctcctg ctccgtgatg cacgaggccc tgcacaacca ctacacccag   1320

aagtccctgt ccctgagccc cggcaag                                        1347


<210> SEQ ID NO 122
<211> LENGTH: 6
<212> TYPE: PRT
<213> ORGANISM: Homo Sapiens

<400> SEQUENCE: 122
```

Gln Gly Val Ser Ser Trp
1 5

<210> SEQ ID NO 123
<211> LENGTH: 3
<212> TYPE: PRT
<213> ORGANISM: Homo Sapiens

<400> SEQUENCE: 123

Gly Ala Ser
1

<210> SEQ ID NO 124
<211> LENGTH: 9
<212> TYPE: PRT
<213> ORGANISM: Homo Sapiens

<400> SEQUENCE: 124

Gln Gln Ala Asn Ser Ile Pro Phe Thr
1 5

<210> SEQ ID NO 125
<211> LENGTH: 11
<212> TYPE: PRT
<213> ORGANISM: Homo Sapiens

<400> SEQUENCE: 125

Arg Ala Ser Gln Gly Val Ser Ser Trp Leu Ala
1 5 10

<210> SEQ ID NO 126
<211> LENGTH: 7
<212> TYPE: PRT
<213> ORGANISM: Homo Sapiens

<400> SEQUENCE: 126

Gly Ala Ser Ser Leu Gln Ser
1 5

<210> SEQ ID NO 127
<211> LENGTH: 9
<212> TYPE: PRT
<213> ORGANISM: Homo Sapiens

<400> SEQUENCE: 127

Gln Gln Ala Asn Ser Ile Pro Phe Thr
1 5

<210> SEQ ID NO 128
<211> LENGTH: 107
<212> TYPE: PRT
<213> ORGANISM: Homo Sapiens

<400> SEQUENCE: 128

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Val Ser Ser Trp
20 25 30

Leu Ala Trp Tyr Gln Gln Lys Ser Gly Lys Ala Pro Lys Leu Leu Ile
35 40 45

Tyr Gly Ala Ser Ser Leu Gln Ser Gly Val Pro Ser Arg Phe Ser Gly
50 55 60

Ser Gly Ser Gly Thr Glu Phe Ile Leu Thr Ile Ser Ser Leu Gln Pro 65 70 75 80

Glu Asp Phe Ala Thr Tyr Tyr Cys Gln Gln Ala Asn Ser Ile Pro Phe
85 90 95

Thr Phe Gly Pro Gly Thr Lys Val Asp Ile Lys
100 105

<210> SEQ ID NO 129
<211> LENGTH: 322
<212> TYPE: DNA
<213> ORGANISM: Homo Sapiens

<400> SEQUENCE: 129
gacatccaga tgacccagtc tccatcttcc gtgtctgcat ctgtcggaga cagagtcacc 60
atcacttgtc gggcgagtca gggtgttagc agctggttag cctggtatca gcagaaatca 120
gggaaagccc ctaagctcct gatctatggt gcatccagtt tgcaaagtgg ggtcccatca 180
agattcagcg gcagtggatc tgggacagag ttcattctca ccatcagcag cctgcagcct 240
gaagattttg caacttacta ttgtcaacag gctaacagta tcccattcac tttcggccct 300
gggaccaaag tggatatcaa ac 322

<210> SEQ ID NO 130
<211> LENGTH: 214
<212> TYPE: PRT
<213> ORGANISM: Homo Sapiens

<400> SEQUENCE: 130

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Val Ser Ser Trp
20 25 30

Leu Ala Trp Tyr Gln Gln Lys Ser Gly Lys Ala Pro Lys Leu Leu Ile
35 40 45

Tyr Gly Ala Ser Ser Leu Gln Ser Gly Val Pro Ser Arg Phe Ser Gly
50 55 60

Ser Gly Ser Gly Thr Glu Phe Ile Leu Thr Ile Ser Ser Leu Gln Pro
65 70 75 80

Glu Asp Phe Ala Thr Tyr Tyr Cys Gln Gln Ala Asn Ser Ile Pro Phe
85 90 95

Thr Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 131
<211> LENGTH: 642
<212> TYPE: DNA
<213> ORGANISM: Homo Sapiens

<400> SEQUENCE: 131
gacatccaga tgacccagtc tccatcttcc gtgtctgcat ctgtcggaga cagagtcacc 60
atcacttgtc gggcgagtca gggtgttagc agctggttag cctggtatca gcagaaatca 120
gggaaagccc ctaagctcct gatctatggt gcatccagtt tgcaaagtgg ggtcccatca 180
agattcagcg gcagtggatc tgggacagag ttcattctca ccatcagcag cctgcagcct 240
gaagattttg caacttacta ttgtcaacag gctaacagta tcccattcac tttcggccct 300
gggaccaaag tggatatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 132
<211> LENGTH: 8
<212> TYPE: PRT
<213> ORGANISM: Homo Sapiens

<400> SEQUENCE: 132

Gly Phe Thr Phe Arg Ile Tyr Gly
1 5

<210> SEQ ID NO 133
<211> LENGTH: 8
<212> TYPE: PRT
<213> ORGANISM: Homo Sapiens

<400> SEQUENCE: 133

Ile Trp Tyr Asp Gly Ser Asn Lys
1 5

<210> SEQ ID NO 134
<211> LENGTH: 11
<212> TYPE: PRT
<213> ORGANISM: Homo Sapiens

<400> SEQUENCE: 134

Ala Arg Asp Met Asp Tyr Phe Gly Met Asp Val
1 5 10

<210> SEQ ID NO 135
<211> LENGTH: 5
<212> TYPE: PRT
<213> ORGANISM: Homo Sapiens

<400> SEQUENCE: 135

Ile Tyr Gly Met His
1 5

<210> SEQ ID NO 136
<211> LENGTH: 17
<212> TYPE: PRT
<213> ORGANISM: Homo Sapiens

<400> SEQUENCE: 136

Val Ile Trp Tyr Asp Gly Ser Asn Lys Tyr Tyr Ala Asp Ser Val Lys
1 5 10 15

Gly

<210> SEQ ID NO 137
<211> LENGTH: 9
<212> TYPE: PRT
<213> ORGANISM: Homo Sapiens

<400> SEQUENCE: 137

Asp Met Asp Tyr Phe Gly Met Asp Val
1 5

<210> SEQ ID NO 138
<211> LENGTH: 118
<212> TYPE: PRT
<213> ORGANISM: Homo Sapiens

<400> SEQUENCE: 138

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Arg Ile Tyr
20 25 30

Gly Met His Trp Val Arg Gln Ala Pro Gly Lys Gly Leu Glu Trp Val
35 40 45

Ala Val Ile Trp Tyr Asp Gly Ser Asn Lys Tyr Tyr Ala Asp Ser Val
50 55 60

Lys Gly Arg Phe Thr Ile Ser Arg Asp Asn Ser Asp Asn Thr Leu Tyr
65 70 75 80

Leu Gln Met Asn Ser Leu Arg Ala Glu Asp Thr Ala Val Tyr Tyr Cys
85 90 95

Ala Arg Asp Met Asp Tyr Phe Gly Met Asp Val Trp Gly Gln Gly Thr
100 105 110

Thr Val Thr Val Ser Ser
115

<210> SEQ ID NO 139
<211> LENGTH: 355
<212> TYPE: DNA
<213> ORGANISM: Homo Sapiens

<400> SEQUENCE: 139
caggtgcagc tggtggagtc tgggggaggc gtggtccagc ctgggaggtc cctgagactc 60
tcctgtgcag cgtctggatt caccttccgt atttatggca tgcactgggt ccgccaggct 120
ccaggcaagg ggctggagtg ggtggcagtt atatggtatg atggaagtaa taaatactat 180
gctgactccg tgaagggccg attcaccatc tccagagaca attccgacaa cacgctgtat 240
ctgcaaatga acagcctgag agccgaggac acggctgtgt attactgtgc gagagatatg 300
gactacttcg gtatggacgt ctggggccaa gggaccacgg tcaccgtctc ctcag 355

<210> SEQ ID NO 140
<211> LENGTH: 448
<212> TYPE: PRT
<213> ORGANISM: Homo Sapiens

<400> SEQUENCE: 140

Gln Val Gln Leu Val Glu Ser Gly Gly Gly Val Val Gln Pro Gly Arg

-continued

```
1               5                   10                  15

Ser Leu Arg Leu Ser Cys Ala Ala Ser Gly Phe Thr Phe Arg Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Asp Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Asp Tyr Phe Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445


<210> SEQ ID NO 141
<211> LENGTH: 1344
<212> TYPE: DNA
<213> ORGANISM: Homo Sapiens

<400> SEQUENCE: 141

caggtgcagc tggtggagtc tgggggaggc gtggtccagc ctgggaggtc cctgagactc      60

tcctgtgcag cgtctggatt caccttccgt atttatggca tgcactgggt ccgccaggct     120

ccaggcaagg ggctggagtg ggtggcagtt atatggtatg atggaagtaa taaatactat     180

gctgactccg tgaagggccg attcaccatc tccagagaca attccgacaa cacgctgtat     240

ctgcaaatga acagcctgag agccgaggac acggctgtgt attactgtgc gagagatatg     300

gactacttcg gtatggacgt ctggggccaa gggaccacgg tcaccgtctc ctcagccagc     360

accaagggcc cctctgtgtt ccctctggcc ccttccagca agtccacctc tggcggaaca     420

gccgctctgg gctgcctcgt gaaggactac ttccccgagc ctgtgaccgt gtcctggaac     480

tctggcgctc tgaccagcgg agtgcacacc ttccctgctg tgctgcagtc ctccggcctg     540

tactccctgt cctccgtcgt gaccgtgcct tccagctctc tgggcaccca gacctacatc     600

tgcaacgtga accacaagcc ctccaacacc aaggtggaca agaaggtgga acccaagtcc     660

tgcgacaaga cccacacctg tccccccttgt cctgcccctg aactgctggg cggaccttcc     720

gtgttcctgt tcccccccaaa gcccaaggac accctgatga tctcccggac ccccgaagtg     780

acctgcgtgg tggtggatgt gtcccacgag gaccctgaag tgaagttcaa ttggtacgtg     840

gacggcgtgg aagtgcacaa cgccaagacc aagcctagag aggaacagta caactccacc     900

taccgggtgg tgtccgtgct gaccgtgctg caccaggatt ggctgaacgg caaagagtac     960

aagtgcaagg tgtccaacaa ggccctgcct gcccccatcg aaaagaccat ctccaaggcc    1020

aagggccagc cccgggaacc ccaggtgtac acactgcccc ctagcaggga cgagctgacc    1080

aagaaccagg tgtccctgac ctgtctcgtg aaaggcttct acccctccga tatcgccgtg    1140

gaatgggagt ccaacggcca gcctgagaac aactacaaga ccaccccccc tgtgctggac    1200

tccgacggct cattcttcct gtacagcaag ctgacagtgg acaagtcccg gtggcagcag    1260

ggcaacgtgt tctcctgctc cgtgatgcac gaggccctgc acaaccacta cacccagaag    1320

tccctgtccc tgagccccgg caag                                           1344


<210> SEQ ID NO 142
<211> LENGTH: 6
<212> TYPE: PRT
<213> ORGANISM: Homo Sapiens

<400> SEQUENCE: 142

Gln Gly Ile Arg Asn Asp
1               5


<210> SEQ ID NO 143
<211> LENGTH: 3
<212> TYPE: PRT
<213> ORGANISM: Homo Sapiens

<400> SEQUENCE: 143

Ala Ala Ser
1
```

<210> SEQ ID NO 144
<211> LENGTH: 9
<212> TYPE: PRT
<213> ORGANISM: Homo Sapiens

<400> SEQUENCE: 144

Leu Gln His Asn Ser Tyr Pro Arg Thr
1               5

<210> SEQ ID NO 145
<211> LENGTH: 11
<212> TYPE: PRT
<213> ORGANISM: Homo Sapiens

<400> SEQUENCE: 145

Arg Ala Ser Gln Gly Ile Arg Asn Asp Leu Gly
1               5                   10

<210> SEQ ID NO 146
<211> LENGTH: 7
<212> TYPE: PRT
<213> ORGANISM: Homo Sapiens

<400> SEQUENCE: 146

Ala Ala Ser Ser Leu Gln Ser
1               5

<210> SEQ ID NO 147
<211> LENGTH: 9
<212> TYPE: PRT
<213> ORGANISM: Homo Sapiens

<400> SEQUENCE: 147

Leu Gln His Asn Ser Tyr Pro Arg Thr
1               5

<210> SEQ ID NO 148
<211> LENGTH: 107
<212> TYPE: PRT
<213> ORGANISM: Homo Sapiens

<400> SEQUENCE: 148

Asp Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys
            100                 105

<210> SEQ ID NO 149
<211> LENGTH: 322
<212> TYPE: DNA
<213> ORGANISM: Homo Sapiens

<400> SEQUENCE: 149

```
gacctccaga tgacccagtc tccatcctcc ctgtctgcat ctgtaggaga cagagtcacc     60

atcacttgcc gggcaagtca gggcattaga aatgatttag gctggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatagtt accctcggac gttcggccaa    300

gggaccaagg tggaaatcaa ac                                             322
```

<210> SEQ ID NO 150
<211> LENGTH: 214
<212> TYPE: PRT
<213> ORGANISM: Homo Sapiens

<400> SEQUENCE: 150

```
Asp Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 151
<211> LENGTH: 642
<212> TYPE: DNA
<213> ORGANISM: Homo Sapiens

<400> SEQUENCE: 151

```
gacctccaga tgacccagtc tccatcctcc ctgtctgcat ctgtaggaga cagagtcacc     60

atcacttgcc gggcaagtca gggcattaga aatgatttag gctggtatca gcagaaacca    120

gggaaagccc ctaagcgcct gatctatgct gcatccagtt tgcaaagtgg ggtcccatca    180
```

-continued

```
aggttcagcg gcagtggatc tgggacagaa ttcactctca caatcagcag cctgcagcct    240

gaagattttg caacttatta ctgtctacag cataatagtt accctcggac gttcggccaa    300

gggaccaagg tggaaatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                        642
```

```
<210> SEQ ID NO 152
<211> LENGTH: 9
<212> TYPE: PRT
<213> ORGANISM: Homo Sapiens

<400> SEQUENCE: 152

Gly Gly Ser Ile Ser Ser Ser Asp Trp
1               5


<210> SEQ ID NO 153
<211> LENGTH: 7
<212> TYPE: PRT
<213> ORGANISM: Homo Sapiens

<400> SEQUENCE: 153

Ile Phe His Ser Gly Asn Thr
1               5


<210> SEQ ID NO 154
<211> LENGTH: 8
<212> TYPE: PRT
<213> ORGANISM: Homo Sapiens

<400> SEQUENCE: 154

Val Arg Asp Gly Ser Gly Ser Tyr
1               5


<210> SEQ ID NO 155
<211> LENGTH: 6
<212> TYPE: PRT
<213> ORGANISM: Homo Sapiens

<400> SEQUENCE: 155

Ser Ser Asp Trp Trp Ser
1               5


<210> SEQ ID NO 156
<211> LENGTH: 16
<212> TYPE: PRT
<213> ORGANISM: Homo Sapiens

<400> SEQUENCE: 156

Glu Ile Phe His Ser Gly Asn Thr Asn Tyr Asn Pro Ser Leu Lys Ser
1               5                   10                  15


<210> SEQ ID NO 157
<211> LENGTH: 6
<212> TYPE: PRT
<213> ORGANISM: Homo Sapiens

<400> SEQUENCE: 157
```

Asp Gly Ser Gly Ser Tyr
1 5

<210> SEQ ID NO 158
<211> LENGTH: 115
<212> TYPE: PRT
<213> ORGANISM: Homo Sapiens

<400> SEQUENCE: 158

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asp Trp Trp Ser Trp Val Arg Gln Pro Pro Gly Lys Gly Leu Glu Trp
35 40 45

Ile Gly Glu Ile Phe His Ser Gly Asn Thr Asn Tyr Asn Pro Ser Leu
50 55 60

Lys Ser Arg Val Thr Ile Ser Val Asp Lys Ser Lys Asn Gln Ile Ser
65 70 75 80

Leu Arg Leu Asn Ser Val Thr Ala Ala Asp Thr Ala Val Tyr Tyr Cys
85 90 95

Val Arg Asp Gly Ser Gly Ser Tyr Trp Gly Gln Gly Thr Leu Val Thr
100 105 110

Val Ser Ser
115

<210> SEQ ID NO 159
<211> LENGTH: 346
<212> TYPE: DNA
<213> ORGANISM: Homo Sapiens

<400> SEQUENCE: 159
caggtgcagc tgcaggagtc gggcccagga ctggtgaagc cttcggggac cctgtccctc 60
acctgcgctg tctctggtgg ctccatcagc agtagtgact ggtggagttg ggtccgccag 120
cccccaggga aggggctgga gtggattggg gaaatctttc atagtgggaa caccaactac 180
aacccgtccc tcaagagtcg agtcaccata tcagtagaca agtccaagaa ccagatctcc 240
ctgaggctga actctgtgac cgccgcggac acggccgtgt attactgtgt gagagatggt 300
tcggggagtt actggggcca gggaaccctg gtcaccgtct cctcag 346

<210> SEQ ID NO 160
<211> LENGTH: 445
<212> TYPE: PRT
<213> ORGANISM: Homo Sapiens

<400> SEQUENCE: 160

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asp Trp Trp Ser Trp Val Arg Gln Pro Pro Gly Lys Gly Leu Glu Trp
35 40 45

Ile Gly Glu Ile Phe His Ser Gly Asn Thr Asn Tyr Asn Pro Ser Leu
50 55 60

Lys Ser Arg Val Thr Ile Ser Val Asp Lys Ser Lys Asn Gln Ile Ser
65 70 75 80

Leu Arg Leu Asn Ser Val Thr Ala Ala Asp Thr Ala Val Tyr Tyr Cys

```
                85                  90                  95

Val Arg Asp Gly Ser Gly Ser Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 161
<211> LENGTH: 1335
<212> TYPE: DNA
<213> ORGANISM: Homo Sapiens

<400> SEQUENCE: 161

caggtgcagc tgcaggagtc gggcccagga ctggtgaagc cttcggggac cctgtccctc      60

acctgcgctg tctctggtgg ctccatcagc agtagtgact ggtggagttg ggtccgccag     120
```

cccccaggga aggggctgga gtggattggg gaaatctttc atagtgggaa caccaactac 180
aacccgtccc tcaagagtcg agtcaccata tcagtagaca agtccaagaa ccagatctcc 240
ctgaggctga actctgtgac cgccgcggac acggccgtgt attactgtgt gagagatggt 300
tcggggagtt actggggcca gggaaccctg gtcaccgtct cctcagccag caccaagggc 360
ccctctgtgt tccctctggc cccttccagc aagtccacct ctggcggaac agccgctctg 420
ggctgcctcg tgaaggacta cttccccgag cctgtgaccg tgtcctggaa ctctggcgct 480
ctgaccagcg gagtgcacac cttccctgct gtgctgcagt cctccggcct gtactccctg 540
tcctccgtcg tgaccgtgcc ttccagctct ctgggcaccc agacctacat ctgcaacgtg 600
aaccacaagc cctccaacac caaggtggac aagaaggtgg aacccaagtc ctgcgacaag 660
acccacacct gtcccccttg tcctgcccct gaactgctgg gcggaccttc cgtgttcctg 720
ttccccccaa agcccaagga caccctgatg atctcccgga cccccgaagt gacctgcgtg 780
gtggtggatg tgtcccacga ggaccctgaa gtgaagttca attggtacgt ggacggcgtg 840
gaagtgcaca acgccaagac caagcctaga gaggaacagt acaactccac ctaccgggtg 900
gtgtccgtgc tgaccgtgct gcaccaggat tggctgaacg gcaaagagta caagtgcaag 960
gtgtccaaca aggccctgcc tgcccccatc gaaaagacca tctccaaggc caagggccag 1020
ccccgggaac cccaggtgta cacactgccc cctagcaggg acgagctgac caagaaccag 1080
gtgtccctga cctgtctcgt gaaaggcttc taccccctccg atatcgccgt ggaatgggag 1140
tccaacggcc agcctgagaa caactacaag accacccccc ctgtgctgga ctccgacggc 1200
tcattcttcc tgtacagcaa gctgacagtg gacaagtccc ggtggcagca gggcaacgtg 1260
ttctcctgct ccgtgatgca cgaggccctg cacaaccact acacccagaa gtccctgtcc 1320
ctgagccccg gcaag 1335

<210> SEQ ID NO 162
<211> LENGTH: 12
<212> TYPE: PRT
<213> ORGANISM: Homo Sapiens

<400> SEQUENCE: 162

Gln Ser Val Leu Tyr Ser Ser Asn Asn Lys Asn Tyr
1               5                   10

<210> SEQ ID NO 163
<211> LENGTH: 3
<212> TYPE: PRT
<213> ORGANISM: Homo Sapiens

<400> SEQUENCE: 163

Trp Ala Ser
1

<210> SEQ ID NO 164
<211> LENGTH: 8
<212> TYPE: PRT
<213> ORGANISM: Homo Sapiens

<400> SEQUENCE: 164

Gln Gln Tyr Tyr Ser Thr Arg Ser
1               5

<210> SEQ ID NO 165
<211> LENGTH: 17

<212> TYPE: PRT
<213> ORGANISM: Homo Sapiens

<400> SEQUENCE: 165

```
Lys Ser Ser Gln Ser Val Leu Tyr Ser Ser Asn Asn Lys Asn Tyr Leu
1               5                   10                  15

Ala
```

<210> SEQ ID NO 166
<211> LENGTH: 7
<212> TYPE: PRT
<213> ORGANISM: Homo Sapiens

<400> SEQUENCE: 166

```
Trp Ala Ser Thr Arg Glu Ser
1               5
```

<210> SEQ ID NO 167
<211> LENGTH: 8
<212> TYPE: PRT
<213> ORGANISM: Homo Sapiens

<400> SEQUENCE: 167

```
Gln Gln Tyr Tyr Ser Thr Arg Ser
1               5
```

<210> SEQ ID NO 168
<211> LENGTH: 112
<212> TYPE: PRT
<213> ORGANISM: Homo Sapiens

<400> SEQUENCE: 168

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Arg Ser Phe Gly Gln Gly Thr Lys Leu Glu Ile Lys
            100                 105                 110
```

<210> SEQ ID NO 169
<211> LENGTH: 337
<212> TYPE: DNA
<213> ORGANISM: Homo Sapiens

<400> SEQUENCE: 169

```
gacatcgtga tgacccagtc tccagactcc ctggctgtgt ctctgggcga gagggccacc     60

atcaactgca agtccagcca gagtgtttta tacagctcca acaataagaa ctacttagct    120

tggtaccagc agaaaccagg acagcctcct aaactgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcaata ttatagtact    300
```

cgcagttttg gccaggggac caagctggag atcaaac 337

<210> SEQ ID NO 170
<211> LENGTH: 219
<212> TYPE: PRT
<213> ORGANISM: Homo Sapiens

<400> SEQUENCE: 170

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Arg Ser Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 171
<211> LENGTH: 657
<212> TYPE: DNA
<213> ORGANISM: Homo Sapiens

<400> SEQUENCE: 171
gacatcgtga tgacccagtc tccagactcc ctggctgtgt ctctgggcga gagggccacc 60
atcaactgca agtccagcca gagtgtttta tacagctcca acaataagaa ctacttagct 120
tggtaccagc agaaaccagg acagcctcct aaactgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatagtact 300
cgcagttttg gccaggggac caagctggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 172
<211> LENGTH: 10
<212> TYPE: PRT
<213> ORGANISM: Homo Sapiens

<400> SEQUENCE: 172

Gly Gly Ser Ile Ser Ser Ser Ser Tyr Tyr
1 5 10

<210> SEQ ID NO 173
<211> LENGTH: 7
<212> TYPE: PRT
<213> ORGANISM: Homo Sapiens

<400> SEQUENCE: 173

Ile Tyr Ser Thr Gly Tyr Thr
1 5

<210> SEQ ID NO 174
<211> LENGTH: 13
<212> TYPE: PRT
<213> ORGANISM: Homo Sapiens

<400> SEQUENCE: 174

Ala Ile Ser Thr Ala Ala Gly Pro Glu Tyr Phe His Arg
1 5 10

<210> SEQ ID NO 175
<211> LENGTH: 7
<212> TYPE: PRT
<213> ORGANISM: Homo Sapiens

<400> SEQUENCE: 175

Ser Ser Ser Tyr Tyr Cys Gly
1 5

<210> SEQ ID NO 176
<211> LENGTH: 16
<212> TYPE: PRT
<213> ORGANISM: Homo Sapiens

<400> SEQUENCE: 176

Ser Ile Tyr Ser Thr Gly Tyr Thr Tyr Tyr Asn Pro Ser Leu Lys Ser
1 5 10 15

<210> SEQ ID NO 177
<211> LENGTH: 11
<212> TYPE: PRT
<213> ORGANISM: Homo Sapiens

<400> SEQUENCE: 177

Ser Thr Ala Ala Gly Pro Glu Tyr Phe His Arg
1 5 10

<210> SEQ ID NO 178
<211> LENGTH: 120
<212> TYPE: PRT
<213> ORGANISM: Homo Sapiens

<400> SEQUENCE: 178

Gln Leu Gln Glu Ser Gly Pro Gly Leu Val Lys Pro Ser Glu Thr Leu
1 5 10 15

```
Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60

Ser Arg Val Thr Ile Ser Ile Asp Thr Ser Lys Asn Gln Phe Ser Cys
65                  70                  75                  80

Leu Ile Leu Thr Ser Val Thr Ala Ala Asp Thr Ala Val Tyr Tyr Cys
                85                  90                  95

Ala Ile Ser Thr Ala Ala Gly Pro Glu Tyr Phe His Arg Trp Gly Gln
            100                 105                 110

Gly Thr Leu Val Thr Val Ser Ser
        115                 120


<210> SEQ ID NO 179
<211> LENGTH: 361
<212> TYPE: DNA
<213> ORGANISM: Homo Sapiens

<400> SEQUENCE: 179

cagctgcagg agtcgggccc aggcctggtg aagccttcgg agaccctgtc cctcacctgc      60

actgtctctg gtggctccat cagcagtagt agttattact gcggctggat ccgccagccc     120

cctgggaagg ggctggactg gattgggagt atctattcta ctgggtacac ctactacaac     180

ccgtccctca agagtcgagt caccatttcc atagacacgt ccaagaacca gttctcatgc     240

ctgatactga cctctgtgac cgccgcagac acggctgtgt attactgtgc gataagtaca     300

gcagctggcc ctgaatactt ccatcgctgg ggccagggca ccctggtcac cgtctcctca     360

g                                                                     361


<210> SEQ ID NO 180
<211> LENGTH: 450
<212> TYPE: PRT
<213> ORGANISM: Homo Sapiens

<400> SEQUENCE: 180

Gln Leu Gln Glu Ser Gly Pro Gly Leu Val Lys Pro Ser Glu Thr Leu
1               5                   10                  15

Ser Leu Thr Cys Thr Val Ser Gly Gly Ser Ile Ser Ser Ser Ser Tyr
            20                  25                  30

Tyr Cys Gly Trp Ile Arg Gln Pro Pro Gly Lys Gly Leu Asp Trp Ile
        35                  40                  45

Gly Ser Ile Tyr Ser Thr Gly Tyr Thr Tyr Tyr Asn Pro Ser Leu Lys
    50                  55                  60

Ser Arg Val Thr Ile Ser Ile Asp Thr Ser Lys Asn Gln Phe Ser Cys
65                  70                  75                  80

Leu Ile Leu Thr Ser Val Thr Ala Ala Asp Thr Ala Val Tyr Tyr Cys
                85                  90                  95

Ala Ile Ser Thr Ala Ala Gly Pro Glu Tyr Phe His Arg Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 181
<211> LENGTH: 1350
<212> TYPE: DNA
<213> ORGANISM: Homo Sapiens

<400> SEQUENCE: 181

```
cagctgcagg agtcgggccc aggcctggtg aagccttcgg agaccctgtc cctcacctgc     60

actgtctctg gtggctccat cagcagtagt agttattact gcggctggat ccgccagccc    120

cctgggaagg ggctggactg gattgggagt atctattcta ctgggtacac ctactacaac    180

ccgtccctca agagtcgagt caccatttcc atagacacgt ccaagaacca gttctcatgc    240

ctgatactga cctctgtgac cgccgcagac acggctgtgt attactgtgc gataagtaca    300

gcagctggcc ctgaatactt ccatcgctgg ggccagggca ccctggtcac cgtctcctca    360
```

```
gccagcacca agggcccctc tgtgttccct ctggcccctt ccagcaagtc cacctctggc    420

ggaacagccg ctctgggctg cctcgtgaag gactacttcc ccgagcctgt gaccgtgtcc    480

tggaactctg gcgctctgac cagcggagtg cacaccttcc ctgctgtgct gcagtcctcc    540

ggcctgtact ccctgtcctc cgtcgtgacc gtgccttcca gctctctggg cacccagacc    600

tacatctgca acgtgaacca caagccctcc aacaccaagg tggacaagaa ggtggaaccc    660

aagtcctgcg acaagaccca cacctgtccc ccttgtcctg cccctgaact gctgggcgga    720

ccttccgtgt tcctgttccc cccaaagccc aaggacaccc tgatgatctc ccggaccccc    780

gaagtgacct gcgtggtggt ggatgtgtcc cacgaggacc ctgaagtgaa gttcaattgg    840

tacgtggacg gcgtggaagt gcacaacgcc aagaccaagc ctagagagga acagtacaac    900

tccacctacc gggtggtgtc cgtgctgacc gtgctgcacc aggattggct gaacggcaaa    960

gagtacaagt gcaaggtgtc caacaaggcc ctgcctgccc ccatcgaaaa gaccatctcc   1020

aaggccaagg gccagccccg ggaaccccag gtgtacacac tgccccctag cagggacgag   1080

ctgaccaaga accaggtgtc cctgacctgt ctcgtgaaag gcttctaccc ctccgatatc   1140

gccgtggaat gggagtccaa cggccagcct gagaacaact acaagaccac ccccccctgtg  1200

ctggactccg acggctcatt cttcctgtac agcaagctga cagtggacaa gtcccggtgg   1260

cagcagggca acgtgttctc ctgctccgtg atgcacgagg ccctgcacaa ccactacacc   1320

cagaagtccc tgtccctgag ccccggcaag                                    1350
```

<210> SEQ ID NO 182
<211> LENGTH: 12
<212> TYPE: PRT
<213> ORGANISM: Homo Sapiens

<400> SEQUENCE: 182

```
Gln Ser Val Leu Tyr Ser Ser Asn Ser Lys Asn Phe
1               5                   10
```

<210> SEQ ID NO 183
<211> LENGTH: 3
<212> TYPE: PRT
<213> ORGANISM: Homo Sapiens

<400> SEQUENCE: 183

```
Trp Ala Ser
1
```

<210> SEQ ID NO 184
<211> LENGTH: 9
<212> TYPE: PRT
<213> ORGANISM: Homo Sapiens

<400> SEQUENCE: 184

```
Gln Gln Tyr Tyr Ser Thr Pro Arg Thr
1               5
```

<210> SEQ ID NO 185
<211> LENGTH: 17
<212> TYPE: PRT
<213> ORGANISM: Homo Sapiens

<400> SEQUENCE: 185

```
Lys Ser Ser Gln Ser Val Leu Tyr Ser Ser Asn Ser Lys Asn Phe Leu
1               5                   10                  15
```

Ala

<210> SEQ ID NO 186
<211> LENGTH: 7
<212> TYPE: PRT
<213> ORGANISM: Homo Sapiens

<400> SEQUENCE: 186

Trp Ala Ser Thr Arg Gly Ser
1               5

<210> SEQ ID NO 187
<211> LENGTH: 9
<212> TYPE: PRT
<213> ORGANISM: Homo Sapiens

<400> SEQUENCE: 187

Gln Gln Tyr Tyr Ser Thr Pro Arg Thr
1               5

<210> SEQ ID NO 188
<211> LENGTH: 113
<212> TYPE: PRT
<213> ORGANISM: Homo Sapiens

<400> SEQUENCE: 188

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Phe Leu Ala Trp Tyr Gln Gln Lys Pro Gly Gln
        35                  40                  45

Pro Pro Lys Leu Phe Ile Tyr Trp Ala Ser Thr Arg Gly Ser Gly Val
    50                  55                  60

Pro Asp Arg Ile Ser Gly Ser Gly Ser Gly Thr Asp Phe Asn Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 189
<211> LENGTH: 340
<212> TYPE: DNA
<213> ORGANISM: Homo Sapiens

<400> SEQUENCE: 189
gacatcgtga tgacccagtc tccagactcc ctggctgtgt ctctgggcga gagggccacc      60
atcaactgca agtccagcca gagtgtttta tacagctcca acagtaagaa cttcttagct     120
tggtaccagc agaaaccggg acagcctcct aagctgttca tttactgggc atctacccgg     180
ggatccgggg tccctgaccg aatcagtggc agcgggtctg ggacagattt caatctcacc     240
atcagcagcc tgcaggctga agatgtggca gtttattact gtcaacaata ttatagtact     300
cctcggacgt tcggccaagg gaccaaggtg gagatcaaac                           340

<210> SEQ ID NO 190
<211> LENGTH: 220
<212> TYPE: PRT

<213> ORGANISM: Homo Sapiens

<400> SEQUENCE: 190

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Ser Lys Asn Phe Leu Ala Trp Tyr Gln Gln Lys Pro Gly Gln
35 40 45

Pro Pro Lys Leu Phe Ile Tyr Trp Ala Ser Thr Arg Gly Ser Gly Val
50 55 60

Pro Asp Arg Ile Ser Gly Ser Gly Ser Gly Thr Asp Phe Asn Leu Thr
65 70 75 80

Ile Ser Ser Leu Gln Ala Glu Asp Val Ala Val Tyr Tyr Cys Gln Gln
85 90 95

Tyr Tyr Ser Thr Pro Arg Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 191
<211> LENGTH: 660
<212> TYPE: DNA
<213> ORGANISM: Homo Sapiens

<400> SEQUENCE: 191
gacatcgtga tgacccagtc tccagactcc ctggctgtgt ctctgggcga gagggccacc 60
atcaactgca agtccagcca gagtgtttta tacagctcca acagtaagaa cttcttagct 120
tggtaccagc agaaaccggg acagcctcct aagctgttca tttactgggc atctacccgg 180
ggatccgggg tccctgaccg aatcagtggc agcgggtctg ggacagattt caatctcacc 240
atcagcagcc tgcaggctga agatgtggca gtttattact gtcaacaata ttatagtact 300
cctcggacgt tcggccaagg gaccaaggtg gagatcaaac gtacggtggc cgctccctcc 360
gtgttcatct tcccaccttc cgacgagcag ctgaagtccg gcaccgcttc tgtcgtgtgc 420
ctgctgaaca acttctaccc ccgcgaggcc aaggtgcagt ggaaggtgga caacgccctg 480
cagtccggca actcccagga atccgtgacc gagcaggact ccaaggacag cacctactcc 540
ctgtcctcca ccctgaccct gtccaaggcc gactacgaga agcacaaggt gtacgcctgc 600
gaagtgaccc accagggcct gtctagcccc gtgaccaagt ctttcaaccg gggcgagtgt 660

<210> SEQ ID NO 192
<211> LENGTH: 981

<212> TYPE: DNA
<213> ORGANISM: Homo Sapiens

<400> SEQUENCE: 192
gcttccacca agggcccatc cgtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccatgccc atcatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcctgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaggcta accgtggaca agagcaggtg gcaggagggg 900
aatgtcttct catgctccgt gatgcatgag gctctgcaca accactacac acagaagagc 960
ctctccctgt ctctgggtaa a 981

<210> SEQ ID NO 193
<211> LENGTH: 327
<212> TYPE: PRT
<213> ORGANISM: Homo Sapiens

<400> SEQUENCE: 193

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 194
<211> LENGTH: 981
<212> TYPE: DNA
<213> ORGANISM: Homo Sapiens

<400> SEQUENCE: 194
gcttccacca agggcccatc cgtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccgtgccc atcatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcgtgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaggcta accgtggaca agagcaggtg gcaggagggg 900
aatgtcttct catgctccgt gatgcatgag gctctgcaca accactacac gcagaagagc 960
ctctccctgt ctctgggtaa a 981

<210> SEQ ID NO 195
<211> LENGTH: 327
<212> TYPE: PRT
<213> ORGANISM: Homo Sapiens

<400> SEQUENCE: 195

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 196
<211> LENGTH: 981
<212> TYPE: DNA
<213> ORGANISM: Homo Sapiens

<400> SEQUENCE: 196
gcttccacca agggcccatc cgtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180

```
ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaagctc accgtggaca agagcaggtg gcaggagggg    900

aacgtcttct catgctccgt gatgcatgag gctctgcaca accactacac gcagaagagc    960

ctctccctgt ctctgggtaa a                                              981
```

```
<210> SEQ ID NO 197
<211> LENGTH: 327
<212> TYPE: PRT
<213> ORGANISM: Homo Sapiens

<400> SEQUENCE: 197

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
```

```
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 198
<211> LENGTH: 981
<212> TYPE: DNA
<213> ORGANISM: Homo Sapiens

<400> SEQUENCE: 198

gcctccacca agggcccatc cgtcttcccc ctggcgccct gctccaggag cacctccgag      60

agcacggccg ccctgggctg cctggtcaag gactacttcc ccgaaccagt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacgaagacc     240

tacacctgca acgtagatca caagcccagc aacaccaagg tggacaagag agttgagtcc     300

aaatatggtc ccccatgccc accatgccca gcgcctgaat ttgagggggg accatcagtc     360

ttcctgttcc ccccaaaacc caaggacact ctcatgatct cccggacccc tgaggtcacg     420

tgcgtggtgg tggacgtgag ccaggaagac cccgaggtcc agttcaactg gtacgtggat     480

ggcgtggagg tgcataatgc caagacaaag ccgcgggagg agcagttcaa cagcacgtac     540

cgtgtggtca gcgtcctcac cgtcctgcac caggactggc tgaacggcaa ggagtacaag     600

tgcaaggtct ccaacaaagg cctcccgtca tcgatcgaga aaaccatctc caaagccaaa     660

gggcagcccc gagagccaca ggtgtacacc ctgcccccat cccaggagga gatgaccaag     720

aaccaggtca gcctgacctg cctggtcaaa ggcttctacc ccagcgacat cgccgtggag     780

tgggagagca atgggcagcc ggagaacaac tacaagacca cgcctcccgt gctggactcc     840

gacggatcct tcttcctcta cagcaggcta accgtggaca agagcaggtg gcaggagggg     900

aatgtcttct catgctccgt gatgcatgag gctctgcaca accactacac acagaagagc     960

ctctccctgt ctctgggtaa a                                               981


<210> SEQ ID NO 199
<211> LENGTH: 327
<212> TYPE: PRT
<213> ORGANISM: Homo Sapiens

<400> SEQUENCE: 199

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Glu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 200
<211> LENGTH: 981
<212> TYPE: DNA
<213> ORGANISM: Homo Sapiens

<400> SEQUENCE: 200
gcctccacca agggacctag cgtgttccct ctcgcccct gttccaggtc cacaagcgag 60
tccaccgctg ccctcggctg tctggtgaaa gactacttc ccgagcccgt gaccgtctcc 120
tggaatagcg gagccctgac ctccggcgtg cacacatttc ccgccgtgct gcagagcagc 180
ggactgtata gcctgagcag cgtggtgacc gtgcccagct ccagcctcgg caccaaaacc 240
tacacctgca acgtggacca caagccctcc aacaccaagg tggacaagcg ggtggagagc 300
aagtacggcc ccccttgccc tccttgtcct gcccctgagt tcgagggagg accctccgtg 360
ttcctgtttc cccccaaacc caaggacacc ctgatgatct cccggacacc cgaggtgacc 420
tgtgtggtcg tggacgtcag ccaggaggac cccgaggtgc agttcaactg gtatgtggac 480
ggcgtggagg tgcacaatgc caaaaccaag cccagggagg agcagttcaa ttccacctac 540

```
agggtggtga gcgtgctgac cgtcctgcat caggattggc tgaacggcaa ggagtacaag    600
tgcaaggtgt ccaacaaggg actgcccagc tccatcgaga agaccatcag caaggctaag    660
ggccagccga gggagcccca ggtgtatacc ctgcctccta gccaggaaga gatgaccaag    720
aaccaagtgt ccctgacctg cctggtgaag ggattctacc cctccgacat cgccgtggag    780
tgggagagca atggccagcc cgagaacaac tacaaaacaa cccctcccgt gctcgatagc    840
gacggcagct tctttctcta cagccggctg acagtggaca agagcaggtg gcaggagggc    900
aacgtgttct cctgttccgt gatgcacgag gccctgcaca atcactacac ccagaagagc    960
ctctccctgt ccctgggcaa g                                               981
```

<210> SEQ ID NO 201
<211> LENGTH: 981
<212> TYPE: DNA
<213> ORGANISM: Homo Sapiens

<400> SEQUENCE: 201

```
gccagcacca agggcccttc cgtgttcccc ctggcccctt gcagcaggag cacctccgaa     60
tccacagctg ccctgggctg tctggtgaag gactactttc ccgagcccgt gaccgtgagc    120
tggaacagcg gcgctctgac atccggcgtc cacacctttc ctgccgtcct gcagtcctcc    180
ggcctctact ccctgtcctc cgtggtgacc gtgcctagct cctccctcgg caccaagacc    240
tacacctgta acgtggacca caaaccctcc aacaccaagg tggacaaacg ggtcgagagc    300
aagtacggcc ctccctgccc tccttgtcct gcccccgagt tcgaaggcgg acccagcgtg    360
ttcctgttcc ctcctaagcc caaggacacc ctcatgatca gccggacacc cgaggtgacc    420
tgcgtggtgg tggatgtgag ccaggaggac cctgaggtcc agttcaactg gtatgtggat    480
ggcgtggagg tgcacaacgc caagacaaag ccccgggaag agcagttcaa ctccacctac    540
agggtggtca gcgtgctgac cgtgctgcat caggactggc tgaacggcaa ggagtacaag    600
tgcaaggtca gcaataaggg actgcccagc agcatcgaga agaccatctc caaggctaaa    660
ggccagcccc gggaacctca ggtgtacacc ctgcctccca gccaggagga gatgaccaag    720
aaccaggtga gcctgacctg cctggtgaag ggattctacc cttccgacat cgccgtggag    780
tgggagtcca acggccagcc cgagaacaat tataagacca cccctcccgt cctcgacagc    840
gacggatcct tctttctgta ctccaggctg accgtggata agtccaggtg gcaggaaggc    900
aacgtgttca gctgctccgt gatgcacgag gccctgcaca atcactacac ccagaagtcc    960
ctgagcctgt ccctgggaaa g                                               981
```

<210> SEQ ID NO 202
<211> LENGTH: 981
<212> TYPE: DNA
<213> ORGANISM: Homo Sapiens

<400> SEQUENCE: 202

```
gcctccacca agggcccatc cgtcttcccc ctggcgccct gctccaggag cacctccgag     60
agcacggccg ccctgggctg cctggtcaag gactacttcc ccgaaccagt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc accatgccca gcgcctccag ttgcgggggg accatcagtc    360
```

```
ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtca tcgatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggatcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa a                                              981
```

```
<210> SEQ ID NO 203
<211> LENGTH: 327
<212> TYPE: PRT
<213> ORGANISM: Homo Sapiens

<400> SEQUENCE: 203

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 204
<211> LENGTH: 990
<212> TYPE: DNA
<213> ORGANISM: Homo Sapiens

<400> SEQUENCE: 204
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agtggagccc 300
aaatcttgtg acaaaactca cacatgccca ccgtgcccag cacctgaact cgcgggggca 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 205
<211> LENGTH: 330
<212> TYPE: PRT
<213> ORGANISM: Homo Sapiens

<400> SEQUENCE: 205

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 206
<211> LENGTH: 321
<212> TYPE: DNA
<213> ORGANISM: Homo Sapiens

<400> SEQUENCE: 206

cgtacggtgg ccgctccctc cgtgttcatc ttcccacctt ccgacgagca gctgaagtcc      60

ggcaccgctt ctgtcgtgtg cctgctgaac aacttctacc cccgcgaggc caaggtgcag     120

tggaaggtgg acaacgccct gcagtccggc aactcccagg aatccgtgac cgagcaggac     180

tccaaggaca gcacctactc cctgtcctcc accctgaccc tgtccaaggc cgactacgag     240

aagcacaagg tgtacgcctg cgaagtgacc caccagggcc tgtctagccc cgtgaccaag     300

tctttcaacc ggggcgagtg t                                               321


<210> SEQ ID NO 207
<211> LENGTH: 107
<212> TYPE: PRT
<213> ORGANISM: Homo Sapiens

<400> SEQUENCE: 207

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 208
<211> LENGTH: 321
<212> TYPE: DNA
<213> ORGANISM: Homo Sapiens

<400> SEQUENCE: 208

cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggag     180

agcaaggaca gcacctacag cctcagcagc accctgacgc tgagcaaagc agactacgag     240

aaacacaaag tctacgccgg cgaagtcacc catcagggcc tgagctcgcc cgtcacaaag     300

agcttcaaca ggggagagtg t                                               321


<210> SEQ ID NO 209
<211> LENGTH: 107
<212> TYPE: PRT
<213> ORGANISM: Homo Sapiens

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105


<210> SEQ ID NO 210
<211> LENGTH: 321
<212> TYPE: DNA
<213> ORGANISM: Homo Sapiens

<400> SEQUENCE: 210

cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120
```

cggaaggtgg ataacgccct ccaatcgggt aactcccagg agagtgtcac agagcaggag 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg t 321

<210> SEQ ID NO 211
<211> LENGTH: 107
<212> TYPE: PRT
<213> ORGANISM: Homo Sapiens

<400> SEQUENCE: 211

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 212
<211> LENGTH: 321
<212> TYPE: DNA
<213> ORGANISM: Homo Sapiens

<400> SEQUENCE: 212
cgaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaac tctacgcctg cgaagtcacc catcagggcc tgagctcgcc cgtcacaaag 300
agcttcaaca ggggagagtg t 321

<210> SEQ ID NO 213
<211> LENGTH: 107
<212> TYPE: PRT
<213> ORGANISM: Homo Sapiens

<400> SEQUENCE: 213

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 214
<211> LENGTH: 321
<212> TYPE: DNA
<213> ORGANISM: Homo Sapiens

<400> SEQUENCE: 214

```
cgaactgtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcaac accctgacgc tgagcaaagc agactacgag     240

aaacacaaag tctacgcctg cgaagtcacc catcagggcc tgagctcgcc cgtcacaaag     300

agcttcaaca ggggagagtg c                                               321
```

<210> SEQ ID NO 215
<211> LENGTH: 107
<212> TYPE: PRT
<213> ORGANISM: Homo Sapiens

<400> SEQUENCE: 215

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 216
<211> LENGTH: 312
<212> TYPE: DNA
<213> ORGANISM: Homo Sapiens

<400> SEQUENCE: 216

```
cccaaggcca accccacggt cactctgttc ccgccctcct ctgaggagct ccaagccaac      60

aaggccacac tagtgtgtct gatcagtgac ttctacccgg gagctgtgac agtggcttgg     120

aaggcagatg gcagccccgt caaggcggga gtggagacga ccaaaccctc caaacagagc     180

aacaacaagt acgcggccag cagctacctg agcctgacgc ccgagcagtg gaagtcccac     240

agaagctaca gctgccaggt cacgcatgaa gggagcaccg tggagaagac agtggcccct     300

acagaatgtt ca                                                         312
```

<210> SEQ ID NO 217
<211> LENGTH: 104

<212> TYPE: PRT
<213> ORGANISM: Homo Sapiens

<400> SEQUENCE: 217

```
Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 218
<211> LENGTH: 318
<212> TYPE: DNA
<213> ORGANISM: Homo Sapiens

<400> SEQUENCE: 218

```
ggtcagccca aggccaaccc cactgtcact ctgttcccgc cctcctctga ggagctccaa     60

gccaacaagg ccacactagt gtgtctgatc agtgacttct acccgggagc tgtgacagtg    120

gcctggaagg cagatggcag ccccgtcaag gcgggagtgg agaccaccaa accctccaaa    180

cagagcaaca acaagtacgc ggccagcagc tacctgagcc tgacgcccga gcagtggaag    240

tcccacagaa gctacagctg ccaggtcacg catgaaggga gcaccgtgga gaagacagtg    300

gcccctacag aatgttca                                                  318
```

<210> SEQ ID NO 219
<211> LENGTH: 106
<212> TYPE: PRT
<213> ORGANISM: Homo Sapiens

<400> SEQUENCE: 219

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 220
<211> LENGTH: 318
<212> TYPE: DNA

<213> ORGANISM: Homo Sapiens

<400> SEQUENCE: 220
ggtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttca 318

<210> SEQ ID NO 221
<211> LENGTH: 318
<212> TYPE: DNA
<213> ORGANISM: Homo Sapiens

<400> SEQUENCE: 221
ggccagccta aggccgctcc ttctgtgacc ctgttccccc catcctccga ggaactgcag 60
gctaacaagg ccaccctcgt gtgcctgatc agcgacttct accctggcgc cgtgaccgtg 120
gcctggaagg ctgatagctc tcctgtgaag gccggcgtgg aaaccaccac cccttccaag 180
cagtccaaca acaaatacgc cgcctcctcc tacctgtccc tgacccctga gcagtggaag 240
tcccaccggt cctacagctg ccaagtgacc cacgagggct ccaccgtgga aaagaccgtg 300
gctcctaccg agtgctcc 318

<210> SEQ ID NO 222
<211> LENGTH: 318
<212> TYPE: DNA
<213> ORGANISM: Homo Sapiens

<400> SEQUENCE: 222
ggccagccta aagctgcccc cagcgtcacc ctgtttcctc cctccagcga ggagctccag 60
gccaacaagg ccaccctcgt gtgcctgatc tccgacttct atcccggcgc tgtgaccgtg 120
gcttggaaag ccgactccag ccctgtcaaa gccggcgtgg agaccaccac accctccaag 180
cagtccaaca acaagtacgc cgcctccagc tatctctccc tgacccctga gcagtggaag 240
tcccaccggt cctactcctg tcaggtgacc cacgagggct ccaccgtgga aaagaccgtc 300
gcccccaccg agtgctcc 318

<210> SEQ ID NO 223
<211> LENGTH: 106
<212> TYPE: PRT
<213> ORGANISM: Homo Sapiens

<400> SEQUENCE: 223

Gly Gln Pro Lys Ala Asn Pro Thr Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Gly Ser Pro
35 40 45

Val Lys Ala Gly Val Glu Thr Thr Lys Pro Ser Lys Gln Ser Asn Asn
50 55 60

Lys Tyr Ala Ala Ser Ser Tyr Leu Ser Leu Thr Pro Glu Gln Trp Lys
65 70 75 80

-continued

```
Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 224
<211> LENGTH: 318
<212> TYPE: DNA
<213> ORGANISM: Homo Sapiens

<400> SEQUENCE: 224

```
ggtcagccca aggctgcccc ctcggtcact ctgttcccgc cctcctctga ggagcttcaa      60

gccaacaagg ccacactggt gtgtctcata agtgacttct acccgggagc cgtgacagtg     120

gcctggaagg cagatagcag ccccgtcaag gcgggagtgg agaccaccac accctccaaa     180

caaagcaaca acaagtacgc ggccagcagc tatctgagcc tgacgcctga gcagtggaag     240

tcccacagaa gctacagctg ccaggtcacg catgaaggga gcaccgtgga gaagacagtg     300

gcccctacag aatgttca                                                   318
```

<210> SEQ ID NO 225
<211> LENGTH: 106
<212> TYPE: PRT
<213> ORGANISM: Homo Sapiens

<400> SEQUENCE: 225

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 226
<211> LENGTH: 312
<212> TYPE: DNA
<213> ORGANISM: Homo Sapiens

<400> SEQUENCE: 226

```
cccaaggctg ccccctcggt cactctgttc ccaccctcct ctgaggagct tcaagccaac      60

aaggccacac tggtgtgtct cataagtgac ttctacccgg gagccgtgac agttgcctgg     120

aaggcagata gcagccccgt caaggcgggg gtggagacca ccacaccctc caaacaaagc     180

aacaacaagt acgcggccag cagctacctg agcctgacgc ctgagcagtg gaagtcccac     240

aaaagctaca gctgccaggt cacgcatgaa gggagcaccg tggagaagac agttgcccct     300

acggaatgtt ca                                                         312
```

<210> SEQ ID NO 227
<211> LENGTH: 104
<212> TYPE: PRT

<213> ORGANISM: Homo Sapiens

<400> SEQUENCE: 227

Pro Lys Ala Ala Pro Ser Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Ser Ser Pro Val Lys
35 40 45

Ala Gly Val Glu Thr Thr Thr Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Lys Ser Tyr Ser Cys Gln Val Thr His Glu Gly Ser Thr Val Glu Lys
85 90 95

Thr Val Ala Pro Thr Glu Cys Ser
100

<210> SEQ ID NO 228
<211> LENGTH: 318
<212> TYPE: DNA
<213> ORGANISM: Homo Sapiens

<400> SEQUENCE: 228
ggtcagccca aggctgcccc ctcggtcact ctgttcccac cctcctctga ggagcttcaa 60
gccaacaagg ccacactggt gtgtctcata agtgacttct acccggggcc agtgacagtt 120
gcctggaagg cagatagcag ccccgtcaag gcgggggtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacgg aatgttca 318

<210> SEQ ID NO 229
<211> LENGTH: 106
<212> TYPE: PRT
<213> ORGANISM: Homo Sapiens

<400> SEQUENCE: 229

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Pro Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val
85 90 95

Glu Lys Thr Val Ala Pro Thr Glu Cys Ser
100 105

<210> SEQ ID NO 230
<211> LENGTH: 318
<212> TYPE: DNA
<213> ORGANISM: Homo Sapiens

<400> SEQUENCE: 230
ggtcagccca aggctgcccc ctcggtcact ctgttcccac cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacag aatgttca 318

<210> SEQ ID NO 231
<211> LENGTH: 106
<212> TYPE: PRT
<213> ORGANISM: Homo Sapiens

<400> SEQUENCE: 231

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val
85 90 95

Glu Lys Thr Val Ala Pro Thr Glu Cys Ser
100 105

<210> SEQ ID NO 232
<211> LENGTH: 318
<212> TYPE: DNA
<213> ORGANISM: Homo Sapiens

<400> SEQUENCE: 232
ggtcagccca aggctgcccc ctcggtcact ctgttcccgc cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tacctgagcc tgacgcctga gcagtggaag 240
tcccacagaa gctacagctg ccaggtcacg catgaaggga gcaccgtgga gaagacagtg 300
gcccctacag aatgttca 318

<210> SEQ ID NO 233
<211> LENGTH: 106
<212> TYPE: PRT
<213> ORGANISM: Homo Sapiens

<400> SEQUENCE: 233

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro

```
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 234
<211> LENGTH: 318
<212> TYPE: DNA
<213> ORGANISM: Homo Sapiens

<400> SEQUENCE: 234

ggtcagccca aggctgcccc atcggtcact ctgttcccgc cctcctctga ggagcttcaa      60

gccaacaagg ccacactggt gtgcctgatc agtgacttct acccgggagc tgtgaaagtg     120

gcctggaagg cagatggcag ccccgtcaac acgggagtgg agaccaccac accctccaaa     180

cagagcaaca acaagtacgc ggccagcagc tacctgagcc tgacgcctga gcagtggaag     240

tcccacagaa gctacagctg ccaggtcacg catgaaggga gcaccgtgga gaagacagtg     300

gcccctgcag aatgttca                                                   318


<210> SEQ ID NO 235
<211> LENGTH: 106
<212> TYPE: PRT
<213> ORGANISM: Homo Sapiens

<400> SEQUENCE: 235

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105


<210> SEQ ID NO 236
<211> LENGTH: 318
<212> TYPE: DNA
<213> ORGANISM: Homo Sapiens

<400> SEQUENCE: 236

ggtcagccca aggctgcccc atcggtcact ctgttcccac cctcctctga ggagcttcaa      60

gccaacaagg ccacactggt gtgtctcgta agtgacttct acccgggagc cgtgacagtg     120

gcctggaagg cagatggcag ccccgtcaag gtgggagtgg agaccaccaa accctccaaa     180

caaagcaaca acaagtatgc ggccagcagc tacctgagcc tgacgcccga gcagtggaag     240
```

```
tcccacagaa gctacagctg ccgggtcacg catgaaggga gcaccgtgga gaagacagtg    300

gcccctgcag aatgctct                                                   318


<210> SEQ ID NO 237
<211> LENGTH: 106
<212> TYPE: PRT
<213> ORGANISM: Homo Sapiens

<400> SEQUENCE: 237

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 238
<211> LENGTH: 8
<212> TYPE: PRT
<213> ORGANISM: Homo Sapiens

<400> SEQUENCE: 238

Gly Phe Thr Phe Ser Asp Tyr Tyr
1               5


<210> SEQ ID NO 239
<211> LENGTH: 8
<212> TYPE: PRT
<213> ORGANISM: Homo Sapiens

<400> SEQUENCE: 239

Ile Ser Thr Ser Gly Ser Thr Ile
1               5


<210> SEQ ID NO 240
<211> LENGTH: 16
<212> TYPE: PRT
<213> ORGANISM: Homo Sapiens

<400> SEQUENCE: 240

Ala Arg Gly Ile Thr Gly Thr Asn Phe Tyr His Tyr Gly Leu Gly Val
1               5                   10                  15


<210> SEQ ID NO 241
<211> LENGTH: 5
<212> TYPE: PRT
<213> ORGANISM: Homo Sapiens

<400> SEQUENCE: 241

Asp Tyr Tyr Met Ser
1               5


<210> SEQ ID NO 242
```

<211> LENGTH: 17
<212> TYPE: PRT
<213> ORGANISM: Homo Sapiens

<400> SEQUENCE: 242

Tyr Ile Ser Thr Ser Gly Ser Thr Ile Tyr Tyr Ala Asp Ser Val Lys
1 5 10 15

Gly

<210> SEQ ID NO 243
<211> LENGTH: 14
<212> TYPE: PRT
<213> ORGANISM: Homo Sapiens

<400> SEQUENCE: 243

Gly Ile Thr Gly Thr Asn Phe Tyr His Tyr Gly Leu Gly Val
1 5 10

<210> SEQ ID NO 244
<211> LENGTH: 123
<212> TYPE: PRT
<213> ORGANISM: Homo Sapiens

<400> SEQUENCE: 244

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Val Pro Gly Lys Gly Leu Glu Trp Val
35 40 45

Ser Tyr Ile Ser Thr Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Ala Ala Val Tyr His Cys
85 90 95

Ala Arg Gly Ile Thr Gly Thr Asn Phe Tyr His Tyr Gly Leu Gly Val
100 105 110

Trp Gly Gln Gly Thr Thr Val Thr Val Ser Ser
115 120

<210> SEQ ID NO 245
<211> LENGTH: 370
<212> TYPE: DNA
<213> ORGANISM: Homo Sapiens

<400> SEQUENCE: 245
caggtgcagc tggtggagtc tgggggaggc ttggtcaagc ctggagggtc cctgagactc 60
tcctgtgcag cctctggatt caccttcagt gactactaca tgagctggat ccgccaggtt 120
ccagggaagg ggctggagtg ggtttcatac attagtacta gtggtagtac catatactac 180
gcagactctg tgaagggccg attcaccatc tccagggaca acgccaagaa ctcactgtat 240
ctacaaatga acagcctgag agccgaggac gcggccgtgt atcactgtgc gagaggtata 300
actggaacta acttctacca ctacggtttg ggcgtctggg gccaagggac cacggtcacc 360
gtctcctcag 370

<210> SEQ ID NO 246
<211> LENGTH: 453

<212> TYPE: PRT
<213> ORGANISM: Homo Sapiens

<400> SEQUENCE: 246

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Val Pro Gly Lys Gly Leu Glu Trp Val
        35                  40                  45

Ser Tyr Ile Ser Thr Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr His Cys
                85                  90                  95

Ala Arg Gly Ile Thr Gly Thr Asn Phe Tyr His Tyr Gly Leu Gly Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

-continued

```
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

```
<210> SEQ ID NO 247
<211> LENGTH: 1359
<212> TYPE: DNA
<213> ORGANISM: Homo Sapiens

<400> SEQUENCE: 247

caggtgcagc tggtggagtc tgggggaggc ttggtcaagc ctggagggtc cctgagactc     60
tcctgtgcag cctctggatt caccttcagt gactactaca tgagctggat ccgccaggtt    120
ccagggaagg ggctggagtg ggtttcatac attagtacta gtggtagtac catatactac    180
gcagactctg tgaagggccg attcaccatc tccagggaca acgccaagaa ctcactgtat    240
ctacaaatga acagcctgag agccgaggac gcggccgtgt atcactgtgc gagaggtata    300
actggaacta acttctacca ctacggtttg ggcgtctggg gccaagggac cacggtcacc    360
gtctcctcag ccagcaccaa gggcccctct gtgttccctc tggccccttc cagcaagtcc    420
acctctggcg gaacagccgc tctgggctgc ctcgtgaagg actacttccc cgagcctgtg    480
accgtgtcct ggaactctgg cgctctgacc agcggagtgc acaccttccc tgctgtgctg    540
cagtcctccg gcctgtactc cctgtcctcc gtcgtgaccg tgccttccag ctctctgggc    600
acccagacct acatctgcaa cgtgaaccac aagccctcca acaccaaggt ggacaagaag    660
gtggaaccca agtcctgcga caagacccac acctgtcccc cttgtcctgc ccctgaactg    720
ctgggcggac cttccgtgtt cctgttcccc ccaaagccca aggacaccct gatgatctcc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaact ccacctaccg ggtggtgtcc gtgctgaccg tgctgcacca ggattggctg    960
aacggcaaag agtacaagtg caaggtgtcc aacaaggccc tgcctgcccc catcgaaaag   1020
accatctcca aggccaaggg ccagccccgg gaaccccagg tgtacacact gccccctagc   1080
agggacgagc tgaccaagaa ccaggtgtcc ctgacctgtc tcgtgaaagg cttctacccc   1140
tccgatatcg ccgtggaatg ggagtccaac ggccagcctg agaacaacta caagaccacc   1200
ccccctgtgc tggactccga cggctcattc ttcctgtaca gcaagctgac agtggacaag   1260
tcccggtggc agcagggcaa cgtgttctcc tgctccgtga tgcacgaggc cctgcacaac   1320
cactacaccc agaagtccct gtccctgagc cccggcaag                          1359
```

```
<210> SEQ ID NO 248
<211> LENGTH: 6
<212> TYPE: PRT
<213> ORGANISM: Homo Sapiens

<400> SEQUENCE: 248

Gln Gly Ile Asn Ser Trp
1               5
```

<210> SEQ ID NO 249
<211> LENGTH: 3
<212> TYPE: PRT
<213> ORGANISM: Homo Sapiens

<400> SEQUENCE: 249

Ala Ala Ser
1

<210> SEQ ID NO 250
<211> LENGTH: 9
<212> TYPE: PRT
<213> ORGANISM: Homo Sapiens

<400> SEQUENCE: 250

Gln Gln Val Asn Ser Phe Pro Leu Thr
1               5

<210> SEQ ID NO 251
<211> LENGTH: 11
<212> TYPE: PRT
<213> ORGANISM: Homo Sapiens

<400> SEQUENCE: 251

Arg Ala Ser Gln Gly Ile Asn Ser Trp Leu Ala
1               5                   10

<210> SEQ ID NO 252
<211> LENGTH: 7
<212> TYPE: PRT
<213> ORGANISM: Homo Sapiens

<400> SEQUENCE: 252

Ala Ala Ser Thr Leu Gln Ser
1               5

<210> SEQ ID NO 253
<211> LENGTH: 9
<212> TYPE: PRT
<213> ORGANISM: Homo Sapiens

<400> SEQUENCE: 253

Gln Gln Val Asn Ser Phe Pro Leu Thr
1               5

<210> SEQ ID NO 254
<211> LENGTH: 107
<212> TYPE: PRT
<213> ORGANISM: Homo Sapiens

<400> SEQUENCE: 254

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

```
Thr Phe Gly Gly Gly Thr Lys Val Glu Ile Lys
            100                 105


<210> SEQ ID NO 255
<211> LENGTH: 322
<212> TYPE: DNA
<213> ORGANISM: Homo Sapiens

<400> SEQUENCE: 255

gacatccaga tgacccagtc tccatcttcc gtgtctgcat ctgtaggaga cagagtcacc     60

atcacttgtc gggcgagtca gggtattaac agctggttag cctggtatca gcagaaacca    120

gggaaagccc ctaagctcct gatctatgct gcatccactt tgcaaagtgg ggtcccatca    180

aggttcagcg gcagtgggtc tggggcagat ttcactctca ccatcagcag cctgcagcct    240

gaagattttg caacttacta ttgtcaacag gttaacagtt tcccgctcac tttcggcgga    300

gggaccaagg tggagatcaa ac                                             322


<210> SEQ ID NO 256
<211> LENGTH: 214
<212> TYPE: PRT
<213> ORGANISM: Homo Sapiens

<400> SEQUENCE: 256

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Val Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 257
<211> LENGTH: 642
<212> TYPE: DNA
<213> ORGANISM: Homo Sapiens
```

<400> SEQUENCE: 257
gacatccaga tgacccagtc tccatcttcc gtgtctgcat ctgtaggaga cagagtcacc 60
atcacttgtc gggcgagtca gggtattaac agctggttag cctggtatca gcagaaacca 120
gggaaagccc ctaagctcct gatctatgct gcatccactt tgcaaagtgg ggtcccatca 180
aggttcagcg gcagtgggtc tggggcagat ttcactctca ccatcagcag cctgcagcct 240
gaagattttg caacttacta ttgtcaacag gttaacagtt tcccgctcac tttcggcgga 300
gggaccaagg tggagatcaa acgtacggtg gccgctccct ccgtgttcat cttcccacct 360
tccgacgagc agctgaagtc cggcaccgct tctgtcgtgt gcctgctgaa caacttctac 420 cccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 258
<211> LENGTH: 8
<212> TYPE: PRT
<213> ORGANISM: Homo Sapiens

<400> SEQUENCE: 258

Gly Phe Thr Phe Ser Tyr Tyr Ala
1 5

<210> SEQ ID NO 259
<211> LENGTH: 8
<212> TYPE: PRT
<213> ORGANISM: Homo Sapiens

<400> SEQUENCE: 259

Ile Ser Gly Gly Gly Gly Asn Thr
1 5

<210> SEQ ID NO 260
<211> LENGTH: 16
<212> TYPE: PRT
<213> ORGANISM: Homo Sapiens

<400> SEQUENCE: 260

Ala Lys Asp Arg Met Lys Gln Leu Val Arg Ala Tyr Tyr Phe Asp Tyr
1 5 10 15

<210> SEQ ID NO 261
<211> LENGTH: 5
<212> TYPE: PRT
<213> ORGANISM: Homo Sapiens

<400> SEQUENCE: 261

Tyr Tyr Ala Met Ser
1 5

<210> SEQ ID NO 262
<211> LENGTH: 17
<212> TYPE: PRT
<213> ORGANISM: Homo Sapiens

<400> SEQUENCE: 262

Thr Ile Ser Gly Gly Gly Gly Asn Thr His Tyr Ala Asp Ser Val Lys
1 5 10 15

Gly

<210> SEQ ID NO 263
<211> LENGTH: 14
<212> TYPE: PRT
<213> ORGANISM: Homo Sapiens

<400> SEQUENCE: 263

Asp Arg Met Lys Gln Leu Val Arg Ala Tyr Tyr Phe Asp Tyr
1               5                   10

<210> SEQ ID NO 264
<211> LENGTH: 123
<212> TYPE: PRT
<213> ORGANISM: Homo Sapiens

<400> SEQUENCE: 264

Glu Val Pro Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser
        115                 120

<210> SEQ ID NO 265
<211> LENGTH: 370
<212> TYPE: DNA
<213> ORGANISM: Homo Sapiens

<400> SEQUENCE: 265
gaggtgccgc tggtggagtc tgggggaggc ttggtacagc ctggggggtc cctgagactc      60
tcctgtgcag cctctggatt cacgtttagc tactatgcca tgagctgggt ccgtcaggct     120
ccagggaagg ggctggactg ggtctcaact attagtggtg gtggtggtaa cacacactac     180
gcagactccg tgaagggccg attcactata tccagagaca attccaagaa cacgctgtat     240
ctgcacatga acagcctgag agccgaagac acggccgtct attactgtgc gaaggatcgg     300
atgaaacagc tcgtccgggc ctactacttt gactactggg gccagggaac cctggtcacc     360
gtctcctcag                                                            370

<210> SEQ ID NO 266
<211> LENGTH: 453
<212> TYPE: PRT
<213> ORGANISM: Homo Sapiens

<400> SEQUENCE: 266

Glu Val Pro Leu Val Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Asp Trp Val
        35                  40                  45

Ser Thr Ile Ser Gly Gly Gly Gly Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Glu Asp Thr Ala Val Tyr Tyr Cys
                85                  90                  95

Ala Lys Asp Arg Met Lys Gln Leu Val Arg Ala Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
```

435 440 445

Leu Ser Pro Gly Lys
450

<210> SEQ ID NO 267
<211> LENGTH: 1359
<212> TYPE: DNA
<213> ORGANISM: Homo Sapiens

<400> SEQUENCE: 267
gaggtgccgc tggtggagtc tgggggaggc ttggtacagc ctgggggtc cctgagactc 60 tcctgtgcag cctctggatt cacgtttagc tactatgcca tgagctgggt ccgtcaggct 120
ccagggaagg ggctggactg ggtctcaact attagtggtg gtggtggtaa cacacactac 180
gcagactccg tgaagggccg attcactata tccagagaca attccaagaa cacgctgtat 240
ctgcacatga acagcctgag agccgaagac acggccgtct attactgtgc gaaggatcgg 300
atgaaacagc tcgtccgggc ctactacttt gactactggg gccagggaac cctggtcacc 360
gtctcctcag ccagcaccaa gggcccctct gtgttccctc tggcccettc cagcaagtcc 420 acctctggcg gaacagccgc tctgggctgc ctcgtgaagg actacttccc cgagcctgtg 480
accgtgtcct ggaactctgg cgctctgacc agcggagtgc acaccttccc tgctgtgctg 540
cagtcctccg gcctgtactc cctgtcctcc gtcgtgaccg tgccttccag ctctctgggc 600
acccagacct acatctgcaa cgtgaaccac aagccctcca acaccaaggt ggacaagaag 660
gtggaaccca agtcctgcga caagacccac acctgtcccc cttgtcctgc ccctgaactg 720
ctgggcggac cttccgtgtt cctgttcccc ccaaagccca aggacaccct gatgatctcc 780
cggacccccg aagtgacctg cgtggtggtg gatgtgtccc acgaggaccc tgaagtgaag 840
ttcaattggt acgtggacgg cgtggaagtg cacaacgcca agaccaagcc tagagaggaa 900
cagtacaact ccacctaccg ggtggtgtcc gtgctgaccg tgctgcacca ggattggctg 960
aacggcaaag agtacaagtg caaggtgtcc aacaaggccc tgcctgcccc catcgaaaag 1020
accatctcca aggccaaggg ccagccccgg gaaccccagg tgtacacact gcccccctagc 1080 agggacgagc tgaccaagaa ccaggtgtcc ctgacctgtc tcgtgaaagg cttctacccc 1140
tccgatatcg ccgtggaatg ggagtccaac ggccagcctg agaacaacta caagaccacc 1200
ccccctgtgc tggactccga cggctcattc ttcctgtaca gcaagctgac agtggacaag 1260
tcccggtggc agcagggcaa cgtgttctcc tgctccgtga tgcacgaggc cctgcacaac 1320
cactacaccc agaagtccct gtccctgagc cccggcaag 1359

<210> SEQ ID NO 268
<211> LENGTH: 6
<212> TYPE: PRT
<213> ORGANISM: Homo Sapiens

<400> SEQUENCE: 268

Gln Asp Ile Ser Thr Tyr
1 5

<210> SEQ ID NO 269
<211> LENGTH: 3
<212> TYPE: PRT
<213> ORGANISM: Homo Sapiens

<400> SEQUENCE: 269

Gly Thr Ser

1

<210> SEQ ID NO 270
<211> LENGTH: 9
<212> TYPE: PRT
<213> ORGANISM: Homo Sapiens

<400> SEQUENCE: 270

Gln Gln Leu His Thr Asp Pro Ile Thr
1 5

<210> SEQ ID NO 271
<211> LENGTH: 11
<212> TYPE: PRT
<213> ORGANISM: Homo Sapiens

<400> SEQUENCE: 271

Trp Ala Ser Gln Asp Ile Ser Thr Tyr Leu Gly
1 5 10

<210> SEQ ID NO 272
<211> LENGTH: 7
<212> TYPE: PRT
<213> ORGANISM: Homo Sapiens

<400> SEQUENCE: 272

Gly Thr Ser Ser Leu Gln Ser
1 5

<210> SEQ ID NO 273
<211> LENGTH: 9
<212> TYPE: PRT
<213> ORGANISM: Homo Sapiens

<400> SEQUENCE: 273

Gln Gln Leu His Thr Asp Pro Ile Thr
1 5

<210> SEQ ID NO 274
<211> LENGTH: 107
<212> TYPE: PRT
<213> ORGANISM: Homo Sapiens

<400> SEQUENCE: 274

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Ile Ser Thr Tyr
20 25 30

Leu Gly Trp Tyr Gln Gln Lys Pro Gly Lys Ala Pro Lys Leu Leu Ile
35 40 45

Tyr Gly Thr Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Leu His Thr Asp Pro Ile
85 90 95

Thr Phe Gly Gln Gly Thr Arg Leu Glu Ile Lys
100 105

<210> SEQ ID NO 275
<211> LENGTH: 322
<212> TYPE: DNA

<213> ORGANISM: Homo Sapiens

<400> SEQUENCE: 275
gacatccagt tgacccagtc tccatccttc ctgtctgcat ctgtaggaga cagagtcacc 60
atcacttgct gggccagtca ggacattagc acttatttag gctggtatca gcaaaaacca 120
gggaaagccc ctaagctcct gatctatggt acatccagtt tgcaaagtgg ggtcccatca 180
aggttcagcg gcagtggatc tgggacagaa ttcactctca caatcagcag cctgcagcct 240
gaagattttg caacttatta ctgtcaacag cttcatactg acccgatcac cttcggccaa 300
gggacacgac tggagatcaa ac 322

<210> SEQ ID NO 276
<211> LENGTH: 214
<212> TYPE: PRT
<213> ORGANISM: Homo Sapiens

<400> SEQUENCE: 276

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Ile Ser Thr Tyr
20 25 30

Leu Gly Trp Tyr Gln Gln Lys Pro Gly Lys Ala Pro Lys Leu Leu Ile
35 40 45

Tyr Gly Thr Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Leu His Thr Asp Pro Ile
85 90 95

Thr Phe Gly Gln Gly Thr Arg Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 277
<211> LENGTH: 642
<212> TYPE: DNA
<213> ORGANISM: Homo Sapiens

<400> SEQUENCE: 277
gacatccagt tgacccagtc tccatccttc ctgtctgcat ctgtaggaga cagagtcacc 60
atcacttgct gggccagtca ggacattagc acttatttag gctggtatca gcaaaaacca 120
gggaaagccc ctaagctcct gatctatggt acatccagtt tgcaaagtgg ggtcccatca 180

```
aggttcagcg gcagtggatc tgggacagaa ttcactctca caatcagcag cctgcagcct    240

gaagattttg caacttatta ctgtcaacag cttcatactg acccgatcac cttcggccaa    300

gggacacgac tggagatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 278
<211> LENGTH: 8
<212> TYPE: PRT
<213> ORGANISM: Homo Sapiens

<400> SEQUENCE: 278

Gly Phe Thr Phe Ser Ser Tyr Trp
1               5


<210> SEQ ID NO 279
<211> LENGTH: 8
<212> TYPE: PRT
<213> ORGANISM: Homo Sapiens

<400> SEQUENCE: 279

Ile Lys Gln Asp Gly Ser Glu Lys
1               5


<210> SEQ ID NO 280
<211> LENGTH: 12
<212> TYPE: PRT
<213> ORGANISM: Homo Sapiens

<400> SEQUENCE: 280

Ala Arg Val Arg Gln Trp Ser Asp Tyr Ser Asp Tyr
1               5                   10


<210> SEQ ID NO 281
<211> LENGTH: 5
<212> TYPE: PRT
<213> ORGANISM: Homo Sapiens

<400> SEQUENCE: 281

Ser Tyr Trp Met Asn
1               5


<210> SEQ ID NO 282
<211> LENGTH: 17
<212> TYPE: PRT
<213> ORGANISM: Homo Sapiens

<400> SEQUENCE: 282

Asn Ile Lys Gln Asp Gly Ser Glu Lys Tyr Tyr Val Asp Ser Val Lys
1               5                   10                  15

Gly


<210> SEQ ID NO 283
<211> LENGTH: 10
<212> TYPE: PRT
<213> ORGANISM: Homo Sapiens
```

<400> SEQUENCE: 283

Val Arg Gln Trp Ser Asp Tyr Ser Asp Tyr
1               5                   10

<210> SEQ ID NO 284
<211> LENGTH: 119
<212> TYPE: PRT
<213> ORGANISM: Homo Sapiens

<400> SEQUENCE: 284

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gln Trp Ser Asp Tyr Ser Asp Tyr Trp Gly Gln Gly
            100                 105                 110

Thr Pro Val Thr Val Ser Ser
        115

<210> SEQ ID NO 285
<211> LENGTH: 358
<212> TYPE: DNA
<213> ORGANISM: Homo Sapiens

<400> SEQUENCE: 285
gaggtgcacc tggtggagtc tgggggaggc ttggtccagc ctggggggtc cctgagactc      60
tcctgtgcag cctctggatt cacctttagt agctattgga tgaactgggt ccgccaggct     120
ccagggaagg ggctggagtg ggtggccaac ataaagcaag atggaagtga gaaatactat     180
gtggactctg tgaagggccg cttcaccgtc tccagagaca acgccaagaa ctcactgtat     240
ctgcaaatga acagcctgag agccgaggac acggctgtgt attactgtgc gagagttcga     300
caatggtccg actactctga ctactggggc cagggaaccc cggtcaccgt ctcctcag       358

<210> SEQ ID NO 286
<211> LENGTH: 449
<212> TYPE: PRT
<213> ORGANISM: Homo Sapiens

<400> SEQUENCE: 286

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Val Ser Arg Asp Asn Ala Lys Asn Ser Leu Tyr

-continued

```
65                  70                  75                  80

Leu Gln Met Asn Ser Leu Arg Ala Glu Asp Thr Ala Val Tyr Tyr Cys
                85                  90                  95

Ala Arg Val Arg Gln Trp Ser Asp Tyr Ser Asp Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 287
<211> LENGTH: 1347
<212> TYPE: DNA
<213> ORGANISM: Homo Sapiens -continued

<400> SEQUENCE: 287

```
gaggtgcacc tggtggagtc tgggggaggc ttggtccagc ctggggggtc cctgagactc     60
tcctgtgcag cctctggatt cacctttagt agctattgga tgaactgggt ccgccaggct    120
ccagggaagg ggctggagtg ggtggccaac ataaagcaag atggaagtga gaaatactat    180
gtggactctg tgaagggccg cttcaccgtc tccagagaca acgccaagaa ctcactgtat    240
ctgcaaatga acagcctgag agccgaggac acggctgtgt attactgtgc gagagttcga    300
caatggtccg actactctga ctactggggc cagggaaccc cggtcaccgt ctcctcagcc    360
agcaccaagg gccccctctgt gttccctctg gccccttcca gcaagtccac ctctggcgga    420
acagccgctc tgggctgcct cgtgaaggac tacttccccg agcctgtgac cgtgtcctgg    480
aactctggcg ctctgaccag cggagtgcac accttccctg ctgtgctgca gtcctccggc    540
ctgtactccc tgtcctccgt cgtgaccgtg ccttccagct ctctgggcac ccagacctac    600
atctgcaacg tgaaccacaa gccctccaac accaaggtgg acaagaaggt ggaacccaag    660
tcctgcgaca agacccacac ctgtcccccct tgtcctgccc ctgaactgct gggcggacct    720
tccgtgttcc tgttcccccc aaagcccaag gacaccctga tgatctcccg gacccccgaa    780
gtgacctgcg tggtggtgga tgtgtcccac gaggaccctg aagtgaagtt caattggtac    840
gtggacggcg tggaagtgca caacgccaag accaagccta gagaggaaca gtacaactcc    900
acctaccggg tggtgtccgt gctgaccgtg ctgcaccagg attggctgaa cggcaaagag    960
tacaagtgca aggtgtccaa caaggccctg cctgccccca tcgaaaagac catctccaag   1020
gccaagggcc agccccggga accccaggtg tacacactgc cccctagcag ggacgagctg   1080
accaagaacc aggtgtccct gacctgtctc gtgaaaggct tctacccctc cgatatcgcc   1140
gtggaatggg agtccaacgg ccagcctgag aacaactaca agaccacccc ccctgtgctg   1200
gactccgacg gctcattctt cctgtacagc aagctgacag tggacaagtc ccggtggcag   1260
cagggcaacg tgttctcctg ctccgtgatg cacgaggccc tgcacaacca ctacacccag   1320
aagtccctgt ccctgagccc cggcaag                                       1347
```

<210> SEQ ID NO 288
<211> LENGTH: 6
<212> TYPE: PRT
<213> ORGANISM: Homo Sapiens

<400> SEQUENCE: 288

```
Gln Gly Ile Ser Ser Trp
1               5
```

<210> SEQ ID NO 289
<211> LENGTH: 3
<212> TYPE: PRT
<213> ORGANISM: Homo Sapiens

<400> SEQUENCE: 289

```
Ala Ala Ser
1
```

<210> SEQ ID NO 290
<211> LENGTH: 9
<212> TYPE: PRT
<213> ORGANISM: Homo Sapiens

<400> SEQUENCE: 290

```
Gln Gln Ala Asn Ser Phe Pro Phe Thr
```

1 5

<210> SEQ ID NO 291
<211> LENGTH: 11
<212> TYPE: PRT
<213> ORGANISM: Homo Sapiens

<400> SEQUENCE: 291

Arg Ala Ser Gln Gly Ile Ser Ser Trp Leu Ala
1 5 10

<210> SEQ ID NO 292
<211> LENGTH: 7
<212> TYPE: PRT
<213> ORGANISM: Homo Sapiens

<400> SEQUENCE: 292

Ala Ala Ser Ser Leu Gln Ser
1 5

<210> SEQ ID NO 293
<211> LENGTH: 9
<212> TYPE: PRT
<213> ORGANISM: Homo Sapiens

<400> SEQUENCE: 293

Gln Gln Ala Asn Ser Phe Pro Phe Thr
1 5

<210> SEQ ID NO 294
<211> LENGTH: 107
<212> TYPE: PRT
<213> ORGANISM: Homo Sapiens

<400> SEQUENCE: 294

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Phe
85 90 95

Thr Phe Gly Pro Gly Thr Lys Val Asp Ile Lys
100 105

<210> SEQ ID NO 295
<211> LENGTH: 322
<212> TYPE: DNA
<213> ORGANISM: Homo Sapiens

<400> SEQUENCE: 295
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tcccattcac tttcggccct 300
gggaccaaag tggatatcaa ac 322

<210> SEQ ID NO 296
<211> LENGTH: 214
<212> TYPE: PRT
<213> ORGANISM: Homo Sapiens

<400> SEQUENCE: 296

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Phe
85 90 95

Thr Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 297
<211> LENGTH: 642
<212> TYPE: DNA
<213> ORGANISM: Homo Sapiens

<400> SEQUENCE: 297
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tcccattcac tttcggccct 300
gggaccaaag tggatatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480

```
gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 298
<211> LENGTH: 214
<212> TYPE: PRT
<213> ORGANISM: Homo Sapiens

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 299
<211> LENGTH: 453
<212> TYPE: PRT
<213> ORGANISM: Homo Sapiens

<400> SEQUENCE: 299

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80
```

-continued

```
Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 300
<211> LENGTH: 347
<212> TYPE: PRT
<213> ORGANISM: Homo Sapiens

<400> SEQUENCE: 300

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Pro Thr Ser Ser Ser Thr Lys Lys Thr
    210                 215                 220

Gln Leu Gln Leu Glu His Leu Leu Leu Asp Leu Gln Met Ile Leu Asn
225                 230                 235                 240

Gly Ile Asn Asn Tyr Lys Asn Pro Lys Leu Thr Arg Met Leu Thr Phe
                245                 250                 255

Lys Phe Tyr Met Pro Lys Lys Ala Thr Glu Leu Lys His Leu Gln Cys
            260                 265                 270

Leu Glu Glu Glu Leu Lys Pro Leu Glu Glu Val Leu Asn Leu Ala Gln
        275                 280                 285

Ser Lys Asn Phe His Leu Arg Pro Arg Asp Leu Ile Ser Asn Ile Asn
    290                 295                 300

Val Ile Val Leu Glu Leu Lys Gly Ser Glu Thr Thr Phe Met Cys Glu
305                 310                 315                 320

Tyr Ala Asp Glu Thr Ala Thr Ile Val Glu Phe Leu Asn Arg Trp Ile
                325                 330                 335

Thr Phe Cys Gln Ser Ile Ile Ser Thr Leu Thr
            340                 345


<210> SEQ ID NO 301
<211> LENGTH: 133
<212> TYPE: PRT
<213> ORGANISM: Homo Sapiens

<400> SEQUENCE: 301

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

<210> SEQ ID NO 302
<211> LENGTH: 586
<212> TYPE: PRT
<213> ORGANISM: Homo Sapiens

<400> SEQUENCE: 302

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Val Pro Gly Lys Gly Leu Glu Trp Val
35 40 45

Ser Gly Ile Ser Trp Ile Arg Thr Gly Ile Gly Tyr Ala Asp Ser Val
50 55 60

Lys Gly Arg Phe Thr Ile Phe Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Lys Asp Met Lys Gly Ser Gly Thr Tyr Gly Gly Trp Phe Asp Thr
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Ala Gly Ala Pro Ser Val Phe Leu Phe Pro Pro Lys Pro Lys Asp Thr
245 250 255

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Ala Pro Thr Ser Ser Ser Thr Lys Lys Thr Gln
    450                 455                 460

Leu Gln Leu Glu His Leu Leu Leu Asp Leu Gln Met Ile Leu Asn Gly
465                 470                 475                 480

Ile Asn Asn Tyr Lys Asn Pro Lys Leu Thr Arg Met Leu Thr Phe Lys
                485                 490                 495

Phe Tyr Met Pro Lys Lys Ala Thr Glu Leu Lys His Leu Gln Cys Leu
            500                 505                 510

Glu Glu Glu Leu Lys Pro Leu Glu Glu Val Leu Asn Leu Ala Gln Ser
        515                 520                 525

Lys Asn Phe His Leu Arg Pro Arg Asp Leu Ile Ser Asn Ile Asn Val
    530                 535                 540

Ile Val Leu Glu Leu Lys Gly Ser Glu Thr Thr Phe Met Cys Glu Tyr
545                 550                 555                 560

Ala Asp Glu Thr Ala Thr Ile Val Glu Phe Leu Asn Arg Trp Ile Thr
                565                 570                 575

Phe Cys Gln Ser Ile Ile Ser Thr Leu Thr
            580                 585
```

<210> SEQ ID NO 303
<211> LENGTH: 14
<212> TYPE: PRT
<213> ORGANISM: Homo Sapiens

<400> SEQUENCE: 303

```
Ala Pro Thr Ser Thr Gln Leu Gln Leu Glu Leu Leu Leu Asp
1               5                   10
```

<210> SEQ ID NO 304
<211> LENGTH: 11
<212> TYPE: PRT
<213> ORGANISM: Homo Sapiens

<400> SEQUENCE: 304

Thr Gln Leu Gln Leu Glu His Leu Leu Leu Asp
1 5 10

<210> SEQ ID NO 305
<211> LENGTH: 17
<212> TYPE: PRT
<213> ORGANISM: Homo Sapiens

<400> SEQUENCE: 305

Ala Pro Thr Ser Lys Lys Thr Gln Leu Gln Leu Glu His Leu Leu Leu
1 5 10 15

Asp

<210> SEQ ID NO 306
<211> LENGTH: 19
<212> TYPE: PRT
<213> ORGANISM: Homo Sapiens

<400> SEQUENCE: 306

Pro Thr Ser Ser Ser Thr Lys Lys Thr Gln Leu Gln Leu Glu His Leu
1 5 10 15

Leu Leu Asp

<210> SEQ ID NO 307
<211> LENGTH: 18
<212> TYPE: PRT
<213> ORGANISM: Homo Sapiens

<400> SEQUENCE: 307

Thr Ser Ser Ser Thr Lys Lys Thr Gln Leu Gln Leu Glu His Leu Leu
1 5 10 15

Leu Asp

<210> SEQ ID NO 308
<211> LENGTH: 17
<212> TYPE: PRT
<213> ORGANISM: Homo Sapiens

<400> SEQUENCE: 308

Ser Ser Ser Thr Lys Lys Thr Gln Leu Gln Leu Glu His Leu Leu Leu
1 5 10 15

Asp

<210> SEQ ID NO 309
<211> LENGTH: 16
<212> TYPE: PRT
<213> ORGANISM: Homo Sapiens

<400> SEQUENCE: 309

Ser Ser Thr Lys Lys Thr Gln Leu Gln Leu Glu His Leu Leu Leu Asp
1 5 10 15

<210> SEQ ID NO 310
<211> LENGTH: 15
<212> TYPE: PRT
<213> ORGANISM: Homo Sapiens

<400> SEQUENCE: 310

Ser Thr Lys Lys Thr Gln Leu Gln Leu Glu His Leu Leu Leu Asp
1 5 10 15

<210> SEQ ID NO 311
<211> LENGTH: 14
<212> TYPE: PRT
<213> ORGANISM: Homo Sapiens

<400> SEQUENCE: 311

Thr Lys Lys Thr Gln Leu Gln Leu Glu His Leu Leu Leu Asp
1 5 10

<210> SEQ ID NO 312
<211> LENGTH: 13
<212> TYPE: PRT
<213> ORGANISM: Homo Sapiens

<400> SEQUENCE: 312

Lys Lys Thr Gln Leu Gln Leu Glu His Leu Leu Leu Asp
1 5 10

<210> SEQ ID NO 313
<211> LENGTH: 12
<212> TYPE: PRT
<213> ORGANISM: Homo Sapiens

<400> SEQUENCE: 313

Lys Thr Gln Leu Gln Leu Glu His Leu Leu Leu Asp
1 5 10

<210> SEQ ID NO 314
<211> LENGTH: 19
<212> TYPE: PRT
<213> ORGANISM: Homo Sapiens

<400> SEQUENCE: 314

Ala Pro Thr Ser Ser Ser Thr Lys Thr Gln Leu Gln Leu Glu His Leu
1 5 10 15

Leu Leu Asp

<210> SEQ ID NO 315
<211> LENGTH: 18
<212> TYPE: PRT
<213> ORGANISM: Homo Sapiens

<400> SEQUENCE: 315

Ala Pro Thr Ser Ser Ser Thr Thr Gln Leu Gln Leu Glu His Leu Leu
1 5 10 15

Leu Asp

<210> SEQ ID NO 316
<211> LENGTH: 17
<212> TYPE: PRT
<213> ORGANISM: Homo Sapiens

<400> SEQUENCE: 316

Ala Pro Thr Ser Ser Ser Thr Gln Leu Gln Leu Glu His Leu Leu Leu
1 5 10 15

Asp

<210> SEQ ID NO 317
<211> LENGTH: 16
<212> TYPE: PRT
<213> ORGANISM: Homo Sapiens

<400> SEQUENCE: 317

Ala Pro Thr Ser Ser Thr Gln Leu Gln Leu Glu His Leu Leu Leu Asp
1 5 10 15

<210> SEQ ID NO 318
<211> LENGTH: 14
<212> TYPE: PRT
<213> ORGANISM: Homo Sapiens

<400> SEQUENCE: 318

Ala Pro Thr Thr Gln Leu Gln Leu Glu His Leu Leu Leu Asp
1 5 10

<210> SEQ ID NO 319
<211> LENGTH: 13
<212> TYPE: PRT
<213> ORGANISM: Homo Sapiens

<400> SEQUENCE: 319

Ala Pro Thr Gln Leu Gln Leu Glu His Leu Leu Leu Asp
1 5 10

<210> SEQ ID NO 320
<211> LENGTH: 12
<212> TYPE: PRT
<213> ORGANISM: Homo Sapiens

<400> SEQUENCE: 320

Ala Thr Gln Leu Gln Leu Glu His Leu Leu Leu Asp
1 5 10

<210> SEQ ID NO 321
<211> LENGTH: 15
<212> TYPE: PRT
<213> ORGANISM: Homo Sapiens

<400> SEQUENCE: 321

Ala Thr Lys Lys Thr Gln Leu Gln Leu Glu His Leu Leu Leu Asp
1 5 10 15

<210> SEQ ID NO 322
<211> LENGTH: 15
<212> TYPE: PRT
<213> ORGANISM: Homo Sapiens

<400> SEQUENCE: 322

Ala Pro Lys Lys Thr Gln Leu Gln Leu Glu His Leu Leu Leu Asp
1 5 10 15

<210> SEQ ID NO 323
<211> LENGTH: 15
<212> TYPE: PRT
<213> ORGANISM: Homo Sapiens

<400> SEQUENCE: 323

Ala Pro Thr Lys Thr Gln Leu Gln Leu Glu His Leu Leu Leu Asp
1 5 10 15

<210> SEQ ID NO 324
<211> LENGTH: 113
<212> TYPE: PRT
<213> ORGANISM: Homo Sapiens

<400> SEQUENCE: 324

```
Leu Gln Met Ile Leu Asn Gly Ile Asn Asn Tyr Lys Asn Pro Lys Leu
1               5                   10                  15

Thr Arg Met Leu Thr Phe Lys Phe Tyr Met Pro Lys Lys Ala Thr Glu
            20                  25                  30

Leu Lys His Leu Gln Cys Leu Glu Glu Glu Leu Lys Pro Leu Glu Glu
        35                  40                  45

Val Leu Asn Leu Ala Gln Ser Lys Asn Phe His Leu Arg Pro Arg Asp
    50                  55                  60

Leu Ile Ser Asn Ile Asn Val Ile Val Leu Glu Leu Lys Gly Ser Glu
65                  70                  75                  80

Thr Thr Phe Met Cys Glu Tyr Ala Asp Glu Thr Ala Thr Ile Val Glu
                85                  90                  95

Phe Leu Asn Arg Trp Ile Thr Phe Cys Gln Ser Ile Ile Ser Thr Leu
            100                 105                 110

Thr


<210> SEQ ID NO 325
<211> LENGTH: 290
<212> TYPE: PRT
<213> ORGANISM: Mus Musculus

<400> SEQUENCE: 325

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255
```

```
Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290


<210> SEQ ID NO 326
<211> LENGTH: 226
<212> TYPE: PRT
<213> ORGANISM: Mus Musculus

<400> SEQUENCE: 326

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His His His His
    210                 215                 220

His His
225


<210> SEQ ID NO 327
<211> LENGTH: 251
<212> TYPE: PRT
<213> ORGANISM: Homo Sapiens

<400> SEQUENCE: 327

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45
```

Asn Ser Ser His Ser Ser Trp Asp Asn Gln Cys Gln Cys Thr Ser Ser
50 55 60

Ala Thr Arg Asn Thr Thr Lys Gln Val Thr Pro Gln Pro Glu Glu Gln
65 70 75 80

Lys Glu Arg Lys Thr Thr Glu Met Gln Ser Pro Met Gln Pro Val Asp
85 90 95

Gln Ala Ser Leu Pro Gly His Cys Arg Glu Pro Pro Pro Trp Glu Asn
100 105 110

Glu Ala Thr Glu Arg Ile Tyr His Phe Val Val Gly Gln Met Val Tyr
115 120 125

Tyr Gln Cys Val Gln Gly Tyr Arg Ala Leu His Arg Gly Pro Ala Glu
130 135 140

Ser Val Cys Lys Met Thr His Gly Lys Thr Arg Trp Thr Gln Pro Gln
145 150 155 160

Leu Ile Cys Thr Gly Glu Met Glu Thr Ser Gln Phe Pro Gly Glu Glu
165 170 175

Lys Pro Gln Ala Ser Pro Glu Gly Arg Pro Glu Ser Glu Thr Ser Cys
180 185 190

Leu Val Thr Thr Thr Asp Phe Gln Ile Gln Thr Glu Met Ala Ala Thr
195 200 205

Met Glu Thr Ser Ile Phe Thr Thr Glu Tyr Gln Val Ala Val Ala Gly
210 215 220

Cys Val Phe Leu Leu Ile Ser Val Leu Leu Leu Ser Gly Leu Thr Trp
225 230 235 240

Gln Arg Arg Gln Arg Lys Ser Arg Arg Thr Ile
245 250

<210> SEQ ID NO 328
<211> LENGTH: 525
<212> TYPE: PRT
<213> ORGANISM: Homo Sapiens

<400> SEQUENCE: 328

Ala Val Asn Gly Thr Ser Gln Phe Thr Cys Phe Tyr Asn Ser Arg Ala
1 5 10 15

Asn Ile Ser Cys Val Trp Ser Gln Asp Gly Ala Leu Gln Asp Thr Ser
20 25 30

Cys Gln Val His Ala Trp Pro Asp Arg Arg Arg Trp Asn Gln Thr Cys
35 40 45

Glu Leu Leu Pro Val Ser Gln Ala Ser Trp Ala Cys Asn Leu Ile Leu
50 55 60

Gly Ala Pro Asp Ser Gln Lys Leu Thr Thr Val Asp Ile Val Thr Leu
65 70 75 80

Arg Val Leu Cys Arg Glu Gly Val Arg Trp Arg Val Met Ala Ile Gln
85 90 95

Asp Phe Lys Pro Phe Glu Asn Leu Arg Leu Met Ala Pro Ile Ser Leu
100 105 110

Gln Val Val His Val Glu Thr His Arg Cys Asn Ile Ser Trp Glu Ile
115 120 125

Ser Gln Ala Ser His Tyr Phe Glu Arg His Leu Glu Phe Glu Ala Arg
130 135 140

Thr Leu Ser Pro Gly His Thr Trp Glu Glu Ala Pro Leu Leu Thr Leu
145 150 155 160

Lys Gln Lys Gln Glu Trp Ile Cys Leu Glu Thr Leu Thr Pro Asp Thr
165 170 175

Gln Tyr Glu Phe Gln Val Arg Val Lys Pro Leu Gln Gly Glu Phe Thr
180 185 190

Thr Trp Ser Pro Trp Ser Gln Pro Leu Ala Phe Arg Thr Lys Pro Ala
195 200 205

Ala Leu Gly Lys Asp Thr Ile Pro Trp Leu Gly His Leu Leu Val Gly
210 215 220

Leu Ser Gly Ala Phe Gly Phe Ile Ile Leu Val Tyr Leu Leu Ile Asn
225 230 235 240

Cys Arg Asn Thr Gly Pro Trp Leu Lys Lys Val Leu Lys Cys Asn Thr
245 250 255

Pro Asp Pro Ser Lys Phe Phe Ser Gln Leu Ser Ser Glu His Gly Gly
260 265 270

Asp Val Gln Lys Trp Leu Ser Ser Pro Phe Pro Ser Ser Ser Phe Ser
275 280 285

Pro Gly Gly Leu Ala Pro Glu Ile Ser Pro Leu Glu Val Leu Glu Arg
290 295 300

Asp Lys Val Thr Gln Leu Leu Leu Gln Gln Asp Lys Val Pro Glu Pro
305 310 315 320

Ala Ser Leu Ser Ser Asn His Ser Leu Thr Ser Cys Phe Thr Asn Gln
325 330 335

Gly Tyr Phe Phe Phe His Leu Pro Asp Ala Leu Glu Ile Glu Ala Cys
340 345 350

Gln Val Tyr Phe Thr Tyr Asp Pro Tyr Ser Glu Glu Asp Pro Asp Glu
355 360 365

Gly Val Ala Gly Ala Pro Thr Gly Ser Ser Pro Gln Pro Leu Gln Pro
370 375 380

Leu Ser Gly Glu Asp Asp Ala Tyr Cys Thr Phe Pro Ser Arg Asp Asp
385 390 395 400

Leu Leu Leu Phe Ser Pro Ser Leu Leu Gly Gly Pro Ser Pro Pro Ser
405 410 415

Thr Ala Pro Gly Gly Ser Gly Ala Gly Glu Glu Arg Met Pro Pro Ser
420 425 430

Leu Gln Glu Arg Val Pro Arg Asp Trp Asp Pro Gln Pro Leu Gly Pro
435 440 445

Pro Thr Pro Gly Val Pro Asp Leu Val Asp Phe Gln Pro Pro Pro Glu
450 455 460

Leu Val Leu Arg Glu Ala Gly Glu Glu Val Pro Asp Ala Gly Pro Arg
465 470 475 480

Glu Gly Val Ser Phe Pro Trp Ser Arg Pro Pro Gly Gln Gly Glu Phe
485 490 495

Arg Ala Leu Asn Ala Arg Leu Pro Leu Asn Thr Asp Ala Tyr Leu Ser
500 505 510

Leu Gln Glu Leu Gln Gly Gln Asp Pro Thr His Leu Val
515 520 525

<210> SEQ ID NO 329
<211> LENGTH: 347
<212> TYPE: PRT
<213> ORGANISM: Homo Sapiens

<400> SEQUENCE: 329

Leu Asn Thr Thr Ile Leu Thr Pro Asn Gly Asn Glu Asp Thr Thr Ala
1 5 10 15

Asp Phe Phe Leu Thr Thr Met Pro Thr Asp Ser Leu Ser Val Ser Thr 20 25 30

Leu Pro Leu Pro Glu Val Gln Cys Phe Val Phe Asn Val Glu Tyr Met
35 40 45

Asn Cys Thr Trp Asn Ser Ser Ser Glu Pro Gln Pro Thr Asn Leu Thr
50 55 60

Leu His Tyr Trp Tyr Lys Asn Ser Asp Asn Asp Lys Val Gln Lys Cys
65 70 75 80

Ser His Tyr Leu Phe Ser Glu Glu Ile Thr Ser Gly Cys Gln Leu Gln
85 90 95

Lys Lys Glu Ile His Leu Tyr Gln Thr Phe Val Val Gln Leu Gln Asp
100 105 110

Pro Arg Glu Pro Arg Arg Gln Ala Thr Gln Met Leu Lys Leu Gln Asn
115 120 125

Leu Val Ile Pro Trp Ala Pro Glu Asn Leu Thr Leu His Lys Leu Ser
130 135 140

Glu Ser Gln Leu Glu Leu Asn Trp Asn Asn Arg Phe Leu Asn His Cys
145 150 155 160

Leu Glu His Leu Val Gln Tyr Arg Thr Asp Trp Asp His Ser Trp Thr
165 170 175

Glu Gln Ser Val Asp Tyr Arg His Lys Phe Ser Leu Pro Ser Val Asp
180 185 190

Gly Gln Lys Arg Tyr Thr Phe Arg Val Arg Ser Arg Phe Asn Pro Leu
195 200 205

Cys Gly Ser Ala Gln His Trp Ser Glu Trp Ser His Pro Ile His Trp
210 215 220

Gly Ser Asn Thr Ser Lys Glu Asn Pro Phe Leu Phe Ala Leu Glu Ala
225 230 235 240

Val Val Ile Ser Val Gly Ser Met Gly Leu Ile Ile Ser Leu Leu Cys
245 250 255

Val Tyr Phe Trp Leu Glu Arg Thr Met Pro Arg Ile Pro Thr Leu Lys
260 265 270

Asn Leu Glu Asp Leu Val Thr Glu Tyr His Gly Asn Phe Ser Ala Trp
275 280 285

Ser Gly Val Ser Lys Gly Leu Ala Glu Ser Leu Gln Pro Asp Tyr Ser
290 295 300

Glu Arg Leu Cys Leu Val Ser Glu Ile Pro Pro Lys Gly Gly Ala Leu
305 310 315 320

Gly Glu Gly Pro Gly Ala Ser Pro Cys Asn Gln His Ser Pro Tyr Trp
325 330 335

Ala Pro Pro Cys Tyr Thr Leu Lys Pro Glu Thr
340 345

<210> SEQ ID NO 330
<211> LENGTH: 152
<212> TYPE: PRT
<213> ORGANISM: Homo Sapiens

<400> SEQUENCE: 330

Asp Cys Asp Ile Glu Gly Lys Asp Gly Lys Gln Tyr Glu Ser Val Leu
1 5 10 15

Met Val Ser Ile Asp Gln Leu Leu Asp Ser Met Lys Glu Ile Gly Ser
20 25 30

Asn Cys Leu Asn Asn Glu Phe Asn Phe Phe Lys Arg His Ile Cys Asp
35 40 45

```
Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 331
<211> LENGTH: 133
<212> TYPE: PRT
<213> ORGANISM: Homo Sapiens

<400> SEQUENCE: 331

Gly Ile His Val Phe Ile Leu Gly Cys Phe Ser Ala Gly Leu Pro Lys
1               5                   10                  15

Thr Glu Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser
    130


<210> SEQ ID NO 332
<211> LENGTH: 133
<212> TYPE: PRT
<213> ORGANISM: Homo Sapiens

<400> SEQUENCE: 332

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80
```

```
Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130


<210> SEQ ID NO 333
<211> LENGTH: 127
<212> TYPE: PRT
<213> ORGANISM: Homo Sapiens

<400> SEQUENCE: 333

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 334
<211> LENGTH: 171
<212> TYPE: PRT
<213> ORGANISM: Homo Sapiens

<400> SEQUENCE: 334

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Glu Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140
```

Arg Met Glu Ile Met Lys Ser Leu Phe Leu Ser Thr Asn Met Gln Glu
145 150 155 160

Arg Leu Arg Ser Lys Asp Arg Asp Leu Gly Ser
165 170

<210> SEQ ID NO 335
<211> LENGTH: 177
<212> TYPE: PRT
<213> ORGANISM: Homo Sapiens

<400> SEQUENCE: 335

Gly Pro Gln Arg Glu Glu Phe Pro Arg Asp Leu Ser Leu Ile Ser Pro
1 5 10 15

Leu Ala Gln Ala Val Arg Ser Ser Ser Arg Thr Pro Ser Asp Lys Pro
20 25 30

Val Ala His Val Val Ala Asn Pro Gln Ala Glu Gly Gln Leu Gln Trp
35 40 45

Leu Asn Arg Arg Ala Asn Ala Leu Leu Ala Asn Gly Val Glu Leu Arg
50 55 60

Asp Asn Gln Leu Val Val Pro Ser Glu Gly Leu Tyr Leu Ile Tyr Ser
65 70 75 80

Gln Val Leu Phe Lys Gly Gln Gly Cys Pro Ser Thr His Val Leu Leu
85 90 95

Thr His Thr Ile Ser Arg Ile Ala Val Ser Tyr Gln Thr Lys Val Asn
100 105 110

Leu Leu Ser Ala Ile Lys Ser Pro Cys Gln Arg Glu Thr Pro Glu Gly
115 120 125

Ala Glu Ala Lys Pro Trp Tyr Glu Pro Ile Tyr Leu Gly Gly Val Phe
130 135 140

Gln Leu Glu Lys Gly Asp Arg Leu Ser Ala Glu Ile Asn Arg Pro Asp
145 150 155 160

Tyr Leu Asp Phe Ala Glu Ser Gly Gln Val Tyr Phe Gly Ile Ile Ala
165 170 175

Leu

<210> SEQ ID NO 336
<211> LENGTH: 197
<212> TYPE: PRT
<213> ORGANISM: Homo Sapiens

<400> SEQUENCE: 336

Arg Asn Leu Pro Val Ala Thr Pro Asp Pro Gly Met Phe Pro Cys Leu
1 5 10 15

His His Ser Gln Asn Leu Leu Arg Ala Val Ser Asn Met Leu Gln Lys
20 25 30

Ala Arg Gln Thr Leu Glu Phe Tyr Pro Cys Thr Ser Glu Glu Ile Asp
35 40 45

His Glu Asp Ile Thr Lys Asp Lys Thr Ser Thr Val Glu Ala Cys Leu
50 55 60

Pro Leu Glu Leu Thr Lys Asn Glu Ser Cys Leu Asn Ser Arg Glu Thr
65 70 75 80

Ser Phe Ile Thr Asn Gly Ser Cys Leu Ala Ser Arg Lys Thr Ser Phe
85 90 95

Met Met Ala Leu Cys Leu Ser Ser Ile Tyr Glu Asp Leu Lys Met Tyr
100 105 110

Gln Val Glu Phe Lys Thr Met Asn Ala Lys Leu Leu Met Asp Pro Lys

```
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 337
<211> LENGTH: 306
<212> TYPE: PRT
<213> ORGANISM: Homo Sapiens

<400> SEQUENCE: 337

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285
```

-continued

Gln Asp Arg Tyr Tyr Ser Ser Ser Trp Ser Glu Trp Ala Ser Val Pro
    290                 295                 300

Cys Ser
305

<210> SEQ ID NO 338
<211> LENGTH: 103
<212> TYPE: PRT
<213> ORGANISM: Homo Sapiens

<400> SEQUENCE: 338

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80

Lys Lys His Gln Lys Lys Lys Val Leu Lys Val Arg Lys Ser Gln Arg
                85                  90                  95

Ser Arg Gln Lys Lys Thr Thr
            100

<210> SEQ ID NO 339
<211> LENGTH: 77
<212> TYPE: PRT
<213> ORGANISM: Homo Sapiens

<400> SEQUENCE: 339

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 340
<211> LENGTH: 330
<212> TYPE: PRT
<213> ORGANISM: Homo Sapiens

<400> SEQUENCE: 340

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr

```
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 341
<211> LENGTH: 996
<212> TYPE: DNA
<213> ORGANISM: Homo Sapiens

<400> SEQUENCE: 341

gccagcacca agggcccctc tgtgttccct ctggcccctt ccagcaagtc cacctctggc      60

ggaacagccg ctctgggctg cctcgtgaag gactacttcc ccgagcctgt gaccgtgtcc     120

tggaactctg gcgctctgac cagcggagtg cacaccttcc ctgctgtgct gcagtcctcc     180

ggcctgtact ccctgtcctc cgtcgtgacc gtgccttcca gctctctggg cacccagacc     240

tacatctgca acgtgaacca caagccctcc aacaccaagg tggacaagaa ggtggaaccc     300

aagtcctgcg acaagaccca cacctgtccc ccttgtcctg cccctgaact gctgggcgga     360

ccttccgtgt tcctgttccc cccaaagccc aaggacaccc tgatgatctc ccggaccccc     420

gaagtgacct gcgtggtggt ggatgtgtcc cacgaggacc ctgaagtgaa gttcaattgg     480

tacgtggacg gcgtggaagt gcacaacgcc aagaccaagc ctagagagga acagtacaac     540

tccacctacc gggtggtgtc cgtgctgacc gtgctgcacc aggattggct gaacggcaaa     600

gagtacaagt gcaaggtgtc caacaaggcc ctgcctgccc ccatcgaaaa gaccatctcc     660
```

-continued

```
aaggccaagg gccagccccg ggaaccccag gtgtacacac tgccccctag cagggacgag    720

ctgaccaaga accaggtgtc cctgacctgt ctcgtgaaag gcttctaccc ctccgatatc    780

gccgtggaat gggagtccaa cggccagcct gagaacaact acaagaccac ccccctgtg    840

ctggactccg acggctcatt cttcctgtac agcaagctga cagtggacaa gtcccggtgg    900

cagcagggca acgtgttctc ctgctccgtg atgcacgagg ccctgcacaa ccactacacc    960

cagaagtccc tgtccctgag ccccggcaag tgatga                              996


<210> SEQ ID NO 342
<211> LENGTH: 450
<212> TYPE: PRT
<213> ORGANISM: Homo Sapiens

<400> SEQUENCE: 342

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Ile Arg Thr Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Gly Gly Trp Phe Asp Thr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Leu Ala Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
```

305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Arg Leu Thr Val Asp
405 410 415

Lys Ser Arg Trp Gln Glu Gly Asn Val Phe Ser Cys Ser Val Met His
420 425 430

Glu Ala Leu His Asn His Tyr Thr Gln Lys Ser Leu Ser Leu Ser Leu
435 440 445

Gly Lys
450

<210> SEQ ID NO 343
<211> LENGTH: 8
<212> TYPE: PRT
<213> ORGANISM: Homo Sapiens

<400> SEQUENCE: 343

Gly Phe Thr Phe Ser Asn Tyr Ala
1 5

<210> SEQ ID NO 344
<211> LENGTH: 8
<212> TYPE: PRT
<213> ORGANISM: Homo Sapiens

<400> SEQUENCE: 344

Ile Ser Phe Ser Gly Gly Thr Thr
1 5

<210> SEQ ID NO 345
<211> LENGTH: 14
<212> TYPE: PRT
<213> ORGANISM: Homo Sapiens

<400> SEQUENCE: 345

Ala Lys Asp Glu Ala Pro Ala Gly Ala Thr Phe Phe Asp Ser
1 5 10

<210> SEQ ID NO 346
<211> LENGTH: 5
<212> TYPE: PRT
<213> ORGANISM: Homo Sapiens

<400> SEQUENCE: 346

Asn Tyr Ala Met Ser
1 5

<210> SEQ ID NO 347
<211> LENGTH: 17
<212> TYPE: PRT
<213> ORGANISM: Homo Sapiens

<400> SEQUENCE: 347

Ala Ile Ser Phe Ser Gly Gly Thr Thr Tyr Tyr Ala Asp Ser Val Lys
1 5 10 15

Gly

<210> SEQ ID NO 348
<211> LENGTH: 12
<212> TYPE: PRT
<213> ORGANISM: Homo Sapiens

<400> SEQUENCE: 348

Asp Glu Ala Pro Ala Gly Ala Thr Phe Phe Asp Ser
1 5 10

<210> SEQ ID NO 349
<211> LENGTH: 121
<212> TYPE: PRT
<213> ORGANISM: Homo Sapiens

<400> SEQUENCE: 349

Glu Val Gln Leu Ala Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ser Trp Val Arg Gln Thr Pro Gly Lys Gly Leu Glu Trp Val
35 40 45

Ser Ala Ile Ser Phe Ser Gly Gly Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu His Met Asn Ser Leu Arg Ala Asp Asp Thr Ala Val Tyr Tyr Cys
85 90 95

Ala Lys Asp Glu Ala Pro Ala Gly Ala Thr Phe Phe Asp Ser Trp Gly
100 105 110

Gln Gly Thr Leu Val Thr Val Ser Ser
115 120

<210> SEQ ID NO 350
<211> LENGTH: 364
<212> TYPE: DNA
<213> ORGANISM: Homo Sapiens

<400> SEQUENCE: 350
gaagtgcaac tggcggagtc tgggggaggc ttggtacagc cggggggtc cctgagactc 60 tcctgtgcag cctctggatt cacctttagc aactatgcca tgagttgggt ccgccagact 120
ccaggaaagg ggctggagtg ggtctcagct attagtttta gtggtggtac tacatactac 180
gctgactccg tgaagggccg gttcaccatc tccagagaca attccaagaa cacgctgtat 240
ttgcacatga acagcctgag agccgatgac acggccgtat attactgtgc gaaagatgag 300
gcaccagctg gcgcaacctt ctttgactcc tggggccagg gaacgctggt caccgtctcc 360
tcag 364

<210> SEQ ID NO 351
<211> LENGTH: 448
<212> TYPE: PRT
<213> ORGANISM: Homo Sapiens

<400> SEQUENCE: 351

```
Glu Val Gln Leu Ala Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Gly Lys Gly Leu Glu Trp Val
        35                  40                  45

Ser Ala Ile Ser Phe Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu His Met Asn Ser Leu Arg Ala Asp Asp Thr Ala Val Tyr Tyr Cys
                85                  90                  95

Ala Lys Asp Glu Ala Pro Ala Gly Ala Thr Phe Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

```
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 352
<211> LENGTH: 1344
<212> TYPE: DNA
<213> ORGANISM: Homo Sapiens

<400> SEQUENCE: 352

gaagtgcaac tggcggagtc tgggggaggc ttggtacagc cggggggtc cctgagactc     60

tcctgtgcag cctctggatt cacctttagc aactatgcca tgagttgggt ccgccagact    120

ccaggaaagg ggctggagtg ggtctcagct attagtttta gtggtggtac tacatactac    180

gctgactccg tgaagggccg gttcaccatc tccagagaca attccaagaa cacgctgtat    240

ttgcacatga acagcctgag agccgatgac acggccgtat attactgtgc gaaagatgag    300

gcaccagctg gcgcaacctt ctttgactcc tggggccagg gaacgctggt caccgtctcc    360

tcagccagca ccaagggccc ttccgtgttc cccctggccc cttgcagcag gagcacctcc    420

gaatccacag ctgccctggg ctgtctggtg aaggactact tccccgagcc cgtgaccgtg    480

agctggaaca gcggcgctct gacatccggc gtccacacct ttcctgccgt cctgcagtcc    540

tccggcctct actccctgtc ctccgtggtg accgtgccta gctcctccct cggcaccaag    600

acctacacct gtaacgtgga ccacaaaccc tccaacacca aggtggacaa acgggtcgag    660

agcaagtacg gccctccctg ccctccttgt cctgcccccg agttcgaagg cggacccagc    720

gtgttcctgt tccctcctaa gcccaaggac accctcatga tcagccggac acccgaggtg    780

acctgcgtgg tggtggatgt gagccaggag gaccctgagg tccagttcaa ctggtatgtg    840

gatggcgtgg aggtgcacaa cgccaagaca aagccccggg aagagcagtt caactccacc    900

tacagggtgg tcagcgtgct gaccgtgctg catcaggact ggctgaacgg caaggagtac    960

aagtgcaagg tcagcaataa gggactgccc agcagcatcg agaagaccat ctccaaggct   1020

aaaggccagc ccgggaacc tcaggtgtac accctgcctc ccagccagga ggagatgacc   1080

aagaaccagg tgagcctgac ctgcctggtg aagggattct acccttccga catcgccgtg   1140

gagtgggagt ccaacggcca gcccgagaac aattataaga ccacccctcc cgtcctcgac   1200

agcgacggat ccttctttct gtactccagg ctgaccgtgg ataagtccag gtggcaggaa   1260

ggcaacgtgt tcagctgctc cgtgatgcac gaggccctgc acaatcacta cacccagaag   1320

tccctgagcc tgtccctggg aaag                                         1344


<210> SEQ ID NO 353
<211> LENGTH: 6
<212> TYPE: PRT
<213> ORGANISM: Homo Sapiens

<400> SEQUENCE: 353

Gln Gly Ile Arg Arg Trp
1               5


<210> SEQ ID NO 354
<211> LENGTH: 3
<212> TYPE: PRT
<213> ORGANISM: Homo Sapiens

<400> SEQUENCE: 354
```

```
Gly Ala Ser
1


<210> SEQ ID NO 355
<211> LENGTH: 9
<212> TYPE: PRT
<213> ORGANISM: Homo Sapiens

<400> SEQUENCE: 355

Gln Gln Ala Asn Ser Phe Pro Ile Thr
1               5


<210> SEQ ID NO 356
<211> LENGTH: 11
<212> TYPE: PRT
<213> ORGANISM: Homo Sapiens

<400> SEQUENCE: 356

Arg Ala Ser Gln Gly Ile Arg Arg Trp Leu Ala
1               5                   10


<210> SEQ ID NO 357
<211> LENGTH: 7
<212> TYPE: PRT
<213> ORGANISM: Homo Sapiens

<400> SEQUENCE: 357

Gly Ala Ser Ser Leu Gln Ser
1               5


<210> SEQ ID NO 358
<211> LENGTH: 9
<212> TYPE: PRT
<213> ORGANISM: Homo Sapiens

<400> SEQUENCE: 358

Gln Gln Ala Asn Ser Phe Pro Ile Thr
1               5


<210> SEQ ID NO 359
<211> LENGTH: 107
<212> TYPE: PRT
<213> ORGANISM: Homo Sapiens

<400> SEQUENCE: 359

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Arg Trp
            20                  25                  30

Leu Ala Trp Tyr Gln Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Ser Gly Ser Gly Thr Asp Phe Thr Leu Ile Ile Thr Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105


<210> SEQ ID NO 360
<211> LENGTH: 322
```

<212> TYPE: DNA
<213> ORGANISM: Homo Sapiens

<400> SEQUENCE: 360
gacatccaga tgacccagtc tccatcttcc gtgtctgcat ctgtaggaga cagagtcacc 60
atcacttgtc gggcgagtca gggtattagg aggtggttag cctggtatca gcagaaacca 120
gggaaagccc ctaaactcct gatctctggt gcatccagtt tgcaaagtgg ggtcccatca 180
aggttcagcg gcagtggatc tgggacagat ttcactctca tcattaccag tctgcagcct 240
gaagattttg caacttacta ttgtcaacag gctaacagtt tcccgatcac cttcggccaa 300
gggacacgac tggagatcaa ac 322

<210> SEQ ID NO 361
<211> LENGTH: 214
<212> TYPE: PRT
<213> ORGANISM: Homo Sapiens

<400> SEQUENCE: 361

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Arg Arg Trp
20 25 30

Leu Ala Trp Tyr Gln Gln Lys Pro Gly Lys Ala Pro Lys Leu Leu Ile
35 40 45

Ser Gly Ala Ser Ser Leu Gln Ser Gly Val Pro Ser Arg Phe Ser Gly
50 55 60

Ser Gly Ser Gly Thr Asp Phe Thr Leu Ile Ile Thr Ser Leu Gln Pro
65 70 75 80

Glu Asp Phe Ala Thr Tyr Tyr Cys Gln Gln Ala Asn Ser Phe Pro Ile
85 90 95

Thr Phe Gly Gln Gly Thr Arg Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 362
<211> LENGTH: 642
<212> TYPE: DNA
<213> ORGANISM: Homo Sapiens

<400> SEQUENCE: 362
gacatccaga tgacccagtc tccatcttcc gtgtctgcat ctgtaggaga cagagtcacc 60
atcacttgtc gggcgagtca gggtattagg aggtggttag cctggtatca gcagaaacca 120

```
gggaaagccc ctaaactcct gatctctggt gcatccagtt tgcaaagtgg ggtcccatca    180

aggttcagcg gcagtggatc tgggacagat ttcactctca tcattaccag tctgcagcct    240

gaagattttg caacttacta ttgtcaacag gctaacagtt tcccgatcac cttcggccaa    300

gggacacgac tggagatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642


<210> SEQ ID NO 363
<211> LENGTH: 8
<212> TYPE: PRT
<213> ORGANISM: Homo Sapiens

<400> SEQUENCE: 363

Gly Tyr Thr Phe Ser Thr Phe Gly
1               5


<210> SEQ ID NO 364
<211> LENGTH: 8
<212> TYPE: PRT
<213> ORGANISM: Homo Sapiens

<400> SEQUENCE: 364

Ile Ser Ala Tyr Asn Gly Asp Thr
1               5


<210> SEQ ID NO 365
<211> LENGTH: 14
<212> TYPE: PRT
<213> ORGANISM: Homo Sapiens

<400> SEQUENCE: 365

Ala Arg Ser Ser Gly His Tyr Tyr Tyr Tyr Gly Met Asp Val
1               5                   10


<210> SEQ ID NO 366
<211> LENGTH: 121
<212> TYPE: PRT
<213> ORGANISM: Homo Sapiens

<400> SEQUENCE: 366

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Phe
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Asp Thr Asn Tyr Ala Gln Asn Leu
    50                  55                  60

Gln Gly Arg Val Ile Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ser Gly His Tyr Tyr Tyr Tyr Gly Met Asp Val Trp Gly
            100                 105                 110
```

Gln Gly Thr Thr Val Thr Val Ser Ser
        115                 120

<210> SEQ ID NO 367
<211> LENGTH: 363
<212> TYPE: DNA
<213> ORGANISM: Homo Sapiens

<400> SEQUENCE: 367
caggttcagg tggtgcagtc tggagctgag gtgaagaagc ctggggcctc agtgaaggtc 60
tcctgcaagg cttctggtta caccttttcc acctttggta tcacctgggt gcgacaggcc 120
cctggacaag ggcttgaatg gatgggatgg atcagcgctt acaatggtga cacaaactat 180
gcacagaatc tccagggcag agtcatcatg accacagaca catccacgag cacagcctac 240
atggagctga ggagcctgag atctgacgac acggccgttt attactgtgc gaggagcagt 300
ggccactact actactacgg tatggacgtc tggggccaag ggaccacggt caccgtctcc 360
tca 363

<210> SEQ ID NO 368
<211> LENGTH: 451
<212> TYPE: PRT
<213> ORGANISM: Homo Sapiens

<400> SEQUENCE: 368

Gln Val Gln Val Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Phe
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Asp Thr Asn Tyr Ala Gln Asn Leu
    50                  55                  60

Gln Gly Arg Val Ile Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ser Gly His Tyr Tyr Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

-continued

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 369
<211> LENGTH: 1359
<212> TYPE: DNA
<213> ORGANISM: Homo Sapiens

<400> SEQUENCE: 369

caggttcagg tggtgcagtc tggagctgag gtgaagaagc ctggggcctc agtgaaggtc      60

tcctgcaagg cttctggtta caccttttcc acctttggta tcacctgggt gcgacaggcc     120

cctggacaag ggcttgaatg gatgggatgg atcagcgctt acaatggtga cacaaactat     180

gcacagaatc tccagggcag agtcatcatg accacagaca catccacgag cacagcctac     240

atggagctga ggagcctgag atctgacgac acggccgttt attactgtgc gaggagcagt     300

ggccactact actactacgg tatggacgtc tggggccaag ggaccacggt caccgtctcc     360

tcagccagca ccaagggccc ctctgtgttc cctctggccc cttccagcaa gtccacctct     420

ggcggaacag ccgctctggg ctgcctcgtg aaggactact tccccgagcc tgtgaccgtg     480

tcctggaact ctggcgctct gaccagcgga gtgcacacct tccctgctgt gctgcagtcc     540

tccggcctgt actccctgtc ctccgtcgtg accgtgcctt ccagctctct gggcacccag     600

acctacatct gcaacgtgaa ccacaagccc tccaacacca aggtggacaa gaaggtggaa     660

cccaagtcct gcgacaagac ccacacctgt ccccccttgtc ctgcccctga actgctgggc     720

ggaccttccg tgttcctgtt ccccccaaag cccaaggaca ccctgatgat ctcccggacc     780

cccgaagtga cctgcgtggt ggtggatgtg tcccacgagg accctgaagt gaagttcaat     840

tggtacgtgg acggcgtgga agtgcacaac gccaagacca agcctagaga ggaacagtac     900
```

aactccacct accgggtggt gtccgtgctg accgtgctgc accaggattg gctgaacggc 960
aaagagtaca agtgcaaggt gtccaacaag gccctgcctg cccccatcga aaagaccatc 1020
tccaaggcca agggccagcc ccgggaaccc caggtgtaca cactgccccc tagcagggac 1080
gagctgacca agaaccaggt gtccctgacc tgtctcgtga aaggcttcta cccctccgat 1140
atcgccgtgg aatgggagtc caacggccag cctgagaaca actacaagac cacccccccct 1200 gtgctggact ccgacggctc attcttcctg tacagcaagc tgacagtgga caagtcccgg 1260
tggcagcagg gcaacgtgtt ctcctgctcc gtgatgcacg aggccctgca caaccactac 1320
acccagaagt ccctgtccct gagccccggc aagtgatga 1359

<210> SEQ ID NO 370
<211> LENGTH: 11
<212> TYPE: PRT
<213> ORGANISM: Homo Sapiens

<400> SEQUENCE: 370

Gln Ser Leu Leu His Ser Asn Glu Tyr Asn Tyr
1 5 10

<210> SEQ ID NO 371
<211> LENGTH: 3
<212> TYPE: PRT
<213> ORGANISM: Homo Sapiens

<400> SEQUENCE: 371

Leu Gly Ser
1

<210> SEQ ID NO 372
<211> LENGTH: 9
<212> TYPE: PRT
<213> ORGANISM: Homo Sapiens

<400> SEQUENCE: 372

Met Gln Ser Leu Gln Thr Pro Leu Thr
1 5

<210> SEQ ID NO 373
<211> LENGTH: 112
<212> TYPE: PRT
<213> ORGANISM: Homo Sapiens

<400> SEQUENCE: 373

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Glu Tyr Asn Tyr Leu Asp Trp Tyr Leu Gln Lys Pro Gly Gln Ser
35 40 45

Pro Gln Leu Leu Ile Phe Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Thr Arg Val Glu Ala Glu Asp Val Gly Ile Tyr Tyr Cys Met Gln Ser
85 90 95

Leu Gln Thr Pro Leu Thr Phe Gly Gly Gly Thr Lys Val Glu Ile Lys
100 105 110

<210> SEQ ID NO 374
<211> LENGTH: 336
<212> TYPE: DNA
<213> ORGANISM: Homo Sapiens

<400> SEQUENCE: 374

```
gatattgtga tgactcagtc tccactctcc ctgcccgtca cccctggaga gccggcctcc      60
atctcctgca ggtctagtca gagcctcctg catagtaatg aatacaacta tttggattgg     120
tacctgcaga agccagggca gtctccacag ctcctgatct ttttgggttc taatcgggcc     180
tccggggtcc ctgacaggtt cagtggcagt ggatcaggca cagattttac actgaaaatc     240
accagagtgg aggctgagga tgttggaatt tattactgca tgcaatctct acaaactccg     300
ctcactttcg gcggagggac caaggtggag atcaaa                               336
```

<210> SEQ ID NO 375
<211> LENGTH: 219
<212> TYPE: PRT
<213> ORGANISM: Homo Sapiens

<400> SEQUENCE: 375

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Glu Tyr Asn Tyr Leu Asp Trp Tyr Leu Gln Lys Pro Gly Gln Ser
        35                  40                  45

Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Ile Tyr Tyr Cys Met Gln Ser
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 376
<211> LENGTH: 657
<212> TYPE: DNA
<213> ORGANISM: Homo Sapiens

<400> SEQUENCE: 376

```
gatattgtga tgactcagtc tccactctcc ctgcccgtca cccctggaga gccggcctcc      60
```

-continued atctcctgca ggtctagtca gagcctcctg catagtaatg aatacaacta tttggattgg 120
tacctgcaga agccagggca gtctccacag ctcctgatct tttgggttc taatcgggcc 180 tccggggtcc ctgacaggtt cagtggcagt ggatcaggca cagattttac actgaaaatc 240
accagagtgg aggctgagga tgttggaatt tattactgca tgcaatctct acaaactccg 300
ctcactttcg gcggagggac caaggtggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 377
<211> LENGTH: 8
<212> TYPE: PRT
<213> ORGANISM: Homo Sapiens

<400> SEQUENCE: 377

Gly Tyr Thr Phe Thr Ser Tyr Gly
1 5

<210> SEQ ID NO 378
<211> LENGTH: 8
<212> TYPE: PRT
<213> ORGANISM: Homo Sapiens

<400> SEQUENCE: 378

Ile Ser Ala Tyr Asn Gly Asn Thr
1 5

<210> SEQ ID NO 379
<211> LENGTH: 17
<212> TYPE: PRT
<213> ORGANISM: Homo Sapiens

<400> SEQUENCE: 379

Ala Arg Ser Thr Tyr Phe Tyr Gly Ser Gly Thr Leu Tyr Gly Met Asp
1 5 10 15

Val

<210> SEQ ID NO 380
<211> LENGTH: 124
<212> TYPE: PRT
<213> ORGANISM: Homo Sapiens

<400> SEQUENCE: 380

Gln Val Gln Leu Val Gln Ser Gly Gly Glu Val Lys Lys Pro Gly Ala
1 5 10 15

Ser Val Lys Val Ser Cys Lys Ala Ser Gly Tyr Thr Phe Thr Ser Tyr
20 25 30

Gly Phe Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

-continued

```
Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
            100                 105                 110

Val Trp Gly Gln Gly Thr Thr Val Thr Val Ser Ser
        115                 120
```

<210> SEQ ID NO 381
<211> LENGTH: 372
<212> TYPE: DNA
<213> ORGANISM: Homo Sapiens

<400> SEQUENCE: 381

```
caggttcaac tggtgcagtc tggaggtgag gtgaagaagc ctggggcctc agtgaaggtc     60

tcctgcaagg cttctggtta cacctttacc agctatggtt tcagctgggt gcgacaggcc    120

cctggacaag gactagagtg gatgggatgg atcagcgctt acaatggtaa cacaaactat    180

gcacagaagc tccagggcag agtcaccatg accacagaca catccacgag cacagcctac    240

atggagctga ggagcttgag atctgacgac acggccgtgt attactgtgc gagatctacg    300

tatttctatg gttcggggac cctctacggt atggacgtct ggggccaagg gaccacggtc    360

accgtctcct ca                                                          372
```

<210> SEQ ID NO 382
<211> LENGTH: 454
<212> TYPE: PRT
<213> ORGANISM: Homo Sapiens

<400> SEQUENCE: 382

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
```

```
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 383
<211> LENGTH: 1368
<212> TYPE: DNA
<213> ORGANISM: Homo Sapiens

<400> SEQUENCE: 383

```
caggttcaac tggtgcagtc tggaggtgag gtgaagaagc ctggggcctc agtgaaggtc     60

tcctgcaagg cttctggtta cacctttacc agctatggtt tcagctgggt gcgacaggcc    120

cctggacaag gactagagtg gatgggatgg atcagcgctt acaatggtaa cacaaactat    180

gcacagaagc tccagggcag agtcaccatg accacagaca catccacgag cacagcctac    240

atggagctga ggagcttgag atctgacgac acggccgtgt attactgtgc gagatctacg    300

tatttctatg gttcggggac cctctacggt atggacgtct ggggccaagg gaccacggtc    360

accgtctcct cagccagcac caagggcccc tctgtgttcc ctctggcccc ttccagcaag    420

tccacctctg gcggaacagc cgctctgggc tgcctcgtga aggactactt ccccgagcct    480

gtgaccgtgt cctggaactc tggcgctctg accagcggag tgcacacctt ccctgctgtg    540

ctgcagtcct ccggcctgta ctccctgtcc tccgtcgtga ccgtgccttc cagctctctg    600

ggcacccaga cctacatctg caacgtgaac cacaagccct ccaacaccaa ggtggacaag    660

aaggtggaac ccaagtcctg cgacaagacc cacacctgtc cccccttgtcc tgcccctgaa    720
```

-continued

```
ctgctgggcg gaccttccgt gttcctgttc cccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020

aagaccatct ccaaggccaa gggccagccc cgggaacccc aggtgtacac actgccccct   1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

acccccccctg tgctggactc cgacggctca ttcttcctgt acagcaagct gacagtggac   1260

aagtcccggt ggcagcaggg caacgtgttc tcctgctccg tgatgcacga ggccctgcac   1320

aaccactaca cccagaagtc cctgtccctg agccccggca agtgatga                1368


<210> SEQ ID NO 384
<211> LENGTH: 11
<212> TYPE: PRT
<213> ORGANISM: Homo Sapiens

<400> SEQUENCE: 384

Gln Ser Leu Leu His Ser Asp Gly Tyr Asn Tyr
1               5                   10


<210> SEQ ID NO 385
<211> LENGTH: 3
<212> TYPE: PRT
<213> ORGANISM: Homo Sapiens

<400> SEQUENCE: 385

Leu Gly Ser
1


<210> SEQ ID NO 386
<211> LENGTH: 9
<212> TYPE: PRT
<213> ORGANISM: Homo Sapiens

<400> SEQUENCE: 386

Met Gln Ala Leu Gln Thr Pro Leu Ser
1               5


<210> SEQ ID NO 387
<211> LENGTH: 112
<212> TYPE: PRT
<213> ORGANISM: Homo Sapiens

<400> SEQUENCE: 387

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

```
                85                  90                  95

Leu Gln Thr Pro Leu Ser Phe Gly Gln Gly Thr Lys Leu Glu Ile Lys
            100                 105                 110


<210> SEQ ID NO 388
<211> LENGTH: 336
<212> TYPE: DNA
<213> ORGANISM: Homo Sapiens

<400> SEQUENCE: 388

gatattgtga tgactcagtc tccactctcc ctgcccgtca cccctggaga gccggcctcc      60

atctcctgca ggtctagtca gagcctcctg catagtgatg gatacaactg tttggattgg     120

tacctgcaga agccagggca gtctccacag ctcctgatct atttgggttc tactcgggcc     180

tccgggttcc ctgacaggtt cagtggcagt ggatcaggca cagattttac actgaaaatc     240

agcagagtgg aggctgagga tgttggggtt tattactgca tgcaagctct acaaactccg     300

tgcagttttg gccaggggac caagctggag atcaaa                               336


<210> SEQ ID NO 389
<211> LENGTH: 219
<212> TYPE: PRT
<213> ORGANISM: Homo Sapiens

<400> SEQUENCE: 389

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 390
<211> LENGTH: 657
<212> TYPE: DNA
```

<213> ORGANISM: Homo Sapiens

<400> SEQUENCE: 390
gatattgtga tgactcagtc tccactctcc ctgcccgtca cccctggaga gccggcctcc 60
atctcctgca ggtctagtca gagcctcctg catagtgatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
tgcagttttg gccaggggac caagctggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 391
<211> LENGTH: 8
<212> TYPE: PRT
<213> ORGANISM: Homo Sapiens

<400> SEQUENCE: 391

Gly Tyr Thr Phe Thr Ser Tyr Gly
1 5

<210> SEQ ID NO 392
<211> LENGTH: 8
<212> TYPE: PRT
<213> ORGANISM: Homo Sapiens

<400> SEQUENCE: 392

Ile Ser Ala Tyr Asn Gly Asn Thr
1 5

<210> SEQ ID NO 393
<211> LENGTH: 17
<212> TYPE: PRT
<213> ORGANISM: Homo Sapiens

<400> SEQUENCE: 393

Ala Arg Ser Thr Tyr Phe Tyr Gly Ser Gly Thr Leu Tyr Gly Met Asp
1 5 10 15

Val

<210> SEQ ID NO 394
<211> LENGTH: 124
<212> TYPE: PRT
<213> ORGANISM: Homo Sapiens

<400> SEQUENCE: 394

Gln Val Gln Leu Val Gln Ser Gly Gly Glu Val Lys Lys Pro Gly Ala
1 5 10 15

Ser Val Lys Val Ser Cys Lys Ala Ser Gly Tyr Thr Phe Thr Ser Tyr
20 25 30

Gly Phe Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu

```
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
            100                 105                 110

Val Trp Gly Gln Gly Thr Thr Val Thr Val Ser Ser
        115                 120


<210> SEQ ID NO 395
<211> LENGTH: 372
<212> TYPE: DNA
<213> ORGANISM: Homo Sapiens

<400> SEQUENCE: 395

caggttcaac tggtgcagtc tggaggtgag gtgaagaagc ctggggcctc agtgaaggtc     60

tcctgcaagg cttctggtta cacctttacc agctatggtt tcagctgggt gcgacaggcc    120

cctggacaag gactagagtg gatgggatgg atcagcgctt acaatggtaa cacaaactat    180

gcacagaagc tccagggcag agtcaccatg accacagaca catccacgag cacagcctac    240

atggagctga ggagcttgag atctgacgac acggccgtgt attactgtgc gagatctacg    300

tatttctatg gttcggggac cctctacggt atggacgtct ggggccaagg gaccacggtc    360

accgtctcct ca                                                        372


<210> SEQ ID NO 396
<211> LENGTH: 454
<212> TYPE: PRT
<213> ORGANISM: Homo Sapiens

<400> SEQUENCE: 396

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Tyr Phe Tyr Gly Ser Gly Thr Leu Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 397
<211> LENGTH: 1368
<212> TYPE: DNA
<213> ORGANISM: Homo Sapiens

<400> SEQUENCE: 397
caggttcaac tggtgcagtc tggaggtgag gtgaagaagc ctggggcctc agtgaaggtc 60
tcctgcaagg cttctggtta cacctttacc agctatggtt tcagctgggt gcgacaggcc 120
cctggacaag gactagagtg gatgggatgg atcagcgctt acaatggtaa cacaaactat 180
gcacagaagc tccagggcag agtcaccatg accacagaca catccacgag cacagcctac 240
atggagctga ggagcttgag atctgacgac acggccgtgt attactgtgc gagatctacg 300
tatttctatg gttcggggac cctctacggt atggacgtct ggggccaagg gaccacggtc 360
accgtctcct cagccagcac caagggcccc tctgtgttcc ctctggcccc ttccagcaag 420
tccacctctg gcggaacagc cgctctgggc tgcctcgtga aggactactt ccccgagcct 480
gtgaccgtgt cctggaactc tggcgctctg accagcggag tgcacacctt ccctgctgtg 540
ctgcagtcct ccggcctgta ctccctgtcc tccgtcgtga ccgtgccttc cagctctctg 600

```
ggcacccaga cctacatctg caacgtgaac cacaagccct ccaacaccaa ggtggacaag    660

aaggtggaac ccaagtcctg cgacaagacc cacacctgtc cccccttgtcc tgcccctgaa    720

ctgctgggcg gaccttccgt gttcctgttc cccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020

aagaccatct ccaaggccaa gggccagccc cgggaacccc aggtgtacac actgcccccct   1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

acccccccctg tgctggactc cgacggctca ttcttcctgt acagcaagct gacagtggac   1260

aagtcccggt ggcagcaggg caacgtgttc tcctgctccg tgatgcacga ggccctgcac   1320

aaccactaca cccagaagtc cctgtccctg agccccggca agtgatga                1368
```

<210> SEQ ID NO 398
<211> LENGTH: 11
<212> TYPE: PRT
<213> ORGANISM: Homo Sapiens

<400> SEQUENCE: 398

```
Gln Ser Leu Leu His Ser Asp Gly Tyr Asn Cys
1               5                   10
```

<210> SEQ ID NO 399
<211> LENGTH: 3
<212> TYPE: PRT
<213> ORGANISM: Homo Sapiens

<400> SEQUENCE: 399

```
Leu Gly Ser
1
```

<210> SEQ ID NO 400
<211> LENGTH: 9
<212> TYPE: PRT
<213> ORGANISM: Homo Sapiens

<400> SEQUENCE: 400

```
Met Gln Ala Leu Gln Thr Pro Cys Ser
1               5
```

<210> SEQ ID NO 401
<211> LENGTH: 112
<212> TYPE: PRT
<213> ORGANISM: Homo Sapiens

<400> SEQUENCE: 401

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Cys Leu Asp Trp Tyr Leu Gln Lys Pro Gly Gln Ser
        35                  40                  45

Pro Gln Leu Leu Ile Tyr Leu Gly Ser Thr Arg Ala Ser Gly Phe Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110


<210> SEQ ID NO 402
<211> LENGTH: 336
<212> TYPE: DNA
<213> ORGANISM: Homo Sapiens

<400> SEQUENCE: 402

gatattgtga tgactcagtc tccactctcc ctgcccgtca cccctggaga gccggcctcc      60

atctcctgca ggtctagtca gagcctcctg catagtgatg gatacaactg tttggattgg     120

tacctgcaga agccagggca gtctccacag ctcctgatct atttgggttc tactcgggcc     180

tccgggttcc ctgacaggtt cagtggcagt ggatcaggca cagattttac actgaaaatc     240

agcagagtgg aggctgagga tgttggggtt tattactgca tgcaagctct acaaactccg     300

tgcagttttg gccaggggac caagctggag atcaaa                               336


<210> SEQ ID NO 403
<211> LENGTH: 219
<212> TYPE: PRT
<213> ORGANISM: Homo Sapiens

<400> SEQUENCE: 403

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Cys Leu Asp Trp Tyr Leu Gln Lys Pro Gly Gln Ser
        35                  40                  45

Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 404
<211> LENGTH: 657
<212> TYPE: DNA
<213> ORGANISM: Homo Sapiens

<400> SEQUENCE: 404
gatattgtga tgactcagtc tccactctcc ctgcccgtca cccctggaga gccggcctcc 60
atctcctgca ggtctagtca gagcctcctg catagtgatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
tgcagttttg gccaggggac caagctggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 405
<211> LENGTH: 8
<212> TYPE: PRT
<213> ORGANISM: Homo Sapiens

<400> SEQUENCE: 405

Gly Val Thr Phe Asp Asp Tyr Gly
1 5

<210> SEQ ID NO 406
<211> LENGTH: 8
<212> TYPE: PRT
<213> ORGANISM: Homo Sapiens

<400> SEQUENCE: 406

Ile Asn Trp Asn Gly Gly Asp Thr
1 5

<210> SEQ ID NO 407
<211> LENGTH: 17
<212> TYPE: PRT
<213> ORGANISM: Homo Sapiens

<400> SEQUENCE: 407

Ala Arg Asp Phe Tyr Gly Ser Gly Ser Tyr Tyr His Val Pro Phe Asp
1 5 10 15

Tyr

<210> SEQ ID NO 408
<211> LENGTH: 124
<212> TYPE: PRT
<213> ORGANISM: Homo Sapiens

<400> SEQUENCE: 408

Glu Val Gln Leu Val Glu Ser Gly Gly Gly Val Val Arg Pro Gly Gly
1 5 10 15

Ser Leu Arg Leu Ser Cys Val Ala Ser Gly Val Thr Phe Asp Asp Tyr
20 25 30

```
Gly Met Ser Trp Val Arg Gln Ala Pro Gly Lys Gly Leu Glu Trp Val
        35                  40                  45

Ser Gly Ile Asn Trp Asn Gly Gly Asp Thr Asp Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Phe Tyr Gly Ser Gly Ser Tyr Tyr His Val Pro Phe Asp
            100                 105                 110

Tyr Trp Gly Gln Gly Ile Leu Val Thr Val Ser Ser
            115                 120
```

<210> SEQ ID NO 409
<211> LENGTH: 372
<212> TYPE: DNA
<213> ORGANISM: Homo Sapiens

<400> SEQUENCE: 409

```
gaggtgcagc tggtggagtc tgggggaggt gtggtacggc ctggggggtc cctgagactc    60
tcctgtgtag cctctggagt caccttttgat gattatggca tgagctgggt ccgccaagct   120
ccagggaagg ggctggartg ggtctctggt attaattgga atggtggcga cacagattat   180
tcagactctg tgaagggccg attcaccatc tccagagaca acgccaagaa ctccctgtat   240
ctacaaatga atagtctgag agccgaggac acggccttgt attactgtgc gagggatttc   300
tatggttcgg ggagttatta tcacgttcct tttgactact ggggccaggg aatcctggtc   360
accgtctcct ca                                                        372
```

<210> SEQ ID NO 410
<211> LENGTH: 454
<212> TYPE: PRT
<213> ORGANISM: Homo Sapiens

<400> SEQUENCE: 410

```
Glu Val Gln Leu Val Glu Ser Gly Gly Gly Val Val Arg Pro Gly Gly
1               5                   10                  15

Ser Leu Arg Leu Ser Cys Val Ala Ser Gly Val Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Asp Thr Asp Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Phe Tyr Gly Ser Gly Ser Tyr Tyr His Val Pro Phe Asp
            100                 105                 110

Tyr Trp Gly Gln Gly Ile Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160
```

-continued

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Asp Glu Leu Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly Lys
450

<210> SEQ ID NO 411
<211> LENGTH: 1368
<212> TYPE: DNA
<213> ORGANISM: Homo Sapiens

<400> SEQUENCE: 411
gaggtgcagc tggtggagtc tgggggaggt gtggtacggc ctggggggtc cctgagactc 60
tcctgtgtag cctctggagt cacctttgat gattatggca tgagctgggt ccgccaagct 120
ccagggaagg ggctggartg ggtctctggt attaattgga atggtggcga cacagattat 180
tcagactctg tgaagggccg attcaccatc tccagagaca acgccaagaa ctccctgtat 240
ctacaaatga atagtctgag agccgaggac acggccttgt attactgtgc gagggatttc 300
tatggttcgg ggagttatta tcacgttcct tttgactact ggggccaggg aatcctggtc 360
accgtctcct cagccagcac caagggcccc tctgtgttcc ctctggcccc ttccagcaag 420

```
tccacctctg gcggaacagc cgctctgggc tgcctcgtga aggactactt ccccgagcct    480

gtgaccgtgt cctggaactc tggcgctctg accagcggag tgcacacctt ccctgctgtg    540

ctgcagtcct ccggcctgta ctccctgtcc tccgtcgtga ccgtgccttc cagctctctg    600

ggcacccaga cctacatctg caacgtgaac cacaagccct ccaacaccaa ggtggacaag    660

aaggtggaac ccaagtcctg cgacaagacc cacacctgtc cccccttgtcc tgcccctgaa    720

ctgctgggcg gaccttccgt gttcctgttc cccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020

aagaccatct ccaaggccaa gggccagccc cgggaacccc aggtgtacac actgcccccct   1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

acccccccctg tgctggactc cgacggctca ttcttcctgt acagcaagct gacagtggac   1260

aagtcccggt ggcagcaggg caacgtgttc tcctgctccg tgatgcacga ggccctgcac   1320

aaccactaca cccagaagtc cctgtccctg agccccggca agtgatga                 1368
```

<210> SEQ ID NO 412
<211> LENGTH: 7
<212> TYPE: PRT
<213> ORGANISM: Homo Sapiens

<400> SEQUENCE: 412

```
Gln Ser Val Ser Arg Ser Tyr
1               5
```

<210> SEQ ID NO 413
<211> LENGTH: 3
<212> TYPE: PRT
<213> ORGANISM: Homo Sapiens

<400> SEQUENCE: 413

```
Gly Ala Ser
1
```

<210> SEQ ID NO 414
<211> LENGTH: 9
<212> TYPE: PRT
<213> ORGANISM: Homo Sapiens

<400> SEQUENCE: 414

```
His Gln Tyr Asp Met Ser Pro Phe Thr
1               5
```

<210> SEQ ID NO 415
<211> LENGTH: 108
<212> TYPE: PRT
<213> ORGANISM: Homo Sapiens

<400> SEQUENCE: 415

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30
```

```
Tyr Leu Ala Trp Tyr Gln Gln Lys Arg Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asp Gly Ser Gly Thr Asp Phe Thr Leu Ser Ile Ser Arg Leu Glu
65                  70                  75                  80

Pro Glu Asp Phe Ala Val Tyr Tyr Cys His Gln Tyr Asp Met Ser Pro
                85                  90                  95

Phe Thr Phe Gly Pro Gly Thr Lys Val Asp Ile Lys
            100                 105


<210> SEQ ID NO 416
<211> LENGTH: 324
<212> TYPE: DNA
<213> ORGANISM: Homo Sapiens

<400> SEQUENCE: 416

gaaattgtgt tgacgcagtc tccagggacc ctgtctttgt ctccagggga aagagccacc      60

ctctcctgca gggccagtca gagtgttagc agaagctact tagcctggta ccagcagaaa     120

cgtggccagg ctcccaggct cctcatctat ggtgcatcca gcagggccac tggcatccca     180

gacaggttca gtggcgatgg gtctgggaca gacttcactc tctccatcag cagactggag     240

cctgaagatt ttgcagtgta ttactgtcac cagtatgata tgtcaccatt cactttcggc     300

cctgggacca aagtggatat caaa                                            324


<210> SEQ ID NO 417
<211> LENGTH: 215
<212> TYPE: PRT
<213> ORGANISM: Homo Sapiens

<400> SEQUENCE: 417

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Arg Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Asp Gly Ser Gly Thr Asp Phe Thr Leu Ser Ile Ser Arg Leu Glu
65                  70                  75                  80

Pro Glu Asp Phe Ala Val Tyr Tyr Cys His Gln Tyr Asp Met Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 418
<211> LENGTH: 645
<212> TYPE: DNA
<213> ORGANISM: Homo Sapiens

<400> SEQUENCE: 418
gaaattgtgt tgacgcagtc tccagggacc ctgtctttgt ctccagggga aagagccacc 60
ctctcctgca gggccagtca gagtgttagc agaagctact tagcctggta ccagcagaaa 120
cgtggccagg ctcccaggct cctcatctat ggtgcatcca gcagggccac tggcatccca 180
gacaggttca gtggcgatgg gtctgggaca gacttcactc tctccatcag cagactggag 240
cctgaagatt ttgcagtgta ttactgtcac cagtatgata tgtcaccatt cactttcggc 300
cctgggacca aagtggatat caaacgtacg gtggccgctc cctccgtgtt catcttccca 360
ccttccgacg agcagctgaa gtccggcacc gcttctgtcg tgtgcctgct gaacaacttc 420
tacccccgcg aggccaaggt gcagtggaag gtggacaacg ccctgcagtc cggcaactcc 480
caggaatccg tgaccgagca ggactccaag gacagcacct actccctgtc ctccaccctg 540
accctgtcca aggccgacta cgagaagcac aaggtgtacg cctgcgaagt gacccaccag 600
ggcctgtcta gccccgtgac caagtctttc aaccggggcg agtgt 645

<210> SEQ ID NO 419
<211> LENGTH: 8
<212> TYPE: PRT
<213> ORGANISM: Homo Sapiens

<400> SEQUENCE: 419

Gly Leu Thr Phe Asp Asp Tyr Gly
1               5

<210> SEQ ID NO 420
<211> LENGTH: 8
<212> TYPE: PRT
<213> ORGANISM: Homo Sapiens

<400> SEQUENCE: 420

Ile Asn Trp Asn Gly Asp Asn Thr
1               5

<210> SEQ ID NO 421
<211> LENGTH: 17
<212> TYPE: PRT
<213> ORGANISM: Homo Sapiens

<400> SEQUENCE: 421

Ala Arg Asp Tyr Tyr Gly Ser Gly Ser Tyr Tyr Asn Val Pro Phe Asp
1               5                   10                  15

Tyr

<210> SEQ ID NO 422
<211> LENGTH: 124
<212> TYPE: PRT
<213> ORGANISM: Homo Sapiens

<400> SEQUENCE: 422

```
Glu Val Gln Leu Val Glu Ser Gly Gly Gly Val Val Arg Pro Gly Gly
1               5                   10                  15

Ser Leu Arg Leu Ser Cys Ala Ala Ser Gly Leu Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Asn Trp Asn Gly Asp Asn Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Tyr Tyr Gly Ser Gly Ser Tyr Tyr Asn Val Pro Phe Asp
            100                 105                 110

Tyr Trp Gly Gln Gly Thr Leu Val Thr Val Ser Ser
        115                 120


<210> SEQ ID NO 423
<211> LENGTH: 372
<212> TYPE: DNA
<213> ORGANISM: Homo Sapiens

<400> SEQUENCE: 423

gaggtgcagc tggtggagtc tgggggaggt gtggtacggc ctggggggtc cctgagactc      60

tcctgtgcag cctctggact cacctttgat gattatggca tgagctgggt ccgccaagtt     120

ccagggaagg ggctggagtg ggtctctggt attaattgga atggtgataa cacagattat     180

gcagactctg tgaagggccg attcaccatc tccagagaca acgccaagaa ctccctgtat     240

ctgcaaatga acagtctgag agccgaggac acggccttgt attactgtgc gagggattac     300

tatggttcgg ggagttatta taacgttcct tttgactact ggggccaggg aaccctggtc     360

accgtctcct ca                                                         372


<210> SEQ ID NO 424
<211> LENGTH: 454
<212> TYPE: PRT
<213> ORGANISM: Homo Sapiens

<400> SEQUENCE: 424

Glu Val Gln Leu Val Glu Ser Gly Gly Gly Val Val Arg Pro Gly Gly
1               5                   10                  15

Ser Leu Arg Leu Ser Cys Ala Ala Ser Gly Leu Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Asn Trp Asn Gly Asp Asn Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Tyr Tyr Gly Ser Gly Ser Tyr Tyr Asn Val Pro Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
```

130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Asp Glu Leu Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly Lys
450

<210> SEQ ID NO 425
<211> LENGTH: 1368
<212> TYPE: DNA
<213> ORGANISM: Homo Sapiens

<400> SEQUENCE: 425
gaggtgcagc tggtggagtc tgggggaggt gtggtacggc ctgggggtc cctgagactc 60 tcctgtgcag cctctggact cacctttgat gattatggca tgagctgggt ccgccaagtt 120
ccagggaagg ggctggagtg ggtctctggt attaattgga atggtgataa cacagattat 180
gcagactctg tgaagggccg attcaccatc tccagagaca acgccaagaa ctccctgtat 240
ctgcaaatga acagtctgag agccgaggac acggccttgt attactgtgc gagggattac 300

-continued

```
tatggttcgg ggagttatta taacgttcct tttgactact ggggccaggg aaccctggtc    360

accgtctcct cagccagcac caagggcccc tctgtgttcc ctctggcccc ttccagcaag    420

tccacctctg gcggaacagc cgctctgggc tgcctcgtga aggactactt ccccgagcct    480

gtgaccgtgt cctggaactc tggcgctctg accagcggag tgcacacctt ccctgctgtg    540

ctgcagtcct ccggcctgta ctccctgtcc tccgtcgtga ccgtgccttc cagctctctg    600

ggcacccaga cctacatctg caacgtgaac cacaagccct ccaacaccaa ggtggacaag    660

aaggtggaac ccaagtcctg cgacaagacc cacacctgtc cccccttgtcc tgcccctgaa   720

ctgctgggcg gaccttccgt gttcctgttc cccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020

aagaccatct ccaaggccaa gggccagccc cgggaacccc aggtgtacac actgcccccct  1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

acccccccctg tgctggactc cgacggctca ttcttcctgt acagcaagct gacagtggac  1260

aagtcccggt ggcagcaggg caacgtgttc tcctgctccg tgatgcacga ggccctgcac   1320

aaccactaca cccagaagtc cctgtccctg agccccggca agtgatga                1368
```

<210> SEQ ID NO 426
<211> LENGTH: 7
<212> TYPE: PRT
<213> ORGANISM: Homo Sapiens

<400> SEQUENCE: 426

```
Gln Ser Val Ser Ser Ser Tyr
1               5
```

<210> SEQ ID NO 427
<211> LENGTH: 3
<212> TYPE: PRT
<213> ORGANISM: Homo Sapiens

<400> SEQUENCE: 427

```
Gly Ala Ser
1
```

<210> SEQ ID NO 428
<211> LENGTH: 8
<212> TYPE: PRT
<213> ORGANISM: Homo Sapiens

<400> SEQUENCE: 428

```
Gln Gln Tyr Gly Ser Ser Pro Phe
1               5
```

<210> SEQ ID NO 429
<211> LENGTH: 107
<212> TYPE: PRT
<213> ORGANISM: Homo Sapiens

<400> SEQUENCE: 429

```
Glu Ile Val Leu Thr Gln Ser Pro Gly Thr Leu Ser Leu Ser Pro Gly
```

```
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Ser Ser Pro
                85                  90                  95

Phe Phe Gly Pro Gly Thr Lys Val Asp Ile Lys
            100                 105


<210> SEQ ID NO 430
<211> LENGTH: 321
<212> TYPE: DNA
<213> ORGANISM: Homo Sapiens

<400> SEQUENCE: 430

gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatatat ggtgcatcca gcagggccac tggcatccca    180

gacaggttca gtggcagtgg gtctgggaca gacttcactc tcaccatcag aagactggag    240

cctgaagatt ttgcagtgta ttactgtcag cagtatggta gttcaccatt cttcggccct    300

gggaccaaag tggatatcaa a                                              321


<210> SEQ ID NO 431
<211> LENGTH: 323
<212> TYPE: DNA
<213> ORGANISM: Homo Sapiens

<400> SEQUENCE: 431

gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatatat ggtgcatcca gcagggccac tggcatccca    180

gacaggttca gtggcagtgg gtctgggaca gacttcactc tcaccatcag aagactggag    240

cctgaagatt ttgcagtgta ttactgtcag cagtatggta gttcaccatt cacttcggcc    300

ctgggaccaa agtggatatc aaa                                            323


<210> SEQ ID NO 432
<211> LENGTH: 214
<212> TYPE: PRT
<213> ORGANISM: Homo Sapiens

<400> SEQUENCE: 432

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Arg Arg Leu Glu
65 70 75 80

Pro Glu Asp Phe Ala Val Tyr Tyr Cys Gln Gln Tyr Gly Ser Ser Pro
85 90 95

Phe Phe Gly Pro Gly Thr Lys Val Asp Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 433
<211> LENGTH: 642
<212> TYPE: DNA
<213> ORGANISM: Homo Sapiens

<400> SEQUENCE: 433
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatatat ggtgcatcca gcagggccac tggcatccca 180
gacaggttca gtggcagtgg gtctgggaca gacttcactc tcaccatcag aagactggag 240
cctgaagatt ttgcagtgta ttactgtcag cagtatggta gttcaccatt cttcggccct 300
gggaccaaag tggatatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 434
<211> LENGTH: 644
<212> TYPE: DNA
<213> ORGANISM: Homo Sapiens

<400> SEQUENCE: 434
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatatat ggtgcatcca gcagggccac tggcatccca 180
gacaggttca gtggcagtgg gtctgggaca gacttcactc tcaccatcag aagactggag 240
cctgaagatt ttgcagtgta ttactgtcag cagtatggta gttcaccatt cacttcggcc 300

-continued

```
ctgggaccaa agtggatatc aaacgtacgg tggccgctcc ctccgtgttc atcttcccac    360

cttccgacga gcagctgaag tccggcaccg cttctgtcgt gtgcctgctg aacaacttct    420

acccccgcga ggccaaggtg cagtggaagg tggacaacgc cctgcagtcc ggcaactccc    480

aggaatccgt gaccgagcag gactccaagg acagcaccta ctccctgtcc tccaccctga    540

ccctgtccaa ggccgactac gagaagcaca aggtgtacgc ctgcgaagtg acccaccagg    600

gcctgtctag ccccgtgacc aagtctttca accggggcga gtgt                     644


<210> SEQ ID NO 435
<211> LENGTH: 8
<212> TYPE: PRT
<213> ORGANISM: Homo Sapiens

<400> SEQUENCE: 435

Gly Tyr Thr Phe Asn Ser Tyr Gly
1               5


<210> SEQ ID NO 436
<211> LENGTH: 8
<212> TYPE: PRT
<213> ORGANISM: Homo Sapiens

<400> SEQUENCE: 436

Ile Ser Val His Asn Gly Asn Thr
1               5


<210> SEQ ID NO 437
<211> LENGTH: 17
<212> TYPE: PRT
<213> ORGANISM: Homo Sapiens

<400> SEQUENCE: 437

Ala Arg Ala Gly Tyr Asp Ile Leu Thr Asp Phe Ser Asp Ala Phe Asp
1               5                   10                  15

Ile


<210> SEQ ID NO 438
<211> LENGTH: 124
<212> TYPE: PRT
<213> ORGANISM: Homo Sapiens

<400> SEQUENCE: 438

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Gly Ile Ile Trp Val Arg Gln Ala Pro Gly Gln Gly Leu Glu Trp Met
        35                  40                  45

Gly Trp Ile Ser Val His Asn Gly Asn Thr Asn Cys Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Thr Asp Asp Thr Ala Val Tyr Tyr Cys
                85                  90                  95

Ala Arg Ala Gly Tyr Asp Ile Leu Thr Asp Phe Ser Asp Ala Phe Asp
            100                 105                 110

Ile Trp Gly His Gly Thr Met Val Thr Val Ser Ser
        115                 120
```

<210> SEQ ID NO 439
<211> LENGTH: 372
<212> TYPE: DNA
<213> ORGANISM: Homo Sapiens

<400> SEQUENCE: 439
caggttcagt tggtgcagtc tggagctgag gtgaagaagc ctggggcctc agtgaaggtc 60
tcctgcaagg cttctggtta cacctttaat agttatggta tcatctgggt gcgacaggcc 120
cctggacaag ggcttgagtg gatgggatgg atcagcgttc acaatggtaa cacaaactgt 180
gcacagaagc tccagggtag agtcaccatg accacagaca catccacgag cacagcctac 240
atggagctga ggagcctgag aactgacgac acggccgtgt attactgtgc gagagcgggt 300
tacgatattt tgactgattt ttccgatgct tttgatatct ggggccacgg gacaatggtc 360
accgtctctt ca 372

<210> SEQ ID NO 440
<211> LENGTH: 454
<212> TYPE: PRT
<213> ORGANISM: Homo Sapiens

<400> SEQUENCE: 440

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Asn Ser Tyr
20 25 30

Gly Ile Ile Trp Val Arg Gln Ala Pro Gly Gln Gly Leu Glu Trp Met
35 40 45

Gly Trp Ile Ser Val His Asn Gly Asn Thr Asn Cys Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Thr Asp Asp Thr Ala Val Tyr Tyr Cys
85 90 95

Ala Arg Ala Gly Tyr Asp Ile Leu Thr Asp Phe Ser Asp Ala Phe Asp
100 105 110

Ile Trp Gly His Gly Thr Met Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp

```
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 441
<211> LENGTH: 1368
<212> TYPE: DNA
<213> ORGANISM: Homo Sapiens

<400> SEQUENCE: 441

```
caggttcagt tggtgcagtc tggagctgag gtgaagaagc ctggggcctc agtgaaggtc     60

tcctgcaagg cttctggtta cacctttaat agttatggta tcatctgggt gcgacaggcc    120

cctggacaag ggcttgagtg gatgggatgg atcagcgttc acaatggtaa cacaaactgt    180

gcacagaagc tccagggtag agtcaccatg accacagaca catccacgag cacagcctac    240

atggagctga ggagcctgag aactgacgac acggccgtgt attactgtgc gagagcgggt    300

tacgatattt tgactgattt ttccgatgct tttgatatct ggggccacgg gacaatggtc    360

accgtctctt cagccagcac caagggcccc tctgtgttcc ctctggcccc ttccagcaag    420

tccacctctg gcggaacagc cgctctgggc tgcctcgtga aggactactt ccccgagcct    480

gtgaccgtgt cctggaactc tggcgctctg accagcggag tgcacacctt ccctgctgtg    540

ctgcagtcct ccggcctgta ctccctgtcc tccgtcgtga ccgtgccttc cagctctctg    600

ggcacccaga cctacatctg caacgtgaac cacaagccct ccaacaccaa ggtggacaag    660

aaggtggaac ccaagtcctg cgacaagacc cacacctgtc cccccttgtcc tgcccctgaa    720

ctgctgggcg gaccttccgt gttcctgttc ccccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020
```

```
aagaccatct ccaaggccaa gggccagccc cgggaacccc aggtgtacac actgcccccct   1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

accccccctg tgctggactc cgacggctca ttcttcctgt acagcaagct gacagtggac   1260

aagtcccggt ggcagcaggg caacgtgttc tcctgctccg tgatgcacga ggccctgcac   1320

aaccactaca cccagaagtc cctgtccctg agccccggca agtgatga                 1368
```

```
<210> SEQ ID NO 442
<211> LENGTH: 6
<212> TYPE: PRT
<213> ORGANISM: Homo Sapiens

<400> SEQUENCE: 442

Gln Asn Ile Asn Asn Phe
1               5


<210> SEQ ID NO 443
<211> LENGTH: 3
<212> TYPE: PRT
<213> ORGANISM: Homo Sapiens

<400> SEQUENCE: 443

Ala Ala Ser
1


<210> SEQ ID NO 444
<211> LENGTH: 8
<212> TYPE: PRT
<213> ORGANISM: Homo Sapiens

<400> SEQUENCE: 444

Gln Gln Ser Tyr Gly Ile Pro Trp
1               5


<210> SEQ ID NO 445
<211> LENGTH: 106
<212> TYPE: PRT
<213> ORGANISM: Homo Sapiens

<400> SEQUENCE: 445

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Phe
            20                  25                  30

Leu Asn Trp Tyr Gln Gln Lys Glu Gly Lys Gly Pro Lys Leu Leu Ile
        35                  40                  45

Tyr Ala Ala Ser Ser Leu Gln Arg Gly Ile Pro Ser Thr Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ile Cys Gln Gln Ser Tyr Gly Ile Pro Trp
                85                  90                  95

Val Gly Gln Gly Thr Lys Val Glu Ile Lys
            100                 105


<210> SEQ ID NO 446
<211> LENGTH: 318
<212> TYPE: DNA
```

<213> ORGANISM: Homo Sapiens

<400> SEQUENCE: 446
gacatccaga tgacccagtc tccatcctcc ctgtctgcat ctgtaggaga cagagtcacc 60
atcacttgcc gggcaagtca gaacattaat aactttttaa attggtatca gcagaaagaa 120
gggaaaggcc ctaagctcct gatctatgca gcatccagtt tgcaaagagg gataccatca 180
acgttcagtg gcagtggatc tgggacagac ttcactctca ccatcagcag tctgcaacct 240
gaagattttg caacttacat ctgtcaacag agctacggta tcccgtgggt cggccaaggg 300
accaaggtgg aaatcaaa 318

<210> SEQ ID NO 447
<211> LENGTH: 213
<212> TYPE: PRT
<213> ORGANISM: Homo Sapiens

<400> SEQUENCE: 447

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Asn Asn Phe
20 25 30

Leu Asn Trp Tyr Gln Gln Lys Glu Gly Lys Gly Pro Lys Leu Leu Ile
35 40 45

Tyr Ala Ala Ser Ser Leu Gln Arg Gly Ile Pro Ser Thr Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Ile Cys Gln Gln Ser Tyr Gly Ile Pro Trp
85 90 95

Val Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 448
<211> LENGTH: 639
<212> TYPE: DNA
<213> ORGANISM: Homo Sapiens

<400> SEQUENCE: 448
gacatccaga tgacccagtc tccatcctcc ctgtctgcat ctgtaggaga cagagtcacc 60
atcacttgcc gggcaagtca gaacattaat aactttttaa attggtatca gcagaaagaa 120
gggaaaggcc ctaagctcct gatctatgca gcatccagtt tgcaaagagg gataccatca 180

-continued

```
acgttcagtg gcagtggatc tgggacagac ttcactctca ccatcagcag tctgcaacct    240

gaagattttg caacttacat ctgtcaacag agctacggta tcccgtgggt cggccaaggg    300

accaaggtgg aaatcaaacg tacggtggcc gctccctccg tgttcatctt cccaccttcc    360

gacgagcagc tgaagtccgg caccgcttct gtcgtgtgcc tgctgaacaa cttctacccc    420

cgcgaggcca aggtgcagtg gaaggtggac aacgccctgc agtccggcaa ctcccaggaa    480

tccgtgaccg agcaggactc caaggacagc acctactccc tgtcctccac cctgaccctg    540

tccaaggccg actacgagaa gcacaaggtg tacgcctgcg aagtgaccca ccagggcctg    600

tctagccccg tgaccaagtc tttcaaccgg ggcgagtgt                           639
```

```
<210> SEQ ID NO 449
<211> LENGTH: 8
<212> TYPE: PRT
<213> ORGANISM: Homo Sapiens

<400> SEQUENCE: 449

Gly Phe Thr Phe Ser Asp Tyr Phe
1               5


<210> SEQ ID NO 450
<211> LENGTH: 8
<212> TYPE: PRT
<213> ORGANISM: Homo Sapiens

<400> SEQUENCE: 450

Ile Ser Ser Ser Gly Ser Thr Ile
1               5


<210> SEQ ID NO 451
<211> LENGTH: 21
<212> TYPE: PRT
<213> ORGANISM: Homo Sapiens

<400> SEQUENCE: 451

Ala Arg Asp His Tyr Asp Gly Ser Gly Ile Tyr Pro Leu Tyr Tyr Tyr
1               5                   10                  15

Tyr Gly Leu Asp Val
            20


<210> SEQ ID NO 452
<211> LENGTH: 128
<212> TYPE: PRT
<213> ORGANISM: Homo Sapiens

<400> SEQUENCE: 452

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Arg Gly Arg Phe Thr Ile Ser Arg Asp Asn Ala Lys Tyr Ser Leu Tyr
65                  70                  75                  80

Leu Gln Met Asn Ser Leu Arg Ser Glu Asp Thr Ala Val Tyr Tyr Cys
                85                  90                  95
```

```
Ala Arg Asp His Tyr Asp Gly Ser Gly Ile Tyr Pro Leu Tyr Tyr Tyr
            100                 105                 110

Tyr Gly Leu Asp Val Trp Gly Gln Gly Thr Thr Val Thr Val Ser Ser
        115                 120                 125


<210> SEQ ID NO 453
<211> LENGTH: 384
<212> TYPE: DNA
<213> ORGANISM: Homo Sapiens

<400> SEQUENCE: 453

caggtgcagc tggtggagtc tgggggaggc ttggtcaagc ctggagggtc cctgagactc      60

tcctgtgcag cctctggatt caccttcagt gactacttca tgagctggat ccgccaggcg     120

ccagggaagg ggctggagtg gatttcatac attagttcta gtggtagtac catatactac     180

gcagactctg tgaggggccg attcaccatc tccagggaca acgccaagta ctcactgtat     240

ctgcaaatga acagcctgag atccgaggac acggccgtgt attactgtgc gagagatcac     300

tacgatggtt cggggattta tcccctctac tactattacg gtttggacgt ctggggccag     360

gggaccacgg tcaccgtctc ctca                                            384


<210> SEQ ID NO 454
<211> LENGTH: 458
<212> TYPE: PRT
<213> ORGANISM: Homo Sapiens

<400> SEQUENCE: 454

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Arg Gly Arg Phe Thr Ile Ser Arg Asp Asn Ala Lys Tyr Ser Leu Tyr
65                  70                  75                  80

Leu Gln Met Asn Ser Leu Arg Ser Glu Asp Thr Ala Val Tyr Tyr Cys
                85                  90                  95

Ala Arg Asp His Tyr Asp Gly Ser Gly Ile Tyr Pro Leu Tyr Tyr Tyr
            100                 105                 110

Tyr Gly Leu Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
```

-continued

```
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 455
<211> LENGTH: 1380
<212> TYPE: DNA
<213> ORGANISM: Homo Sapiens

<400> SEQUENCE: 455

```
caggtgcagc tggtggagtc tgggggaggc ttggtcaagc ctggagggtc cctgagactc     60

tcctgtgcag cctctggatt caccttcagt gactacttca tgagctggat ccgccaggcg    120

ccagggaagg ggctggagtg gatttcatac attagttcta gtggtagtac catatactac    180

gcagactctg tgaggggccg attcaccatc tccagggaca acgccaagta ctcactgtat    240

ctgcaaatga acagcctgag atccgaggac acggccgtgt attactgtgc gagagatcac    300

tacgatggtt cggggattta tcccctctac tactattacg gtttggacgt ctggggccag    360

gggaccacgg tcaccgtctc ctcagccagc accaagggcc cctctgtgtt ccctctggcc    420

ccttccagca agtccacctc tggcggaaca gccgctctgg gctgcctcgt gaaggactac    480

ttccccgagc ctgtgaccgt gtcctggaac tctggcgctc tgaccagcgg agtgcacacc    540

ttccctgctg tgctgcagtc ctccggcctg tactccctgt cctccgtcgt gaccgtgcct    600

tccagctctc tgggcaccca gacctacatc tgcaacgtga accacaagcc ctccaacacc    660

aaggtggaca agaaggtgga acccaagtcc tgcgacaaga cccacacctg tccccccttgt    720

cctgcccctg aactgctggg cggaccttcc gtgttcctgt tcccccccaaa gcccaaggac    780

accctgatga tctcccggac ccccgaagtg acctgcgtgg tggtggatgt gtcccacgag    840
```

-continued

```
gaccctgaag tgaagttcaa ttggtacgtg gacggcgtgg aagtgcacaa cgccaagacc    900

aagcctagag aggaacagta caactccacc taccgggtgg tgtccgtgct gaccgtgctg    960

caccaggatt ggctgaacgg caaagagtac aagtgcaagg tgtccaacaa ggccctgcct   1020

gcccccatcg aaaagaccat ctccaaggcc aagggccagc cccgggaacc ccaggtgtac   1080

acactgcccc ctagcaggga cgagctgacc aagaaccagg tgtccctgac ctgtctcgtg   1140

aaaggcttct acccctccga tatcgccgtg gaatgggagt ccaacggcca gcctgagaac   1200

aactacaaga ccaccccccc tgtgctggac tccgacggct cattcttcct gtacagcaag   1260

ctgacagtgg acaagtcccg gtggcagcag ggcaacgtgt tctcctgctc cgtgatgcac   1320

gaggccctgc acaaccacta cacccagaag tccctgtccc tgagccccgg caagtgatga   1380


<210> SEQ ID NO 456
<211> LENGTH: 11
<212> TYPE: PRT
<213> ORGANISM: Homo Sapiens

<400> SEQUENCE: 456

Gln Ser Leu Leu His Ser Asn Gly Tyr Asn Tyr
1               5                   10


<210> SEQ ID NO 457
<211> LENGTH: 3
<212> TYPE: PRT
<213> ORGANISM: Homo Sapiens

<400> SEQUENCE: 457

Leu Gly Ser
1


<210> SEQ ID NO 458
<211> LENGTH: 9
<212> TYPE: PRT
<213> ORGANISM: Homo Sapiens

<400> SEQUENCE: 458

Met Gln Ala Leu Gln Thr Pro Arg Ser
1               5


<210> SEQ ID NO 459
<211> LENGTH: 111
<212> TYPE: PRT
<213> ORGANISM: Homo Sapiens

<400> SEQUENCE: 459

Ile Val Met Thr Gln Ser Pro Leu Ser Leu Pro Val Thr Pro Gly Glu
1               5                   10                  15

Pro Ala Ser Ile Ser Cys Arg Ser Ser Gln Ser Leu Leu His Ser Asn
            20                  25                  30

Gly Tyr Asn Tyr Leu Asp Tyr Tyr Leu Gln Lys Pro Gly Gln Ser Pro
        35                  40                  45

Gln Leu Leu Ile Tyr Leu Gly Ser Tyr Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Ala Leu
                85                  90                  95

Gln Thr Pro Arg Ser Phe Gly Gln Gly Thr Thr Leu Glu Ile Lys
```

100 105 110

<210> SEQ ID NO 460
<211> LENGTH: 333
<212> TYPE: DNA
<213> ORGANISM: Homo Sapiens

<400> SEQUENCE: 460
attgtgatga ctcagtctcc actctcccta cccgtcaccc ctggagagcc ggcctccatc 60
tcctgcaggt ctagtcagag cctcctgcat agtaatggat acaactattt ggattattac 120
ctgcagaagc cagggcagtc tccacagctc ctgatctatt tgggttctta tcgggcctcc 180
ggggtccctg acaggttcag tggcagtgga tcaggcacag attttacact gaaaatcagc 240
agagtggagg ctgaggatgt tggggtttat tactgcatgc aagctctaca aactcctcgc 300
agttttggcc aggggaccac gctggagatc aaa 333

<210> SEQ ID NO 461
<211> LENGTH: 218
<212> TYPE: PRT
<213> ORGANISM: Homo Sapiens

<400> SEQUENCE: 461

Ile Val Met Thr Gln Ser Pro Leu Ser Leu Pro Val Thr Pro Gly Glu
1 5 10 15

Pro Ala Ser Ile Ser Cys Arg Ser Ser Gln Ser Leu Leu His Ser Asn
20 25 30

Gly Tyr Asn Tyr Leu Asp Tyr Tyr Leu Gln Lys Pro Gly Gln Ser Pro
35 40 45

Gln Leu Leu Ile Tyr Leu Gly Ser Tyr Arg Ala Ser Gly Val Pro Asp
50 55 60

Arg Phe Ser Gly Ser Gly Ser Gly Thr Asp Phe Thr Leu Lys Ile Ser
65 70 75 80

Arg Val Glu Ala Glu Asp Val Gly Val Tyr Tyr Cys Met Gln Ala Leu
85 90 95

Gln Thr Pro Arg Ser Phe Gly Gln Gly Thr Thr Leu Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 462
<211> LENGTH: 654
<212> TYPE: DNA
<213> ORGANISM: Homo Sapiens

<400> SEQUENCE: 462

```
attgtgatga ctcagtctcc actctcccta cccgtcaccc ctggagagcc ggcctccatc     60

tcctgcaggt ctagtcagag cctcctgcat agtaatggat acaactattt ggattattac    120

ctgcagaagc cagggcagtc tccacagctc ctgatctatt tgggttctta tcgggcctcc    180

ggggtccctg acaggttcag tggcagtgga tcaggcacag attttacact gaaaatcagc    240

agagtggagg ctgaggatgt tggggtttat tactgcatgc aagctctaca aactcctcgc    300

agttttggcc aggggaccac gctggagatc aaacgtacgg tggccgctcc ctccgtgttc    360

atcttcccac cttccgacga gcagctgaag tccggcaccg cttctgtcgt gtgcctgctg    420

aacaacttct acccccgcga ggccaaggtg cagtggaagg tggacaacgc cctgcagtcc    480

ggcaactccc aggaatccgt gaccgagcag gactccaagg acagcaccta ctccctgtcc    540

tccaccctga ccctgtccaa ggccgactac gagaagcaca aggtgtacgc ctgcgaagtg    600

acccaccagg gcctgtctag ccccgtgacc aagtctttca accggggcga gtgt          654
```

```
<210> SEQ ID NO 463
<211> LENGTH: 10
<212> TYPE: PRT
<213> ORGANISM: Homo Sapiens

<400> SEQUENCE: 463

Gly Phe Ser Leu Ser Thr Thr Gly Val Gly
1               5                   10


<210> SEQ ID NO 464
<211> LENGTH: 7
<212> TYPE: PRT
<213> ORGANISM: Homo Sapiens

<400> SEQUENCE: 464

Ile Tyr Trp Asp Asp Asp Lys
1               5


<210> SEQ ID NO 465
<211> LENGTH: 16
<212> TYPE: PRT
<213> ORGANISM: Homo Sapiens

<400> SEQUENCE: 465

Thr His Gly Tyr Gly Ser Ala Ser Tyr Tyr His Tyr Gly Met Asp Val
1               5                   10                  15


<210> SEQ ID NO 466
<211> LENGTH: 124
<212> TYPE: PRT
<213> ORGANISM: Homo Sapiens

<400> SEQUENCE: 466

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Thr
            20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80
```

```
Val Leu Thr Met Thr Asn Met Asp Pro Val Asp Thr Ala Thr Tyr Phe
                85                  90                  95

Cys Thr His Gly Tyr Gly Ser Ala Ser Tyr Tyr His Tyr Gly Met Asp
            100                 105                 110

Val Trp Gly Gln Gly Thr Thr Val Thr Val Ser Ser
        115                 120


<210> SEQ ID NO 467
<211> LENGTH: 372
<212> TYPE: DNA
<213> ORGANISM: Homo Sapiens

<400> SEQUENCE: 467

cagatcacct tgaaggagtc tggtcctacg ctggtgaaac ccacacagac cctcacgctg      60

acctgcacct tctctgggtt ctcactcagc actactggag tgggtgtggg ctggatccgt     120

cagcccccag gaaaggccct ggagtggctt gcagtcattt attgggatga tgataagcgc     180

tacagcccat ctctgaagag cagactcacc atcaccaagg acacctccaa aaaccaggtg     240

gtccttacaa tgaccaacat ggaccctgtg gacacagcca catatttctg tacacacgga     300

tatggttcgg cgagttatta ccactacggt atggacgtct ggggccaagg gaccacggtc     360

accgtctcct ca                                                         372


<210> SEQ ID NO 468
<211> LENGTH: 454
<212> TYPE: PRT
<213> ORGANISM: Homo Sapiens

<400> SEQUENCE: 468

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Thr
            20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Thr His Gly Tyr Gly Ser Ala Ser Tyr Tyr His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
```

| | | | | | | | | | | |
|---|---|---|---|---|---|---|---|---|---|---|
| | | | 210 | | | 215 | | | 220 | |

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
 245 250 255

Thr Leu Met Ile Ser Arg Thr Pro Glu Val Thr Cys Val Val Val Asp
 260 265 270

Val Ser His Glu Asp Pro Glu Val Lys Phe Asn Trp Tyr Val Asp Gly
 275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
 325 330 335

Ala Pro Ile Glu Lys Thr Ile Ser Lys Ala Lys Gly Gln Pro Arg Glu
 340 345 350

Pro Gln Val Tyr Thr Leu Pro Pro Ser Arg Asp Glu Leu Thr Lys Asn
 355 360 365

Gln Val Ser Leu Thr Cys Leu Val Lys Gly Phe Tyr Pro Ser Asp Ile
 370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
 405 410 415

Leu Thr Val Asp Lys Ser Arg Trp Gln Gln Gly Asn Val Phe Ser Cys
 420 425 430

Ser Val Met His Glu Ala Leu His Asn His Tyr Thr Gln Lys Ser Leu
 435 440 445

Ser Leu Ser Pro Gly Lys
 450

<210> SEQ ID NO 469
<211> LENGTH: 1368
<212> TYPE: DNA
<213> ORGANISM: Homo Sapiens

<400> SEQUENCE: 469

| | |
|---|---|
| cagatcacct tgaaggagtc tggtcctacg ctggtgaaac ccacacagac cctcacgctg | 60 |
| acctgcacct tctctgggtt ctcactcagc actactggag tgggtgtggg ctggatccgt | 120 |
| cagcccccag gaaaggccct ggagtggctt gcagtcattt attgggatga tgataagcgc | 180 |
| tacagcccat ctctgaagag cagactcacc atcaccaagg acacctccaa aaaccaggtg | 240 |
| gtccttacaa tgaccaacat ggaccctgtg gacacagcca catatttctg tacacacgga | 300 |
| tatggttcgg cgagttatta ccactacggt atggacgtct ggggccaagg gaccacggtc | 360 |
| accgtctcct cagccagcac caagggcccc tctgtgttcc ctctggcccc ttccagcaag | 420 |
| tccacctctg gcggaacagc cgctctgggc tgcctcgtga aggactactt ccccgagcct | 480 |
| gtgaccgtgt cctggaactc tggcgctctg accagcggag tgcacacctt ccctgctgtg | 540 |
| ctgcagtcct ccggcctgta ctccctgtcc tccgtcgtga ccgtgccttc cagctctctg | 600 |
| ggcacccaga cctacatctg caacgtgaac cacaagccct ccaacaccaa ggtggacaag | 660 |
| aaggtggaac ccaagtcctg cgacaagacc cacacctgtc ccccttgtcc tgcccctgaa | 720 |

```
ctgctgggcg gaccttccgt gttcctgttc cccccaaagc ccaaggacac cctgatgatc    780

tcccggaccc ccgaagtgac ctgcgtggtg gtggatgtgt cccacgagga ccctgaagtg    840

aagttcaatt ggtacgtgga cggcgtggaa gtgcacaacg ccaagaccaa gcctagagag    900

gaacagtaca actccaccta ccgggtggtg tccgtgctga ccgtgctgca ccaggattgg    960

ctgaacggca aagagtacaa gtgcaaggtg tccaacaagg ccctgcctgc ccccatcgaa   1020

aagaccatct ccaaggccaa gggccagccc cgggaacccc aggtgtacac actgcccccct   1080

agcagggacg agctgaccaa gaaccaggtg tccctgacct gtctcgtgaa aggcttctac   1140

ccctccgata tcgccgtgga atgggagtcc aacggccagc ctgagaacaa ctacaagacc   1200

acccccccctg tgctggactc cgacggctca ttcttcctgt acagcaagct gacagtggac   1260

aagtcccggt ggcagcaggg caacgtgttc tcctgctccg tgatgcacga ggccctgcac   1320

aaccactaca cccagaagtc cctgtccctg agccccggca agtgatga                1368
```

<210> SEQ ID NO 470
<211> LENGTH: 6
<212> TYPE: PRT
<213> ORGANISM: Homo Sapiens

<400> SEQUENCE: 470

```
Gln Ser Val Thr Asn Tyr
1               5
```

<210> SEQ ID NO 471
<211> LENGTH: 3
<212> TYPE: PRT
<213> ORGANISM: Homo Sapiens

<400> SEQUENCE: 471

```
Asp Ala Ser
1
```

<210> SEQ ID NO 472
<211> LENGTH: 9
<212> TYPE: PRT
<213> ORGANISM: Homo Sapiens

<400> SEQUENCE: 472

```
Gln His Arg Ser Asn Trp Pro Leu Thr
1               5
```

<210> SEQ ID NO 473
<211> LENGTH: 107
<212> TYPE: PRT
<213> ORGANISM: Homo Sapiens

<400> SEQUENCE: 473

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Leu
```

```
                85                  90                  95

Thr Phe Gly Gly Gly Thr Lys Val Glu Ile Lys
            100                 105
```

<210> SEQ ID NO 474
<211> LENGTH: 322
<212> TYPE: DNA
<213> ORGANISM: Homo Sapiens

<400> SEQUENCE: 474

```
gaaattgtat tgacacagtc tccagccacc ctgtctttgt ctccagggga aagagccacc      60

ctctcctgca gggccagtca gagtgttacc aactacttag cctggcacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcac cgtagcaact ggcctctcac tttcggcgga     300

gggaccaagg tggagatcaa ac                                              322
```

<210> SEQ ID NO 475
<211> LENGTH: 214
<212> TYPE: PRT
<213> ORGANISM: Homo Sapiens

<400> SEQUENCE: 475

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 476
<211> LENGTH: 643
<212> TYPE: DNA

<213> ORGANISM: Homo Sapiens

<400> SEQUENCE: 476
gaaattgtat tgacacagtc tccagccacc ctgtctttgt ctccagggga aagagccacc 60
ctctcctgca gggccagtca gagtgttacc aactacttag cctggcacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcac cgtagcaact ggcctctcac tttcggcgga 300
gggaccaagg tggagatcaa accgtacggt ggccgctccc tccgtgttca tcttcccacc 360
ttccgacgag cagctgaagt ccggcaccgc ttctgtcgtg tgcctgctga acaacttcta 420
cccccgcgag gccaaggtgc agtggaaggt ggacaacgcc ctgcagtccg gcaactccca 480
ggaatccgtg accgagcagg actccaagga cagcacctac tccctgtcct ccaccctgac 540
cctgtccaag gccgactacg agaagcacaa ggtgtacgcc tgcgaagtga cccaccaggg 600
cctgtctagc cccgtgacca agtctttcaa ccggggcgag tgt 643

<210> SEQ ID NO 477
<211> LENGTH: 10
<212> TYPE: PRT
<213> ORGANISM: Homo Sapiens

<400> SEQUENCE: 477

Gly Phe Ser Leu Ser Thr Ser Gly Val Gly
1 5 10

<210> SEQ ID NO 478
<211> LENGTH: 7
<212> TYPE: PRT
<213> ORGANISM: Homo Sapiens

<400> SEQUENCE: 478

Ile Tyr Trp Asp Asp Asp Lys
1 5

<210> SEQ ID NO 479
<211> LENGTH: 16
<212> TYPE: PRT
<213> ORGANISM: Homo Sapiens

<400> SEQUENCE: 479

Thr His Gly Tyr Gly Ser Ala Ser Tyr Tyr His Tyr Gly Met Asp Val
1 5 10 15

<210> SEQ ID NO 480
<211> LENGTH: 124
<212> TYPE: PRT
<213> ORGANISM: Homo Sapiens

<400> SEQUENCE: 480

Gln Ile Thr Leu Lys Glu Ser Gly Pro Thr Leu Val Lys Pro Thr Gln
1 5 10 15

Thr Leu Thr Leu Thr Cys Thr Phe Ser Gly Phe Ser Leu Ser Thr Ser
20 25 30

Gly Val Gly Val Gly Trp Ile Arg Gln Pro Pro Gly Lys Ala Leu Glu
35 40 45

Trp Leu Ala Val Ile Tyr Trp Asp Asp Asp Lys Arg Tyr Ser Pro Ser
50 55 60

```
Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Thr His Gly Tyr Gly Ser Ala Ser Tyr Tyr His Tyr Gly Met Asp
            100                 105                 110

Val Trp Gly Gln Gly Thr Thr Val Thr Val Ser Ser
        115                 120


<210> SEQ ID NO 481
<211> LENGTH: 372
<212> TYPE: DNA
<213> ORGANISM: Homo Sapiens

<400> SEQUENCE: 481

cagatcacct tgaaggagtc tggtcctacg ctggtgaaac ccacacagac cctcacgctg      60

acctgcacct tctctgggtt ctcactcagc actagtggag tgggtgtggg ctggatccgt     120

cagcccccag gaaaggccct ggagtggctt gcagtcattt attgggatga tgataagcgc     180

tacagcccat ctctgaagag caggctcacc atcaccaagg acacctccaa aaaccaggtg     240

gtccttacaa tgaccaacat ggaccctgtg gacacagcca catatttctg tacacacgga     300

tatggttcgg cgagttatta ccactacggt atggacgtct ggggccaagg gaccacggtc     360

accgtctcct ca                                                         372


<210> SEQ ID NO 482
<211> LENGTH: 454
<212> TYPE: PRT
<213> ORGANISM: Homo Sapiens

<400> SEQUENCE: 482

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Val Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Thr His Gly Tyr Gly Ser Ala Ser Tyr Tyr His Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
```

```
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 483
<211> LENGTH: 1368
<212> TYPE: DNA
<213> ORGANISM: Homo Sapiens

<400> SEQUENCE: 483

```
cagatcacct tgaaggagtc tggtcctacg ctggtgaaac ccacacagac cctcacgctg     60

acctgcacct tctctgggtt ctcactcagc actagtggag tgggtgtggg ctggatccgt    120

cagcccccag gaaaggccct ggagtggctt gcagtcattt attgggatga tgataagcgc    180

tacagcccat ctctgaagag caggctcacc atcaccaagg acacctccaa aaaccaggtg    240

gtccttacaa tgaccaacat ggaccctgtg gacacagcca catatttctg tacacacgga    300

tatggttcgg cgagttatta ccactacggt atggacgtct ggggccaagg gaccacggtc    360

accgtctcct cagccagcac caagggcccc tctgtgttcc ctctggcccc ttccagcaag    420

tccacctctg gcggaacagc cgctctgggc tgcctcgtga aggactactt ccccgagcct    480

gtgaccgtgt cctggaactc tggcgctctg accagcggag tgcacacctt ccctgctgtg    540

ctgcagtcct ccggcctgta ctccctgtcc tccgtcgtga ccgtgccttc cagctctctg    600

ggcacccaga cctacatctg caacgtgaac cacaagccct ccaacaccaa ggtggacaag    660
```

aaggtggaac ccaagtcctg cgacaagacc cacacctgtc cccctgtcc tgcccctgaa 720 ctgctgggcg gaccttccgt gttcctgttc cccccaaagc ccaaggacac cctgatgatc 780
tcccggaccc ccgaagtgac ctgcgtggtg gtggatgtgt cccacgagga ccctgaagtg 840
aagttcaatt ggtacgtgga cggcgtggaa gtgcacaacg ccaagaccaa gcctagagag 900
gaacagtaca actccaccta ccgggtggtg tccgtgctga ccgtgctgca ccaggattgg 960
ctgaacggca aagagtacaa gtgcaaggtg tccaacaagg ccctgcctgc ccccatcgaa 1020
aagaccatct ccaaggccaa gggccagccc cgggaacccc aggtgtacac actgcccccct 1080 agcagggacg agctgaccaa gaaccaggtg tccctgacct gtctcgtgaa aggcttctac 1140
ccctccgata tcgccgtgga atgggagtcc aacggccagc ctgagaacaa ctacaagacc 1200
accccccctg tgctggactc cgacggctca ttcttcctgt acagcaagct gacagtggac 1260
aagtcccggt ggcagcaggg caacgtgttc tcctgctccg tgatgcacga ggccctgcac 1320
aaccactaca cccagaagtc cctgtccctg agccccggca agtgatga 1368

<210> SEQ ID NO 484
<211> LENGTH: 6
<212> TYPE: PRT
<213> ORGANISM: Homo Sapiens

<400> SEQUENCE: 484

Gln Ser Val Thr Asn Tyr
1               5

<210> SEQ ID NO 485
<211> LENGTH: 3
<212> TYPE: PRT
<213> ORGANISM: Homo Sapiens

<400> SEQUENCE: 485

Asp Ala Ser
1

<210> SEQ ID NO 486
<211> LENGTH: 9
<212> TYPE: PRT
<213> ORGANISM: Homo Sapiens

<400> SEQUENCE: 486

Gln Gln Arg Ser Asn Trp Pro Leu Thr
1               5

<210> SEQ ID NO 487
<211> LENGTH: 107
<212> TYPE: PRT
<213> ORGANISM: Homo Sapiens

<400> SEQUENCE: 487

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105


<210> SEQ ID NO 488
<211> LENGTH: 321
<212> TYPE: DNA
<213> ORGANISM: Homo Sapiens

<400> SEQUENCE: 488

gaaattgtgt tgacacagtc tccagccacc ctgtctttgt ctccagggga aagagccacc      60

ctctcctgca gggccagtca gagtgttacc aactacttag cctggcacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag cgtagcaact ggcctctcac tttcggcgga     300

gggaccaagg tggagatcaa a                                               321


<210> SEQ ID NO 489
<211> LENGTH: 214
<212> TYPE: PRT
<213> ORGANISM: Homo Sapiens

<400> SEQUENCE: 489

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Asn Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 490
<211> LENGTH: 642
<212> TYPE: DNA
<213> ORGANISM: Homo Sapiens

<400> SEQUENCE: 490

```
gaaattgtgt tgacacagtc tccagccacc ctgtctttgt ctccagggga aagagccacc     60

ctctcctgca gggccagtca gagtgttacc aactacttag cctggcacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag cgtagcaact ggcctctcac tttcggcgga    300

gggaccaagg tggagatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642
```

<210> SEQ ID NO 491
<211> LENGTH: 8
<212> TYPE: PRT
<213> ORGANISM: Homo Sapiens

<400> SEQUENCE: 491

```
Gly Phe Thr Phe Ser Asp Tyr Tyr
1               5
```

<210> SEQ ID NO 492
<211> LENGTH: 8
<212> TYPE: PRT
<213> ORGANISM: Homo Sapiens

<400> SEQUENCE: 492

```
Ile Ser Ser Ser Gly Ser Thr Ile
1               5
```

<210> SEQ ID NO 493
<211> LENGTH: 20
<212> TYPE: PRT
<213> ORGANISM: Homo Sapiens

<400> SEQUENCE: 493

```
Ala Arg Asp Phe Tyr Asp Ile Leu Thr Asp Ser Pro Tyr Phe Tyr Tyr
1               5                   10                  15

Gly Val Asp Val
            20
```

<210> SEQ ID NO 494
<211> LENGTH: 127
<212> TYPE: PRT
<213> ORGANISM: Homo Sapiens

<400> SEQUENCE: 494

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Val Tyr Tyr Cys
                85                  90                  95

Ala Arg Asp Phe Tyr Asp Ile Leu Thr Asp Ser Pro Tyr Phe Tyr Tyr
            100                 105                 110

Gly Val Asp Val Trp Gly Gln Gly Thr Thr Val Thr Val Ser Ser
        115                 120                 125


<210> SEQ ID NO 495
<211> LENGTH: 381
<212> TYPE: DNA
<213> ORGANISM: Homo Sapiens

<400> SEQUENCE: 495

caggtgcagc tggtggagtc tgggggaggc ttggtcaagc ctggagggtc cctgagactc      60

tcctgtgcag cctctggatt caccttcagt gactactaca tgagctggat ccgccaggct     120

ccagggaagg ggctggagtg ggtttcatac attagtagta gtggtagtac catatactac     180

gcagactctg tgaagggccg attcaccatc tccagggaca acgccaagaa ctcactgtat     240

ctgcaaatta acagcctgag agccgaggac acggccgtgt attactgtgc gagagatttt     300

tacgatattt tgactgatag tccgtacttc tactacggtg tggacgtctg gggccaaggg     360

accacggtca ccgtctcctc a                                               381


<210> SEQ ID NO 496
<211> LENGTH: 457
<212> TYPE: PRT
<213> ORGANISM: Homo Sapiens

<400> SEQUENCE: 496

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Val Tyr Tyr Cys
                85                  90                  95

Ala Arg Asp Phe Tyr Asp Ile Leu Thr Asp Ser Pro Tyr Phe Tyr Tyr
            100                 105                 110

Gly Val Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

-continued

```
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455
```

<210> SEQ ID NO 497
<211> LENGTH: 1377
<212> TYPE: DNA
<213> ORGANISM: Homo Sapiens

<400> SEQUENCE: 497

```
caggtgcagc tggtggagtc tgggggaggc ttggtcaagc ctggagggtc cctgagactc      60

tcctgtgcag cctctggatt caccttcagt gactactaca tgagctggat ccgccaggct     120

ccagggaagg ggctggagtg ggtttcatac attagtagta gtggtagtac catatactac     180

gcagactctg tgaagggccg attcaccatc tccagggaca acgccaagaa ctcactgtat     240

ctgcaaatta acagcctgag agccgaggac acggccgtgt attactgtgc gagagatttt     300

tacgatattt tgactgatag tccgtacttc tactacggtg tggacgtctg gggccaaggg     360

accacggtca ccgtctcctc agccagcacc aagggcccct ctgtgttccc tctggcccct     420

tccagcaagt ccacctctgg cggaacagcc gctctgggct gcctcgtgaa ggactacttc     480
```

```
cccgagcctg tgaccgtgtc ctggaactct ggcgctctga ccagcggagt gcacaccttc    540

cctgctgtgc tgcagtcctc cggcctgtac tccctgtcct ccgtcgtgac cgtgccttcc    600

agctctctgg gcacccagac ctacatctgc aacgtgaacc acaagccctc caacaccaag    660

gtggacaaga aggtggaacc caagtcctgc gacaagaccc acacctgtcc cccttgtcct    720

gcccctgaac tgctgggcgg accttccgtg ttcctgttcc ccccaaagcc caaggacacc    780

ctgatgatct cccggacccc cgaagtgacc tgcgtggtgg tggatgtgtc ccacgaggac    840

cctgaagtga agttcaattg gtacgtggac ggcgtggaag tgcacaacgc caagaccaag    900

cctagagagg aacagtacaa ctccacctac cgggtggtgt ccgtgctgac cgtgctgcac    960

caggattggc tgaacggcaa agagtacaag tgcaaggtgt ccaacaaggc cctgcctgcc   1020

cccatcgaaa agaccatctc caaggccaag ggccagcccc gggaacccca ggtgtacaca   1080

ctgcccccta gcagggacga gctgaccaag aaccaggtgt ccctgacctg tctcgtgaaa   1140

ggcttctacc cctccgatat cgccgtggaa tgggagtcca acggccagcc tgagaacaac   1200

tacaagacca cccccccctgt gctggactcc gacggctcat tcttcctgta cagcaagctg   1260

acagtggaca agtcccggtg gcagcagggc aacgtgttct cctgctccgt gatgcacgag   1320

gccctgcaca accactacac ccagaagtcc ctgtccctga gccccggcaa gtgatga      1377
```

```
<210> SEQ ID NO 498
<211> LENGTH: 11
<212> TYPE: PRT
<213> ORGANISM: Homo Sapiens

<400> SEQUENCE: 498

Gln Ser Leu Leu His Ser Asn Gly Tyr Asn Tyr
1               5                   10


<210> SEQ ID NO 499
<211> LENGTH: 3
<212> TYPE: PRT
<213> ORGANISM: Homo Sapiens

<400> SEQUENCE: 499

Leu Gly Ser
1


<210> SEQ ID NO 500
<211> LENGTH: 9
<212> TYPE: PRT
<213> ORGANISM: Homo Sapiens

<400> SEQUENCE: 500

Met Gln Ala Leu Gln Thr Pro Arg Thr
1               5


<210> SEQ ID NO 501
<211> LENGTH: 112
<212> TYPE: PRT
<213> ORGANISM: Homo Sapiens

<400> SEQUENCE: 501

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
```

```
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110


<210> SEQ ID NO 502
<211> LENGTH: 336
<212> TYPE: DNA
<213> ORGANISM: Homo Sapiens

<400> SEQUENCE: 502

gatattgtga tgactcagtc tccactctcc ctgcccgtca cccctggaga gccggcctcc      60

atctcctgca ggtctagtca gagcctcctg catagtaatg gatacaacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct acaaactcct     300

cggacgttcg gccaagggac caaggtggaa atcaaa                               336


<210> SEQ ID NO 503
<211> LENGTH: 219
<212> TYPE: PRT
<213> ORGANISM: Homo Sapiens

<400> SEQUENCE: 503

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

-continued

```
        195                 200                 205

Pro Val Thr Lys Ser Phe Asn Arg Gly Glu Cys
    210                 215


<210> SEQ ID NO 504
<211> LENGTH: 657
<212> TYPE: DNA
<213> ORGANISM: Homo Sapiens

<400> SEQUENCE: 504

gatattgtga tgactcagtc tccactctcc ctgcccgtca cccctggaga gccggcctcc      60

atctcctgca ggtctagtca gagcctcctg catagtaatg gatacaacta tttggattgg     120

tacctgcaga agccagggca gtctccacag ctcctgatct atttgggttc taatcgggcc     180

tccggggtcc ctgacaggtt cagtggcagt ggatcaggca cagattttac actgaaaatc     240

agcagagtgg aggctgagga tgttggggtt tattactgca tgcaagctct acaaactcct     300

cggacgttcg gccaagggac caaggtggaa atcaaacgta cggtggccgc tccctccgtg     360

ttcatcttcc caccttccga cgagcagctg aagtccggca ccgcttctgt cgtgtgcctg     420

ctgaacaact tctacccccg cgaggccaag gtgcagtgga aggtggacaa cgccctgcag     480

tccggcaact cccaggaatc cgtgaccgag caggactcca aggacagcac ctactccctg     540

tcctccaccc tgaccctgtc caaggccgac tacgagaagc acaaggtgta cgcctgcgaa     600

gtgacccacc agggcctgtc tagccccgtg accaagtctt tcaaccgggg cgagtgt        657


<210> SEQ ID NO 505
<211> LENGTH: 239
<212> TYPE: PRT
<213> ORGANISM: Homo Sapiens

<400> SEQUENCE: 505

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190
```

-continued

```
Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Ile Glu Gly
    210                 215                 220

Arg Asp Tyr Lys Asp Asp Asp Asp Lys His His His His His His
225                 230                 235
```

<210> SEQ ID NO 506
<211> LENGTH: 179
<212> TYPE: PRT
<213> ORGANISM: Homo Sapiens

<400> SEQUENCE: 506

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu
```

<210> SEQ ID NO 507
<211> LENGTH: 121
<212> TYPE: PRT
<213> ORGANISM: Homo Sapiens

<400> SEQUENCE: 507

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
```

```
            100                 105                 110

Ser Gln Leu Cys Cys Gln Leu Lys Phe
        115                 120


<210> SEQ ID NO 508
<211> LENGTH: 199
<212> TYPE: PRT
<213> ORGANISM: Homo Sapiens

<400> SEQUENCE: 508

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 509
<211> LENGTH: 33
<212> TYPE: PRT
<213> ORGANISM: Homo Sapiens

<400> SEQUENCE: 509

Lys Tyr Ser Ser Ser Val His Asp Pro Asn Gly Glu Tyr Met Phe Met
1               5                   10                  15

Arg Ala Val Asn Thr Ala Lys Lys Ser Arg Leu Thr Asp Val Thr Leu
            20                  25                  30

Met


<210> SEQ ID NO 510
<211> LENGTH: 128
<212> TYPE: PRT
<213> ORGANISM: Mus Musculus

<400> SEQUENCE: 510

Glu Ile Asn Gly Ser Ala Asp His Arg Met Phe Ser Phe His Asn Gly
1               5                   10                  15
```

-continued

```
Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr His Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys Ile Val Val Gln Val Thr Glu
        115                 120                 125


<210> SEQ ID NO 511
<211> LENGTH: 121
<212> TYPE: PRT
<213> ORGANISM: Mus Musculus

<400> SEQUENCE: 511

Glu Ile Asn Gly Ser Ala Asp His Arg Met Phe Ser Phe His Asn Gly
1               5                   10                  15

Gly Val Gln Ile Ser Cys Lys Tyr Pro Glu Thr Val Gln Gln Leu Lys
            20                  25                  30

Met Arg Leu Phe Arg Glu Arg Glu Val Leu Cys Glu Leu Thr Lys Thr
        35                  40                  45

Lys Gly Ser Gly Asn Ala Val Ser Ile Lys Asn Pro Met Leu Cys Leu
    50                  55                  60

Tyr His Leu Ser Asn Asn Ser Val Ser Phe Phe Leu Asn Asn Pro Asp
65                  70                  75                  80

Ser Ser Gln Gly Ser Tyr Tyr Phe Cys Ser Leu Ser Ile Phe Asp Pro
                85                  90                  95

Pro Pro Phe Gln Glu Arg Asn Leu Ser Gly Gly Tyr Leu His Ile Tyr
            100                 105                 110

Glu Ser Gln Leu Cys Cys Gln Leu Lys
        115                 120


<210> SEQ ID NO 512
<211> LENGTH: 147
<212> TYPE: PRT
<213> ORGANISM: Mus Musculus

<400> SEQUENCE: 512

Met Gly Trp Ser Cys Ile Ile Leu Phe Leu Val Ala Thr Ala Thr Gly
1               5                   10                  15

Val His Ser Glu Ile Asn Gly Ser Ala Asp His Arg Met Phe Ser Phe
            20                  25                  30

His Asn Gly Gly Val Gln Ile Ser Cys Lys Tyr Pro Glu Thr Val Gln
        35                  40                  45

Gln Leu Lys Met Arg Leu Phe Arg Glu Arg Glu Val Leu Cys Glu Leu
    50                  55                  60

Thr Lys Thr Lys Gly Ser Gly Asn Ala Val Ser Ile Lys Asn Pro Met
65                  70                  75                  80

Leu Cys Leu Tyr His Leu Ser Asn Asn Ser Val Ser Phe Phe Leu Asn
                85                  90                  95
```

```
Asn Pro Asp Ser Ser Gln Gly Ser Tyr Tyr Phe Cys Ser Leu Ser Ile
            100                 105                 110

Phe Asp Pro Pro Pro Phe Gln Glu Arg Asn Leu Ser Gly Gly Tyr Leu
        115                 120                 125

His Ile Tyr Glu Ser Gln Leu Cys Cys Gln Leu Lys Ile Val Val Gln
    130                 135                 140

Val Thr Glu
145
```

<210> SEQ ID NO 513
<211> LENGTH: 199
<212> TYPE: PRT
<213> ORGANISM: Cynomologus

<400> SEQUENCE: 513

```
Met Lys Ser Gly Leu Trp Tyr Phe Phe Leu Phe Cys Leu His Met Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Lys Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp Arg Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Thr Phe Val Val Val Cys Ile Phe Gly Cys Ile Leu
145                 150                 155                 160

Ile Cys Trp Leu Thr Lys Lys Lys Tyr Ser Ser Thr Val His Asp Pro
                165                 170                 175

Asn Gly Glu Tyr Met Phe Met Arg Ala Val Asn Thr Ala Lys Lys Ser
            180                 185                 190

Arg Leu Thr Gly Thr Thr Pro
        195
```

<210> SEQ ID NO 514
<211> LENGTH: 120
<212> TYPE: PRT
<213> ORGANISM: Cynomologus

<400> SEQUENCE: 514

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Lys Val Ser Ile Lys Ser Leu Lys Phe Cys His
    50                  55                  60
```

Ser Gln Leu Ser Asn Asn Ser Val Ser Phe Phe Leu Tyr Asn Leu Asp
65 70 75 80

Arg Ser His Ala Asn Tyr Tyr Phe Cys Asn Leu Ser Ile Phe Asp Pro
85 90 95

Pro Pro Phe Lys Val Thr Leu Thr Gly Gly Tyr Leu His Ile Tyr Glu
100 105 110

Ser Gln Leu Cys Cys Gln Leu Lys
115 120

<210> SEQ ID NO 515
<211> LENGTH: 240
<212> TYPE: PRT
<213> ORGANISM: Homo Sapiens

<400> SEQUENCE: 515

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Asn Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr Trp Ser
225 230 235 240

<210> SEQ ID NO 516
<211> LENGTH: 302
<212> TYPE: PRT
<213> ORGANISM: Homo Sapiens

<400> SEQUENCE: 516

Met Arg Leu Gly Ser Pro Gly Leu Leu Phe Leu Leu Phe Ser Ser Leu
1 5 10 15

Arg Ala Asp Thr Gln Glu Lys Glu Val Arg Ala Met Val Gly Ser Asp
20 25 30

-continued

```
Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300
```

<210> SEQ ID NO 517
<211> LENGTH: 113
<212> TYPE: PRT
<213> ORGANISM: Homo Sapiens

<400> SEQUENCE: 517

```
Leu Gln Met Ile Leu Asn Gly Ile Asn Asn Tyr Lys Asn Pro Lys Leu
1               5                   10                  15

Thr Ala Met Leu Thr Phe Lys Phe Tyr Met Pro Lys Lys Ala Thr Glu
            20                  25                  30

Leu Lys His Leu Gln Cys Leu Glu Glu Glu Leu Lys Pro Leu Glu Glu
        35                  40                  45

Val Leu Asn Leu Ala Gln Ser Lys Asn Phe His Leu Arg Pro Arg Asp
    50                  55                  60

Leu Ile Ser Asn Ile Asn Val Ile Val Leu Glu Leu Lys Gly Ser Glu
65                  70                  75                  80

Thr Thr Phe Met Cys Glu Tyr Ala Asp Glu Thr Ala Thr Ile Val Glu
                85                  90                  95

Phe Leu Asn Arg Trp Ile Thr Phe Cys Gln Ser Ile Ile Ser Thr Leu
            100                 105                 110
```

Thr

<210> SEQ ID NO 518
<211> LENGTH: 113
<212> TYPE: PRT
<213> ORGANISM: Homo Sapiens

<400> SEQUENCE: 518

Leu Gln Met Ile Leu Asn Gly Ile Asn Asn Tyr Lys Asn Pro Lys Leu
1 5 10 15

Thr Gln Met Leu Thr Phe Lys Phe Tyr Met Pro Lys Lys Ala Thr Glu
20 25 30

Leu Lys His Leu Gln Cys Leu Glu Glu Glu Leu Lys Pro Leu Glu Glu
35 40 45

Val Leu Asn Leu Ala Gln Ser Lys Asn Phe His Leu Arg Pro Arg Asp
50 55 60

Leu Ile Ser Asn Ile Asn Val Ile Val Leu Glu Leu Lys Gly Ser Glu
65 70 75 80

Thr Thr Phe Met Cys Glu Tyr Ala Asp Glu Thr Ala Thr Ile Val Glu
85 90 95

Phe Leu Asn Arg Trp Ile Thr Phe Cys Gln Ser Ile Ile Ser Thr Leu
100 105 110

Thr

<210> SEQ ID NO 519
<211> LENGTH: 336
<212> TYPE: DNA
<213> ORGANISM: Homo Sapiens

<400> SEQUENCE: 519
gatattgtga tgactcagtc tccactctcc ctgcccgtca cccctggaga gccggcctcc 60
atctcctgca ggtctagtca gagcctcctg catagtgatg gatacaacta tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
ctcagttttg gccaggggac caagctggag atcaaa 336

<210> SEQ ID NO 520
<211> LENGTH: 657
<212> TYPE: DNA
<213> ORGANISM: Homo Sapiens

<400> SEQUENCE: 520
gatattgtga tgactcagtc tccactctcc ctgcccgtca cccctggaga gccggcctcc 60
atctcctgca ggtctagtca gagcctcctg catagtgatg gatacaacta tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
ctcagttttg gccaggggac caagctggag atcaaacgta cggtggccgc tccctccgtg 360
ttcatcttcc caccttccga cgagcagctg aagtccggca ccgcttctgt cgtgtgcctg 420
ctgaacaact tctacccccg cgaggccaag gtgcagtgga aggtggacaa cgccctgcag 480
tccggcaact cccaggaatc cgtgaccgag caggactcca aggacagcac ctactccctg 540
tcctccaccc tgaccctgtc caaggccgac tacgagaagc acaaggtgta cgcctgcgaa 600
gtgacccacc agggcctgtc tagccccgtg accaagtctt tcaaccgggg cgagtgt 657

<210> SEQ ID NO 521
<211> LENGTH: 372
<212> TYPE: DNA
<213> ORGANISM: Homo Sapiens

<400> SEQUENCE: 521
gaggtgcagc tggtggagtc tgggggaggt gtggtacggc ctgggggtc cctgagactc 60 tcctgtgtag cctctggagt cacctttgat gattatggca tgagctgggt ccgccaagct 120
ccagggaagg ggctggagtg ggtctctggt attaattgga atggtggcga cacagattat 180
tcagactctg tgaagggccg attcaccatc tccagagaca acgccaagaa ctccctgtat 240
ctacaaatga atagtctgag agccgaggac acggccttgt attactgtgc gagggatttc 300
tatggttcgg ggagttatta tcacgttcct tttgactact ggggccaggg aatcctggtc 360
accgtctcct ca 372

<210> SEQ ID NO 522
<211> LENGTH: 1368
<212> TYPE: DNA
<213> ORGANISM: Homo Sapiens

<400> SEQUENCE: 522
gaggtgcagc tggtggagtc tgggggaggt gtggtacggc ctgggggtc cctgagactc 60 tcctgtgtag cctctggagt cacctttgat gattatggca tgagctgggt ccgccaagct 120
ccagggaagg ggctggagtg ggtctctggt attaattgga atggtggcga cacagattat 180
tcagactctg tgaagggccg attcaccatc tccagagaca acgccaagaa ctccctgtat 240
ctacaaatga atagtctgag agccgaggac acggccttgt attactgtgc gagggatttc 300
tatggttcgg ggagttatta tcacgttcct tttgactact ggggccaggg aatcctggtc 360
accgtctcct cagccagcac caagggcccc tctgtgttcc ctctggcccc ttccagcaag 420
tccacctctg gcggaacagc cgctctgggc tgcctcgtga aggactactt ccccgagcct 480
gtgaccgtgt cctggaactc tggcgctctg accagcggag tgcacacctt ccctgctgtg 540
ctgcagtcct ccggcctgta ctccctgtcc tccgtcgtga ccgtgccttc cagctctctg 600
ggcacccaga cctacatctg caacgtgaac cacaagccct ccaacaccaa ggtggacaag 660
aaggtggaac ccaagtcctg cgacaagacc cacacctgtc ccccttgtcc tgcccctgaa 720
ctgctgggcg gaccttccgt gttcctgttc cccccaaagc ccaaggacac cctgatgatc 780
tcccggaccc ccgaagtgac ctgcgtggtg gtggatgtgt cccacgagga ccctgaagtg 840
aagttcaatt ggtacgtgga cggcgtggaa gtgcacaacg ccaagaccaa gcctagagag 900
gaacagtaca actccaccta ccgggtggtg tccgtgctga ccgtgctgca ccaggattgg 960
ctgaacggca aagagtacaa gtgcaaggtg tccaacaagg ccctgcctgc ccccatcgaa 1020
aagaccatct ccaaggccaa gggccagccc cgggaacccc aggtgtacac actgccccct 1080
agcagggacg agctgaccaa gaaccaggtg tccctgacct gtctcgtgaa aggcttctac 1140
ccctccgata tcgccgtgga atgggagtcc aacggccagc ctgagaacaa ctacaagacc 1200
accccccctg tgctggactc cgacggctca ttcttcctgt acagcaagct gacagtggac 1260
aagtcccggt ggcagcaggg caacgtgttc tcctgctccg tgatgcacga ggccctgcac 1320

-continued aaccactaca cccagaagtc cctgtccctg agccccggca agtgatga 1368

<210> SEQ ID NO 523
<211> LENGTH: 990
<212> TYPE: DNA
<213> ORGANISM: Homo Sapiens

<400> SEQUENCE: 523
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggtaaa 990

<210> SEQ ID NO 524
<211> LENGTH: 330
<212> TYPE: PRT
<213> ORGANISM: Homo Sapiens

<400> SEQUENCE: 524

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 525
<211> LENGTH: 990
<212> TYPE: DNA
<213> ORGANISM: Homo Sapiens

<400> SEQUENCE: 525

gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acatcttctc atgctccgtg atgcatgagg ctctgcacaa ccactacacg    960

cagaagagcc tctccctgtc tccgggtaaa                                     990
```

<210> SEQ ID NO 526
<211> LENGTH: 330
<212> TYPE: PRT
<213> ORGANISM: Homo Sapiens

<400> SEQUENCE: 526

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Ile Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 527
<211> LENGTH: 978
<212> TYPE: DNA
<213> ORGANISM: Homo Sapiens

<400> SEQUENCE: 527
gcctccacca agggcccatc ggtcttcccc ctggcgccct gctccaggag cacctccgag 60

```
agcacagccg ccctgggctg cctggtcaag gactacttcc ccgaaccggt gacggtgtcg    120

tggaactcag gcgctctgac cagcggcgtg cacaccttcc cagctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttgagcgc    300

aaatgttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt tgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatcgc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900

gtcttctcat gctccgtgat gcatgaggct ctgcacaacc actacacgca gaagagcctc    960

tccctgtctc cgggtaaa                                                  978


<210> SEQ ID NO 528
<211> LENGTH: 326
<212> TYPE: PRT
<213> ORGANISM: Homo Sapiens

<400> SEQUENCE: 528

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 529
<211> LENGTH: 978
<212> TYPE: DNA
<213> ORGANISM: Homo Sapiens

<400> SEQUENCE: 529

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cggctgtcct acagtcctca     180

ggactctact ccctcagcag cgtggtgacc gtgacctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

atggaggtgc ataatgccaa gacaaagcca cgggaggagc agttcaacag cacgttccgt     540

gtggtcagcg tcctcaccgt cgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatcgc cgtggagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacaca gaagagcctc     960

tccctgtctc cgggtaaa                                                   978


<210> SEQ ID NO 530
<211> LENGTH: 326
<212> TYPE: PRT
<213> ORGANISM: Homo Sapiens

<400> SEQUENCE: 530

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 531
<211> LENGTH: 978
<212> TYPE: DNA
<213> ORGANISM: Homo Sapiens

<400> SEQUENCE: 531

```
gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cagctgtcct acagtcctca     180

ggactctact ccctcagcag cgtggtgacc gtgccctcca gcagcttggg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360
```

-continued

```
ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt tgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatcgc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900

gtcttctcat gctccgtgat gcatgaggct ctgcacaacc actacacgca gaagagcctc    960

tccctgtctc cgggtaaa                                                  978


<210> SEQ ID NO 532
<211> LENGTH: 326
<212> TYPE: PRT
<213> ORGANISM: Homo Sapiens

<400> SEQUENCE: 532

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

```
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 533
<211> LENGTH: 978
<212> TYPE: DNA
<213> ORGANISM: Homo Sapiens

<400> SEQUENCE: 533

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cggctgtcct acagtcctca     180

ggactctact ccctcagcag cgtggtgacc gtgccctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

gtggaggtgc ataatgccaa gacaaagcca cgggaggagc agttcaacag cacgttccgt     540

gtggtcagcg tcctcaccgt cgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatctc cgtggagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacaca gaagagcctc     960

tccctgtctc cgggtaaa                                                   978


<210> SEQ ID NO 534
<211> LENGTH: 326
<212> TYPE: PRT
<213> ORGANISM: Homo Sapiens

<400> SEQUENCE: 534

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80
```

-continued

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 535
<211> LENGTH: 318
<212> TYPE: DNA
<213> ORGANISM: Homo Sapiens

<400> SEQUENCE: 535

ggtcagccca aggctgcccc ctcggtcact ctgttcccac cctcctctga ggagcttcaa      60

gccaacaagg ccacactggt gtgtctcgta agtgacttca acccgggagc cgtgacagtg     120

gcctggaagg cagatggcag ccccgtcaag gtgggagtgg agaccaccaa accctccaaa     180

caaagcaaca acaagtatgc ggccagcagc tacctgagcc tgacgcccga gcagtggaag     240

tcccacagaa gctacagctg ccgggtcacg catgaaggga gcaccgtgga gaagacagtg     300

gcccctgcag aatgctct                                                    318


<210> SEQ ID NO 536
<211> LENGTH: 106
<212> TYPE: PRT
<213> ORGANISM: Homo Sapiens

<400> SEQUENCE: 536

Gly Gln Pro Lys Ala Ala Pro Ser Val Thr Leu Phe Pro Pro Ser Ser
1               5                   10                  15
```

```
Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 537
<211> LENGTH: 990
<212> TYPE: DNA
<213> ORGANISM: Homo Sapiens

<400> SEQUENCE: 537

gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gggtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 538
<211> LENGTH: 106
<212> TYPE: PRT
<213> ORGANISM: Homo Sapiens

<400> SEQUENCE: 538

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

```
Lys Tyr Ala Ala Ser Ser Tyr Leu Ser Leu Thr Pro Glu Gln Trp Lys
65              70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 539
<211> LENGTH: 663
<212> TYPE: PRT
<213> ORGANISM: Homo Sapiens

<400> SEQUENCE: 539

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65              70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145             150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Thr Gln Pro Gly Lys Ser Leu Lys Leu Ser Cys Glu Ala Ser Gly
225             230                 235                 240

Phe Thr Phe Ser Ser Phe Thr Met His Trp Val Arg Gln Ser Pro Gly
                245                 250                 255

Lys Gly Leu Glu Trp Val Ala Phe Ile Arg Ser Gly Ser Gly Ile Val
            260                 265                 270

Phe Tyr Ala Asp Ala Val Arg Gly Arg Phe Thr Ile Ser Arg Asp Asn
        275                 280                 285

Ala Lys Asn Leu Leu Phe Leu Gln Met Asn Asp Leu Lys Ser Glu Asp
    290                 295                 300

Thr Ala Met Tyr Tyr Cys Ala Arg Arg Pro Leu Gly His Asn Thr Phe
305             310                 315                 320

Asp Ser Trp Gly Gln Gly Thr Leu Val Thr Val Ser Ser Ala Ser Thr
```

-continued

```
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Glu
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
385                 390                 395                 400

Val Val Thr Val Pro Ser Ser Ser Leu Gly Thr Gln Thr Tyr Ile Cys
                405                 410                 415

Asn Val Asn His Lys Pro Ser Asn Thr Lys Val Asp Lys Lys Val Glu
            420                 425                 430

Pro Lys Ser Cys Asp Lys Thr His Thr Cys Pro Pro Cys Pro Ala Pro
        435                 440                 445

Glu Leu Leu Gly Gly Pro Ser Val Phe Leu Phe Pro Pro Lys Pro Lys
    450                 455                 460

Asp Thr Leu Met Ile Ser Arg Thr Pro Glu Val Thr Cys Val Val Val
465                 470                 475                 480

Asp Val Ser His Glu Asp Pro Glu Val Lys Phe Asn Trp Tyr Val Asp
                485                 490                 495

Gly Val Glu Val His Asn Ala Lys Thr Lys Pro Arg Glu Glu Gln Tyr
            500                 505                 510

Asn Ser Thr Tyr Arg Val Val Ser Val Leu Thr Val Leu His Gln Asp
        515                 520                 525

Trp Leu Asn Gly Lys Glu Tyr Lys Cys Lys Val Ser Asn Lys Ala Leu
    530                 535                 540

Pro Ala Pro Ile Glu Lys Thr Ile Ser Lys Ala Lys Gly Gln Pro Arg
545                 550                 555                 560

Glu Pro Gln Val Tyr Thr Leu Pro Pro Ser Arg Asp Glu Leu Thr Lys
                565                 570                 575

Asn Gln Val Ser Leu Thr Cys Leu Val Lys Gly Phe Tyr Pro Ser Asp
            580                 585                 590

Ile Ala Val Glu Trp Glu Ser Asn Gly Gln Pro Glu Asn Asn Tyr Lys
        595                 600                 605

Thr Thr Pro Pro Val Leu Asp Ser Asp Gly Ser Phe Phe Leu Tyr Ser
    610                 615                 620

Lys Leu Thr Val Asp Lys Ser Arg Trp Gln Gln Gly Asn Val Phe Ser
625                 630                 635                 640

Cys Ser Val Met His Glu Ala Leu His Asn His Tyr Thr Gln Lys Ser
                645                 650                 655

Leu Ser Leu Ser Pro Gly Lys
            660


<210> SEQ ID NO 540
<211> LENGTH: 215
<212> TYPE: PRT
<213> ORGANISM: Homo Sapiens

<400> SEQUENCE: 540

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Phe
            20                  25                  30
```

-continued

```
Tyr Met Ala Trp Val Arg Gln Ala Pro Lys Lys Gly Leu Glu Trp Val
        35                  40                  45

Ala Ser Ile Ser Tyr Glu Gly Ser Ser Thr Tyr Tyr Gly Asp Ser Val
    50                  55                  60

Met Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ala Arg Gln Arg Glu Ala Asn Trp Glu Asp Trp Gly Gln Gly Val Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val
    210                 215


<210> SEQ ID NO 541
<211> LENGTH: 220
<212> TYPE: PRT
<213> ORGANISM: Homo Sapiens

<400> SEQUENCE: 541

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 542
<211> LENGTH: 667
<212> TYPE: PRT
<213> ORGANISM: Homo Sapiens

<400> SEQUENCE: 542

Asp Ile Val Met Thr Gln Ser Pro Ser Ser Leu Ala Val Ser Pro Gly
1 5 10 15

Glu Lys Val Thr Met Thr Cys Lys Ser Ser Gln Ser Leu Tyr Tyr Ser
20 25 30

Gly Val Lys Glu Asn Leu Leu Ala Trp Tyr Gln Gln Lys Pro Gly Gln
35 40 45

Ser Pro Lys Leu Leu Ile Tyr Tyr Ala Ser Ile Arg Phe Thr Gly Val
50 55 60

Pro Asp Arg Phe Thr Gly Ser Gly Ser Gly Thr Asp Tyr Thr Leu Thr
65 70 75 80

Ile Thr Ser Val Gln Ala Glu Asp Met Gly Gln Tyr Phe Cys Gln Gln
85 90 95

Gly Ile Asn Asn Pro Leu Thr Phe Gly Asp Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys Glu Val Gln Leu
210 215 220

Val Glu Ser Gly Gly Gly Leu Val Gln Pro Gly Arg Ser Leu Lys Leu
225 230 235 240

Ser Cys Ala Ala Ser Gly Phe Thr Phe Ser Asp Phe Tyr Met Ala Trp
245 250 255

Val Arg Gln Ala Pro Lys Lys Gly Leu Glu Trp Val Ala Ser Ile Ser
260 265 270

Tyr Glu Gly Ser Ser Thr Tyr Tyr Gly Asp Ser Val Met Gly Arg Phe
275 280 285

Thr Ile Ser Arg Asp Asn Ala Lys Ser Thr Leu Tyr Leu Gln Met Asn
290 295 300

Ser Leu Arg Ser Glu Asp Thr Ala Thr Tyr Tyr Cys Ala Arg Gln Arg
305 310 315 320

Glu Ala Asn Trp Glu Asp Trp Gly Gln Gly Val Met Val Thr Val Ser
325 330 335

Ser Ala Ser Thr Lys Gly Pro Ser Val Phe Pro Leu Ala Pro Ser Ser

```
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445

Cys Pro Ala Pro Glu Leu Leu Gly Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
            500                 505                 510

Glu Glu Gln Tyr Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Asp
                565                 570                 575

Glu Leu Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly Lys
            660                 665


<210> SEQ ID NO 543
<211> LENGTH: 217
<212> TYPE: PRT
<213> ORGANISM: Homo Sapiens

<400> SEQUENCE: 543

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45
```

```
Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215
```

<210> SEQ ID NO 544
<211> LENGTH: 214
<212> TYPE: PRT
<213> ORGANISM: Homo Sapiens

<400> SEQUENCE: 544

```
Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 545
<211> LENGTH: 663
<212> TYPE: PRT
<213> ORGANISM: Homo Sapiens

<400> SEQUENCE: 545

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys Glu Val Gln Leu Val Glu Ser Gly Gly Gly
    210                 215                 220

Leu Thr Gln Pro Gly Lys Ser Leu Lys Leu Ser Cys Glu Ala Ser Gly
225                 230                 235                 240

Phe Thr Phe Ser Ser Phe Thr Met His Trp Val Arg Gln Ser Pro Gly
                245                 250                 255

Lys Gly Leu Glu Trp Val Ala Phe Ile Arg Ser Gly Ser Gly Ile Val
            260                 265                 270

Phe Tyr Ala Asp Ala Val Arg Gly Arg Phe Thr Ile Ser Arg Asp Asn
        275                 280                 285

Ala Lys Asn Leu Leu Phe Leu Gln Met Asn Asp Leu Lys Ser Glu Asp
    290                 295                 300

Thr Ala Met Tyr Tyr Cys Ala Arg Arg Pro Leu Gly His Asn Thr Phe
305                 310                 315                 320

Asp Ser Trp Gly Gln Gly Thr Leu Val Thr Val Ser Ser Ala Lys Thr
                325                 330                 335

Thr Ala Pro Ser Val Tyr Pro Leu Ala Pro Val Cys Gly Asp Thr Thr
            340                 345                 350

Gly Ser Ser Val Thr Leu Gly Cys Leu Val Lys Gly Tyr Phe Pro Glu
```

-continued

```
        355                 360                 365

Pro Val Thr Leu Thr Trp Asn Ser Gly Ser Leu Ser Ser Gly Val His
    370                 375                 380

Thr Phe Pro Ala Val Leu Gln Ser Asp Leu Tyr Thr Leu Ser Ser Ser
385                 390                 395                 400

Val Thr Val Thr Ser Ser Thr Trp Pro Ser Gln Ser Ile Thr Cys Asn
                405                 410                 415

Val Ala His Pro Ala Ser Ser Thr Lys Val Asp Lys Lys Ile Glu Pro
            420                 425                 430

Arg Gly Pro Thr Ile Lys Pro Cys Pro Pro Cys Lys Cys Pro Ala Pro
        435                 440                 445

Asn Leu Leu Gly Gly Pro Ser Val Phe Ile Phe Pro Pro Lys Ile Lys
    450                 455                 460

Asp Val Leu Met Ile Ser Leu Ser Pro Ile Val Thr Cys Val Val Val
465                 470                 475                 480

Asp Val Ser Glu Asp Asp Pro Asp Val Gln Ile Ser Trp Phe Val Asn
                485                 490                 495

Asn Val Glu Val His Thr Ala Gln Thr Gln Thr His Arg Glu Asp Tyr
            500                 505                 510

Asn Ser Thr Leu Arg Val Val Ser Ala Leu Pro Ile Gln His Gln Asp
        515                 520                 525

Trp Met Ser Gly Lys Glu Phe Lys Cys Lys Val Asn Asn Lys Asp Leu
    530                 535                 540

Pro Ala Pro Ile Glu Arg Thr Ile Ser Lys Pro Lys Gly Ser Val Arg
545                 550                 555                 560

Ala Pro Gln Val Tyr Val Leu Pro Pro Pro Glu Glu Glu Met Thr Lys
                565                 570                 575

Lys Gln Val Thr Leu Thr Cys Met Val Thr Asp Phe Met Pro Glu Asp
            580                 585                 590

Ile Tyr Val Glu Trp Thr Asn Asn Gly Lys Thr Glu Leu Asn Tyr Lys
        595                 600                 605

Asn Thr Glu Pro Val Leu Asp Ser Asp Gly Ser Tyr Phe Met Tyr Ser
    610                 615                 620

Lys Leu Arg Val Glu Lys Lys Asn Trp Val Glu Arg Asn Ser Tyr Ser
625                 630                 635                 640

Cys Ser Val Val His Glu Gly Leu His Asn His His Thr Thr Lys Ser
                645                 650                 655

Phe Ser Arg Thr Pro Gly Lys
            660


<210> SEQ ID NO 546
<211> LENGTH: 214
<212> TYPE: PRT
<213> ORGANISM: Homo Sapiens

<400> SEQUENCE: 546

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Phe
            20                  25                  30

Tyr Met Ala Trp Val Arg Gln Ala Pro Lys Lys Gly Leu Glu Trp Val
        35                  40                  45

Ala Ser Ile Ser Tyr Glu Gly Ser Ser Thr Tyr Tyr Gly Asp Ser Val
    50                  55                  60
```

```
Met Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ala Arg Gln Arg Glu Ala Asn Trp Glu Asp Trp Gly Gln Gly Val Met
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile
    210


<210> SEQ ID NO 547
<211> LENGTH: 220
<212> TYPE: PRT
<213> ORGANISM: Homo Sapiens

<400> SEQUENCE: 547

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220
```

<210> SEQ ID NO 548
<211> LENGTH: 667
<212> TYPE: PRT
<213> ORGANISM: Homo Sapiens

<400> SEQUENCE: 548

```
Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys Glu Val Gln Leu
    210                 215                 220

Val Glu Ser Gly Gly Gly Leu Val Gln Pro Gly Arg Ser Leu Lys Leu
225                 230                 235                 240

Ser Cys Ala Ala Ser Gly Phe Thr Phe Ser Asp Phe Tyr Met Ala Trp
                245                 250                 255

Val Arg Gln Ala Pro Lys Lys Gly Leu Glu Trp Val Ala Ser Ile Ser
            260                 265                 270

Tyr Glu Gly Ser Ser Thr Tyr Tyr Gly Asp Ser Val Met Gly Arg Phe
        275                 280                 285

Thr Ile Ser Arg Asp Asn Ala Lys Ser Thr Leu Tyr Leu Gln Met Asn
    290                 295                 300

Ser Leu Arg Ser Glu Asp Thr Ala Thr Tyr Tyr Cys Ala Arg Gln Arg
305                 310                 315                 320

Glu Ala Asn Trp Glu Asp Trp Gly Gln Gly Val Met Val Thr Val Ser
                325                 330                 335

Ser Ala Lys Thr Thr Ala Pro Ser Val Tyr Pro Leu Ala Pro Val Cys
            340                 345                 350

Gly Asp Thr Thr Gly Ser Ser Val Thr Leu Gly Cys Leu Val Lys Gly
        355                 360                 365

Tyr Phe Pro Glu Pro Val Thr Leu Thr Trp Asn Ser Gly Ser Leu Ser
```

370 375 380

Ser Gly Val His Thr Phe Pro Ala Val Leu Gln Ser Asp Leu Tyr Thr
385 390 395 400

Leu Ser Ser Ser Val Thr Val Thr Ser Ser Thr Trp Pro Ser Gln Ser
405 410 415

Ile Thr Cys Asn Val Ala His Pro Ala Ser Ser Thr Lys Val Asp Lys
420 425 430

Lys Ile Glu Pro Arg Gly Pro Thr Ile Lys Pro Cys Pro Pro Cys Lys
435 440 445

Cys Pro Ala Pro Asn Leu Leu Gly Gly Pro Ser Val Phe Ile Phe Pro
450 455 460

Pro Lys Ile Lys Asp Val Leu Met Ile Ser Leu Ser Pro Ile Val Thr
465 470 475 480

Cys Val Val Val Asp Val Ser Glu Asp Asp Pro Asp Val Gln Ile Ser
485 490 495

Trp Phe Val Asn Asn Val Glu Val His Thr Ala Gln Thr Gln Thr His
500 505 510

Arg Glu Asp Tyr Asn Ser Thr Leu Arg Val Val Ser Ala Leu Pro Ile
515 520 525

Gln His Gln Asp Trp Met Ser Gly Lys Glu Phe Lys Cys Lys Val Asn
530 535 540

Asn Lys Asp Leu Pro Ala Pro Ile Glu Arg Thr Ile Ser Lys Pro Lys
545 550 555 560

Gly Ser Val Arg Ala Pro Gln Val Tyr Val Leu Pro Pro Pro Glu Glu
565 570 575

Glu Met Thr Lys Lys Gln Val Thr Leu Thr Cys Met Val Thr Asp Phe
580 585 590

Met Pro Glu Asp Ile Tyr Val Glu Trp Thr Asn Asn Gly Lys Thr Glu
595 600 605

Leu Asn Tyr Lys Asn Thr Glu Pro Val Leu Asp Ser Asp Gly Ser Tyr
610 615 620

Phe Met Tyr Ser Lys Leu Arg Val Glu Lys Lys Asn Trp Val Glu Arg
625 630 635 640

Asn Ser Tyr Ser Cys Ser Val Val His Glu Gly Leu His Asn His His
645 650 655

Thr Thr Lys Ser Phe Ser Arg Thr Pro Gly Lys
660 665

<210> SEQ ID NO 549
<211> LENGTH: 216
<212> TYPE: PRT
<213> ORGANISM: Homo Sapiens

<400> SEQUENCE: 549

Glu Val Gln Leu Val Glu Ser Gly Gly Gly Leu Thr Gln Pro Gly Lys
1 5 10 15

Ser Leu Lys Leu Ser Cys Glu Ala Ser Gly Phe Thr Phe Ser Ser Phe
20 25 30

Thr Met His Trp Val Arg Gln Ser Pro Gly Lys Gly Leu Glu Trp Val
35 40 45

Ala Phe Ile Arg Ser Gly Ser Gly Ile Val Phe Tyr Ala Asp Ala Val
50 55 60

Arg Gly Arg Phe Thr Ile Ser Arg Asp Asn Ala Lys Asn Leu Leu Phe
65 70 75 80

-continued

```
Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile
    210                 215


<210> SEQ ID NO 550
<211> LENGTH: 214
<212> TYPE: PRT
<213> ORGANISM: Homo Sapiens

<400> SEQUENCE: 550

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 551
```

<211> LENGTH: 659
<212> TYPE: PRT
<213> ORGANISM: Homo Sapiens

<400> SEQUENCE: 551

```
Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Thr Gln Pro Gly Lys Ser Leu Lys Leu Ser Cys Glu Ala Ser Gly
225                 230                 235                 240

Phe Thr Phe Ser Ser Phe Thr Met His Trp Val Arg Gln Ser Pro Gly
                245                 250                 255

Lys Gly Leu Glu Trp Val Ala Phe Ile Arg Ser Gly Ser Gly Ile Val
            260                 265                 270

Phe Tyr Ala Asp Ala Val Arg Gly Arg Phe Thr Ile Ser Arg Asp Asn
        275                 280                 285

Ala Lys Asn Leu Leu Phe Leu Gln Met Asn Asp Leu Lys Ser Glu Asp
    290                 295                 300

Thr Ala Met Tyr Tyr Cys Ala Arg Arg Pro Leu Gly His Asn Thr Phe
305                 310                 315                 320

Asp Ser Trp Gly Gln Gly Thr Leu Val Thr Val Ser Ser Ala Ser Thr
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Glu
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
```

385 390 395 400

Val Val Thr Val Pro Ser Ser Ser Leu Gly Thr Gln Thr Tyr Ile Cys
405 410 415

Asn Val Asn His Lys Pro Ser Asn Thr Lys Val Asp Lys Lys Val Glu
420 425 430

Pro Lys Ser Cys Asp Lys Thr His Thr Cys Pro Pro Asn Leu Leu Gly
435 440 445

Gly Pro Ser Val Phe Ile Phe Pro Pro Lys Ile Lys Asp Val Leu Met
450 455 460

Ile Ser Leu Ser Pro Ile Val Thr Cys Val Val Val Asp Val Ser Glu
465 470 475 480

Asp Asp Pro Asp Val Gln Ile Ser Trp Phe Val Asn Asn Val Glu Val
485 490 495

His Thr Ala Gln Thr Gln Thr His Arg Glu Asp Tyr Asn Ser Thr Leu
500 505 510

Arg Val Val Ser Ala Leu Pro Ile Gln His Gln Asp Trp Met Ser Gly
515 520 525

Lys Glu Phe Lys Cys Lys Val Asn Asn Lys Asp Leu Pro Ala Pro Ile
530 535 540

Glu Arg Thr Ile Ser Lys Pro Lys Gly Ser Val Arg Ala Pro Gln Val
545 550 555 560

Tyr Val Leu Pro Pro Pro Glu Glu Glu Met Thr Lys Lys Gln Val Thr
565 570 575

Leu Thr Cys Met Val Thr Asp Phe Met Pro Glu Asp Ile Tyr Val Glu
580 585 590

Trp Thr Asn Asn Gly Lys Thr Glu Leu Asn Tyr Lys Asn Thr Glu Pro
595 600 605

Val Leu Asp Ser Asp Gly Ser Tyr Phe Met Tyr Ser Lys Leu Arg Val
610 615 620

Glu Lys Lys Asn Trp Val Glu Arg Asn Ser Tyr Ser Cys Ser Val Val
625 630 635 640

His Glu Gly Leu His Asn His His Thr Thr Lys Ser Phe Ser Arg Thr
645 650 655

Pro Gly Lys

<210> SEQ ID NO 552
<211> LENGTH: 215
<212> TYPE: PRT
<213> ORGANISM: Homo Sapiens

<400> SEQUENCE: 552

Glu Val Gln Leu Val Glu Ser Gly Gly Gly Leu Val Gln Pro Gly Arg
1 5 10 15

Ser Leu Lys Leu Ser Cys Ala Ala Ser Gly Phe Thr Phe Ser Asp Phe
20 25 30

Tyr Met Ala Trp Val Arg Gln Ala Pro Lys Lys Gly Leu Glu Trp Val
35 40 45

Ala Ser Ile Ser Tyr Glu Gly Ser Ser Thr Tyr Tyr Gly Asp Ser Val
50 55 60

Met Gly Arg Phe Thr Ile Ser Arg Asp Asn Ala Lys Ser Thr Leu Tyr
65 70 75 80

Leu Gln Met Asn Ser Leu Arg Ser Glu Asp Thr Ala Thr Tyr Tyr Cys
85 90 95

Ala Arg Gln Arg Glu Ala Asn Trp Glu Asp Trp Gly Gln Gly Val Met

```
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val
    210                 215


<210> SEQ ID NO 553
<211> LENGTH: 220
<212> TYPE: PRT
<213> ORGANISM: Homo Sapiens

<400> SEQUENCE: 553

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 554
<211> LENGTH: 663
<212> TYPE: PRT
<213> ORGANISM: Homo Sapiens
```

<400> SEQUENCE: 554

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Glu Val Gln Leu
    210                 215                 220

Val Glu Ser Gly Gly Gly Leu Val Gln Pro Gly Arg Ser Leu Lys Leu
225                 230                 235                 240

Ser Cys Ala Ala Ser Gly Phe Thr Phe Ser Asp Phe Tyr Met Ala Trp
                245                 250                 255

Val Arg Gln Ala Pro Lys Lys Gly Leu Glu Trp Val Ala Ser Ile Ser
            260                 265                 270

Tyr Glu Gly Ser Ser Thr Tyr Tyr Gly Asp Ser Val Met Gly Arg Phe
        275                 280                 285

Thr Ile Ser Arg Asp Asn Ala Lys Ser Thr Leu Tyr Leu Gln Met Asn
    290                 295                 300

Ser Leu Arg Ser Glu Asp Thr Ala Thr Tyr Tyr Cys Ala Arg Gln Arg
305                 310                 315                 320

Glu Ala Asn Trp Glu Asp Trp Gly Gln Gly Val Met Val Thr Val Ser
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

```
Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445

Asn Leu Leu Gly Gly Pro Ser Val Phe Ile Phe Pro Pro Lys Ile Lys
    450                 455                 460

Asp Val Leu Met Ile Ser Leu Ser Pro Ile Val Thr Cys Val Val Val
465                 470                 475                 480

Asp Val Ser Glu Asp Asp Pro Asp Val Gln Ile Ser Trp Phe Val Asn
                485                 490                 495

Asn Val Glu Val His Thr Ala Gln Thr Gln Thr His Arg Glu Asp Tyr
            500                 505                 510

Asn Ser Thr Leu Arg Val Val Ser Ala Leu Pro Ile Gln His Gln Asp
        515                 520                 525

Trp Met Ser Gly Lys Glu Phe Lys Cys Lys Val Asn Asn Lys Asp Leu
    530                 535                 540

Pro Ala Pro Ile Glu Arg Thr Ile Ser Lys Pro Lys Gly Ser Val Arg
545                 550                 555                 560

Ala Pro Gln Val Tyr Val Leu Pro Pro Pro Glu Glu Glu Met Thr Lys
                565                 570                 575

Lys Gln Val Thr Leu Thr Cys Met Val Thr Asp Phe Met Pro Glu Asp
            580                 585                 590

Ile Tyr Val Glu Trp Thr Asn Asn Gly Lys Thr Glu Leu Asn Tyr Lys
        595                 600                 605

Asn Thr Glu Pro Val Leu Asp Ser Asp Gly Ser Tyr Phe Met Tyr Ser
    610                 615                 620

Lys Leu Arg Val Glu Lys Lys Asn Trp Val Glu Arg Asn Ser Tyr Ser
625                 630                 635                 640

Cys Ser Val Val His Glu Gly Leu His Asn His His Thr Thr Lys Ser
                645                 650                 655

Phe Ser Arg Thr Pro Gly Lys
            660


<210> SEQ ID NO 555
<211> LENGTH: 217
<212> TYPE: PRT
<213> ORGANISM: Homo Sapiens

<400> SEQUENCE: 555

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
```

```
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val
    210                 215


<210> SEQ ID NO 556
<211> LENGTH: 214
<212> TYPE: PRT
<213> ORGANISM: Homo Sapiens

<400> SEQUENCE: 556

Asp Ile Gln Met Thr Gln Ser Pro Ala Ser Leu Ser Ala Ser Leu Gly
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 557
<211> LENGTH: 659
<212> TYPE: PRT
<213> ORGANISM: Homo Sapiens

<400> SEQUENCE: 557

Asp Ile Gln Met Thr Gln Ser Pro Ala Ser Leu Ser Ala Ser Leu Gly
```

-continued

```
1               5                   10                  15

Glu Thr Val Thr Ile Gln Cys Arg Ala Ser Glu Asp Ile Tyr Ser Gly
            20                  25                  30

Leu Ala Trp Phe Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Ser Met Gln Thr
65                  70                  75                  80

Glu Asp Glu Gly Val Tyr Phe Cys Gln Gln Gly Leu Lys Tyr Pro Pro
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Thr Gln Pro Gly Lys Ser Leu Lys Leu Ser Cys Glu Ala Ser Gly
225                 230                 235                 240

Phe Thr Phe Ser Ser Phe Thr Met His Trp Val Arg Gln Ser Pro Gly
                245                 250                 255

Lys Gly Leu Glu Trp Val Ala Phe Ile Arg Ser Gly Ser Gly Ile Val
            260                 265                 270

Phe Tyr Ala Asp Ala Val Arg Gly Arg Phe Thr Ile Ser Arg Asp Asn
        275                 280                 285

Ala Lys Asn Leu Leu Phe Leu Gln Met Asn Asp Leu Lys Ser Glu Asp
    290                 295                 300

Thr Ala Met Tyr Tyr Cys Ala Arg Arg Pro Leu Gly His Asn Thr Phe
305                 310                 315                 320

Asp Ser Trp Gly Gln Gly Thr Leu Val Thr Val Ser Ser Ala Ser Thr
                325                 330                 335

Lys Gly Pro Ser Val Phe Pro Leu Ala Pro Ser Ser Lys Ser Thr Ser
            340                 345                 350

Gly Gly Thr Ala Ala Leu Gly Cys Leu Val Lys Asp Tyr Phe Pro Glu
        355                 360                 365

Pro Val Thr Val Ser Trp Asn Ser Gly Ala Leu Thr Ser Gly Val His
    370                 375                 380

Thr Phe Pro Ala Val Leu Gln Ser Ser Gly Leu Tyr Ser Leu Ser Ser
385                 390                 395                 400

Val Val Thr Val Pro Ser Ser Ser Leu Gly Thr Gln Thr Tyr Ile Cys
                405                 410                 415

Asn Val Asn His Lys Pro Ser Asn Thr Lys Val Asp Lys Lys Val Glu
            420                 425                 430
```

Pro Lys Ser Cys Asp Lys Thr His Thr Cys Pro Pro Asn Leu Leu Gly
435 440 445

Gly Pro Ser Val Phe Ile Phe Pro Pro Lys Ile Lys Asp Val Leu Met
450 455 460

Ile Ser Leu Ser Pro Ile Val Thr Cys Val Val Val Asp Val Ser Glu
465 470 475 480

Asp Asp Pro Asp Val Gln Ile Ser Trp Phe Val Asn Asn Val Glu Val
485 490 495

His Thr Ala Gln Thr Gln Thr His Arg Glu Asp Tyr Asn Ser Thr Leu
500 505 510

Arg Val Val Ser Ala Leu Pro Ile Gln His Gln Asp Trp Met Ser Gly
515 520 525

Lys Glu Phe Lys Cys Lys Val Asn Asn Lys Asp Leu Pro Ala Pro Ile
530 535 540

Glu Arg Thr Ile Ser Lys Pro Lys Gly Ser Val Arg Ala Pro Gln Val
545 550 555 560

Tyr Val Leu Pro Pro Pro Glu Glu Glu Met Thr Lys Lys Gln Val Thr
565 570 575

Leu Thr Cys Met Val Thr Asp Phe Met Pro Glu Asp Ile Tyr Val Glu
580 585 590

Trp Thr Asn Asn Gly Lys Thr Glu Leu Asn Tyr Lys Asn Thr Glu Pro
595 600 605

Val Leu Asp Ser Asp Gly Ser Tyr Phe Met Tyr Ser Lys Leu Arg Val
610 615 620

Glu Lys Lys Asn Trp Val Glu Arg Asn Ser Tyr Ser Cys Ser Val Val
625 630 635 640

His Glu Gly Leu His Asn His His Thr Thr Lys Ser Phe Ser Arg Thr
645 650 655

Pro Gly Lys

<210> SEQ ID NO 558
<211> LENGTH: 215
<212> TYPE: PRT
<213> ORGANISM: Homo Sapiens

<400> SEQUENCE: 558

Glu Val Gln Leu Val Glu Ser Gly Gly Gly Leu Val Gln Pro Gly Arg
1 5 10 15

Ser Leu Lys Leu Ser Cys Ala Ala Ser Gly Phe Thr Phe Ser Asp Phe
20 25 30

Tyr Met Ala Trp Val Arg Gln Ala Pro Lys Lys Gly Leu Glu Trp Val
35 40 45

Ala Ser Ile Ser Tyr Glu Gly Ser Ser Thr Tyr Tyr Gly Asp Ser Val
50 55 60

Met Gly Arg Phe Thr Ile Ser Arg Asp Asn Ala Lys Ser Thr Leu Tyr
65 70 75 80

Leu Gln Met Asn Ser Leu Arg Ser Glu Asp Thr Ala Thr Tyr Tyr Cys
85 90 95

Ala Arg Gln Arg Glu Ala Asn Trp Glu Asp Trp Gly Gln Gly Val Met
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val
    210                 215


<210> SEQ ID NO 559
<211> LENGTH: 220
<212> TYPE: PRT
<213> ORGANISM: Homo Sapiens

<400> SEQUENCE: 559

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 560
<211> LENGTH: 663
<212> TYPE: PRT
<213> ORGANISM: Homo Sapiens

<400> SEQUENCE: 560

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30
```

-continued

```
Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Glu Val Gln Leu
    210                 215                 220

Val Glu Ser Gly Gly Gly Leu Val Gln Pro Gly Arg Ser Leu Lys Leu
225                 230                 235                 240

Ser Cys Ala Ala Ser Gly Phe Thr Phe Ser Asp Phe Tyr Met Ala Trp
                245                 250                 255

Val Arg Gln Ala Pro Lys Lys Gly Leu Glu Trp Val Ala Ser Ile Ser
            260                 265                 270

Tyr Glu Gly Ser Ser Thr Tyr Tyr Gly Asp Ser Val Met Gly Arg Phe
        275                 280                 285

Thr Ile Ser Arg Asp Asn Ala Lys Ser Thr Leu Tyr Leu Gln Met Asn
    290                 295                 300

Ser Leu Arg Ser Glu Asp Thr Ala Thr Tyr Tyr Cys Ala Arg Gln Arg
305                 310                 315                 320

Glu Ala Asn Trp Glu Asp Trp Gly Gln Gly Val Met Val Thr Val Ser
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
        355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
            420                 425                 430

Lys Lys Val Glu Pro Lys Ser Cys Asp Lys Thr His Thr Cys Pro Pro
        435                 440                 445
```

```
Asn Leu Leu Gly Gly Pro Ser Val Phe Ile Phe Pro Pro Lys Ile Lys
    450                 455                 460

Asp Val Leu Met Ile Ser Leu Ser Pro Ile Val Thr Cys Val Val Val
465                 470                 475                 480

Asp Val Ser Glu Asp Asp Pro Asp Val Gln Ile Ser Trp Phe Val Asn
                485                 490                 495

Asn Val Glu Val His Thr Ala Gln Thr Gln Thr His Arg Glu Asp Tyr
            500                 505                 510

Asn Ser Thr Leu Arg Val Val Ser Ala Leu Pro Ile Gln His Gln Asp
        515                 520                 525

Trp Met Ser Gly Lys Glu Phe Lys Cys Lys Val Asn Asn Lys Asp Leu
    530                 535                 540

Pro Ala Pro Ile Glu Arg Thr Ile Ser Lys Pro Lys Gly Ser Val Arg
545                 550                 555                 560

Ala Pro Gln Val Tyr Val Leu Pro Pro Pro Glu Glu Glu Met Thr Lys
                565                 570                 575

Lys Gln Val Thr Leu Thr Cys Met Val Thr Asp Phe Met Pro Glu Asp
            580                 585                 590

Ile Tyr Val Glu Trp Thr Asn Asn Gly Lys Thr Glu Leu Asn Tyr Lys
        595                 600                 605

Asn Thr Glu Pro Val Leu Asp Ser Asp Gly Ser Tyr Phe Met Tyr Ser
    610                 615                 620

Lys Leu Arg Val Glu Lys Lys Asn Trp Val Glu Arg Asn Ser Tyr Ser
625                 630                 635                 640

Cys Ser Val Val His Glu Gly Leu His Asn His His Thr Thr Lys Ser
                645                 650                 655

Phe Ser Arg Thr Pro Gly Lys
            660


<210> SEQ ID NO 561
<211> LENGTH: 217
<212> TYPE: PRT
<213> ORGANISM: Homo Sapiens

<400> SEQUENCE: 561

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val
210 215

<210> SEQ ID NO 562
<211> LENGTH: 214
<212> TYPE: PRT
<213> ORGANISM: Homo Sapiens

<400> SEQUENCE: 562

Asp Ile Gln Met Thr Gln Ser Pro Ala Ser Leu Ser Ala Ser Leu Gly
1 5 10 15

Glu Thr Val Thr Ile Gln Cys Arg Ala Ser Glu Asp Ile Tyr Ser Gly
20 25 30

Leu Ala Trp Phe Gln Gln Lys Pro Gly Lys Ser Pro Gln Leu Leu Ile
35 40 45

Tyr Gly Ala Ser Ser Leu Gln Asp Gly Val Pro Ser Arg Phe Ser Gly
50 55 60

Ser Gly Ser Gly Thr Gln Tyr Ser Leu Lys Ile Ser Ser Met Gln Thr
65 70 75 80

Glu Asp Glu Gly Val Tyr Phe Cys Gln Gln Gly Leu Lys Tyr Pro Pro
85 90 95

Thr Phe Gly Ser Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 563
<211> LENGTH: 364
<212> TYPE: DNA
<213> ORGANISM: Homo Sapiens

<400> SEQUENCE: 563
caggttcaac tgatgcagtc tggaactgag gtgaagaagc ctggggcctc agtgaaggtc 60
tcctgcaaga cttctggtta cacctttacc acctatggta tcacttgggt gcgacaggcc 120
cctggacaag ggcttgagtg gatgggatgg atcagcgctt acagtggtga cacagactat 180
gcacagaagt tccagggcag agtcaccgtg acaacagaca catccacgaa cacagcctac 240
atggagttga ggagcctgaa atctgacgac acggccgtgt attattgtgc gagaagtagt 300
ggctggcccc accactacgg tatggacgtc tggggccaag ggaccacggt caccgtctcc 360
tcag 364

<210> SEQ ID NO 564
<211> LENGTH: 121
<212> TYPE: PRT
<213> ORGANISM: Homo Sapiens

<400> SEQUENCE: 564

Gln Val Gln Leu Met Gln Ser Gly Thr Glu Val Lys Lys Pro Gly Ala
1 5 10 15

Ser Val Lys Val Ser Cys Lys Thr Ser Gly Tyr Thr Phe Thr Thr Tyr
20 25 30

Gly Ile Thr Trp Val Arg Gln Ala Pro Gly Gln Gly Leu Glu Trp Met
35 40 45

Gly Trp Ile Ser Ala Tyr Ser Gly Asp Thr Asp Tyr Ala Gln Lys Phe
50 55 60

Gln Gly Arg Val Thr Val Thr Thr Asp Thr Ser Thr Asn Thr Ala Tyr
65 70 75 80

Met Glu Leu Arg Ser Leu Lys Ser Asp Asp Thr Ala Val Tyr Tyr Cys
85 90 95

Ala Arg Ser Ser Gly Trp Pro His His Tyr Gly Met Asp Val Trp Gly
100 105 110

Gln Gly Thr Thr Val Thr Val Ser Ser
115 120

<210> SEQ ID NO 565
<211> LENGTH: 8
<212> TYPE: PRT
<213> ORGANISM: Homo Sapiens

<400> SEQUENCE: 565

Gly Tyr Thr Phe Thr Thr Tyr Gly
1 5

<210> SEQ ID NO 566
<211> LENGTH: 8
<212> TYPE: PRT
<213> ORGANISM: Homo Sapiens

<400> SEQUENCE: 566

Ile Ser Ala Tyr Ser Gly Asp Thr
1 5

<210> SEQ ID NO 567
<211> LENGTH: 14
<212> TYPE: PRT
<213> ORGANISM: Homo Sapiens

<400> SEQUENCE: 567

Ala Arg Ser Ser Gly Trp Pro His His Tyr Gly Met Asp Val
1 5 10

<210> SEQ ID NO 568
<211> LENGTH: 373
<212> TYPE: DNA
<213> ORGANISM: Homo Sapiens

<400> SEQUENCE: 568

-continued

```
caggttcaac tggtgcagtc tggaggtgag gtgaaaaagc ctggggcctc agtgaaggtc      60

tcctgcaagg cttctggtta cacctttacc agctatggtt tcagctgggt gcgacaggcc     120

cctggacaag gactagagtg gatgggatgg atcagcgctt acaatggtaa cacaaactat     180

gcacagaagc tccagggcag agtctccatg accacagaca catccacgag cacagcctac     240

atggagctga ggagcttgag atctgacgac acggccgtgt atttctgtgc gcgatctacg     300

tcttactatg gttcggggac cctatacggt atggacgtct ggggccaagg gaccacggtc     360

accgtctcct cag                                                        373
```

<210> SEQ ID NO 569
<211> LENGTH: 124
<212> TYPE: PRT
<213> ORGANISM: Homo Sapiens

<400> SEQUENCE: 569

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Ser Thr Ser Tyr Tyr Gly Ser Gly Thr Leu Tyr Gly Met Asp
            100                 105                 110

Val Trp Gly Gln Gly Thr Thr Val Thr Val Ser Ser
        115                 120
```

<210> SEQ ID NO 570
<211> LENGTH: 17
<212> TYPE: PRT
<213> ORGANISM: Homo Sapiens

<400> SEQUENCE: 570

```
Ala Arg Ser Thr Ser Tyr Tyr Gly Ser Gly Thr Leu Tyr Gly Met Asp
1               5                   10                  15

Val
```

<210> SEQ ID NO 571
<211> LENGTH: 373
<212> TYPE: DNA
<213> ORGANISM: Homo Sapiens

<400> SEQUENCE: 571

```
caggttcaac tggtgcagtc tggaggtgag gtgaagaagc ctggggcctc agtgaaggtc      60

tcctgcaagg cttctggtta cacctttacc agctatggtt tcagctgggt gcgacaggcc     120

cctggacaag gactagagtg gatgggatgg atcagcgctt acaatggtaa cacaaactat     180

gcacagaagc tccagggcag agtctccatg accacagaca catccacgag cacagcctac     240

atggagctga ggagcttgag atctgacgac acggccgtgt attactgtgc gcgatctacg     300

tcttactatg gttcggggac cctctacggt atggacgtct ggggccaagg gaccacggtc     360
```

accgtctcct cag 373

<210> SEQ ID NO 572
<211> LENGTH: 124
<212> TYPE: PRT
<213> ORGANISM: Homo Sapiens

<400> SEQUENCE: 572

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Ser Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Thr Ser Tyr Tyr Gly Ser Gly Thr Leu Tyr Gly Met Asp
            100                 105                 110

Val Trp Gly Gln Gly Thr Thr Val Thr Val Ser Ser
        115                 120
```

<210> SEQ ID NO 573
<211> LENGTH: 373
<212> TYPE: DNA
<213> ORGANISM: Homo Sapiens

<400> SEQUENCE: 573

```
caggttcaac tggtgcagtc tggaggtgag gtgaaaaagc ctggggcctc agtgaaggtc      60

tcctgcaagg cttctggtta cacctttacc agctatggtt tcagctgggt gcgacaggcc     120

cctggacaag gactagagtg gatgggatgg atcagcgctt acaatggtaa cacaaactat     180

gcacagaagc tccagggcag agtctccatg accacagaca catccacgag cacagcctac     240

atggagctga ggagcttgag atctgacgac acggccgtgt atttctgtgc gcgatctacg     300

tcttactatg gttcggggac cctatacggt atggacgtct ggggccaagg gaccacggtc     360

accgtctcct cag                                                        373
```

<210> SEQ ID NO 574
<211> LENGTH: 124
<212> TYPE: PRT
<213> ORGANISM: Homo Sapiens

<400> SEQUENCE: 574

```
Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Ser Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Phe Cys
                85                  90                  95

Ala Arg Ser Thr Ser Tyr Tyr Gly Ser Gly Thr Leu Tyr Gly Met Asp
            100                 105                 110

Val Trp Gly Gln Gly Thr Thr Val Thr Val Ser Ser
        115                 120
```

<210> SEQ ID NO 575
<211> LENGTH: 373
<212> TYPE: DNA
<213> ORGANISM: Homo Sapiens

<400> SEQUENCE: 575

```
caggttcaac tggtgcagtc tggaggtgag gtgaaaaagc ctcgggcctc agtgaaggtc     60

tcctgcaagg cttctggtta cacctttacc agctatgtgt tcagctgggt gcgacatgcc    120

gctggacaag gactagagtg gatgggatgg atcagcggtt acaatggtaa cacaaactat    180

gcacagaagc tccagtgcgg agtctcgatg accgcagaca catccacgag cacagcctac    240

atggagctga ggagcttgag atctgacgac acggccgtgt atttctgtgc gcgatctacg    300

tcttactatg gtgcggggac cctatacggt atggacgtct ggggccaagg gaccacggtc    360

accgtctcct cag                                                       373
```

<210> SEQ ID NO 576
<211> LENGTH: 124
<212> TYPE: PRT
<213> ORGANISM: Homo Sapiens

<400> SEQUENCE: 576

```
Gln Val Gln Leu Val Gln Ser Gly Gly Glu Val Lys Lys Pro Arg Ala
1               5                   10                  15

Ser Val Lys Val Ser Cys Lys Ala Ser Gly Tyr Thr Phe Thr Ser Tyr
            20                  25                  30

Val Phe Ser Trp Val Arg His Ala Ala Gly Gln Gly Leu Glu Trp Met
        35                  40                  45

Gly Trp Ile Ser Gly Tyr Asn Gly Asn Thr Asn Tyr Ala Gln Lys Leu
    50                  55                  60

Gln Cys Gly Val Ser Met Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Ser Thr Ser Tyr Tyr Gly Ala Gly Thr Leu Tyr Gly Met Asp
            100                 105                 110

Val Trp Gly Gln Gly Thr Thr Val Thr Val Ser Ser
        115                 120
```

<210> SEQ ID NO 577
<211> LENGTH: 8
<212> TYPE: PRT
<213> ORGANISM: Homo Sapiens

<400> SEQUENCE: 577

```
Gly Tyr Thr Phe Thr Ser Tyr Val
1               5
```

<210> SEQ ID NO 578
<211> LENGTH: 8
<212> TYPE: PRT
<213> ORGANISM: Homo Sapiens

<400> SEQUENCE: 578

Ile Ser Gly Tyr Asn Gly Asn Thr
1 5

<210> SEQ ID NO 579
<211> LENGTH: 17
<212> TYPE: PRT
<213> ORGANISM: Homo Sapiens

<400> SEQUENCE: 579

Ala Arg Ser Thr Ser Tyr Tyr Gly Ala Gly Thr Leu Tyr Gly Met Asp
1 5 10 15

Val

<210> SEQ ID NO 580
<211> LENGTH: 373
<212> TYPE: DNA
<213> ORGANISM: Homo Sapiens

<400> SEQUENCE: 580
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttgt attactgtgc ggccgattac 300
tatggttcgg ggagttatta taacgtcccc tttgactact ggggccaggg aaccctggtc 360
accgtctcct cag 373

<210> SEQ ID NO 581
<211> LENGTH: 124
<212> TYPE: PRT
<213> ORGANISM: Homo Sapiens

<400> SEQUENCE: 581

Glu Val Gln Leu Val Glu Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Ala Asp Tyr Tyr Gly Ser Gly Ser Tyr Tyr Asn Val Pro Phe Asp
100 105 110

Tyr Trp Gly Gln Gly Thr Leu Val Thr Val Ser Ser
115 120

<210> SEQ ID NO 582
<211> LENGTH: 8
<212> TYPE: PRT
<213> ORGANISM: Homo Sapiens

<400> SEQUENCE: 582

Gly Phe Thr Phe Asp Asp Tyr Gly
1 5

<210> SEQ ID NO 583
<211> LENGTH: 8
<212> TYPE: PRT
<213> ORGANISM: Homo Sapiens

<400> SEQUENCE: 583

Ile Asn Trp Asn Gly Gly Ser Thr
1 5

<210> SEQ ID NO 584
<211> LENGTH: 17
<212> TYPE: PRT
<213> ORGANISM: Homo Sapiens

<400> SEQUENCE: 584

Ala Ala Asp Tyr Tyr Gly Ser Gly Ser Tyr Tyr Asn Val Pro Phe Asp
1 5 10 15

Tyr

<210> SEQ ID NO 585
<211> LENGTH: 373
<212> TYPE: DNA
<213> ORGANISM: Homo Sapiens

<400> SEQUENCE: 585
gaggtgcagc tggtggagtc tgggggaggt gtgatacggc ctggggggtc cctgagactc 60
tcctgtgcag cctctggatt cacctttgat gattatggca tgagctgggt ccgccaagct 120
ccagggaagg ggctggagtg ggtctctggt attaattgga ttggtgataa cacagattat 180
gcagactctg tgaagggccg attcaccatc tccagagaca acgccaagaa ctccctatat 240
ctgcaaatga acagtctgag agccgaggac acggccttgt attactgtgc gagagattac 300
tttggttcgg ggagttatta taacgttccc tttgactact ggggccaggg aaccctggtc 360
accgtctcct cag 373

<210> SEQ ID NO 586
<211> LENGTH: 124
<212> TYPE: PRT
<213> ORGANISM: Homo Sapiens

<400> SEQUENCE: 586

Glu Val Gln Leu Val Glu Ser Gly Gly Gly Val Ile Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Ile Gly Asp Asn Thr Asp Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Arg Asp Tyr Phe Gly Ser Gly Ser Tyr Tyr Asn Val Pro Phe Asp
100 105 110

Tyr Trp Gly Gln Gly Thr Leu Val Thr Val Ser Ser
            115                 120

<210> SEQ ID NO 587
<211> LENGTH: 8
<212> TYPE: PRT
<213> ORGANISM: Homo Sapiens

<400> SEQUENCE: 587

Ile Asn Trp Ile Gly Asp Asn Thr
1               5

<210> SEQ ID NO 588
<211> LENGTH: 17
<212> TYPE: PRT
<213> ORGANISM: Homo Sapiens

<400> SEQUENCE: 588

Ala Arg Asp Tyr Phe Gly Ser Gly Ser Tyr Tyr Asn Val Pro Phe Asp
1               5                   10                  15

Tyr

<210> SEQ ID NO 589
<211> LENGTH: 337
<212> TYPE: DNA
<213> ORGANISM: Homo Sapiens

<400> SEQUENCE: 589
gatattgtga tgactcagtc tccactctcc ctgcccgtca cccctggaga gccggcctcc    60
atctcctgca ggtctagtca gagcctcctg catagtaatg gattcaacta tttcgattgg   120
tacctgcaga agccaggaca gtctccacag ctcctgatct ttttggtttc taatcgggcc   180
tccggggtcc ctgacaggtt cagtggcagt ggatcaggca cagattttac actgaaaatc   240
agcagagtgg aggctgagga tgttgggatt tattactgca tgcaagctct acaaactccg   300
ctcactttcg gcggagggac caaggtggag atcaaac                            337

<210> SEQ ID NO 590
<211> LENGTH: 112
<212> TYPE: PRT
<213> ORGANISM: Homo Sapiens

<400> SEQUENCE: 590

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Phe Asp Trp Tyr Leu Gln Lys Pro Gly Gln Ser
        35                  40                  45

Pro Gln Leu Leu Ile Phe Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 591

<211> LENGTH: 11
<212> TYPE: PRT
<213> ORGANISM: Homo Sapiens

<400> SEQUENCE: 591

Gln Ser Leu Leu His Ser Asn Gly Phe Asn Tyr
1 5 10

<210> SEQ ID NO 592
<211> LENGTH: 3
<212> TYPE: PRT
<213> ORGANISM: Homo Sapiens

<400> SEQUENCE: 592

Leu Val Ser
1

<210> SEQ ID NO 593
<211> LENGTH: 9
<212> TYPE: PRT
<213> ORGANISM: Homo Sapiens

<400> SEQUENCE: 593

Met Gln Ala Leu Gln Thr Pro Leu Thr
1 5

<210> SEQ ID NO 594
<211> LENGTH: 337
<212> TYPE: DNA
<213> ORGANISM: Homo Sapiens

<400> SEQUENCE: 594
gatattgtga tgactcagtc tccactctcc ctgcccgtca cccctggaga gccggcctcc 60
atctcctgca ggtctagtca gagcctcctg catagtaatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
tgcagttttg gccaggggac caagctggag atcaaac 337

<210> SEQ ID NO 595
<211> LENGTH: 112
<212> TYPE: PRT
<213> ORGANISM: Homo Sapiens

<400> SEQUENCE: 595

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Cys Leu Asp Trp Tyr Leu Gln Lys Pro Gly Gln Ser
35 40 45

Pro Gln Leu Leu Ile Tyr Leu Gly Ser Thr Arg Ala Ser Gly Phe Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Cys Ser Phe Gly Gln Gly Thr Lys Leu Glu Ile Lys
100 105 110

<210> SEQ ID NO 596
<211> LENGTH: 11
<212> TYPE: PRT
<213> ORGANISM: Homo Sapiens

<400> SEQUENCE: 596

Gln Ser Leu Leu His Ser Asn Gly Tyr Asn Cys
1               5                   10

<210> SEQ ID NO 597
<211> LENGTH: 337
<212> TYPE: DNA
<213> ORGANISM: Homo Sapiens

<400> SEQUENCE: 597
gatattgtga tgactcagtc tccactctcc ctgcccgtca cccctggaga gccggcctcc 60
atctcctgca ggtctagtca gagcctcctg catagtaatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
tgcagttttg gccaggggac caagctggag atcaaac 337

<210> SEQ ID NO 598
<211> LENGTH: 112
<212> TYPE: PRT
<213> ORGANISM: Homo Sapiens

<400> SEQUENCE: 598

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Cys Leu Asp Trp Tyr Leu Gln Lys Pro Gly Gln Ser
        35                  40                  45

Pro Gln Leu Leu Ile Tyr Leu Gly Ser Thr Arg Ala Ser Gly Phe Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

<210> SEQ ID NO 599
<211> LENGTH: 337
<212> TYPE: DNA
<213> ORGANISM: Homo Sapiens

<400> SEQUENCE: 599
gatattgtga tgactcagtc tccactctcc ctgcccgtca cccctggaga gccggcctcc 60
atctcctgca ggtctagtca gagcctcctg catagtaatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattctac actgaaaatc 240
agcagagtgg aggctgagga tgttggggtt tattactgca tgcaagctct acaaactccg 300

-continued tgcagttttg gccaggggac caagctggag atcaaac 337

<210> SEQ ID NO 600
<211> LENGTH: 112
<212> TYPE: PRT
<213> ORGANISM: Homo Sapiens

<400> SEQUENCE: 600

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Cys Leu Asp Trp Tyr Leu Gln Lys Pro Gly Gln Ser
35 40 45

Pro Gln Leu Leu Ile Tyr Leu Gly Ser Thr Arg Ala Ser Gly Phe Pro
50 55 60

Asp Arg Phe Ser Gly Ser Gly Ser Gly Thr Asp Ser Thr Leu Lys Ile
65 70 75 80

Ser Arg Val Glu Ala Glu Asp Val Gly Val Tyr Tyr Cys Met Gln Ala
85 90 95

Leu Gln Thr Pro Cys Ser Phe Gly Gln Gly Thr Lys Leu Glu Ile Lys
100 105 110

<210> SEQ ID NO 601
<211> LENGTH: 337
<212> TYPE: DNA
<213> ORGANISM: Homo Sapiens

<400> SEQUENCE: 601
gatattgtga tgactcagtc tccactctcc ctgcccgtca cccctggaga gccggcctcc 60
atctcctgca ggtctagtca gagcctcctg catagtaatg gatacaactg tttggattgg 120
tacctgcaga agccagggca gtctccacag ctcctgatct atttgggttc tactcgggcc 180
tccgggttcc ctgacaggtt cagtggcagt ggatcaggca cagattttac actgaaaatc 240
agcagagtgg aggctgagga tgttggggtt tattactgca tgcaagctct acaaactccg 300
tgcagttttg gccaggggac caagctggag atcaaac 337

<210> SEQ ID NO 602
<211> LENGTH: 112
<212> TYPE: PRT
<213> ORGANISM: Homo Sapiens

<400> SEQUENCE: 602

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Cys Leu Asp Trp Tyr Leu Gln Lys Pro Gly Gln Ser
35 40 45

Pro Gln Leu Leu Ile Tyr Leu Gly Ser Thr Arg Ala Ser Gly Phe Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Cys Ser Phe Gly Gln Gly Thr Lys Leu Glu Ile Lys
100 105 110

<210> SEQ ID NO 603
<211> LENGTH: 325
<212> TYPE: DNA
<213> ORGANISM: Homo Sapiens

<400> SEQUENCE: 603
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccttt cactttcggc 300
cctgggacca aagtggatat caaac 325

<210> SEQ ID NO 604
<211> LENGTH: 108
<212> TYPE: PRT
<213> ORGANISM: Homo Sapiens

<400> SEQUENCE: 604

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Phe Thr Phe Gly Pro Gly Thr Lys Val Asp Ile Lys
100 105

<210> SEQ ID NO 605
<211> LENGTH: 9
<212> TYPE: PRT
<213> ORGANISM: Homo Sapiens

<400> SEQUENCE: 605

Gln Gln Tyr Gly Ser Ser Pro Phe Thr
1 5

<210> SEQ ID NO 606
<211> LENGTH: 325
<212> TYPE: DNA
<213> ORGANISM: Homo Sapiens

<400> SEQUENCE: 606
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggaa 240
cctgaagatt ttgcagtata ttactgtcac cagtatggta attcaccatt cactttcggc 300
cctgggacca aagtggatat caaac 325

<210> SEQ ID NO 607
<211> LENGTH: 108
<212> TYPE: PRT
<213> ORGANISM: Homo Sapiens

<400> SEQUENCE: 607

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Asn Ser Pro
                85                  90                  95

Phe Thr Phe Gly Pro Gly Thr Lys Val Asp Ile Lys
            100                 105

<210> SEQ ID NO 608
<211> LENGTH: 9
<212> TYPE: PRT
<213> ORGANISM: Homo Sapiens

<400> SEQUENCE: 608

His Gln Tyr Gly Asn Ser Pro Phe Thr
1               5

<210> SEQ ID NO 609
<211> LENGTH: 11
<212> TYPE: PRT
<213> ORGANISM: Homo Sapiens
<220> FEATURE:
<221> NAME/KEY: MISC_FEATURE
<222> LOCATION: (1)..(1)
<223> OTHER INFORMATION: X = any amino acid.
<220> FEATURE:
<221> NAME/KEY: MISC_FEATURE
<222> LOCATION: (5)..(5)
<223> OTHER INFORMATION: X = any amino acid.
<220> FEATURE:
<221> NAME/KEY: MISC_FEATURE
<222> LOCATION: (8)..(8)
<223> OTHER INFORMATION: X = any amino acid.
<220> FEATURE:
<221> NAME/KEY: MISC_FEATURE
<222> LOCATION: (9)..(9)
<223> OTHER INFORMATION: X = is either present or absent, and if
      present, may be any amino acid.

<400> SEQUENCE: 609

Xaa Gly Ser Gly Xaa Tyr Gly Xaa Xaa Phe Asp
1               5                   10

<210> SEQ ID NO 610
<211> LENGTH: 478
<212> TYPE: PRT
<213> ORGANISM: Artificial Sequence
<220> FEATURE:
<223> OTHER INFORMATION: ICOSL-Fc fusion protein

<400> SEQUENCE: 610

Asp Thr Gln Glu Lys Glu Val Arg Ala Met Val Gly Ser Asp Val Glu
1 5 10 15

Leu Ser Cys Ala Cys Pro Glu Gly Ser Arg Phe Asp Leu Asn Asp Val
20 25 30

Tyr Val Tyr Trp Gln Thr Ser Glu Ser Lys Thr Val Val Thr Tyr His
35 40 45

Ile Pro Gln Asn Ser Ser Leu Glu Asn Val Asp Ser Arg Tyr Arg Asn
50 55 60

Arg Ala Leu Met Ser Pro Ala Gly Met Leu Arg Gly Asp Phe Ser Leu
65 70 75 80

Arg Leu Phe Asn Val Thr Pro Gln Asp Glu Gln Lys Phe His Cys Leu
85 90 95

Val Leu Ser Gln Ser Leu Gly Phe Gln Glu Val Leu Ser Val Glu Val
100 105 110

Thr Leu His Val Ala Ala Asn Phe Ser Val Pro Val Val Ser Ala Pro
115 120 125

His Ser Pro Ser Gln Asp Glu Leu Thr Phe Thr Cys Thr Ser Ile Asn
130 135 140

Gly Tyr Pro Arg Pro Asn Val Tyr Trp Ile Asn Lys Thr Asp Asn Ser
145 150 155 160

Leu Leu Asp Gln Ala Leu Gln Asn Asp Thr Val Phe Leu Asn Met Arg
165 170 175

Gly Leu Tyr Asp Val Val Ser Val Leu Arg Ile Ala Arg Thr Pro Ser
180 185 190

Val Asn Ile Gly Cys Cys Ile Glu Asn Val Leu Leu Gln Gln Asn Leu
195 200 205

Thr Val Gly Ser Gln Thr Gly Asn Asp Ile Gly Glu Arg Asp Lys Ile
210 215 220

Thr Glu Asn Pro Val Ser Thr Gly Glu Lys Asn Ala Ala Thr Trp Ser
225 230 235 240

Asp Ile Glu Gly Arg Met Asp Pro Lys Ser Cys Asp Lys Thr His Thr
245 250 255

Cys Pro Pro Cys Pro Ala Pro Glu Leu Leu Gly Gly Pro Ser Val Phe
260 265 270

Leu Phe Pro Pro Lys Pro Lys Asp Thr Leu Met Ile Ser Arg Thr Pro
275 280 285

Glu Val Thr Cys Val Val Val Asp Val Ser His Glu Asp Pro Glu Val
290 295 300

Lys Phe Asn Trp Tyr Val Asp Gly Val Glu Val His Asn Ala Lys Thr
305 310 315 320

Lys Pro Arg Glu Glu Gln Tyr Asn Ser Thr Tyr Arg Val Val Ser Val
325 330 335

Leu Thr Val Leu His Gln Asp Trp Leu Asn Gly Lys Glu Tyr Lys Cys
340 345 350

Lys Val Ser Asn Lys Ala Leu Pro Ala Pro Ile Glu Lys Thr Ile Ser
355 360 365

Lys Ala Lys Gly Gln Pro Arg Glu Pro Gln Val Tyr Thr Leu Pro Pro
370 375 380

Ser Arg Asp Glu Leu Thr Lys Asn Gln Val Ser Leu Thr Cys Leu Val
385 390 395 400

Lys Gly Phe Tyr Pro Ser Asp Ile Ala Val Glu Trp Glu Ser Asn Gly
405 410 415

-continued

```
Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```